US006921759B2

(12) United States Patent
Anthony et al.

(10) Patent No.: US 6,921,759 B2
(45) Date of Patent: Jul. 26, 2005

(54) AZA- AND POLYAZA-NAPHTHALENYL CARBOXAMIDES USEFUL AS HIV INTEGRASE INHIBITORS

(75) Inventors: Neville J. Anthony, Hatfield, PA (US); Robert P. Gomez, Perkasie, PA (US); Steven D. Young, Lansdale, PA (US); Melissa Egbertson, Ambler, PA (US); John S. Wai, Harleysville, PA (US); Linghang Zhuang, Chalfont, PA (US); Mark Embrey, North Wales, PA (US); Jeffrey Y. Melamed, Doylestown, PA (US); H. Marie Langford, Lansdale, NJ (US); James P. Guare, Quakertown, PA (US); Thorsten E. Fisher, Hatfield, PA (US); Samson M. Jolly, Quakertown, PA (US); Michelle S. Kuo, Gwynedd Valley, PA (US); Debra S. Perlow, East Greenville, PA (US); Jennifer J. Bennett, East Norriton, PA (US); Timothy W. Funk, Ephrata, PA (US)

(73) Assignee: Merck & Co., Inc., Rahway, NJ (US)

( * ) Notice: Subject to any disclaimer, the term of this patent is extended or adjusted under 35 U.S.C. 154(b) by 119 days.

(21) Appl. No.: 09/973,853

(22) Filed: Oct. 10, 2001

(65) Prior Publication Data

US 2003/0055071 A1 Mar. 20, 2003

Related U.S. Application Data

(60) Provisional application No. 60/281,656, filed on Apr. 5, 2001, and provisional application No. 60/239,707, filed on Oct. 12, 2000.

(51) Int. Cl.$^7$ .................... A61P 31/00; A61K 31/4375; C07D 471/02
(52) U.S. Cl. ................ 514/211.03; 514/211.08; 514/218; 514/222.2; 514/222.5; 514/228.2; 514/234.5; 514/249; 514/253.04; 514/274; 514/275; 514/300; 514/303; 540/488; 540/489; 540/492; 540/545; 544/3; 544/8; 544/58.6; 544/127; 544/310; 544/331; 544/349; 544/362; 546/118; 546/9; 546/123
(58) Field of Search ............. 514/211.03, 211.08, 514/218, 222.2, 222.5, 228.2, 234.5, 249, 253.04, 274, 275, 300, 303; 540/488, 489, 492, 545; 544/3, 8, 58.6, 127, 310, 331, 349, 362; 546/118, 119, 123

(56) References Cited

U.S. PATENT DOCUMENTS

| 3,945,995 | A | 3/1976 | Yamada et al. .......... 260/239.1 |
|---|---|---|---|
| 4,416,884 | A | 11/1983 | Ishikawa et al. ............ 424/250 |
| 4,996,213 | A | 2/1991 | Mendes et al. ............. 514/300 |
| 5,294,620 | A | 3/1994 | Ratcliffe et al. ............ 514/300 |
| 5,633,362 | A | 5/1997 | Nagarajan et al. ......... 536/23.1 |
| 5,753,666 | A | 5/1998 | Beasley et al. ............. 514/258 |
| 5,766,944 | A | 6/1998 | Ruiz .......................... 435/325 |
| 5,945,431 | A | 8/1999 | Jin et al. ..................... 514/300 |
| 6,211,376 | B1 | 4/2001 | Romines et al. ............ 546/172 |
| 6,262,055 | B1 | 7/2001 | Young et al. ............... 514/252 |
| 6,294,547 | B1 | 9/2001 | Oka et al. ................... 514/292 |
| 6,306,891 | B1 | 10/2001 | Selnick et al. .............. 514/423 |
| 6,380,249 | B1 | 4/2002 | Young et al. ............... 514/530 |
| 6,525,042 | B1 | 2/2003 | Kobayashi et al. .... 514/212.03 |

FOREIGN PATENT DOCUMENTS

| WO | WO 96/25399 | 8/1996 |
|---|---|---|
| WO | WO 98/11073 | 3/1998 |
| WO | WO 98/13350 | 4/1998 |
| WO | WO 99/10347 | 3/1999 |
| WO | WO 99/15526 A2 | 4/1999 |
| WO | WO 99/32450 | 7/1999 |
| WO | WO 00/03992 A1 | 1/2000 |
| WO | WO 01/00578 A1 | 1/2001 |
| WO | WO 02/04443 | 1/2002 |
| WO | WO 02/06246 A1 | 1/2002 |
| WO | PCT/US 02/25666 | 8/2002 |
| WO | PCT/US 02/27151 | 8/2002 |
| WO | WO 03/035076 A1 | 5/2003 |
| WO | WO 03/035077 A1 | 5/2003 |

OTHER PUBLICATIONS

Pommier et al., Retroviral Integrase Inhibitors Year 2000: Update and Perspectives, Antiviral Research, vol. 47, pp. 139–148, Sep. 2000.*

De Clercq, Erik, New Anti–HIV Agents and Targets, Medicinal Research Reviews, vol. 22, No. 6, pp. 531–565, 2002.*

J. Bedard et al., "Antiviral Properties of a Series of 1,6–Naphthyridine and 7,8–Dihydroisoquinoline Derivatives Exhibiting Potent Activity Against Human Cytomegalovirus", 2000, vol. 44, Antimicrobial Agents and Chemotherapy.

CAPLUS Accession No. 2001:923611, Kiyama et al., "Dual divalent metal ion chelators as HIV integrase inhibitors", abstract of WO 01/95905, Assignee: Shionogi & Co., Ltd. (2001).

Abstract of WO 02/070486 from http://ipdl.wipo.int (Fuji et al., "Nitrogen–Containing Heteroaryl Compounds Having HIV Integrase Inhibitory Activity", Assignee: Shionogi & Co., Ltd.), 2002.

(Continued)

*Primary Examiner*—Brenda Coleman

(57) ABSTRACT

Aza- and polyaza-naphthalenyl carboxamide derivatives including certain quinoline carboxamide and naphthyridine carboxamide derivatives are described. These compounds are inhibitors of HIV integrase and inhibitors of HIV replication, and are useful in the prevention or treatment of infection by HIV and the treatment of AIDS, as compounds or pharmaceutically acceptable salts, or as ingredients in pharmaceutical compositions, optionally in combination with other antivirals, immunomodulators, antibiotics or vaccines. Methods of preventing, treating or delaying the onset of AIDS and methods of preventing or treating infection by HIV are also described.

23 Claims, No Drawings

OTHER PUBLICATIONS

L. Chan et al., "Discovery of 1,6–Naphthyridines as a Novel Class of Potent and Selective Human Cytomegalovirus Inhibitors", J. Med. Chem., vol. 42, No. 16, pp. 3023–3025 (1999).

Derwent Abstract No. 2002–732783, M. Fuji, "New Nitrogenous Heteroaromatic Compounds Are HIV Integrase Inhibitors For Treating HIV Infections, AIDS and AIDS–related Diseases", Abstract of WO 02/070491, Assignee: Shionogi & Co., Ltd. (2002).

M. Ouali et al., "Modeling of the Inhibition of Retroviral Integrases by Styrylquinoline Derivatives", J. Med. Chem., vol. 43, pp. 1949–1957 (2000).

CAPLUS Accession No. 2001:923611, R. Kiyama et al., "Dual Divalent Metal Ion Chelators as HIV Integrase Inhibitors", Abstract of WO 01/95905, Assignee: Shionogi & Co., Ltd., Japan (2001).

L. Ratner et al., "Complete Nucleotide sequence of the AIDS virus, HTLV–III", Nature, vol. 313, pp. 277–284 (Jan. 24, 1985).

H. Toh et al., "Close structural resemblance between putative polymerase of a Drosophila transposable genetic element 17.6 and pol gene product of Moloney murine leukaemia virus", The EMBO Journal, vol. 4, No. 5, pp. 1267–1272 (1985).

M. D. Power et al., "Nucleotide Sequence of SRV–1, Type D Simian Acquired Immune Deficiency Syndrome Retrovirus", Science, vol. 231, pp. 1567–1572 (1986).

L. H. Pearl et al., "A structural model for the retroviral proteases", Nature, vol. 329, pp. 351–354 (Sep. 24, 1987).

Derwent Abstract No. 97–048296/05 (Abstract of JP 08301849–A, Takeda Chem. Ind. Ltd., "New heterocyclic carboxamide derivs.—useful in pharmaceuticals as tachykinin receptor inhibitors"), 1996.

Chemical Abstracts No. 33–2525 ; (Abstract of Otiai et al., "Synthesis of 2,5 naphthyridine derivatives. II", J. Pharm. Soc. Japan, vol. 58, pp. 764–770 (1938)).

U.S. Appl. No. 10/333,431, filed Jul. 11, 2001, Gardelli et al.

U.S. Appl. No. 10/218,537, filed Aug. 14, 2002, Anthony et al.

* cited by examiner

AZA- AND POLYAZA-NAPHTHALENYL CARBOXAMIDES USEFUL AS HIV INTEGRASE INHIBITORS

This application claims the benefit of U.S. Provisional Application No. 60/239,707, filed Oct. 12, 2000, and U.S. Provisional Application No. 60/281,656, filed Apr. 5, 2001, the disclosures of which are hereby incorporated by reference in their entireties.

FIELD OF THE INVENTION

The present invention is directed to aza- and polyaza-naphthalenyl carboxamides and pharmaceutically acceptable salts thereof, their synthesis, and their use as inhibitors of the HIV integrase enzyme. The compounds of the present invention include 7-(N-substituted carboxamido)-8-hydroxy-1,6-naphthyridines and quinoxalines. The compounds and pharmaceutically acceptable salts thereof of the present invention are useful for preventing or treating infection by HIV and for treating AIDS.

References are made throughout this application to various published documents in order to more fully describe the state of the art to which this invention pertains. The disclosures of these references are hereby incorporated by reference in their entireties.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhbitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:

Chemical Abstracts No. 33-2525 discloses the preparation of 5-chloro-8-hydroxy-1,6-naphthyridine-7-carboxylic acid amide from the corresponding methyl ester.

Derwent Abstract No. 97-048296 is an abstract of Japanse Published Application No. 08301849. The abstract discloses certain heterocyclic carboxamide derivatives. The derivatives are said to be useful as tachykinin receptor inhibitors. N-(3,5-bis(trifluoromethyl)benzyl-1,2-dihydro-N,2-dimethyl-1-oxo-4-pyrrolidino-3-isoquinoline carboxamide is specifically disclosed.

WO 98/13350 discloses certain quinoline derivatives which inhibit vascular endothelial growth factor. The reference also discloses certain 1,8-naphthryidine derivatives; i.e., Examples 53 and 54 respectively describe preparations of 2-acetamido-5-(2-fluoro-5-hydroxy-4-methylanilino)-1, 8-naphthyridine and 2-amino-5-(2-fluoro-5-hydroxy-4-methylanilino)-1,8-naphthyridine.

WO 99/32450 discloses 4-hydroxyquinoline-2-carboxamide derivatives which are proposed for use in treating herpes virus infections.

WO 98/11073 discloses 8-hydroxyquinoline-7-carboxamides which are proposed for use in treating herpes virus infections.

SUMMARY OF THE INVENTION

The present invention is directed to novel aza- and polyazanaphthalenyl carboxamides. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts or hydrates (when appropriate), or as pharmaceutical composition ingredients, whether or not in combination with other HIV/AIDS antivirals, anti-infectives, immunomodulators, antibiotics or vaccines. More particularly, the present invention includes a compound of Formula (I):

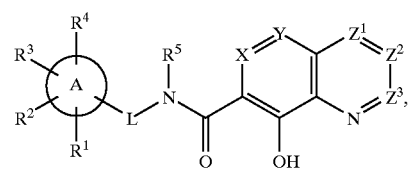

wherein A is phenyl or phenyl fused to a carbocycle to form a fused carbocyclic ring system;
A is substituted by $R^1$, $R^2$, $R^3$, and $R^4$;
L is a linker connecting a ring atom of A to the nitrogen of the —N($R^5$)— moiety, wherein L is
  (i) a single bond,
  (ii) —($C_{1-6}$ alkyl)-,
  (iii) —($C_{2-6}$ alkenyl)-,
  (iv) —($C_{0-6}$ alkyl)($C_{3-6}$ cycloalkyl)($C_{0-6}$ alkyl)-, or
  (v) —($C_{0-6}$ alkyl)-M—($C_{0-6}$ alkyl)-, wherein M is —N($R^a$)—, —OC(=O)—, or —C(=O)O—; wherein the alkenyl in (iii) and the alkyls in (ii), (iv), and (v) are independently and optionally substituted with 1, 2, or 3 substituents independently selected from the group consisting of halogen, —OH, —$C_{1-6}$ alkyl, —O—$C_{1-6}$ alkyl, —$CO_2R^a$, —$CO_2(CH_2)_{1-2}R^k$, —$C_{1-6}$ alkyl-$OR^a$, —$R^k$, —$(CH_2)_{1-2}R^k$, —CH($OR^a$)—$R^k$, and —CH(N($R^a$)$_2$)—$R^k$;

X is N or C—$Q^1$;
Y is N or C—$Q^2$, provided that X and Y are not both N;
$Z^1$ is N or C—$Q^3$;
$Z^2$ is N or C—$Q^4$;
$Z^3$ is N or CH;
$Q^1$, $Q^2$, $Q^3$, and $Q^4$ are as defined in (i) or (ii) as follows:

(i) each of $Q^1$, $Q^2$, $Q^3$, and $Q^4$ is independently
- (1) —H,
- (2) —$C_{1-6}$ alkyl,
- (3) —$C_{1-6}$ haloalkyl,
- (4) —O—$C_{1-6}$ alkyl,
- (5) —O—$C_{1-6}$ haloalkyl,
- (6) halo,
- (7) —CN,
- (8) —$C_{1-6}$ alkyl-$OR^a$,
- (9) —$C_{0-6}$ alkyl-C(=O)$R^a$,
- (10) —$C_{0-6}$ alkyl-$CO_2R^a$,
- (11) —$C_{0-6}$ alkyl-$SR^a$,
- (12) —N($R^a$)$_2$,
- (13) —$C_{1-6}$ alkyl-N($R^a$)$_2$,
- (14) —$C_{0-6}$ alkyl-C(=O)N($R^a$)$_2$,
- (15) —$C_{0-6}$ alkyl-G—$C_{1-6}$ alkyl-C(=O)N($R^a$)$_2$, wherein G is O, S, N($R^a$), or N($SO_2R^a$),
- (16) —N($R^a$)—C($R^a$)=O,
- (17) —$C_{1-6}$ alkyl-N($R^a$)—C($R^a$)=O,
- (18) —C(=O)—N($R^a$)—$C_{1-6}$ alkyl-[C(=O)]$_{0-1}$—N($R^a$)$_2$,
- (19) —C(=O)—N($R^a$)—$C_{1-6}$ alkyl substituted with 1 or 2—$OR^a$,
- (20) —$C_{0-6}$ alkyl-$SO_2R^a$,
- (21) —$C_{0-6}$ alkyl-N($R^a$)$SO_2R^a$,
- (22) —$C_{2-6}$ alkenyl,
- (23) —$C_{2-6}$ alkenyl-C(=O)—N($R^a$)$_2$,
- (24) —$C_{2-5}$ alkynyl,
- (25) —$C_{2-5}$ alkynyl-$CH_2$N($R^a$)$_2$,
- (26) —$C_{2-5}$ alkynyl-$CH_2OR^a$,
- (27) —$C_{2-5}$ alkynyl-$CH_2$S(O)$_n$—$R^a$, or

(28) 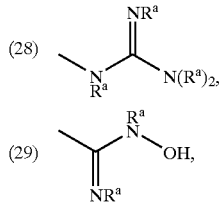

(29)

- (30) —C(=N$R^a$)—N($R^a$)$_2$,
- (31) —N($R^a$)—$C_{1-6}$ alkyl-S(O)$_n R^a$,
- (32) —N($R^a$)—$C_{1-6}$ alkyl-$OR^a$,
- (33) —N($R^a$)—$C_{1-6}$ alkyl-N($R^a$)$_2$,
- (34) —N($R^a$)—$C_{1-6}$ alkyl-N($R^a$)—C($R^a$)=O,
- (35) —N($R^a$)—$C_{0-6}$ alkyl-[C(=O)]$_{1-2}$N($R^a$)$_2$,
- (36) —N($R^a$)—$C_{1-6}$ alkyl-$CO_2R^a$,
- (37) —N($R^a$)C(=O)N($R^a$)—$C_{1-6}$ alkyl-C(=O)N($R^a$)$_2$,
- (38) —N($R^a$)C(=O)—$C_{1-6}$ alkyl-N($R^a$)$_2$,
- (39) —N($R^a$)—$SO_2$—N($R^a$)$_2$,
- (40) —$R^k$,
- (41) —$C_{1-6}$ alkyl substituted with $R^k$,
- (42) —$C_{1-6}$ haloalkyl substituted with $R^k$,
- (43) —$C_{2-5}$ alkenyl-$R^k$,
- (44) —$C_{2-5}$ alkynyl-$R^k$,
- (45) —$C_{0-6}$ alkyl-O—$R^k$,
- (46) —$C_{0-6}$ alkyl-O—$C_{1-6}$ alkyl-$R^k$,
- (47) —$C_{0-6}$ alkyl-S(O)$_n$—$R^k$,
- (48) —$C_{0-6}$ alkyl-S(O)$_n$—$C_{1-6}$ alkyl-$R^k$,
- (49) —O—$C_{1-6}$ alkyl-$OR^k$,
- (50) —O—$C_{1-6}$ alkyl-O—$C_{1-6}$ alkyl-$R^k$,
- (51) —O—$C_{1-6}$ alkyl-S(O)$_n R^k$,
- (52) —$C_{0-6}$ alkyl-N($R^c$)—$R^k$,
- (53) —$C_{0-6}$ alkyl-N($R^c$)—$C_{1-6}$ alkyl substituted with one or two $R^k$ groups,
- (54) —$C_{0-6}$ alkyl-N($R^c$)—$C_{1-6}$ alkyl-$OR^k$,
- (55) —$C_{0-6}$ alkyl-C(=O)—$R^k$,
- (56) —$C_{0-6}$ alkyl-C(=O)N($R^a$)—$R^k$,
- (57) —$C_{0-6}$ alkyl-N($R^a$)C(=O)—$R^k$,
- (58) —$C_{0-6}$ alkyl-C(=O)N($R^a$)—$C_{1-6}$ alkyl-$R^k$, or
- (59) —$C_{0-6}$ alkyl-N($R^a$)—$C_{0-6}$ alkyl-S(O)$_n R^k$;

(ii) alternatively, $Q^2$ and $Q^3$ together with the carbon atoms to which they are attached and the fused ring carbon atom attached therebetween form a 5- or 6-membered monocyclic carbocycle or a 5- or 6-membered monocyclic heterocycle, wherein the heterocycle contains 1 or 2 heteroatoms selected from nitrogen, oxygen and sulfur, and wherein either the carbocycle or heterocycle is optionally substituted with from 1 to 3 substituents independently selected from
- (1) —$C_{1-6}$ alkyl,
- (3) —$C_{1-6}$ haloalkyl,
- (4) —O—$C_{1-6}$ alkyl,
- (5) —O—$C_{1-6}$ haloalkyl,
- (6) halo,
- (7) —CN,
- (8) —$C_{1-6}$ alkyl-$OR^a$,
- (9) —$C_{1-6}$ alkyl-S(O)$_n R^a$,
- (10) —$C_{1-6}$ alkyl-N($R^a$)$_2$,
- (11) —$C_{1-6}$ alkyl-C(=O)—N($R^a$)$_2$,
- (12) —$C_{1-6}$ alkyl-$CO_2R^a$,
- (13) oxo,
- (14) —$R^k$, and
- (15) —$C_{1-6}$ alkyl substituted with $R^k$; and $Q^1$ and $Q^4$ are independently as defined in (i) above;
each of $R^1$ and $R^2$ is independently:
- (1) —H,
- (2) —$C_{1-6}$ alkyl,
- (3) —$C_{1-6}$ haloalkyl,
- (4) —O—$C_{1-6}$ alkyl,
- (5) —O—$C_{1-6}$ haloalkyl,
- (6) —OH
- (7) halo,
- (8) —$NO_2$,
- (9) —CN,
- (10) —$C_{1-6}$ alkyl-$OR^a$,
- (11) —$C_{0-6}$ alkyl-C(=O)$R^a$,
- (12) —$C_{0-6}$ alkyl-$CO_2R^a$,
- (13) —$C_{0-6}$ alkyl-$SR^a$,
- (14) —N($R^a$)$_2$,
- (15) —$C_{1-6}$ alkyl-N($R^a$)$_2$,
- (16) —$C_{0-6}$ alkyl-C(=O)N($R^a$)$_2$,
- (17) —$C_{1-6}$ alkyl-N($R^a$)—C($R^a$)=O,
- (18) —$SO_2R^a$,
- (19) —N($R^a$)$SO_2R^a$,
- (20) —$C_{2-5}$ alkenyl,
- (21) —O—$C_{1-6}$ alkyl-$OR^a$,
- (22) —O—$C_{1-6}$ alkyl-$SR^a$,
- (23) —O—$C_{1-6}$ alkyl-NH—$CO_2R^a$,
- (24) —O—$C_{2-6}$ alkyl-N($R^a$)$_2$,
- (25) —N($R^a$)—$C_{1-6}$ alkyl-$SR^a$,
- (26) —N($R^a$)—$C_{1-6}$ alkyl-$OR^a$,

(27) —N(R$^a$)—C$_{1-6}$ alkyl-N(R$^a$)$_2$,
(28) —N(R$^a$)—C$_{1-6}$ alkyl-N(R$^a$)—C(R$^a$)=O,
(29) —R$^k$,
(30) —C$_{1-6}$ alkyl substituted with 1 or 2 R$^k$ groups,
(31) —C$_{1-6}$ haloalkyl substituted with 1 or 2 R$^k$ groups,
(32) —C$_{2-5}$ alkenyl-R$^k$,
(33) —C$_{2-5}$ alkynyl-R$^k$,
(34) —O—R$^k$,
(35) —O—C$_{1-6}$ alkyl-R$^k$,
(36) —S(O)$_n$—R$^k$,
(37) —S(O)$_n$—C$_{1-6}$ alkyl-R$^k$,
(38) —O—C$_{1-6}$ alkyl-OR$^k$,
(39) —O—C$_{1-6}$ alkyl-O—C$_{1-6}$ alkyl-R$^k$,
(40) —O—C$_{1-6}$ alkyl-S(O)$_n$R$^k$,
(41) —C$_{1-6}$ alkyl (OR$^b$)(R$^k$),
(42) —C$_{1-6}$ alkyl (OR$^b$)(—C$_{1-6}$ alkyl-R$^k$),
(43) —C$_{0-6}$ alkyl-N(R$^b$)(R$^k$),
(44) —C$_{0-6}$ alkyl-N(R$^b$)(—C$_{1-6}$ alkyl-R$^k$),
(45) —C$_{1-6}$ alkyl S(O)$_n$—R$^k$,
(46) —C$_{1-6}$ alkyl S(O)$_n$—C$_{1-6}$ alkyl-R$^k$,
(47) —C$_{0-6}$ alkyl C(O)—R$^k$, or
(48) —C$_{0-6}$ alkyl C(O)—C$_{1-6}$ alkyl-R$^k$,
each of R$^3$ and R$^4$ is independently
(1) —H,
(2) halo,
(3) —CN,
(4) —NO$_2$,
(5) —OH,
(6) C$_{1-6}$ alkyl,
(7) C$_{1-6}$ haloalkyl,
(8) —O—C$_{1-6}$ alkyl,
(9) —O—C$_{1-6}$ haloalkyl,
(10) —C$_{1-6}$ alkyl-OR$^a$,
(11) —C$_{0-6}$ alkyl-C(=O)R$^a$,
(12) —C$_{0-6}$ alkyl-CO$_2$R$^a$,
(13) —C$_{0-6}$ alkyl-SR$^a$,
(14) —N(R$^a$)$_2$,
(15) —C$_{1-6}$ alkyl-N(R$^a$)$_2$,
(16) —C$_{0-6}$ alkyl-C(=O)N(R$^a$)$_2$,
(17) —SO$_2$R$^a$,
(18) —N(R$^a$)SO$_2$R$^a$,
(19) —C$_{2-5}$ alkenyl,
(20) —O—C$_{1-6}$ alkyl-OR$^a$,
(21) —O—C$_{1-6}$ alkyl-SR$^a$,
(22) —O—C$_{1-6}$ alkyl-NH—CO$_2$R$^a$, or
(23) —O—C$_{2-6}$ alkyl-N(R$^a$)$_2$;
R$^5$ is
(1) —H,
(2) —C$_{1-6}$ alkyl, optionally substituted with from 1 to 5 substituents independently selected from halogen, —O—C$_{1-6}$ alkyl, —O—C$_{1-6}$ haloalkyl, —N(R$^a$)$_2$, and —CO$_2$R$^a$;
(3) aryl optionally substituted with from 1 to 5 substituents independently selected from halogen, C$_{1-6}$ alkyl, C$_{1-6}$ haloalkyl, —O—C$_{1-6}$ alkyl, —O—C$_{1-6}$ haloalkyl, —S—C$_{1-6}$ alkyl, —CN, and —OH, or
(4) —C$_{1-6}$ alkyl substituted with R$^k$;
each R$^a$ is independently —H, —C$_{1-6}$ alkyl, or —C$_{1-6}$ haloalkyl;

each R$^b$ is independently:
(1) —H,
(2) —C$_{1-4}$ alkyl,
(3) —C$_{1-4}$haloalkyl,
(4) —R$^k$,
(5) —C$_{2-3}$ alkenyl,
(6) —C$_{1-4}$ alkyl-R$^k$,
(7) —C$_{2-3}$ alkenyl-R$^k$,
(8) —S(O)$_n$—R$^k$, or
(9) —C(O)—R$^k$;
each R$^c$ is independently
(1) —H,
(2) —C$_{1-6}$ alkyl,
(3) —C$_{1-6}$ alkyl substituted with —N(R$^a$)$_2$, or
(4) —C$_{1-4}$ alkyl-aryl, wherein aryl is optionally substituted with 1 to 5 substituents independently selected from halogen, C$_{1-6}$ alkyl, C$_{1-6}$ haloalkyl, —O—C$_{1-6}$ alkyl, —O—C$_{1-6}$ haloalkyl, —S—C$_{1-6}$ alkyl, —CN, and —OH;
each R$^k$ is independently carbocycle or heterocycle, wherein the carbocycle and heterocycle are unsubstituted or substituted with from 1 to 5 substituents each of which is independently selected from
(a) halogen,
(b) —C$_{1-6}$ alkyl,
(c) —C$_{1-6}$ haloalkyl,
(d) —O—C$_{1-6}$ alkyl,
(e) —O—C$_{1-6}$ haloalkyl,
(f) —S—C$_{1-6}$ alkyl,
(g) —CN,
(h) —OH,
(i) oxo,
(j) —C$_{0-6}$ alkyl-C(=O)N(R$^a$)$_2$,
(k) —C$_{0-6}$ alkyl-C(=O)R$^a$,
(l) —N(R$^a$)—C(=O)R$^a$,
(m) —N(R$^a$)—CO$_2$R$^a$,
(n) —C$_{1-6}$ alkyl-N(R$^a$)—C(=O)R$^a$,
(o) —N(R$^a$)$_2$,
(p) —C$_{1-6}$ alkyl-N(R$^a$)$_2$,
(q) —C$_{1-6}$ alkyl-OR$^a$,
(r) —C$_{0-6}$ alkyl-CO$_2$R$^a$,
(s) —C$_{0-6}$ alkyl-O—C$_{1-6}$ alkyl-OR$^a$,
(t) —SO$_2$R$^a$,
(u) —SO$_2$N(R$^a$)$_2$,
(v) —C$_{0-6}$ alkyl-CO$_2$—C$_{2-5}$ alkenyl,
(w) aryl,
(x) aryloxy-,
(y) —C$_{1-4}$ alkyl substituted with aryl,
(z) heteromonocycle,
(aa) —C$_{1-4}$ alkyl substituted with a heteromonocycle,
(bb) heteromonocyclylcarbonyl-C$_{0-6}$ alkyl-, and
(cc) N-heteromonocyclyl-N—C$_{1-6}$ alkyl-amino-;
wherein the aryl group in (w) aryl, (x) aryloxy, and (y) —C$_{1-4}$ alkyl substituted with aryl, is optionally substituted with from 1 to 4 substituents independently selected from halogen, C$_{1-6}$ alkyl, —O—C$_{1-6}$ alkyl, C$_{1-6}$ alkyl substituted with N(R$^a$)$_2$, C$_{1-6}$ haloalkyl, and —OH; and
wherein the heteromonocyclyl group in (z) heteromonocycle, (aa) —C$_{1-4}$ alkyl substituted with a heteromonocycle, (bb) heteromonocyclyl-carbonyl-C$_{0-6}$ alkyl-, and (cc) N-heteromonocyclyl-N—C$_{1-6}$ alkyl-amino- is optionally substituted with from 1 to 4 substituents independently selected from halogen, C$_{1-6}$ alkyl, —O—C$_{1-6}$ alkyl, C$_{1-6}$ haloalkyl, oxo, and —OH; and each n is independently an integer equal to 0, 1 or 2;
and with the proviso that when Z$^1$ is C—Q$^3$, Z$^2$ is C—Q$^4$, Z$^3$ is CH, and X is C—Q$^1$, then Y is not C—Q$^2$;
or a pharmaceutically acceptable salt thereof.

An aspect of the invention is a compound of Formula (I) as just defined above, except that part (i) of the definition of Q$^1$, Q$^2$, Q$^3$, and Q$^4$ does not include (59) —C$_{0-6}$ alkyl-N(R$^a$)—C$_{0-6}$ alkyl-S(O)$_n$R$^k$.

A first embodiment of the invention is a compound of Formula (I), wherein each of Q$^1$, Q$^2$, Q$^3$, and Q$^4$ is independently
(1) —H,
(2) —C$_{1-6}$ alkyl,
(3) —C$_{1-6}$ fluoroalkyl,
(4) —O—C$_{1-6}$ alkyl,
(5) —O—C$_{1-6}$ fluoroalkyl,
(6) halo,
(7) —CN,
(8) —C$_{1-6}$ alkyl-OR$^a$,
(9) —C$_{0-6}$ alkyl-C(=O)R$^a$,
(10) —C$_{0-6}$ alkyl-CO$_2$R$^a$,
(11) —C$_{0-6}$ alkyl-SR$^a$,
(12) —N(R$^a$)$_2$,
(13) —C$_{1-6}$ alkyl —N(R$^a$)$_2$,
(14) —C$_{0-6}$ alkyl-C(=O)N(R$^a$)$_2$,
(15) —C$_{1-6}$ alkyl-N(R$^a$)—C(R$^a$)=O,
(16) —SO$_2$R$^a$,
(17) —N(R$^a$)SO$_2$R$^a$,
(18) —C$_{2-5}$ alkynyl,
(19) —C$_{2-5}$ alkynyl-CH$_2$N(R$^a$)$_2$,
(20) —C$_{2-5}$ alkynyl-CH$_2$OR$^a$,

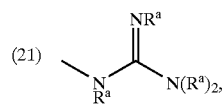

(22) —N(R$^a$)—C$_{1-6}$ alkyl-SR$^a$,
(23) —N(R$^a$)—C$_{1-6}$ alkyl-OR$^a$,
(24) —N(R$^a$)—C$_{1-6}$ alkyl-N(R$^a$)$_2$,
(25) —N(R$^a$)—C$_{1-6}$ alkyl-N(R$^a$)—C(R$^a$)=O,
(26) —R$^k$,
(27) —C$_{1-6}$ alkyl substituted with R$^k$,
(28) —C$_{1-6}$ fluoroalkyl substituted with R$^k$,
(29) —C$_{2-5}$ alkenyl-R$^k$,
(30) —C$_{2-5}$ alkynyl-R$^k$,
(31) —O—R$^k$,
(32) —O—C$_{1-4}$ alkyl-R$^k$,
(33) —S(O)$_n$—R$^k$,
(34) —S(O)$_n$—C$_{1-4}$ alkyl-R$^k$,
(35) —O—C$_{1-6}$ alkyl-OR$^k$,
(36) —O—C$_{1-6}$ alkyl-O—C$_{1-4}$ alkyl-R$^k$,
(37) —O—C$_{1-6}$ alkyl-SR$^k$,
(38) —N(R$^c$)—R$^k$,
(39) —N(R$^c$)—C$_{1-6}$ alkyl substituted with one or two R$^k$ groups,
(40) —N(R$^c$)—C$_{1-6}$ alkyl-OR$^k$,
(41) —C(=O)N(R$^a$)—C$_{1-6}$ alkyl-R$^k$,
(42) —C$_{2-5}$ alkynyl-CH$_2$S(O)$_n$—R$^a$, or
(43) —C(=NR$^a$)—N(R$^a$)$_2$;
each of R$^1$ and R$^2$ is independently:
(1) —H,
(2) —C$_{1-6}$ alkyl,
(3) —C$_{1-6}$ fluoroalkyl,
(4) —O—C$_{1-6}$ alkyl,
(5) —O—C$_{1-6}$ fluoroalkyl,
(6) —OH
(7) halo,
(8) —NO$_2$,
(9) —CN,
(10) —C$_{1-6}$ alkyl—OR$^a$,
(11) —C$_{0-6}$ alkyl-C(=O)R$^a$,
(12) —C$_{0-6}$ alkyl-CO$_2$R$^a$,
(13) —C$_{0-6}$ alkyl-SR$^a$,
(14) —N(R$^a$)$_2$,
(15) —C$_{1-6}$ alkyl-N(R$^a$)$_2$,
(16) —C$_{0-6}$ alkyl-C(=O)N(R$^a$)$_2$,
(17) —C$_{1-6}$ alkyl-N(R$^a$)—C(R$^a$)=O,
(18) —SO$_2$R$^a$,
(19) —N(R$^a$)SO$_2$R$^a$,
(20) —C$_{2-5}$ alkenyl,
(21) —O—C$_{1-6}$ alkyl-OR$^a$,
(22) —O—C$_{1-6}$ alkyl-SR$^a$,
(23) —O—C$_{1-6}$ alkyl-NH—CO$_2$R$^a$,
(24) —O—C$_{2-6}$ alkyl-N(R$^a$)$_2$,
(25) —N(R$^a$)—C$_{1-6}$ alkyl-SR$^a$,
(26) —N(R$^a$)—C$_{1-6}$ alkyl-OR$^a$,
(27) —N(R$^a$)—C$_{1-6}$ alkyl-N(R$^a$)$_2$,
(28) —N(R$^a$)—C$_{1-6}$ alkyl-N(R$^a$)—C(R$^a$)=O,
(29) R$^k$,
(30) —C$_{1-6}$ alkyl substituted with 1 or 2 R$^k$ groups,
(31) —C$_{1-6}$ fluoroalkyl substituted with 1 or 2 R$^k$ groups,
(32) —C$_{2-5}$ alkenyl-R$^k$,
(33) —C$_{2-5}$ alkynyl-R$^k$,
(34) —O—R$^k$,
(35) —O—C$_{1-4}$ alkyl-R$^k$,
(36) —S(O)$_n$—R$^k$,
(37) —S(O)$_n$—C$_{1-4}$ alkyl-R$^k$,
(38) —O—C$_{1-6}$ alkyl-OR$^k$,
(39) —O—C$_{1-6}$ alkyl-O—C$_{1-4}$ alkyl-R$^k$,
(40) —O—C$_{1-6}$ alkyl-SR$^k$,
(41) —C$_{1-6}$ alkyl (OR$^b$)(R$^k$),
(42) —C$_{1-6}$ alkyl (OR$^b$)(—C$_{1-4}$ alkyl-R$^k$),
(43) —C$_{0-6}$ alkyl-N(R$^b$)(R$^k$),
(44) —C$_{0-6}$ alkyl-N(R$^b$)(—C$_{1-4}$ alkyl-R$^k$),
(45) —C$_{1-6}$ alkyl S(O)$_n$—R$^k$,
(46) —C$_{1-6}$ alkyl S(O)$_n$—C$_{1-4}$ alkyl-R$^k$,
(47) —C$_{0-6}$ alkyl C(O)—R$^k$, or
(48) —C$_{0-6}$ alkyl C(O)—C$_{1-4}$ alkyl-R$^k$, each of $R^3$ and $R^4$ is independently
- (1) —H,
- (2) halo,
- (3) —CN,
- (4) —NO$_2$,
- (5) —OH,
- (6) C$_{1-6}$ alkyl,
- (7) C$_{1-6}$ fluoroalkyl,
- (8) —O—C$_{1-6}$ alkyl,
- (9) —O—C$_{1-6}$ fluoroalkyl,
- (10) —C$_{1-6}$ alkyl-OR$^a$,
- (11) —C$_{0-6}$ alkyl-C(=O)R$^a$,
- (12) —C$_{0-6}$ alkyl-CO$_2$R$^a$,
- (13) —C$_{0-6}$ alkyl-SR$^a$,
- (14) —N(R$^a$)$_2$,
- (15) —C$_{1-6}$ alkyl-N(R$^a$)$_2$,
- (16) —C$_{0-6}$ alkyl-C(=O)N(R$^a$)$_2$,
- (17) —SO$_2$R$^a$,
- (18) —N(R$^a$)SO$_2$R$^a$,
- (19) —C$_{2-5}$ alkenyl,
- (20) —O—C$_{1-6}$ alkyl-OR$^a$,
- (21) —O—C$_{1-6}$ alkyl-SR$^a$,
- (22) —O—C$_{1-6}$ alkyl-NH—CO$_2$R$^a$, or
- (23) —O—C$_{2-6}$ alkyl-N(R$^a$)$_2$;

$R^5$ is
- (1) —H,
- (2) —C$_{1-6}$ alkyl, optionally substituted with from 1 to 3 substituents independently selected from halogen, —O—C$_{1-6}$ alkyl, —O—C$_{1-6}$ fluoroalkyl, —N(R$^a$)$_2$, and —CO$_2$R$^a$;
- (3) aryl optionally substituted with from 1 to 5 substituents independently selected from halogen, C$_{1-6}$ alkyl, C$_{1-6}$ fluoroalkyl, —O—C$_{1-6}$ alkyl, —O—C$_{1-6}$ fluoroalkyl, —S—C$_{1-6}$ alkyl, —CN, and —OH, or
- (4) —C$_{1-6}$ alkyl substituted with R$^k$;

each R$^a$ is independently —H, —C$_{1-6}$ alkyl, or —C$_{1-6}$ fluoroalkyl;

each R$^b$ is independently:
- (1) —H,
- (2) —C$_{1-4}$ alkyl,
- (3) —C$_{1-4}$ fluoroalkyl,
- (4) —R$^k$,
- (5) —C$_{2-3}$ alkenyl,
- (6) —C$_{1-4}$ alkyl-R$^k$,
- (7) —C$_{2-3}$ alkenyl-R$^k$,
- (8) —S(O)$_n$—R$^k$, or
- (9) —C(O)—R$^k$;

each R$^c$ is independently
- (1) —H,
- (2) —C$_{1-6}$ alkyl,
- (3) —C$_{1-6}$ alkyl substituted with —N(R$^a$)$_2$, or
- (4) —C$_{1-4}$ alkyl-aryl, wherein aryl is optionally substituted with 1 to 5 substituents independently selected from halogen, C$_{1-6}$ alkyl, C$_{1-6}$ fluoroalkyl, —O—C$_{1-6}$ alkyl, —O—C$_{1-6}$ fluoroalkyl, —S—C$_{1-6}$ alkyl, —CN, and —OH; and each R$^k$ is independently carbocycle or heterocycle, wherein the carbocycle and heterocycle are unsubstituted or substituted with from 1 to 5 substituents each of which is independently selected from
- (a) halogen,
- (b) C$_{1-6}$ alkyl,
- (c) C$_{1-6}$ fluoroalkyl,
- (d) —O—C$_{1-6}$ alkyl,
- (e) —O—C$_{1-6}$ fluoroalkyl,
- (f) —S—C$_{1-6}$ alkyl,
- (g) —CN,
- (h) —OH,
- (i) oxo,
- (j) —(CH$_2$)$_{0-3}$C(=O)N(R$^a$)$_2$,
- (k) —(CH$_2$)$_{0-3}$C(=O)R$^a$,
- (l) —N(R$^a$)—C(=O)R$^a$,
- (m) —N(R$^a$)—C(=O)OR$^a$,
- (n) —(CH$_2$)$_{1-3}$N(R$^a$)—C(=O)R$^a$,
- (o) —N(R$^a$)$_2$,
- (p) —C$_{1-6}$ alkyl-N(R$^a$)$_2$,
- (q) aryl,
- (r) aryloxy-,
- (s) —C$_{1-4}$ alkyl substituted with aryl,
- (t) heteromonocycle,
- (u) —C$_{1-4}$ alkyl substituted with a heteromonocycle,
- (v) heteromonocyclylcarbonyl-C$_{0-6}$ alkyl-, and
- (w) N-heteromonocyclyl-N—C$_{1-6}$ alkyl-amino-;

wherein the aryl group in (q) aryl, (r) aryloxy, and (s) —C$_{1-4}$ alkyl substituted with aryl, is optionally substituted with from 1 to 3 substituents independently selected from halogen, C$_{1-6}$ alkyl, —O—C$_{1-6}$ alkyl, C$_{1-6}$ alkyl substituted with N(R$^a$)$_2$, C$_{1-6}$ fluoroalkyl, and —OH; and wherein the heteromonocyclyl group in (t) heteromonocycle, (u) —C$_{1-4}$ alkyl substituted with a heteromonocycle, (v) heteromonocyclyl-carbonyl-C$_{0-6}$ alkyl-, and (w) N-heteromonocyclyl-N—C$_{1-6}$ alkyl-amino- is optionally substituted with from 1 to 3 substituents independently selected from halogen, C$_{1-6}$ alkyl, —O—C$_{1-6}$ alkyl, C$_{1-6}$ fluoroalkyl, oxo, and —OH;

and all other variables are as originally defined;
and with the proviso that when $Z^1$ is C—Q$^3$, $Z^2$ is C—Q$^4$, $Z^3$ is CH, and X is C—Q$^1$, then Y is not C—Q$^2$;
or a pharmaceutically acceptable salt thereof.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the aza- and polyazanaphthalenyl carboxamides of Formula (I) above. These compounds and pharmaceutically acceptable salts thereof are HIV integrase inhibitors.

A second embodiment of the invention is a compound of Formula (I), wherein

A is phenyl or a fused carbocyclic ring system selected from the group consisting of

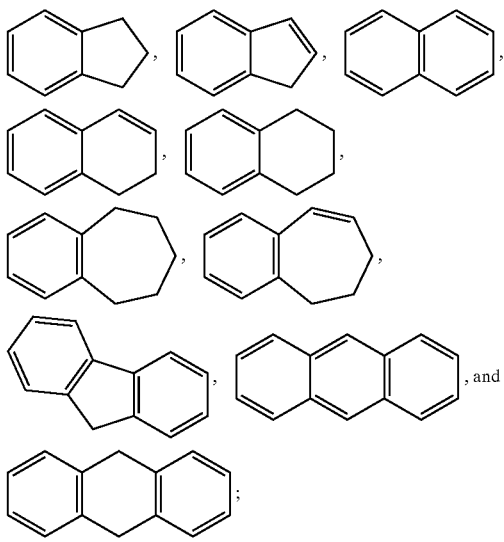

L is
(i) a single bond;
(ii) —$(CH_2)_{1-5}$—, which is optionally substituted with 1 or 2 substituents independently selected from the group consisting of halogen, —OH, —$C_{1-6}$ alkyl, —O—$C_{1-6}$ alkyl, —$CO_2R^a$, —$CO_2(CH_2)_{1-2}R^k$, —$C_{1-6}$ alkyl-$OR^a$, —$R^k$, —$(CH_2)_{1-2}R^k$, —$CH(OR^a)$—$R^k$, and —$CH(N(R^a)_2)$—$R^k$;
(iii) —$(CH_2)_{0-2}$—CH=CH—$(CH_2)_{1-2}$—, which is optionally substituted with 1, 2 or 3 substituents independently selected from the group consisting of halogen, —OH, —$C_{1-6}$ alkyl, and —O—$C_{1-6}$ alkyl;

(iv) 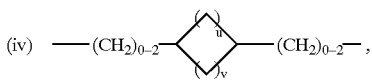

wherein u and v are each integers having a value from 0 to 4, provided that the sum of u+v is 1, 2, 3 or 4; or
(v) a heteroatom-containing chain which is —$(CH_2)_{0-3}N(R^a)$—$(CH_2)_{1-3}$—, —$(CH_2)_{1-2}$—$OC(=O)$—$(CH_2)_{1-2}$—, or —$(CH_2)_{1-2}$—$C(=O)O$—$(CH_2)_{1-2}$—;

$R^5$ is
(1) —H,
(2) —$C_{1-4}$ alkyl, optionally substituted with from 1 to 5 substituents independently selected from halogen, —O—$C_{1-6}$ alkyl, —O—$C_{1-6}$ haloalkyl, —$N(R^a)_2$, and —$CO_2R^a$;
(3) phenyl optionally substituted with from 1 to 5 substituents independently selected from halogen, $C_{1-6}$ alkyl, $C_{1-6}$ haloalkyl, —O—$C_{1-6}$ alkyl, —O—$C_{1-6}$ haloalkyl, —S—$C_{1-6}$ alkyl, —CN, and —OH, or
(4) —$C_{1-4}$ alkyl substituted with $R^k$;

each $R^a$ is independently —H or —$C_{1-6}$ alkyl;
each $R^c$ is independently
(1) —H,
(2) —$C_{1-4}$ alkyl,
(3) —$C_{1-4}$ alkyl substituted with —$N(R^a)_2$, or
(4) —$C_{1-4}$ alkyl-phenyl, wherein the phenyl is optionally substituted with 1 to 5 substituents independently selected from halogen, $C_{1-6}$ alkyl, $C_{1-6}$ haloalkyl, —O—$C_{1-6}$ alkyl, —O—$C_{1-6}$ haloalkyl, —S—$C_{1-6}$ alkyl, —CN, and —OH;

each $R^k$ is independently:
(1) aryl selected from phenyl and naphthyl, wherein aryl is unsubstituted or substituted with from 1 to 5 substituents independently selected from:
(a) halogen,
(b) $C_{1-6}$ alkyl,
(c) $C_{1-6}$ haloalkyl,
(d) —O—$C_{1-6}$ alkyl,
(e) —O—$C_{1-6}$ haloalkyl,
(f) phenyl,
(g) —S—$C_{1-6}$ alkyl,
(h) —CN,
(i) —OH,
(j) phenyloxy, unsubstituted or substituted with from 1 to 3 substituents independently selected from:
(i) halogen,
(ii) $C_{1-6}$ alkyl,
(iii) $C_{1-6}$ haloalkyl, and
(iv) —OH,
(k) —$N(R^a)_2$,
(l) —$C_{1-6}$ alkyl-$N(R^a)_2$,
(m) —$R^t$,
(p) —$(CH_2)_{0-3}C(=O)N(R^a)_2$, and
(q) —$(CH_2)_{0-3}C(=O)R^a$;
(2) —$C_{3-7}$ cycloalkyl, unsubstituted or substituted with from 1 to 3 substituents independently selected from:
(a) halogen,
(b) $C_{1-6}$ alkyl,
(c) —O—$C_{1-6}$ alkyl,
(d) $C_{1-6}$ haloalkyl,
(e) —O—$C_{1-6}$ haloalkyl,
(f) —CN,
(h) phenyl, and
(j) —OH;
(3) —$C_{3-7}$ cycloalkyl fused with a phenyl ring, unsubstituted or substituted with from 1 to 5 substituents independently selected from:
(a) halogen,
(b) $C_{1-6}$ alkyl,
(c) —O—$C_{1-6}$ alkyl,
(d) $C_{1-6}$ haloalkyl,
(e) —O—$C_{1-6}$ haloalkyl,
(f) —CN, and
(g) —OH;
(4) a 5- or 6- membered heteroaromatic ring containing from 1 to 4 heteroatoms independently selected from oxygen, nitrogen and sulfur, wherein the heteroaromatic ring is unsubstituted or substituted on nitrogen or carbon with from 1 to 5 substituents independently selected from:
(a) halogen,
(b) $C_{1-6}$ alkyl,
(c) $C_{1-6}$ haloalkyl,
(d) —O—$C_{1-6}$ alkyl,
(e) —O—$C_{1-6}$ haloalkyl,
(f) phenyl,
(g) —S—$C_{1-6}$ alkyl,
(h) —CN,
(i) —OH,
(j) phenyloxy, unsubstituted or substituted with from 1 to 3 substituents independently selected from:
(i) halogen,
(ii) $C_{1-6}$ alkyl,

13

(iii) $C_{1-6}$ haloalkyl, and
(iv) —OH,
(k) —N($R^a$)$_2$,
(l) —$C_{1-6}$ alkyl-N($R^a$)$_2$,
(m) —$R^t$,
(n) oxo,
(o) —(CH$_2$)$_{0-3}$C(=O)N($R^a$)$_2$, and
(p) —(CH$_2$)$_{0-3}$C(=O)$R^a$;
(5) a 5- or 6- or 7- or 8-membered heterocyclic ring selected from a saturated heterocyclic ring and a mono- or poly-unsaturated non-aromatic heterocyclic ring, wherein the heterocyclic ring contains from 1 to 4 heteroatoms independently selected from oxygen, nitrogen and sulfur, and wherein the heterocyclic ring is unsubstituted or substituted with from 1 to 5 substituents independently selected from:
(a) halogen,
(b) $C_{1-6}$ alkyl,
(c) —O—$C_{1-6}$ alkyl,
(d) $C_{1-6}$ haloalkyl,
(e) —O—$C_{1-6}$ haloalkyl,
(f) —CN,
(g) oxo,
(h) phenyl
(i) benzyl,
(j) phenylethyl,
(k) —OH,
(l) —(CH$_2$)$_{0-3}$C(=O)N($R^a$)$_2$,
(m) —(CH$_2$)$_{0-3}$C(=O)$R^a$,
(n) —N($R^a$)—C(=O)$R^a$,
(o) —N($R^a$)—CO$_2R^a$,
(p) —(CH$_2$)$_{1-3}$N($R^a$)—C(=O)$R^a$,
(q) —N($R^a$)$_2$,
(r) —(CH$_2$)$_{1-3}$N($R^a$)$_2$,
(s) —(CH$_2$)$_{1-3}$—O$R^a$,
(t) —(CH$_2$)$_{0-3}$CO$_2R^a$,
(u) —(CH$_2$)$_{0-3}$—O—(CH$_2$)$_{1-3}$—O$R^a$,
(v) —SO$_2R^a$,
(w) —SO$_2$N($R^a$)$_2$,
(x) —(CH$_2$)$_{0-3}$C(=O)O(CH$_2$)$_{1-2}$CH=CH$_2$,
(y) $R^t$,
(z) —(CH$_2$)$_{0-3}$C(=O)$R^t$,
(aa) —N($R^a$)$R^t$, and
(bb) —(CH$_2$)$_{1-3}R^t$; or
(6) an 8- to 10- membered heterobicyclic ring containing from 1 to 4 heteroatoms independently selected from oxygen, nitrogen and sulfur, wherein the heterobicyclic ring is saturated or unsaturated and is unsubstituted or substituted with from 1 to 5 substituents independently selected from:
(a) halogen,
(b) $C_{1-6}$ alkyl,
(c) —O—$C_{1-6}$ alkyl,
(d) $C_{1-6}$ haloalkyl,
(e) —O—$C_{1-6}$ haloalkyl,
(f) —CN,
(g) =O, and
(h) —OH; and
$R^t$ is naphthyl or a 5- or 6-membered heteromonocylic ring containing from 1 to 4 nitrogen atoms, wherein the heteromonocyclic ring is saturated or unsaturated, and wherein either the naphthyl or the heteromonocyclic ring is unsubstituted or substituted with from 1 to 4 substituents independently selected from halogen, oxo, $C_{1-4}$ alkyl, and —O—$C_{1-4}$ alkyl;
and all other variables are as originally defined or as defined in the first embodiment;

14 and with the proviso that when $Z^1$ is C—$Q^3$, $Z^2$ is C—$Q^4$, $Z^3$ is CH, and X is C—$Q^1$, then Y is not C—$Q^2$;
or a pharmaceutically acceptable salt thereof.

A third embodiment of the invention is a compound of Formula (I), wherein

A is phenyl or a fused carbocyclic ring system selected from the group consisting of

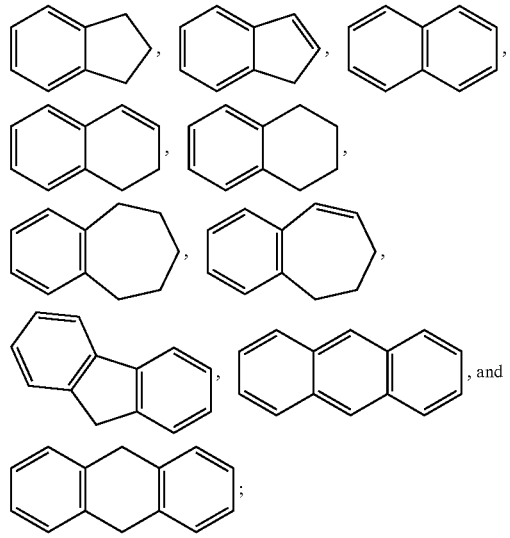

L is
(i) a single bond;
(ii) —(CH$_2$)$_{1-5}$—, which is optionally substituted with 1 or 2 substituents independently selected from the group consisting of halogen, —OH, —$C_{1-6}$ alkyl, —O—$C_{1-6}$ alkyl, —CO$_2R^a$, —CO$_2$(CH$_2$)$_{1-2}R^k$, —$C_{1-6}$ alkyl-O$R^a$, —$R^k$, —(CH$_2$)$_{1-2}R^k$, —CH(O$R^a$)—$R^k$, and —CH(N($R^a$)$_2$)—$R^k$;
(iii) —(CH$_2$)$_{0-2}$—CH=CH—(CH$_2$)$_{1-2}$—, which is optionally substituted with 1 or 2 substituents independently selected from the group consisting of halogen, —OH, —$C_{1-6}$ alkyl, and —O—$C_{1-6}$ alkyl;

(iv) 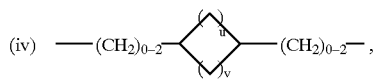

wherein u and v are each integers having a value from 0 to 4, provided that the sum of u+v is 1, 2, 3 or 4; or
(v) a heteroatom-containing chain which is —(CH$_2$)$_{0-3}$N($R^a$)—(CH$_2$)$_{1-3}$—, —(CH$_2$)$_{1-2}$—OC(=O)—(CH$_2$)$_{1-2}$—, or —(CH$_2$)$_{1-2}$—C(=O)O—(CH$_2$)$_{1-2}$—;
$R^5$ is
(1) —H,
(2) —$C_{1-4}$ alkyl, optionally substituted with from 1 to 3 substituents independently selected from halogen, —O—$C_{1-6}$ alkyl, —O—$C_{1-6}$ fluoroalkyl, —N($R^a$)$_2$, and —CO$_2R^a$;
(3) phenyl optionally substituted with from 1 to 5 substituents independently selected from halogen, $C_{1-6}$ alkyl, $C_{1-6}$ fluoroalkyl, —O—$C_{1-6}$ alkyl, —O—$C_{1-6}$ fluoroalkyl, —S—$C_{1-6}$ alkyl, —CN, and —OH, or
(4) —$C_{1-4}$ alkyl substituted with $R^k$;
each $R^a$ is independently —H or —$C_{1-6}$ alkyl;
each $R^c$ is independently (1) —H,
(2) —C$_{1-4}$ alkyl,
(3) —C$_{1-4}$ alkyl substituted with —N(R$^a$)$_2$, or
(4) —C$_{1-4}$ alkyl-phenyl, wherein the phenyl is optionally substituted with 1 to 5 substituents independently selected from halogen, C$_{1-6}$ alkyl, C$_{1-6}$ fluoroalkyl, —O—C$_{1-6}$ alkyl, —O—C$_{1-6}$ fluoroalkyl, —S—C$_{1-6}$ alkyl, —CN, and —OH;

each R$^k$ is independently:
(1) aryl selected from phenyl and naphthyl, wherein aryl is unsubstituted or substituted with from 1 to 5 substituents independently selected from:
(a) halogen,
(b) C$_{1-6}$ alkyl,
(c) C$_{1-6}$ fluoroalkyl,
(d) —O—C$_{1-6}$ alkyl,
(e) —O—C$_{1-6}$ fluoroalkyl,
(f) phenyl,
(g) —S—C$_{1-6}$ alkyl,
(h) —CN,
(i) —OH,
(j) phenyloxy, unsubstituted or substituted with from 1 to 3 substituents independently selected from:
  (i) halogen,
  (ii) C$_{1-6}$ alkyl,
  (iii) C$_{1-6}$ fluoroalkyl, and
  (iv) —OH,
(k) —N(R$^a$)$_2$,
(l) —C$_{1-6}$ alkyl-N(R$^a$)$_2$,
(m) R$^t$,
(p) —(CH$_2$)$_{0-3}$C(=O)N(R$^a$)$_2$, and
(q) —(CH$_2$)$_{0-3}$C(=O)R$^a$;
(2) —C$_{3-7}$ cycloalkyl, unsubstituted or substituted with from 1 to 3 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(h) phenyl, and
(j) —OH;
(3) —C$_{3-7}$ cycloalkyl fused with a phenyl ring, unsubstituted or substituted with from 1 to 5 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN, and
(g) —OH;
(4) a 5- or 6- membered heteroaromatic ring containing from 1 to 4 heteroatoms independently selected from oxygen, nitrogen and sulfur, wherein the heteroaromatic ring is unsubstituted or substituted on nitrogen or carbon with from 1 to 5 substituents independently selected from:
(a) halogen,
(b) C$_{1-6}$ alkyl,
(c) C$_{1-6}$ fluoroalkyl,
(d) —O—C$_{1-6}$ alkyl,
(e) —O—C$_{1-6}$ fluoroalkyl,
(f) phenyl,
(g) —S—C$_{1-6}$ alkyl,
(h) —CN,
(i) —OH,
(j) phenyloxy, unsubstituted or substituted with from 1 to 3 substituents independently selected from:
  (i) halogen,
  (ii) C$_{1-6}$ alkyl,
  (iii) C$_{1-6}$ fluoroalkyl, and
  (iv) —OH,
(k) —N(R$^a$)$_2$,
(l) —C$_{1-6}$ alkyl-N(R$^a$)$_2$,
(m) R$^t$,
(n) oxo,
(o) —(CH$_2$)$_{0-3}$C(=O)N(R$^a$)$_2$, and
(p) —(CH$_2$)$_{0-3}$C(=O)R$^a$;
(5) a 5- or 6- membered saturated heterocyclic ring containing 1 or 2 heteroatoms independently selected from oxygen, nitrogen and sulfur, wherein the heterocyclic ring is unsubstituted or substituted with from 1 to 4 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(g) oxo,
(h) phenyl
(i) benzyl,
(j) phenylethyl,
(k) —OH,
(l) —(CH$_2$)$_{0-3}$C(=O)N(R$^a$)$_2$,
(m) —(CH$_2$)$_{0-3}$C(=O)R$^a$,
(n) —N(R$^a$)—C(=O)R$^a$,
(o) —N(R$^a$)—C(=O)OR$^a$,
(p) —(CH$_2$)$_{1-3}$N(R$^a$)—C(=O)R$^a$,
(q) —N(R$^a$)$_2$,
(r) —(CH$_2$)$_{1-3}$N(R$^a$)$_2$,
(s) —(CH$_2$)$_{0-3}$C(=O)R$^t$,
(t) —R$^t$,
(u) —N(R$^a$)R$^t$, and
(v) —(CH$_2$)$_{1-3}$R$^t$; or
(6) an 8- to 10- membered heterobicyclic ring containing from 1 to 4 heteroatoms independently selected from oxygen, nitrogen and sulfur, wherein the heterobicyclic ring is saturated or unsaturated and is unsubstituted or substituted with from 1 to 5 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(g) =O, and
(h) —OH; and R$^t$ is naphthyl or a 5- or 6-membered heteromonocyclic ring containing from 1 to 4 nitrogen atoms, wherein the heteromonocyclic ring is saturated or unsaturated, and wherein either the naphthyl or the heteromonocyclic ring is unsubstituted or substituted with 1 or 2 substituents independently selected from halogen, oxo, C$_{1-4}$ alkyl, and —O—C$_{1-4}$ alkyl;

and all other variables are as originally defined or as defined in the first embodiment;

and with the proviso that when Z$^1$ is C—Q$^3$, Z$^2$ is C—Q$^4$, Z$^3$ is CH, and X is C—Q$^1$, then Y is not C—Q$^2$;

or a pharmaceutically acceptable salt thereof.

A fourth embodiment of the present invention is a compound of Formula (I), wherein each $R^k$ is independently:

(1) aryl selected from phenyl and naphthyl, wherein aryl is unsubstituted or substituted with from 1 to 4 substituents independently selected from:
 (a) halogen,
 (b) $C_{1-6}$ alkyl,
 (c) $C_{1-6}$ haloalkyl,
 (d) —O—$C_{1-6}$ alkyl,
 (e) —O—$C_{1-6}$ haloalkyl,
 (f) phenyl,
 (g) —S—$C_{1-6}$ alkyl,
 (h) —CN,
 (i) —OH,
 (j) phenyloxy, unsubstituted or substituted with from 1 to 3 substituents independently selected from:
  (i) halogen,
  (ii) $C_{1-6}$ alkyl,
  (iii) $C_{1-6}$ haloalkyl, and
  (iv) —OH,
 (k) —N($R^a$)$_2$,
 (l) —$C_{1-6}$ alkyl-N($R^a$)$_2$,
 (m) $R^t$,
 (p) —(CH$_2$)$_{0-3}$C(=O)N($R^a$)$_2$, and
 (q) —(CH$_2$)$_{0-3}$C(=O)$R^a$;

(2) —$C_{3-6}$ cycloalkyl, unsubstituted or substituted with from 1 to 3 substituents independently selected from:
 (a) halogen,
 (b) $C_{1-6}$ alkyl,
 (c) —O—$C_{1-6}$ alkyl,
 (d) $C_{1-6}$ haloalkyl,
 (e) —O—$C_{1-6}$ haloalkyl,
 (f) —CN,
 (h) phenyl, and
 (j) —OH;

(3) —$C_{3-6}$ cycloalkyl fused with a phenyl ring, unsubstituted or substituted with from 1 to 4 substituents independently selected from:
 (a) halogen,
 (b) $C_{1-6}$ alkyl,
 (c) —O—$C_{1-6}$ alkyl,
 (d) $C_{1-6}$ haloalkyl,
 (e) —O—$C_{1-6}$ haloalkyl,
 (f) —CN, and
 (g) —OH;

(4) a 5- or 6- membered heteroaromatic ring selected from thienyl, pyridyl, pyridyl N-oxide, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with from 1 to 4 substituents independently selected from:
 (a) halogen,
 (b) $C_{1-6}$ alkyl,
 (c) $C_{1-6}$ haloalkyl,
 (d) —O—$C_{1-6}$ alkyl,
 (e) —O—$C_{1-6}$ haloalkyl,
 (f) phenyl,
 (g) —S—$C_{1-6}$ alkyl,
 (h) —CN,
 (i) —OH,
 (j) phenyloxy, unsubstituted or substituted with from 1 to 3 substituents independently selected from:
  (i) halogen,
  (ii) $C_{1-6}$ alkyl,
  (iii) $C_{1-6}$ haloalkyl, and
  (iv) —OH,
 (k) —N($R^a$)$_2$,
 (l) —$C_{1-6}$ alkyl-N($R^a$)$_2$,
 (m) —$R^t$,
 (n) oxo,
 (o) —(CH$_2$)$_{0-3}$C(=O)N($R^a$)$_2$, and
 (p) —(CH$_2$)$_{0-3}$C(=O)$R^a$;

(5) a 5- or 6- or 7- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, azepanyl, thiadiazepanyl, dithiazepanyl, diazepanyl, and thiadiazinanyl; and wherein the heterocyclic ring is unsubstituted or substituted with from 1 to 4 substituents independently selected from:
 (a) halogen,
 (b) $C_{1-6}$ alkyl,
 (c) —O—$C_{1-6}$ alkyl,
 (d) $C_{1-6}$ haloalkyl,
 (e) —O—$C_{1-6}$ haloalkyl,
 (f) —CN,
 (g) oxo,
 (h) phenyl
 (i) benzyl,
 (j) phenylethyl,
 (k) —OH,
 (l) —(CH$_2$)$_{0-3}$C(=O)N($R^a$)$_2$,
 (m) —(CH$_2$)$_{0-3}$C(=O)$R^a$,
 (n) —N($R^a$)—C(=O)$R^a$,
 (o) —N($R^a$)—CO$_2$$R^a$,
 (p) —(CH$_2$)$_{1-3}$N($R^a$)—C(=O)$R^a$,
 (q) —N($R^a$)$_2$,
 (r) —(CH$_2$)$_{1-3}$N($R^a$)$_2$,
 (s) —(CH$_2$)$_{1-3}$—O$R^a$,
 (t) —(CH$_2$)$_{0-3}$CO$_2$$R^a$,
 (u) —(CH$_2$)$_{0-3}$—O—(CH$_2$)$_{1-3}$—O$R^a$,
 (v) —SO$_2$$R^a$,
 (w) —SO$_2$N($R^a$)$_2$,
 (x) —(CH$_2$)$_{0-3}$C(=O)O(CH$_2$)$_{1-2}$CH=CH$_2$,
 (y) —$R^t$,
 (z) —(CH$_2$)$_{0-3}$C(=O)$R^t$,
 (aa) —N($R^a$)$R^t$, and
 (bb) —(CH$_2$)$_{1-3}$$R^t$;

(6) a mono-unsaturated heterocyclic ring which is:

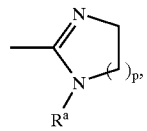

wherein p is an integer from zero to 4 and wherein each ring carbon is optionally and independently substituted with —$C_{1-4}$ alkyl; or (7) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, isochromanyl, hexahydropyrazolo[4,3-c]pyridinyl, hexahydropurinyl, hexahydrooxazolo[3,4a]pyrazinyl, and 1,2,3,4-tetrahydro-1,8-naphthyridinyl; and wherein the bicyclic ring is unsubstituted or substituted with from 1 to 4 substituents independently selected from:
(a) halogen,
(b) $C_{1-6}$ alkyl,
(c) —O—$C_{1-6}$ alkyl,
(d) $C_{1-6}$ haloalkyl,
(e) —O—$C_{1-6}$ haloalkyl,
(f) —CN,
(g) =O, and
(h) —OH; and $R^t$ is naphthyl or a 5- or 6-membered heteromonocylic ring selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; and wherein the naphthyl or the heteromonocyclic ring is unsubstituted or substituted with from 1 to 4 substituents independently selected from halogen, oxo, $C_{1-4}$ alkyl, and —O—$C_{1-4}$ alkyl;
and all other variables are as originally defined or as defined in any one of the preceding embodiments;
and with the proviso that when $Z^1$ is C—$Q^3$, $Z^2$ is C—$Q^4$, $Z^3$ is CH, and X is C—$Q^1$, then Y is not C—$Q^2$;
or a pharmaceutically acceptable salt thereof.

In an aspect of the fourth embodiment, the compound of Formula (I) is as just defined above, except that in part (5) of the definition of $R^k$, the 5- or 6- or 7-membered saturated heterocyclic ring is selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, and azepanyl.

A fifth embodiment of the present invention is a compound of Formula I, wherein each $R^k$ is independently:
(1) aryl selected from phenyl and naphthyl, wherein aryl is unsubstituted or substituted with from 1 to 4 substituents independently selected from:
(a) halogen,
(b) $C_{1-6}$ alkyl,
(c) $C_{1-6}$ fluoroalkyl,
(d) —O—$C_{1-6}$ alkyl,
(e) —O—$C_{16}$ fluoroalkyl,
(f) phenyl,
(g) —S—$C_{1-6}$ alkyl,
(h) —CN,
(i) —OH,
(j) phenyloxy, unsubstituted or substituted with from 1 to 3 substituents independently selected from:
(i) halogen,
(ii) $C_{1-6}$ alkyl,
(iii) $C_{1-6}$ fluoroalkyl, and
(iv) —OH,
(k) —N($R^a$)$_2$,
(l) —$C_{1-6}$ alkyl-N($R^a$)$_2$,
(m) —$R^t$,
(p) —(CH$_2$)$_{0-3}$C(=O)N($R^a$)$_2$, and
(q) —(CH$_2$)$_{0-3}$C(=O)$R^a$;
(2) —$C_{3-6}$ cycloalkyl, unsubstituted or substituted with from 1 to 3 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(h) phenyl, and
(j) —OH;
(3) —$C_{3-6}$ cycloalkyl fused with a phenyl ring, unsubstituted or substituted with from 1 to 4 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN, and
(g) —OH;
(4) a 5- or 6- membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with from 1 to 4 substituents independently selected from:
(a) halogen,
(b) $C_{1-6}$ alkyl,
(c) $C_{1-6}$ fluoroalkyl,
(d) —O—$C_{1-6}$ alkyl,
(e) —O—$C_{1-6}$ fluoroalkyl,
(f) phenyl,
(g) —S—$C_{1-6}$ alkyl,
(h) —CN,
(i) —OH,
(j) phenyloxy, unsubstituted or substituted with from 1 to 3 substituents independently selected from:
(i) halogen,
(ii) $C_{1-6}$ alkyl,
(iii) $C_{1-6}$ fluoroalkyl, and
(iv) —OH,
(k) —N($R^a$)$_2$,
(l) —$C_{1-6}$ alkyl-N($R^a$)$_2$,
(m) —$R^t$,
(n) oxo,
(o) —(CH$_2$)$_{0-3}$C(=O)N($R^a$)$_2$, and
(p) —(CH$_2$)$_{0-3}$C(=O)$R^a$;
(5) a 5- or 6- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, and pyrazolidinyl, wherein the heterocyclic ring is unsubstituted or substituted with from 1 to 3 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) =O,
(h) phenyl
(i) benzyl,
(j) phenylethyl,
(k) —OH,
(l) —(CH$_2$)$_{0-3}$C(=O)N($R^a$)$_2$,
(m) —(CH$_2$)$_{0-3}$C(=O)$R^a$,
(n) N($R^a$)—C(=O)$R^a$,
(o) N($R^a$)—C(=O)O$R^a$,
(p) (CH$_2$)$_{1-3}$N($R^a$)—C(=O)$R^a$,
(q) N($R^a$)$_2$, (r) $(CH_2)_{1-3}N(R^a)_2$,
(s) $-(CH_2)_{0-3}C(=O)R^t$,
(t) $-R^t$,
(u) $-N(R^a)R^t$, and
(v) $-(CH_2)_{1-3}R^t$; or (6) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, and isochromanyl, wherein the bicyclic ring is unsubstituted or substituted with 1 or 2 substituents independently selected from:
 (a) halogen,
 (b) $C_{1-6}$ alkyl,
 (c) $-O-C_{1-6}$ alkyl,
 (d) $C_{1-6}$ fluoroalkyl,
 (e) $-O-C_{1-6}$ fluoroalkyl,
 (f) $-CN$,
 (g) $=O$, and
 (h) $-OH$; and $R^t$ is naphthyl or a 5- or 6-membered heteromonocylic ring selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; and wherein the naphthyl or the heteromonocyclic ring is unsubstituted or substituted with 1 or 2 substituents independently selected from halogen, oxo, $C_{1-4}$ alkyl, and $-O-C_{1-4}$ alkyl;

and all other variables are as originally defined or as defined in any one of the first, second, or third embodiments;

and with the proviso that when $Z^1$ is $C-Q^3$, $Z^2$ is $C-Q^4$, $Z^3$ is CH, and X is $C-Q^1$, then Y is not $C-Q^2$;

or a pharmaceutically acceptable salt thereof.

A sixth embodiment of the present invention is a compound of Formula (I), wherein X is N;
Y is $C-Q^2$;
$Z^1$ is $C-Q^3$;
$Z^2$ is $C-Q^4$;
$Z^3$ is CH;
$Q^2$, $Q^3$, and $Q^4$ are as defined in (i) or (ii) as follows:
 (i) $Q^2$ is
  (1) $-H$,
  (2) $-C_{1-6}$ alkyl,
  (3) $-C_{1-6}$ fluoroalkyl,
  (4) $-O-C_{1-6}$ alkyl,
  (5) $-O-C_{1-6}$ fluoroalkyl,
  (6) halo,
  (7) $-CN$,
  (8) $-C_{1-6}$ alkyl-$OR^a$,
  (9) $-C_{0-6}$ alkyl-$C(=O)R^a$,
  (10) $-C_{0-6}$ alkyl-$CO_2R^a$,
  (11) $-C_{0-6}$ alkyl-$SR^a$,
  (12) $-N(R^a)_2$,
  (13) $-C_{1-6}$ alkyl-$N(R^a)_2$,
  (14) $-C_{0-6}$ alkyl-$C(=O)N(R^a)_2$,
  (15) $-C_{0-6}$ alkyl-G-$C_{1-6}$ alkyl-$C(=O)N(R^a)_2$, wherein G is O, S, $N(R^a)$, or $N(SO_2R^a)$,
  (16) $-N(R^a)-C(R^a)=O$,
  (17) $-C_{1-6}$ alkyl-$N(R^a)-C(R^a)=O$,
  (18) $-C(=O)-N(R^a)-C_{1-6}$ alkyl-$[C(=O)]_{0-1}-N(R^a)_2$,
  (19) $-C(=O)-N(R^a)-C_{1-6}$ alkyl substituted with 1 or 2 $-OR^a$,
  (20) $-SO_2R^a$,
  (21) $-N(R^a)SO_2R^a$,
  (22) $-C_{2-6}$ alkenyl,
  (23) $-C_{2-6}$ alkenyl-$C(=O)-N(R^a)_2$,
  (24) $-C_{2-5}$ alkynyl,
  (25) $-C_{2-5}$ alkynyl-$CH_2N(R^a)_2$,
  (26) $-C_{2-5}$ alkynyl-$CH_2OR^a$,
  (27) $-C_{2-5}$ alkynyl-$CH_2S(O)_n-R^a$,

(28) 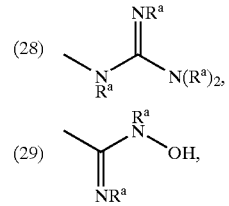

(29)

(30) $-C(=NR^a)-N(R^a)_2$,
  (31) $-N(R^a)-C_{1-6}$ alkyl-$SR^a$,
  (32) $-N(R^a)-C_{1-6}$ alkyl-$OR^a$,
  (33) $-N(R^a)-C_{1-6}$ alkyl-$N(R^a)_2$,
  (34) $-N(R^a)-C_{1-6}$ alkyl-$N(R^a)-C(R^a)=O$,
  (35) $-N(R^a)-C_{0-6}$ alkyl-$[C(=O)]_{1-2}N(R^a)_2$,
  (36) $-N(R^a)-C_{1-6}$ alkyl-$CO_2R^a$,
  (37) $-N(R^a)C(=O)N(R^a)-C_{1-6}$ alkyl-$C(=O)N(R^a)_2$,
  (38) $-N(R^a)C(=O)-C_{1-6}$ alkyl-$N(R^a)_2$,
  (39) $-N(R^a)-SO_2-N(R^a)_2$,
  (40) $-R^k$,
  (41) $-C_{1-6}$ alkyl substituted with $R^k$,
  (42) $-C_{1-6}$ fluoroalkyl substituted with $R^k$,
  (43) $-C_{2-5}$ alkenyl-$R^k$,
  (44) $-C_{2-5}$ alkynyl-$R^k$,
  (45) $-O-R^k$,
  (46) $-O-C_{1-4}$ alkyl-$R^k$,
  (47) $-S(O)_n-R^k$,
  (48) $-S(O)_n-C_{1-4}$ alkyl-$R^k$,
  (49) $-O-C_{1-6}$ alkyl-$OR^k$,
  (50) $-O-C_{1-6}$ alkyl-$O-C_{1-4}$ alkyl-$R^k$,
  (51) $-O-C_{1-6}$ alkyl-$S(O)_nR^k$,
  (52) $-N(R^c)-R^k$,
  (53) $-N(R^c)-C_{1-6}$ alkyl substituted with one or two $R^k$ groups,
  (54) $-N(R^c)-C_{1-6}$ alkyl-$OR^k$,
  (55) $-C(=O)-R^k$,
  (56) $-C(=O)N(R^a)-R^k$,
  (57) $-N(R^a)C(=O)-R^k$,
  (58) $-C(=O)N(R^a)-C_{1-6}$ alkyl-$R^k$, or
  (59) $-N(R^a)-C_{0-6}$ alkyl-$S(O)_nR^k$; and each of $Q^3$ and $Q^4$ is independently:
 (1) $-H$,
 (2) $-C_{1-6}$ alkyl,
 (3) $-C_{1-6}$ fluoroalkyl,
 (4) $-O-C_{1-6}$ alkyl,
 (5) $-O-C_{1-6}$ fluoroalkyl,
 (6) halo,
 (7) $-CN$,
 (8) $-C_{1-6}$ alkyl-$OR^a$,
 (9) $-C_{0-6}$ alkyl-$C(=O)R^a$,
 (10) $-C_{0-6}$ alkyl-$CO_2R^a$,
 (11) $-SR^a$,
 (12) $-N(R^a)_2$,

(13) —C$_{1-6}$ alkyl —N(R$^a$)$_2$,
(14) —C$_{0-6}$ alkyl-C(=O)N(R$^a$)$_2$,
(15) —SO$_2$R$^a$,
(16) —N(R$^a$)SO$_2$R$^a$,
(17) —R$^k$, or
(18) —C$_{1-6}$ alkyl substituted with R$^k$; or (ii) alternatively, Q$^2$ and Q$^3$ together with the carbon atoms to which they are attached and the fused ring carbon atom therebetween form a 5- or 6-membered monocyclic carbocycle or a 5- or 6-membered monocyclic heterocycle, wherein the heterocycle contains 1 or 2 heteroatoms selected from nitrogen, oxygen and sulfur, and wherein either the carbocycle or heterocycle is optionally substituted with from 1 to 3 substituents independently selected from
(1) —C$_{1-6}$alkyl,
(3) —C$_{1-6}$ fluoroalkyl,
(4) —O—C$_{1-6}$ alkyl,
(5) —O—C$_{1-6}$ fluoroalkyl,
(6) halo,
(7) —CN,
(8) —C$_{1-6}$ alkyl-OR$^a$,
(9) —C$_{1-6}$ alkyl-SR$^a$,
(10) —C$_{1-6}$ alkyl-N(R$^a$)$_2$,
(11) —C$_{1-6}$ alkyl-C(=O)—N(R$^a$)$_2$,
(12) —C$_{1-6}$ alkyl-CO$_2$R$^a$,
(13) oxo,
(14) —R$^k$, and
(15) —C$_{1-6}$ alkyl substituted with R$^k$; and Q$^4$ is as defined in (i) above;
and all other variables are as originally defined or as defined in any one of the preceding embodiments;
or a pharmaceutically acceptable salt thereof.

In an aspect of the sixth embodiment, the compound of Formula (I) is as just defined above, except that part (i) of the definition of Q$^2$, Q$^3$, and Q$^4$ does not include (59) —N(R$^a$)—C$_{0-6}$ alkyl-S(O)$_n$R$^k$.

A seventh embodiment of the present invention is a compound of Formula I, wherein X is N;
Y is C—Q$^2$;
Z$^1$ is C—Q$^3$;
Z$^2$ is C—Q$^4$;
Z$^3$ is CH;
Q$^2$ is
(1) —H,
(2) —C$_{1-6}$ alkyl,
(3) —C$_{1-6}$ fluoroalkyl,
(4) —O—C$_{1-6}$ alkyl,
(5) —O—C$_{1-6}$ fluoroalkyl,
(6) halo,
(7) —CN,
(8) —C$_{1-6}$ alkyl-OR$^a$,
(9) —C$_{0-6}$ alkyl-C(=O)R$^a$,
(10) —C$_{0-6}$ alkyl-CO$_2$R$^a$,
(11) —C$_{0-6}$ alkyl-SR$^a$,
(12) —N(R$^a$)$_2$,
(13) —C$_{1-6}$ alkyl —N(R$^a$)$_2$,
(14) —C$_{0-6}$ alkyl-C(=O)N(R$^a$)$_2$,
(15) —C$_{1-6}$ alkyl-N(R$^a$)—C(R$^a$)=O,
(16) —SO$_2$R$^a$,
(17) —N(R$^a$)SO$_2$R$^a$,
(18) —C$_{2-5}$ alkynyl,
(19) —C$_{2-5}$ alkynyl-CH$_2$N(R$^a$)$_2$,
(20) —C$_{2-5}$ alkynyl-CH$_2$OR$^a$,

(21) 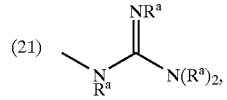

(22) —N(R$^a$)—C$_{1-6}$ alkyl-SR$^a$,
(23) —N(R$^a$)—C$_{1-6}$ alkyl-OR$^a$,
(24) —N(R$^a$)—C$_{1-6}$ alkyl-N(R$^a$)$_2$,
(25) —N(R$^a$)—C$_{1-6}$ alkyl-N(R$^a$)—C(R$^a$)=O,
(26) R$^k$,
(27) —C$_{1-6}$ alkyl substituted with R$^k$,
(28) —C$_{1-6}$ fluoroalkyl substituted with R$^k$,
(29) —C$_{2-5}$ alkenyl-R$^k$,
(30) —C$_{2-5}$ alkynyl-R$^k$,
(31) —O—R$^k$,
(32) —O—C$_{1-4}$ alkyl-R$^k$,
(33) —S(O)$_n$—R$^k$,
(34) —S(O)$_n$—C$_{1-4}$ alkyl-R$^k$,
(35) —O—C$_{1-6}$ alkyl-OR$^k$,
(36) —O—C$_{1-6}$ alkyl-O—C$_{1-4}$ alkyl-R$^k$,
(37) —O—C$_{1-6}$ alkyl-SR$^k$,
(38) —N(R$^c$)—R$^k$,
(39) —N(R$^c$)—C$_{1-6}$ alkyl substituted with one or two R$^k$ groups,
(40) —N(R$^c$)—C$_{1-6}$ alkyl-OR$^k$,
(41) —C(=O)N—C$_{1-6}$ alkyl-R$^k$,
(42) —C$_{2-5}$ alkynyl-CH$_2$S(O)$_n$—R$^a$,
(43) —C(=NR$^a$)—N(R$^a$)$_2$, or

(44) 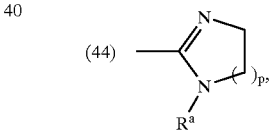

wherein p is an integer from zero to 3;
each of Q$^3$ and Q$^4$ is independently:
(1) —H,
(2) —C$_{1-6}$ alkyl,
(3) —C$_{1-6}$ fluoroalkyl,
(4) —O—C$_{1-6}$ alkyl,
(5) —O—C$_{1-6}$ fluoroalkyl,
(6) halo,
(7) —CN,
(8) —C$_{1-6}$ alkyl-OR$^a$,
(9) —C$_{0-6}$ alkyl-C(=O)R$^a$,
(10) —C$_{0-6}$ alkyl-CO$_2$R$^a$,
(11) —SR$^a$,
(12) —N(R$^a$)$_2$,
(13) —C$_{1-6}$ alkyl —N(R$^a$)$_2$,
(14) —C$_{0-6}$ alkyl-C(=O)N(R$^a$)$_2$,
(15) —SO$_2$R$^a$,
(16) —N(R$^a$)SO$_2$R$^a$

(17) $R^k$, or

(18) —$C_{1-6}$ alkyl substituted with $R^k$;

and all other variables are as defined in any one of the first, second, third, fourth, or fifth embodiments;

or a pharmaceutically acceptable salt thereof.

An eighth embodiment of the present invention is a compound of Formual (I), wherein
X is N;
Y is C—$Q^2$;
$Z^1$ is C—$Q^3$;
$Z^2$ is C—$Q^4$; and
$Z^3$ is CH;
and all other variables are as originally defined or as defined in any of the preceding embodiments;
or a pharmaceutically acceptable salt thereof.

In an aspect of the eighth embodiment, A is phenyl, and $Q^3$ and $Q^4$ are both —H.

A ninth embodiment of the present invention is a compound of Formula I, wherein:

$Q^3$ is:
  (1) —H,
  (2) —$C_{1-6}$ alkyl,
  (3) —$C_{1-6}$ fluoroalkyl,
  (4) —O—$C_{1-6}$ alkyl,
  (5) —O—$C_{1-6}$ fluoroalkyl,
  (6) halo,
  (7) —CN,
  (8) —$C_{1-6}$ alkyl-$OR^a$,
  (9) —$C_{0-6}$ alkyl-C(=O)$R^a$,
  (10) —$C_{0-6}$ alkyl-$CO_2R^a$,
  (11) —$SR^a$,
  (12) —N($R^a$)$_2$,
  (13) —$C_{1-6}$ alkyl —N($R^a$)$_2$,
  (14) —$C_{0-6}$ alkyl-C(=O)N($R^a$)$_2$,
  (15) —$SO_2R^a$,
  (16) —N($R^a$)$SO_2R^a$
  (17) —$R^k$, or
  (18) —$C_{1-6}$ alkyl substituted with $R^k$;

$Q^4$ is:
  (1) —H,
  (2) —$C_{1-6}$ alkyl,
  (3) —$C_{1-6}$ fluoroalkyl,
  (4) —O—$C_{1-6}$ alkyl,
  (5) —O—$C_{1-6}$ fluoroalkyl,
  (6) halo,
  (7) —CN,
  (8) —$C_{1-6}$ alkyl-$OR^a$,
  (9) —$C_{0-6}$ alkyl-C(=O)$R^a$,
  (10) —$C_{0-6}$ alkyl-$CO_2R^a$,
  (11) —$SR^a$,
  (12) —N($R^a$)$_2$,
  (13) —$C_{1-6}$ alkyl —N($R^a$)$_2$,
  (14) —$C_{0-6}$ alkyl-C(=O)N($R^a$)$_2$,
  (15) —$SO_2R^a$, or
  (16) —N($R^a$)$SO_2R^a$;

and all other variables are as defined in the seventh embodiment;
or a pharmaceutically acceptable salt thereof.

In an aspect of the ninth embodiment, $Q^3$ and $Q^4$ are both —H.

A tenth embodiment of the present invention is a compound of Formula (II):

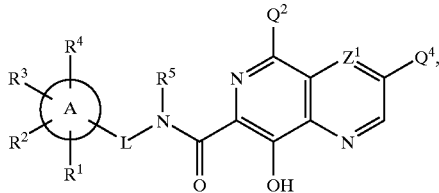

(II)

wherein

A is

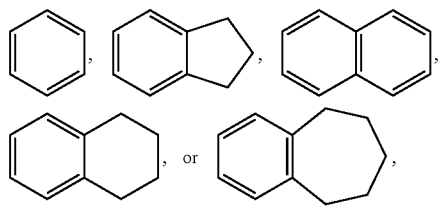

L is
  (i) a single bond;
  (ii) —(CH$_2$)$_{1-3}$—, which is optionally substituted with 1 or 2 substituents independently selected from the group consisting of halogen, —OH, —$C_{1-4}$ alkyl, —O—$C_{1-4}$ alkyl, —$CO_2CH_3$, —$CO_2CH_2$-phenyl, phenyl, benzyl, —(CH$_2$)$_{1-2}$OH, —CH(OH)-phenyl, and —CH(NH$_2$)-phenyl;
  (iii) —(CH$_2$)$_{0-1}$—CH=CH—(CH$_2$)—, which is optionally substituted with 1 or 2 substituents independently selected from the group consisting of halogen, —OH, —$C_{1-4}$ alkyl, and —O—$C_{1-4}$ alkyl;

(iv) 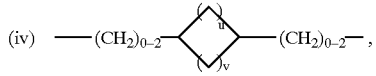

wherein u and v are each integers having a value of from 0 to 4, provided that the sum of u+v is 1, 2, 3 or 4; or
  (v) a heteroatom-containing chain which is —N($R^a$)—(CH$_2$)$_{1-2}$—, —CH$_2$—OC(=O)—CH$_2$—, or —CH$_2$—C(=O)O—CH$_2$—;

$Z^1$ is N or C—$Q^3$;
$Q^2$ and $Q^3$ are as defined in (i) or (ii) as follows:
  (i) $Q^2$ is
    (1) —H,
    (2) —$C_{1-4}$ alkyl,
    (3) —$C_{1-4}$ fluoroalkyl,
    (4) —O—$C_{1-4}$ alkyl,
    (5) —O—$C_{1-4}$ fluoroalkyl,
    (6) halo,
    (7) —CN,
    (8) —$C_{1-4}$ alkyl-$OR^a$,
    (9) —(CH$_2$)$_{0-2}$C(=O)$R^a$,
    (10) —(CH$_2$)$_{0-2}$CO$_2R^a$,
    (11) —(CH$_2$)$_{0-2}$$SR^a$,
    (12) —N($R^a$)$_2$,

(13) —$C_{1-4}$ alkyl —$N(R^a)_2$,
(14) —$(CH_2)_{0-2}C(=O)N(R^a)_2$,
(15) —G—$C_{1-6}$ alkyl-$C(=O)N(R^a)_2$, wherein G is O, S, $N(R^a)$, or $N(SO_2R^a)$,
(16) —$N(R^a)$—$C(R^a)$=O,
(17) —$(CH_2)_{1-3}$—$N(R^a)$—$C(R^a)$=O,
(18) —$C(=O)$—$N(R^a)$—$(CH_2)_{1-3}$—$[C(=O)]_{0-1}$—$N(R^a)_2$,
(19) —$C(=O)$—$N(R^a)$—$C_{1-4}$ alkyl substituted with 1 or 2-$OR^a$,
(20) —$SO_2R^a$,
(21) —$N(R^a)SO_2R^a$,
(22) —$C_{2-4}$ alkenyl,
(23) —$C_{2-4}$ alkenyl-$C(=O)$—$N(R^a)_2$,
(24) —$C_{2-3}$ alkynyl,
(25) —C≡C—$CH_2N(R^a)_2$,
(26) —C≡C—$CH_2OR^a$,
(27) —C≡C—$CH_2SR^a$,
(28) —C≡C—$CH_2SO_2R^a$,

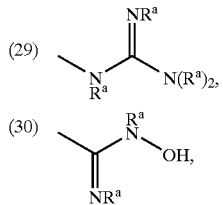

(29)

(30)

(31) —$N(R^a)$—$C_{1-4}$ alkyl-$SR^a$,
(32) —$N(R^a)$—$C_{1-4}$ alkyl-$OR^a$,
(33) —$N(R^a)$—$C_{1-4}$ alkyl-$N(R^a)_2$,
(34) —$N(R^a)$—$C_{1-4}$ alkyl-$N(R^a)$—$C(R^a)$=O,
(35) —$N(R^a)$—$C_{0-4}$ alkyl-$[C(=O)]_{1-2}N(R^a)_2$,
(36) —$N(R^a)$—$C_{1-4}$ alkyl-$CO_2R^a$,
(37) —$N(R^a)C(=O)N(R^a)$—$C_{1-4}$ alkyl-$C(=O)N(R^a)_2$,
(38) —$N(R^a)C(=O)$—$C_{1-4}$ alkyl-$N(R^a)_2$,
(39) —$N(R^a)$—$SO_2$—$N(R^a)_2$,
(40) —$R^k$,
(41) —$C_{1-4}$ alkyl substituted with $R^k$,
(42) —$C_{1-4}$ fluoroalkyl substituted with $R^k$,
(43) —$C_{2-5}$ alkenyl-$R^k$,
(44) —$C_{2-5}$ alkynyl-$R^k$,
(45) —$OR^k$,
(46) —O—$C_{1-4}$ alkyl-$R^k$,
(47) —$S(O)_n$—$R^k$,
(48) —$S(O)_n$—$C_{1-4}$ alkyl-$R^k$,
(49) —O—$C_{1-4}$ alkyl-$OR^k$,
(50) —O—$C_{1-4}$ alkyl-O—$C_{1-4}$ alkyl-$R^k$,
(51) —O—$C_{1-4}$ alkyl-$S(O)_nR^k$,
(52) —$N(R^c)$—$R^k$,
(53) —$N(R^c)$—$C_{1-4}$ alkyl substituted with one or two $R^k$ groups,
(54) —$N(R^c)$—$C_{1-4}$ alkyl-$OR^k$,
(55) —$C(=O)$—$R^k$,
(56) —$C(=O)N(R^a)$—$R^k$,
(57) —$N(R^a)C(=O)$—$R^k$,
(58) —$C(=O)N(R^a)$—$C_{1-4}$ alkyl-$R^k$, or
(59) —$N(R^a)$—$C_{0-4}$ alkyl-$S(O)_nR^k$;

$Q^3$ is
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo selected from —F, —Cl, and —Br,
(7) —CN,
(8) —$C_{1-4}$ alkyl-$OR^a$, or
(9) —$C_{1-4}$ alkyl substituted with $R^k$; or
(ii) alternatively, $Q^2$ and $Q^3$ together with the carbon atoms to which they are attached and the fused ring carbon atom attached therebetween form a 5- or 6-membered monocyclic heterocycle, wherein the heterocycle contains 1 or 2 heteroatoms selected from nitrogen, oxygen and sulfur, and wherein the heterocycle is optionally substituted with from 1 to 3 substituents independently selected from
(1) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo,
(7) —CN,
(8) —$C_{1-4}$ alkyl-$OR^a$,
(9) —$C_{1-4}$ alkyl-$S(O)_nR^a$,
(10) —$C_{1-4}$ alkyl-$N(R^a)_2$,
(11) —$C_{1-4}$ alkyl-$C(=O)$—$N(R^a)_2$,
(12) —$C_{1-4}$ alkyl-$CO_2R^a$,
(13) oxo,
(14) —$R^k$, and
(15) —$C_{1-4}$ alkyl substituted with $R^k$;

$Q^4$ is:
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo selected from —F, —Cl, and —Br,
(7) —CN,
(8) —$C_{1-6}$ alkyl-$OR^a$,
(9) —$N(R^a)_2$, or
(10) —$C_{1-6}$ alkyl —$N(R^a)_2$;

each of $R^1$ and $R^2$ is independently:
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) —OH,
(7) halo,
(8) —CN,
(9) —$C_{1-4}$ alkyl-$OR^a$,
(10) —$(CH_2)_{0-2}C(=O)R^a$,
(11) —$(CH_2)_{0-2}CO_2R^a$,
(12) —$(CH_2)_{0-2}SR^a$,
(13) —$N(R^a)_2$,
(14) —$C_{1-4}$ alkyl $N(R^a)_2$,
(15) —$(CH_2)_{0-2}C(=O)N(R^a)_2$,
(16) —$C_{1-4}$ alkyl-$N(R^a)$—$C(R^a)$=O,
(17) —$SO_2R^a$,
(18) —$N(R^a)SO_2R^a$,
(19) —O—$C_{1-4}$ alkyl-$OR^a$,
(20) —O—$C_{1-4}$ alkyl-$SR^a$,
(21) —O—$C_{1-4}$ alkyl-NH—$CO_2R^a$,
(22) —O—$C_{2-4}$ alkyl-$N(R^a)_2$,
(23) —$N(R^a)$—$C_{1-4}$ alkyl-$SR^a$,
(24) —$N(R^a)$—$C_{1-4}$ alkyl-$OR^a$,

(25) —N(R$^a$)—C$_{1-4}$ alkyl-N(R$^a$)$_2$,
(26) —N(R$^a$)—C$_{1-4}$ alkyl-N(R$^a$)—C(R$^a$)=O,
(27) —R$^k$,
(28) —C$_{1-4}$ alkyl substituted with 1 or 2 R$^k$ groups,
(29) —C$_{1-4}$ fluoroalkyl substituted with 1 or 2 R$^k$ groups,
(30) —O—R$^k$,
(31) —O—C$_{1-4}$ alkyl-R$^k$,
(32) —S(O)$_n$—R$^k$,
(33) —S(O)$_n$—C$_{1-4}$ alkyl-R$^k$,
(34) —O—C$_{1-4}$ alkyl-OR$^k$,
(35) —O—C$_{1-4}$ alkyl-O—C$_{1-4}$ alkyl-R$^k$,
(36) —O—C$_{1-4}$ alkyl-S(O)$_n$R$^k$, or
(37) —C$_{0-4}$ alkyl-N(R$^b$)(R$^k$);
each of R$^3$ and R$^4$ is independently
  (1) —H,
  (2) halo,
  (3) —CN,
  (4) —OH,
  (5) C$_{1-4}$alkyl,
  (6) C$_{1-4}$ fluoroalkyl,
  (7) —O—C$_{1-4}$ alkyl,
  (8) —O—C$_{1-4}$ fluoroalkyl,
  (9) —C$_{1-4}$ alkyl-OR$^a$,
  (10) —O—C$_{1-4}$ alkyl-OR$^a$,
  (11) —O—C$_{1-4}$ alkyl-SR$^a$,
  (12) —O—C$_{1-4}$ alkyl-NH—CO$_2$R$^a$, or
  (13) —O—C$_{2-4}$ alkyl-N(R$^a$)$_2$;
R$^5$ is
  (1) —H,
  (2) —C$_{1-4}$ alkyl, optionally substituted with 1 or 2 substituents independently selected from halogen, —O—C$_{1-4}$ alkyl, —O—C$_{1-4}$ fluoroalkyl, —N(R$^a$)$_2$, and —CO$_2$R$^a$;
  (3) phenyl optionally substituted with from 1 to 3 substituents independently selected from halogen, C$_{1-4}$ alkyl, C$_{1-4}$ fluoroalkyl, —O—C$_{1-4}$ alkyl, —O—C$_{1-4}$ fluoroalkyl, —S—C$_{1-4}$ alkyl, —CN, and —OH, or
  (4) —C$_{1-4}$ alkyl substituted with phenyl;
each R$^a$ is independently —H or —C$_{1-4}$ alkyl;
each R$^b$ is independently:
  (1) —H,
  (2) —C$_{1-4}$ alkyl,
  (3) —C$_{1-4}$ fluoroalkyl,
  (4) —R$^k$,
  (5) —C$_{1-4}$ alkyl-R$^k$,
  (6) —S(O)$_n$—R$^k$, or
  (7) —C(=O)—R$^k$;
each R$^c$ is independently
  (1) —H,
  (2) —C$_{1-4}$ alkyl,
  (3) —C$_{1-4}$ alkyl substituted with —N(R$^a$)$_2$, or
  (4) —C$_{1-4}$ alkyl-phenyl, wherein the phenyl is optionally substituted with 1 to 3 substituents independently selected from halogen, C$_{1-4}$ alkyl, C$_{1-4}$ fluoroalkyl, —O—C$_{1-4}$ alkyl, —O—C$_{1-4}$ fluoroalkyl, —S—C$_{1-4}$ alkyl, —CN, and —OH;
each R$^k$ is independently:
  (1) aryl selected from phenyl and naphthyl, wherein aryl is unsubstituted or substituted with from 1 to 5 substituents independently selected from:
    (a) halogen,
    (b) C$_{1-6}$ alkyl,
    (c) C$_{1-6}$ fluoroalkyl,
    (d) —O—C$_{1-6}$ alkyl,
    (e) —O—C$_{1-6}$ fluoroalkyl,
    (f) phenyl,
    (g) —S—C$_{1-6}$ alkyl,
    (h) —CN,
    (i) —OH,
    (j) phenyloxy, unsubstituted or substituted with from 1 to 3 substituents independently selected from:
      (i) halogen,
      (ii) C$_{1-6}$ alkyl,
      (iii) C$_{1-6}$ fluoroalkyl, and
      (iv) —OH,
    (k) —N(R$^a$)$_2$,
    (l) —C$_{1-6}$ alkyl-N(R$^a$)$_2$,
    (m) —R$^t$,
    (p) —(CH$_2$)$_{0-3}$C(=O)N(R$^a$)$_2$, and
    (q) —(CH$_2$)$_{0-3}$C(=O)R$^a$;
  (2) —C$_{3-7}$ cycloalkyl, unsubstituted or substituted with from 1 to 3 substituents independently selected from:
    (a) halogen,
    (b) C$_{1-6}$ alkyl,
    (c) —O—C$_{1-6}$ alkyl,
    (d) C$_{1-6}$ fluoroalkyl,
    (e) —O—C$_{1-6}$ fluoroalkyl,
    (f) —CN,
    (h) phenyl, and
    (j) —OH;
  (3) —C$_{3-7}$ cycloalkyl fused with a phenyl ring, unsubstituted or substituted with from 1 to 5 substituents independently selected from:
    (a) halogen,
    (b) C$_{1-6}$ alkyl,
    (c) —O—C$_{1-6}$ alkyl,
    (d) C$_{1-6}$ fluoroalkyl,
    (e) —O—C$_{1-6}$ fluoroalkyl,
    (f) —CN, and
    (g) —OH;
  (4) a 5- or 6- membered heteroaromatic ring containing from 1 to 4 heteroatoms independently selected from oxygen, nitrogen and sulfur, wherein the heteroaromatic ring is unsubstituted or substituted on nitrogen or carbon with from 1 to 5 substituents independently selected from:
    (a) halogen,
    (b) C$_{1-6}$ alkyl,
    (c) C$_{1-6}$ fluoroalkyl,
    (d) —O—C$_{1-6}$ alkyl,
    (e) —O—C$_{1-6}$ fluoroalkyl,
    (f) phenyl,
    (g) —S—C$_{1-6}$ alkyl,
    (h) —CN,
    (i) —OH,
    (j) phenyloxy, unsubstituted or substituted with from 1 to 3 substituents independently selected from:
      (i) halogen,
      (ii) C$_{1-6}$ alkyl,
      (iii) C$_{1-6}$ fluoroalkyl, and
      (iv) —OH,
    (k) —N(R$^a$)$_2$,
    (l) —C$_{1-6}$ alkyl-N(R$^a$)$_2$,
    (m) —R$^t$,
    (n) oxo,
    (o) —(CH$_2$)$_{0-3}$C(=O)N(R$^a$)$_2$, and
    (p) —(CH$_2$)$_{0-3}$C(=O)R$^a$;

(5) a 5- or 6- or 7- membered saturated heterocyclic ring containing from 1 to 3 heteroatoms independently selected from oxygen, nitrogen and sulfur, wherein the heterocyclic ring is unsubstituted or substituted with from 1 to 4 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) oxo,
(h) phenyl
(i) benzyl,
(j) phenylethyl,
(k) —OH,
(l) —$(CH_2)_{0-3}C(=O)N(R^a)_2$,
(m) —$(CH_2)_{0-3}C(=O)R^a$,
(n) —$N(R^a)$—$C(=O)R^a$,
(o) —$N(R^a)$—$CO_2R^a$,
(p) —$(CH_2)_{1-3}N(R^a)$—$C(=O)R^a$,
(q) —$N(R^a)_2$,
(r) —$(CH_2)_{1-3}N(R^a)_2$,
(s) —$(CH_2)_{1-3}$—$OR^a$,
(t) —$(CH_2)_{0-3}CO_2R^a$,
(u) —$(CH_2)_{0-3}$—O—$(CH_2)_{1-3}$—$OR^a$,
(v) —$SO_2R^a$,
(w) —$SO_2N(R^a)_2$,
(x) —$(CH_2)_{0-3}C(=O)O(CH_2)_{1-2}CH=CH_2$,
(y) —$R^t$,
(z) —$(CH_2)_{0-3}C(=O)R^t$,
(aa) —$N(R^a)R^t$, and
(bb) —$(CH_2)_{1-3}R^t$; or
(6) an 8- to 10- membered heterobicyclic ring containing from 1 to 4 heteroatoms independently selected from oxygen, nitrogen and sulfur, wherein the heterobicyclic ring is saturated or unsaturated, and is unsubstituted or substituted with from 1 to 5 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) =O, and
(h) —OH;
$R^t$ is naphthyl or a 5- or 6-membered heteromonocylic ring containing from 1 to 4 nitrogen atoms, wherein the heteromonocyclic ring is saturated or unsaturated, and wherein the naphthyl or the heteromonocyclic ring is unsubstituted or substituted with from 1 to 4 substituents independently selected from halogen, oxo, $C_{1-4}$ alkyl, and —O—$C_{1-4}$ alkyl; and
n is an integer equal to 0, 1 or 2;
or a pharmaceutically acceptable salt thereof.

In an aspect of the tenth embodiment, the compound of Formula (II) is as just defined above, except that part (i) of the definition of $Q^2$ does not include (59) —$N(R^a)$—$C_{0-4}$ alkyl-$S(O)_nR^k$.

An eleventh embodiment of the present invention is a compound of Formula (II), wherein A is

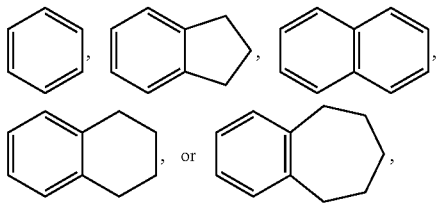

L is
(i) a single bond;
(ii) —$(CH_2)_{1-3}$—, which is optionally substituted with 1 or 2 substituents independently selected from the group consisting of —OH, —$C_{1-4}$ alkyl, —O—$C_{1-4}$ alkyl, —$CO_2CH_3$, —$CO_2CH_2$-phenyl, phenyl, benzyl, —$(CH_2)_{1-2}OH$, —CH(OH)-phenyl, and —$CH(NH_2)$-phenyl;
(iii) —$(CH_2)_{0-1}$—CH=CH—$(CH_2)$—, which is optionally substituted with 1 or 2 substituents independently selected from the group consisting of halogen, —OH, —$C_1'$-4 alkyl, and —O—$C_{1-4}$ alkyl;

(iv) 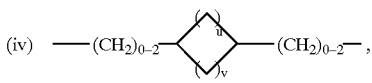

wherein u and v are each integers having a value of from 0 to 4, provided that the sum of u+v is 1, 2, 3 or 4; or
(v) a heteroatom-containing chain which is —$N(R^a)$—$(CH_2)_{1-2}$—, —$CH_2$—$OC(=O)$—$CH_2$—, or —$CH_2$—$C(=O)O$—$CH_2$—;
$Z^1$ is N or C—$Q^3$;
$Q^2$ is
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo,
(7) —CN,
(8) —$C_{1-4}$ alkyl-$OR^a$,
(9) —$(CH_2)_{0-2}C(=O)R^a$,
(10) —$(CH_2)_{0-2}CO_2R^a$,
(11) —$(CH_2)_{0-2}SR^a$,
(12) —$N(R^a)_2$,
(13) —$C_{1-4}$ alkyl —$N(R^a)_2$,
(14) —$(CH_2)_{0-2}C(=O)N(R^a)_2$,
(15) —$SO_2R^a$,
(16) —$N(R^a)SO_2R^a$,
(17) —$C_{2-3}$ alkynyl,
(18) —C≡C—$CH_2N(R^a)_2$,
(19) —C≡C—$CH_2OR^a$,
(20) —$N(R^a)$—$C_{1-4}$ alkyl-$SR^a$,
(21) —$N(R^a)$—$C_{1-4}$ alkyl-$OR^a$,
(22) —$N(R^a)$—$C_{1-4}$ alkyl-$N(R^a)_2$,
(23) —$N(R^a)$—$C_{1-4}$ alkyl-$N(R^a)$—$C(R^a)=O$,
(24) —$R^k$,
(25) —$C_{1-4}$ alkyl substituted with $R^k$,

(26) —$C_{1-4}$ fluoroalkyl substituted with $R^k$,
(27) —$C_{2-5}$ alkenyl-$R^k$,
(28) —$C_{2-5}$ alkynyl-$R^k$,
(29) —O—$R^k$,
(30) —O—$C_{1-4}$ alkyl-$R^k$,
(31) —S(O)$_n$—$R^k$,
(32) —N($R^c$)—$R^k$,
(33) —N($R^c$)—$C_{1-4}$ alkyl substituted with one or two $R^k$ groups,
(34) —N($R^c$)—$C_{1-4}$ alkyl-O$R^k$,
(35) —C(=O)N—$C_{1-4}$ alkyl-$R^k$,
(36) —C≡C—$CH_2$S$R^a$, or
(37) —C≡C—$CH_2$S$O_2R^a$;

$Q^3$ is
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo selected from —F, —Cl, and —Br,
(7) —CN,
(8) —$C_{1-4}$ alkyl-O$R^a$, or
(9) —$C_{1-4}$ alkyl substituted with $R^k$;

$Q^4$ is:
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo selected from —F, —Cl, and —Br,
(7) —CN,
(8) —$C_{1-6}$ alkyl-O$R^a$,
(9) —N($R^a$)$_2$, or
(10) —$C_{1-6}$ alkyl —N($R^a$)$_2$;

each of $R^1$ and $R^2$ is independently:
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) —OH,
(7) halo,
(8) —CN,
(9) —$C_{1-4}$ alkyl-O$R^a$,
(10) —(CH$_2$)$_{0-2}$C(=O)$R^a$,
(11) —(CH$_2$)$_{0-2}$CO$_2R^a$,
(12) —(CH$_2$)$_{0-2}$S$R^a$,
(13) —N($R^a$)$_2$,
(14) —$C_{1-4}$ alkyl N($R^a$)$_2$,
(15) —(CH$_2$)$_{0-2}$C(=O)N($R^a$)$_2$,
(16) —$C_{1-4}$ alkyl-N($R^a$)—C($R^a$)=O,
(17) —SO$_2R^a$,
(18) —N($R^a$)SO$_2R^a$,
(19) —O—$C_{1-4}$ alkyl-O$R^a$,
(20) —O—$C_{1-4}$ alkyl-S$R^a$,
(21) —O—$C_{1-4}$ alkyl-NH—CO$_2R^a$,
(22) —O—$C_{2-4}$ alkyl-N($R^a$)$_2$,
(23) —N($R^a$)—$C_{1-4}$ alkyl-S$R^a$,
(24) —N($R^a$)—$C_{1-4}$ alkyl-O$R^a$,
(25) —N($R^a$)—$C_{1-4}$ alkyl-N($R^a$)$_2$,
(26) —N($R^a$)—$C_{1-4}$ alkyl-N($R^a$)—C($R^a$)=O,
(27) —$R^k$,
(28) —$C_{1-4}$ alkyl substituted with 1 or 2 $R^k$ groups,
(29) —$C_{1-4}$ fluoroalkyl substituted with 1 or 2 $R^k$ groups,
(30) —O—$R^k$,
(31) —O—$C_{1-4}$ alkyl-$R^k$,
(32) —S(O)$_n$—$R^k$,
(33) —S(O)$_n$—$C_{1-4}$ alkyl-$R^k$,
(34) —O—$C_{1-4}$ alkyl-O$R^k$,
(35) —O—$C_{1-4}$ alkyl-O—$C_{1-4}$ alkyl-$R^k$,
(36) —O—$C_{1-4}$ alkyl-S$R^k$, or
(37) —$C_{0-4}$ alkyl-N($R^b$)($R^k$);

each of $R^3$ and $R^4$ is independently
(1) —H,
(2) halo,
(3) —CN,
(4) —OH,
(5) $C_{1-4}$ alkyl,
(6) $C_{1-4}$ fluoroalkyl,
(7) —O—$C_{1-4}$ alkyl,
(8) —O—$C_{1-4}$ fluoroalkyl,
(9) —$C_{1-4}$ alkyl-O$R^a$,
(10) —O—$C_{1-4}$ alkyl-O$R^a$,
(11) —O—$C_{1-4}$ alkyl-S$R^a$,
(12) —O—$C_{1-4}$ alkyl-NH—CO$_2R^a$, or
(13) —O—$C_{2-4}$ alkyl-N($R^a$)$_2$;

$R^5$ is
(1) —H,
(2) —$C_{1-4}$ alkyl, optionally substituted with 1 or 2 substituents independently selected from halogen, —O—$C_{1-4}$ alkyl, —O—$C_{1-4}$ fluoroalkyl, —N($R^a$)$_2$, and —CO$_2R^a$;
(3) phenyl optionally substituted with from 1 to 3 substituents independently selected from halogen, $C_{1-4}$ alkyl, $C_{1-4}$ fluoroalkyl, —O—$C_{1-4}$ alkyl, —O—$C_{1-4}$ fluoroalkyl, —S—$C_{1-4}$ alkyl, —CN, and —OH, or
(4) —$C_{1-4}$ alkyl substituted with phenyl;

each $R^a$ is independently —H or —$C_{1-4}$ alkyl;
each $R^b$ is independently:
(1) —H,
(2) —$C_{1-4}$ alkyl,
(3) —$C_{1-4}$ fluoroalkyl,
(4) —$R^k$,
(5) —$C_{1-4}$ alkyl-$R^k$,
(6) —S(O)$_n$—$R^k$, or
(7) —C(=O)—$R^k$;

each $R^c$ is independently
(1) —H,
(2) —$C_{1-4}$ alkyl,
(3) —$C_{1-4}$ alkyl substituted with —N($R^a$)$_2$, or
(4) —$C_{1-4}$ alkyl-phenyl, wherein the phenyl is optionally substituted with 1 to 3 substituents independently selected from halogen, $C_{1-4}$ alkyl, $C_{1-4}$ fluoroalkyl, —O—$C_{1-4}$ alkyl, —O—$C_{1-4}$ fluoroalkyl, —S—$C_{1-4}$ alkyl, —CN, and —OH;

each $R^k$ is independently:
  (1) aryl selected from phenyl and naphthyl, wherein aryl is unsubstituted or substituted with from 1 to 5 substituents independently selected from:
     (a) halogen,
     (b) $C_{1-6}$ alkyl,
     (c) $C_{1-6}$ fluoroalkyl,
     (d) —O—$C_{1-6}$ alkyl,
     (e) —O—$C_{1-6}$ fluoroalkyl,
     (f) phenyl,
     (g) —S—$C_{1-6}$ alkyl,
     (h) —CN,
     (i) —OH,
     (j) phenyloxy, unsubstituted or substituted with from 1 to 3 substituents independently selected from:
        (i) halogen,
        (ii) $C_{1-6}$ alkyl,
        (iii) $C_{1-6}$ fluoroalkyl, and
        (iv) —OH,
     (k) —N($R^a$)$_2$,
     (l) —$C_{1-6}$ alkyl-N($R^a$)$_2$,
     (m) $R^t$,
     (p) —(CH$_2$)$_{0-3}$C(=O)N($R^a$)$_2$, and
     (q) —(CH$_2$)$_{0-3}$C(=O)$R^a$;
  (2) —$C_{3-7}$ cycloalkyl, unsubstituted or substituted with from 1 to 3 substituents independently selected from:
     (a) halogen,
     (b) $C_{1-6}$ alkyl,
     (c) —O—$C_{1-6}$ alkyl,
     (d) $C_{1-6}$ fluoroalkyl,
     (e) —O—$C_{1-6}$ fluoroalkyl,
     (f) —CN,
     (h) phenyl, and
     (j) —OH;
  (3) —$C_{3-7}$ cycloalkyl fused with a phenyl ring, unsubstituted or substituted with from 1 to 5 substituents independently selected from:
     (a) halogen,
     (b) $C_{1-6}$ alkyl,
     (c) —O—$C_{1-6}$ alkyl,
     (d) $C_{1-6}$ fluoroalkyl,
     (e) —O—$C_{1-6}$ fluoroalkyl,
     (f) —CN, and
     (g) —OH;
  (4) a 5- or 6- membered heteroaromatic ring containing from 1 to 4 heteroatoms independently selected from oxygen, nitrogen and sulfur, wherein the heteroaromatic ring is unsubstituted or substituted on nitrogen or carbon with from 1 to 5 substituents independently selected from:
     (a) halogen,
     (b) $C_{1-6}$ alkyl,
     (c) $C_{1-6}$ fluoroalkyl,
     (d) —O—$C_{1-6}$ alkyl,
     (e) —O—$C_{1-6}$ fluoroalkyl,
     (f) phenyl,
     (g) —S—$C_{1-6}$ alkyl,
     (h) —CN,
     (i) —OH,
     (j) phenyloxy, unsubstituted or substituted with from 1 to 3 substituents independently selected from:
        (i) halogen,
        (ii) $C_{1-6}$ alkyl,
        (iii) $C_{1-6}$ fluoroalkyl, and
        (iv) —OH,
     (k) —N($R^a$)$_2$,
     (l) —$C_{1-6}$ alkyl-N($R^a$)$_2$,
     (m) —$R^t$,
     (n) oxo,
     (o) —(CH$_2$)$_{0-3}$C(=O)N($R^a$)$_2$, and
     (p) —(CH$_2$)$_{0-3}$C(=O)$R^a$;
  (5) a 5- or 6- membered saturated heterocyclic ring containing 1 or 2 heteroatoms independently selected from oxygen, nitrogen and sulfur, wherein the heterocyclic ring is unsubstituted or substituted with from 1 to 4 substituents independently selected from:
     (a) halogen,
     (b) $C_{1-6}$ alkyl,
     (c) —O—$C_{1-6}$ alkyl,
     (d) $C_{1-6}$ fluoroalkyl,
     (e) —O—$C_{1-6}$ fluoroalkyl,
     (f) —CN,
     (g) oxo,
     (h) phenyl,
     (i) benzyl,
     (j) phenylethyl,
     (k) —OH,
     (l) —(CH$_2$)$_{0-3}$C(=O)N($R^a$)$_2$,
     (m) —(CH$_2$)$_{0-3}$C(=O)$R^a$,
     (n) —N($R^a$)—C(=O)$R^a$,
     (o) —N($R^a$)—C(=O)O$R^a$,
     (p) —(CH$_2$)$_{1-3}$N($R^a$)—C(=O)$R^a$,
     (q) —N($R^a$)$_2$,
     (r) —(CH$_2$)$_{1-3}$N($R^a$)$_2$,
     (s) —(CH$_2$)$_{0-3}$C(=O)$R^t$,
     (t) —$R^t$,
     (u) —N($R^a$)$R^t$, and
     (v) —(CH$_2$)$_{1-3}R^t$; or
  (6) an 8- to 10- membered heterobicyclic ring containing from 1 to 4 heteroatoms independently selected from oxygen, nitrogen and sulfur, wherein the heterobicyclic ring is saturated or unsaturated, and is unsubstituted or substituted with from 1 to 5 substituents independently selected from:
     (a) halogen,
     (b) $C_{1-6}$ alkyl,
     (c) —O—$C_{1-6}$ alkyl,
     (d) $C_{1-6}$ fluoroalkyl,
     (e) —O—$C_{1-6}$ fluoroalkyl,
     (f) —CN,
     (g) =O, and
     (h) —OH;
$R^t$ is naphthyl or a 5- or 6-membered heteromonocylic ring containing from 1 to 4 nitrogen atoms, wherein the heteromonocyclic ring is saturated or unsaturated, and wherein the naphthyl or the heteromonocyclic ring is unsubstituted or substituted with 1 or 2 substituents independently selected from halogen, oxo, $C_{1-4}$ alkyl, and —O—$C_{1-4}$ alkyl; and
n is an integer equal to 0, 1 or 2;
or a pharmaceutically acceptable salt thereof.

A twelfth embodiment of the present invention is a compound of Formula (II), wherein $Z^1$ is CH;
$Q^2$ is
  (1) —H,
  (2) —$C_{1-4}$ alkyl,
  (3) —(CH$_2$)$_{0-2}$CF$_3$,
  (4) —O—$C_{1-4}$ alkyl,
  (5) —O—(CH$_2$)$_{0-2}$CF$_3$,
  (6) halo selected from —F, —Cl and —Br,
  (7) —CN, (8) —$(CH_2)_{1-3}OR^a$,
(9) —$(CH_2)_{0-2}C(=O)R^a$,
(10) —$(CH_2)_{0-2}CO_2R^a$, (11) —$(CH_2)_{0-2}SR^a$,
(12) —$N(R^a)_2$,
(13) —$(CH_2)_{1-3}N(R^a)_2$,
(14) —$(CH_2)_{0-2}C(=O)N(R^a)_2$,
(15) —G—$(CH_2)_{1-2}$—$C(=O)N(R^a)_2$, wherein G is O, S, $N(R^a)$, or $N(SO_2R^a)$,
(16) —$N(R^a)$—$C(R^a)$=O,
(17) —$(CH_2)_{1-2}$—$N(R^a)$—$C(R^a)$=O,
(18) —$C(=O)$—$N(R^a)$—$(CH_2)_{1-3}$—$[C(=O)]_{0-1}$—$N(R^a)_2$,
(19) —$C(=O)$—$N(R^a)$—$(CH_2)_{1-2}H$ substituted with 1 or 2-$OR^a$,
(20) —$SO_2R^a$,
(21) —$N(R^a)SO_2R^a$,
(22) —CH=CH—$(CH_2)_{0-1}$—$C(=O)$—$N(R^a)_2$,
(23) —C≡C—$CH_2OR^a$,
(24) —C≡C—$CH_2SR^a$,
(25) —C≡C—$CH_2SO_2R^a$

(26) 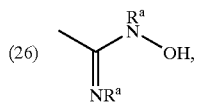

(27) —$N(R^a)$—$(CH_2)_{1-4}SR^a$,
(28) —$N(R^a)$—$(CH_2)_{1-4}OR^a$,
(29) —$N(R^a)$—$(CH_2)_{1-4}$—$N(R^a)_2$,
(30) —$N(R^a)$—$(CH_2)_{1-4}N(R^a)$—$C(R^a)$=O,
(31) —$N(R^a)$—$(CH_2)_{0-2}$—$[C(=O)]_{1-2}N(R^a)_2$,
(32) —$N(R^a)$—$(CH_2)_{1-4}$—$CO_2R^a$,
(33) —$N(R^a)C(=O)N(R^a)$—$(CH_2)_{1-4}$—$C(=O)N(R^a)_2$,
(34) —$N(R^a)C(=O)$—$(CH_2)_{1-4}$—$N(R^a)_2$,
(35) —$N(R^a)$—$SO_2N(R^a)_2$,
(36) —$R^k$,
(37) —$(CH_2)_{1-4}R^k$,
(38) —C≡C—$CH_2R^k$,
(39) —O—$R^k$,
(40) —$S(O)_n$—$R^k$,
(41) —$N(R^c)$—$R^k$,
(42) —$N(R^c)$—$(CH_2)_{1-4}H$ substituted with one or two $R^k$ groups,
(43) —$N(R^c)$—$(CH_2)_{1-4}OR^k$,
(44) —$C(=O)$—$R^k$,
(45) —$C(=O)N(R^a)$—$R^k$,
(46) —$N(R^a)C(=O)$—$R^k$, or
(47) —$C(=O)N(R^a)$—$(CH_2)_{1-4}R^k$; and
(48) —$N(R^a)$—$S(O)_nR^k$;
$Q^4$ is —H;
each of $R^1$ and $R^2$ is independently:
(1) —H,
(2) —$C_{1-4}$ alkyl,
(3) —$(CH_2)_{0-2}CF_3$,
(4) —O—$C_{1-4}$ alkyl,
(5) —O—$(CH_2)_{0-2}CF_3$,
(6) —OH,
(7) halo selected from —F, —Cl and —Br, (8) —CN,
(9) —$(CH_2)_{1-3}OR^a$,
(10) —$(CH_2)_{0-2}C(=O)R^a$,
(11) —$(CH_2)_{0-2}CO_2R^a$,
(12) —$(CH_2)_{0-2}SR^a$,
(13) —$N(R^a)_2$,
(14) —$(CH_2)_{1-3}N(R^a)_2$,
(15) —$(CH_2)_{0-2}C(=O)N(R^a)_2$,
(16) —$C_{1-4}$ alkyl-$N(R^a)$—$C(R^a)$=O,
(17) —$SO_2R^a$,
(18) —$N(R^a)SO_2R^a$,
(19) —O—$(CH_2)_{1-4}OR^a$,
(20) —O—$(CH_2)_{1-4}SR^a$,
(21) —O—$(CH_2)_{1-4}NH$—$CO_2R^a$,
(22) —O—$(CH_2)_{2-4}N(R^a)_2$,
(23) —$N(R^a)$—$(CH_2)_{1-4}SR^a$,
(24) —$N(R^a)$—$(CH_2)_{1-4}OR^a$,
(25) —$N(R^a)$—$(CH_2)_{1-4}N(R^a)_2$,
(26) —$N(R^a)$—$(CH_2)_{1-4}N(R^a)$—$C(R^a)$=O,
(27) —$R^k$,
(28) —$(CH_2)_{1-4}H$ substituted with 1 or 2 $R^k$ groups,
(29) —O—$R^k$,
(30) —O—$(CH_2)_{1-4}R^k$,
(31) —$S(O)_n$—$R^k$,
(32) —$S(O)_n$—$(CH_2)_{1-4}R^k$,
(33) —O—$(CH_2)_{1-4}OR^k$,
(34) —O—$(CH_2)_{1-4}$—O—$(CH_2)_{1-4}R^k$,
(35) —O—$(CH_2)_{1-4}SR^k$, or
(36) —$(CH_2)_{0-4}N(R^b)(R^k)$;
each of $R^3$ and $R^4$ is independently
(1) —H,
(2) halo selected from —F, —Cl and —Br,
(3) —CN,
(4) —OH,
(5) $C_{1-4}$ alkyl,
(6) —$(CH_2)_{0-2}CF_3$,
(7) —O—$C_{1-4}$ alkyl, or
(8) —$O(CH_2)_{0-2}CF_3$; and
$R^5$ is
(1) —H,
(2) —$C_{1-4}$ alkyl,
(3) —$(CH_2)_{1-4}N(R^a)_2$,
(4) —$(CH_2)_{1-4}CO_2R^a$,
(5) phenyl optionally substituted with from 1 to 3 substituents independently selected from halogen, $C_{1-4}$ alkyl, —$(CH_2)_0$-$2CF_3$, —O—$C_{1-4}$ alkyl, —$O(CH_2)_{0-2}CF_3$, —S—$C_{1-4}$ alkyl, —CN, and —OH, or
(6) —$(CH_2)_{1-4}$-phenyl;
and all other variables are as defined in either the tenth embodiment or the eleventh embodiment;
or a pharmaceutically acceptable salt thereof.

A thirteenth embodiment of the present invention is a compound of Formula II, wherein:

$Z^1$ is CH;
$Q^2$ is
(1) —H,
(2) —$C_{1-4}$ alkyl, (3) —(CH$_2$)$_{0-2}$CF$_3$,
(4) —O—C$_{1-4}$ alkyl,
(5) —O—(CH$_2$)$_{0-2}$CF$_3$,
(6) halo selected from —F, —Cl and —Br,
(7) —CN,
(8) —(CH$_2$)$_{1-3}$OR$^a$,
(9) —(CH$_2$)$_{0-2}$C(=O)R$^a$,
(10) —(CH$_2$)$_{0-2}$CO$_2$R$^a$,
(11) —(CH$_2$)$_{0-2}$SR$^a$,
(12) —N(R$^a$)$_2$,
(13) —(CH$_2$)$_{1-3}$N(R$^a$)$_2$,
(14) —(CH$_2$)$_{0-2}$C(=O)N(R$^a$)$_2$,
(15) —SO$_2$R$^a$,
(16) —N(R$^a$)SO$_2$R$^a$,
(17) —C≡C—CH$_2$OR$^a$,
(18) —N(R$^a$)—(CH$_2$)$_{1-4}$SR$^a$,
(19) —N(R$^a$)—(CH$_2$)$_{1-4}$OR$^a$,
(20) —N(R$^a$) (CH$_2$)$_{1-4}$—N(R$^a$)$_2$,
(21) —N(R$^a$)—(CH$_2$)$_{1-4}$N(R$^a$)—C(R$^a$)=O,
(22) —R$^k$,
(23) —(CH$_2$)$_{1-4}$R$^k$,
(24) —C≡C—CH$_2$R$^k$,
(25) —O—R$^k$,
(26) —S(O)$_n$—R$^k$,
(27) —N(R$^c$)—R$^k$,
(28) —N(R$^c$)—(CH$_2$)$_{1-4}$H substituted with one or two R$^k$ groups,
(29) —N(R$^c$)—(CH$_2$)$_{1-4}$OR$^k$,
(30) —C(=O)N—(CH$_2$)$_{1-4}$R$^k$,
(31) —C≡C—CH$_2$SR$^a$, or
(32) —C≡C—CH$_2$SO$_2$R$^a$;
Q$^4$ is —H;
each of R$^1$ and R$^2$ is independently:
(1) —H,
(2) —C$_{1-4}$ alkyl,
(3) —(CH$_2$)$_{0-2}$CF$_3$,
(4) —O—C$_{114}$ alkyl,
(5) —O—(CH$_2$)$_{0-2}$CF$_3$,
(6) —OH,
(7) halo selected from —F, —Cl and —Br,
(8) —CN,
(9) —(CH$_2$)$_{1-3}$OR$^a$,
(10) —(CH$_2$)$_{0-2}$C(=O)R$^a$,
(11) —(CH$_2$)$_{0-2}$CO$_2$R$^a$,
(12) —(CH$_2$)$_{0-2}$SR$^a$,
(13) —N(R$^a$)$_2$,
(14) —(CH$_2$)$_{1-3}$N(R$^a$)$_2$,
(15) —(CH$_2$)$_{0-2}$C(=O)N(R$^a$)$_2$,
(16) —C$_{1-4}$ alkyl-N(R$^a$)—C(R$^a$)=O,
(17) —SO$_2$R$^a$,
(18) —N(R$^a$)SO$_2$R$^a$,
(19) —O—(CH$_2$)$_{1-4}$OR$^a$,
(20) —O—(CH$_2$)$_{1-4}$SR$^a$,
(21) —O—(CH$_2$)$_{1-4}$NH—CO$_2$R$^a$,
(22) —O—(CH$_2$)$_{2-4}$N(R$^a$)$_2$,
(23) —N(R$^a$)—(CH$_2$)$_{1-4}$SR$^a$,
(24) —N(R$^a$)—(CH$_2$)$_{1-4}$OR$^a$,
(25) —N(R$^a$)—(CH$_2$)$_{1-4}$N(R$^a$)$_2$,
(26) —N(R$^a$)—(CH$_2$)$_{1-4}$N(R$^a$)—C(R$^a$)=O,
(27) —R$^k$,
(28) —(CH$_2$)$_{1-4}$H substituted with 1 or 2 R$^k$ groups,
(29) —O—R$^k$,
(30) —O—(CH$_2$)$_{1-4}$R$^k$,
(31) —S(O)$_n$—R$^k$,
(32) —S(O)$_n$—(CH$_2$)$_{1-4}$R$^k$,
(33) —O—(CH$_2$)$_{1-4}$OR$^k$,
(34) —O—(CH$_2$)$_{1-4}$—O—(CH$_2$)$_{1-4}$R$^k$,
(35) —O—(CH$_2$)$_{1-4}$SR$^k$, or
(36) —(CH$_2$)$_{0-4}$N(R$^b$)(R$^k$);
each of R$^3$ and R$^4$ is independently
(1) —H,
(2) halo selected from —F, —Cl and —Br,
(3) —CN,
(4) —OH,
(5) C$_{1-4}$ alkyl,
(6) —(CH$_2$)$_{0-2}$CF$_3$,
(7) —O—C$_{1-4}$ alkyl, or
(8) —O(CH$_2$)$_{0-2}$CF$_3$,
R$^5$ is
(1) —H,
(2) —C$_{1-4}$ alkyl,
(3) —(CH$_2$)$_{1-4}$N(R$^a$)$_2$,
(4) —(CH$_2$)$_{1-4}$CO$_2$R$^a$,
(5) phenyl optionally substituted with from 1 to 3 substituents independently selected from halogen, C$_{1-4}$ alkyl, —(CH$_2$)$_0$-2CF$_3$, —O—C$_{1-4}$ alkyl, —O(CH$_2$)$_0$-2CF$_3$, —S—C$_{1-4}$ alkyl, —CN, and —OH, or
(6) —(CH$_2$)$_{1-4}$-phenyl;
each R$^a$ is independently —H or —C$_{1-4}$ alkyl;
each R$^b$ is independently:
(1) —H,
(2) —C$_{1-4}$ alkyl,
(3) —CF$_3$,
(4) —R$^k$, or
(5) —(CH$_2$)$_{1-4}$—R$^k$;
each R$^c$ is independently
(1) —H,
(2) —C$_{1-4}$ alkyl,
(3) —(CH$_2$)$_{1-4}$N(R$^a$)$_2$, or
(4) —(CH$_2$)$_{1-4}$-phenyl, wherein the phenyl is optionally substituted with 1 to 3 substituents independently selected from halogen, C$_{1-4}$ alkyl, C$_{1-4}$ fluoroalkyl, —O—C$_{1-4}$ alkyl, —O—C$_{1-4}$ fluoroalkyl, —S—C$_{1-4}$ alkyl, —CN, and —OH; and
each R$^k$ is independently:
(1) aryl selected from phenyl and naphthyl, wherein aryl is unsubstituted or substituted with from 1 to 4 substituents independently selected from:
(a) halogen,
(b) C$_{1-4}$ alkyl,
(c) C$_{1-4}$ fluoroalkyl,
(d) —O—C$_{1-4}$ alkyl,
(e) —O—C$_{1-4}$ fluoroalkyl,
(f) phenyl,
(g) —S—C$_{1-4}$ alkyl,
(h) —CN,
(i) —OH, (j) phenyloxy, unsubstituted or substituted with from 1 to 3 substituents independently selected from:
  (i) halogen,
  (ii) $C_{1-4}$ alkyl,
  (iii) $C_{1-4}$ fluoroalkyl, and
  (iv) —OH,
(k) —N($R^a$)$_2$,
(l) —$C_{1-4}$ alkyl-N($R^a$)$_2$,
(m) —$R^t$,
(p) —(CH$_2$)$_{0-3}$C(=O)N($R^a$)$_2$, and
(q) —(CH$_2$)$_{0-3}$C(=O)$R^a$;

(2) —$C_{3-6}$ cycloalkyl, unsubstituted or substituted with from 1 to 3 substituents independently selected from:
  (a) halogen,
  (b) $C_{1-4}$ alkyl,
  (c) —O—$C_{1-4}$ alkyl,
  (d) $C_{1-4}$ fluoroalkyl,
  (e) —O—$C_{1-4}$ fluoroalkyl,
  (f) —CN,
  (h) phenyl, and
  (j) —OH;

(3) —$C_{3-6}$ cycloalkyl fused with a phenyl ring, unsubstituted or substituted with from 1 to 4 substituents independently selected from:
  (a) halogen,
  (b) $C_{1-4}$ alkyl,
  (c) —O—$C_{1-4}$ alkyl,
  (d) $C_{1-4}$ fluoroalkyl,
  (e) —O—$C_{1-4}$ fluoroalkyl,
  (f) —CN, and
  (g) —OH;

(4) a 5- or 6- membered heteroaromatic ring selected from thienyl, pyridyl, imidazolyl, pyrrolyl, pyrazolyl, thiazolyl, isothiazolyl, oxazolyl, isooxazolyl, pyrazinyl, pyirimidinyl, triazolyl, tetrazolyl,furanyl, and pyridazinyl, wherein the heteroaromatic ring is unsubstituted or substituted on nitrogen or carbon with from 1 to 4 substituents independently selected from:
  (a) halogen,
  (b) $C_{1-4}$ alkyl,
  (c) $C_{1-4}$ fluoroalkyl,
  (d) —O—$C_{1-4}$ alkyl,
  (e) —O—$C_{1-4}$ fluoroalkyl,
  (f) phenyl,
  (g) —S—$C_{1-4}$ alkyl,
  (h) —CN,
  (i) —OH,
  (j) phenyloxy, unsubstituted or substituted with from 1 to 3 substituents independently selected from:
    (i) halogen,
    (ii) $C_{1-4}$ alkyl,
    (iii) $C_{1-4}$ fluoroalkyl, and
    (iv) —OH,
  (k) —N($R^a$)$_2$,
  (l) —$C_{1-4}$ alkyl-N($R^a$)$_2$,
  (m) —$R^t$,
  (n) oxo,
  (o) —(CH$_2$)$_{0-3}$C(=O)N($R^a$)$_2$, and
  (p) —(CH$_2$)$_{0-3}$C(=O)$R^a$;

(5) a 5- or 6- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, and pyrazolidinyl, wherein the heterocyclic ring is unsubstituted or substituted with from 1 to 3 substituents independently selected from:
  (a) halogen,
  (b) $C_{1-4}$ alkyl,
  (c) —O—$C_{1-4}$ alkyl,
  (d) $C_{1-4}$ fluoroalkyl,
  (e) —O—$C_{1-4}$ fluoroalkyl,
  (f) —CN,
  (g) =O,
  (h) phenyl,
  (i) benzyl,
  (j) phenylethyl,
  (k) —OH,
  (l) —(CH$_2$)$_{0-3}$C(=O)N($R^a$)$_2$,
  (m) —(CH$_2$)$_{0-3}$C(=O)$R^a$,
  (n) N($R^a$)—C(=O)$R^a$,
  (o) N($R^a$)—C(=O)O$R^a$,
  (p) (CH$_2$)$_{1-3}$N($R^a$)—C(=O)$R^a$,
  (q) N($R^a$)$_2$,
  (r) (CH$_2$)$_{1-3}$N($R^a$)$_2$,
  (s) —(CH$_2$)$_{0-3}$C(=O)$R^t$,
  (t) —$R^t$,
  (u) —N($R^a$)$R^t$, and
  (v) —(CH$_2$)$_{1-3}R^t$; or (6) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[11,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, and isochromanyl, wherein the bicyclic ring is unsubstituted or substituted with 1 or 2 substituents independently selected from:
  (a) halogen,
  (b) $C_{1-4}$ alkyl,
  (c) —O—$C_{1-4}$ alkyl,
  (d) $C_{1-4}$ fluoroalkyl,
  (e) —O—$C_{1-4}$ fluoroalkyl,
  (f) —CN,
  (g) =O , and
  (h) —OH;

$R^t$ is naphthyl or a 5- or 6-membered heteromonocylic ring selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; and wherein the naphthyl or the heteromonocyclic ring is unsubstituted or substituted with 1 or 2 substituents independently selected from halogen, oxo, $C_{1-4}$ alkyl, and —O—$C_{1-4}$ alkyl;

and all other variables are as defined in the eleventh embodiment;

or a pharmaceutically acceptable salt thereof.

A fourteenth embodiment of the present invention is compounds of Formula (III):

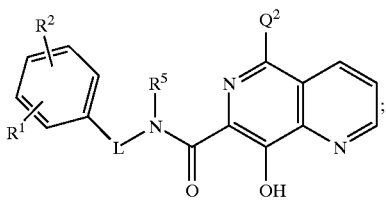

(III)

wherein each of the variables is as defined in any one of the tenth, eleventh, twelfth or thirteenth embodiments; or, alternatively, as originally defined or as defined in any other preceding embodiment containing any one or more of the variables; or a pharmaceutically acceptable salt thereof.

A fifteenth embodiment of the present invention is compounds of Formula (III), wherein:

L is
  (i) a single bond;
  (ii) $-(CH_2)_{1-3}-$, which is optionally substituted with 1 or 2 substituents independently selected from the group consisting of $-OH$, methyl, ethyl, $-CO_2CH_3$, $-CO_2CH_2$-phenyl, phenyl, benzyl, $-(CH_2)_{1-2}OH$, $-CH(OH)$-phenyl, and $-CH(NH_2)$-phenyl; or

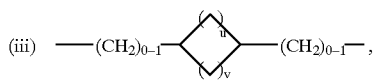

(iii)

wherein u and v are each integers having a value of from 0 to 3, provided that the sum of u+v is 1, 2, 3 or 4;

$Q^2$ is
  (1) $-H$,
  (2) methyl,
  (3) ethyl,
  (4) $CF_3$,
  (5) methoxy,
  (6) ethoxy
  (7) $-OCF_3$
  (8) halo selected from $-F$, $-Cl$ and $-Br$,
  (9) $-CN$,
  (10) $-CH_2OH$,
  (11) $-CH_2OCH_3$
  (12) $-(CH_2)_{0-2}CO_2CH_3$,
  (13) $-SR^a$,
  (14) $-N(R^a)_2$,
  (15) $-SO_2R^a$,
  (16) $-C\equiv C-CH_2OR^a$,
  (17) $-N(R^a)-(CH_2)_{1-3}SR^a$,
  (18) $-N(R^a)-(CH_2)_{1-3}OR^a$,
  (19) $-N(R^a)-(CH_2)_{1-3}N(R^a)_2$,
  (20) $-N(R^a)-(CH_2)_{1-3}N(R^a)-C(R^a)=O$,
  (21) $-R^k$,
  (22) $-(CH_2)_{1-4}R^k$,
  (23) $-C\equiv C-CH_2R^k$,
  (24) $-O-R^k$,
  (25) $-S-R^k$,
  (26) $-SO_2-R^k$,
  (27) $-N(R^c)-R^k$,
  (28) $-N(R^c)-(CH_2)_{1-4}H$ substituted with one or two $R^k$ groups,
  (29) $-N(R^c)-(CH_2)_{1-4}OR^k$,
  (30) $-C(=O)N-(CH_2)_{1-4}R^k$,
  (31) $-C\equiv C-CH_2SR^a$, or
  (32) $-C\equiv C-CH_2SO_2R^a$;

each of $R^1$ and $R^2$ is independently:
  (1) $-H$,
  (2) methyl,
  (3) ethyl,
  (4) $CF_3$,
  (5) methoxy,
  (6) ethoxy
  (7) $-OCF_3$
  (8) halo selected from $-F$, $-Cl$ and $-Br$,
  (9) $-CN$,
  (10) $-CH_2OR^a$,
  (11) $-CO_2R^a$,
  (12) $-SR^a$,
  (13) $-N(R^a)_2$,
  (14) $-(CH_2)_{1-3}N(R^a)_2$,
  (15) $-SO_2R^a$,
  (16) $-(CH_2)_{1-2}N(R^a)-C(R^a)=O$,
  (17) $-R^k$,
  (18) $-(CH_2)_{1-3}H$ substituted with 1 or 2 $R^k$ groups,
  (19) $-O-R^k$, or
  (20) $-O-(CH_2)_{1-3}R^k$;

$R^5$ is
  (1) $-H$,
  (2) methyl,
  (3) $-(CH_2)_{1-2}N(R^a)_2$,
  (4) $-(CH_2)_{1-2}CO_2CH_3$, or
  (5) $-(CH_2)_{1-2}CO_2CH_2CH_3$;
  (6) phenyl, or
  (7) benzyl;

each $R^a$ is independently $-H$ or $-C_{1-4}$ alkyl;
each $R^c$ is independently $-H$, $-C_{1-4}$ alkyl, or $-(CH_2)_{1-3}N(R^a)_2$;
each $R^k$ is independently:
  (1) phenyl which is unsubstituted or substituted with from 1 to 4 substituents independently selected from:
    (a) halogen selected from $-F$, $-Cl$, and $-Br$,
    (b) methyl,
    (c) $-CF_3$,
    (d) methoxy,
    (e) $-OCF_3$,
    (f) phenyl,
    (g) $-S-CH_3$,
    (h) $-CN$,
    (i) $-OH$,
    (j) phenyloxy, unsubstituted or substituted with from 1 to 3 substituents independently selected from:
      (i) halogen selected from $-F$, $-Cl$, and $-Br$,
      (ii) methyl,
      (iii) $-CF_3$, and
      (iv) $-OH$,
    (k) $-N(R^a)_2$,
    (l) $-(CH_2)_{1-3}N(R^a)_2$,
    (m) $-R^t$, (p) —(CH$_2$)$_{0-3}$C(=O)N(R$^a$)$_2$, and
(q) —(CH$_2$)$_{0-3}$C(=O)R$^a$;

(2) —C$_{3-6}$ cycloalkyl, unsubstituted or substituted with from 1 to 3 substituents independently selected from:
(a) halogen selected from —F, —Cl, and —Br,
(b) methyl,
(c) —CF$_3$,
(d) methoxy,
(e) —OCF$_3$,
(f) —CN,
(h) phenyl, and
(j) —OH;

(3) a 5- or 6- membered heteroaromatic ring selected from thienyl, pyridyl, imidazolyl, pyrrolyl, pyrazolyl, thiazolyl, isothiazolyl, oxazolyl, isooxazolyl, pyrazinyl, pyirimidinyl, triazolyl, tetrazolyl, furanyl, and pyridazinyl, wherein the heteroaromatic ring is unsubstituted or substituted on nitrogen or carbon with 1 or 2 substituents independently selected from:
(a) halogen selected from —F, —Cl, and —Br,
(b) methyl,
(c) —CF$_3$,
(d) methoxy,
(e) —OCF$_3$,
(f) phenyl,
(g) —S—C$_{1-6}$ alkyl,
(h) —CN,
(i) —OH,
(j) phenyloxy, unsubstituted or substituted with from 1 to 3 substituents independently selected from:
(i) halogen selected from —F, —Cl, and —Br,
(ii) methyl,
(iii) —CF$_3$, and
(iv) —OH,
(k) —N(R$^a$)$_2$,
(l) —C$_{1-6}$ alkyl-N(R$^a$)$_2$,
(m) R$^t$,
(n) oxo,
(o) —(CH$_2$)$_{0-3}$C(=O)N(R$^a$)$_2$, and
(p) —(CH$_2$)$_{0-3}$C(=O)R$^a$;

(4) a 5- or 6- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, and pyrazolidinyl, wherein the heterocyclic ring is unsubstituted or substituted with 1 or 2 substituents independently selected from:
(a) halogen selected from —F, —Cl, and —Br,
(b) methyl,
(c) —CF$_3$,
(d) methoxy,
(e) —OCF$_3$,
(f) —CN,
(g) =O,
(h) phenyl,
(i) benzyl,
(j) phenylethyl,
(k) —OH,
(l) —(CH$_2$)$_{0-3}$C(=O)N(R$^a$)$_2$,
(m) —(CH$_2$)$_{0-3}$C(=O)R$^a$,
(n) N(R$^a$)—C(=O)R$^a$,
(o) N(R$^a$)—C(=O)OR$^a$,
(p) (CH$_2$)$_{1-3}$N(R$^a$)—C(=O)R$^a$,
(q) N(R$^a$)$_2$,
(r) (CH$_2$)$_{1-3}$N(R$^a$)$_2$,
(s) —(CH$_2$)$_{0-3}$C(=O)R$^t$,
(t) —R$^t$,
(u) —N(R$^a$)R$^t$, and
(v) —(CH$_2$)$_{1-3}$R$^t$; and (5) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, and isochromanyl, wherein the bicyclic ring is unsubstituted or substituted with 1 or 2 substituents independently selected from:
(a) halogen selected from —F, —Cl, and —Br,
(b) methyl,
(c) —CF$_3$,
(d) methoxy,
(e) —OCF$_3$,
(f) —CN,
(g) =O, and
(h) —OH;

R$^t$ is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;
or a pharmaceutically acceptable salt thereof.

A sixteenth embodiment of the present invention is a compound of Formula (III), wherein L is
(i) a single bond;
(ii) —(CH$_2$)$_{1-3}$—, which is optionally substituted with 1 or 2 substituents independently selected from the group consisting of —F, —Cl, —Br, —OH, methyl, ethyl, —CO$_2$CH$_3$, —CO$_2$CH$_2$-phenyl, phenyl, benzyl, —(CH$_2$)$_{1-2}$OH, —CH(OH)-phenyl, and —CH(NH$_2$)-phenyl; or (iii) 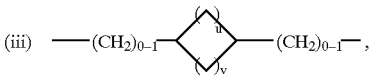

wherein u and v are each integers having a value of from 0 to 3, provided that the sum of u+v is 1, 2, 3 or 4;

each of R$^1$ and R$^2$ is independently:
(1) —H,
(2) methyl,
(3) ethyl,
(4) CF$_3$,
(5) methoxy,
(6) ethoxy
(7) —OCF$_3$
(8) halo selected from —F, —Cl and —Br,
(9) —CN,
(10) —CH$_2$OR$^a$,
(11) —CO$_2$R$^a$,
(12) —SR$^a$,
(13) —N(R$^a$)$_2$,

(14) —(CH$_2$)$_{1-3}$N(R$^a$)$_2$,
(15) —SO$_2$R$^a$,
(16) —(CH$_2$)$_{1-2}$N(R$^a$)—C(R$^a$)=O,
(17) —R$^k$,
(18) —(CH$_2$)$_{1-3}$H substituted with 1 or 2 R$^k$ groups,
(19) —O—R$^k$, or
(20) —O—(CH$_2$)$_{1-3}$R$^k$;

R$^5$ is
(1) —H,
(2) methyl,
(3) —(CH$_2$)$_{1-2}$N(R$^a$)$_2$,
(4) —(CH$_2$)$_{1-2}$CO$_2$CH$_3$, or
(5) —(CH$_2$)$_{1-2}$CO$_2$CH$_2$CH$_3$;
(6) phenyl, or
(7) benzyl;

each R$^a$ is independently —H or —C$_{1-4}$ alkyl;
each R$^c$ is independently
(1) —H,
(2) —C$_{1-4}$ alkyl,
(3) —(CH$_2$)$_{1-4}$N(R$^a$)$_2$, or
(4) —(CH$_2$)$_{1-4}$-phenyl, wherein the phenyl is optionally substituted with 1 to 3 substituents independently selected from halogen, C$_{1-4}$ alkyl, C$_{1-4}$ fluoroalkyl, —O—C$_{1-4}$ alkyl, —O—C$_{1-4}$ fluoroalkyl, —S—C$_{1-4}$ alkyl, —CN, and —OH; and each R$^k$ is independently:
(1) aryl selected from phenyl and naphthyl, wherein aryl is unsubstituted or substituted with from 1 to 4 substituents independently selected from:
  (a) halogen,
  (b) C$_{1-4}$ alkyl,
  (c) C$_{1-4}$ fluoroalkyl,
  (d) —O—C$_{1-4}$ alkyl,
  (e) —O—C$_{1-4}$ fluoroalkyl,
  (f) phenyl,
  (g) —S—C$_{1-4}$ alkyl,
  (h) —CN,
  (i) —OH,
  (j) phenyloxy, unsubstituted or substituted with from 1 to 3 substituents independently selected from:
    (i) halogen,
    (ii) C$_{1-4}$ alkyl,
    (iii) C$_{1-4}$ fluoroalkyl, and
    (iv) —OH,
  (k) —N(R$^a$)$_2$,
  (l) —C$_{1-4}$ alkyl-N(R$^a$)$_2$,
  (m) R$^t$,
  (p) —(CH$_2$)$_{0-3}$C(=O)N(R$^a$)$_2$, and
  (q) —(CH$_2$)$_{0-3}$C(=O)R$^a$;
(2) —C$_{3-6}$ cycloalkyl, unsubstituted or substituted with from 1 to 3 substituents independently selected from:
  (a) halogen,
  (b) C$_{1-4}$ alkyl,
  (c) —O—C$_{1-4}$ alkyl,
  (d) C$_{1-4}$ fluoroalkyl,
  (e) —O—C$_{1-4}$ fluoroalkyl,
  (f) —CN,
  (h) phenyl, and
  (j) —OH;
(3) —C$_{3-6}$ cycloalkyl fused with a phenyl ring, unsubstituted or substituted with from 1 to 4 substituents independently selected from:
  (a) halogen,
  (b) C$_{1-4}$ alkyl,
  (c) —O—C$_{1-4}$ alkyl,
  (d) C$_{1-4}$ fluoroalkyl,
  (e) —O—C$_{1-4}$ fluoroalkyl,
  (f) —CN, and
  (g) —OH;
(4) a 5- or 6- membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with from 1 to 4 substituents independently selected from:
  (a) halogen,
  (b) C$_{1-4}$ alkyl,
  (c) C$_{1-4}$ fluoroalkyl,
  (d) —O—C$_{1-4}$ alkyl,
  (e) —O—C$_{1-4}$ fluoroalkyl,
  (f) phenyl,
  (g) —S—C$_{1-4}$ alkyl,
  (h) —CN,
  (i) —OH,
  (j) phenyloxy, unsubstituted or substituted with from 1 to 3 substituents independently selected from:
    (i) halogen,
    (ii) C$_{1-4}$ alkyl,
    (iii) C$_{1-4}$ fluoroalkyl, and
    (iv) —OH,
  (k) —N(R$^a$)$_2$,
  (l) —C$_{1-4}$ alkyl-N(R$^a$)$_2$,
  (m) R$^t$,
  (n) oxo,
  (o) —(CH$_2$)$_{0-3}$C(=O)N(R$^a$)$_2$, and
  (p) —(CH$_2$)$_{0-3}$C(=O)R$^a$;
(5) a 5- or 6- or 7- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, azepanyl, thiadiazepanyl, dithiazepanyl, diazepanyl, and thiadiazinanyl, and wherein the heterocyclic ring is unsubstituted or substituted with from 1 to 4 substituents independently selected from:
  (a) halogen,
  (b) C$_{1-6}$ alkyl,
  (c) —O—C$_{1-6}$ alkyl,
  (d) C$_{1-6}$ fluoroalkyl,
  (e) —O—C$_{1-6}$ fluoroalkyl,
  (f) —CN,
  (g) oxo,
  (h) phenyl
  (i) benzyl,
  (j) phenylethyl,
  (k) —OH,
  (l) —(CH$_2$)$_{0-3}$C(=O)N(R$^a$)$_2$,
  (m) —(CH$_2$)$_{0-3}$C(=O)R$^a$,
  (n) —N(R$^a$)—C(=O)R$^a$,
  (o) —N(R$^a$)—CO$_2$R$^a$,
  (p) —(CH$_2$)$_{1-3}$N(R$^a$)—C(=O)R$^a$,
  (q) —N(R$^a$)$_2$,
  (r) —(CH$_2$)$_{1-3}$N(R$^a$)$_2$,
  (s) —(CH$_2$)$_{1-3}$—OR$^a$,
  (t) —(CH$_2$)$_{0-3}$CO$_2$R$^a$,
  (u) —(CH$_2$)$_{0-3}$—O—(CH$_2$)$_{1-3}$—OR$^a$,
  (v) —SO$_2$R$^a$,
  (w) —SO$_2$N(R$^a$)$_2$, (x) —(CH$_2$)$_{0-3}$C(=O)O(CH$_2$)$_{1-2}$CH=CH$_2$,
(y) —R$^t$,
(z) —(CH$_2$)$_{0-3}$C(=O)R$^t$,
(aa) —N(R$^a$)R$^t$, and
(bb) —(CH$_2$)$_{1-3}$R$^t$; or
(6) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, isochromanyl, hexahydropyrazolo[4,3-c]pyridinyl, hexahydropurinyl, hexahydrooxazolo[3,4a]pyrazinyl, and 1,2,3,4-tetrahydro-1,8-naphthyridinyl; and wherein the bicyclic ring is unsubstituted or substituted with from 1 to 3 substituents independently selected from:
(a) halogen,
(b) C$_{1-4}$ alkyl,
(c) —O—C$_{1-4}$ alkyl,
(d) C$_{1-4}$ fluoroalkyl,
(e) —O—C$_{1-4}$ fluoroalkyl,
(f) —CN,
(g) =O, and
(h) —OH;
R$^t$ is naphthyl or a 5- or 6-membered heteromonocylic ring selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; and wherein the naphthyl or the heteromonocyclic ring is unsubstituted or substituted with 1 or 2 substituents independently selected from halogen, oxo, C$_{1-4}$ alkyl, and —C$_{1-4}$ alkyl;
and Q$^2$ is as originally defined or as defined in any one of the preceding embodiments;
or a pharmaceutically acceptable salt thereof.

In an aspect of the sixteenth embodiment, the compound of Formula (III) is as just defined above, except that in part (5) of the definition of R$^k$, the 5- or 6- or 7- membered saturated heterocyclic ring is selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, and azepanyl.

A first class of the present invention is compounds of Formula (IV):

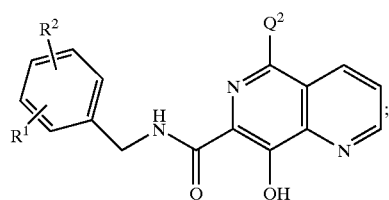

(IV)

wherein each of the variables is as defined in any one of the tenth, eleventh, twelfth, thirteenth, fourteenth, fifteenth, or sixteenth embodiments; or, alternatively, as originally defined, or as defined in any of the other preceding embodiments containing the variables;
or a pharmaceutically acceptable salt thereof.

A first sub-class of the present invention is compounds of Formula (V):

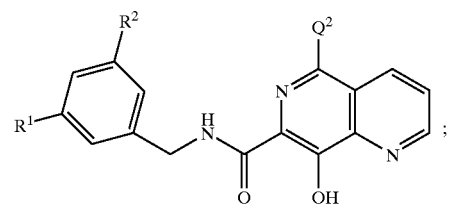

(V)

wherein each of the variables is as defined in either the fifteenth embodiment or the sixteenth embodiment; or, alternatively, as originally defined, or as defined in any of the other preceding embodiments or classes containing the variables;
or a pharmaceutically acceptable salt thereof.

A second sub-class of the present invention is compounds of Formula (V), wherein:

Q$^2$ is
(1) —H,
(2) methyl,
(3) ethyl,
(4) CF$_3$,
(5) methoxy,
(6) ethoxy
(7) —OCF$_3$
(8) halo selected from —F, —Cl and —Br,
(9) —CN,
(10) —CH$_2$OH,
(11) —CH$_2$OCH$_3$,
(12) —SR$^a$,
(13) —N(R$^a$)$_2$,
(14) —N(H)CH$_2$CH$_2$CH$_3$,
(15) —SO$_2$R$^a$,
(16) —C≡C—CH$_2$OR$^a$,
(17) —N(R$^a$)—(CH$_2$)$_{1-3}$SR$^a$,
(18) —N(R$^a$)—(CH$_2$)$_{1-3}$OR$^a$,
(19) —N(R$^a$)—(CH$_2$)$_{1-3}$N(R$^a$)$_2$,
(20) —N(R$^a$)—(CH$_2$)$_{1-3}$N(R$^a$)—C(R$^a$)=O,
(21) —R$^k$,
(22) —(CH$_2$)$_{1-4}$R$^k$,
(23) —C≡C—CH$_2$R$^k$,
(24) —S—R$^k$,
(25) —SO$_2$—R$^k$,
(26) —N(R$^c$)—R$^k$,
(27) —N(R$^c$)—(CH$_2$)$_{1-4}$H substituted with one or two R$^k$ groups,
(28) —N(R$^c$)—(CH$_2$)$_{1-4}$OR$^k$,
(29) —C≡C—CH$_2$SR$^a$, or
(30) —C≡C—CH$_2$SO$_2$R$^8$;
R$^1$ is:
(1) —H,
(2) methyl,
(3) ethyl,
(4) CF$_3$, (5) methoxy,
(6) ethoxy
(7) —OCF$_3$
(8) halo selected from —F and —Cl,
(9) —CN,
(10) —CH$_2$OR$^a$,
(11) —CO$_2$R$^a$,
(12) —SR$^a$,
(13) —N(R$^a$)$_2$,
(14) —(CH$_2$)$_{1-3}$N(R$^a$)$_2$,
(15) —SO$_2$R$^a$,
(16) —R$^k$,
(17) —(CH$_2$)$_{1-3}$R$^k$,
(18) —O—R$^k$, or
(19) —O—(CH$_2$)$_{1-3}$R$^k$;

R$^2$ is:
(1) —H,
(2) methyl,
(3) ethyl,
(4) CF$_3$,
(5) methoxy,
(6) ethoxy
(7) —OCF$_3$
(8) halo selected from —F and —Cl,
(9) —CN,
(10) —CH$_2$OR$^a$,
(11) —CO$_2$R$^a$,
(12) —SR$^a$,
(13) —N(R$^a$)$_2$,
(14) —(CH$_2$)$_{1-3}$N(R$^a$)$_2$, or
(15) —SO$_2$R$^a$;

each R$^a$ is independently —H or methyl;
each R$^c$ is independently —H, methyl, or —(CH$_2$)$_{1-3}$N(R$^a$)$_2$;
each R$^k$ is independently:
  (1) phenyl which is unsubstituted or substituted with from 1 to 2 substituents independently selected from:
    (a) halogen selected from —F, —Cl, and —Br,
    (b) methyl,
    (c) —CF$_3$,
    (d) methoxy,
    (e) —OCF$_3$,
    (f) phenyl,
    (g) —S—CH$_3$,
    (h) —CN,
    (i) —OH,
    (j) phenyloxy
    (k) —N(R$^a$)$_2$,
    (l) —(CH$_2$)$_{1-3}$N(R$^a$)$_2$,
    (m) R$^t$,
    (p) —(CH$_2$)$_{0-3}$C(=O)N(R$^a$)$_2$, and
    (q) —(CH$_2$)$_{0-3}$C(=O)R$^a$;
  (2) —C$_{3-6}$ cycloalkyl;
  (3) a 5- or 6- membered heteroaromatic ring selected from thienyl, pyridyl, imidazolyl, pyrrolyl, pyrazolyl, thiazolyl, isothiazolyl, pyrazinyl, pyirimidinyl, triazolyl, and tetrazolyl, wherein the heteroaromatic ring is unsubstituted or substituted on nitrogen or carbon with 1 or 2 substituents independently selected from:
    (a) halogen selected from —F, —Cl, and —Br,
    (b) methyl,
    (c) —CF$_3$,
    (d) methoxy,
    (e) —OCF$_3$,
    (f) —S—C$_{1-6}$ alkyl,
    (g) —CN,
    (h) —OH,
    (i) —N(R$^a$)$_2$,
    (j) —C$_{1-6}$ alkyl-N(R$^a$)$_2$,
    (k) —R$^t$,
    (l) oxo,
    (m) —(CH$_2$)$_{0-3}$C(=O)N(R$^a$)$_2$, and
    (n) —(CH$_2$)$_{0-3}$C(=O)R$^a$;
  (4) a 5- or 6- membered saturated heterocyclic ring selected from piperidinyl, morpholinyl, thiomorpholinyl, thiazolidinyl, isothiazolidinyl, pyrrolidinyl, imidazolidinyl and, piperazinyl, wherein the heterocyclic ring is unsubstituted or substituted with 1 or 2 substituents independently selected from:
    (a) halogen selected from —F, —Cl, and —Br,
    (b) methyl,
    (c) —CF$_3$,
    (d) methoxy,
    (e) —OCF$_3$,
    (f) —CN,
    (g) =O,
    (h) phenyl,
    (i) benzyl,
    (j) phenylethyl,
    (k) —OH,
    (l) —(CH$_2$)$_{0-3}$C(=O)N(R$^a$)$_2$,
    (m) —(CH$_2$)$_{0-3}$C(=O)R$^a$,
    (n) N(R$^a$)—C(=O)R$^a$,
    (o) N(R$^a$)—C(=O)OR$^a$,
    (p) N(R$^a$)—C(=O)OC(CH$_3$)$_3$,
    (q) (CH$_2$)$_{1-3}$N(R$^a$)—C(=O)R$^a$,
    (r) N(R$^a$)$_2$,
    (s) (CH$_2$)$_{1-3}$N(R$^a$)$_2$,
    (t) —(CH$_2$)$_{0-3}$C(=O)R$^t$,
    (u) —R$^t$,
    (v) —N(R$^a$)R$^t$, and
    (w) —(CH$_2$)$_{1-3}$R$^t$; and
  (5) an 8- to 10- membered heterobicyclic ring selected from indolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, and quinazolinyl, wherein the bicyclic ring is unsubstituted or substituted with 1 or 2 substituents independently selected from:
    (a) halogen selected from —F, —Cl, and —Br,
    (b) methyl,
    (c) —CF$_3$,
    (d) methoxy,
    (e) —OCF$_3$,
    (f) —CN,
    (g) =O, and
    (h) —OH;

R$^t$ is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;
or a pharmaceutically acceptable salt thereof.

An aspect of the second sub-class is a compound of Formula (VI):

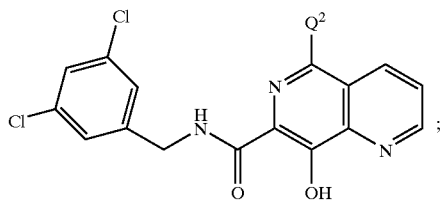

(VI)

wherein $Q^2$ is as defined in the second sub-class;
or a pharmaceutically acceptable salt thereof.

A seventeenth embodiment of the present invention is a compound of Formula (IV), wherein $Q^2$ is
(1) —H,
(2) methyl,
(3) ethyl,
(4) $CF_3$,
(5) methoxy,
(6) ethoxy
(7) —$OCF_3$
(8) halo selected from —F, —Cl and —Br,
(9) —CN,
(10) —$CH_2OH$,
(11) —$CH_2OCH_3$,
(12) —$(CH_2)_{0-2}C(=O)CH_3$,
(13) —$(CH_2)_{0-2}CO_2CH_3$,
(14) —$SR^a$,
(15) —$N(R^a)_2$,
(16) —$(CH_2)_{1-2}N(R^a)_2$,
(17) —$(CH_2)_{0-2}C(=O)N(R^a)_2$,
(18) —S—$CH_2$—$C(=O)N(R^a)_2$,
(19) —O—$CH_2$—$C(=O)N(R^a)_2$,
(20) —$N(SO_2R^a)$—$CH_2$—$C(=O)N(R^a)_2$,
(21) —$N(R^a)$—$C(R^a)=O$,
(22) —$C(=O)$—$N(R^a)$—$(CH_2)_{1-2}$—$C(=)N(R^a)_2$,
(23) —$C(=O)$—$N(R^a)$—$(CH_2)_{1-2}OR^a$,
(24) —$C(=O)$—$N(R^a)$—$(CH_2)_{1-3}$—$N(R^a)_2$,
(25) —$SO_2R^a$,
(26) —$N(R^a)SO_2R^a$,
(27) —CH=CH—$C(=O)$—$N(R^a)_2$,
(28) —C≡C—$CH_2OR^a$,
(29) —C≡C—$CH_2SR^a$,
(30) —C≡C—$CH_2SO_2R^a$ (31)

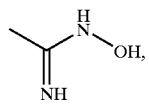

(32) —$N(R^a)$—$(CH_2)_{1-3}SR^a$,
(33) —$N(R^a)$—$(CH_2)_{1-3}OR^a$,

(34) —$N(R^a)$—$(CH_2)_{1-3}N(R^a)_2$,
(35) —$N(R^a)$—$(CH_2)_{1-3}N(R^a)$—$C(R^a)=O$,
(36) —$N(R^a)CH_2$—$C(=O)N(R^a)_2$,
(37) —$N(R^a)$—$C(=O)$—$C(=O)$—$N(R^a)_2$,
(38) —$N(R^a)$—$C(=O)$—$N(R^a)_2$,
(39) —$N(R^a)$—$(CH_2)_{1-2}$—$CO_2R^a$,
(40) —$N(R^a)$—$C(=O)$—$N(R^a)$—$(CH_2)_{1-2}$—$C(=O)$—$N(R^a)_2$,
(41) —$N(R^a)$—$C(=O)$—$(CH_2)_{1-2}$—$C(=O)$—$N(R^a)_2$,
(42) —$N(R^a)$—$SO_2$—$N(R^a)_2$,
(43) —$R^k$,
(44) —$(CH_2)_{1-4}R^k$,
(45) —C≡C—$CH_2R^k$,
(46) —O—$R^k$,
(47) —S—$R^k$,
(48) —$SO_2$—$R^k$,
(49) —$N(R^c)$—$R^k$,
(50) —$N(R^c)$—$(CH_2)_{1-4}H$ substituted with one or two $R^k$ groups,
(51) —$N(R^c)$—$(CH_2)_{1-4}OR^k$,
(52) —$C(=O)$—$R^k$,
(53) —$C(=O)N(R^a)$—$R^k$,
(54) —$N(R^a)$—$C(=O)$—$R^k$,
(55) —$C(=O)N(R^a)$—$(CH_2)_{1-4}R^k$, or
(56) —$N(R^a)$—$SO_2R^k$,
each of $R^1$ and $R^2$ is independently:
(1) —H,
(2) methyl,
(3) ethyl,
(4) $CF_3$,
(5) methoxy,
(6) ethoxy
(7) —$OCF_3$
(8) halo selected from —F and —Cl,
(9) —CN,
(10) —$CH_2OR^a$,
(11) —$CO_2R^a$,
(12) —$SR^a$,
(13) —$N(R^a)_2$,
(14) —$(CH_2)_{1-3}N(R^a)_2$,
(15) —$SO_2R^a$,
(16) —$R^k$,
(17) —$(CH_2)_{1-3}R^k$,
(18) —O—$R^k$, or
(19) —O—$(CH_2)_{1-3}R^k$;
each $R^a$ is independently —H or —$C_{1-4}$ alkyl;
each $R^c$ is independently —H, —$C_{1-4}$ alkyl, or —$(CH_2)_{1-3}N(R^a)_2$;
each $R^k$ is independently:
(1) phenyl which is unsubstituted or substituted with from 1 to 4 substituents independently selected from:
(a) halogen selected from —F, —Cl, and —Br,
(b) methyl or ethyl,
(c) —$CF_3$,
(d) methoxy,
(e) —$OCF_3$,
(f) phenyl,
(g) —S—$CH_3$,
(h) —CN, (i) —OH,
(j) phenyloxy
(k) —N(R$^a$)$_2$,
(l) —(CH$_2$)$_{1-3}$N(R$^a$)$_2$,
(m) —R$^t$,
(p) —(CH$_2$)$_{0-3}$C(=O)N(R$^a$)$_2$, and
(q) —(CH$_2$)$_{0-3}$C(=O)R$^a$;

(2) —C$_{3-6}$ cycloalkyl, (3) a 5- or 6- membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with 1 or 2 substituents independently selected from:
  (a) halogen selected from —F, —Cl, and —Br,
  (b) methyl or ethyl,
  (c) —CF$_3$,
  (d) methoxy,
  (e) —OCF$_3$,
  (f) —S—C$_{1-6}$ alkyl,
  (g) —CN,
  (h) —OH,
  (i) —N(R$^a$)$_2$,
  (j) —C$_{1-6}$ alkyl-N(R$^a$)$_2$,
  (k) R$^t$,
  (l) oxo,
  (m) —(CH$_2$)$_{0-3}$C(=O)N(R$^a$)$_2$, and
  (n) —(CH$_2$)$_{0-3}$C(=O)R$^a$;

(4) a 5- or 6- or 7- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, azepanyl, thiadiazepanyl, dithiazepanyl, diazepanyl; and wherein the heterocyclic ring is unsubstituted or substituted with 1 to 4 substituents independently selected from:
  (a) halogen selected from —F, —Cl, and —Br,
  (b) methyl or ethyl,
  (c) —CF$_3$,
  (d) methoxy,
  (e) —OCF$_3$,
  (f) —CN,
  (g) =O ,
  (h) phenyl,
  (i) benzyl,
  (j) phenylethyl,
  (k) —OH,
  (l) —(CH$_2$)$_{0-3}$C(=O)N(R$^a$)$_2$,
  (m) —(CH$_2$)$_{0-3}$C(=O)R$^a$,
  (n) N(R$^a$)—C(=O)R$^a$,
  (o) N(R$^a$)—CO$_2$R$^a$,
  (p) (CH$_2$)$_{1-3}$N(R$^a$)—C(=O)R$^a$,
  (q) N(R$^a$)$_2$,
  (r) (CH$_2$)$_{1-3}$N(R$^a$)$_2$,
  (s) SO$_2$R$^a$,
  (t) —(CH$_2$)$_{0-3}$C(=O)R$^t$,
  (u) —R$^t$,
  (v) —N(R$^a$)R$^t$, and
  (w) —(CH$_2$)$_{1-3}$R$^t$; and (5) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[11,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, isochromanyl, and 1,2,3,4-tetrahydro-1,8-naphthyridinyl, wherein the bicyclic ring is unsubstituted or substituted with 1 or 2 substituents independently selected from:
  (a) halogen selected from —F, —Cl, and —Br,
  (b) methyl or ethyl,
  (c) —CF$_3$,
  (d) methoxy,
  (e) —OCF$_3$,
  (f) —CN,
  (g) =O, and
  (h) —OH;

R$^t$ is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;

or a pharmaceutically acceptable salt thereof.

In an aspect of the seventeenth embodiment, the compound of Formula (IV) is as just defined above, except that:
  the definition of Q$^2$ does not include (56) —N(R$^a$)SO$_2$R$^k$;
  parts (1)(b), (2(b), (3(b), (4(b), (5(b), and (6)(b) of the definition of R$^k$ is methyl, instead of methyl or ethyl; and
  in part (5) of the definition of R$^k$, the 5- or 6- or 7- membered saturated heterocyclic ring is selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, and azepanyl.

In another aspect of the seventeenth embodiment, R$^1$ and R$^2$ in the compound of Formula (IV) are both chloro. In a feature of this aspect, the compound is a compound of Formula (VI) wherein Q$^2$ is as defined in the seventeenth embodiment.

A second class of the present invention is a compound of Formula (VII):

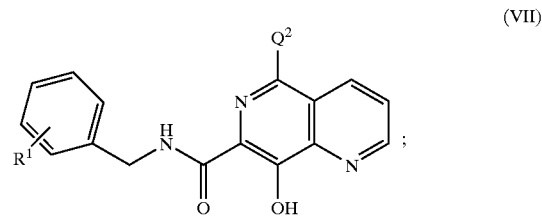

wherein the variables are as defined in the seventeenth embodiment; or, alternatively, as originally defined, or as defined in any of the other preceding embodiments, classes, or sub-classes containing the variables;
or a pharmaceutically acceptable salt thereof.

A third sub-class of the present invention is compounds of Formula (V-A):

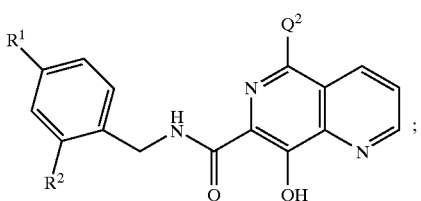

(V-A)

wherein each of the variables is as defined in the seventeenth embodiment, or, alternatively, as originally defined, or as defined in any of the other preceding embodiments, classes, or sub-classes containing the variables;
or a pharmaceutically acceptable salt thereof.

A fourth sub-class of the present invention is compounds of Formula (V-A), wherein $R^1$ is H or F, and $R^2$ is H or $-SO_2CH_3$, with the proviso that $R^1$ and $R^2$ are not both H; and $Q^2$ is as defined in the seventeenth embodiment, or as originally defined, or as defined in any of the other preceding embodiments, classes, or sub-classes containing $Q^2$;
or a pharmaceutically acceptable salt thereof.

A fifth sub-class of the present invention is a compound of Formula (VIII):

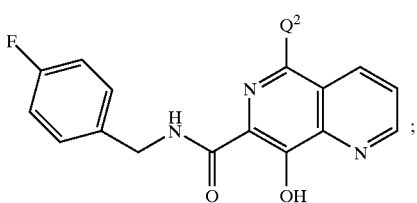

(VIII)

wherein $Q^2$ is as defined in the second class, or as originally defined or as defined in any of the other preceding embodiments, classes, or sub-classes containing $Q^2$;
or a pharmaceutically acceptable salt thereof.

In an aspect of each of the preceding classes and sub-classes, $Q^2$ is:
(1) $-C(=O)N(R^a)_2$,
(2) $-CH_2C(=O)N(R^a)_2$,
(3) $-CH_2CH_2C(=O)N(R^a)_2$,
(4) $-S-CH_2-C(=O)N(R^a)_2$,
(5) $-O-CH_2-C(=O)N(R^a)_2$,
(6) $-N(R^a)-C(R^a)=O$,
(7) $-N(SO_2R^a)-CH_2-C(=O)N(R^a)_2$,
(8) $-N(R^a)-C(=O)-C(=O)-N(R^a)_2$,
(9) $-N(R^a)SO_2R^a$,
(10) $-CH=CH-C(=O)-N(R^a)_2$,
(11) $-N(R^a)CH_2-C(=O)N(R^a)_2$,
(12) $-N(R^a)-C(=O)-N(R^a)_2$,
(13) $-R^k$,
(14) $-(CH_2)_{1-3}R^k$, or
(15) $-N(R^c)-(CH_2)_{1-3}R^k$,
each $R^a$ is independently $-H$ or $-C_{1-4}$ alkyl;
each $R^c$ is independently $-H$ or $-C_{1-4}$ alkyl; and
$R^k$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, 1,2-thiazinanyl, 1,4-thiazepanyl, 1,2,5-thiadiazepanyl, 1,5,2-dithiazepanyl, 1,4-diazepanyl, and 1,2,6-thiadiazinanyl, wherein the heterocyclic ring is unsubstituted or substituted with 1 to 4 substituents independently selected from:
(a) methyl or ethyl,
(b) =O,
(c) $-C(=O)N(R^a)_2$,
(d) $-CH_2C(=O)N(R^a)_2$,
(e) $-C(=O)R^a$, or
(f) $-SO_2R^a$;
or a pharmaceutically acceptable salt thereof.

In a feature of each these aspects, $R^k$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, 1,2-thiazinanyl, 1,4-thiazepanyl, and 1,2,5-thiadiazepanyl, wherein the heterocyclic ring is unsubstituted or substituted with 1 to 4 substituents independently selected from:
(a) methyl,
(b) =O,
(c) $-C(=O)N(R^a)_2$, or
(d) $-CH_2C(=O)N(R^a)_2$.

In another aspect of each of the preceding classes and sub-classes, $Q^2$ is:
(1) $-C(=O)N(R^a)_2$,
(2) $-CH_2C(=O)N(R^a)_2$,
(3) $-CH_2CH_2C(=O)N(R^a)_2$,
(4) $-S-CH_2-C(=O)N(R^a)_2$,
(5) $-O-CH_2-C(=O)N(R^a)_2$,
(6) $-N(SO_2R^a)-CH_2-C(=O)N(R^a)_2$,
(7) $-N(R^a)-C(=O)-C(=O)-N(R^a)_2$,
(8) $-N(R^a)SO_2R^a$,
(9) $-CH=CH-C(=O)-N(R^a)_2$,
(10) $-N(R^a)CH_2-C(=O)N(R^a)_2$,
(11) $-N(R^a)-C(=O)-N(R^a)_2$,
(12) $-R^k$,
(13) $-(CH_2)_{1-2}R^k$, or
(14) $-NH-(CH_2)_{1-2}R^k$;
each $R^a$ is independently methyl, ethyl, or isopropyl; and $R^k$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, 1,2-thiazinanyl, 1,4-thiazepanyl, 1,2,5-thiadiazepanyl, 1,5,2-dithiazepanyl, 1,4-diazepanyl, and 1,2,6-thiadiazinanyl, wherein the heterocyclic ring is unsubstituted or substituted with 1 to 4 substituents independently selected from:
(a) methyl or ethyl,
(b) =O,
(c) $-C(=O)NH_2$, (d) —C(=O)CH₃, or
(e) —SO₂CH₃;
or a pharmaceutically acceptable salt thereof.

In a feature of each these aspects, $R^k$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, 1,2-thiazinanyl, 1,4-thiazepanyl, and 1,2,5-thiadiazepanyl, wherein the heterocyclic ring is unsubstituted or substituted with 1 to 4 substituents independently selected from:
(a) methyl,
(b) =O, or
(c) —C(=O)NH₂.

An eighteenth embodiment of the present invention is a compound of Formula (IX):

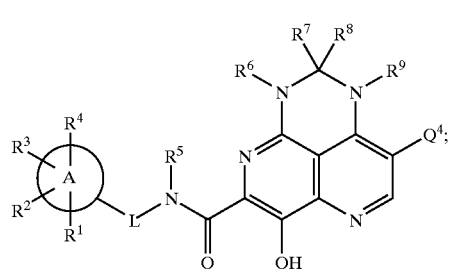

(IX)

wherein each of $R^6$ and $R^9$ is independently:
(1) —H
(2) —C₁₋₄ alkyl,
(3) —C₁₋₄ fluoroalkyl,
(4) —C₁₋₄ alkyl-OR$^a$,
(5) —C₁₋₄ alkyl-S(O)$_n$R$^a$,
(6) —C₁₋₄ alkyl-N(R$^a$)₂,
(7) —C₁₋₄ alkyl-C(=O)—N(R$^a$)₂,
(8) —C₁₋₄ alkyl-CO₂R$^a$, and
(9) —C₁₋₄ alkyl substituted with $R^k$; and
each of $R^7$ and $R^8$ is independently:
(1) —H
(2) —C₁₋₄ alkyl,
(3) —C₁₋₄ fluoroalkyl,
(4) —C₁₋₄ alkyl-OR$^a$,
(5) —C₁₋₄ alkyl-SR$^a$,
(6) —C₁₋₄ alkyl-N(R$^a$)₂,
(7) —C₁₋₄ alkyl-C(=O)—N(R$^a$)₂,
(8) —C₁₋₄ alkyl-CO₂R$^a$, and
(9) —C₁₋₄ alkyl substituted with $R^k$;
or $R^7$ and $R^8$ together form oxo;
and all other variables are as originally defined or as defined in any of the preceding embodiments;
or a pharmaceutically acceptable salt thereof.

A third class of the present invention is compounds of Formula (X):

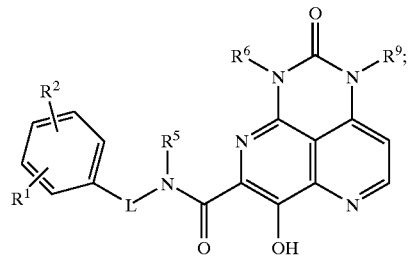

(X)

wherein each of the variables is as defined in the eighteenth embodiment;
or a pharmaceutically acceptable salt thereof.

A sub-class of the third class is a compound of Formula (XI):

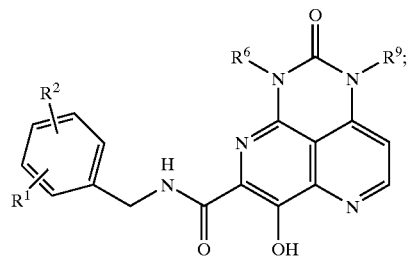

(XI)

wherein each of the variables is as defined in the third class;
or a pharmaceutically acceptable salt thereof.

Another sub-class of the third class is a compound of Formula (XII):

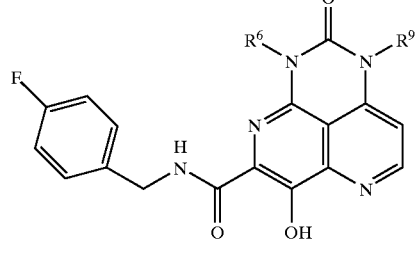

(XII)

wherein each of the variables is as defined in the third class;
or a pharmaceutically acceptable salt thereof.

An aspect of the sub-class is a compound of Formula (XII), wherein $R^6$ is:
(1) —H
(2) methyl,
(3) ethyl
(4) —CF₃,
(4) —(CH₂)₁₋₃—OR$^a$,
(5) —(CH₂)₁₋₃—SR$^a$,
(6) —(CH₂)₁₋₃—SO₂R$^a$,
(7) —(CH₂)₁₋₃—N(R$^a$)₂, (8) —(CH$_2$)$_{1-3}$—C(=O)—N(R$^a$)$_2$, or
(9) —(CH$_2$)$_{1-3}$—CO$_2$R$^a$;
R$^9$ is:
(1) —H
(2) methyl,
(3) ethyl,
(4) —CF$_3$,
(4) —(CH$_2$)$_{1-3}$—OR$^a$,
(5) —(CH$_2$)$_{1-3}$—SR$^a$,
(6) —(CH$_2$)$_{1-3}$—SO$_2$R$^a$,
(7) —(CH$_2$)$_{1-3}$—N(R$^a$)$_2$,
(8) —(CH$_2$)$_{1-3}$—C(=O)—N(R$^a$)$_2$,
(9) —(CH$_2$)$_{1-3}$—CO$_2$R$^a$, or
(10) —(CH$_2$)$_{1-3}$—R$^k$;
each R$^a$ is independently —H, methyl, or ethyl;
R$^k$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, and pyrazolidinyl; and wherein the heterocyclic ring is unsubstituted or substituted with from 1 to 3 substituents independently selected from:
(a) halogen selected from —F, —Cl, and —Br,
(b) methyl,
(c) —CF$_3$,
(d) methoxy,
(e) —OCF$_3$,
(f) —CN, and
(g) =O;
or a pharmaceutically acceptable salt thereof.

Exemplary compounds of the invention include compounds selected from the group consisting of N-(3,5-dichlorobenzyl)-8-hydroxy-1,6-naphthyridine-7-carboxamide;
N-(2,5-dichlorobenzyl)-8-hydroxy-1,6-naphthyridine-7-carboxamide;
N-[(1R,S)-2,3-dihydro-1H-inden-1-yl]-8-hydroxy-1,6-naphthyridine-7-carboxamide;
N-[2-(3-chlorophenyl)ethyl]-8-hydroxy-1,6-naphthyridine-7-carboxamide;
N-[2-(2-chlorophenyl)ethyl]-8-hydroxy-1,6-naphthyridine-7-carboxamide;
N-[2-(1,1'-biphenyl-4-yl)ethyl]-8-hydroxy-1,6-naphthyridine-7-carboxamide;
8-hydroxy-N-[2-(4-phenoxyphenyl)ethyl]-1,6-naphthyridine-7-carboxamide;
8-hydroxy-N-(3-phenylpropyl)-1,6-naphthyridine-7-carboxamide;
N-(1,1'-biphenyl-2-ylmethyl)-8-hydroxy-1,6-naphthyridine-7-carboxamide;
N-(1,1'-biphenyl-3-ylmethyl)-8-hydroxy-1,6-naphthyridine-7-carboxamide;
8-hydroxy-N-phenyl-1,6-naphthyridine-7-carboxamide;
8 N-(2-chlorobenzyl)-8-hydroxy-1,6-naphthyridine-7-carboxamide;
N-benzyl-8-hydroxy-N-methyl-1,6-naphthyridine-7-carboxamide;
8-hydroxy-N-(1-methyl-1-phenylethyl)-1,6-naphthyridine-7-carboxamide;
8-hydroxy-N-(2-phenylethyl)-1,6-naphthyridine-7-carboxamide;
8-hydroxy-N-(1-naphthylmethyl)-1,6-naphthyridine-7-carboxamide;
N-benzyl-8-hydroxy-N-phenyl-1,6-naphthyridine-7-carboxamide;
N-(3-chlorobenzyl)-8-hydroxy-1,6-naphthyridine-7-carboxamide;
N-(4-chlorobenzyl)-8-hydroxy-1,6-naphthyridine-7-carboxamide;
Methyl (2S)-{[(8-hydroxy-1,6-naphthyridin-7-yl)carbonyl]amino}(phenyl)ethanoate;
Ethyl N-benzyl-N-[(8-hydroxy-1,6-naphthyridin-7-yl)carbonyl]glycinate;
N-benzyl-8-hydroxy-N-(2-phenylethyl)-1,6-naphthyridine-7-carboxamide;
N-(1,2-diphenylethyl)-8-hydroxy-1,6-naphthyridine-7-carboxamide;
N-(2,3-dihydro-1H-inden-2-yl)-8-hydroxy-1,6-naphthyridine-7-carboxamide;
N-benzyl-8-hydroxy-1,6-naphthyridine-7-carboxamide;
N-(2-anilinoethyl)-8-hydroxy-1,6-naphthyridine-7-carboxamide;
N-(2,2-diphenylethyl)-8-hydroxy-1,6-naphthyridine-7-carboxamide;
N-(3,3-diphenylpropyl)-8-hydroxy-1,6-naphthyridine-7-carboxamide;
N-(2-chloro-6-phenoxybenzyl)-8-hydroxy-1,6-naphthyridine-7-carboxamide;
Methyl (2R)-{[(8-hydroxy-1,6-naphthyridin-7-yl)carbonyl]amino}(phenyl)ethanoate;
8-hydroxy-N-(1,2,3,4-tetrahydronaphthalen-1-yl)-1,6-naphthyridine-7-carboxamide;
N-(2,3-dihydro-1H-inden-1-ylmethyl)-8-hydroxy-1,6-naphthyridine-7-carboxamide;
8-hydroxy-N-(6,7,8,9-tetrahydro-5H-benzo[a][7]annulen-6-ylmethyl)-1,6-naphthyridine-7-carboxamide;
8-hydroxy-N-[2-(1-naphthylamino)ethyl]-1,6-naphthyridine-7-carboxamide;
N-(2,3-dihydro-1H-inden-2-ylmethyl)-8-hydroxy-1,6-naphthyridine-7-carboxamide;
8-hydroxy-N-[(1R)-1-phenylethyl]-1,6-naphthyridine-7-carboxamide;
8-hydroxy-N-[(1S)-1-phenylethyl]-1,6-naphthyridine-7-carboxamide;
8-hydroxy-N-(3-hydroxy-1-phenylpropyl)-1,6-naphthyridine-7-carboxamide;
N-[2-(4-chlorophenyl)ethyl]-8-hydroxy-1,6-naphthyridine-7-carboxamide;
8-hydroxy-N-[(1R)-2-hydroxy-1-phenylethyl]-1,6-naphthyridine-7-carboxamide;
N-[(1S)-1-benzyl-2-hydroxyethyl]-8-hydroxy-1,6-naphthyridine-7-carboxamide;
N-[(1R)-1-benzyl-2-hydroxyethyl]-8-hydroxy-1,6-naphthyridine-7-carboxamide;
8-hydroxy-N-(2-hydroxy-2-phenylethyl)-1,6-naphthyridine-7-carboxamide;
5-chloro-N-(3,5-dichlorobenzyl)-8-hydroxy-1,6-naphthyridine-7-carboxamide;
N-(3,5-dichlorobenzyl)-8-hydroxy-5-piperidin-1-yl-1,6-naphthyridine-7-carboxamide;
N-(3,5-dichlorobenzyl)-8-hydroxy-5-phenyl-1,6-naphthyridine-7-carboxamide;
N-(3,5-dichlorobenzyl)-8-hydroxy-5-(1H-imidazol-1-yl)-1,6-naphthyridine-7-carboxamide;
N-(3,5-dichlorobenzyl)-8-hydroxy-5-morpholin-4-yl-1,6-naphthyridine-7-carboxamide;
(±)-8-hydroxy-N-[(cis)-3-phenyl-2,3-dihydro-1H-inden-1-yl]-1,6-naphthyridine-7-carboxamide
5-bromo-N-(3,5-dichlorobenzyl)-8-hydroxy-1,6-naphthyridine-7-carboxamide;

N-(benzyl)-8-hydroxy-5-phenyl-1,6-naphthyridine-7-carboxamide;
N-(2,3-dihydro-1H-inden-1-yl)-8-hydroxy-5-phenyl-1,6-naphthyridine-7-carboxamide;
8-hydroxy-N-(1-naphthylmethyl)-5-phenyl-1,6-naphthyridine-7-carboxamide;
N-(2,5-dichlorobenzyl)-8-hydroxy-5-phenyl-1,6-naphthyridine-7-carboxamide;
N-(3-chlorobenzyl)-8-hydroxy-5-phenyl-1,6-naphthyridine-7-carboxamide;
N-[(1S)-2,3-dihydro-1H-inden-1-yl]-8-hydroxy-1,6-naphthyridine-7-carboxamide;
N-(3,5-dichlorobenzyl)-8-hydroxy-5-phenoxy-1,6-naphthyridine-7-carboxamide;
N-(3,5-dichlorobenzyl)-8-hydroxy-5-(4-methylpiperazin-1-yl)-1,6-naphthyridine-7-carboxamide;
5-(4-benzylpiperazin-1-yl)-N-(3,5-dichlorobenzyl)-8-hydroxy-1,6-naphthyridine-7-carboxamide;
N-(3,5-dichlorobenzyl)-5-{4-[2-(formylamino)ethyl]piperazin-1-yl}-8-hydroxy-1,6-naphthyridine-7-carboxamide;
N-(3,5-dichlorobenzyl)-8-hydroxy-5-(4-pyridin-2-ylpiperazin-1-yl)-1,6-naphthyridine-7-carboxamide;
N-(3,5-dichlorobenzyl)-8-hydroxy-5-(4-pyrrolidin-1-ylpiperidin-1-yl)-1,6-naphthyridine-7-carboxamide;
5-anilino-N-(3,5-dichlorobenzyl)-8-hydroxy-1,6-naphthyridine-7-carboxamide;
N-(3,5-dichlorobenzyl)-5-{[3-(formylamino)propyl]amino}-8-hydroxy-1,6-naphthyridine-7-carboxamide;
N-(3,5-dichlorobenzyl)-5-{[2-(dimethylamino)ethyl]amino}-8-hydroxy-1,6-naphthyridine-7-carboxamide;
N-(3,5-dichlorobenzyl)-8-hydroxy-5-[(2-morpholin-4-ylethyl)amino]-1,6-naphthyridine-7-carboxamide;
5-[(1-benzylpiperidin-4-yl)amino]-N-(3,5-dichlorobenzyl)-8-hydroxy-1,6-naphthyridine-7-carboxamide;
N-(3,5-dichlorobenzyl)-5-[[2-(dimethylamino)ethyl](methyl)amino]-8-hydroxy-1,6-naphthyridine-7-carboxamide;
8-Hydroxy-5-phenylsulfanyl-[1,6]naphthyridine-7-carboxylic acid 3,5-dichlorobenzylamide;
5-benzenesulfonyl-8-hydroxy-[1,6]naphthyridine-7-carboxylic acid 3,5-dichlorobenzylamide;
tert-butyl 1-(7-{[(3,5-dichlorobenzyl)amino]carbonyl}-8-hydroxy-1,6-naphthyridin-5-yl)pyrrolidin-3-ylcarbamate;
5-(3-aminopyrrolidin-1-yl)-N-(3,5-dichlorobenzyl)-8-hydroxy-1,6-naphthyridine-7-carboxamide trifluoroacetate;
N-(3,5-dichlorobenzyl)-8-hydroxy-5-(4H-1,2,4-triazol-4-yl)-1,6-naphthyridine-7-carboxamide;
N-(3,5-dichlorobenzyl)-8-hydroxy-5-(1H-1,2,4-triazol-1-yl)-1,6-naphthyridine-7-carboxamide;
N-(3,5-dichlorobenzyl)-8-hydroxy-5-(3-hydroxypyrrolidin-1-yl)-1,6-naphthyridine-7-carboxamide;
5-[3-(acetylamino)pyrrolidin-1-yl]-N-(3,5-dichlorobenzyl)-8-hydroxy-1,6-naphthyridine-7-carboxamide;
N-(3,5-dichlorobenzyl)-5-(4-formylpiperazin-1-yl)-8-hydroxy-1,6-naphthyridine-7-carboxamide;
1-(7-{[(3,5-dichlorobenzyl)amino]carbonyl}-8-hydroxy-1,6-naphthyridin-5-yl)piperazine;
8-Hydroxy-5-(3-hydroxy-prop-1-ynyl)-[1,6]naphthyridine-7-carboxylic acid 3,5-dichloro-benzylamide;
1-(7-{[(3,5-dichlorobenzyl)amino]carbonyl}-8-hydroxy-1,6-naphthyridin-5-yl)-4-(2-oxo-2-pyrrolidin-1-ylethyl)piperazine
8-Hydroxy-5-(3-piperidin-1-yl-prop-1-ynyl)-[1,6]naphthyridine-7-carboxylic acid 3,5-dichlorobenzylamide;
N-(3,5-dichlorobenzyl)-8-hydroxy-5-thiomorpholin-4-yl-1,6-naphthyridine-7-carboxamide;
5-[3-(aminocarbonyl)piperidin-1-yl]-N-(3,5-dichlorobenzyl)-8-hydroxy-1,6-naphthyridine-7-carboxamide;
1-(7-{[(3,5-dichlorobenzyl)amino]carbonyl}-8-hydroxy-1,6-naphthyridin-5-yl)-4-(2-phenylethyl)piperazine;
4-[(7-{[(3,5-dichlorobenzyl)amino]carbonyl}-8-hydroxy-1,6-naphthyridin-5-yl)amino]pyridine;
5-[(cyclopropylmethyl)amino]-N-(3,5-dichlorobenzyl)-8-hydroxy-1,6-naphthyridine-7-carboxamide;
N-(3,5-dichlorobenzyl)-5-{[2-(formylamino)ethyl]amino}-8-hydroxy-1,6-naphthyridine-7-carboxamide;
2-[(7-{[(3,5-dichlorobenzyl)amino]carbonyl}-8-hydroxy-1,6-naphthyridin-5-yl)amino]ethanamine;
N-(3,5-dichlorobenzyl)-8-hydroxy-5-[(2-methoxyethyl)amino]-1,6-naphthyridine-7-carboxamide;
N-(3,5-dichlorobenzyl)-8-hydroxy-5-{[2-(methylthio)ethyl]amino}-1,6-naphthyridine-7-carboxamide;
1-{2-[(7-{[(3,5-dichlorobenzyl)amino]carbonyl}-8-hydroxy-1,6-naphthyridin-5-yl)amino]ethyl}pyrrolidine;
1N-(3,5-dichlorobenzyl)-8-hydroxy-5-pyrrolidin-1-yl-1,6-naphthyridine-7-carboxamide;
3-{2-[(7-{[(3,5-dichlorobenzyl)amino]carbonyl}-8-hydroxy-1,6-naphthyridin-5-yl)amino]ethyl}pyridine;
1-{3-[(7-{[(3,5-dichlorobenzyl)amino]carbonyl}-8-hydroxy-1,6-naphthyridin-5-yl)amino]propyl}-H-imidazoline;
1-{3-[(7-{[(3,5-dichlorobenzyl)amino]carbonyl}-8-hydroxy-1,6-naphthyridin-5-yl)amino]propyl}pyrrolidine;
1-(2-aminoethyl)-4-(7-{[(3,5-dichlorobenzyl)amino]carbonyl}-8-hydroxy-1,6-naphthyridin-5-yl)piperazine;
N-(3,5-dichlorobenzyl)-8-hydroxy-5-[(2-phenoxyethyl)amino]-1,6-naphthyridine-7-carboxamide;
N-(3,5-dichlorobenzyl)-8-hydroxy-5-{[3-(2-oxopyrrolidin-1-yl)propyl]amino}-1,6-naphthyridine-7-carboxamide;
2-[benzyl(7-{[(3,5-dichlorobenzyl)amino]carbonyl}-8-hydroxy-1,6-naphthyridin-5-yl)amino]ethanamine;
1-{3-[(7-{[(3,5-dichlorobenzyl)amino]carbonyl}-8-hydroxy-1,6-naphthyridin-5-yl)amino]propyl}-4-methylpiperazine;
1:1 mixture of 1-(7-{[(3,5-dichlorobenzyl)amino]carbonyl}-8-hydroxy-1,6-naphthyridin-5-yl)-1H-imidazo[4,5-b]pyridine and 3-(7-{[(3,5-dichlorobenzyl)amino]carbonyl}-8-hydroxy-1,6-naphthyridin-5-yl)-3H-imidazo[4,5-b]pyridine;
N-(3,5-dichlorobenzyl)-8-hydroxy-5-{[4-(3-methyl-2-oxoimidazolidin-1-yl)phenyl]amino}-1,6-naphthyridine-7-carboxamide;
N-(3,5-dichlorobenzyl)-8-hydroxy-5-(1,4,6,7-tetrahydro-5H-pyrazolo[4,3-c]pyridin-5-yl)-1,6-naphthyridine-7-carboxamide;
N-(3,5-dichlorobenzyl)-8-hydroxy-5-({[(2R)-5-oxopyrrolidin-2-yl]methyl}amino)-1,6-naphthyridine-7-carboxamide;
N-(3,5-dichlorobenzyl)-8-hydroxy-5-{[(5-oxo-4,5-dihydro-1H-1,2,4-triazol-3-yl)methyl]amino}-1,6-naphthyridine-7-carboxamide;
2-(7-{[(3,5-dichlorobenzyl)amino]carbonyl}-8-hydroxy-1,6-naphthyridin-5-yl)octahydropyrrolo[1,2-a]pyrazine;
N-(3,5-dichlorobenzyl)-8-hydroxy-5-[4-(pyrimidin-2-ylamino)piperidin-1-yl]-1,6-naphthyridine-7-carboxamide
2-{2-[(7-{[(3,5-dichlorobenzyl)amino]carbonyl}-8-hydroxy-1,6-naphthyridin-5-yl)(methyl)amino]ethyl}pyridine;

N-(3,5-dichlorobenzyl)-5-(dimethylamino)-8-hydroxy-1,6-naphthyridine-7-carboxamide;
8-Hydroxy-5-(3-morpholin-4-yl-prop-1-ynyl)-[1,6]naphthyridine-7-carboxylic acid 3,5-dichloro-benzylamide;
N-(3,5-difluorobenzyl)-8-hydroxy-5-(methylsulfonyl)-1,6-naphthyridine-7-carboxamide;
5-cyano-N-(2,3-dimethoxybenzyl)-8-hydroxy-1,6-naphthyridine-7-carboxamide;
N-(3,5-dichlorobenzyl)-8-hydroxy-5-thien-2-yl-1,6-naphthyridine-7-carboxamide;
8-hydroxy-5-phenylsulfanyl-[1,6]naphthyridine-7-carboxylic acid 2-methylsulfanylbenzylamide;
N-(2,3-dimethoxybenzyl)-8-hydroxy-5-(methylsulfonyl)-1,6-naphthyridine-7-carboxamide;
N-(3,5-dichlorobenzyl)-8-hydroxy-5-[(2-hydroxyethyl)amino]-1,6-naphthyridine-7-carboxamide;
N-(3,5-dichlorobenzyl)-8-hydroxy-5-(propylamino)-1,6-naphthyridine-7-carboxamide;
N-(3,5-dichlorobenzyl)-8-hydroxy-5-[(1H-imidazol-4-ylethyl)amino]-1,6-naphthyridine-7-carboxamide;
N-(3,5-dichlorobenzyl)-8-hydroxy-5-[(3-phenylprop-1-yl)amino]-1,6-naphthyridine-7-carboxamide;
N-(3,5-dichlorobenzyl)-8-hydroxy-5-[(3-morpholin-4-ylpropyl)amino]-1,6-naphthyridine-7-carboxamide;
N-(3,5-dichlorobenzyl)-8-hydroxy-5-[4-(pyridin-2-ylmethyl)piperazin-1-yl]-1,6-naphthyridine-7-carboxamide;
N-(3,5-dichlorobenzyl)-8-hydroxy-5-[(2-morpholin-4-yl-2-pyridin-3-ylethyl)amino]-1,6-naphthyridine-7-carboxamide;
N-(2,3-dimethoxybenzyl)-5-{[4-(dimethylamino)phenyl]thio}-8-hydroxy-1,6-naphthyridine-7-carboxamide;
8-hydroxy-6-methyl-[1,6]naphthyridine-7-carboxylic acid 3,5-dichloro-benzylamide;
8-hydroxy-6-methyl-[1,6]naphthyridine-7-carboxylic acid 4-fluoro-benzylamide;
5-bromo-N-(4-fluorobenzyl)-8-hydroxy-1,6-naphthyridine-7-carboxamide;
1-(7-{[(4-fluorobenzyl)amino]carbonyl}-8-hydroxy-1,6-naphthyridin-5-yl)-4-methylpiperazine;
1-(7-{[(4-fluorobenzyl)amino]carbonyl}-8-hydroxy-1,6-naphthyridin-5-yl)piperazine;
5-[[2-(dimethylamino)-2-oxoethyl](methyl)amino]-N-(4-fluorobenzyl)-8-hydroxy-1,6-naphthyridine-7-carboxamide;
N-1-(7-{[(4-fluorobenzyl)amino]carbonyl}-8-hydroxy-1,6-naphthyridin-5-yl)-N-1-,N-2-,N-2-trimethylethanediamide;
N-(4-fluorobenzyl)-5-(2,6-dioxohexahydropyrimidin-4-yl)-8-hydroxy-[1,6]napthyridine-7-carboxamide;
5-(1,3-dimethyl-2,6-dioxohexahydro-4-pyrimidinyl)-N-(4-fluorobenzyl)-8-hydroxy[1,6]-naphthyridine-7-carboxamide;
5-(1-methyl-2,6-dioxohexahydro-4-pyrimidinyl)-N-(4-fluorobenzyl)-8-hydroxy[1,6]-naphthyridine-7-carboxamide;
5-(3-methyl-2,6-dioxohexahydro-4-pyrimidinyl)-N-(4-fluorobenzyl)-8-hydroxy[1,6]-naphthyridine-7-carboxamide;
N-(4-fluorobenzyl)-8-hydroxy-5-(5-oxo-1,4-thiazepan-7-yl)[1,6]naphthyridine-7-carboxamide;
N-(4-fluorobenzyl)-8-hydroxy-5-(1-oxido-5-oxo-1,4-thiazepan-7-yl)-[1,6]naphthyridine-7-carboxamide;
N-(4-fluorobenzyl)-8-hydroxy-5-(1,1-dioxido-5-oxo-1,4-thiazepan-7-yl)[1,6]-naphthyridine-7-carboxamide;
N-(4-fluorobenzyl)-5-{[2-(dimethylamino)-2-oxoethyl]sulfanyl}-8-hydroxy-[1,6]napthyridine-7-carboxamide;
N-(4-fluorobenzyl)-5-[2-(dimethylamino)-2-oxoethoxy]-8-hydroxy-[1,6]naphthyridine-7-carboxamide;
N-(4-fluorobenzyl)-5-{[2-(dimethylamino)-2-oxoethyl](methylsulfonyl)amino}-8-hydroxy-[1,6]naphthyridine-7-carboxamide;
N-(4-fluorobenzyl)-5-[3-(dimethylamino)-3-oxopropyl]-8-hydroxy-[1,6]napthyridine-7-carboxamide;
N-(4-fluorobenzyl)-5-[(1E)-3-(dimethylamino)-3-oxo-1-propenyl]-8-hydroxy-[1,6]napthyridine-7-carboxamide;
N-(4-fluorobenzyl)-5-[2-(3-oxo-1-piperazinyl)ethyl]-8-hydroxy-[1,6]napthyridine-7-carboxamide;
N-(4-fluorobenzyl)-5-[2-(2-oxo-1-imidazolidinyl)ethyl]-8-hydroxy-[1,6]napthyridine-7-carboxamide;
N-(4-fluorobenzyl)-5-[2-(2-oxo-1-piperazinyl)ethyl]-8-hydroxy-[1,6]napthyridine-7-carboxamide;
5-(1,1-dioxido-1,2-thiazinan-2-yl)-N-(4-fluorobenzyl)-8-hydroxy-1,6-naphthyridine-7-carboxamide;
5-(1,1-dioxidoisothiazolidin-2-yl)-N-(4-fluorobenzyl)-8-hydroxy-1,6-naphthyridine-7-carboxamide;
N-(4-fluorobenzyl)-8-hydroxy-5-[methyl(methylsulfonyl)amino]-1,6-naphthyridine-7-carboxamide;
5-[acetyl(methyl)amino]-N-(4-fluorobenzyl)-8-hydroxy-1,6-naphthyridine-7-carboxamide;
5-[[(dimethylamino)carbonyl](methyl)amino]-N-(4-fluorobenzyl)-8-hydroxy-1,6-naphthyridine-7-carboxamide;
N-(4-fluorobenzyl)-6-hydroxy-3-methyl-1-(2-morpholin-4-ylethyl)-2-oxo-2,3-dihydro-1H-pyrimido[4,5,6-de]-1,6-naphthyridine-5-carboxamide;
N-(4-fluorobenzyl)-8-hydroxy-5-thiomorpholin-4-yl-1,6-naphthyridine-7-carboxamide;
5-(1,1-dioxidothiomorpholin-4-yl)-N-(4-fluorobenzyl)-8-hydroxy-1,6-naphthyridine-7-carboxamide;
N-(4-fluorobenzyl)-8-hydroxy-5-(4-methyl-3-oxopiperazin-1-yl)-1,6-naphthyridine-7-carboxamide;
1-(7-{[4-fluorobenzyl)amino]carbonyl}-8-hydroxy-1,6-naphthyridin-5-yl-L-prolinamide;
N-(4-fluorobenzyl)-8-hydroxy-5-(2-oxotetrahydropyrimidin-1(2H)-yl)-1,6-naphthyridine-7-carboxamide;
N-(4-fluorobenzyl)-8-hydroxy-5-(2-oxoimidazolidin-1-yl)-1,6-naphthyridine-7-carboxamide;
N-7-(4-fluorobenzyl)-8-hydroxy-N 5, N 5-dimethyl-1,6-naphthyridine-5,7-dicarboxamide;
N 7-(4-fluorobenzyl)-8-hydroxy-N 5-isopropyl-N 5-methyl-1,6-naphthyridine-5,7-dicarboxamide;
N 7-(4-fluorobenzyl)-8-hydroxy-N 5-(2-morpholin-4-ylethyl)-1,6-naphthyridine-5,7-dicarboxamide;
N 5-[2-(dimethylamino)-2-oxoethyl]-N 7-(4-fluorobenzyl)-8-hydroxy-N 5-methyl-1,6-naphthyridine-5,7-dicarboxamide;
N-(4-fluorobenzyl)-5-(1,1-dioxido-4-oxo-1,2,5-thiadiazepan-2-yl)-8-hydroxy-[1,6]napthyridine-7-carboxamide;
N-(4-fluorobenzyl)-5-(1,1-dioxido-5-methyl-4-oxo-1,2,5-thiadiazepan-2-yl)-8-hydroxy-[1,6]napthyridine-7-carboxamide;
N-(4-fluorobenzyl)-5-(1,1-dioxido-5-ethyl-4-oxo-1,2,5-thiadiazepan-2-yl)-8-hydroxy-[1,6]napthyridine-7-carboxamide;
N-(4-fluorobenzyl)-5-(1,1-dioxido-1,5,2-dithiazepan-2-yl)-8-hydroxy-[1,6]napthyridine-7-carboxamide;
N-(4-fluorobenzyl)-5-(1,1,5,5-tetraoxido-1,5,2-dithiazepan-2-yl)-8-hydroxy-[1,6]napthyridine-7-carboxamide;
N-(4-fluorobenzyl)-5-(1,4-dimethyl-7-oxo-1,4-diazepan-5-yl)-8-hydroxy-[1,6]-napthyridine-7-carboxamide;
N-(4-fluorobenzyl)-5-(1-methyl-7-oxo-1,4-diazepan-5-yl)-8-hydroxy-[1,6]-naphthyridine-7-carboxamide;

N-(4-Fluorobenzyl)-5-(7-oxo-1,4-diazepan-5-yl)-8-hydroxy-[1,6]-napthyridine-7-carboxamide
N-(4-fluorobenzyl)-5-[4-(methylsulfonyl)thiomorpholin-2-yl]-8-hydroxy-[1,6]napthyridine-7-carboxamide;
N-(4-fluorobenzyl)-5-[4-(methylsulfonyl)-1-oxidothiomorpholin-2-yl]-8-hydroxy-[1,6]napthyridine-7-carboxamide;
N-(4-fluorobenzyl)-5-[4-(methylsulfonyl)-1,1-dioxidothiomorpholin-2-yl]-8-hydroxy-[1,6]napthyridine-7-carboxamide;
N-(4-fluorobenzyl)-5-(2-Acetyl-1-methylpyrazolidin-3-yl)-8-hydroxy-[1,6]napthyridine-7-carboxamide;
N-(4-fluorobenzyl)-5-(1,1-dioxido-1,2,5-thiadiazepan-2-yl)-8-hydroxy-[1,6]napthyridine-7-carboxamide;
N-(4-fluorobenzyl)-8-hydroxy-5-[5-(methylsulfonyl)-1,1-dioxido-1,2,5-thiadiazepan-2-yl]-1,6-naphthyridine-7-carboxamide;
N-(4-fluorobenzyl)-8-hydroxy-5(6-methyl-1,1-dioxido-1,2,6-thiadiazinan-2yl)-1,6-naphthyridine-7-carboxamide;
N-(4-fluorobenzyl)-8-hydroxy-5-{methyl [(1-methyl-1H-imidazol-4-yl)sulfonyl]amino}-1,6-naphthyridine-7-carboxamide;
N-[4-fluoro-2-(methylsulfonyl)benzyl]-8-hydroxy-5-{methyl [(1-methyl-1H-imidazol-4-yl)sulfonyl]amino}-1,6-naphthyridine-7-carboxamide;
N-7-[4-fluoro-2-(methylsulfonyl)benzyl]-8-hydroxy-N-5-,N-5-dimethyl-1,6-naphthyridine-5,7-dicarboxamide;
N-[4-fluoro-2-(methylsulfonyl)benzyl]-8-hydroxy-5-(1,1-dioxido-1,2-thiazinan-2-yl)-1,6-naphthyridine-7-carboxamide
N-(2-(methylsulfonyl)benzyl)-5-(1,1-dioxido-1,2-thiazinan-2-yl)-8-hydroxy-1,6-naphthyridine-7-carboxamide;
N-(2-[(dimethylaminosulfonyl]-4-fluorobenzyl)-5-(1,1-dioxido-1,2-thiazinan-2-yl)-8-hydroxy-1,6-naphthyridine-7-carboxamide;
N-(4-fluorobenzyl)-8-hydroxy-5-(1-methyl-5-oxopyrrolidin-3-yl)-1,6-naphthyridine-7-carboxamide;
and pharmaceutically acceptable salts thereof.

In one aspect, the present invention is a compound selected from the group consisting of 1-(7-{[(4-fluorobenzyl)amino]carbonyl}-8-hydroxy-1,6-naphthyridin-5-yl)-4-methylpiperazine;
1-(7-{[(4-fluorobenzyl)amino]carbonyl}-8-hydroxy-1,6-naphthyridin-5-yl)piperazine;
N-(3,5-dichlorobenzyl)-5-(4-formylpiperazin-1-yl)-8-hydroxy-1,6-naphthyridine-7-carboxamide;
N-(3,5-dichlorobenzyl)-5-{4-[2-(formylamino)ethyl]piperazin-1-yl}-8-hydroxy-1,6-naphthyridine-7-carboxamide;
N-(3,5-dichlorobenzyl)-8-hydroxy-5-[4-(pyridin-2-ylmethyl)piperazin-1-yl]-1,6-naphthyridine-7-carboxamide;
1-(7-{[(3,5-dichlorobenzyl)amino]carbonyl}-8-hydroxy-1,6-naphthyridin-5-yl)-4-(2-oxo-2-pyrrolidin-1-ylethyl)piperazine;
1-(7-{[(3,5-dichlorobenzyl)amino]carbonyl}-8-hydroxy-1,6-naphthyridin-5-yl)piperazine;
2-(7-{[(3,5-dichlorobenzyl)amino]carbonyl}-8-hydroxy-1,6-naphthyridin-5-yl)octahydropyrrolo[1,2-a]pyrazine;
N-(3,5-dichlorobenzyl)-8-hydroxy-5-(1,4,6,7-tetrahydro-5H-pyrazolo[4,3-c]pyridin-5-yl)-1,6-naphthyridine-7-carboxamide;
N-(3,5-dichlorobenzyl)-8-hydroxy-5-{[4-(3-methyl-2-oxoimidazolidin-1-yl)phenyl]amino}-1,6-naphthyridine-7-carboxamide;
5-[3-(aminocarbonyl)piperidin-1-yl]-N-(3,5-dichlorobenzyl)-8-hydroxy-1,6-naphthyridine-7-carboxamide;
N-(3,5-dichlorobenzyl)-8-hydroxy-5-(4-pyrrolidin-1-ylpiperidin-1-yl)-1,6-naphthyridine-7-carboxamide;
N-(3,5-dichlorobenzyl)-8-hydroxy-5-[(2-morpholin-4-ylethyl)amino]-1,6-naphthyridine-7-carboxamide;
N-(3,5-dichlorobenzyl)-8-hydroxy-5-(4-methylpiperazin-1-yl)-1,6-naphthyridine-7-carboxamide;
8-hydroxy-6-methyl-[1,6]naphthyridine-7-carboxylic acid 3,5-dichloro-benzylamide;
N-(3,5-dichlorobenzyl)-8-hydroxy-5-[4-(pyrimidin-2-ylamino)piperidin-1-yl]-1,6-naphthyridine-7-carboxamide
N-(3,5-dichlorobenzyl)-8-hydroxy-5-[(3-morpholin-4-ylpropyl)amino]-1,6-naphthyridine-7-carboxamide;
N-(3,5-dichlorobenzyl)-8-hydroxy-5-[(2-morpholin-4-yl-2-pyridin-3-ylethyl)amino]-1,6-naphthyridine-7-carboxamide;
2-{2-[(7-{[(3,5-dichlorobenzyl)amino]carbonyl}-8-hydroxy-1,6-naphthyridin-5-yl)(methyl)amino]ethyl}pyridine;
N-(3,5-dichlorobenzyl)-8-hydroxy-5-(4-pyridin-2-ylpiperazin-1-yl)-1,6-naphthyridine-7-carboxamide;
and pharmaceutically acceptable salts thereof.

In another aspect, the present invention is a compound selected from the group consisting of 5-[[2-(dimethylamino)-2-oxoethyl](methyl)amino]-N-(4-fluorobenzyl)-8-hydroxy-1,6-naphthyridine-7-carboxamide;
N-1-(7-{[(4-fluorobenzyl)amino]carbonyl}-8-hydroxy-1,6-naphthyridin-5-yl)-N-1-,N-2-,N-2-trimethylethanediamide;
N-(4-fluorobenzyl)-5-(2,6-dioxohexahydropyrimidin-4-yl)-8-hydroxy-[1,6]napthyridine-7-carboxamide;
5-(1,3-dimethyl-2,6-dioxohexahydro-4-pyrimidinyl)-N-(4-fluorobenzyl)-8-hydroxy[1,6]-naphthyridine-7-carboxamide;
5-(1-methyl-2,6-dioxohexahydro-4-pyrimidinyl)-N-(4-fluorobenzyl)-8-hydroxy[1,6]-naphthyridine-7-carboxamide;
5-(3-methyl-2,6-dioxohexahydro-4-pyrimidinyl)-N-(4-fluorobenzyl)-8-hydroxy[1,6]-naphthyridine-7-carboxamide;
N-(4-fluorobenzyl)-8-hydroxy-5-(5-oxo-1,4-thiazepan-7-yl)[1,6]naphthyridine-7-carboxamide;
N-(4-fluorobenzyl)-8-hydroxy-5-(1-oxido-5-oxo-1,4-thiazepan-7-yl)-[1,6]naphthyridine-7-carboxamide;
N-(4-fluorobenzyl)-8-hydroxy-5-(1,1-dioxido-5-oxo-1,4-thiazepan-7-yl)[1,6]-naphthyridine-7-carboxamide;
N-(4-fluorobenzyl)-5-{[2-(dimethylamino)-2-oxoethyl]sulfanyl}-8-hydroxy-[1,6]napthyridine-7-carboxamide;
N-(4-fluorobenzyl)-5-[2-(dimethylamino)-2-oxoethoxy]-8-hydroxy-[1,6]napthyridine-7-carboxamide;
N-(4-fluorobenzyl)-5-{[2-(dimethylamino)-2-oxoethyl](methylsulfonyl)amino}-8-hydroxy-[1,6]napthyridine-7-carboxamide;
N-(4-fluorobenzyl)-5-[3-(dimethylamino)-3-oxopropyl]-8-hydroxy-[1,6]napthyridine-7-carboxamide;
N-(4-fluorobenzyl)-5-[(1E)-3-(dimethylamino)-3-oxo-1-propenyl]-8-hydroxy-[1,6]napthyridine-7-carboxamide;
N-(4-fluorobenzyl)-5-[2-(3-oxo-1-piperazinyl)ethyl]-8-hydroxy-[1,6]napthyridine-7-carboxamide;
N-(4-fluorobenzyl)-5-[2-(2-oxo-1-imidazolidinyl)ethyl]-8-hydroxy-[1,6]napthyridine-7-carboxamide;

N-(4-fluorobenzyl)-5-[2-(2-oxo-1-piperazinyl)ethyl]-8-hydroxy-[1,6]napthyridine-7-carboxamide;
5-(1,1-dioxido-1,2-thiazinan-2-yl)-N-(4-fluorobenzyl)-8-hydroxy-1,6-naphthyridine-7-carboxamide;
5-(1,1-dioxidoisothiazolidin-2-yl)-N-(4-fluorobenzyl)-8-hydroxy-1,6-naphthyridine-7-carboxamide;
N-(4-fluorobenzyl)-8-hydroxy-5-[methyl(methylsulfonyl)amino]-1,6-naphthyridine-7-carboxamide;
5-[acetyl(methyl)amino]-N-(4-fluorobenzyl)-8-hydroxy-1,6-naphthyridine-7-carboxamide;
5-[[(dimethylamino)carbonyl](methyl)amino]-N-(4-fluorobenzyl)-8-hydroxy-1,6-naphthyridine-7-carboxamide;
N-(4-fluorobenzyl)-6-hydroxy-3-methyl-1-(2-morpholin-4-ylethyl)-2-oxo-2,3-dihydro-1H-pyrimido[4,5,6-de]-1,6-naphthyridine-5-carboxamide;
N-(4-fluorobenzyl)-8-hydroxy-5-thiomorpholin-4-yl-1,6-naphthyridine-7-carboxamide;
5-(1,1-dioxidothiomorpholin-4-yl)-N-(4-fluorobenzyl)-8-hydroxy-1,6-naphthyridine-7-carboxamide;
N-(4-fluorobenzyl)-8-hydroxy-5-(4-methyl-3-oxopiperazin-1-yl)-1,6-naphthyridine-7-carboxamide;
1-(7-{[(4-fluorobenzyl)amino]carbonyl}-8-hydroxy-1,6-naphthyridin-5-yl-L-prolinamide;
N-(4-fluorobenzyl)-8-hydroxy-5-(2-oxotetrahydropyrimidin-1 (2H)-yl)-1,6-naphthyridine-7-carboxamide;
N-(4-fluorobenzyl)-8-hydroxy-5-(2-oxoimidazolidin-1-yl)-1,6-naphthyridine-7-carboxamide;
N-7-(4-fluorobenzyl)-8-hydroxy-N 5,N 5-dimethyl-1,6-naphthyridine-5,7-dicarboxamide;
N 7-(4-fluorobenzyl)-8-hydroxy-N 5-isopropyl-N 5-methyl-1,6-naphthyridine-5,7-dicarboxamide;
N 7-(4-fluorobenzyl)-8-hydroxy-N 5-(2-morpholin-4-ylethyl)-1,6-naphthyridine-5,7-dicarboxamide;
N 5-[2-(dimethylamino)-2-oxoethyl]-N 7-(4-fluorobenzyl)-8-hydroxy-N 5-methyl-1,6-naphthyridine-5,7-dicarboxamide;
N-(4-fluorobenzyl)-5-(1,1-dioxido-4-oxo-1,2,5-thiadiazepan-2-yl)-8-hydroxy-[1,6]napthyridine-7-carboxamide;
and pharmaceutically acceptable salts thereof.

In still another aspect, the present invention is a compound selected from the group consisting of N-(4-fluorobenzyl)-5-(1,1-dioxido-5-methyl-4-oxo-1,2,5-thiadiazepan-2-yl)-8-hydroxy-[1,6]napthyridine-7-carboxamide;
N-(4-fluorobenzyl)-5-(1,1-dioxido-5-ethyl-4-oxo-1,2,5-thiadiazepan-2-yl)-8-hydroxy-[1,6]napthyridine-7-carboxamide;
N-(4-fluorobenzyl)-5-(1,1-dioxido-1,5,2-dithiazepan-2-yl)-8-hydroxy-[1,6]napthyridine-7-carboxamide;
N-(4-fluorobenzyl)-5-(1,1,5,5-tetraoxido-1,5,2-dithiazepan-2-yl)-8-hydroxy-[1,6]napthyridine-7-carboxamide;
N-(4-fluorobenzyl)-5-(1,4-dimethyl-7-oxo-1,4-diazepan-5-yl)-8-hydroxy-[1,6]-napthyridine-7-carboxamide;
N-(4-fluorobenzyl)-5-(1-methyl-7-oxo-1,4-diazepan-5-yl)-8-hydroxy-[1,6]-napthyridine-7-carboxamide;
N-(4-Fluorobenzyl)-5-(7-oxo-1,4-diazepan-5-yl)-8-hydroxy-[1,6]-napthyridine-7-carboxamide
N-(4-fluorobenzyl)-5-[4-(methylsulfonyl)thiomorpholin-2-yl]-8-hydroxy-[1,6]napthyridine-7-carboxamide;
N-(4-fluorobenzyl)-5-[4-(methylsulfonyl)-1-oxidothiomorpholin-2-yl]-8-hydroxy-[1,6]napthyridine-7-carboxamide;
N-(4-fluorobenzyl)-5-[4-(methylsulfonyl)-1,1-dioxidothiomorpholin-2-yl]-8-hydroxy-[1,6]napthyridine-7-carboxamide;
N-(4-fluorobenzyl)-5-(2-Acetyl-1-methylpyrazolidin-3-yl)-8-hydroxy-[1,6]napthyridine-7-carboxamide;
N-(4-fluorobenzyl)-5-(1,1-dioxido-1,2,5-thiadiazepan-2-yl)-8-hydroxy-[1,6]napthyridine-7-carboxamide;
N-(4-fluorobenzyl)-8-hydroxy-5-[5-(methylsulfonyl)-1,1-dioxido-1,2,5-thiadiazepan-2-yl]-1,6-naphthyridine-7-carboxamide;
N-(4-fluorobenzyl)-8-hydroxy-5(6-methyl-1,1-dioxido-1,2,6-thiadiazinan-2yl)-1,6-naphthyridine-7-carboxamide;
N-(4-fluorobenzyl)-8-hydroxy-5-{methyl [(1-methyl-1H-imidazol-4-yl)sulfonyl]amino}-1,6-naphthyridine-7-carboxamide;
N-[4-fluoro-2-(methylsulfonyl)benzyl]-8-hydroxy-5-{methyl [(1-methyl-1H-imidazol-4-yl)sulfonyl]amino}-1,6-naphthyridine-7-carboxamide;
N-7-[4-fluoro-2-(methylsulfonyl)benzyl]-8-hydroxy-N-5-, N-5-dimethyl-1,6-naphthyridine-5,7-dicarboxamide;
N-[4-fluoro-2-(methylsulfonyl)benzyl]-8-hydroxy-5-(1,1-dioxido-1,2-thiazinan-2-yl)-1,6-naphthyridine-7-carboxamide
N-(2-(methylsulfonyl)benzyl)-5-(1,1-dioxido-1,2-thiazinan-2-yl)-8-hydroxy-1,6-naphthyridine-7-carboxamide;
N-(2-[(dimethylaminosulfonyl]-4-fluorobenzyl)-5-(1,1-dioxido-1,2-thiazinan-2-yl)-8-hydroxy-1,6-naphthyridine-7-carboxamide;
N-(4-fluorobenzyl)-8-hydroxy-5-(1-methyl-5-oxopyrrolidin-3-yl)-1,6-naphthyridine-7-carboxamide;
and pharmaceutically acceptable salts thereof.

Other embodiments of the present invention include the following:

(a) A pharmaceutical composition comprising a compound of Formula (I) and a pharmaceutically acceptable carrier.

(b) The pharmaceutical composition of (a), further comprising at least one antiviral selected from the group consisting of HIV protease inhibitors, non-nucleoside HIV reverse transcriptase inhibitors, and nucleoside HIV reverse transcriptase inhibitors.

(c) A method of inhibiting HIV integrase in a subject in need thereof which comprises administering to the subject a therapeutically effective amount of a compound of Formula (I).

(d) A method of preventing or treating infection by HIV in a subject in need thereof which comprises administering to the subject a therapeutically effective amount of a compound of Formula (I).

(e) The method of (d), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(f) A method of preventing, treating or delaying the onset of AIDS in a subject in need thereof which comprises administering to the subject a therapeutically effective amount of a compound of Formula (I).

(g) The method of (f), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (h) A method of inhibiting HIV integrase in a subject in need thereof which comprises administering to the subject a therapeutically effective amount of the composition of (a) or (b).

(i) A method of preventing or treating infection by HIV in a subject in need thereof which comprises administering to the subject a therapeutically effective amount of the composition of (a) or (b).

(j) A method of preventing, treating or delaying the onset of AIDS in a subject in need thereof which comprises administering to the subject a therapeutically effective amount of the composition of (a) or (b).

Still other embodiments of the present invention include the following:

(k) A pharmaceutical composition which comprises the product prepared by combining (e.g., mixing) an effective amount of a compound of Formula (I) and a pharmaceutically acceptable carrier.

(l) A combination useful for inhibiting HIV integrase, for treating or preventing infection by HIV, or for preventing, treating or delaying the onset of AIDS, which is a therapeutically effective amount of a compound of Formula (I) and a therapeutically effective amount of an HIV infection/AIDS treatment agent selected from the group consisting of HIV/AIDS antiviral agents, immunomodulators, and anti-infective agents.

(m) The combination of (l), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

Additional embodiments of the invention include the pharmaceutical compositions and methods set forth in (a)–(j) above and the compositions and combinations set forth in (k)–(m), wherein the compound employed therein is a compound of one of the embodiments, classes, sub-classes, or aspects of compounds described above. In all of these embodiments, the compound may optionally be used in the form of a pharmaceutically acceptable salt.

The present invention also includes use of a compound of Formula (I-A):

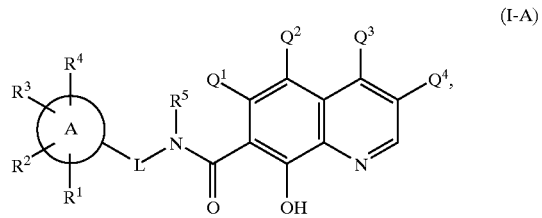

(I-A)

or a pharmaceutically acceptable salt thereof, for inhibiting HIV integrase, for preventing or treating infection by HIV or for preventing, treating or delaying the onset of AIDS in a subject in need thereof; wherein A, $R^1$, $R^2$, $R^3$, $R^4$, $R^5$, L, $Q^1$, $Q^2$, $Q^3$, and $Q^4$ are each independently as originally defined above or as defined in any of the foregoing embodiments, classes, sub-classes, or aspects. In one aspect, the compound of Formula (I-A) is selected from the group consisting of: benzyl 8-hydroxyquinoline-7-carboxamide; 1-methyl-3-phenylpropyl 8-hydroxyquinoline-7-carboxamide; 2-phenylcyclopropyl 8-hydroxyquinoline-7-carboxamide; 1-indanyl 8-hydroxyquinoline-7-carboxamide; N-[(2E)-3-phenyl-2-propenyl]8-hydroxyquinoline-7-carboxamide; benzyl 8-hydroxyquinoline-7-carboxamide; and pharmaceutically acceptable salts thereof.

The present invention also include embodiments for compounds of Formula (I-A) analogous to embodiments (a)–(m) for compounds of Formula (I).

As used herein, the term "$C_{1-6}$ alkyl" (or "$C_1$–$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "$C_0$" as employed in expressions such as "$C_{0-6}$ alkyl" means a direct covalent bond. Similarly, when an integer defining the presence of a certain number of ring atoms in a cyclic group is equal to zero, it means that the ring atoms adjacent thereto in the cyclic group are connected directly by a bond. For example, when L is

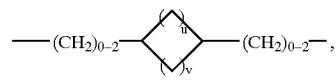

wherein u and v are each integers having a value from 0 to 4, provided that the sum of u+v is 1, 2, 3 or 4, L has the following structure when u is 1 and v is zero:

The term "$C_{2-5}$ alkenyl" (or "$C_2$–$C_5$ alkenyl") means linear or branched chain alkenyl groups having from 2 to 5 carbon atoms and includes all of the pentenyl isomers as well as 1-butenyl, 2-butenyl, 3-butenyl, isobutenyl, 1-propenyl, 2-propenyl, and ethenyl (or vinyl). Similar terms such as "$C_{2-3}$ alkenyl" have an analogous meaning.

The term "$C_{2-5}$ alkynyl" (or "$C_2$–$C_5$ alkynyl") means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

The term "$C_{3-7}$ cycloalkyl" (or "$C_3$–$C_7$ cycloalkyl") means a cyclic ring of an alkane having three to seven total carbon atoms (i.e., cyclopropyl, cyclobutyl, cyclopentyl, cyclohexyl, or cycloheptyl). The term "$C_{3-6}$ cycloalkyl" refers to a cyclic ring selected from cyclopropyl, cyclobutyl, cyclopentyl, and cyclohexyl. Terms such as "$C_3$–$C_5$ cycloalkyl" have an analogous meaning.

The term "halogen" (or "halo") refers to fluorine, chlorine, bromine and iodine (alternatively, fluoro, chloro, bromo, and iodo).

The term "thio" (also referred to as "thioxo") means divalent sulfur; i.e., =S.

The term "$C_{1-6}$ haloalkyl" (which may alternatively be referred to as "$C_1$–$C_6$ haloalkyl" or "halogenated $C_1$–$C_6$ alkyl") means a $C_1$ to $C_6$ linear or branched alkyl group as defined above with one or more halogen substituents. The term "$C_{1-4}$ haloalkyl" has an analogous meaning.

The term "$C_{1-6}$ fluoroalkyl" (which may alternatively be referred to as "$C_1$–$C_6$ fluoroalkyl" or "fluorinated $C_1$–$C_6$ alkyl") means a $C_1$ to $C_6$ linear or branched alkyl group as defined above with one or more fluorine substituents. The term "$C_{1-4}$ fluoroalkyl" (or "$C_1$–$C_4$ fluoroalkyl" or "fluorinated $C_1$–$C_4$ alkyl") has an analogous meaning. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "carbocycle" (and variations thereof such as "carbocyclic" or "carbocyclyl") as used herein broadly refers to a $C_3$ to $C_8$ monocyclic, saturated or unsaturated ring or a $C_7$ to $C_{12}$ bicyclic ring system in which the rings are independent or fused and in which each ring is saturated or unsaturated. The carbocycle may be attached at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A subset of the fused bicyclic carbocycles are those bicyclic carbocycles in which one ring is a benzene ring and the other ring is saturated or unsaturated, with attachment via any carbon atom that results in a stable compound. Representative examples of this subset include the following:

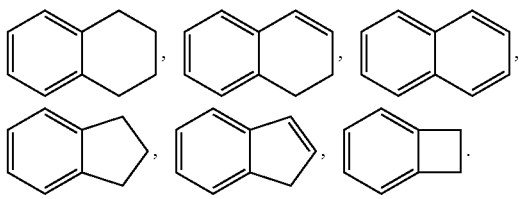

As used herein, the term "fused carbocyclic ring system" refers to a carbocycle as defined above which is fused to a phenyl ring. Representative examples include:

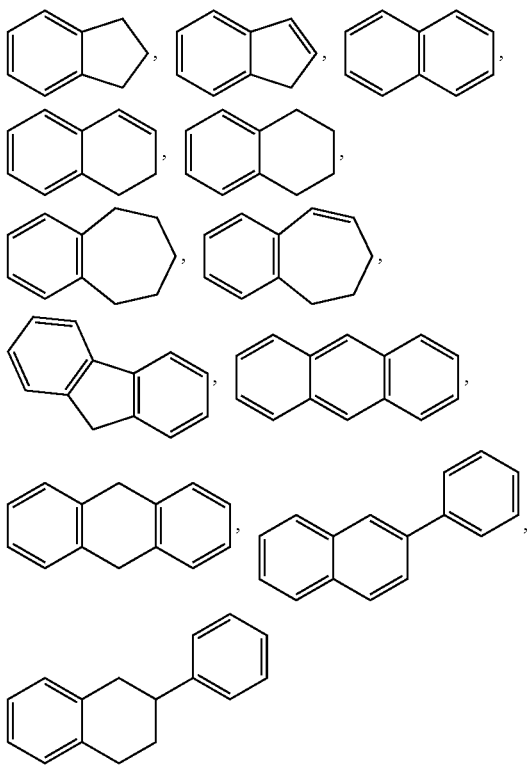

The term "aryl" refers to aromatic mono- and polycarbocyclic ring systems, wherein the individual carbocyclic rings in the polyring systems may be fused or attached to each other via a single bond. Suitable aryl groups include, but are not limited to, phenyl, naphthyl, and biphenylenyl.

The term "heterocycle" (and variations thereof such as "heterocyclic" or "heterocyclyl") broadly refers to a 4- to 8-membered monocyclic ring system, 7- to 12-membered bicyclic ring system, or an 11 to 16-membered tricyclic ring system, any ring of which is saturated or unsaturated, and which consists of carbon atoms and one or more heteroatoms selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results. Representative examples of heterocyclics include piperidinyl, piperazinyl, azepinyl, pyrrolyl, pyrrolidinyl, pyrazolyl, pyrazolidinyl, imidazolyl, imidazolidinyl, triazolyl, tetrazolyl, imidazolinyl, pyridyl (or pyridinyl), pyrazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, quinoxazolinyl, isothiazolidinyl, quinolinyl, isoquinolinyl, benzimidazolyl, thiadazolyl, benzopyranyl, benzothiazolyl, benzoazolyl, furyl (or furanyl), tetrahydrofuryl (or tetrahydrofuranyl), tetrahydropuranyl, thienyl (alternatively thiophenyl), benzothiophenyl, oxadiazolyl, and benzo-1,3-dioxacyclopentyl (alternatively, 1,3-benzodioxolyl). Representative examples of heterocyclics also include tetrahydrothienyl, tetrahydrodioxothienyl, thiadiazinanyl, dioxothiadiazinanyl, thiazinanyl, dioxothiazinanyl, dioxothiazolidinyl, and isodioxothiazolidinyl. Representative examples of heterocyclics also include the following bicyclics: indolyl, benzotriazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinoxalinyl, quinazolinyl, cinnolinyl, chromanyl, and isochromanyl. Additional representative examples of bicyclics include the following: phthalazinyl, purinyl, 1,6-naphthyridinyl, 1,8-napthyridinyl, dihydroindolyl, dihydroisoindolyl, tetrahydroquinolyl, tetrahydroisoquinolyl, imidazo[1,2-a]pyrimidinyl, 2,3-dihydroimidazo[2,1-b][1,3]thiazolyl, benzazepinyl, dihydrobenazepinyl, benzodiazepinyl, dihydrobenzodiazepinyl, and tetrahydrobenzodiazepinyl. Representative examples of heterocyclics also include the following tricyclics: phenothiazinyl, carbazolyl, beta-carbolinyl, tetrahydro-beta-carbolinyl, acridinyl, phenazinyl, and phenoxazinyl.

Representative examples of heterocyclics also include the following saturated monocyclics: hexahydropyrimidinyl, thiazinanyl (e.g., 1,2-thiazinanyl, alternatively named tetrahydro-1,2-thiazinyl), thiazepanyl (e.g., 1,4-thiazepanyl, alternatively named hexahydro-1,4-thiazepinyl), azepanyl (alternatively hexahydroazepinyl), thiadiazepanyl (e.g., 1,2,5-thiadiazepanyl), dithiazepanyl (e.g., 1,5,2,-dithiazepanyl), diazepanyl (e.g., 1,4-diazepanyl), and thiadiazinanyl (e.g., 1,2,6-thiadiazinanyl).

A representative unsaturated heterocycle is

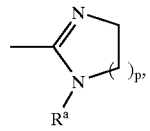

wherein p is an integer from zero to 4 and $R^a$ is as defined above, and wherein each ring carbon is optionally and independently substituted with —$C_{1-4}$ alkyl.

Representative examples of heterocyclics also include the following bicyclics: hexahydropyrazolo[4,3-c]pyridinyl (e.g., 3a,4,5,6,7,7a-hexahydro-1H-pyrazolo[4,3c]pyridinyl), hexahydropurinyl (e.g., 2,3,4,5,6,7-hexahydro-1H-purinyl), hexahydrooxazolo[3,4a]pyrazinyl, and 1,2,3,4-tetrahydro-1,8-naphthyridinyl.

Fused ring heterocycles form a subset of the heterocycles as defined above; e.g., the term "fused bicyclic heterocycle" refers to a heteroatom-containing bicyclic ring system as defined in the preceding paragraph in which two adjacent atoms are shared by both rings. A subset of the fused bicyclic heterocycles is the fused bicyclic heterocycle containing carbon atoms and one or more heteroatoms selected from nitrogen, oxygen and sulfur, wherein one ring is a benzene ring and the other is a saturated or unsaturated heteroatom-containing ring. Representative examples of this subset include, but are not limited to, the following:

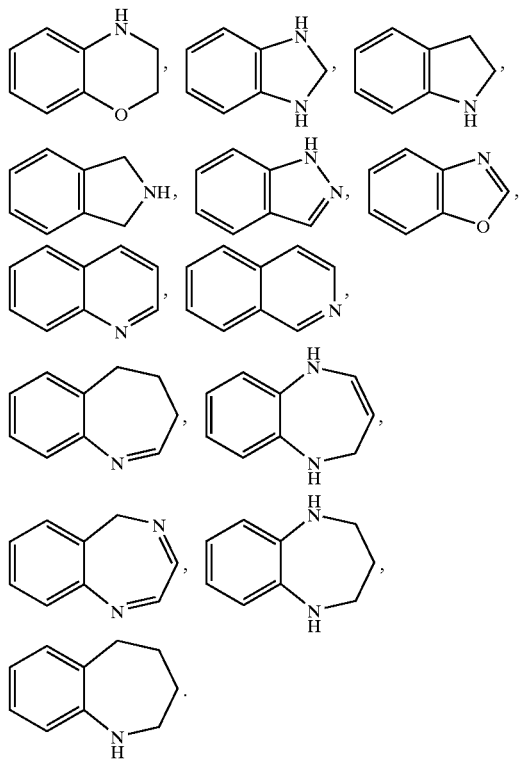

The term "heteromonocycle" (and variations thereof such as "heteromonocyclyl" or "heteromonocyclic") refers to a 4- to 8-membered monocyclic ring which is saturated or unsaturated, and which consists of carbon atoms and one or more heteroatoms selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure. Representative examples of monoheterocycles are disclosed above.

Heteroaromatics form another subset of the heterocycles as defined above; i.e., the term "heteroaromatic" (alternatively "heteroaryl") generally refers to a heterocycle as defined above in which the ring system (whether mono- or poly-cyclic) is an aromatic ring system. The term "heteroaromatic ring" refers to a monocyclic heterocycle as defined above which is an aromatic heterocycle. Representative examples of heteroaromatics include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Unless expressly set forth to the contrary, an "unsaturated" ring is a partially or fully unsaturated ring. For example, an "unsaturated monocyclic $C_6$ carbocycle" refers to cyclohexene, cyclohexadiene, and benzene.

The present invention includes pharmaceutical compositions useful for inhibiting HIV integrase, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. Additionally, the present invention is directed to a pharmaceutical composition comprising a therapeutically effective amount of a compound of the present invention in combination with a therapeutically effective amount of an agent for treating HIV infection or AIDS selected from:

(1) an antiviral agent useful for treating or preventing HIV infection or for treating AIDS (also referred to herein as an HIV/AIDS antiviral agent),
(2) an anti-infective agent, and
(3) an immunomodulator.

The present invention also includes a compound of the present invention for use in (a) inhibiting HIV protease, (b) preventing or treating infection by HIV, or (c) preventing, treating or delaying the onset of AIDS or ARC. The present invention also includes the use of a compound of the present invention as described above as a medicament for (a) inhibiting HIV integrase, (b) preventing or treating infection by HIV, or (c) preventing, treating or delaying the onset of AIDS or ARC. The present invention further includes the use of any of the HIV integrase inhibiting compounds of the present invention as described above in combination with one or more HIV/AIDS treatment agents selected from an HIV/AIDS antiviral agent, an anti-infective agent, and an immunomodulator as a medicament for (a) inhibiting HIV integrase, (b) preventing or treating infection by HIV, or (c) preventing, treating or delaying the onset of AIDS or ARC, said medicament comprising an effective amount of the HIV integrase inhibitor compound and an effective amount of the one or more treatment agents.

The present invention also includes the use of a compound of the present invention as described above in the preparation of a medicament for (a) inhibiting HIV integrase, (b) preventing or treating infection by HIV, or (c) preventing, treating or delaying the onset of AIDS or ARC.

The present invention further includes the use of any of the HIV integrase inhibiting compounds of the present invention as described above in combination with one or more HIV/AIDS treatment agents selected from an HIV/AIDS antiviral agent, an anti-infective agent, and an immunomodulator for the manufacture of a medicament for (a) inhibiting HIV integrase, (b) preventing or treating infection by HIV, or (c) preventing, treating or delaying the onset of AIDS or ARC, said medicament comprising an effective amount of the HIV integrase inhibitor compound and an effective amount of the one or more treatment agents.

The compounds of the present invention may have asymmetric centers and may occur, except when specifically noted, as mixtures of stereoisomers or as individual diastereomers, or enantiomers, with all isomeric forms being included in the present invention.

When any variable (e.g., $R^a$, $R^b$, $R^c$, $R^k$, etc.) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "phenyl ring, unsubstituted or substituted with from 1 to 5 substituents . . . ") includes mono- and poly-substitution by a named substituent to the extent such single and multiple substitution is chemically allowed. For example, a carbocycle or heterocycle substituted with more than one substituent can have multiple substituents on the same ring atom to the extent it is chemically permitted. A ring sulfur atom in a saturated heterocycle can, for example, typically be substituted with 1 (—S(=O)—) or 2 oxo groups (—SO₂—).

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The present invention also provides for the use of a compound of Formula (I) or (I-A) to make a pharmaceutical composition useful for inhibiting HIV integrase and in the treatment of AIDS or ARC.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylene-diamine, chloroprocaine, diethanolamine, procaine, N-benzylphenethyl-amine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The term "administration" and variants thereof (e.g., "administering" a compound) in reference to a compound of the invention each mean providing the compound or a prodrug of the compound to the individual in need of treatment. When a compound of the invention or prodrug thereof is provided in combination with one or more other active agents (e.g., antiviral agents useful for treating HIV infection or AIDS), "administration" and its variants are each understood to include concurrent and sequential provision of the compound or prodrug thereof and other agents.

Thus, in accordance with the present invention there is further provided a method of treating and a pharmaceutical composition for treating HIV infection and AIDS. The treatment involves administering to a subject in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant the carrier, diluent or excipient must be compatible with the other ingredients of the formulation and not deleterious to the recipient thereof.

The term "subject," (alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. When the active compound (i.e., active ingredient) is administered as the salt, references to the amount of active ingredient are to the free acid or free base form of the compound.

These pharmaceutical compositions may be in the form of orally-administrable suspensions or tablets or capsules, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 0.1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of HIV infection or AIDS. For example, the compounds of this invention may be effectively administered, whether at periods of pre-exposure and/or post-exposure, in combination with effective amounts of the HIV/AIDS antivirals, imunomodulators, antiinfectives, or vaccines useful for treating HIV infection or AIDS, such as those in the following Table.

| Drug Name | Manufacturer | Indication |
|---|---|---|
| ANTIVIRALS | | |
| Amprenavir 141 W94 GW 141 | Glaxo Wellcome | HIV infection, AIDS, ARC (protease inhibitor) |
| Abacavir GW 1592 1592U89 | Glaxo Welcome | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL, HIV positive, AIDS |
| Alpha Interferon | Glaxo Wellcome | Kaposi's sarcoma, HIV, in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |

-continued

| Drug Name | Manufacturer | Indication |
|---|---|---|
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| mozenavir (DMP-450) | AVID (Camden, NJ) | HIV infection, AIDS, ARC (protease inhibitor) |
| EL10 | Elan Corp, PLC (Gainesville, GA) | HIV infection |
| Efavirenz (DMP 266) (−) 6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |

-continued

| Drug Name | Manufacturer | Indication |
| --- | --- | --- |
| Ritonavir (ABT-538) | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma in combination with other therapies (reverse transcriptase inhibitor) |
| ABT-378; Lopinavir | Abbott | HIV infection, AIDS, ARC (protease inhibitor) |
| ABT-378/r; contains lopinavir and ritonavir; Kaletra | Abbott | HIV infection, AIDS, ARC (protease inhibitor) |
| JE2147/AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infection, AIDS, ARC (fusion inhibitor) |
| atazanavir (BMS 232632) | Bristol-Myers-Squibb | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |
| DPC 681 & DPC 684 | DuPont | HIV infection, AIDS, ARC (protease inhibitors) |
| DPC 961 & DPC 083 | DuPont | HIV infection AIDS, ARC (nonnucleoside reverse transcriptase inhibitors) |
| Trizivir (contains abacavir, lamivudine, and zidovudine) | GlaxoSmithKline | HIV infection, AIDS, ARC (reverse transcriptase inhibitors) |
| tipranavir (PNU-140690) | Boehringer Ingeiheim (purchased from Pharmacia & Upjohn) | HIV infection, AIDS, ARC (protease inhibitor) |
| tenofovir disoproxil fumarate | Gilead | HIV infection, AIDS, ARC (reverse transcriptase inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4 + cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte | Hoeschst-Roussel | AIDS |

-continued

| Drug Name | Manufacturer | Indication |
|---|---|---|
| Macrophage Colony Stimulating Factor | Immunex | |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK & F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Omidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |
| Intraconazole-R51211 | Janssen Pharm. | histoplasmosis; cryptococcal meningitis |
| Trimetrexate | Warner-Lambert | PCP |

-continued

| Drug Name | Manufacturer | Indication |
|---|---|---|
| | OTHER | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of the compounds of this invention with HIV/AIDS antivirals, immunomodulators, anti-infectives or vaccines is not limited to the list in the above Table, but includes in principle any combination with any pharmaceutical composition useful for the treatment of HIV infection or AIDS. When employed in combination with the compounds of the invention, the HIV/AIDS antivirals and other agents are typically employed in their conventional dosage ranges and regimens as reported in the art, including the dosages described in the *Physicians' Desk Reference*, 54th edition, Medical Economics Company, 2000. The dosage ranges for a compound of the invention in these combinations are the same as those set forth above just before the Table.

Preferred combinations are simultaneous or sequential treatments of a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is the sulfate salt of indinavir, which is N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Still another preferred protease inhibitor is Compound A, which is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)piperazinyl))pentaneamide, preferably administered as the sulfate salt. Compound A can be prepared as described in U.S. Pat. No. 5,646,148. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include a compound of the present invention with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

Another preferred combination is a compound of the present invention with indinavir and Compound A and optionally with one or more of efavirenz, AZT, 3TC, ddI and ddC. In one embodiment of this combination, the weight ratio of indinavir to Compound A is from about 1:1 to about 1:2, wherein the amount of indinavir employed is in the range of from about 200 to about 1000 mg. Indinavir and Compound A can be administered concurrently or sequentially in either order from one to three times per day.

In such combinations the compound of the present invention and other active agents may be administered together or separately. In addition, the administration of one agent may be prior to, concurrent to, or subsequent to the administration of other agent(s).

Abbreviations used in the instant specification, particularly the Schemes and Examples, include the following:
Ac=acetyl
BOP=benzotriazol-1-yloxytris-(dimethylamino) phosphonium hexafluorophosphate
DBU=1,8-diazabicyclo[5.4.0]undec-7-ene
DEA=diethylamine
DEAD=diethylazodicarboxylate
DMF=N,N-dimethylformamide
DMPU=1,3-dimethyl-3,4,5,6-tetrahydro-2(1H)-pyrimidinone
DMSO=dimethylsulfoxide
EDC=1-ethyl-3-(3-dimethylaminopropyl) carbodiimide
EDTA=ethylenediaminetetraacetic acid
ES MS=electrospray mass spectrometry
Et=ethyl
EtOAc=ethyl acetate
EtOH=ethanol
FAB HRMS=fast atom bombardment high resolution mass spectroscopy
FAB MS=fast atom bombardment mass spectroscopy
HOBt=1-hydroxy benzotriazole hydrate
HPLC=high performance liquid chromatography
i-Pr=isopropyl
Me=methyl
MsCl=methanesulfonyl chloride (or mesyl chloride)
NBS=N-bromosuccinimide
NIS=N-iodosuccinimide
NMR=nuclear magnetic resonance
Ph=phenyl
PMBCl=p-methoxybenzyl chloride
rt and RT=room temperature TFA=trifluoroacetic acid
THF=tetrahydrofuran The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The compounds of the present invention can be prepared by the coupling of suitable (poly)azanaphthenyl carboxylic acids (or acid derivatives such as acid halides or esters) with the appropriate amines, as represented by the following general scheme:

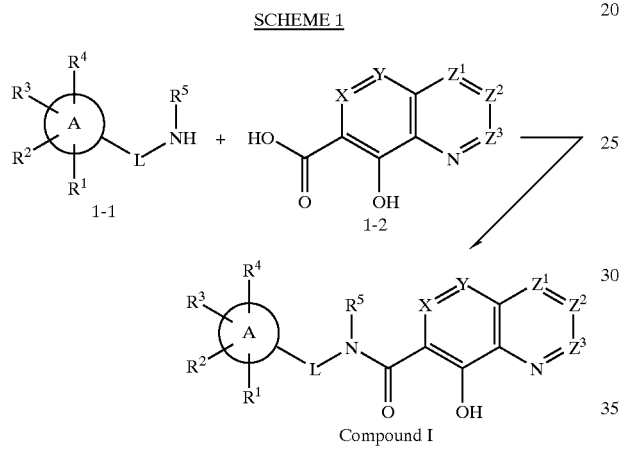

Methods for coupling carboxylic acids with amines to form carboxamides are well known in the art. Suitable methods are described, for example, in Jerry March, *Advanced Organic Chemistry*, 3rd edition, John Wiley & Sons, 1985, pp. 370–376. Amines of formula 1-1 can be prepared using the methods described in Richard Larock, *Comprehensive Organic Transformations*, VCH Publishers Inc, 1989, pp 385–438, or routine variations thereof. Azanaphthenyl and polyazanaphthenyl carboxylic acids of formula 1-2 can be prepared using methods described in Ochiai et al., *Chem. Ber.* 1937, 70: 2018, 2023; Albert et al., *J. Chem. Soc.* 1952, 4985, 4991; and Barlin et al., *Aust. J. Chem.* 1990, 43: 1175–1181; or routine variations thereof. Schemes 2–16 below illustrate and expand upon the chemistry portrayed in Scheme 1.

In Scheme 2, following the procedure set forth in Ornstein et al., *J. Med. Chem.* 1989, 32: 827–833, a cyclic anhydride such as quinolinic anhydride (i.e., $Z^1=Z^2=Z^3=CH$ in 2-1) can be opened with isopropanol to provide mono acid 2-2, which can be converted to the corresponding acyl chloride 2-3 (e.g., by refluxing thionyl chloride). Acyl chloride 2-3 can then be reduced (e.g., with $NaBH_4$ or $LiBH_4$) to the corresponding alcohol 2-4, which can be converted to the corresponding bromide through the action of bromine in the presence of triphenylphosphine. Alkylation of the bromide with the sodium anion of phenylsulfonamide 2-5 in a polar aprotic solvent like DMF can provide sulfonamide 2-6, which can be treated with a base (e.g., alkali metal alkoxide such as sodium methoxide) to provide the bicyclic ester 2-7 via a Dieckmann cyclization. Saponification of the ester (e.g., with aqueous NaOH at reflux) will afford the acid 2-8. The acid 2-8 can be activated with triphosgene and coupled with a variety of amines to provide the compounds of the invention 2-9.

The starting anhydrides of formula 2-1 can be prepared via methods described in Philips et al., *Justus Liebigs Ann. Chem.* 1895, 288: 2535; Bemthsen et al., *Chem.Ber.* 1887; 20: 1209; Bly et al., *J. Org. Chem.* 1964, 29: 2128–2135; and Krapcho et al., *J. Heterocycl. Chem.* 1993, 30: 1597–1606; or routine variations thereof.

SCHEME 2

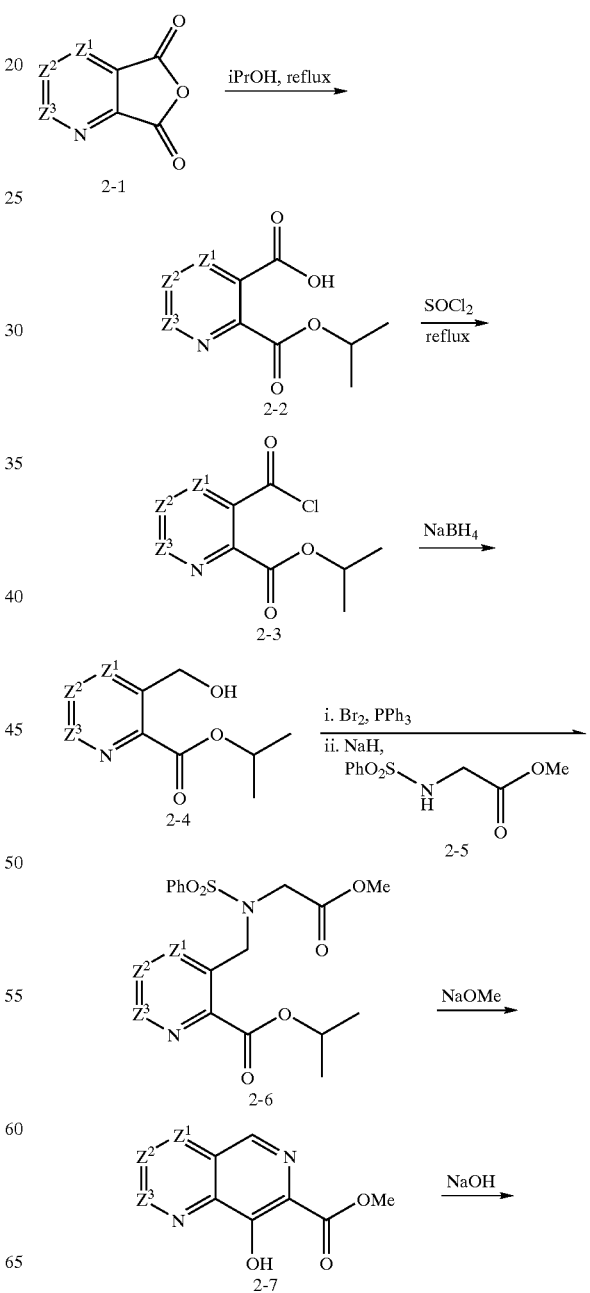

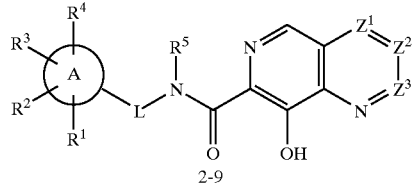

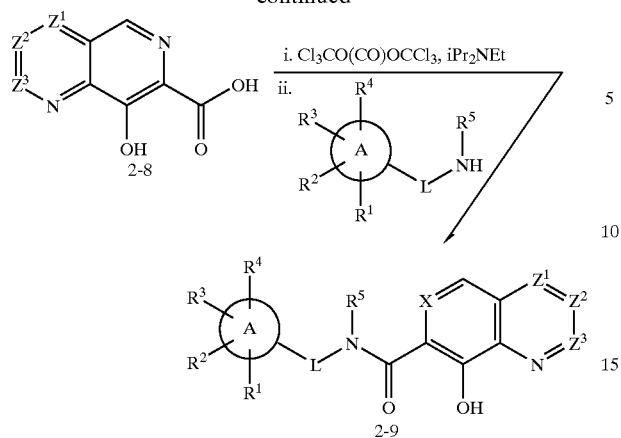

Scheme 3 depicts an alternative synthesis in which alcohol 2-4 can undergo the Mitsunobu reaction with the phenylsulfonamide of glycine methyl ester to provide 3-1. The sulfonamide 3-1 can again be elaborated to provide the acid 2-8, which can be coupled with a variety of amines using standard reagents to provide the compounds of the invention 2-9.

Scheme 3A depicts (for a napthyridine core) a variation of the synthesis shown in Scheme 3, wherein the acid 3A-2 is reacted with ethyl chloroformate to form the mixed anhydride 3A-3, which is reduced to alcohol 3A-4.

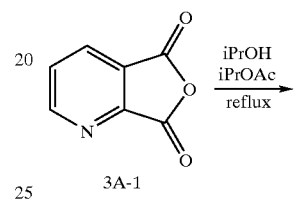

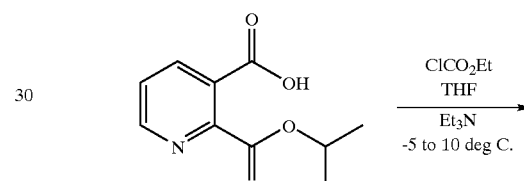

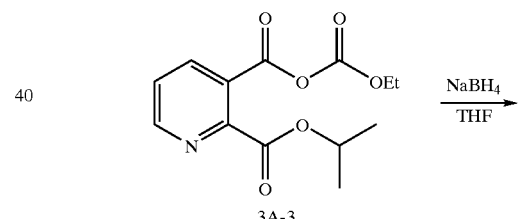

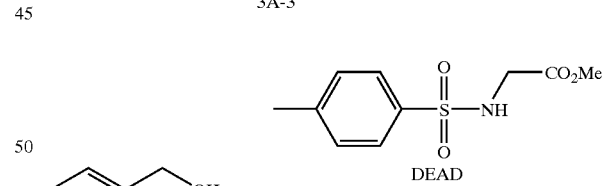

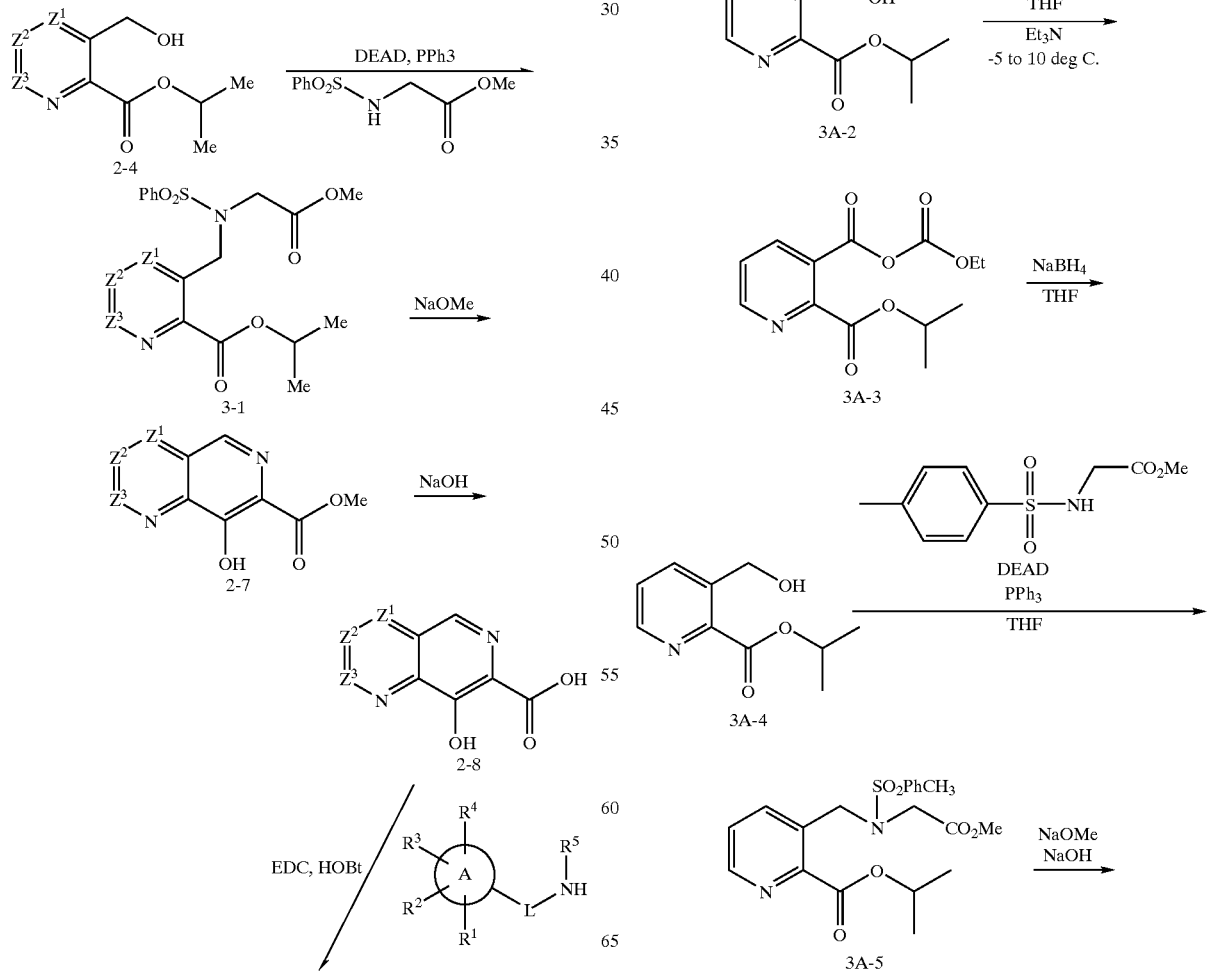

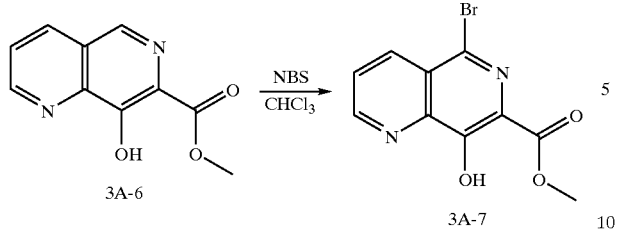

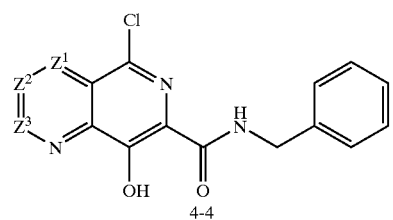

Halogen substituted compounds of the present invention can be prepared as shown in Scheme 4. The acid chloride 2-3 can be reacted with glycine methyl ester to provide the amide 4-1. Dieckmann cyclization of the ester 4-1 with a sodium alkoxide base in an alcoholic solvent like methanol will provide phenol 4-2., which can be reacted with phosphorous oxychloride, followed by methanolysis of the intermediate phosphonate esters to provide 4-3. The ester bond of 4-3 can react selectively with suitable amines in refluxing nonpolar aromatic solvents (e.g., benzylamine refluxed in toluene is depicted in Scheme 4) to provide the corresponding halogenated derivative 4-4.

The preparation of compounds that feature additional substituents can be achieved as shown in Scheme 5. Oxidation of the alcohol 2-4 with manganese dioxide in an inert solvent such as methylene chloride will provide aldehyde 5-1. The addition of Grignard reagents (such as phenyl magnesium bromide) to aldehyde moiety 5-1 can occur regioselectively to provide the alcohol 5-2, which can then be elaborated to the compounds of the invention 5-6.

SCHEME 4

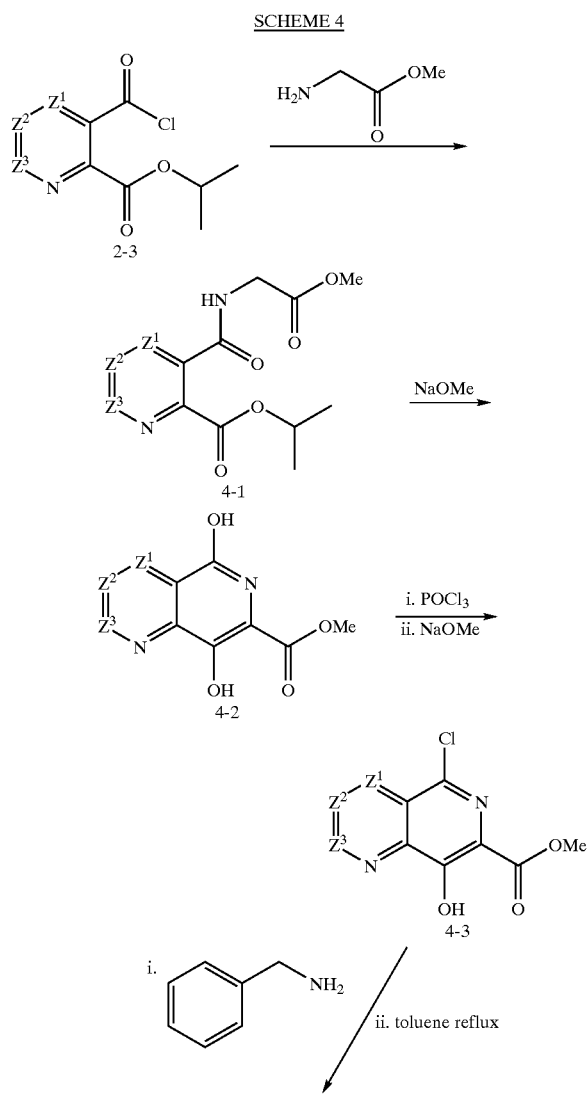

SCHEME 5

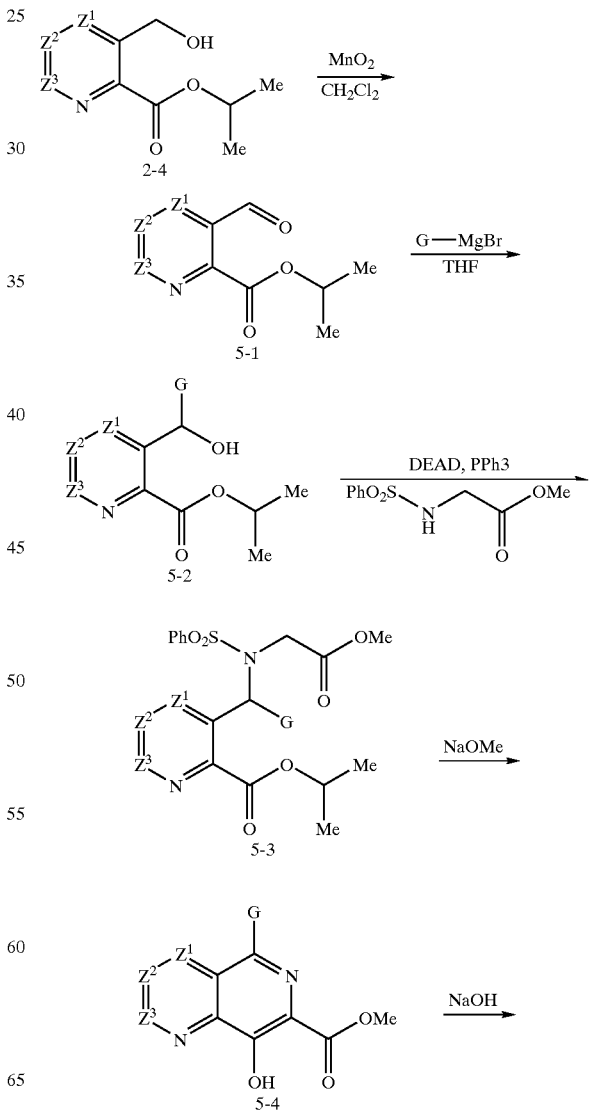

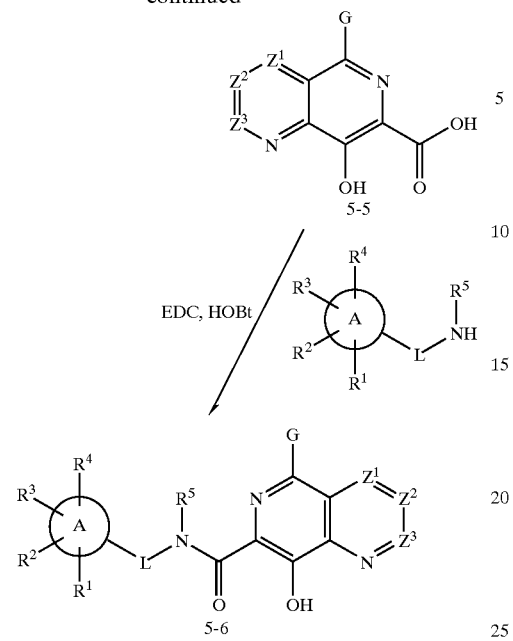

[G = unsubstituted or substituted alkyl, carbocycle (e.g., aryl), or heterocycle (e.g., heteroaryl)]

A further synthetic route to prepare compounds that are the subject of the invention is shown in Scheme 6. This methodology allows access to naphthyridine derivatives that are substituted at the 2, 3, 4 and 5 positions. Briefly, a 2-substituted 5-hydroxypyridine derivative 6-1 can be treated with bromine to undergo bromination at the 6 position to afford 6-2, which can be converted to the methoxypyridine 6-3 and then oxidized to the corresponding N-oxide 6-4. The N-oxide can be nitrated to provide 6-5. Reduction of 6-5 with iron in the presence of ammonium chloride can provide the aniline 6-6, which can be reacted with an alpha,beta-unsaturated aldehyde or ketone in the presence of an acid catalyst like sulfuric acid to provide 6-7 via an annulation. The bromide 6-7 can be elaborated to the amide 6-9 via a sequence of carbonylation and amidation reactions.

2-Substituted 5-hydroxypyridine derivatives of formula 6-1 can be prepared via methods described in Sorm et al., *Collect. Czech. Chem. Commun.* 1949, 14: 331,342; and Saksena et al., *Tetrahedron Lett.* 1993, 34: 3267–3270: or routine variations thereof.

SCHEME 6

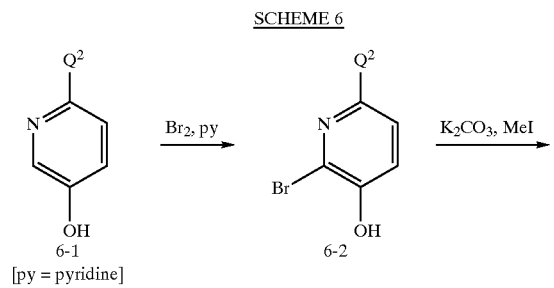

[py = pyridine]

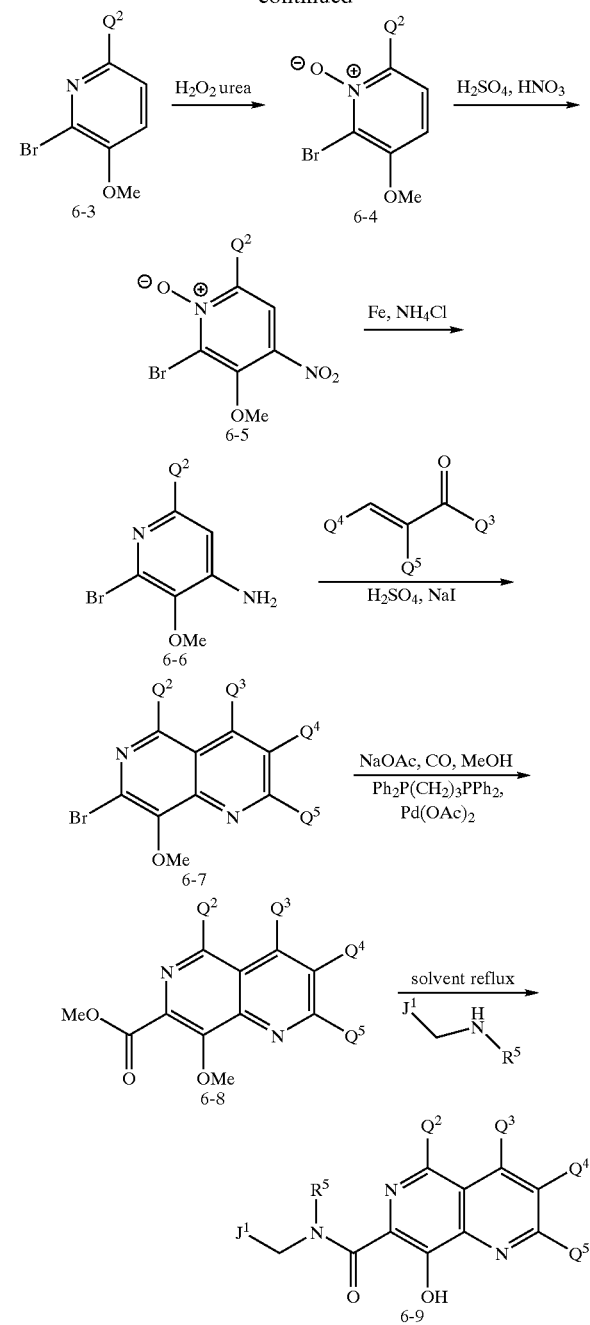

[$J^1$ = (un)substituted aryl]

Compounds of the invention that comprise an amino substituent at the position can be prepared in the manner set forth in Schemes 7 and 8. Bromination of the phenol 7-1 occurs regioselectively upon treatment with NBS in an inert solvent like methylene chloride to afford 7-2. Reaction of this bromide with an amine at elevated temperatures in the presence of a polar solvent such as DMPU affords compounds of the invention 7-3. Similar reaction of the bromide 7-2 (Scheme 8) with a diamine such as ethylene diamine in DMF as solvent will afford the formylated derivative 8-1 in addition to the expected diaminoethane derivative.

SCHEME 7

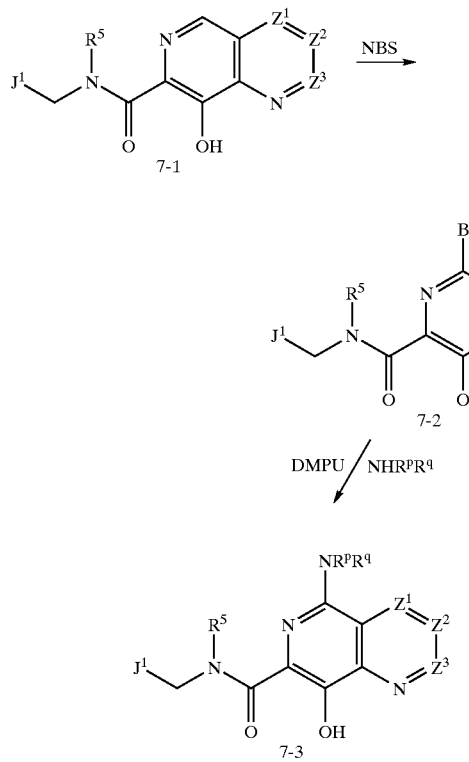

[ J¹ = (un)substituted aryl
Rᵖ, Rᵠ = H; alkyl; alkyl substituted with, e.g., OH, alkoxy, carbocycle, or heterocycle; (un)substituted carbocycle, or (un)substituted heterocycle ]

SCHEME 8

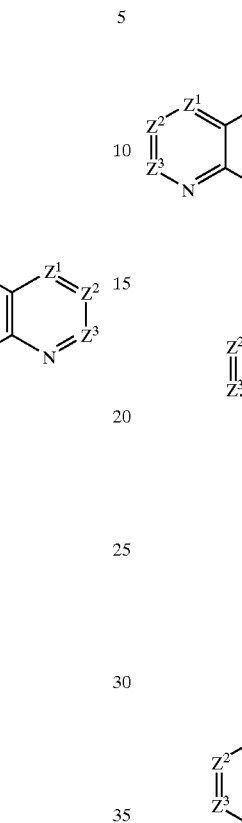

Preparation of aryl and heteroaryl derivatives via palladium cross coupling of the chloride 9-1 and the requisite boronic acids are depicted in Scheme 9.

SCHEME 9

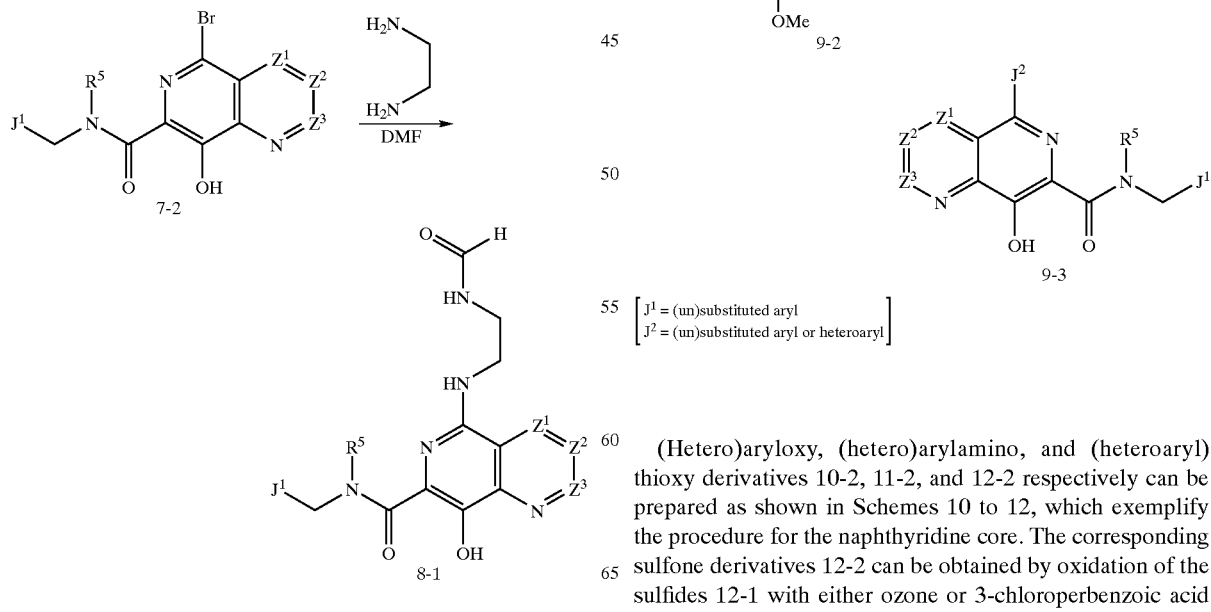

[ J¹ = (un)substituted aryl
J² = (un)substituted aryl or heteroaryl ]

(Hetero)aryloxy, (hetero)arylamino, and (heteroaryl)thioxy derivatives 10-2, 11-2, and 12-2 respectively can be prepared as shown in Schemes 10 to 12, which exemplify the procedure for the naphthyridine core. The corresponding sulfone derivatives 12-2 can be obtained by oxidation of the sulfides 12-1 with either ozone or 3-chloroperbenzoic acid as shown in Scheme 12.

SCHEME 10

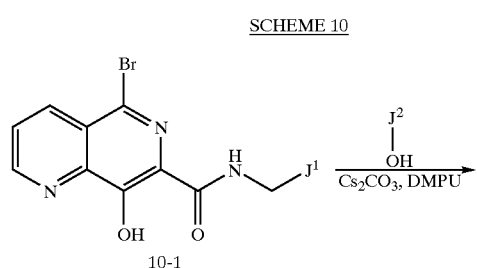

SCHEME 11

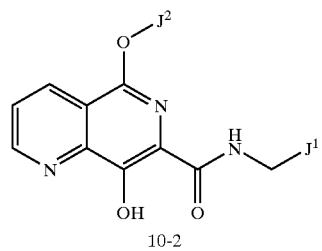

SCHEME 12

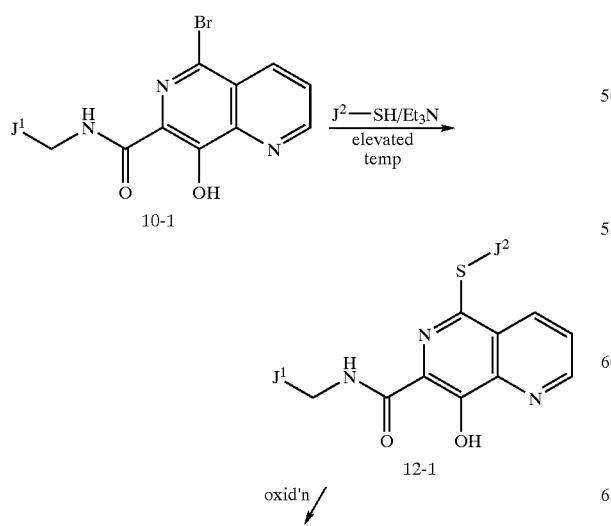

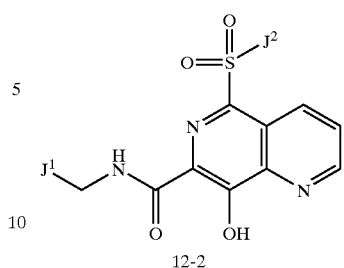

Preparation of compounds of the invention substituted with an acetylene can be prepared according to Scheme 13, which exemplifies the procedure for the naphthyridine core. Following protection of the iodide 13-2 as its benzoate 13-3, the acetylenic group (for example propynol) can be appended by employing a suitable palladium catalyst in the presence of copper iodide. Aminolysis of the ester 13-4 will afford the amide 13-5 with concomitant deprotection of the benzoate ester. Alternately the ester 13-4 can be converted to the corresponding amine and sulfone derivatives as shown in Schemes 14 and 15. Scheme 16 shows that the preparation of the nitrile derivative 16-2 can be achieved via a palladium catalyzed cyanation of the iodide 13-4.

SCHEME 13

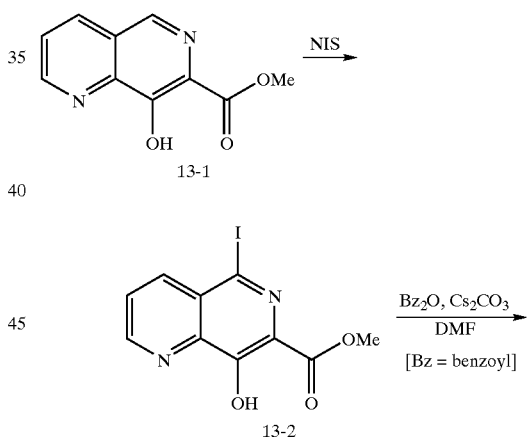

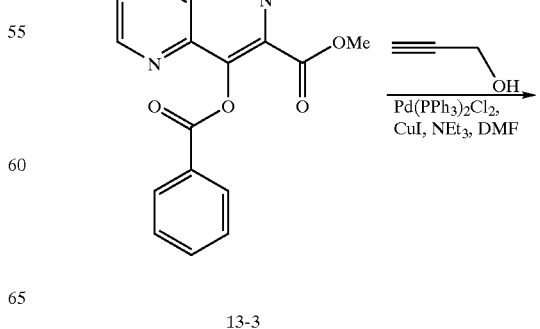

101
-continued
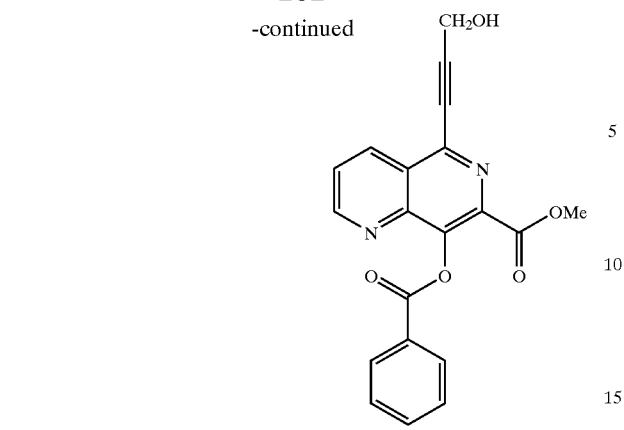
13-4
i. NaOH
ii. Triphosgene, NiPr₂Et
$J^1 \overset{H}{\underset{}{N}} R^5$
13-5
SCHEME 14
13-4
i. MsCl, NEt₃, CHCl₃
ii. K₂CO₃
   amine
14-1
$J^1 \overset{H}{\underset{}{N}} R^5$
102
-continued
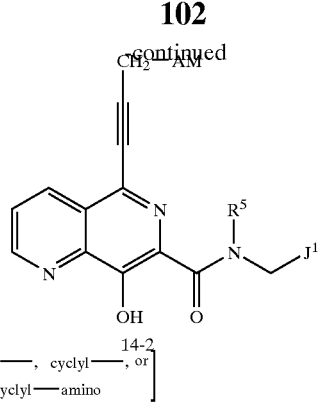
14-2
[AM = acyclyl—, cyclyl—, or heterocyclyl—amino]
SCHEME 15
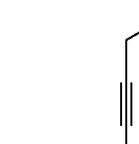
13-4
i. MsCl, NEt₃, CHCl₃
ii. K₂CO₃
   $R^a$—SH
iii. Oxone
15-1
$J^1 \overset{H}{\underset{}{N}} R^5$
15-2

SCHEME 16

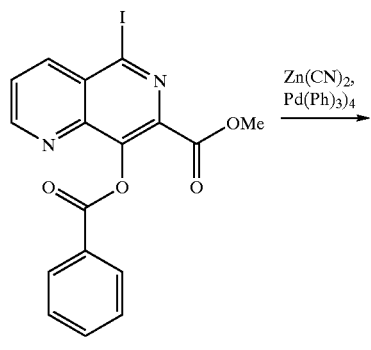

13-4

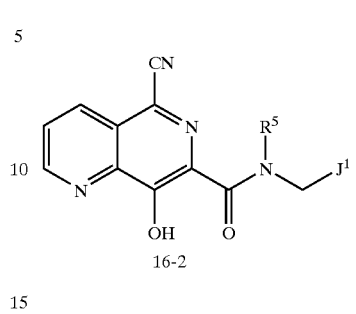

16-2

16-1

Preparation of compounds of the invention substituted with a sulfonamide can be prepared according to Scheme 17, which exemplifies the procedure for the naphthyridine core. The preparation includes halogenation of an alkyl 8-hydroxy-naphthyridine carboxylate (17-1) with a halogenation agent such as N-bromosuccinimide, coupling the halogenated ester (17-2) with substituted or unsubstituted benzylamine, and then condensing the 5-halo-8-hydroxy-naphthyridine carboxamide (17-3) with a sulfonamide (17-4) at elevated temperature (e.g., about 120° C.) in the presence of a copper promoter (e.g., copper(I) oxide) to afford the desired sulfonamidonaphthyridine product (17-5).

SCHEME 17

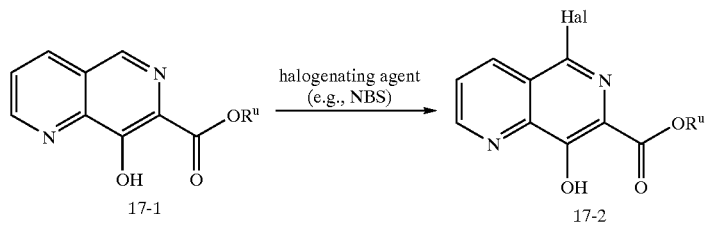

17-1
[R$^u$ = alkyl; e.g., CH$_3$]

17-2

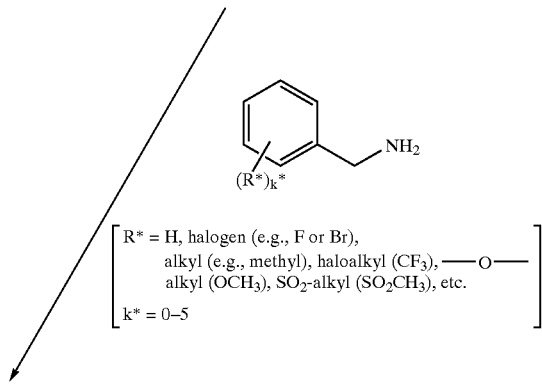

[R* = H, halogen (e.g., F or Br),
alkyl (e.g., methyl), haloalkyl (CF$_3$), —O—alkyl (OCH$_3$), SO$_2$-alkyl (SO$_2$CH$_3$), etc.
k* = 0–5]

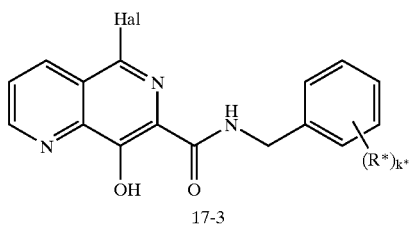

17-3

[Hal = halogen; e.g., Br]

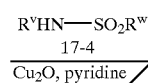

$R^v$ = H or alkyl (e.g., methyl)
$R^w$ = alkyl
Alternatively, $R^v$ and $R^w$ together with the
—$NSO_2$— moiety to which they are attached
form a sultam of formula:

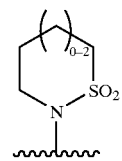

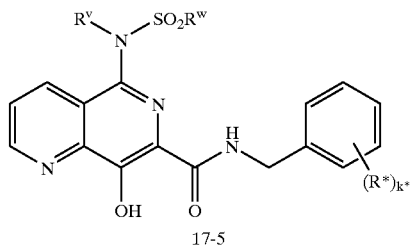

17-5

In the processes for preparing compounds of the present invention set forth in the foregoing schemes, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 1991. The protecting groups may be removed at a convenient subsequent stage using methods known in the art. Alternatively the interfering group can be introduced into the molecule subsequent to the reaction step of concern. For example, if one or more of the substituents $R^1$, $R^2$, $R^3$, and $R^4$ in compound 1-1 can interfere with the coupling reaction between compounds 1-1 and 1-2 of Scheme 1, the substituent can be incorporated into the molecule in a post-coupling step to afford Compound I.

The following examples serve only to illustrate the invention and its practice. The examples are not to be construed as limitations on the scope or spirit of the invention.

EXAMPLE 1
N-(3,5-dichlorobenzyl)-8-hydroxy-1,6-naphthyridine-7-carboxamide

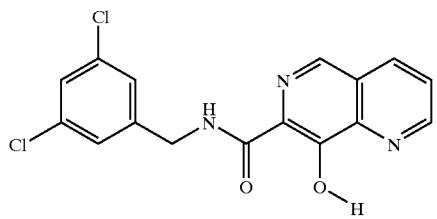

Step 1: Preparation of 3-{[Methoxycarbonylmethyl-(toluene-4-sulfonyl)-amino]-methyl}-pyridine-2-carboxylic acid isopropyl ester Isopropyl 3-(hydroxymethyl)pyridine-2-carboxylate, (200 g, 1.02 mol; prepared as in P. Ornstein et. al. *J. Med. Chem.* 1989, 32, 827), methyl N-[(4-methylphenyl)sulfonyl] glycinate (249 g, 1.02 mol), and triphenylphosphine (403 g, 1.5 mol) were dissolved in dry THF (3000 mls) and cooled to zero degrees under N2. The diethylazodicarboxylate (DEAD) (267.6 g, 1.5 mol) was dissolved in dry THF (250 mls) and placed in a 500 ml addition funnel. The DEAD was added dropwise over 1 hour. The ice bath was removed and the reaction was allowed to warm slowly to RT. After 2 hours, the reaction was checked by HPLC and some glycinate remained. More starting reagents were added and the reaction was left to stir at RT. After 30 min, the reaction was checked again and saw a very small amount of the glycinate remaining. Concentrated reaction down to a reddish-orange oil that was carried onto the next step.

Step 2: Preparation of methyl 8-hydroxy-1,6-naphthyridine-7-carboxylate

3-{[Methoxycarbonylmethyl-(toluene-4-sulfonyl)-amino]-methyl}-pyridine-2-carboxylic acid isopropyl ester (1.02 mol) was dissolved in dry methanol (4000 ml) and cooled to zero degrees under nitrogen. Then via addition funnel, sodium methoxide (137.8 g, 2.5 mol) was added slowly to avoid any exotherm. The reaction was stirred at zero degrees, and checked by HPLC after 1.5 hours and was found to be completed. The solvent was removed in vacuo to obtain a reddish-orange oil, which was partitioned between water (1L) and ethyl acetate (1L). The organic layer was back extracted with saturated sodium bicarbonate solution. The pH of the aqueous layer was adjusted to 7, and the layer was maintained at this pH while extracting with methylene chloride. The organic layer was dried with Na2SO4, filtered, and the solvent was removed in vacuo to obtain a tan solid. The solid was dissolved in hot ethyl acetate, and the solution was filtered while hot to filter out any insoluble material. The product precipitated upon cooling. The precipitate was then filtered and dried in a vacuum oven. The filtrate was recrystallized by concentrating the filtrate and redissolving the resulting solid in a minimal amount of methylene chloride. Sufficient ethyl acetate was added to turn the solution slightly cloudy, after which the solution was boiled to reduce the volume, cooled, and the resulting crystals were filtered out and dried in a vacuum oven.

1H NMR (CDCl3, 500 MHz) δ 11.794 (5H,s), 9.2 (1H, dd, J=1.7 and 6.1 Hz), 8.8 (1H,s), 8.3 (1H, dd, J=1.5 and 9.7 Hz), 7.7 (1H, dd, J=4.2 and 12.4 Hz), 4.1 (3H,s) ppm. ES MS exact mass calculated for C10H8N 2O3 204.1869 (MH+), found 205.1.

Step 3: Preparation of N-(3,5-dichlorobenzyl)-8-hydroxy-1,6-naphthyridine-7-carboxamide A slurry of the ester from step 2 (3.0 g, 0.0147 mol) and 3,5,dichlorobenzylamine (2.85 g, 0.016 mol) in toluene (45 mL) were heated at reflux for 18 hrs. Upon cooling to room temperature, the resulting solids were collected by filtration and washed 3 times with methanol (50 ml; 30 ml and 20 ml) to afford the title compound as a white solid.

$^1$H NMR (CDCl$_3$, 400 MHz) δ 13.1 (1H, s), 9.20 (1H, d, J=4.2 Hz), 8.68 (1H, s), 8.49 (1H, brs), 8.29 (1H, d, J=8.3 Hz), 7.67 (1H, dd, J=8.3 and 4.2 Hz), 7.35–7.22 (3H, m), 4.67 (2H, d, J=5.4 Hz) ppm. FAB MS calcd for C$_{16}$H$_{11}$N$_3$O$_2$Cl$_2$ 348 (MH$^+$), found 348. FAB HRMS exact mass calcd for C$_{16}$H$_{11}$N$_3$O$_2$Cl$_2$ 348.0301 (MH$^+$), found 348.0294.

EXAMPLE 2

N-(2,5-dichlorobenzyl)-8-hydroxy-1,6-naphthyridine-7-carboxamide

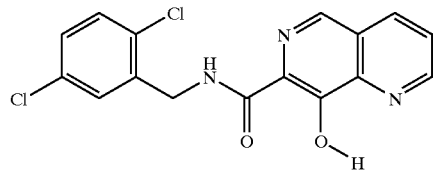

Step 1: Preparation of 8-hydroxy-1,6-naphthyridine-7-carboxylic Acid

To a slurry of methyl 8-hydroxy-1,6-naphthyridine-7-carboxylate from Example 1 step 2 (1.50 g, 7.35 mmol) in methanol (45 ml) was added lithium hydroxide (22.0 ml of a 1M aq. solution, 22.0 mmol) and the reaction was heated at 100° C. for 7 hrs. Upon cooling to room temperature, hydrochloric acid (22.0 ml of a 1M aq. solution, 22.0 mmol) was added and the reaction stirred for 16 hrs. The mixture was concentrated to a volume of 50 ml and neutralized with dilute NaHCO$_3$ (pH=7) The resulting precipitate was collected by filtration and washed with water and dried in vacuo to afford the title compound.

FAB MS calcd for C$_9$H$_6$N$_2$O$_3$ 191 (MH$^+$), found 191. $^1$H NMR (d$_6$DMSO, 400 MHz) δ 9.20 (1H, m), 8.72 (1H, s), 8.58 (1H, m), 7.80 (1H, dd, J=8.3 and 4.2 Hz) ppm.

Step 2: Preparation of N-(2,5-dichlorobenzyl)-8-hydroxy-1,6-naphthyridine-7-carboxamide Triphosgene (0.556 g, 1.87 mmol) was added over 20 mins to a solution of the acid from step 1. (0.89 g, 4.68 mmol) and diisopropylethylamine 3.26 ml, 18.7 mmol) in DMF (22 ml) at 0° C. The dark solution was allowed to warm to room temperature and stirred a further 1 hr. 2,5-dichlorobenzylamine (0.142 ml, 1.05 mmol) was treated with a portion of the above solution (0.58 ml, 0.07 mmol) and the resulting mixture was stirred at room temperature for 16 hrs. The solution was treated with trifluroacetic acid (TFA) (0.025 ml) and purified by preparative HPLC. (Gilson semi preparative HPLC system and a YMC Combiprep Pro Column (50×20 mm I.D., C18, S-5 um, 120A) (available from Waters) eluting with 5–95% acetonitrile/water (0.1% TFA) at 15 ml/min) to afford the title compound after lyophilization.

$^1$H NMR (d$_6$DMSO, 400 MHz) δ 9.90 (1H, br t, J=5.0 Hz)), 9.20 (1H, d, J=4.0 Hz), 8.95 (1H, s), 8.65 (1H, d, J=8.0 Hz), 7.85 (1H, dd, J=8.0 and 4.0 Hz), 7.54 (1H, d, J=8.0 Hz), 7.50–7.30 (2H, m), 4.64 (2H, d, J=5.0 Hz) ppm. FAB MS calcd for C$_{16}$H$_{11}$N$_3$O$_2$Cl$_2$ 348 (MH$^+$), found 348. FAB HRMS exact mass calcd for C$_{16}$H$_{11}$N$_3$O$_2$Cl$_2$ 348.0301 (MH$^+$), found 348.0294.

EXAMPLE 3

N-[(1R,S)-2,3-dihydro-1H-inden-1-yl]-8-hydroxy-1,6-naphthyridine-7-carboxamide

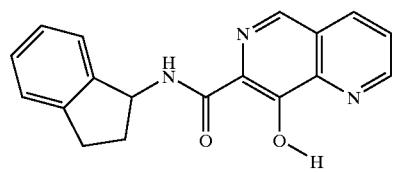

The title compound was prepared using the procedure described in Example 2, Step 2 replacing 2,5 dichlorobenzylamine with 1(R,S) aminoindane.

$^1$H NMR (d$_6$DMSO, 400 MHz) δ 9.41 (1H, d, J=8.2 Hz), 9.18 (1H, d, J=4.2 Hz), 8.90 (1H, s), 8.63 (1H, d, J=8.2 Hz), 7.85 (1H, dd, J=8.2 and 4.2 Hz), 7.35–7.10 (4H, m), 5.63 (1H, q, J=8.2 Hz), 3.20–2.80 (2H, m), 2.60–2.40 (1H, m), 2.30–2.10 (1H, m) ppm. FAB MS calcd for C$_{18}$H$_{15}$N$_3$O$_2$ 306 (MH$^+$), found 306. FAB HRMS exact mass calcd for C$_{18}$H$_{15}$N$_3$O$_2$ 306.1237 (MH$^+$), found 306.1230

EXAMPLE 4

N-[2-(3-chlorophenyl)ethyl]-8-hydroxy-1,6-naphthyridine-7-carboxamide

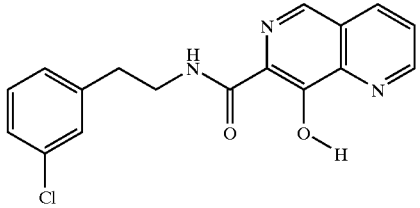

The title compound was prepared using the procedure described in Example 2, Step 2 replacing 2,5 dichlorobenzylamine with 3 chlorophenethylamine.

$^1$H NMR (d$_6$DMSO, 400 MHz) δ 9.39 (1H, m), 9.17 (1H, d, J=4.2 Hz), 8.91 (1H, s), 8.61 (1H, d, J=8.3 Hz), 7.84 (1H, dd, J=8.3 and 4.2 Hz), 7.40–7.20 (4H, m), 3.63 (2H, m), 2.96 (2H, t, J=7.2 Hz) ppm. FAB MS calcd for C$_{17}$H$_{14}$N$_3$O$_2$Cl 328 (MH$^+$), found 328. FAB HRMS exact mass calcd for C$_{17}$H$_{14}$N$_3$O$_2$Cl 328.0847 (MH$^+$), found 328.0841.

EXAMPLE 5

N-[2-(2-chlorophenyl)ethyl]-8-hydroxy-1,6-naphthyridine-7-carboxamide

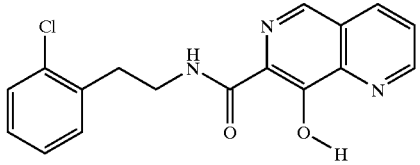

The title compound was prepared using the procedure described in Example 2, Step 2 replacing 2,5 dichlorobenzylamine with 2 chlorophenethylamine.

$^1$H NMR (d$_6$DMSO, 400 MHz) δ 9.45 (1H, m), 9.17 (1H, d, J=4.2 Hz), 8.91 (1H, s), 8.61 (1H, d, J=8.3 Hz), 7.84 (1H, dd, J=8.3 and 4.2 Hz), 7.60–7.20 (4H, m), 3.65 (2H, m), 3.07 (2H, t, J=7.2 Hz) ppm. FAB MS calcd for C$_{17}$H$_{14}$N$_3$O$_2$Cl 328 (MH$^+$), found 328. FAB HRMS exact mass calcd for C$_{17}$H$_{14}$N$_3$O$_2$Cl 328.0847 (MH$^+$), found 328.0842.

EXAMPLE 6

N-[2-(1,1'-biphenyl-4-yl)ethyl]-8-hydroxy-1,6-naphthyridine-7-carboxamide

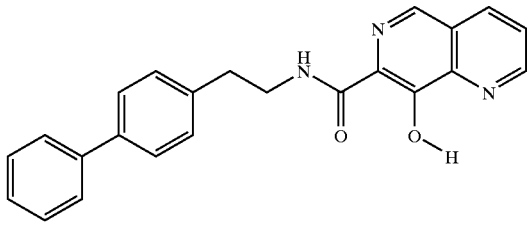

The title compound was prepared using the procedure described in Example 2, Step 2 replacing 2,5 dichlorobenzylamine with 4 phenylphenethylamine.

$^1$H NMR (d$_6$DMSO, 400 MHz) δ 9.41 (1H, m), 9.17 (1H, d, J=4.2 Hz), 8.91 (1H, s), 8.61 (1H, d, J=8.2 Hz), 7.84 (1H, dd, J=8.2 and 4.2 Hz), 7.64 (2H, d, J=7.4 Hz), 7.61(2H, d, J=8.0 Hz), 7.45(2H, d, J=7.6 Hz), 7.40–7.30 (3H, m), 3.65 (2H, m), 2.99 (2H, t, J=7.3 Hz) ppm. FAB MS calcd for C$_{23}$H$_{19}$N$_3$O$_2$ 370 (MH$^+$), found 370. FAB HRMS exact mass calcd for C$_{23}$H$_{19}$N$_3$O$_2$ 370.1550 (MH$^+$), found 370.1554.

EXAMPLE 7

8-hydroxy-N-[2-(4-phenoxyphenyl)ethyl]-1,6-naphthyridine-7-carboxamide

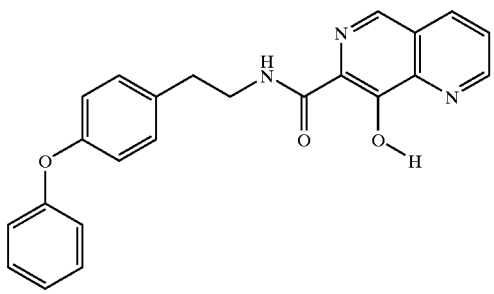

The title compound was prepared using the procedure described in Example 2, Step 2 replacing 2,5 dichlorobenzylamine with 4 phenoxyphenethylamine.

$^1$H NMR (d$_6$DMSO, 400 MHz) δ 9.38 (1H, m), 9.17 (1H, d, J=4.2 Hz), 8.91 (1H, s), 8.61 (1H, d, J=8.3 Hz), 7.84 (1H, dd, J=8.3 and 4.2 Hz), 7.36 (2H, t, J=7.5 Hz), 7.29 (2H, d, J=8.2 Hz), 7.10 (1H, dt, J=7.4 and 1.0 Hz), 7.00–6.90 (4H, m), 3.61 (2H, m), 2.92 (2H, t, J=7.4 Hz) ppm. FAB MS calcd for C$_{23}$H$_{19}$N$_3$O$_3$ 386 (MH$^+$), found 386. FAB HRMS exact mass calcd for C$_{23}$H$_{19}$N$_3$O$_3$ 386.1499 (MH$^+$), found 386.1495.

EXAMPLE 8

8-hydroxy-N-(3-phenylpropyl)-1,6-naphthyridine-7-carboxamide

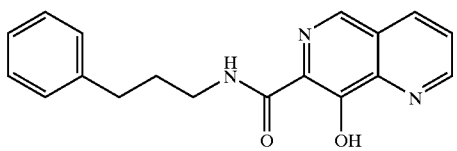

The title compound was prepared using the procedure described in Example 2, Step 2 replacing 2,5 dichlorobenzylamine with 3-phenylproplyanine.

$^1$H NMR (DMSO-d6, 400 MHz) δ 9.38 (1H, t, J=5.5 Hz), 9.16 (1H, d, J=4.2 Hz), 8.91 (1H, s), 8.61 (1H, d, J=8.2 Hz), 7.83 (1H, dd, J=4.2 and 8.2 Hz), 7.25 (4H, m), 7.17 (1H, t, 7 Hz), 3.41 (2H, m), 2.65 (2H, t, J=7.5 Hz) and 1.92 (2H, quintet, J=7.3 Hz) ppm. FAB MS calcd for C$_{18}$H$_{17}$N$_3$O$_2$ 308.1 (MH$^+$), found 308.1. FAB HRMS exact mass calcd for C$_{18}$H$_{17}$N$_3$O$_2$ 308.1394 (MH$^+$), found 308.1379.

EXAMPLE 9

N-(1,1'-biphenyl-2-ylmethyl)-8-hydroxy-1,6-naphthyridine-7-carboxamide

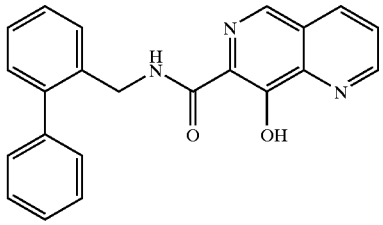

The title compound was prepared using the procedure described in Example 2, Step 2 replacing 2,5 dichlorobenzylamine with 2-phenylbenzylamine.

$^1$H NMR (DMSO-d6, 400 MHz) δ 9.68 (1H, br s), 9.16 (1H, d, J=4.2 Hz), 8.91 (1H, s), 8.61 (1H, d, J=8.4 Hz), 7.83 (1H, dd, J=4.2 and 8.2 Hz), 7.31–7.51 (8H, m), 7.24 (1H, m) and 4.54 (2H, m) ppm. FAB MS calcd for $C_{22}H_{17}N_3O_2$ 356.1 (MH$^+$), found 356.1. FAB HRMS exact mass calcd for $C_{22}H_{17}N_3O_2$ 356.1394 (MH$^+$), found 356.1416.

EXAMPLE 10

N-(1,1'-biphenyl-3-ylmethyl)-8-hydroxy-1,6-naphthyridine-7-carboxamide

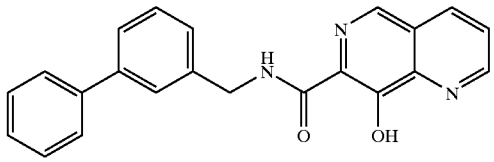

The title compound was prepared using the procedure described in Example 2, Step 2 replacing 2,5 dichlorobenzylamine with 3-phenylbenzylamine.

$^1$H NMR (DMSO-d6, 400 MHz). 9.93 (1H, br s), 9.16 (1H, d, J=4.4 Hz), 8.93 (1H, s), 8.62 (1H, d, J=8.2 Hz), 7.83 (1H, dd, J=4.2 and 8.2 Hz), 7.70 (1H, s), 7.64 (2H, d, 8.4 Hz), 7.56 (1H, d, 7.3 Hz), 7.33–7.51 (5H, m) and 4.64 (2H, m)ppm. FAB MS calcd for $C_{22}H_{17}N_3O_2$ 356.1 (MH$^+$), found 356.1. FAB HRMS exact mass calcd for $C_{22}H_{17}N_3O_2$ 356.1394 (MH$^+$), found 356.1410.

EXAMPLE 11

8-hydroxy-N-phenyl-1,6-naphthyridine-7-carboxamide

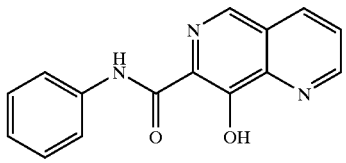

The title compound was prepared using the procedure described in Example 2, Step 2 replacing 2,5 dichlorobenzylamine with aniline.

$^1$H NMR (DMSO-d6, 400 MHz) δ 11.0 (1H, br s), 9.19 (1H, br s), 9.00 (1H, br s), 8.65 (1H, d, J=8.0 Hz), 7.88 (3H, m), 7.41 (2H, t, J=7.7 Hz), 7.19 (1H, t, J=7.0)ppm. FAB MS calcd for $C_{15}H_{11}N_3O_2$ 266.1 (MH$^+$), found 266.1. FAB HRMS exact mass calcd for $C_{15}H_{11}N_3O_2$ 266.0924 (MH$^+$), found 266.0926.

EXAMPLE 12

8 N-(2-chlorobenzyl)-8-hydroxy-1,6-naphthyridine-7-carboxamide

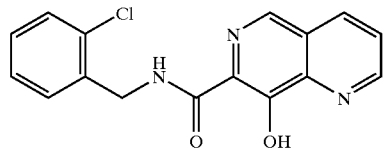

The title compound was prepared using the procedure described in Example 2, Step 2 replacing 2,5 dichlorobenzylamine with 2-chlorobenzylamine.

$^1$H NMR (DMSO-d6, 400 MHz) δ 9.84 (1H, br s), 9.18 (1H, d, J=4.3 Hz), 8.96 (1H, s), 8.64 (1H, d, J=8.3 Hz), 7.85 (1H, dd, J=8.3 and 4.3 Hz), 7.48 (1H, m), 7.38 (1H, m), 7.33 (2H, m), 4.65 (2H, m)ppm. FAB MS calcd for $C_{16}H_{12}ClN_3O_2$ 314.1 (MH$^+$), found 314.1. FAB HRMS exact mass calcd for $C_{16}H_{12}ClN_3O_2$ 314.0691 (MH$^+$), found 314.0702.

EXAMPLE 13

N-benzyl-8-hydroxy-N-methyl-1,6-naphthyridine-7-carboxamide

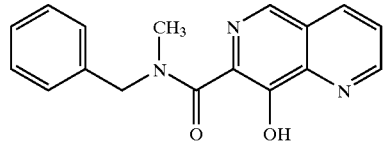

The title compound was prepared using the procedure described in Example 2, Step 2 replacing 2,5 dichlorobenzylamine with N-methylbenzylamine.

$^1$H NMR (DMSO-d6, 400 MHz) δ 9.14 (1H, m), 8.91 (1H, 2s), 8.60 (1H, 2d, J=8.4 Hz), 7.78 (1H, m), 7.32–7.44 (5H, m), 4.76 (1.15H, s), 4.46 (0.85H, s), 2.91 (1.7 h, s) and 2.79 (1.3H, s)ppm. FAB MS calcd for $C_{17}H_{15}N_3O_2$ 294.1 (MH$^+$), found 294.1. FAB HRMS exact mass calcd for $C_{17}H_{15}N_3O_2$ 294.1237 (MH$^+$), found 294.1244.

EXAMPLE 14

8-hydroxy-N-(1-methyl-1-phenylethyl)-1,6-naphthyridine-7-carboxamide

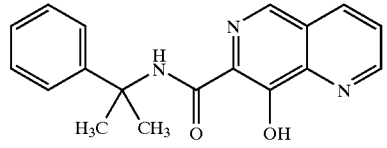

The title compound was prepared using the procedure described in Example 2, Step 2 replacing 2,5 dichlorobenzylamine with cumylamine.

$^1$H NMR (DMSO-d6, 400 MHz) δ 0.16 (1H, br s), 8.94 (1H, s), 8.62 (1H, d, J=8.2 Hz), 7.83 (1H, m), 7.46 (2H, d,

J=7.1 Hz), 7.34 (2H, t, J=7.6 Hz), 7.23 (1H, m) and 1.80 (6H, s)ppm. FAB MS calcd for $C_{18}H_{17}N_3O_2$ 308.1 (MH⁺), found 308.1. FAB HRMS exact mass calcd for $C_{18}H_{17}N_3O_2$ 308.1394 (MH⁺), found 308.1378.

EXAMPLE 15

8-hydroxy-N-(2-phenylethyl)-1,6-naphthyridine-7-carboxamide

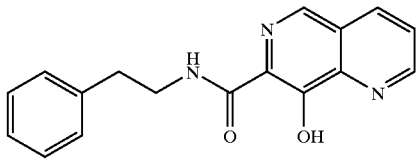

The title compound was prepared using the procedure described in Example 2, Step 2 replacing 2,5 dichlorobenzylamine with phenethylamine.

¹H NMR (DMSO-d6, 400 MHz) δ 9.36 (1H, br s), 9.16 (1H, d, J=4.2 Hz), 8.90 (1H, s), 8.61 (1H, d, J=8.2 Hz), 7.83 (1H, dd, J=4.2 and 8.2 Hz), 7.25–7.36 (4H, m), 7.21(1H, m), 3.61(2H, m) and 2.94 (2H, t, 7.5 Hz) ppm. FAB MS calcd for $C_{17}H_{15}N_3O_2$ 294.1 (MH⁺), found 294.1.

EXAMPLE 16

8-hydroxy-N-(1-naphthylmethyl)-1,6-naphthyridine-7-carboxamide

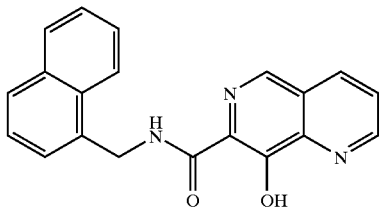

The title compound was prepared using the procedure described in Example 2, Step 2 replacing 2,5 dichlorobenzylamine with 1-naphthalenemethylamine.

¹H NMR (DMSO-d6, 400 MHz) δ 9.86 (1H, br s), 9.17 (1H, d, J=3.7 Hz), 8.92 (1H, s), 8.62 (1H, d, J=8.2 Hz), 8.31 (1H, d, J=8.2 Hz), 7.97 (1H, d, J=7.7 Hz), 7.87 (1H, d, J=8.2 Hz), 7.84 (1H, dd, J=4.2 and 8.2 Hz), 7.61 (1H, m), 7.56 (2H, m), 7.49 (1H, t, J=7.7 Hz), and 5.05 (2H, d, J=4.2 Hz) ppm. FAB MS calcd for $C_{20}H_{15}N_3O_2$ 330.1 (MH⁺), found 330.1.

EXAMPLE 17

N-benzyl-8-hydroxy-N-phenyl-1,6-naphthyridine-7-carboxamide

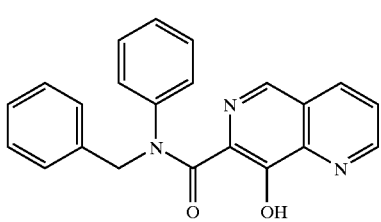

The title compound was prepared using the procedure described in Example 2, Step 2 replacing 2,5 dichlorobenzylamine with N-phenylbenzylamine.

¹H NMR (d₆DMSO, 400 MHz) δ 10.79 (1H, m), 9.04 (1H, s), 8.69 (1H, m), 8.46 (1H, m), 7.68 (1H, m), 7.50–6.90 (7H, m), 6.70–6.40 (3H, m), 5.14 (2H, m) ppm. FAB MS calcd for $C_{22}H_{17}N_3O_2$ 386 (MH⁺), found 356. FAB HRMS exact mass calcd for $C_{22}H_{17}N_3O_2$ 356.13935 (MH⁺), found 356.13689.

EXAMPLE 18

N-(3-chlorobenzyl)-8-hydroxy-1,6-naphthyridine-7-carboxamide

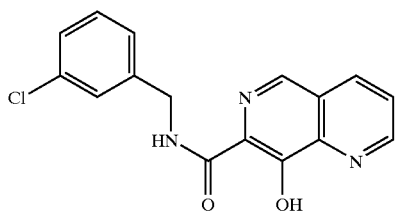

The title compound was prepared using the procedure described in Example 2, Step 2 replacing 2,5 dichlorobenzylamine with 3-chlorobenzylamine.

¹H NMR (d₆DMSO, 400 MHz) δ 9.94(1H, br t, J=5.6 Hz)), 9.17 (1H, d, J=4.2 Hz), 8.93 (1H, s), 8.63 (1H, d, J=8.3 Hz), 7.85 (1H, dd, J=8.3 and 4.2 Hz), 7.45(1H, s), 7.50–7.30 (3H, m), 4.58 (2H, d, J=6.0 Hz) ppm. FAB MS calcd for $C_{16}H_{12}ClN_3O_2$ 314 (MH⁺), found 314.

EXAMPLE 19

N-(4-chlorobenzyl)-8-hydroxy-1,6-naphthyridine-7-carboxamide

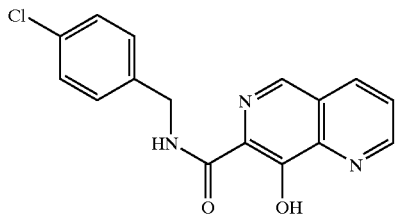

The title compound was prepared using the procedure described in Example 2, Step 2 replacing 2,5 dichlorobenzylamine with 4-chlorobenzylanine.

¹H NMR (d₆DMSO, 400 MHz) δ 9.92 (1H, br t, J=5.0 Hz), 9.17 (1H, d, J=4.3 Hz), 8.93 (1H, s), 8.63 (1H, d, J=8.3 Hz), 7.85 (1H, ddd, J=8.3, 4.2 and 1.5 Hz), 7.41(4H, s), 4.58 (2H, d, J=6.3 Hz) ppm. FAB MS calcd for $C_{16}H_{12}ClN_3O_2$ 314 (MH⁺), found 314. FAB HRMS exact mass calcd for $C_{16}H_{12}ClN_3O_2$ 314.0691 (MH⁺), found 314.06908.

EXAMPLE 20

Methyl (2S)-{[(8-hydroxy-1,6-naphthyridin-7-yl)carbonyl]amino}(phenyl)ethanoate

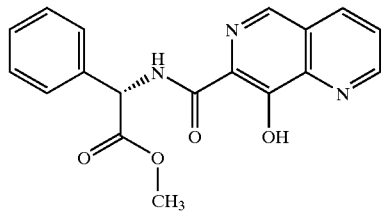

The title compound was prepared using the procedure described in Example 2, Step 2 replacing 2,5 dichlorobenzylamine with S(+)-2-phenylglycine methyl ester.

$^1$H NMR (d$_6$DMSO, 400 MHz) δ 9.82 (1H, m), 9.17 (1H, d, J=4.2 Hz), 8.94 (1H, s), 8.64 (1H, d, J=8.2 Hz), 7.85 (1H, ddd, J=8.2, 4.2 and 1.5 Hz), 7.60–7.30 (5H, m), 5.82 (1H, d, J=7.5 Hz), 3.72 (3H, s) ppm. FAB MS calcd for C$_{18}$H$_{15}$N$_3$O$_4$ 338(MH$^+$), found 338. FAB HRMS exact mass calcd for C$_{18}$H$_{15}$N$_3$O$_4$ 338.11353 (MH$^+$), found 338.11418.

EXAMPLE 21

Ethyl N-benzyl-N-[(8-hydroxy-1,6-naphthyridin-7-yl)carbonyl]glycinate

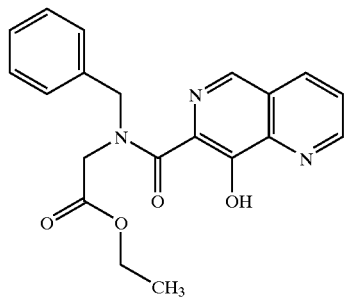

The title compound was prepared using the procedure described in Example 2, Step 2 replacing 2,5 dichlorobenzylamine with N-benzylglycine ethyl ester.

$^1$H NMR (d$_6$DMSO, 400 MHz) δ 9.15 (1H, m), 8.90 (0.5H, s), 8.85 (0.5H, s), 8.59 (1H, m), 7.80 (1H, m), 7.50–7.20 (5H, m), 4.85 (1H, s), 4.60 (1H, s), 4.23 (1H, s), 4.20–4.09 (2H, m), 4.02 (1H, q, J=7.0 Hz), 1.21 (1H, t, J=7.0 Hz), 1.08 (1H, t, J=7.0 Hz) ppm. FAB MS calcd for C$_{18}$H$_{15}$N$_3$O$_4$ 366 (MH$^+$), found 366. FAB HRMS exact mass calcd for C$_{18}$H$_{15}$N$_3$O$_4$ 366.144833 (MH$^+$), found 366.144987.

EXAMPLE 22

N-benzyl-8-hydroxy-N-(2-phenylethyl)-1,6-naphthyridine-7-carboxamide

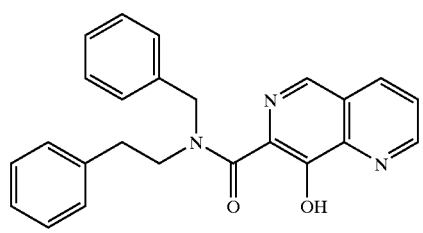

The title compound was prepared using the procedure described in Example 2, Step 2 replacing 2,5 dichlorobenzylamine with N-benzyl-2-phenethylamine.

$^1$H NMR (d$_6$DMSO, 400 MHz) δ 9.25–9.15 (1H, m), 8.99 (0.6H, s), 8.92 (0.4H, s), 8.64 (0.6H, d, J=8.3 Hz), 8.59 (0.4H, d, J=8.3 Hz), 7.90–7.75 (1H, m), 7.50–7.00(10H, m), 6.85 (1H, d, J=7.3 Hz), 4.77 (1.2H, s), 4.41 (0.8H, s), 3.52 (0.8H, t, J=8.0 Hz), 3.34 (1.2H, t, J=8.0 Hz), 2.86 (0.8H, t, J=8.0 Hz), 2.79 (1.2H, t, J=8.0 Hz) ppm. FAB MS calcd for C$_{24}$H$_{21}$N$_3$O$_2$ 384 (MH$^+$), found 384. FAB HRMS exact mass calcd for C$_{24}$H$_{21}$N$_3$O$_2$ 384.17074 (MH$^+$), found 384.17065.

EXAMPLE 23

N-(1,2-diphenylethyl)-8-hydroxy-1,6-naphthyridine-7-carboxamide

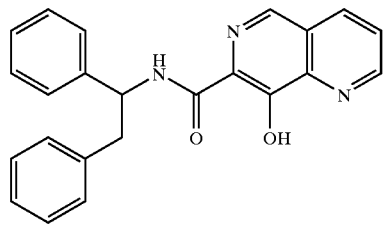

The title compound was prepared using the procedure described in Example 2, Step 2 replacing 2,5 dichlorobenzylamine with 1,2-diphenethylamine.

$^1$H NMR (d$_6$DMSO, 400 MHz) δ 9.77 (1H, d, J=9.0 Hz), 9.14 (1H, d, J=4.2 Hz), 8.93 (1H, s), 8.60 (1H, d, J=8.3 Hz), 7.85 (1H, ddd, J=8.3, 4.2 and 0.8 Hz), 7.56 (2H, d, J=7.7 Hz), 7.40–7.00 (8H, m), 5.37 (1H, m), 3.44 (1H, dd, J=10 and 13.6 Hz), 3.16 (1H, dd, J=10 and 5.4 Hz) ppm. FAB MS calcd for C$_{23}$H$_{19}$N$_3$O$_2$ 370 (MH$^+$), found 370. FAB HRMS exact mass calcd for C$_{23}$H$_{19}$N$_3$O$_2$ 370.155003 (MH$^+$), found 370.155737.

EXAMPLE 24

N-(2,3-dihydro-1H-inden-2-yl)-8-hydroxy-1,6-naphthyridine-7-carboxamide

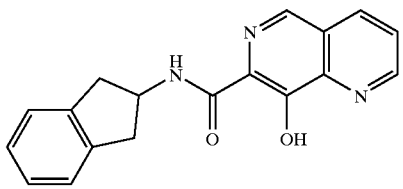

The title compound was prepared using the procedure described in Example 2, Step 2 replacing 2,5 dichlorobenzylamine with 2-aminoindane hydrochloride.

$^1$H NMR (d$_6$DMSO, 400 MHz) δ 9.64 (1H, d, J=7.8 Hz), 9.17 (1H, d, J=3.6 Hz), 8.90 (1H, s), 8.61 (1H, d, J=8.3 Hz), 7.84 (1H, ddd, J=8.3, 4.2 and 1.0 Hz), 7.30–7.10 (4H, m), 4.83 (1H, q, J=7.7), 3.25 (2H, dd, J=7.6 and 13.6 Hz), 3.14 (2H, dd, J=7.6 and 15.6 Hz) ppm. FAB MS calcd for C$_{18}$H$_{15}$N$_3$O$_2$ 306 (MH$^+$), found 306. FAB HRMS exact mass calcd for C$_{18}$H$_{15}$N$_3$O$_2$ 306.123703 (MH$^+$), found 306.122288.

EXAMPLE 25

N-benzyl-8-hydroxy-1,6-naphthyridine-7-carboxamide

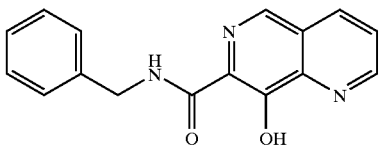

The title compound was prepared using the procedure described in Example 2, Step 2 replacing 2,5 dichlorobenzylamine with benzylamine.

$^1$H NMR (CD3OD, 400 MHz) δ 9.13 (1H, d, J=4.3 Hz), 8.88 (1H, s), 8.66 (1H, d, J=8.3 Hz), 7.87 (1H, dd, J=4.5 and 8.4 Hz), 7.43 (2H, d, J=9.7 Hz), 7.33 (2H, m), 7.26 (1H, m), and 4.67 (2H, s) ppm. FAB MS calcd for C$_{16}$H$_{13}$N$_3$O$_2$ 280.1 (MH$^+$), found 280.0.

EXAMPLE 26

N-(2-anilinoethyl)-8-hydroxy-1,6-naphthyridine-7-carboxamide

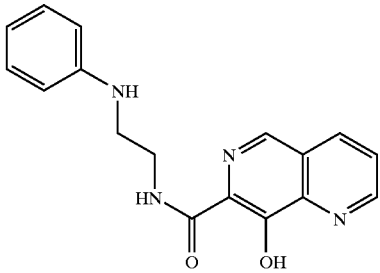

The title compound was prepared using the procedure described in Example 2, Step 2 replacing 2,5 dichlorobenzylamine with N-phenethyldiamine.

$^1$H NMR (d$_6$DMSO, 400 MHz) δ 9.44 (1H, t, J=5.7 Hz), 9.17 (1H, d, J=4.2 Hz), 8.92 (1H, s), 8.62 (1H, d, J=8.2 Hz), 7.84 (1H, dd, J=8.3 and 4.2 Hz), 7.10 (2H, t, J=8.2 Hz), 6.68 (2H, d, J=8.2 Hz), 6.58 (1H, t, J=7.1 Hz), 3.57 (2H, q, J=6.0 Hz), 3.29 (2H, t, J=7.6 Hz) ppm. FAB MS calcd for C$_{17}$H$_{16}$N$_4$O$_2$ 309 (MH$^+$), found 309. FAB HRMS exact mass calcd for C$_{17}$H$_{16}$N$_4$O$_2$ 309.1346022 (MH$^+$), found 309.133004.

EXAMPLE 27

N-(2,2-diphenylethyl)-8-hydroxy-1,6-naphthyridine-7-carboxyamide

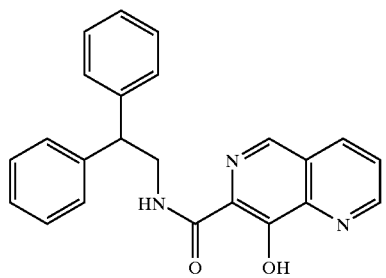

The title compound was prepared using the procedure described in Example 2, Step 2 replacing 2,5 dichlorobenzylamine with 2,2-diphenylethylamine.

$^1$H NMR (d$_6$DMSO, 400 MHz) δ 9.21 (1H, t, J=5.7 Hz), 9.14 (1H, d, J=4.3 Hz), 8.82 (1H, s), 8.57 (1H, d, J=8.4 Hz), 7.81 (1H, dd, J=8.4 and 4.3 Hz), 7.38 (4H, d, J=7.6 Hz), 7.30 (4H, d, J=7.6 Hz), 7.19 (2H, t, J=7.7 Hz), 4.58 (2H, t, J=7.0 Hz), 4.05 (2H, t, J=7.0 Hz) ppm. FAB MS calcd for C$_{23}$H$_{19}$N$_3$O$_2$ 370 (MH$^+$), found 370. FAB HRMS exact mass calcd for C$_{23}$H$_{19}$N$_3$O$_2$ 370.155033 (MH$^+$), found 370.1556930.

EXAMPLE 28

N-(3,3-diphenylpropyl)-8-hydroxy-1,6-naphthyridine-7-carboxamide

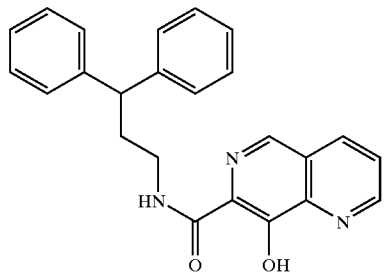

The title compound was prepared using the procedure described in Example 2, Step 2 replacing 2,5 dichlorobenzylamine with 3,3-diphenylpropylamine.

$^1$H NMR (d$_6$DMSO, 400 MHz) δ 9.36 (1H, t, J=5.7 Hz), 9.14 (1H, d, J=4.3 Hz), 8.89 (1H, s), 8.61 (1H, d, J=8.3 Hz), 7.82 (1H, dd, J=8.3 and 4.3 Hz), 7.35 (4H, d, J=7.6 Hz), 7.29 (4H, d, J=7.6 Hz), 7.16 (2H, t, J=7.7 Hz), 4.05 (2H, t, J=7.9 Hz), 3.31 (2H, m) and 2.40 (2H, q, J=7.5 Hz) ppm. FAB MS calcd for C$_{24}$H$_{21}$N$_3$O$_2$ 384 (MH$^+$), found 384. FAB HRMS exact mass calcd for C$_{24}$H$_{21}$N$_3$O$_2$ 384.1707 (MH$^+$), found 384.1708

EXAMPLE 29

N-(2-chloro-6-phenoxybenzyl)-8-hydroxy-1,6-naphthyridine-7-carboxamide

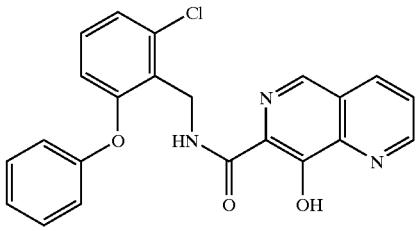

The title compound was prepared using the procedure described in Example 2, Step 2 replacing 2,5 dichlorobenzylamine with 2-aminomethyl-3-chlorodiphenylether.

$^1$H NMR (d$_6$DMSO, 400 MHz) δ 9.21 (1H, m), 9.15 (1H, d, J=4.2 Hz), 8.83 (1H, s), 8.60 (1H, d, J=8.3 Hz), 7.83 (1H, dd, J=8.3 and 4.2 Hz), 7.40–7.25 (4H, m), 7.15–7.00 (3H, m), 6.85 (1H, d, J=7.9 Hz), 4.82 (2H, d, J=5.5 Hz) ppm. FAB MS calcd for C$_{22}$H$_{16}$ClN$_3$O$_3$ 406 (MH$^+$), found 406. FAB HRMS exact mass calcd for C$_{22}$H$_{16}$ClN$_3$O$_3$ 406.09529 (MH$^+$), found 406.0944730.

EXAMPLE 30

Methyl (2R)-{[(8-hydroxy-1,6-naphthyridin-7-yl)carbonyl]amino}(phenyl)ethanoate

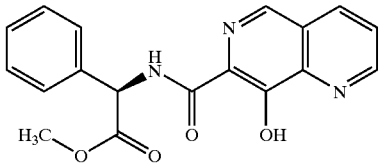

The title compound was prepared using the procedure described in Example 2, Step 2 replacing 2,5 dichlorobenzylamine with R(-)-2-phenylglycine methyl ester hydrochloride.

$^1$H NMR (d$_6$DMSO, 400 MHz) δ 9.82 (1H, m), 9.17 (1H, d, J=4.2 Hz), 8.94 (1H, s), 8.64 (1H, d, J=8.2 Hz), 7.85 (1H, ddd, J=8.2, 4.2 and 1.5 Hz), 7.60–7.30 (5H, m), 5.82 (1H, d, J=7.5 Hz), 3.72 (3H, s) ppm. FAB MS calcd for C$_{18}$H$_{15}$N$_3$O$_4$ 338(MH$^+$), found 338. FAB HRMS exact mass calcd for C$_{18}$H$_{15}$N$_3$O$_4$ 338.1135 (MH$^+$), found 338.1139.

EXAMPLE 31

8-hydroxy-N-(1,2,3,4-tetrahydronaphthalen-1-yl)-1,6-naphthyridine-7-carboxamide

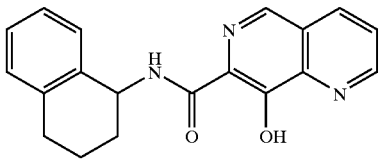

The title compound was prepared using the procedure described in Example 2, Step 2 replacing 2,5 dichlorobenzylamine with 1,2,3,4 tetrahydro-1-napthylamine.

$^1$H NMR (d$_6$DMSO, 400 MHz) δ 9.31(1H, d, J=9.1 Hz), 9.17 (1H, d, J=4.3 Hz), 8.88 (1H, s), 8.61 (1H, d, J=8.3 Hz), 7.84 (1H, dd, J=8.3 and 4.3 Hz), 7.30–7.00 (4H, m), 5.31 (1H, q, J=7.7 Hz), 3.00–2.60 (2H, m), 2.10–1.9 (3H, m), 1.85–1.70 (1H, m) ppm. FAB MS calcd for C$_{19}$H$_{17}$N$_3$O$_2$ 320(MH$^+$), found 320. FAB HRMS exact mass calcd for C$_{19}$H$_{17}$N$_3$O$_2$ 320.1394 (MH$^+$), found 320.1406.

EXAMPLE 32

N-(2,3-dihydro-1H-inden-1-ylmethyl)-8-hydroxy-1,6-naphthyridine-7-carboxamide

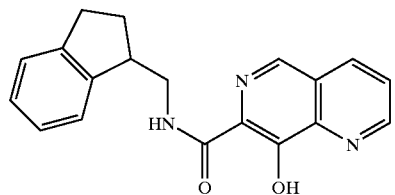

The title compound was prepared using the procedure described in Example 2, Step 2 replacing 2,5 dichlorobenzylamine with 1-(2,3-dihydro-1H-inden-1-yl)methanamine.

$^1$H NMR (d$_6$DMSO, 400 MHz) δ 9.42 (1H, m), 9.17 (1H, d, J=4.1 Hz), 8.92 (1H, s), 8.61 (1H, d, J=8.3 Hz), 7.84 (1H, dd, J=8.3 and 4.1 Hz), 7.40–7.10 (4H, m), 3.80–3.30 (3H, m), 3.05–2.70 (2H, m), 2.30–2.10 (1H, m) and 2.00–1.80 (1H, m) ppm. FAB MS calcd for C$_{19}$H$_{17}$N$_3$O$_2$ 320(MH$^+$), found 320. FAB HRMS exact mass calcd for C$_{19}$H$_{17}$N$_3$O$_2$ 320.1394 (MH$^+$), found 320.1393.

EXAMPLE 33

8-hydroxy-N-(6,7,8,9-tetrahydro-5H-benzo[a][7]annulen-6-ylmethyl)-1,6-naphthyridine-7-carboxamide

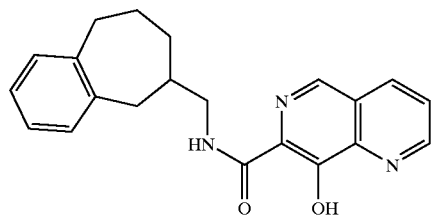

The title compound was prepared using the procedure described in Example 2, Step 2 replacing 2,5 dichlorobenzylamine with 1-(6,7,8,9-tetrahydro-5H-benzo[a][7]annulen-6-yl)methanamine.

$^1$H NMR (d$_6$DMSO, 400 MHz) δ 9.41 (1H, m), 9.16 (1H, dd, J=4.2 and 1.8 Hz), 8.92 (1H, s), 8.61 (1H, dd, J=8.2 and 1.8 Hz), 7.84 (1H, dd, J=8.2 and 4.2 Hz), 7.15–7.00 (4H, m), 3.40–3.20 (2H, m), 2.95–2.60 (4H, m), 2.00–1.75 (3H, m), 1.51 (1H, q, J=9.7 Hz) and 1.35(1H, q, J=9.7 Hz) ppm. FAB MS calcd for C$_{21}$H$_{21}$N$_3$O$_2$ 348 (MH$^+$), found 348. FAB HRMS exact mass calcd for C$_{21}$H$_{21}$N$_3$O$_2$ 348.1707 (MH$^+$), found 348.1691.

EXAMPLE 34

8-hydroxy-N-[2-(1-naphthylamino)ethyl]-1,6-naphthyridine-7-carboxamide

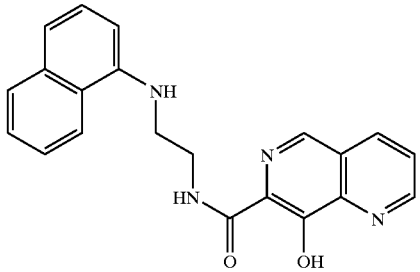

The title compound was prepared using the procedure described in Example 2, Step 2 replacing 2,5 dichlorobenzylamine with N-(1-naphthyl)ethane-1,2-diamine.

$^1$H NMR (d$_6$DMSO, 400 MHz) δ 9.61 (1H, t, J=6.0 Hz), 9.17 (1H, d, J=4.2 Hz), 8.93 (1H, s), 8.62 (1H, d, J=8.3 Hz), 8.15(1H, d, J=9.0 Hz), 7.84 (1H, dd, J=8.3 and 4.2 Hz), 7.77(1H, d, J=9.1 Hz), 7.50–7.35 (2H, m), 7.10 (2H, t, J=8.2 Hz), 7.31 (1H, t, J=8.9 Hz), 7.12(1H, d, J=8.2 Hz), 6.70 (1H, d, J=7.7 Hz), 3.74 (2H, q, J=6.2 Hz), 3.47 (2H, t, J=6.6 Hz) ppm. FAB MS calcd for C$_{21}$H$_{18}$N$_4$O$_2$ 359 (MH$^+$), found 359. FAB HRMS exact mass calcd for C$_{21}$H$_{18}$N$_4$O$_2$ 359.1503 (MH$^+$), found 359.1495.

EXAMPLE 35

N-(2,3-dihydro-1H-inden-2-ylmethyl)-8-hydroxy-1,6-naphthyridine-7-carboxamide

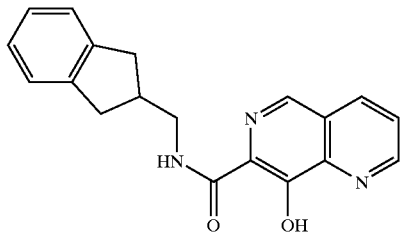

The title compound was prepared using the procedure described in Example 2, Step 2 replacing 2,5 dichlorobenzylamine with 1-(2,3-dihydro-1H-inden-2-yl)methanamine $^1$H NMR (d$_6$DMSO, 400 MHz) δ 9.49 (1H, m), 9.17 (1H, d, J=4.2 Hz), 8.92 (1H, s), 8.61 (1H, d, J=8.4 Hz), 7.84 (1H, dd, J=8.4 and 4.2 Hz), 7.25–7.15 (2H, m), 7.15–7.05 (2H, m), 3.44 (2H, t, J=6.6 Hz), 3.10–2.95 (2H, m), 2.90–2.70 (3H, m) ppm. FAB MS calcd for C$_{19}$H$_{17}$N$_3$O$_2$ 320 (MH$^+$), found 320. FAB HRMS exact mass calcd for C$_{19}$H$_{17}$N$_3$O$_2$ 320.1394 (MH$^+$), found 320.1392.

EXAMPLE 36

8-hydroxy-N-[(1R)-1-phenylethyl]-1,6-naphthyridine-7-carboxamide

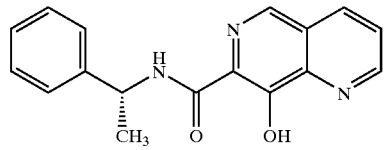

The title compound was prepared using the procedure described in Example 2, Step 2 replacing 2,5 dichlorobenzylamine with (R)-(+)-α-methylbenzylamine.

$^1$H NMR (DMSO-d6, 400 MHz) δ 9.58 (1H, d, J=8.3 Hz), 9.16 (1H, d, J=4.2 Hz), 8.93 (1H, s), 8.62 (1H, d, J=8.3 Hz), 7.84 (1H, dd, J=4.3 and 8.3 Hz), 7.48 (2H, d, J=7.8 Hz), 7.35 (2H, t, J=7.7), 7.25 (1H, t, J=7.4 Hz), 5.26 (1H, m) and 1.60 (3H, d, J=7.0 Hz) ppm. FAB MS calcd for C$_{17}$H$_{15}$N$_3$O$_2$ 294.1 (MH$^+$), found 294.1.

EXAMPLE 37

8-hydroxy-N-[(1S)-1-phenylethyl]-1,6-naphthyridine-7-carboxamide

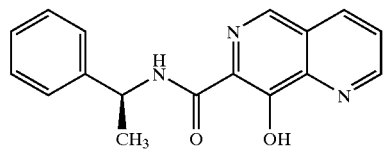

The title compound was prepared using the procedure described in Example 2, Step 2 replacing 2,5 dichlorobenzylamine with (S)-(−)-□□-methylbenzylamine.

$^1$H NMR (DMSO-d6, 400 MHz) δ 9.58 (1H, d, J=8.3 Hz), 9.16 (1H, d, J=4.2 Hz), 8.93 (1H, s), 8.62 (1H, d, J=8.3 Hz), 7.84 (1H, dd, J=4.3 and 8.3 Hz), 7.48 (2H, d, J=7.8 Hz), 7.35 (2H, t, J=7.7), 7.25 (1H, t, J=7.4 Hz), 5.26 (1H, m) and 1.60 (3H, d, J=7.0 Hz) ppm. FAB MS calcd for C$_{17}$H$_{15}$N$_3$O$_2$ 294.1 (MH$^+$), found 294.1.

EXAMPLE 38

8-hydroxy-N-(3-hydroxy-1-phenylpropyl)-1,6-naphthyridine-7-carboxamide

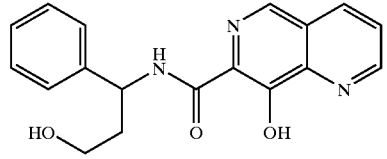

The title compound was prepared using the procedure described in Example 2, Step 2 replacing 2,5 dichlorobenzylamine with 3-amino-3-phenyl-1-propanol.

$^1$H NMR (DMSO-d6, 400 MHz) δ 9.75 (1H, d, J=8.1 Hz), 9.16 (1H, d, J=4.2 Hz), 8.94 (1H, s), 8.61 (1H, d, J=8.3 Hz), 7.83 (1H, dd, J=4.2 and 8.3 Hz), 7.46 (2H, d, J=7.8 Hz), 7.35 (2H, t, J=7.7 Hz), 7.25 (1H, t, J=7.8 Hz), 5.29 (1H, m), 3.45 (2H, t, J=5.8 Hz), 2.20 (1H, m) and 2.05 (1H, m) ppm. FAB MS calcd for C$_{18}$H$_{17}$N$_3$O$_3$ 324.1 (MH$^+$), found 324.1.

EXAMPLE 39

N-[2-(4-chlorophenyl)ethyl]-8-hydroxy-1,6-naphthyridine-7-carboxamide

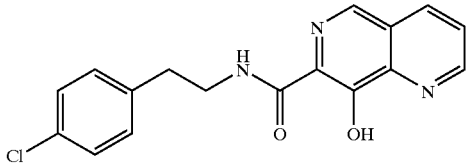

The title compound was prepared using the procedure described in Example 2, Step 2 replacing 2,5 dichlorobenzylamine with 4-chlorophenethylamine.

$^1$H NMR (DMSO-d6, 400 MHz) δ 9.37 (1H, br s), 9.16 (1H, d, J=4.2 Hz), 8.90 (1H, s), 8.61 (1H, d, J=8.3 Hz), 7.83 (1H, dd, J=4.2 and 8.2 Hz), 7.35 (2H, d, J=8.4 Hz), 7.29 (2H, d, J=0.8.4 Hz), 3.61(2H, q, J=7 Hz) and 2.93 (2H, t, J=7 Hz) ppm. FAB MS calcd for $C_{17}H_{14}ClN_3O_2$ 328.1 (MH$^+$), found 328.1.

EXAMPLE 40

8-hydroxy-N-[(1R)-2-hydroxy-1-phenylethyl]-1,6-naphthyridine-7-carboxamide

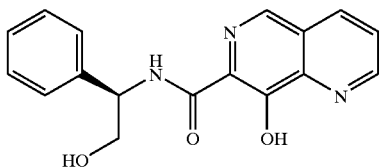

The title compound was prepared using the procedure described in Example 2, Step 2 replacing 2,5 dichlorobenzylamine with (R)-(−)-2-phenyl glycinol.

$^1$H NMR (DMSO-d6, 400 MHz) δ 9.49 (1H, d, 8 Hz), 9.16 (1H, d, J=4.2 Hz), 8.96 (1H, s), 8.64 (1H, d, J=8.3 Hz), 7.85 (1H, dd, J=4.2 and 8.2 Hz), 7.45 (2H, d, J=8.4 Hz), 7.35 (2H, t, J=0.7 Hz), 7.26(1H, t, J=7 Hz), 5.13 (1H, m), 3.88(1H, dd, J=7.5 and 11 Hz) and 3.78 (1H, dd, J=5.6 and 1 Hz) ppm. FAB MS calcd for $C_{17}H_{15}N_3O_3$ 310.1 (MH$^+$), found 310.1.

EXAMPLE 41

N-[(1S)-1-benzyl-2-hydroxyethyl]-8-hydroxy-1,6-naphthyridine-7-carboxamide

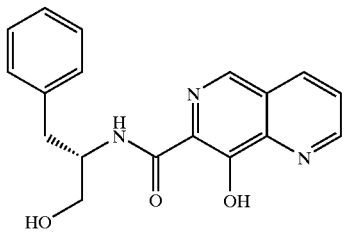

The title compound was prepared using the procedure described in Example 2, Step 2 replacing 2,5 dichlorobenzylamine with (S)-(−)-2-amino-3-phenyl-1-glycinol.

$^1$H NMR (DMSO-d6, 400 MHz) δ 13.7 (1H, s), 9.15 (1H, d, J=4.2 Hz), 8.96 (1H, d, J=8.2 Hz), 8.91 (1H, s), 8.60 (1H, d, J=8.3 Hz), 7.83 (1H, dd, J=4.2 and 8.2 Hz), 7.26 (4H, m), 7.16(1H, m), 5.02 (1H, br s), 4.28 (1H, m), 3.55 (2H, br s) and 2.96 (2H, m) ppm. FAB MS calcd for $C_{18}H_{17}N_3O_3$ 324.1 (MH$^+$), found 324.1.

EXAMPLE 42

N-[(1R)-1-benzyl-2-hydroxyethyl]-8-hydroxy-1,6-naphthyridine-7-carboxamide

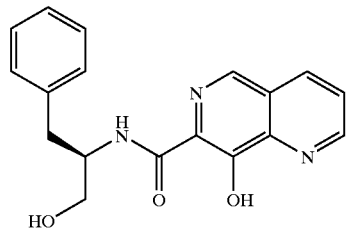

The title compound was prepared using the procedure described in Example 2, Step 2 replacing 2,5 dichlorobenzylamine with (R)-(+)-2-amino-3-phenyl-1-glycinol.

$^1$H NMR (DMSO-d6, 400 MHz) δ 13.7 (1H, s), 9.15 (1H, d, J=4.2 Hz), 8.96 (1H, d, J=8.2 Hz), 8.91 (1H, s), 8.60 (1H, d, J=8.3 Hz), 7.83 (1H, dd, J=4.2 and 8.2 Hz), 7.26 (4H, m), 7.16(1H, m), 5.02 (1H, br s), 4.28 (1H, m), 3.55 (2H, br s) and 2.96 (2H, m) ppm. FAB MS calcd for $C_{18}H_{17}N_3O_3$ 324.1 (MH$^+$), found 324.1.

EXAMPLE 43

8-hydroxy-N-(2-hydroxy-2-phenylethyl)-1,6-naphthyridine-7-carboxamide

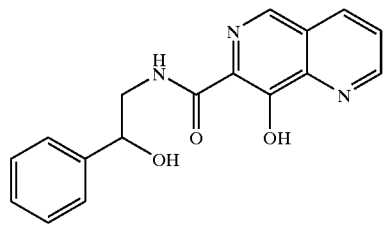

The title compound was prepared using the procedure described in Example 2, Step 2 replacing 2,5 dichlorobenzylamine with 2-amino-1-phenylethanol.

$^1$H NMR (DMSO-d6, 400 MHz) δ 9.17 (1H, d, J=4.2 Hz), 9.08 (1H, br s), 8.91 (1H, s), 8.61 (1H, d, J=8.4 Hz), 7.84 (1H, dd, J=4.4 and 8.2 Hz), 7.42 (2H, d, J=7.2 Hz), 7.35 (2H, t, J=7.4 Hz), 7.26 (1H, t, J=7.2 Hz), 4.88 (1H, dd, J=4.6 and 8.1 Hz), 3.4–3.7 (2H, m) ppm. FAB MS calcd for $C_{17}H_{15}N_3O_3$ 310.1 (MH$^+$), found 310.1.

EXAMPLE 44

5-chloro-N-(3,5-dichlorobenzyl)-8-hydroxy-1,6-naphthyridine-7-carboxamide

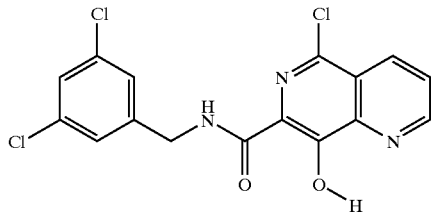

Step 1: Preparation of methyl-N-{[2-(isopropoxycarbonyl)pyridin-3-yl]carbonyl}glycine A solution of isopropyl 3-(chlorocarbonyl)pyridine-2-carboxylate (prepared as in P. Ornstein et. al. *J. Med. Chem.* 1989, 32, 827) (6.577 g, 31.44 mmol) in $CH_2Cl_2$ (50 ml) was added dropwise to a solution of glycine methyl ester hydrochloride (4.34 g, 34.58 mmol) and diisopropylethylamine (12.6 ml, 72.31 mmol) in $CH_2Cl_2$ (65 ml) at 0 C. The reaction was stirred for 16 hrs during which time the ice bath was allowed to expire. The solvent was evaporated in vacuo and the residue was used in the next step without further purification.

FAB MS calcd for $C_{13}H_{16}N_2O_5$ 281 (MH$^+$), found 281.

Step 2: Preparation of Methyl 5,8-dihydroxy-1,6-naphthyridine-7-carboxylate

The crude product from Step 1 (31.44 mmol) was dissolved in methanol (288 ml) and treated with sodium methoxide (28.7 ml of a 4.373M solution in methanol, 125.8 mmol) and heated at reflux for 16 hrs The reaction was cooled to room temperature and neutralized to pH 7 with aq. HCl and the solvent was evaporated in vacuo. The residue was partitioned between water and $CHCl_3$ and the organic layer separated and dried ($Na_2SO_4$). The solvent was evaporated in vacuo to afford the title compound along with its regioisomer, which were used in the next step without further purification.

FAB MS calcd for $C_{10}H_8N_2O_4$ 221 (MH$^+$), found 221.

Step 3: Preparation of methyl 5-chloro-8-hydroxy-1,6-naphthyridine-7-carboxylate The crude material from Step 2 (5.47 g, 24.85 mmol) was suspended in phosphorous oxychloride (45 ml) and heated at 106 C. for 30 mins. The solvent was evaporated in vacuo and the residue was cooled to 0 C. and treated sequentially with methanol (45 mL0 and then with a solution of sodium methoxide until a pH of >12 was obtained. The reaction was stirred for 2 hrs and then neutralised to pH 7 with sat. aq. $NH_4Cl$. The methanol was evaporated in vacuo and the residue was extracted with $CH_2Cl_2$ and dried ($Na_2SO_4$). The solvent was evaporated in vacuo to afford the title compound along with its regioisomer, which were used in the next step without further purification.

FAB MS calcd for $C_{10}H_7ClN_2O_3$ 239 (MH$^+$), found 239.

Step 4: Preparation of Methyl 5-chloro-8-[(4-methoxybenzyl)oxy]-1,6-naphthyridine-7-carboxylate To a slurry of the phenol from Step 3 (7.379 g, 30.79 mmol and cesium carbonate (11.04 g, 33.87 mmol) in DMF (154 ml) was added 4 methoxybenzyl chloride (4.38 ml, 32.33 mmol) at room temperature and the reaction was then warmed to 50 C. and stirred at this temperature for 16 hrs. The reaction mixture was poured into water and extracted into EtOAc and dried ($Na_2SO_4$). The solvent was evaporated in vacuo and the residue was chromatographed (SiO2, gradient elution, 25–30% EtOAc in hexanes) to afford a solid, which was washed with hexanes and then diethyl ether and dried in vacuo to afford the title compound.

FAB MS calcd for $C_{10}H_7ClN_2O_3$ 359 (MH$^+$), found 359.

Step 5: Preparation of 5-chloro-N-(3,5-dichlorobenzyl)-8-hydroxy-1,6-naphthyridine-7-carboxamide The title compound was prepared using the procedure described in Example 1, Step 3 replacing with methyl 8-hydroxy-1,6-naphthyridine-7-carboxylate with methyl 5-chloro-8-[(4-methoxybenzyl)oxy]-1,6-naphthyridine-7-carboxylate from Step 4.

$^1$H NMR (CDCl$_3$, 400 MHz) δ 13.13 (1H, s), 9.25 (1H, d, J=4.2 Hz), 8.61 (1H, d, J=8.5 Hz), 8.23 (1H, brs), 7.77 (1H, dd, J=8.5 and 4.2 Hz), 7.35–7.20 (3H, m), 4.65 (2H, d, J=6.4 Hz) ppm. FAB MS calcd for $C_{16}H_{10}N_3O_2Cl_3$ 383 (MH$^+$), found 383.

EXAMPLE 45

N-(3,5-dichlorobenzyl)-8-hydroxy-5-piperidin-1-yl-1,6-naphthyridine-7-carboxamide

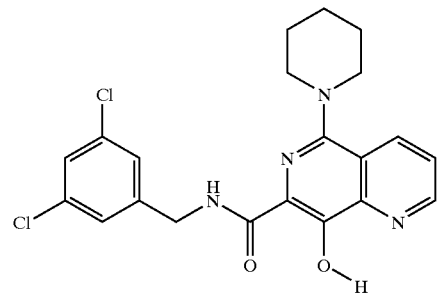

A solution of the chloride from Example 44 Step 5 (40 mg, 0.105 mmol) in piperidine (0.5 ml) was heated at 100 C. for 36 hrs under argon. The resulting solution was cooled to room temperature and the solvent evaporated in vacuo. The residue was dissolved in hot DMF (0.7 ml) and purified by preparative HPLC. (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (CDCl$_3$, 400 MHz) δ 9.30 (1H, s), 8.60 (1H, d, J=8.6 Hz), 8.24 (1H, brs), 7.74 (1H, m), 7.35–7.20 (3H, m), 4.65 (2H, d, J=6.2 Hz), 3.26 (4H, m), 1.84 (4H, m) and 1.71 (2H, m) ppm. FAB MS calcd for $C_{21}H_{20}N_4O_2Cl_2$ 431 (MH$^+$), found 431.

EXAMPLE 46

N-(3,5-dichlorobenzyl)-8-hydroxy-5-phenyl-1,6-naphthyridine-7-carboxamide

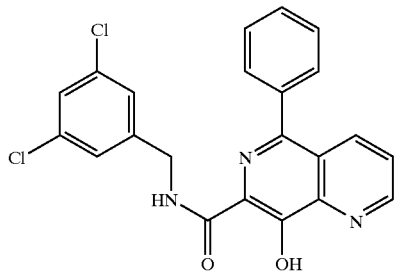

Step 1: Preparation of methyl 8-[(4-methoxybenzyl)oxy]-5-phenyl-1,6-naphthyridine-7-carboxylate A solution of the chloride from Example 44 Step 4 (100 mg, 0.279 mmol), phenyl boronic acid (37.4 mg, 0.307 mmol), tetrakis triphenylphosphine palladium (32.24 mg, 0.0279 mmol) and potassium carbonate (88.95 mg, 0.419 mmol) in DMF (1.7 ml) was stirred at 100 C for 16 hrs. The reaction was allowed to cool to room temperature and pored into water and extracted into $CH_2Cl_2$ and dried ($Na_2SO_4$). The solvent was evaporated in vacuo and the residue was chromatographed ($SiO_2$, gradient elution, 20–30% EtOAc in hexanes) to afford the title compound.

FAB MS calcd for $C_{24}H_{20}N_2O_4$ 401 (MH$^+$), found 401.

Step 2: Preparation of N-(3,5-dichlorobenzyl)-8-hydroxy-5-phenyl-1,6-naphthyridine-7-carboxamide A mixture of the ester from Step 1 (40 mg, 0.10 mmol) and 3,5,dichlorobenzylamine (0.35 g, 2.0 mmol) were heated at 100 C. for 18 hrs. The solvent was evaporated in vacuo and the residue was purified by preparative HPLC. (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (CDCl$_3$, 400 MHz) δ 9.23 (1H, d, J=4.2 Hz), 8.53 (1H, m), 8.42 (1H, d, J=8.6 Hz), 7.70–7.45 (6H, m), 7.30–7.10 (3H, m), 4.66 (2H, d, J=5.4 Hz) ppm. FAB MS calcd for $C_{22}H_{15}N_3O_2Cl_2$ 424 (MH$^+$), found 424.

EXAMPLE 47

N-(3,5-dichlorobenzyl)-8-hydroxy-5-(1H-imidazol-1-yl)-1,6-naphthyridine-7-carboxamide

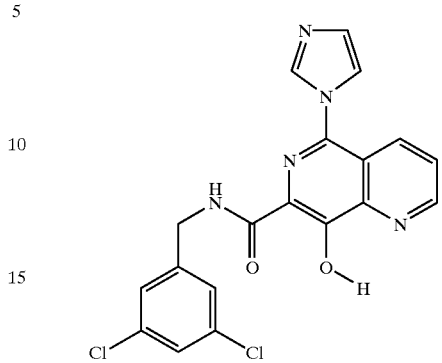

The chloride from Example 44 Step 5 (8.0 mg, 0.021 mmol) and imidazole (80 mg) were fused at 160 C for 1 hr under argon. The residue was dissolved in DMF (0.5 ml) and purified by preparative HPLC. (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (CDCl$_3$, 400 MHz) δ 9.27 (1H, d, J=4.2 Hz), 8.23 (1H, d, J=7.5 Hz), 7.96 (1H, s), 7.73 (1H, dd, J=4.2 and 8.6 Hz), 7.40 (1H, s), 7.38–7.20 (3H, m), 4.66 (2H, d, J=6.2 Hz) ppm. FAB MS calcd for $C_{19}H_{13}N_5O_2Cl_2$ 414 (MH$^+$), found 414.

EXAMPLE 48

N-(3,5-dichlorobenzyl)-8-hydroxy-5-morpholin-4-yl-1,6-naphthyridine-7-carboxamide

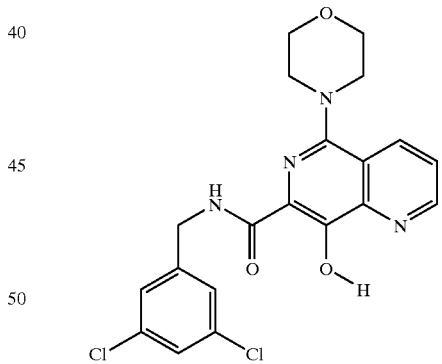

A solution of the chloride from Example 44 Step 5 (14 mg, 0.037 mmol) in morpholine (0.5 ml) was heated at 120C for 36 hrs under argon. The resulting solution was cooled to room temperature and the solvent evaporated in vacuo. The residue was dissolved in hot DMF (0.5 ml) and purified by preparative HPLC. (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (CDCl$_3$, 400 MHz) δ 9.24 (1H, d, J=4.4 Hz), 8.60 (1H, d, J=8.2 Hz), 8.20 (1H, brs), 7.68 (1H, dd, J=4.4 and 8.2 Hz), 7.35–7.20 (3H, m), 4.67 (2H, d, J=6.3 Hz), 3.98

(4H, t, J=4.5 Hz), and 3.28 (4H, t, J=4.5 Hz) ppm. FAB MS calcd for $C_{20}H_{18}N_4O_3Cl_2$ 433 (MH$^+$), found 433.

EXAMPLE 49

8-hydroxy-N-[(cis)-3-phenyl-2,3-dihydro-1H-inden-1-yl]-1,6-naphthyridine-7-carboxamide

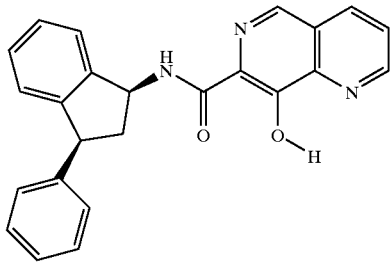

The title compound was prepared using the procedure described in Example 2, Step 2 replacing 2,5 dichlorobenzylamine with cis-3-phenyl-2,3-dihydro-1H-inden-1-amine (Baltrop et al *J. Chem. Soc.* 1956, 2928).

$^1$H NMR (CDCl$_3$, 400 MHz) δ 9.22 (1H, d, J=4.2 Hz), 8.65 (1H, s), 8.41(1H, d, J=9.3 Hz), 8.31 (1H, d, J=8.4 Hz), 7.68 (1H, dd, J=4.2 and 8.4 Hz), 7.41 (1H, d, J=7.0 Hz), 7.38–7.20 (7H, m), 6.98 (1H, d, J=7.7 Hz), 5.76 (1H, q, J=8.4 Hz), 4.35 (1H, t, J=7.2 Hz), 3.17 (1H, dt, J=12.6 and 7.3 Hz), 2.04(1H, dt, J=12.6 and 9.7 Hz) ppm. FAB MS calcd for $C_{24}H_{19}N_3O_2$ 382 (MH$^+$), found 382.

EXAMPLE 50

5-bromo-N-(3,5-dichlorobenzyl)-8-hydroxy-1,6-naphthyridine-7-carboxamide

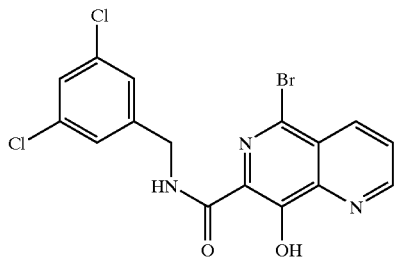

To a solution of N-(3,5-dichlorobenzyl)-8-hydroxy-1,6-naphthyridine-7-carboxamide from Example 1, Step 3 (1.28 g, 3.69 mmol) in CH$_2$Cl$_2$ (100 ml) at room temperature was added N-bromosuccinimide (0.689 g, 3.87 mmol). The reaction was stirred for 4 hrs and then poured into water. The organic phase was washed with water (3×100 ml), and dried (Na$_2$SO$_4$). The solvent was evaporated in vacuo and the residue triturated with CH$_2$Cl$_2$ to afford the title compound as an off white solid.

$^1$H NMR (CDCl$_3$, 400 MHz) δ 13.12 (1H, s), 9.21 (1H, d, J=4.4 Hz), 8.60 (1H, d, J=8.4 Hz), 8.23 (1H, brs), 7.75 (1H, dd, J=4.2 and 8.4 Hz), 7.35–7.20 (3H, m), 4.66 (2H, d, J=6.4 Hz) ppm. FAB MS calcd for $C_{16}H_{10}BrCl_2N_3O_2$ 426 (MH$^+$), found 426.

EXAMPLE 51

N-(benzyl)-8-hydroxy-5-phenyl-1,6-naphthyridine-7-carboxamide

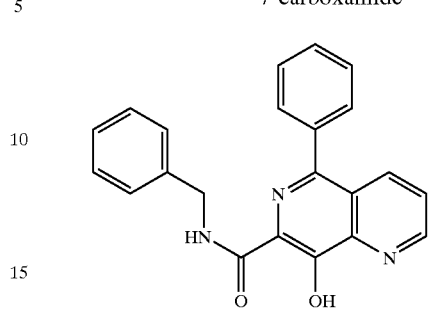

A mixture of the ester from Example 44 Step 1 (21 mg, 0.0524 mmol) and benzylamine (0.0.143 ml, 1.31 mmol) were heated at 100 C for 18 hrs. The reaction was diluted with DMF (0.4 ml) and purified by preparative HPLC. (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (CDCl$_3$, 400 MHz) δ 9.20 (1H, d, J=4.0 Hz), 8.53 (1H, m), 8.42 (1H, dd, J=8.6 and 2.5 Hz), 7.70–7.45 (6H, m), 7.45–7.15 (5H, m), 4.66 (2H, d, J=6.5 Hz) ppm. FAB MS calcd for $C_{22}H_{17}N_3O_2$ 356 (MH$^+$), found 356. FAB HRMS exact mass calcd for $C_{22}H_{17}N_3O_2$ 356.1393533 (MH$^+$), found 356.1386040.

EXAMPLE 52

N-(2,3-dihydro-1H-inden-1-yl)-8-hydroxy-5-phenyl-1,6-naphthyridine-7-carboxamide

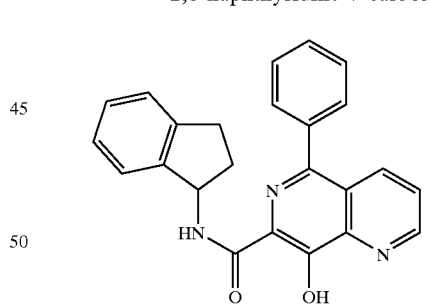

The title compound was prepared using the procedure described in Example 51 replacing benzylamine with aminoindane.

$^1$H NMR (CDCl$_3$, 400 MHz) δ 9.23 (1H, d, J=4.0 Hz), 8.44 (1H, d, J=1.5 Hz), 8.42 (1H, dd, J=8.4, 1.5 Hz), 8.34 (1H, d, J=8.7 Hz), 7.62 (1H, dd, J=8.4 and 4.2 Hz), 7.60–7.45 (4H, m), 7.38 (1H, d, J=7.5 Hz), 7.35–7.15 (5H, m), 5.75 (1H, q, J=8.0 Hz), 3.20–2.90 (2H, m), 2.73 1H, m) and 2.20–1.80 (1H, m) ppm. FAB MS calcd for $C_{24}H_{20}N_3O_2$ 382 (MH$^+$), found 382. FAB HRMS exact mass calcd for $C_{24}H_{20}N_3O_2$ 382.1550033 (MH$^+$), found 382.1549400.

EXAMPLE 53

8-hydroxy-N-(1-naphthylmethyl)-5-phenyl-1,6-naphthyridine-7-carboxamide

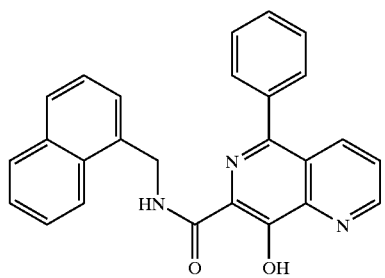

The title compound was prepared using the procedure described in Example 51 replacing benzylamine with 1-napthylmethylamine.

$^1$H NMR (CDCl$_3$, 400 MHz) δ 9.20 (1H, d, J=4.0 Hz), 8.44 (1H, m), 8.37 (1H, dd, J=8.4 and 1.7 Hz), 8.15 (1H, d, J=8.3 Hz), 7.89 (1H, d, J=7.8 Hz), 7.84 (1H, d, J=8.1 Hz), 7.60–7.00 (10H, m), 5.18 (1H, d, J=6.2 Hz) ppm. FAB MS calcd for C$_{26}$H$_{19}$N$_3$O$_2$ 406 (MH$^+$), found 406. FAB HRMS exact mass calcd for C$_{26}$H$_{19}$N$_3$O$_2$ 406.1550033 (MH$^+$), found 406.1562180.

EXAMPLE 54

N-(2,5-dichlorobenzyl)-8-hydroxy-5-phenyl-1,6-naphthyridine-7-carboxamide

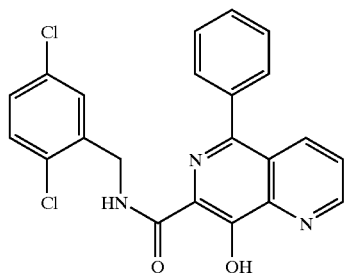

The title compound was prepared using the procedure described in Example 51 replacing benzylamine with 2,5-dichlorobenzylamine.

$^1$H NMR (CDCl$_3$, 400 MHz) δ 9.20 (1H, d, J=4.0 Hz), 8.62 (1H, m), 8.42 (1H, dd, J=8.6, 2.5 Hz), 7.70–7.20 (9H, m), 4.76 (2H, d, J=7.6 Hz) ppm. FAB MS calcd for C$_{22}$H$_{15}$Cl$_2$N$_3$O$_2$ 424 (MH$^+$), found 424. FAB HRMS exact mass calcd for C$_{22}$H$_{15}$Cl$_2$N$_3$O$_2$ 424.0614086 (MH$^+$), found 424.0616930.

EXAMPLE 55

N-(3-chlorobenzyl)-8-hydroxy-5-phenyl-1,6-naphthyridine-7-carboxamide

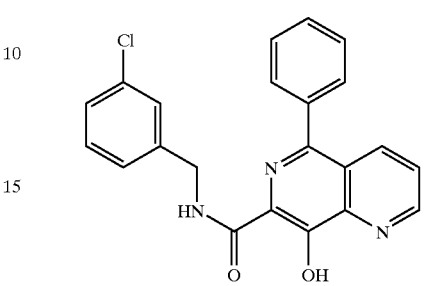

The title compound was prepared using the procedure described in Example 51 replacing benzylamine with 3-chlorobenzylamine.

$^1$H NMR (CDCl$_3$, 400 MHz) δ 9.23 (1H, d, J=2.7 Hz), 8.52 (1H, m), 8.44 (1H, dd, J=8.8 and 1.5 Hz), 7.70–7.20 (10H, m), 4.68 (2H, d, J=6.6 Hz) ppm. FAB MS calcd for C$_{22}$H$_{16}$ClN$_3$O$_2$ 390 (MH$^+$), found 390. FAB HRMS exact mass calcd for C$_{22}$H$_{16}$ClN$_3$O$_2$ 390.1003809 (MH$^+$), found 390.1008681.

EXAMPLE 56

N-[(1S)-2,3-dihydro-1H-inden-1-yl]-8-hydroxy-1,6-naphthyridine-7-carboxamide

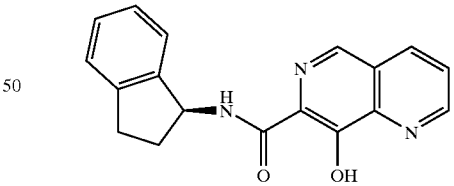

The title compound was prepared using the procedure described in Example 2, Step 2 replacing 2,5 dichlorobenzylamine with 1(S) aminoindane.

$^1$H NMR (d$_6$DMSO, 400 MHz) δ 9.41 (1H, d, J=8.2 Hz), 9.18 (1H, d, J=4.2 Hz), 8.90 (1H, s), 8.63 (1H, d, J=8.2 Hz), 7.85 (1H, dd, J=8.2 and 4.2 Hz), 7.35–7.10 (4H, m), 5.63

(1H, q, J=8.2 Hz), 3.20–2.80 (2H, m), 2.60–2.40 (1H, m), 2.30–2.10 (1H, m) ppm. FAB MS calcd for $C_{18}H_{15}N_3O_2$ 306 (MH$^+$), found 306. FAB HRMS exact mass calcd for $C_{18}H_{15}N_3O_2$ 306.1237 (MH$^+$), found 306.1209

EXAMPLE 57

N-(3,5-dichlorobenzyl)-8-hydroxy-5-phenoxy-1,6-naphthyridine-7-carboxamide

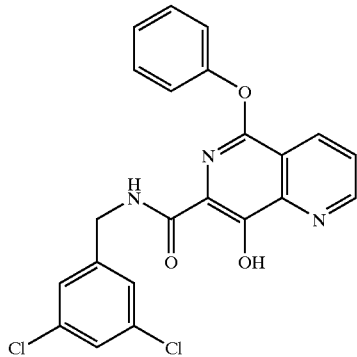

To a solution of 5-bromo-N-(3,5-dichlorobenzyl)-8-hydroxy-1,6-naphthyridine-7-carboxamide from Example 50 (26 mg, 0.068 mmol), phenol (28 mg, 0.304 mmol) and cesium carbonate (198 mg, 0.608 mmol) in DMPU (0.25 ml) was heated at 140C for 8 hrs. The reaction was poured into sat aq. $Na_2CO_3$ and extracted with $CHCl_3$. The organic phase was washed with water and dried ($Na_2SO_4$). The solvent was evaporated in vacuo and the residue dissolved in DMF (0.7 ml) and purified by preparative HPLC. (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (CDCl$_3$, 400 MHz) δ 12.55 (1H, s), 9.31 (1H, d, J=4.4 Hz), 8.80 (1H, d, J=8.4 Hz), 7.78 (1H, dd, J=4.4 and 8.4 Hz), 7.61(1H, t, J=5.5 Hz), 7.44 (2H, t, J=7.9 Hz), 7.35–7.20 (6H, m), 7.10 (2H, d, J=1.8 Hz), 4.49 (2H, d, J=6.2 Hz) ppm. FAB MS calcd for $C_{22}H_{15}Cl_2N_3O_3$ 440 (MH$^+$), found 440.

EXAMPLE 58

N-(3,5-dichlorobenzyl)-8-hydroxy-5-(4-methylpiperazin-1-yl)-1,6-naphthyridine-7-carboxamide

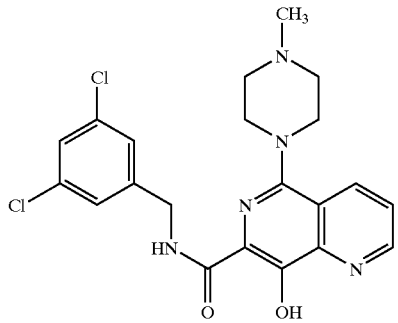

To a solution of 5-bromo-N-(3,5-dichlorobenzyl)-8-hydroxy-1,6-naphthyridine-7-carboxamide from Example 50 (25 mg, 0.060 mmol), N-methyl piperazine (35.2 mg, 0.35 mmol) in DMF (0.25 ml) was heated at 135C for 48 hrs. The reaction mixture was diluted with DMF (0.25 ml) and purified by preparative HPLC. (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (CDCl$_3$, 400 MHz) δ 13.0 (1H, s), 9.21 (1H, d, J=4.2 Hz), 8.36 (1H, dd, J=8.4 and 1.5 Hz), 8.25 (1, t, J=6.4 Hz), 7.65 (1H, dd, J=4.2 and 8.4 Hz), 7.35–7.20 (3H, m), 4.67 (2H, d, J=6.2 Hz), 3.79 (2H, d, J=11.9 Hz), 3.60 (4H, m), 3.19 (2H, m) and 2.96 (3H, s) ppm. FAB MS calcd for $C_{21}H_{21}Cl_2N_5O_3$ 446 (MH$^+$), found 446. FAB HRMS exact mass calc'd for $C_{21}H_{21}Cl_2N_5O_3$ 446.1145 (MH$^+$), found 446.1138.

EXAMPLE 59

5-(4-benzylpiperazin-1-yl)-N-(3,5-dichlorobenzyl)-8-hydroxy-1,6-naphthyridine-7-carboxamide

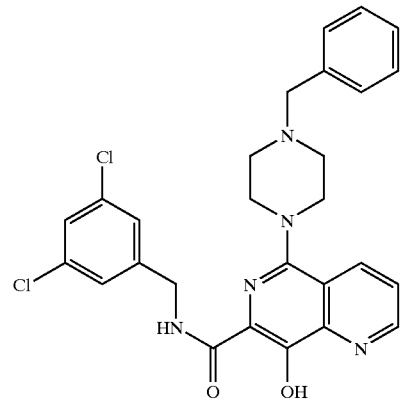

The title compound was prepared using the procedure described in Example 58 replacing N-methyl piperazine with N-benzylpiperazine.

$^1$H NMR (CDCl$_3$, 400 MHz) δ 12.94 (1H, s), 9.21 (1H, dd, J=4.3 and 1.5 Hz), 8.33 (1H, dd, J=8.4 and 1.6 Hz), 8.27(1H, t, J=6.4 Hz), 7.62 (1H, dd, J=4.2 and 8.4 Hz), 7.55–7.40 (5H, m), 7.35–7.20 (3H, m), 4.64 (2H, d, J=6.6 Hz), 4.32 (2H, s), 3.80–3.50 (6H, m), 3.12 (2H, t, J=9.0 Hz) ppm. FAB MS calcd for $C_{27}H_{25}Cl_2N_5O_2$ 522 (MH$^+$), found 522. FAB HRMS exact mass calc'd for $C_{27}H_{25}Cl_2N_5O_2$ 522.1458 (MH$^+$), found 522.1420.

EXAMPLE 60

N-(3,5-dichlorobenzyl)-5-{4-[2-(formylamino)ethyl]piperazin-1-yl}-8-hydroxy-1,6-naphthyridine-7-carboxamide

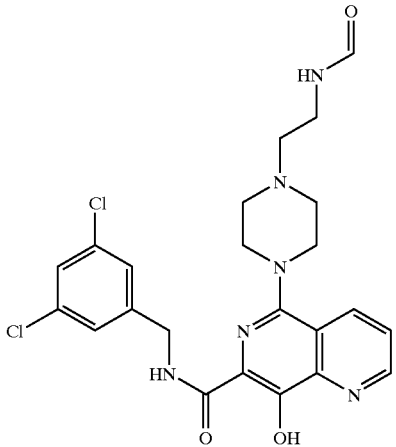

The title compound was prepared using the procedure described in Example 58 replacing N-methyl piperazine with 2-piperazin-1-ylethanamine.

$^1$H NMR (CDCl$_3$, 400 MHz) δ 12.99 (1H, s), 9.20 (1H, dd, J=4.2 and 1.6 Hz), 8.35 (1H, dd, J=8.4 and 1.6 Hz), 8.22 (1H, s), 7.82 (1H, t, J=6.0 Hz), 7.64 (1H, dd, J=4.2 and 8.4 Hz), 7.35–7.40 (3H, m), 4.66 (2H, d, J=6.6 Hz), 4.00–3.10 (12H, m) ppm. FAB MS calcd for C$_{23}$H$_{24}$Cl$_2$N$_6$O$_3$ 503 (MH$^+$), found 503. FAB HRMS exact mass calc'd for C$_{23}$H$_{24}$Cl$_2$N$_6$O$_3$ 503.1360 (MH$^+$), found 503.1371.

EXAMPLE 61

N-(3,5-dichlorobenzyl)-8-hydroxy-5-(4-pyridin-2-ylpiperazin-1-yl)-1,6-naphthyridine-7-carboxamide

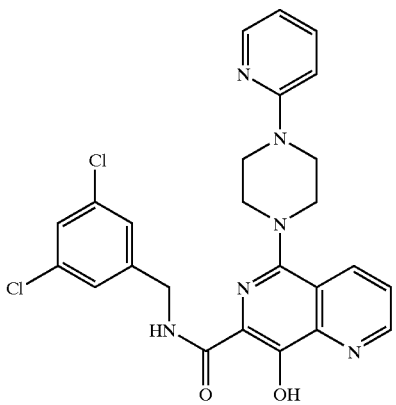

The title compound was prepared using the procedure described in Example 58 replacing N-methyl piperazine with N-pyridin-2-ylpiperazine.

$^1$H NMR (CDCl$_3$, 400 MHz) δ 12.87 (1H, s), 9.20 (1H, dd, J=4.4 and 1.6 Hz), 8.46 (1H, dd, J=8.5 and 1.6 Hz), 8.29 (1H, t, J=6.6 Hz), 7.26 (1H, dd, J=6.1 and 1.8 Hz), 7.89 (1H, m), 7.66 (1H, dd, J=4.4 and 8.5 Hz), 7.35–7.20 (3H, m), 7.04 (1H, d, J=9.1 Hz), 6.92 (1H, t, J=6.5 Hz), 4.66 (2H, d, J=6.4 Hz), 4.02 (4H, t, J=5.0 Hz), 3.50 (4H, t, J=5.0 Hz) ppm. FAB MS calcd for C$_{25}$H$_{22}$Cl$_2$N$_6$O$_3$ 509 (MH$^+$), found 509. FAB HRMS exact mass calc'd for C$_{25}$H$_{22}$Cl$_2$N$_6$O$_3$ 509.1254 (MH$^+$), found 509.1257.

EXAMPLE 62

N-(3,5-dichlorobenzyl)-8-hydroxy-5-(4-pyrrolidin-1-ylpiperidin-1-yl)-1,6-naphthyridine-7-carboxamide

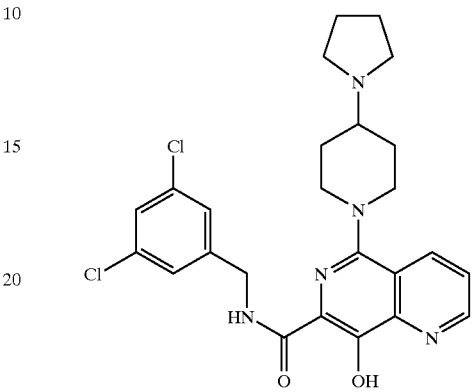

The title compound was prepared using the procedure described in Example 58 replacing N-methyl piperazine with 4-pyrrolidin-1-ylpiperidine.

$^1$H NMR (CDCl$_3$, 400 MHz) δ 12.75 (1H, s), 9.20 (1H, dd, J=4.2 and 1.6 Hz), 8.41 (1H, dd, J=8.4 and 1.6 Hz), 8.15 (1H, t, J=6.4 Hz), 7.64 (1H, dd, J=4.2 and 8.4 Hz), 7.35–7.20 (3H, m), 4.66 (2H, d, J=6.4 Hz), 3.94 (2H, m), 3.70(2H, m) 3.12 (1H, m), 3.00–2.80(2H, m), 2.40–1.80 (8H, m)ppm. FAB MS calcd for C$_{25}$H$_{27}$Cl$_2$N$_5$O$_2$ 500 (MH$^+$), found 500. FAB HRMS exact mass calc'd for C$_{25}$H$_{27}$Cl$_2$N$_5$O$_2$ 500.1615 (MH$^+$), found 500.1626.

EXAMPLE 63

5-anilino-N-(3,5-dichlorobenzyl)-8-hydroxy-1,6-naphthyridine-7-carboxamide

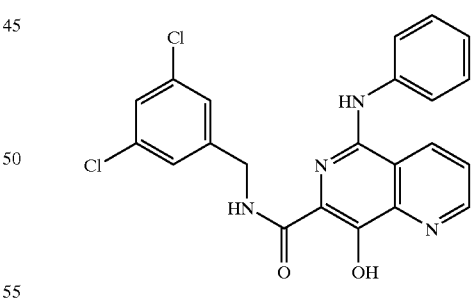

The title compound was prepared using the procedure described in Example 58 replacing N-methyl piperazine with aniline.

$^1$H NMR (CDCl$_3$, 400 MHz) δ 12.30 (1H, s), 9.19 (1H, dd, J=4.2 and 1.5 Hz), 8.32 (1H, dd, J=8.4 and 1.5 Hz), 8.15 (1H, t, J=6.0 Hz), 7.63 (1H, dd, J=4.2 and 8.4 Hz), 7.40–7.00 (8H, m), 4.60 (2H, d, J=6.0 Hz) ppm. FAB MS calcd for C$_{22}$H$_{16}$Cl$_2$N$_4$O$_2$ 439 (MH$^+$), found 439. FAB HRMS exact mass calc'd for C$_{22}$H$_{16}$Cl$_2$N$_4$O$_2$ 439.0723 (MH$^+$), found 439.0700.

EXAMPLE 64

N-(3,5-dichlorobenzyl)-5-{[3-(formylamino)propyl]amino}-8-hydroxy-1,6-naphthyridine-7-carboxamide

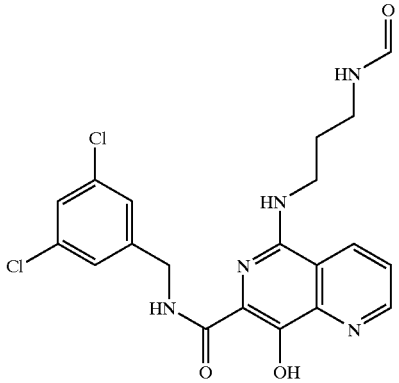

The title compound was prepared using the procedure described in Example 58 replacing N-methyl piperazine with 1,3-diaminopropane.

$^1$H NMR (CDCl$_3$ 400 MHz) δ 9.15 (1H, dd, J=4.4 and 1.5 Hz), 8.48 (1H, d, J=8.8 Hz), 8.35–8.25 (2H, m), 8.15 (1H, t, J=6.0 Hz), 7.63 (1H, dd, J=4.4 and 8.4 Hz), 7.35–7.15 (3H, m), 5.96 (1H, br s), 4.66 (2H, d, J=6.6 Hz), 3.61 (2H, t, J=6.0 Hz), 3.48 (2H, q, =6.0 Hz), 1.91(2H, qnt J=6.0 Hz) ppm. FAB MS calcd for C$_{20}$H$_{19}$Cl$_2$N$_5$O$_3$ 448 (MH$^+$), found 448. FAB HRMS exact mass calc'd for C$_{20}$H$_{19}$Cl$_2$N$_5$O$_3$ 448.0938 (MH$^+$), found 448.0936.

EXAMPLE 65

N-(3,5-dichlorobenzyl)-5-{[2-(dimethylamino)ethyl]amino}-8-hydroxy-1,6-naphthyridine-7-carboxamide

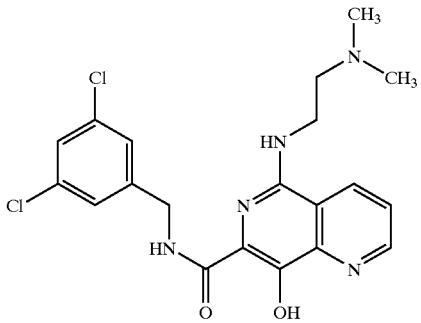

The title compound was prepared using the procedure described in Example 58 replacing N-methyl piperazine with N,N, dimethylaminoethane.

$^1$H NMR (CDCl$_3$, 400 MHz) δ 13.00 (1H, s), 9.10 (1H, d, J=4.2 Hz), 8.54 (1H, d, J=8.4 Hz), 8.23 (1H, t, J=6.0 Hz), 7.58 (1H, dd, J=4.2 and 8.4 Hz), 7.35–7.15 (3H, m), 4.66 (2H, d, J=6.4 Hz) 3.96 (2H, t, J=5.3 Hz), 3.41 (2H, m), 2.93 (6H, s) ppm. FAB MS calcd for C$_{20}$H$_{21}$Cl$_2$N$_5$O$_2$ 434 (MH$^+$), found 434. FAB HRMS exact mass calc'd for C$_{20}$H$_{21}$Cl$_2$N$_5$O$_2$ 434.1145 (MH$^+$), found 434.1147.

EXAMPLE 66

N-(3,5-dichlorobenzyl)-8-hydroxy-5-[(2-morpholin-4-ylethyl)amino]-1,6-naphthyridine-7-carboxamide

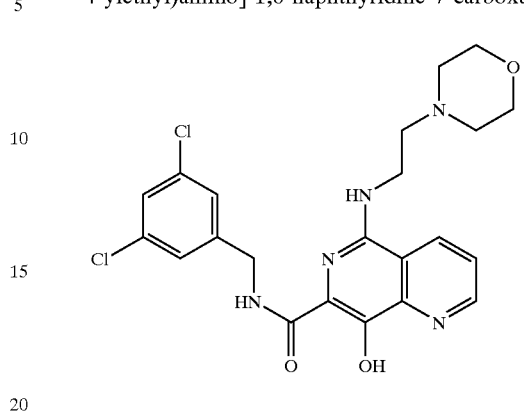

The title compound was prepared using the procedure described in Example 58 replacing N-methyl piperazine with 2-morpholin-4-ylethanamine.

$^1$H NMR (CDCl$_3$, 400 MHz) δ 9.14 (1H, dd, J=4.2 and 1.5 Hz), 8.42 (1H, dd, J=8.4 and 1.5 Hz), 8.33 (1H, t, J=6.0 Hz), 7.58 (1H, dd, J=4.2 and 8.4 Hz), 7.35–7.15 (3H, m), 4.66 (2H, d, J=6.4 Hz) 4.00 (6H, m), 3.60 (2H, m), 3.43 (2H, t, J=5.6 Hz), 2.90 (2H, m) ppm. FAB MS calcd for C$_{22}$H$_{23}$Cl$_2$N$_5$O$_3$ 476 (MH$^+$), found 476. FAB HRMS exact mass calc'd for C$_{22}$H$_{23}$Cl$_2$N$_5$O$_3$ 476.1251 (MH$^+$), found 476.1229.

EXAMPLE 67

5-[(1-benzylpiperidin-4-yl)amino]-N-(3,5-dichlorobenzyl)-8-hydroxy-1,6-naphthyridine-7-carboxamide

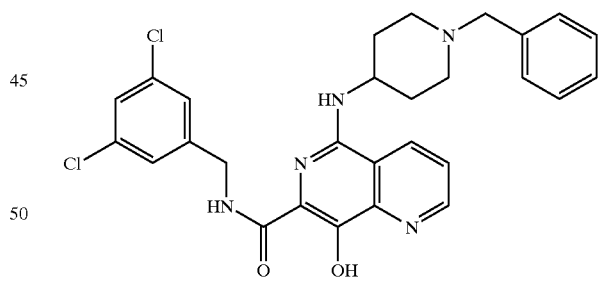

The title compound was prepared using the procedure described in Example 58 replacing N-methyl piperazine with 1-benzylpiperidin-4-amine.

$^1$H NMR (CDCl$_3$, 400 MHz) δ 9.16 (1H, dd, J=4.4 and 1.5 Hz), 8.25 (1H, d, J=8.4 Hz), 7.97 (1H, t, J=6.0 Hz), 7.59 (1H, dd, J=4.4 and 8.4 Hz), 7.55–7.00 (8H, m), 4.66 (2H, d, J=6.0 Hz), 4.45 (1H, m), 4.20 (2H, s), 3.65 (2H, d, J=12.6 Hz), 2.74(2H, m), 2.40–2.00 (4H, m), 2.90 (2H, m) ppm. FAB MS calcd for C$_{28}$H$_{27}$Cl$_2$N$_5$O$_2$ 536 (MH$^+$), found 536. FAB HRMS exact mass calc'd for C$_{28}$H$_{27}$Cl$_2$N$_5$O$_2$ 536.1615 (MH$^+$), found 536.1600.

EXAMPLE 68

N-(3,5-dichlorobenzyl)-5-[[2-(dimethylamino)ethyl](methyl)amino]-8-hydroxy-1,6-naphthyridine-7-carboxamide

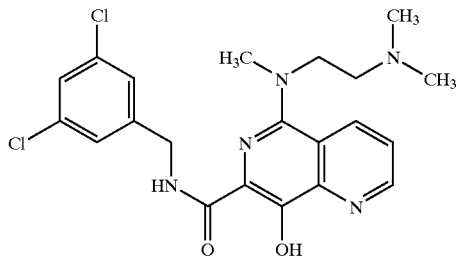

The title compound was prepared using the procedure described in Example 58 replacing N-methyl piperazine with N,N,N'-trimethylethane-1,2-diamine. $^1$H NMR (CDCl$_3$, 400 MHz) δ 9.14 (1H, d, J=4.4 Hz), 8.95 (1H, m), 8.53 (1H, d, J=8.4 and 1.5 Hz), 7.61 (1H, dd, J=4.4 and 8.4 Hz), 7.40–7.10 (3H, m), 4.68 (2H, d, J=6.0 Hz), 3.75 (2H, m), 3.50 (2H, m), 3.07 (3H, s), 2.86 (6H, s) ppm. FAB MS calcd for $C_{21}H_{23}Cl_2N_5O_2$ 448 (MH$^+$), found 448. FAB HRMS exact mass calc'd for $C_{21}H_{23}Cl_2N_5O_2$ 448.1302 (MH$^+$), found 448.1292

EXAMPLE 69

8-Hydroxy-5-phenylsulfanyl-[1,6]naphthyridine-7-carboxylic acid 3,5-dichlorobenzylamide

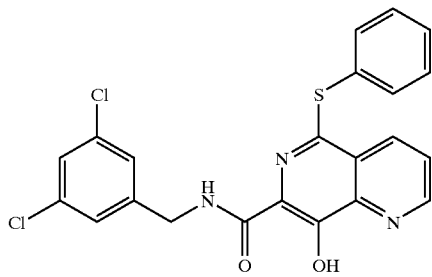

To a 5 mL pyrex pressure vessel with a stirring bar was added 5-bromo-8-hydroxy-[1,6]naphthyridine-7-carboxylic acid 3,5-dichloro-benzylamide (0.055 g, 0.13 mmol), thiophenol (0.056 g, 0.50 mmol) and triethylamine (0.28 mL, 2.00 mmol). The vessel was sealed under nitrogen and the stirred mixture heated in a 135° C. oil bath for 24 h. The cooled reaction mixture was concentrated in vacuo and the residue was chromatographed on silica gel (15 g) using methanol:chloroform (5:95) as eluant to give 8-hydroxy-5-phenylsulfanyl-[1,6]naphthyridine-7-carboxylic acid 3,5-dichlorobenzylamide as a solid.

$^1$H NMR (CDCl$_3$, 300 MHz) δ 12.53 (1H, s), 9.20 (1H, d, J=5 Hz), 8.58 (1H, dd, J=2,8 Hz), 7.66 (1H, dd, J=5, 8 Hz), 7.50 (3H, m), 7.30 (4H, m), 7.08 (1H, s), 4.40 (2H, d, J=6 Hz). FAB MS calc'd for $C_{22}H_{15}Cl_2N_3O_2S$ 456 (MH$^+$), found 456.

EXAMPLE 70

5-benzenesulfonyl-8-hydroxy-[1,6]naphthyridine-7-carboxylic acid 3,5-dichlorobenzylamide

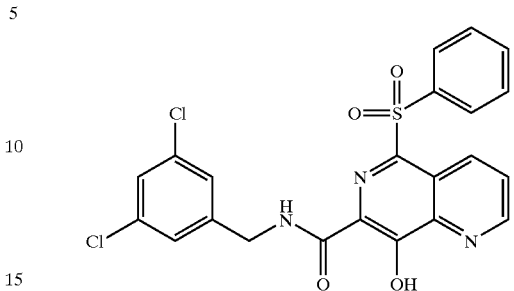

To a 25 mL round bottomed flask with a stirring bar was added 8-hydroxy-5-phenylsulfanyl-[1,6]naphthyridine-7-carboxylic acid 3,5-dichlorobenzylamide (0.04 g, 0.09 mmol) and methanol (7 mL). To this well stirred solution was added a solution of Oxone® (DuPont trademark; potassium peroxymonosulfate) (0.184 g, 0.30 mmol) in water (2 mL). The resulting mixture was stirred vigorously at ambient temperature 20 h. The solvents were removed in vacuo and the residue was triturated with water (10 mL) for 30 min. The solid was collected by filtration on a frit. This material was purified by reverse phase chromatography using water/acetonitrile as eluant to give 5-benzenesulfonyl-8-hydroxy-[1,6]naphthyridine-7-carboxylic acid 3,5-dichlorobenzylamide as a solid.

$^1$H NMR (CDCl$_3$, 300 MHz) δ 9.43 (1H, d, J=9 Hz), 9.26 (1H, d, J=2 Hz), 9.01 (2H, d, J=9 Hz), 7.82 (1H, dd, J=4, 9 Hz), 7.58 (3H, m), 7.48 (1H, s) 7.30 (4H, s), 7.10 (1H, s), 4.48 (2H, d, J=6 Hz). FAB MS calc'd for $C_{22}H_{15}Cl_2N_3O_4S$ 488 (MH$^+$), found 488. FAB HRMS exact mass calc'd for $C_{22}H_{15}Cl_2N_3O_4S$ 488.0233 (MH$^+$), found 488.0239.

EXAMPLE 71 tert-butyl 1-(7-{[(3,5-dichlorobenzyl)amino]carbonyl}-8-hydroxy-1,6-naphthyridin-5-yl)pyrrolidin-3-ylcarbamate

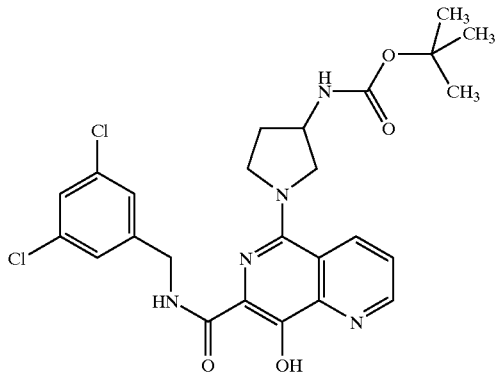

The title compound was prepared using the procedure described in Example 58 replacing N-methyl piperazine with tert-butylpyrrolidin-3-ylcarbamate $^1$H NMR (CDCl$_3$, 400 MHz) δ 9.21 (1H, dd, J=4.4 and 1.5 Hz), 8.62 (1H, d, J=8.6 Hz), 8.21 (1H, t, J=6.0 Hz), 7.61 (1H, dd, J=4.4 and 8.6 Hz), 7.40–7.20 (3H, m), 4.80 (1H, s), 4.66 (2H, d, J=6.4 Hz) 4.38 (1H, m), 3.99 (1H, s), 3.88 (1H, m), 3.74 (1H, m), 3.55 (1H, dd, J=10.8 and 4.0 Hz), 2.5–1.9 (2H, m), 1.45 (9H, s) ppm. FAB MS calcd for $C_{25}H_{27}Cl_2N_5O_4$ 532 (MH$^+$), found 532. FAB HRMS exact mass calc'd for $C_{25}H_{27}Cl_2N_5O_4$ 532.1513 (MH$^+$), found 532.1470.

EXAMPLE 72

5-(3-aminopyrrolidin-1-yl)-N-(3,5-dichlorobenzyl)-8-hydroxy-1,6-naphthyridine-7-carboxamide

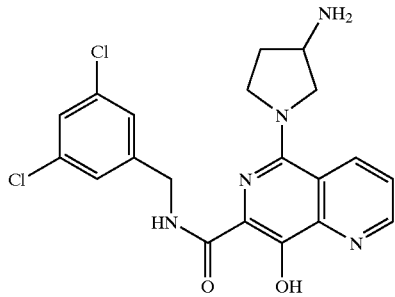

A solution of the derivative prepared in Example 71 (10 mg, 0.0188 mmol) in $CH_2Cl_2$ (2 ml) was treated with trifluroacetic acid (TFA) (0.5 ml) and stirred at room temperature for 1 hr. The solvent was evaporated in vacuo and the residue purified by preparative HPLC (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the trifluoroacetate salt of the title compound after lyophilization.

$^1$H NMR (DMSO-d6, 400 MHz) δ 12.61 (1H, s), 9.32 (1H, t, J=6.6 Hz), 9.09 (1H, dd, J=4.2 and 1.5 Hz), 8.68 (1H, dd, J=8.6 and 1.5 Hz), 8.04 (3H, s), 8.21 (1H, t, J=6.0 Hz), 7.75 (1H, dd, J=4.2 and 8.6 Hz), 7.53 (1H, t, J=1.9 Hz), 7.41 (2H, d, J=1.9 Hz), 4.58 (2H, d, J=6.4 Hz) 4.10–3.90 (3H, m), 3.85–3.60 (2H, m), 2.32 (1H, m), 2.08 (1H, m) ppm. FAB MS calcd for $C_{20}H_{19}Cl_2N_5O_2$ 432 (MH$^+$), found 432. FAB HRMS exact mass calc'd for $C_{20}H_{19}Cl_2N_5O_2$ 432.0989 (MH$^+$), found 432.0994.

EXAMPLE 73

N-(3,5-dichlorobenzyl)-8-hydroxy-5-(4H-1,2,4-triazol-4-yl)-1,6-naphthyridine-7-carboxamide

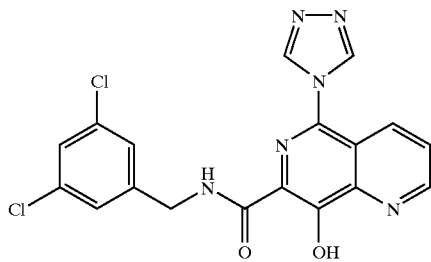

The title compound and its regioisomer 74 were prepared using the procedure described in Example 58 replacing N-methylpiperazine with 1,2,4-triazole.

$^1$H NMR (CD3OD, 400 MHz) δ 9.23 (1H, d, J=4.3 Hz), 9.13 (1H, s), 8.37 (1H, d, J=8.6 Hz), 7.91 (1H, dd, J=4.2 and 8.6 Hz), 7.38 (2H, s), 7.34 1H, s), 4.61 (2H, s)ppm. FAB MS calcd for $C_{15}H_{12}Cl_2N_6O_2$ 415.4 (MH$^+$), found 415.0.

EXAMPLE 74

N-(3,5-dichlorobenzyl)-8-hydroxy-5-(1H-1,2,4-triazol-1-yl)-1,6-naphthyridine-7-carboxamide

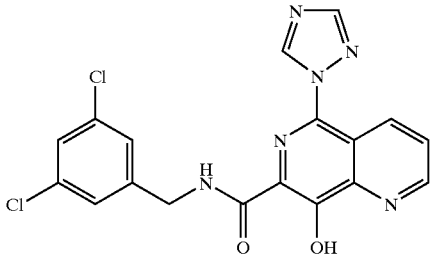

The title compound and its regioisomer 73 were prepared using the procedure described in Example 58 replacing N-methylpiperazine with 1,2,4-triazole.

$^1$H NMR (CD3OD, 400 MHz) δ 9.50 (1H, s), 9.33 (1H, d, J=8.7 Hz), 9.18 (1H, d, J=4.3 Hz), 8.33 (1H, 2), 7.90 (1H, dd, J=4.3 and 8.7 Hz), 7.4 (2H, s), 7.34 (1H, s), 4.64 (2H, s)ppm. FAB MS calcd for $C_{18}H_{12}Cl_2N_6O_2$ 415.4 (MH$^+$), found 415.0. FAB HRMS exact mass calcd for $C_{15}H_{12}Cl_2N_6O_2$ 415.0472 (MH$^+$), found 415.0497

EXAMPLE 75

N-(3,5-dichlorobenzyl)-8-hydroxy-5-(3-hydroxypyrrolidin-1-yl)-1,6-naphthyridine-7-carboxamide

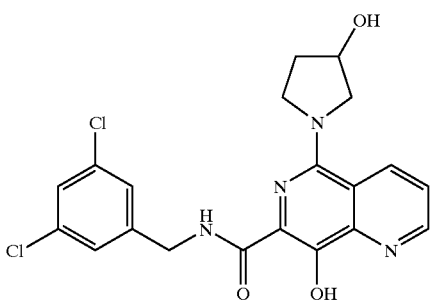

The title compound was prepared using the procedure described in Example 58 replacing N-methylpiperazine with 3-hydroxypyrrolidine.

$^1$H NMR (CD3OD, 400 MHz) δ 8.99 (1H, d, 4.2 Hz), 8.85 (1H, d, J=8.4 Hz), 7.72(1H, dd, J=4.2 and 8.4 Hz), 7.36 (2H, s), 7.34 (1H, s), 4.64 (2H, s), 4.54 (1H, m), 4.09 (2H, m), 3.76 (1H, m), 3.63 (1H, d, J=12 Hz), 2.16 (1H, m) and 2.06 (1H, m)ppm. FAB MS calcd for $C_{20}H_{18}Cl_2N_4O_3$ 433.1 (MH$^+$), found 433.1. FAB HRMS exact mass calcd for $C_{20}H_{18}Cl_2N_4O_3$ 433.0829 (MH$^+$), found 433.0844.

EXAMPLE 76

5-[3-(acetylamino)pyrrolidin-1-yl]-N-(3,5-dichlorobenzyl)-8-hydroxy-1,6-naphthyridine-7-carboxamide

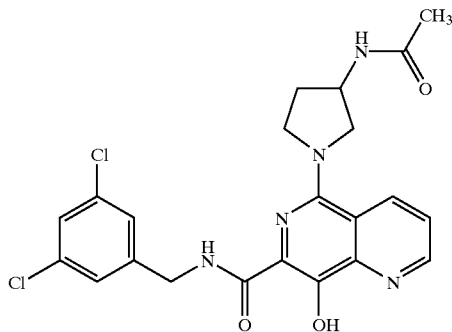

The title compound was prepared using the procedure described in Example 58 replacing N-methylpiperazine with 3-acetamidopyrrolidine.

$^1$H NMR (CD3OD, 400 MHz) δ 9.03 (1H, d, 4.2 Hz), 8.94 (1H, d, J=8.4 Hz), 7.80(1H, dd, J=4.2 and 8.4 Hz), 7.36 (2H, s), 7.34 (1H, s), 4.64 (2H, s), 4.48 (1H, m), 4.12 (1H, dd, J=6.2 and 12 Hz), 4.00 (1H, m), 3.88 (1H, m), 3.63 (1H, m), 2.29 (1H, m), 2.06 (1H, m) and 1.95 (3H, s)ppm. FAB MS calcd for $C_{22}H_{21}Cl_2N_5O_3$ 474.1 (MH$^+$), found 474.1. FAB HRMS exact mass calcd for $C_{22}H_{21}Cl_2N_5O_3$ 474.1094 (MH$^+$), found 474.1122.

EXAMPLE 77

N-(3,5-dichlorobenzyl)-5-(4-formylpiperazin-1-yl)-8-hydroxy-1,6-naphthyridine-7-carboxamide

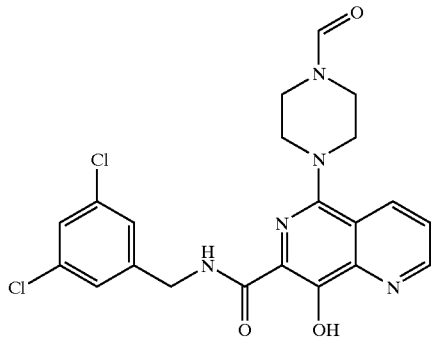

The title compound was prepared using the procedure described in Example 58 replacing N-methylpiperazine with piperazine.

$^1$H NMR (CD3OD, 400 MHz) δ 9.06 (1H, d, 4.2 Hz), 8.69 (1H, d, J=8.4 Hz), 8.13 (1H, s), 7.79(1H, dd, J=4.2 and 8.4 Hz), 7.37 (2H, s), 7.34 (1H, s), 4.63 (2H, s), 3.82 (2H, t, J=5 Hz), 3.73 (2H, t, J=5 Hz) and 3.35 (4H, m)ppm. FAB MS calcd for $C_{21}H_{19}Cl_2N_5O_3$ 460.5 (MH$^+$), found 460.1. FAB HRMS exact mass calcd for $C_{21}H_{19}Cl_2N_5O_3$ 460.0938 (MH$^+$), found 460.0961.

EXAMPLE 78

1-(7-{[(3,5-dichlorobenzyl)amino]carbonyl}-8-hydroxy-1,6-naphthyridin-5-yl)piperazine

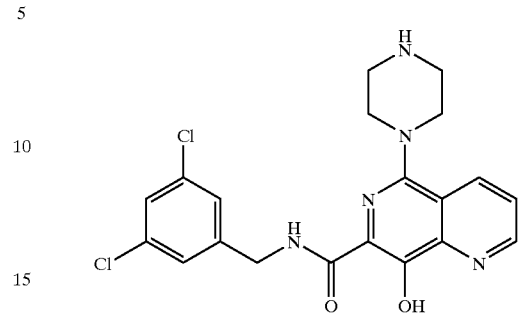

To a solution of 5-bromo-N-(3,5-dichlorobenzyl)-8-hydroxy-1,6-naphthyridine-7-carboxamide from Example 50 (25 mg, 0.060 mmol), piperazine (30.25 mg, 0.35 mmol) in 1-methylpyrrolidinone (0.25 ml) was heated at 135 C for 18 hrs. The resulting mixture was further diluted with DMF (0.25 ml) and TFA (50 ul) and purified by preparative HPLC (Gilson Semi Preparative HPLC System and a YMC Combiprep Pro Column (50×20 mm i.d., C18, S-5 um, 120A) eluting with 5–95% acetonitrile/water (0.1%) at 15 ml/min) to afford the title compound as the piperazin-4-ium trifluoroacetate salt after lyophillization.

$^1$H NMR (CD3OD, 400 MHz) δ 9.09 (1H, d, 4.3 Hz), 8.66 (1H, d, J=8.6 Hz), 7.80(1H, dd, J=4.3 and 8.6 Hz), 7.37 (2H, s), 7.36 (1H, s), 4.65 (2H, s), 3.59 (4H, m) and 3.51 (4H, m)ppm. FAB MS calcd for $C_{20}H_{19}Cl_2N_5O_2$ 432.1 (MH$^+$), found 432.1.

EXAMPLE 79

8-Hydroxy-5-(3-hydroxy-prop-1-ynyl)-[1,6]naphthyridine-7-carboxylic acid 3,5-dichloro-benzylamide

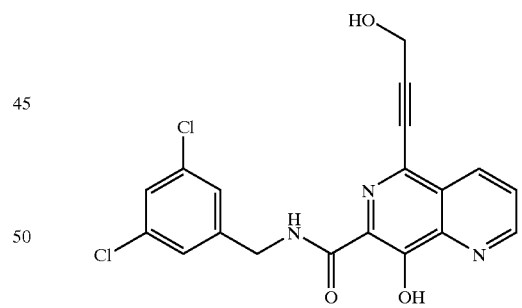

Step 1: Preparation of 5-iodo-8-(1-phenyl-methanoyloxy)-[1,6]naphthyridine-7-carboxylic acid methyl ester To a solution of 8-hydroxy-5-iodo-[1,6]naphthyridine-7-carboxylic acid methyl ester (9.41 g, 28.5 mmol, from Example 112 Step 1) and cesium carbonate (13.9 g, 42.8 mmol) in dry DMF (250 ml), was added benzoic anhydride (9.67 g, 42.8 mmol) and the solution stirred at room temperature for 4 hours. The solvent was removed under reduced pressure and the residue was partitioned between saturated aq. ammonium chloride and extracted into CHCl$_3$. The combined organic extracts were washed with brine, dried over Na$_2$SO$_4$, filtered and and the solvent was evaporated in vacuo. The residue was purified by flash chromatography (40% EtOAc/Hexane gradient elution switching to 1% MeOH/CHCl$_3$) to provide the desired product was a yellow solid.

$^1$H NMR (CDCl$_3$, 400 MHz) δ 9.11 (1H, d, J=4.21 Hz), 8.48 (1H, d, J=8.51 Hz), 8.32 (2H, d, J=8.33 Hz), 7.75–7.67 (2H, m), 7.56 (2H, t, J=7.69 Hz), and 3.93 (3H, s) ppm.

Step 2: Preparation of 5-(3-hydroxy-prop-1-ynyl)-8-(1-phenyl-methanoyloxy)-[1,6]naphthyridine-7-carboxylic acid methyl ester A mixture of 5-iodo-8-(1-phenyl-methanoyloxy)-[1,6] naphthyridine-7-carboxylic acid methyl ester (2.00 g, 4.61 mmol), propargyl alcohol (0.563 mL, 9.67 mmol), dichlorobis(triphenylphosphine)palladium(II) (65 mg, 0.092 mmol), and copper iodide (4 mg, 0.023 mmol) were stirred in triethylamine (13 mL) and dry DMF (5 mL) at 30° C. overnight. The solvent was removed in vacuo and the residue was purified by flash chromatography (50–100% EtOAc/Hexane gradient elution switching to 5% MeOH/CH$_2$Cl$_2$) to provide the desired product was a light brown solid.

$^1$H NMR (d$_6$-DMSO, 400 MHz) δ 9.26 (1H, d, J=4.21 Hz), 8.84 (1H, d, J=8.51 Hz), 8.21 (2H, d, J=8.33 Hz), 7.99 (1H, dd, J=4.21 and 8.51 Hz), 7.83 (1H, m), 7.68 (2H, m), 5.68 (1H, t, J=6.04 Hz), 4.54 (2H, d, J=6.04 Hz), and 3.84 (3H, s) ppm.

Step 3: Preparation of 8-hydroxy-5-(3-hydroxy-prop-1-ynyl)-[1,6]naphthyridine-7-carboxylic acid To a solution of 5-(3-hydroxy-prop-1-ynyl)-8-(1-phenyl-methanoyloxy)-[1,6]naphthyridine-7-carboxylic acid methyl ester (1.00 g, 2.76 mmol) in THF (14 mL) and water (14 mL) was added 1N NaOH (13.8 mL, 13.8 mmol) and the solution was stirred at 50° C. overnight. The THF was removed under reduced pressure and the remaining solution was acidified with 6N HCl to a pH=3. Injected the solution directly onto the Gilson auto-prep running a 95–50% H$_2$O (0.1% TFA)/CH$_3$CN (0.09% TFA) gradient over 35 minutes to obtain the desired compound as a bright yellow solid.

$^1$H NMR (d6-DMSO, 400 MHz) δ 9.22 (1H, d, J=4.22 Hz), 8.73 (1H, d, J=8.51 Hz), 7.95 (1H, dd, J=4.22 and 8.51 Hz), and 4.47 (2H, d, J=1.92 Hz) ppm.

Step 4: Preparation of 8-hydroxy-5-(3-hydroxy-prop-1-ynyl)-[1,6]naphthyridine-7-carboxylic acid 3,5-dichloro-benzylamide Following the general procedure for activation of the acid with triphosgene as in Example 2 gave the title compound as an off-white solid.

$^1$H NMR (d$_6$-DMSO, 400 MHz) δ 9.84 (1H, s), 9.21 (1H, d, J=4.21 Hz), 8.73 (1H, d, J=8.51 Hz), 7.93 (1H, dd, J=4.21 and 8.51 Hz), 7.52 (1H, m), 7.45 (2H, s), 5.57 (1H, s), 4.56 (2H, d, J=6.41 Hz), and 4.49 (2H, s) ppm. FAB HRMS exact mass calcd for C$_{19}$H$_{13}$Cl$_2$N$_3$O$_3$ 402.040673 (MH$^+$), found 402.042519. Anal. Calcd for C$_{19}$H$_{13}$Cl$_2$N$_3$O$_3$·0.20H$_2$O·0.40 TFA: C, 52.68; H, 3.08; N, 9.31. Found: C, 52.68; H, 2.97; N, 9.68.

EXAMPLE 80

1-(7-{[(3,5-dichlorobenzyl)amino]carbonyl}-8-hydroxy-1,6-naphthyridin-5-yl)-4-(2-oxo-2-pyrrolidin-1-ylethyl)piperazine

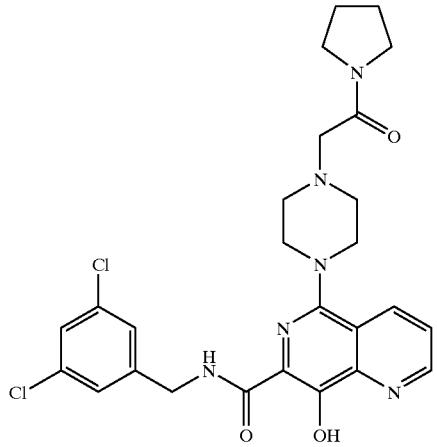

The title compound was prepared as the piperazin-4-ium trifluoroacetate salt using the procedure described in Example 58 replacing N-methylpiperazine with 1-(2-oxo-2-pyrrolidin-1-ylethyl)piperazine.

$^1$H NMR (CD3OD, 400 MHz) δ 9.10 (1H, d, 4.3 Hz), 8.64 (1H, d, J=8.6 Hz), 7.80(1H, dd, J=4.3 and 8.6 Hz), 7.37 (2H, s), 7.36 (1H, s), 4.65 (2H, s), 4.27 (2H, s), 3.51 (4H, m), 3.42–3.96 (8H, br m), 2.05 (2H, m) and 1.94 (2H, m)ppm. FAB MS calcd for C$_{26}$H$_{28}$Cl$_2$N$_6$O$_3$ 543.2 (MH$^+$), found 543.1. FAB HRMS exact mass calcd for C$_{26}$H$_{28}$Cl$_2$N$_6$O$_3$ 543.1673 (MH$^+$), found 543.1678.

EXAMPLE 81

8-Hydroxy-5-(3-piperidin-1-yl-prop-1-ynyl)-[1,6] naphthyridine-7-carboxylic acid 3,5-dichloro-benzylamide

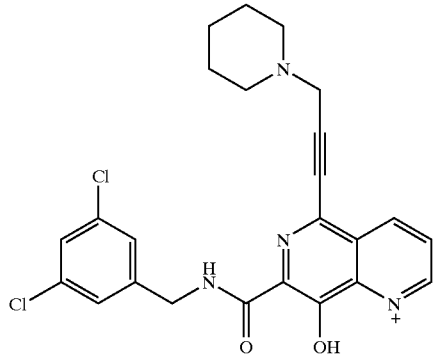

Step 1: Preparation of 5-(3-methanesulfonyloxy-prop-1-ynyl)-8-(1-phenyl-methanoyloxy)-[1,6] naphthyridine-7-carboxylic acid methyl ester A solution of 8-hydroxy-5-(3-hydroxy-prop-1-ynyl)-[1,6] naphthyridine-7-carboxylic acid (200 mg, 0.552 mmol, see Example 79 Step 3), mesyl chloride (94 µL, 1.21 mmol), and triethylamine (84 µL, 0.607 mmol) in dry CHCl$_3$ was stirred for one hour. The reaction was quenched with pH=7 buffer and extracted with CHCl₃. The combined organic extracts were washed with brine, dried over Na₂SO₄, filtered and the solvent was evaporated in vacuo to give the desired product was a light brown oil.

¹H NMR (CDCl₃, 400 MHz) δ 9.19 (1H, m), 8.77 (1H, d, J=8.51 Hz), 8.34 (2H, d, J=7.87 Hz), 7.76 (1H, dd, J=4.21 and 8.51 Hz), 7.71 (1H, t, J=7.51 Hz), 7.58 (2H, t, J=7.69 Hz), 5.23 (2H, s), 3.95 (3H, s), and 3.68 (3H, s) ppm.

Step 2: Preparation of 8-(1-phenyl-methanoyloxy)-5-(3-piperidin-1-yl-prop-1-ynyl)-[1,6]naphthyridine-7-carboxylic acid methyl ester To a stirred mixture of piperdine (207 μL, 2.09 mmol) and potassium carbonate (296 mg, 2.14 mmol) in dry acetonitrile (10 mL) was pipetted in 5-(3-methanesulfonyloxy-prop-1-ynyl)-8-(1-phenyl-methanoyloxy)-[1,6]naphthyridine-7-carboxylic acid methyl ester (230 mg, 0.522 mmol) in acetonitrile (1 mL) and the mixture was stirred at room temperature for 3 hours. The reaction was concentrated, filtered, and purified on the Gilson auto-prep running a 95–50% H₂O (0.1% TFA)/CH₃CN (0.09% TFA) gradient over 30 minutes to obtain the desired compound as a light brown oil.

¹H NMR (CDCl₃, 400 MHz) δ 19.27 (1H, d, J=4.30 Hz), 8.73 (1H, d, J=8.50 Hz), 7.83 (1H, dd, J=4.30 and 8.50 Hz), 4.25 (2H, s), 4.11 (3H, s), 3.83 (4H, m), 2.96–2.89 (2H, m), and 1.98 (4H, m) ppm.

Step 3: Preparation of 8-hydroxy-5-(3-piperidin-1-yl-prop-1-ynyl)-[1,6]naphthyridine-7-carboxylic acid 3,5-dichloro-benzylamide Following the general procedure for addition of 3,5-dichloro-benzylamine to the ester as in Example 1, Step 3 gave the title compound as a brown solid.

¹H NMR (CDCl₃, 400 MHz) δ 9.26 (1H, d, J=4.21 Hz), 8.66 (1H, d, J=8.61 Hz), 8.44 (1H, s), 7.79 (1H, dd, J=4.21 and 8.61 Hz), 7.32 (1H, s), 7.29 (2H, s), 4.66 (2H, d, J=6.41 Hz), 4.30 (2H, s), 3.70 (4H, m), 2.95 (2H, m), and 2.01 (4H, m) ppm. FAB HRMS exact mass calcd for C₂₄H₂₂Cl₂N₄O₂ 469.119258 (MH⁺), found 469.119314. Anal. Calcd for C₂₄H₂₂Cl₂N₄O₂.1.35 MeOH.0.05 TFA: C, 47.39; H, 3.98; N, 7.51. Found: C, 47.40; H, 3.98; N, 7.23.

EXAMPLE 82

N-(3,5-dichlorobenzyl)-8-hydroxy-5-thiomorpholin-4-yl-1,6-naphthyridine-7-carboxamide

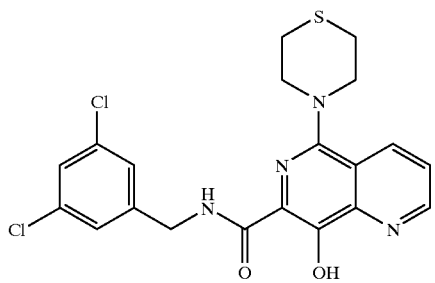

The title compound was prepared using the procedure described in Example 58 replacing N-methylpiperazine with thiomorpholine.

¹H NMR (CD3OD, 400 MHz) δ 9.08 (1H, dd, J=1.5 and 4.4 Hz), 8.64 (1H, dd, J=1.5 and 8.5 Hz), 7.84 (1H, dd, J=4.4 and 8.5 Hz), 7.37 (2H, s), 7.35 (1H, s), 4.64 (2H, s), 3.61 (4H, m) and 2.93 (4H, m) ppm. FAB MS calcd for C₂₀H₁₈Cl₂N₅O₂S 543.2 (MH⁺), found 543.1.

EXAMPLE 83

5-[3-(aminocarbonyl)piperidin-1-yl]-N-(3,5-dichlorobenzyl)-8-hydroxy-1,6-naphthyridine-7-carboxamide

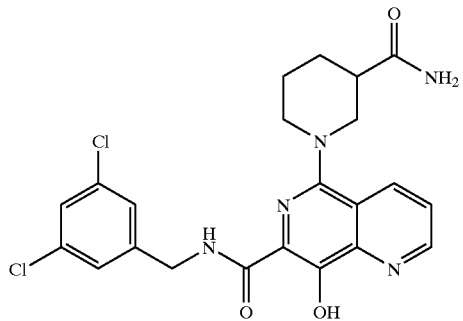

The title compound was prepared using the procedure described in Example 58 replacing N-methylpiperazine with nipecotamide.

¹H NMR (CD3OD, 400 MHz) δ 9.04 (1H, d, 4.2 Hz), 8.62 (1H, d, J=8.4 Hz), 7.76(1H, dd, J=4.2 and 8.4 Hz), 7.38 (2H, s), 7.34 (1H, m), 4.64 (2H, d, J=7.0 Hz), 3.70 (1H, d, J=12 Hz), 3.60 (1H, d, J=12 Hz), 3.17 (1H, m), 2.92 (1H, m), 2.79 (1H, m), 2.09 (1H, m), 1.94 (2H, m) and 1.71 (1H, m)ppm. FAB MS calcd for C₂₂H₂₁Cl₂N₅O₃ 474.1 (MH⁺), found 474.1. FAB HRMS exact mass calcd for C₂₂H₂₁Cl₂N₅O₃ 474.1094 (MH⁺), found 474.1114.

EXAMPLE 84

1-(7-{[(3,5-dichlorobenzyl)amino]carbonyl}-8-hydroxy-1,6-naphthyridin-5-yl)-4-(2-phenylethyl)piperazine

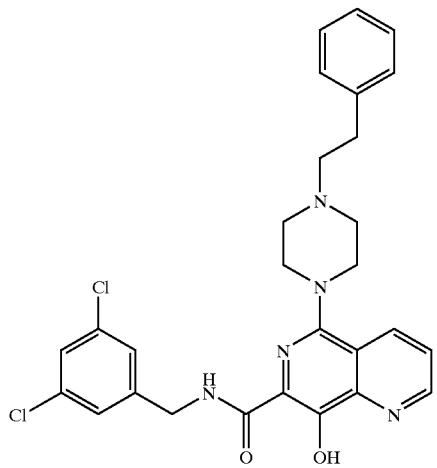

The title compound was prepared as the piperazin-4-ium trifluoroacetate salt using the procedure described in Example 58 replacing N-methylpiperazine with N-phenethylpiperazine.

¹H NMR (CD3OD, 400 MHz) δ 9.10 (1H, dd, 1.65 and 4.2 Hz), 8.65 (1H, dd, J=1.65 and 8.4 Hz), 7.81(1H, dd, J=4.2 and 8.4 Hz), 7.27–7.40 (8H, m), 4.66 (2H, s), 3.93 (2H, d, J=14 Hz), 3.78 (2H, d, J=12 Hz), 3.54 (4H, m), 3.42 (2H, m) and 3.14 (2H, m)ppm. FAB MS calcd for $C_{28}H_{27}Cl_2N_5O_2$ 536.1 (MH$^+$), found 536.1.

EXAMPLE 85

4-[(7-{[(3,5-dichlorobenzyl)amino]carbonyl}-8-hydroxy-1,6-naphthyridin-5-yl)amino]pyridine

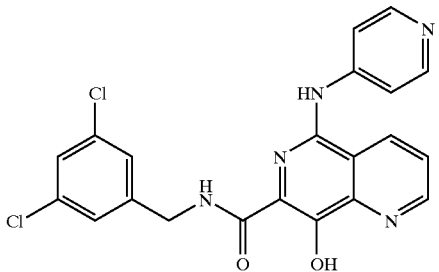

The title compound was prepared as the pyridinium trifluoroacetate salt using the procedure described in Example 58 replacing N-methylpiperazine with 4-aminopyridine.

$^1$H NMR (CD3OD, 400 MHz) δ 9.25 (1H, dd, 1.65 and 4.2 Hz), 8.49 (2H, d, J=5.8 Hz), 8.32 (1H, dd, J=1.65 and 8.7 Hz), 7.92(1H, dd, J=4.2 and 8.7 Hz), 7.37 (2H, d, J=1.7 Hz), 7.35 (1H, d, J=1.7 Hz), 7.05 (2H, d, J=5.8 Hz), 4.62 (2H, s)ppm. FAB MS calcd for $C_{21}H_{15}Cl_2N_5O_2$ 440.1 (MH$^+$), found 440.1. FAB HRMS exact mass calcd for $C_{21}H_{15}Cl_2N_5O_2$ 440.0681 (MH$^+$), found 440.0675.

EXAMPLE 86

5-[(cyclopropylmethyl)amino]-N-(3,5-dichlorobenzyl)-8-hydroxy-1,6-naphthyridine-7-carboxamide

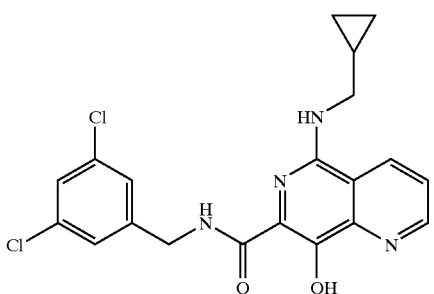

To a solution of 5-bromo-N-(3,5-dichlorobenzyl)-8-hydroxy-1,6-naphthyridine-7-carboxamide from Example 50 (25 mg, 0.060 mmol), cyclopropymethylamine (30.5 ul, 0.35 mmol) in DMPU (0.25 ml) was heated at 135 C. for 48 hrs. The resulting mixture was further diluted with DMF (0.25 ml) and TFA (50 ul) and purified by preparative HPLC (Gilson Semi Preparative HPLC System and a YMC Combiprep Pro Column (50×20 mm i.d., C18, S-5 um, 120A) eluting with 5–95% acetonitrile/water (0.1%) at 15 ml/min) to afford the title comound after lyophillization.

$^1$H NMR (CD3OD, 400 MHz) δ 9.03 (1H, br m), 8.83 (2H, br d, J=8.2 Hz), 7.71 (1H, m), 7.37 (2H, d, J=1.7 Hz), 7.35 (1H, d, J=1.7 Hz), 4.64 (2H, s), 3.48 (2H, d, J=7.0 Hz), 1.23 (1H, m), 0.56 (2H, d, J=7.3 Hz) and 0.34 (2H, d, 4.8 Hz)ppm. FAB MS calcd for $C_{20}H_{18}Cl_2N_4O_2$ 417.1 (MH$^+$), found 417.1. FAB HRMS exact mass calcd for $C_{20}H_{18}Cl_2N_4O_2$ 417.0880 (MH$^+$), found 417.0896.

EXAMPLE 87

N-(3,5-dichlorobenzyl)-5-{[2-(formylamino)ethyl]amino}-8-hydroxy-1,6-naphthyridine-7-carboxamide

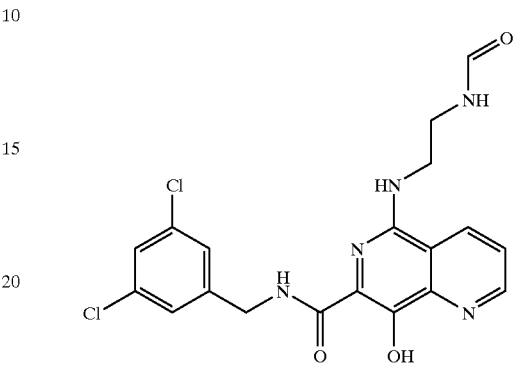

The title compound was prepared using the procedure described in Example 58 replacing N-methylpiperazine with ethylene diamine.

$^1$H NMR (CD3OD, 400 MHz) δ 9.00 (1H, dd, J=1.6 and 4.5 Hz), 8.58 (2H, dd, J=1.6 and 8.5 Hz), 8.11 (1H, s), 7.69 (1H, dd, J=4.5 and 8.5 Hz), 7.40 (2H, d, J=1.8 Hz), 7.32 (1H, d, J=1.8 Hz), 4.65 (2H, s), 3.66 (2H, m) and 3.58 (2H, m)ppm. FAB MS calcd for $C_{19}H_{17}Cl_2N_5O_3$ 434.1 (MH$^+$), found 434.1. FAB HRMS exact mass calcd for $C_{19}H_{17}Cl_2N_5O_3$ 434.0781 (MH$^+$), found 434.0789.

EXAMPLE 88

2-[(7-{[(3,5-dichlorobenzyl)amino]carbonyl}-8-hydroxy-1,6-naphthyridin-5-yl)amino]ethanamine

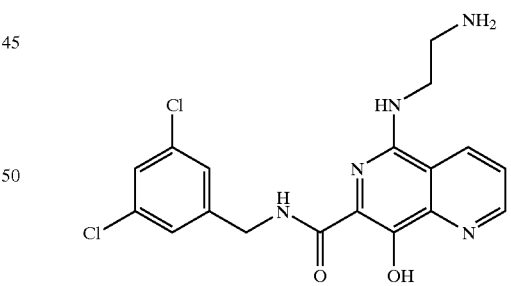

The title compound was prepared as the ethanaminium trifluoroacetate salt using the procedure described in Example 86 replacing cyclopropylmethylamine with ethylene diamine.

$^1$H NMR (CD3OD, 400 MHz) δ 9.04 (1H, d, J=4.6 Hz), 8.57 (2H, d, J=8.4 Hz), 7.71 (1H, d, J=8.4 Hz), 7.36 (3H, s), 4.65 (2H, s), 3.88 (2H, t, J=5.6 Hz) and 3.3(2H, m)ppm. FAB MS calcd for $C_{18}H_{17}Cl_2N_5O_2$ 406.1 (MH$^+$), found 406.1. FAB HRMS exact mass calcd for $C_{18}H_{17}Cl_2N_5O_2$ 406.0832 (MH$^+$), found 406.0846.

EXAMPLE 89

N-(3,5-dichlorobenzyl)-8-hydroxy-5-[(2-methoxyethyl)amino]-1,6-naphthyridine-7-carboxamide

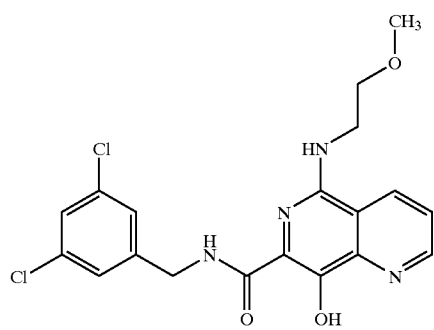

The title compound was prepared using the procedure described in Example 86 replacing cyclopropylmethylamine with 2-methoxyethylamine.

$^1$H NMR (CD3OD, 400 MHz) δ 8.99 (1H, br s), 8.63 (1H, br d, J=8.6 Hz), 7.69 (1H, m), 7.36 (2H, d, J=1.7 Hz), 7.35 (1H, d, J=1.7 Hz), 4.63 (2H, s), 3.81 (2H, t, J=5.5 Hz), 3.68 (2H, m) and 3.39 (3H, s)ppm. FAB MS calcd for $C_{19}H_{18}Cl_2N_4O_3$ 421.1 (MH$^+$), found 421.1. FAB HRMS exact mass calcd for $C_{19}H_{18}Cl_2N_4O_3$ 421.0829 (MH$^+$), found 421.0847.

EXAMPLE 90

N-(3,5-dichlorobenzyl)-8-hydroxy-5-[{2-(methylthio)ethyl]amino}-1,6-naphthyridine-7-carboxamide

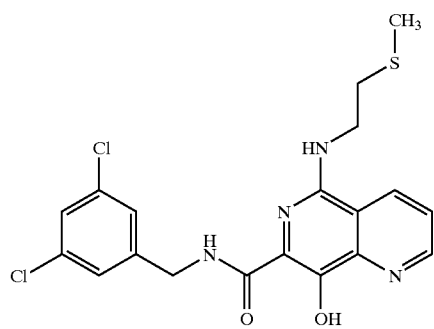

The title compound was prepared using the procedure described in Example 86 replacing cyclopropylmethylamine with 2-methylthioethylamine.

$^1$H NMR (CD3OD, 400 MHz) δ 8.99 (1H, dd, J=1.55 and 4.4 Hz), 8.60 (2H, dd, J=1.55 and 8.5 Hz), 7.69 (1H, dd, J=4.4 and 8.5 Hz), 7.36 (2H, s), 7.35 (1H, d, J=1.8 Hz), 4.63 (2H, s), 3.81 (2H, t, J=7.0 Hz), 3.81 (2H, t, J=7.0 Hz) and 2.10 (3H, s)ppm. FAB MS calcd for $C_{19}H_{18}Cl_2N_4O_2S$ 437.1 (MH$^+$), found 437.0. FAB HRMS exact mass calcd for $C_{19}H_{18}Cl_2N_4O_2S$ 437.0601 (MH$^+$), found 437.0610.

EXAMPLE 91

1-{2-[(7-{[(3,5-dichlorobenzyl)amino]carbonyl}-8-hydroxy-1,6-naphthyridin-5-yl)amino]ethyl}pyrrolidine

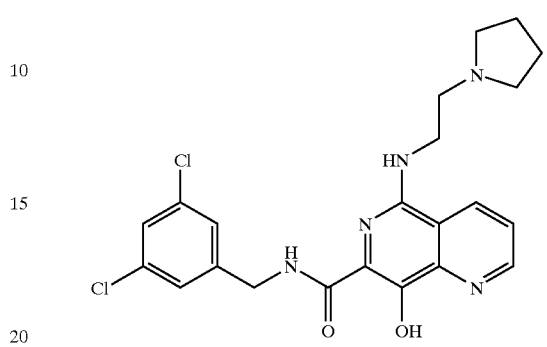

The title compound was prepared as the pyrrolidinium trifluoroacetate salt using the procedure described in Example 86 replacing cyclopropylmethylamine with N-(aminoethyl)pyrrolidine.

$^1$H NMR (CD3OD, 400 MHz) δ 9.07 (1H, dd, J=1.55 and 4.4 Hz), 8.56 (1H, dd, J=1.55 and 8.4 Hz), 7.73 (1H, dd, J=4.4 and 8.4 Hz), 7.38 (2H, s), 7.36 (1H, m), 4.65 (2H, s), 3.90 (2H, t, J=5.1 Hz), 3.49 (2H, t, J=5.1 Hz), 3.3 (4H, m) and 2.11 (4H, m)ppm. FAB MS calcd for $C_{22}H_{23}Cl_2N_5O_2$ 460.1 (MH$^+$), found 460.1. FAB HRMS exact mass calcd for $C_{22}H_{23}Cl_2N_5O_2$ 460.1302 (MH$^+$), found 460.1314.

EXAMPLE 92

1 N-(3,5-dichlorobenzyl)-8-hydroxy-5-pyrrolidin-1-yl-1,6-naphthyridine-7-carboxamide

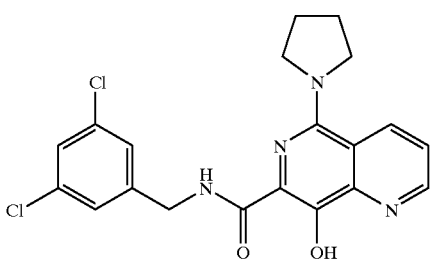

The title compound is formed as a by product in Example 91 and isolated pure during purification.

$^1$H NMR (CD3OD, 400 MHz) δ 9.01 (1H, br s), 8.93 (1H, d, J=8.6 Hz), 7.73 (1H, m), 7.36 (2H, s), 7.34 (1H, m), 4.64 (2H, s), 3.84 (4H, br s) and 2.06 (4H, br s)ppm. FAB MS calcd for $C_{20}H_{18}Cl_2N_4O_2$ 417.1 (MH$^+$), found 417.1. FAB HRMS exact mass calcd for $C_{20}H_{18}Cl_2N_4O_2$ 417.0880 (MH$^+$), found 417.0894.

EXAMPLE 93

3-{2-[(7-{[(3,5-dichlorobenzyl)amino]carbonyl}-8-hydroxy-1,6-naphthyridin-5-yl)amino]ethyl}pyridine

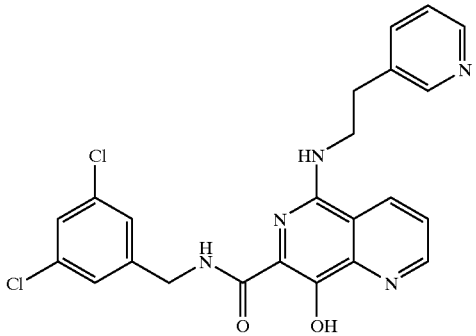

The title compound was prepared as the pyridinium trifluoroacetate salt using the procedure described in Example 86 replacing cyclopropylmethylamine with 3-(aminoethyl)pyridine.

$^1$H NMR (CD3OD, 400 MHz) δ 9.00 (1H, dd, J=1.5 and 4.4 Hz), 8.65 (1H, s), 8.58 (1H, d, J=5.7 Hz), 8.54 (1H, dd, J=1.5 and 8.4 Hz), 8.38 (1H, d, 8 Hz), 7.78 (1H, m), 7.70 (1H, dd, J=4.4 and 8.4 Hz), 7.37 (2H, s), 7.36 (1H, d, J=1.8 Hz), 4.64 (2H, s), 4.02 (2H, t, J=6.5 Hz) and 3.25 (2H, t, J=6.5 Hz)ppm. FAB MS calcd for $C_{23}H_{19}Cl_2N_5O_2$ 468.1 (MH$^+$), found 468.1. FAB HRMS exact mass calcd for $C_{23}H_{19}Cl_2N_5O_2$ 468.0989 (MH$^+$), found 468.1015.

EXAMPLE 94

1-{3-[(7-{[(3,5-dichlorobenzyl)amino]carbonyl}-8-hydroxy-1,6-naphthyridin-5-yl)amino]propyl}-1H-imidazoline

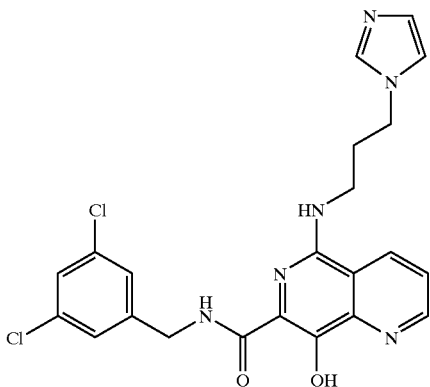

The title compound was prepared as the imidazol-1-ium trifluoroacetate salt using the procedure described in Example 86 replacing cyclopropylmethylamine with 1-(aminopropyl)imidazole.

$^1$H NMR (CD3OD, 400 MHz) δ 9.01 (1H, dd, J=1.5 and 4.4 Hz), 8.86 (1H, s), 8.58 (1H, dd, J=1.5 and 8.4 Hz), 7.71 (1H, dd, J=4.4 and 8.4 Hz), 7.62 (1H, m), 7.50 (1H, m), 7.35 (3H, s), 4.64 (2H, s), 4.40 (2H, t, J=7.4 Hz), 3.74 (2H, t, J=6.4 Hz) and 2.34 (2H, m)ppm. FAB MS calcd for $C_{22}H_{20}Cl_2N_6O_2$ 471.1 (MH$^+$), found 471.1. FAB HRMS exact mass calcd for $C_{22}H_{20}Cl_2N_6O_2$ 471.1098 (MH$^+$), found 471.1111.

EXAMPLE 95

1-{3-[(7-{[(3,5-dichlorobenzyl)amino]carbonyl}-8-hydroxy-1,6-naphthyridin-5-yl)amino]propyl}pyrrolidine

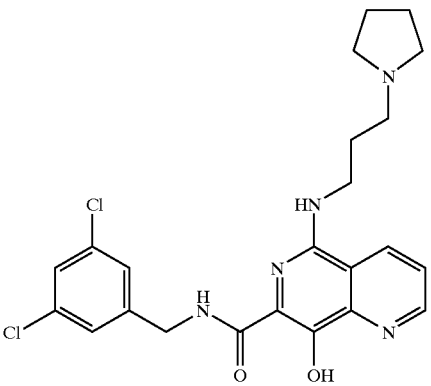

The title compound was prepared as the pyrrolidinium trifluoroacetate salt using the procedure described in Example 58 replacing N-methylpiperazine with N-aminopropylpyrrollidine.

$^1$H NMR (CD3OD, 400 MHz) δ 9.03 (1H, dd, J=1.5 and 4.4 Hz), 8.59 (1H, dd, J=1.5 and 8.4 Hz), 7.71 (1H, dd, J=4.4 and 8.4 Hz), 7.38 (3H, s), 4.65 (2H, s), 3.76 (2H, t, J=6.3 Hz), 3.59 (2H, br s), 3.3 (2H, m), 3.03 (2H, m) and 1.95–2.17 (6H, m)ppm. FAB MS calcd for $C_{23}H_{25}Cl_2N_5O_2$ 474.1 (MH$^+$), found 474.1. FAB HRMS exact mass calcd for $C_{23}H_{25}Cl_2N_5O_2$ 474.1464 (MH$^+$), found 460.1474.

EXAMPLE 96

1-(2-aminoethyl)-4-(7-{[(3,5-dichlorobenzyl)amino]carbonyl}-8-hydroxy-1,6-naphthyridin-5-yl)piperazine

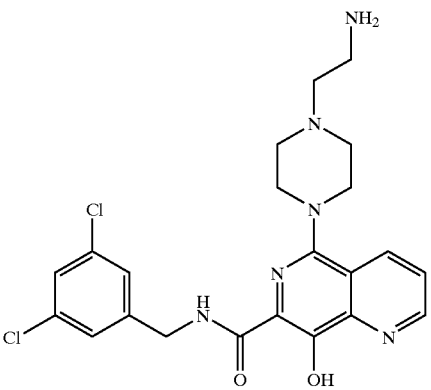

The title compound was prepared as the ethylammonium-piperazin-1-ium bis(trifluoroacetate) salt using the procedure described in Example 86 replacing cyclopropylmethylamine with N-(aminoethyl)piperazine.

$^1$H NMR (CD3OD, 400 MHz) δ 9.06 (1H, dd, J=1.5 and 4.4 Hz), 8.62 (1H, d, J=8.4 Hz), 7.77 (1H, dd, J=4.4 and 8.4 Hz), 7.37 (3H, s), 4.65 (2H, s), 3.45 (4H, br s), 3.16 (2H, m), 3.00 (2H, br m), 2.92 (2H, br m) and 2.85 (2H, br m)ppm. FAB MS calcd for $C_{22}H_{24}Cl_2N_6O_2$ 475.1 (MH$^+$), found 475.1. FAB HRMS exact mass calcd for $C_{22}H_{24}Cl_2N_6O_2$ 475.1416 (MH$^+$), found 475.1419.

EXAMPLE 97

N-(3,5-dichlorobenzyl)-8-hydroxy-5-[(2-phenoxyethyl)amino]-1,6-naphthyridine-7-carboxamide

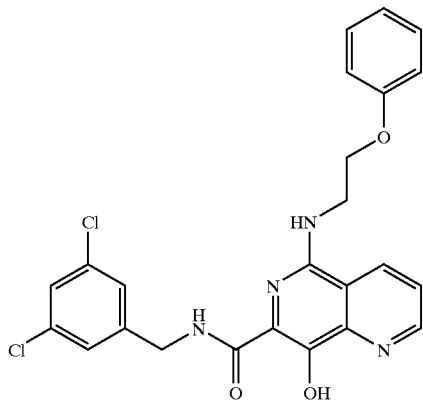

The title compound was prepared using the procedure described in Example 86 replacing cyclopropylmethylamine with 2-phenoxyethylamine.

$^1$H NMR (CD3OD, 400 MHz) δ 9.08 (1H, s), 8.85 (1H, d, J=8.4 Hz), 7.83 (1H, dd, J=4.8 and 8.4 Hz), 7.36 (2H, s), 7.35 (1H, m), 7.22 (2H, m), 6.93 (2H, d, J=7.9 Hz), 6.89 (1H, t, J=7.3 Hz), 4.64 (2H, s), 4.29 (2H, t, J=5.1 Hz) and 4.06 (2H, t, J=5.1 Hz)ppm. FAB MS calcd for $C_{24}H_{20}Cl_2N_4O_3$ 483.1 (MH$^+$), found 483.1. FAB HRMS exact mass calcd for $C_{24}H_{20}Cl_2N_4O_3$ 483.0985 (MH$^+$), found 483.0997.

EXAMPLE 98

N-(3,5-dichlorobenzyl)-8-hydroxy-5-{[3-(2-oxopyrrolidin-1-yl)propyl]amino}-1,6-naphthyridine-7-carboxamide

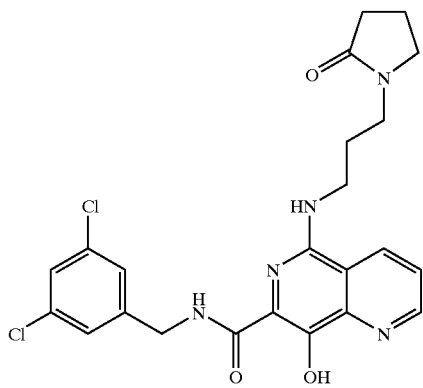

The title compound was prepared using the procedure described in Example 86 replacing cyclopropylmethylamine with 1-(3-aminopropyl)pyrrolidin-2-one.

$^1$H NMR (CD3OD, 400 MHz) δ 9.03 (1H, d, J=4.2 Hz), 8.75 (1H, d, J=8.4 Hz), 7.78 (1H, dd, J=4.2 and 8.4 Hz), 7.37 (2H, d, J=1.6 Hz), 7.35 (1H, d, J=1.6 Hz), 4.64 (2H, s), 3.64 (2H, t, J=6.8 Hz), 3.31 (4H, m), 2.35 (2H, t, J=8.2 Hz) and 1.98 (4H, m)ppm. FAB MS calcd for $C_{23}H_{23}Cl_2N_5O_3$ 488.1 (MH$^+$), found 488.1. FAB HRMS exact mass calcd for $C_{23}H_{23}Cl_2N_5O_3$ 488.1251(MH$^+$), found 488.1265.

EXAMPLE 99

2-[benzyl(7-{[(3,5-dichlorobenzyl)amino]carbonyl}-8-hydroxy-1,6-naphthyridin-5-yl)amino]ethanamine

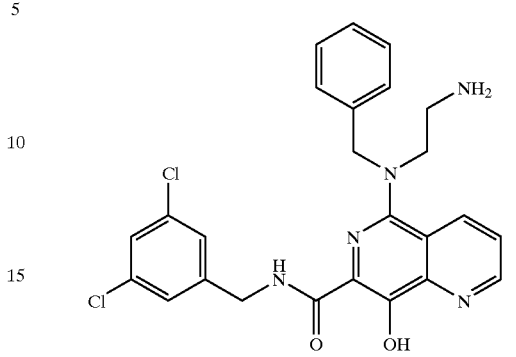

The title compound was prepared as the ethanaminium trifluoroacetate salt using the procedure described in Example 86 replacing cyclopropylmethylamine with N-benzylethylenediamine.

$^1$H NMR (CD3OD, 400 MHz) δ 9.02 (1H, d, J=4.4 Hz), 8.51 (1H, d, J=8.4 Hz), 7.70 (1H, dd, J=4.4 and 8.4 Hz), 7.38 (7H, m), 7.33 (1H, m), 4.64 (2H, s), 4.27 (2H, s), 3.89 (2H, t, J=5.3 Hz) and 3.33 (2H, m)ppm. FAB MS calcd for $C_{25}H_{23}Cl_2N_5O_2$ 496.1 (MH$^+$), found 496.1. FAB HRMS exact mass calcd for $C_{25}H_{23}Cl_2N_5O_2$ 496.1302 (MH$^+$), found 496.1311.

EXAMPLE 100

1-{3-[(7-{[(3,5-dichlorobenzyl)amino]carbonyl}-8-hydroxy-1,6-naphthyridin-5-yl)amino]propyl}-4-methylpiperazine

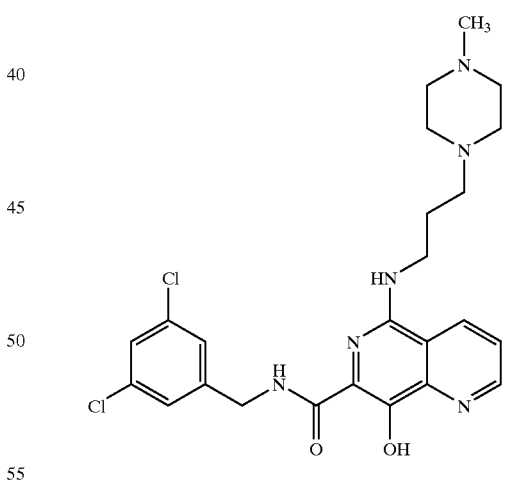

The title compound was prepared as the piperazinedium bis(trifluoroacetate) salt using the procedure described in Example 86 replacing cyclopropylmethylamine with 1-(aminopropyl)-4-methylpiperazine.

$^1$H NMR (CD3OD, 400 MHz) δ 9.03 (1H, dd, J=1.5 and 4.4 Hz), 8.65 (1H, dd, J=1.5 and 8.4 Hz), 7.73 (1H, dd, J=4.4 and 8.4 Hz), 7.37 (3H, s), 4.65 (2H, s), 3.72 (2H, t, J=6.4), 2.6–3.4 (10H, br), 2.72 (3H, s) and 2.01 (2H, t, J=7.3 Hz) ppm. FAB MS calcd for $C_{24}H_{28}Cl_2N_6O_2$ 503.1 (Mt), found 503.1. FAB HRMS exact mass calcd for $C_{24}H_{28}Cl_2N_6O_2$ 503.1724 (MH$^+$), found 503.1721.

EXAMPLE 101

1:1 mixture of 1-(7-{[(3,5-dichlorobenzyl)amino]carbonyl}-8-hydroxy-1,6-naphthyridin-5-yl)-1H-imidazo[4,5-b]pyridine and 3-(7-{[(3,5-dichlorobenzyl)amino]carbonyl}-8-hydroxy-1,6-naphthyridin-5-yl)-3H-imidazo[4,5-b]pyridine

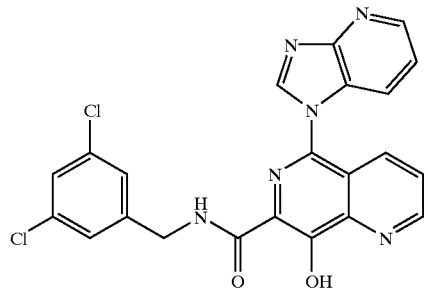

The title compound was prepared as the imidazopyridin-1-ium trifluoroacetate salt using the procedure described in Example 58 replacing N-methylpiperazine with 3H-imidazo[4,5-b]pyridine.

$^1$H NMR (CD3OD, 400 MHz) δ 7.62–9.94 (7H, m), 7.35 (3H, m) and 4.64 (2H, d) ppm. FAB MS calcd for $C_{22}H_{14}Cl_2N_6O_2$ 465.0 (MH$^+$), found 465.0.

EXAMPLE 102

N-(3,5-dichlorobenzyl)-8-hydroxy-5-{[4-(3-methyl-2-oxoimidazolidin-1-yl)phenyl]amino}-1,6-naphthyridine-7-carboxamide

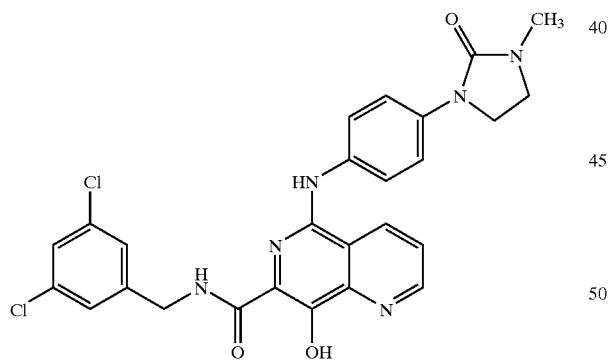

The title compound was prepared using the procedure described in Example 86 replacing cyclopropylmethylamine with 1-(4-aminophenyl)-3-methylimidazolidin-2-one.

$^1$H NMR (CD3OD, 400 MHz) δ 9.07 (1H, d, J=4.4 Hz), 8.87 (1H, d, J=8.4 Hz), 7.80 (1H, dd, J=4.4 and 8.4 Hz), 7.53 (2H, d, J=9.1 Hz), 7.45 (2H, d, 9.1 Hz), 7.38 (1H, d, J=1.8 Hz), 7.35 (2H, d, J=1.8 Hz), 4.59 (2H, s), 3.84 (2H, m), 3.53 (2H, m) and 2.88 (3H, s)ppm. FAB MS calcd for $C_{26}H_{22}Cl_2N_6O_3$ 537.1 (MH$^+$), found 537.1. FAB HRMS exact mass calcd for $C_{26}H_{22}Cl_2N_6O_3$ 537.1203 (MH$^+$), found 537.1210.

EXAMPLE 103

N-(3,5-dichlorobenzyl)-8-hydroxy-5-(1,4,6,7-tetrahydro-5H-pyrazolo[4,3-c]pyridin-5-yl)-1,6-naphthyridine-7-carboxamide

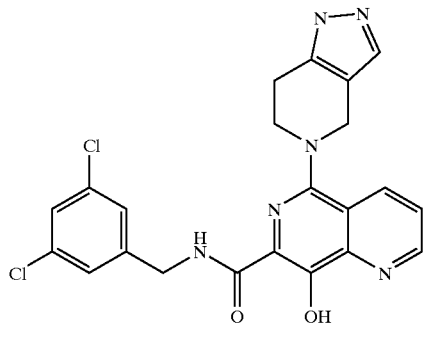

The title compound was prepared using the procedure described in Example 86 replacing cyclopropylmethylamine with 4,5,6,7-tetrahydro-1H-pyrazolo[4,3-c]pyridine.

$^1$H NMR (CD3OD, 400 MHz) δ 9.07 (1H, dd, J=1.5 and 4.4 Hz), 8.66 (1H, dd, J=1.5 and 8.4 Hz), 7.80 (1H, dd, J=4.4 and 8.4 Hz), 7.51 (1H, s), 7.38 (2H, m), 7.35 (1H, m), 4.65 (2H, s), 4.50 (2H, s), 3.67 (2H, t, J=5.6 Hz) and 3.10 (2H, t, J=5.6 Hz)ppm. FAB MS calcd for $C_{22}H_{18}Cl_2N_6O_2$ 469.1 (MH$^+$), found 469.1. FAB HRMS exact mass calcd for $C_{22}H_{18}Cl_2N_6O_2$ 469.0941 (MH$^+$), found 469.0967.

EXAMPLE 104

N-(3,5-dichlorobenzyl)-8-hydroxy-5-({[(2R)-5-oxopyrrolidin-2-yl]methyl}amino)-1,6-naphthyridine-7-carboxamide

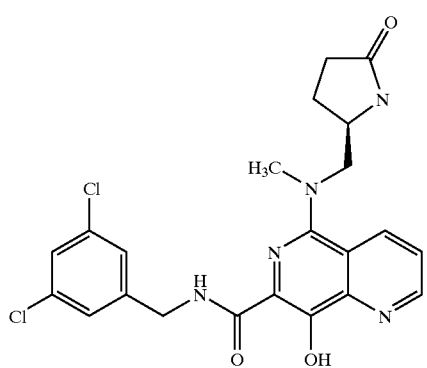

The title compound was prepared using the procedure described in Example 86 replacing cyclopropylmethylamine with (5R)-5-[(methylamino)methyl]-pyrrolidin-2-one.

$^1$H NMR (CD3OD, 400 MHz) δ 9.06 (1H, dd, J=1.5 and 4.4 Hz), 8.82 (1H, dd, J=1.5 and 8.4 Hz), 7.80 (1H, dd, J=4.4 and 8.4 Hz), 7.37 (2H, m), 7.36 (1H, m), 4.66 (2H, m), 4.06 (1H, m), 3.53 (2H, m), 3.28 (2H, m), 3.09 (3H, s) and 2.32 (2H, m)ppm. FAB MS calcd for $C_{22}H_{21}Cl_2N_5O_3$ 474.1 (MH$^+$), found 474.1. FAB HRMS exact mass calcd for $C_{22}H_{21}Cl_2N_5O_3$ 474.1094 (MH$^+$), found 474.1109.

EXAMPLE 105

N-(3,5-dichlorobenzyl)-8-hydroxy-5-{[(5-oxo-4,5-dihydro-1H-1,2,4-triazol-3-yl)methyl]amino}-1,6-naphthyridine-7-carboxamide

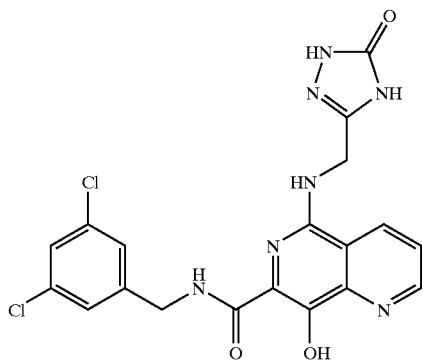

The title compound was prepared using the procedure described in Example 86 replacing cyclopropylmethylamine with 5-(aminomethyl)-2,4-dihydro-3H-1,2,4-triazol-3-one.

$^1$H NMR (CD3OD, 400 MHz) δ 9.02 (1H, dd, J=1.6 and 4.4 Hz), 8.62 (1H, dd, J=1.6 and 8.4 Hz), 7.72 (1H, dd, J=4.4 and 8.4 Hz), 7.36 (2H, m), 7.34 (1H, m), 4.61 (2H, d, J=1.5 Hz)ppm. FAB MS calcd for $C_{19}H_{15}Cl_2N_7O_3$ 460.1 (MH$^+$), found 460.0. FAB HRMS exact mass calcd for $C_{19}H_{15}Cl_2N_7O_3$ 460.0686(MH$^+$), found 460.0692.

EXAMPLE 106

2-(7-{[(3,5-dichlorobenzyl)amino]carbonyl}-8-hydroxy-1,6-naphthyridin-5-yl)octahydropyrrolo[1,2-a]pyrazine

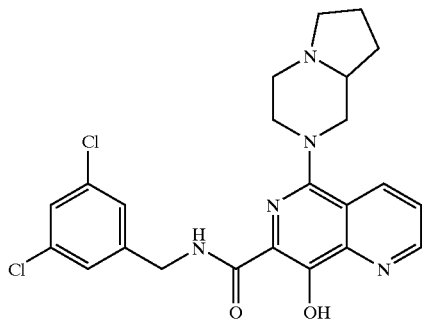

The title compound was prepared as the pyrrolopyrazin-5-ium trifluoroacetate salt using the procedure described in Example 86 replacing cyclopropylmethylamine with octahydropyrrolo[1,2-a]pyrazine.

$^1$H NMR (CD3OD, 400 MHz) δ 9.10 (1H, dd, J=1.5 and 4.4 Hz), 8.64 (1H, dd, J=1.5 and 8.6 Hz), 7.81 (1H, dd, J=4.4 and 8.6 Hz), 7.37 (2H, m), 7.36 (1H, m), 4.65 (2H, s), 3.10–4.17 (9H, m) and 2.30 (4H, m)ppm. FAB MS calcd for $C_{23}H_{23}Cl_2N_5O_2$ 472.1 (MH$^+$), found 472.1. FAB HRMS exact mass calcd for $C_{23}H_{23}Cl_2N_5O_2$ 472.1302 (MH$^+$), found 472.1311.

EXAMPLE 107

N-(3,5-dichlorobenzyl)-8-hydroxy-5-[4-(pyrimidin-2-ylamino)piperidin-1-yl]-1,6-naphthyridine-7-carboxamide

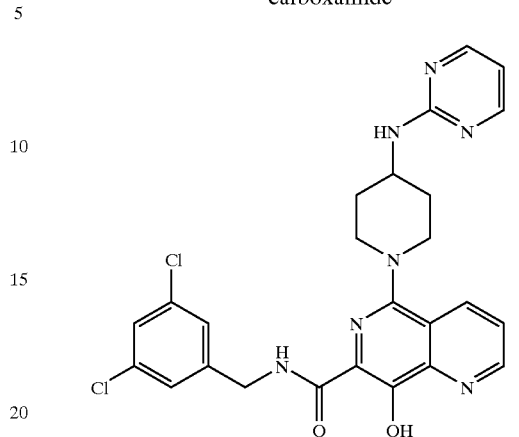

The title compound was prepared as the pyrimidin-2-aminium trifluoroacetate salt using the procedure described in Example 86 replacing cyclopropylmethylamine with tert-butyl $^4$-(pyrimidin-2-ylamino)piperidine-1-carboxylate.

$^1$H NMR (CD3OD, 400 MHz) δ 9.06 (1H, dd, J=1.5 and 4.4 Hz), 8.64 (1H, dd, J=1.5 and 8.4 Hz), 8.39 (2H, d, J=5.0 Hz), 7.78 (1H, dd, J=4.4 and 8.4 Hz), 7.38 (2H, m), 7.35 (1H, m), 6.75 (1H, t, J=5.0 Hz), 4.65 (2H, s), 4.08 (1H, m), 3.73 (2H, d, J=13.5 Hz), 3.16 (2H, m), 2.20 (2H, d, J=11.7 Hz) and 1.96 (2H, m)ppm. FAB MS calcd for $C_{25}H_{23}Cl_2N_7O_2$ 524.1 (MH$^+$), found 524.1. FAB HRMS exact mass calcd for $C_{25}H_{23}Cl_2N_7O_2$ 524.1363 (MH$^+$), found 524.1392.

EXAMPLE 108

2-{2-[(7-{[(3,5-dichlorobenzyl)amino]carbonyl}-8-hydroxy-1,6-naphthyridin-5-yl)(methyl)amino]ethyl}pyridine

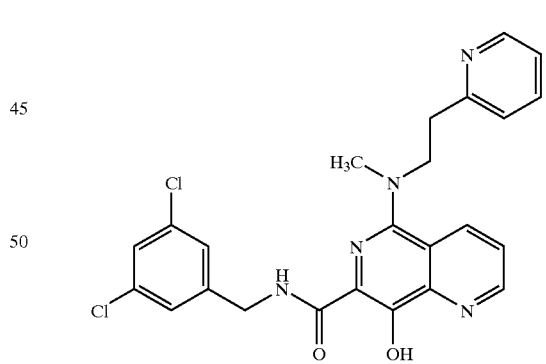

The title compound was prepared as the pyridinium trifluoroacetate salt using the procedure described in Example 58 replacing N-methylpiperazine with (N-methylaminopropyl)pyridine.

$^1$H NMR (CD3OD, 400 MHz) δ 9.02 (1H, dd, J=1.5 and 4.4 Hz), 8.45 (1H, dd, J=1.5 and 8.6 Hz), 8.22 (2H, d, J=7.0 Hz), 8.01 (1H, m), 7.70 (1H, dd, J=4.4 and 8.6 Hz), 7.67 (1H, d, J=7.0 Hz), 7.38 (2H, m), 7.35 (1H, m), 4.66 (2H, s), 3.90 (2H, t, J=6.8 Hz), 3.26 (2H, t, J=6.8 Hz) and 3.09 (3H, s)ppm. FAB MS calcd for $C_{24}H_{21}Cl_2N_5O_2$ 482.1 (MH$^+$), found 482.1.

EXAMPLE 109

N-(3,5-dichlorobenzyl)-5-(dimethylamino)-8-hydroxy-1,6-naphthyridine-7-carboxamide

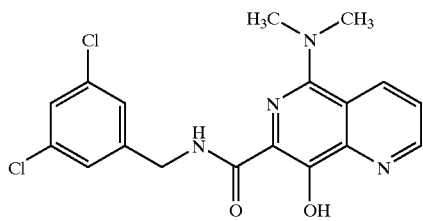

The title compound was obtained as a by-product using the procedure described in Example 58.

$^1$H NMR (CD3OD, 400 MHz) δ 9.04 (1H, d, J=4.4 Hz), 8.81 (1H, d, J=8.4 Hz), 7.81 (1H, dd, J=4.4 and 8.4 Hz), 7.34 (2H, m), 7.30 (1H, m), 4.61 (2H, s) and 3.08 (6H, s)ppm. FAB MS calcd for $C_{18}H_{16}Cl_2N_4O_2$ 391.1 (MH$^+$), found 391.1.

EXAMPLE 110

8-Hydroxy-5-(3-morpholin-4-yl-prop-1-ynyl)-[1,6]naphthyridine-7-carboxylic acid 3,5-dichlorobenzylamide

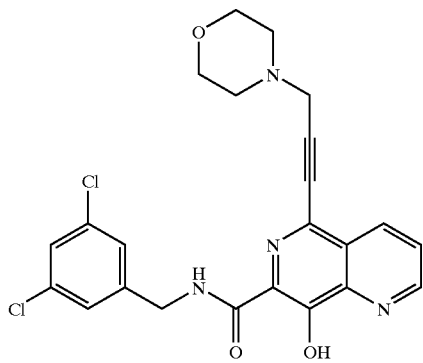

In a method similar to that of Example 81, the title compound was synthesized to give an orange solid.

$^1$H NMR (CDCl$_3$, 400 MHz) δ 9.28 (1H, d, J=4.21 Hz), 8.64 (1H, d, J=8.61 Hz), 8.42 (1H, s), 7.76 (1H, dd, J=4.21 and 8.61 Hz), 7.32 (1H, s), 7.30 (2H, s), 4.67 (2H, d, J=6.41 Hz), 4.22 (2H, s), 4.05 (4H, m), and 3.73 (4H, m) ppm. FAB HRMS exact mass calcd for $C_{23}H_{20}Cl_2N_4O_3$ 471.0985 (MH$^+$), found 471.0966.

EXAMPLE 111

N-(3,5-difluorobenzyl)-8-hydroxy-5-(methylsulfonyl)-1,6-naphthyridine-7-carboxamide

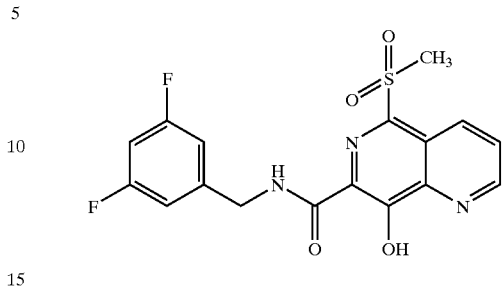

Into a round bottom flask fitted with a nitrogen inlet, condenser and a magnetic stirring bar was placed 5-bromo-N-(3,5-difluorobenzyl)-8-hydroxy-1,6-naphthyridine-7-carboxamide (0.1 g, 0.25 mmol), sodium methanesulfinate (0.061 g, 0.6 mmol) and 2 mL DMF. The mixture was heated to 100° C. for 48 hours, after which time the reaction was cooled, poured into water and extracted with CH$_2$Cl$_2$. The combined organic extracts were washed with brine, dried over Na$_2$SO$_4$, filtered and the solvent removed in vacuo. The resulting crude product was purified by reverse phase HPLC to obtain N-(3,5-difluorobenzyl)-8-hydroxy-5-(methylsulfonyl)-1,6-naphthyridine-7-carboxamide trifluoroacetate salt as a yellow crystalline solid.

$^1$H NMR (CDCl$_3$, 400 MHz) δ 9.34 (1H, d, J=8.7 Hz); 9.29 (1H, d, J=4.1 Hz); 8.17 (1H, m); 7.80 (1H, dd, J=4.2 Hz, 8.8 Hz); 6.92 (2H, d, J=5.8 Hz), 6.77 (1H, t, J=8.8 Hz); 4.72 (2H, d, J=6.5 Hz); 3.38 (3H, s) FAB HRMS exact mass calcd for $C_{17}H_{13}F_2N_3O_4S$ 394.0668 (MH$^+$), found 394.0675.

EXAMPLE 112

5-cyano-N-(2,3-dimethoxybenzyl)-8-hydroxy-1,6-naphthyridine-7-carboxamide

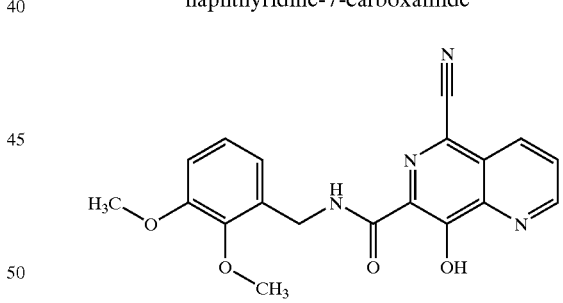

Step 1: Preparation of methyl 8-hydroxy-5-iodo-1,6-naphthyridine-7-carboxylate

The iodide was synthesized in a manner similar to that of Example 113, Step 1 except NIS was used instead of NBS and 2% of the solvent was DMF.

$^1$H NMR (CDCl$_3$, 400 MHz) δ 11.77 (1H, s), 9.17 (1H, d, J=4.4 Hz), 8.44–8.41 (1H, d, J=8.6 Hz), 7.79–7.76 (1H, dd, J=4.3 and 8.5 Hz), and 4.12 (3H, s) ppm.

Step 2: Preparation of methyl 8-(benzoyloxy)-5-iodo-1,6-naphthyridine-7-carboxylate The synthesis of this compound was described in Example 79, Step 1.

Step 3: Preparation of methyl 8-(benzoyloxy)-5-cyano-1,6-naphthyridine-7-carboxylate To a solution of methyl 8-(benzoyloxy)-5-iodo-1,6-naphthyridine-7-carboxylate (750 mg, 1.727 mmol) in anhydrous DMF (10 ml) was added dicyanozinc (142 mg, 1.21 mmol) and tetrakis(triphenylphospine)palladium(0) (299 mg, 0.26 mmol) and the solution was stirred at 85° C. overnight. The reaction was quenched with water and extracted with chloroform three times. The combined organic extracts were dried over sodium sulfate, filtered and concentrated. The residue was purified by flash chromatography (17–55% EtOAc/Hexanes gradient elution) to provide a white solid.

$^1$H NMR (CDCl$_3$, 400 MHz) δ 9.27 (1H, d, J=4.1 Hz), 8.74(1H, d, J=8.5 Hz), 8.32 (2H, d, J=8.3 Hz), 7.88–7.85 (1H, dd, J=4.2 and 8.6 Hz), 7.72 (1H, t, J=7.5 Hz), 7.59 (2H, t, J=7.7 Hz), and 3.97(3H, s) ppm.

Step 4: Preparation of 5-cyano-N-(2,3-dimethoxybenzyl)-8-hydroxy-1,6-naphthyridine-7-carboxamide To a solution of methyl 8-(benzoyloxy)-5-cyano-1,6-naphthyridine-7-carboxylate (264 mg, 0.792 mmol) in anhydrous toluene (12 ml) was added 2,3-dimethoxybenzyl amine (132 mg, 0.79 mmol) and the solution was stirred at reflux under argon overnight. The solvent was removed under reduced pressure to give a brown syrup which was subsequently taken up into ether (10 ml). After stirring for 4 hours the solids were collected by vacuum filtration and dried overnight on an aberhalden to give an off white solid.

$^1$H NMR (CDCl$_3$, 400 MHz) δ 9.26 (1H, d, J=2.8 Hz), 8.59–8.56 (1H, d, J=8.5 Hz), 8.39 (1H, b), 7.82–7.79 (1H, dd, J=4.2 and 8.5 Hz), 7.07 (1H, t, J=7.9 Hz), 6.98 (1H, d, J=6.6 Hz), 6.93 (1H, d, J=8.2 Hz), 4.72 (2H, d, J=6.0 Hz), 3.97 (3H, s) and 3.89(3H, s) ppm. ES HRMS exact mass calcd for C$_{19}$H$_{17}$N$_4$O$_4$ 365.1245 (MH$^+$), found 365.1229.

EXAMPLE 113

N-(3,5-dichlorobenzyl)-8-hydroxy-5-thien-2-yl-1,6-naphthyridine-7-carboxamide

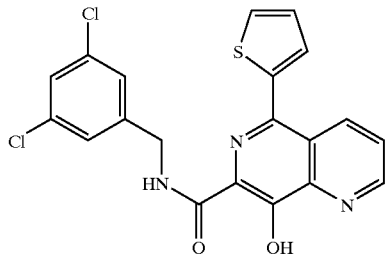

Step 1: Preparation of Methyl-5-bromo-8-hydroxy-1,6-naphthyridine-7-carboxylate To a solution of methyl 8-hydroxy-1,6-naphthyridine-7-carboxylate from Example 1 Step 2 (5.0 g, 24.49 mmol) in CH$_2$Cl$_2$ (100 ml) at room temperature was added N-bromo succinimide (4.36 g, 24.49 mmol). The reaction was stirred for 1 hr. The solids were collected by filtration and dried in vacuo to afford the title compound as an off white solid.

$^1$H NMR (CDCl$_3$, 400 MHz) δ 11.80 (1H, s), 9.23 (1H, dd, J=1.5 and 4.3 Hz), 8.60 (1H, dd, J=1.6 and 8.5 Hz), 7.80 (1H, dd, J=4.4 and 8.5 Hz), 4.12 (3H, s) ppm. FAB MS calcd for C$_{11}$H$_7$Br N$_2$O$_2$ 283 (MH$^+$), found 283.

Step 2: Preparation of Methyl 5-bromo-8-[(4-methoxybenzyl)oxy]-1,6-naphthyridine-7-carboxylate To a slurry of the phenol from Step 1 (0.195 g, 0.69 mmol) and cesium carbonate (2.47 g, 0.76 mmol) in DMF (3.5 ml) was added 4 methoxybenzyl chloride (0.1 ml, 0.72 mmol) at room temperature and the reaction was then warmed to 50 C and stirred at this temperature for 16 hrs. The reaction mixture was quenched with sat. aq. NH4Cl and poured into water and extracted into EtOAc and dried (Na$_2$SO$_4$). The solvent was evaporated in vacuo and the residue was chromatographed (SiO2, gradient elution, 20–30% EtOAc in hexanes) to afford a solid, which was washed with hexanes and then diethyl ether and dried in vacuo to afford the title compound.

FAB MS calcd for C$_{17}$H$_{15}$BrN$_2$O$_4$ 403 (MH$^+$), found 403.

Step 3: Preparation of methyl 8-[(4-methoxybenzyl)oxy]-5-(2-thienyl)-1,6-naphthyridine-7-carboxylate A solution of the bromide from Step 2 (94 mg, 0.24 mmol), 2-thiophene boronic acid (33 mg, 0.26 mmol), potassium fluoride (44.8 mg, 0.78 mmol) and trit-butyl phosphine (4.8 mg, 0.02 mmol) and Pd(dba)$_2$ (6.8 mg, 0.02 mmol) in THF (1.2 ml) was stirred at reflux for 3 hrs. The reaction was allowed to cool to room temperature and poured into water and extracted into CH$_2$Cl$_2$ and dried (Na$_2$SO$_4$).

The solvent was evaporated in vacuo and the residue was chromatographed (SiO2, gradient elution, 20–30% EtOAc in hexanes) to afford the title compound.

FAB MS calcd for C$_{21}$H$_{18}$N$_2$O$_4$S 407 (MH$^+$), found 407.

Step 4: Preparation of N-(3,5-dichlorobenzyl)-8-hydroxy-5-thien-2-yl-1,6-naphthyridine-7-carboxamide The title compound was prepared using the procedure described in Example 1, Step 3 replacing methyl 8-hydroxy-1,6-naphthyridine-7-carboxylate with methyl 8-[(4-methoxybenzyl)oxy]-5-(2-thienyl)-1,6-naphthyridine-7-carboxylate from Step 3.

$^1$H NMR (CDCl$_3$, 400 MHz) δ 13.09 (1H, s), 9.25 (1H, d, J=4.2 Hz), 8.80 (1H, d, J=8.8 Hz), 8.47 (1H, t, J=6.0 Hz), 7.71 (1H, dd, J=8.7 and 4.3 Hz), 7.54 (1H, t, J=6.2 Hz), 7.47 (1H, d, J=3.6 Hz), 7.35–7.15 (4H, m), 4.68 (2H, d, J=6.5 Hz) ppm. FAB MS calcd for C$_{20}$H$_{13}$N$_3$O$_2$ S 430 (MH$^+$), found 430. FAB HRMS exact mass calc'd for C$_{20}$H$_{13}$N$_3$O$_2$ S 430.0179 (MH$^+$), found 430.0192.

EXAMPLE 114

8-hydroxy-5-phenylsulfanyl-[1,6]naphthyridine-7-carboxylic acid 2-methylsulfanylbenzylamide

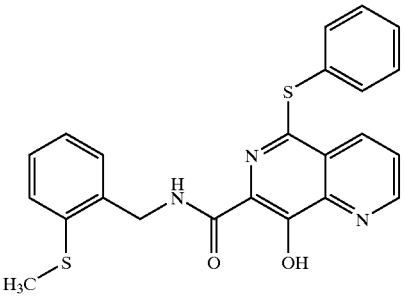

Step 1: Preparation of 8-Hydroxy-5-bromo-[1,6] naphthyridine-7-carboxylic acid 2-methylsulfanylbenzylamide To a 25 mL round bottomed flask with a stirring bar, reflux condenser and a nitrogen inlet was added 5-bromo-8- hydroxy-[1,6]naphthyridine-7-carboxylic acid methyl ester (0.511 g, 1.81 mmol) dry toluene (12.5 mL) and 2-methylthiobenzylamine (0.346 g, 2.26 mmol). This mixture was heated at reflux for 24 h. The mixture was cooled to ambient temperature and the toluene was removed in vacuo. The residue was triturated with a little Et$_2$O/hexane, collected on a frit and dried in vacuo to give 8-hydroxy-5-bromo-[1,6]naphthyridine-7-carboxylic acid 2-methylsulfanylbenzylamide as a crystalline solid.

$^1$H NMR (CDCl$_3$, 300 MHz) δ 9.19 (1H, d, J=5 Hz), 8.55 (1H, dd, J=2,9 Hz), 8.28 (1H, br), 7.71 (1H, dd, J=5,9 Hz), 7.41 (1H, d, J=7 Hz), 7.48 (1H, s) 7.22 (2H, m), 7.18 (2H, m), 4.79 (2H, d, J=6 Hz), 2.54 (3H, s). FAB MS calc'd for C$_{17}$H$_{14}$BrN$_3$O$_2$S 404 (MH$^+$), found 404.

Step 2: Preparation of 8-hydroxy-5-phenylsulfanyl-[1,6]naphthyridine-7-carboxylic acid 2-methylsulfanylbenzylamide To a 5 mL pyrex pressure vessel with a stirring bar was added 8-hydroxy-5-bromo-[1,6]naphthyridine-7-carboxylic acid 2-methylsulfanylbenzylamide (0.22 g, 0.54 mmol), thiophenol (0.181 g, 1.63 mmol) and triethylamine (0.557 mL, 4.00 mmol). The vessel was sealed under nitrogen and the stirred mixture heated in a 135° C. oil bath for 24 h. The cooled reaction mixture was concentrated in vacuo and the residue was chromatographed by reverse phase HPLC using water/acetonitrile as eluant to give 8-hydroxy-5-phenylsulfanyl-[1,6]naphthyridine-7-carboxylic acid 2-methylsulfanylbenzylamide as a solid.

$^1$H NMR (CDCl$_3$, 300 MHz) δ 9.19 (1H, dd, J=2, 5 Hz), 8.59 (1H, dd, J=2,9 Hz), 7.64 (1H, dd, J=5, 9 Hz), 7.56 (1H, br s), 7.51 (2H, dd, J=2, 6 Hz), 7.35 (2H, m), 7.21 (5H, m), 4.57 (2H, d, J=6 Hz), 2.46 (3H, s). FAB MS calc'd for C$_{22}$H$_{15}$cl$_2$N$_3$O$_2$S 434 (MH$^+$), found 434. FAB HRMS exact mass calc'd for C$_{23}$H$_{19}$N$_3$O$_2$S$_2$ 434.0991 (MH$^+$), found 434.0978.

EXAMPLE 115

N-(2,3-dimethoxybenzyl)-8-hydroxy-5-(methylsulfonyl)-1,6-naphthyridine-7-carboxamide

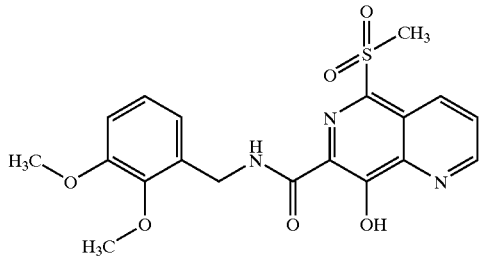

Step 1: Preparation of 5-Bromo-N-(2,3-dimethoxybenzyl)-8-hydroxy-1,6-naphthyridine-7-carboxamide Into a round bottom flask fitted with a gas inlet, condenser and a magnetic stirring bar was placed methyl 8-(benzoyloxy)-5-bromo-1,6-naphthyridine-7-carboxylate (0.4 g, 1.03 mmol), 2,3-dimethoxybenzylamine (0.432 g, 0.38 mL, 2.58 mmol) and 10 mL toluene. This mixture was refluxed for 18 hours, after which the reaction was cooled and the solvent removed in vacuo. The resulting residue was triturated with diethyl ether and filtered to yield 5-bromo-N-(2,3-dimethoxybenzyl)-8-hydroxy-1,6-naphthyridine-7-carboxamide as a light yellow solid.

$^1$H NMR (CDCl$_3$, 400 MHz) δ 9.18 (1H, dd, J=1.6 Hz, 4.2 Hz); 8.53 (1H, dd, J=1.6 Hz, 8.5 Hz); 8.26 (1H, m); 7.72 (1H, dd, J=4.2 Hz, 8.5 Hz); 6.84–7.04 (3H, m); 4.72 (2H, d, J=6.2 Hz); 3.97 (3H, s); 3.89 (3H, s).

Step 2: Preparation of N-(2,3-dimethoxybenzyl)-8-hydroxy-5-(methylsulfonyl)-1,6-naphthyridine-7-carboxamide trifluoroacetate salt In an analogous manner to Example 111, 5-bromo-N-(2,3-dimethoxybenzyl)-8-hydroxy-1,6-naphthyridine-7-carboxamide (0.1 g, 0.24 mmol) and sodium methanesulfinate (0.057 g, 0.56 mmol) were reacted in 2 mL DMF to give N-(2,3-dimethoxybenzyl)-8-hydroxy-5-(methylsulfonyl)-1,6-naphthyridine-7-carboxamide trifluoroacetate salt.

$^1$H NMR (CDCl$_3$, 400 MHz) δ 19.20–9.26 (2H, m); 8.35 (1H, m); 7.75 (1H, dd, J=4.2 Hz, 8.7 Hz); 7.06 (1H, t, J=7.9 Hz); 6.91–6.97 (2H, m) 4.72 (1H, d, J=6.2 Hz); 3.97 (3H, s); 3.88 (3H, s); 3.45 (3H, s) FAB HRMS exact mass calcd for C$_{19}$H$_{19}$N$_3$O$_6$S 418.1067 (MH$^+$), found 418.1061

EXAMPLE 116

N-(3,5-dichlorobenzyl)-8-hydroxy-5-[(2-hydroxyethyl)amino]-1,6-naphthyridine-7-carboxamide

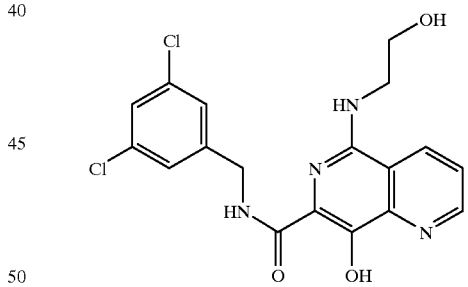

The title compound was prepared using the procedure described in Example 93 replacing 2-pyridin-3-ylethanamine with 1,2-aminoethanol.

$^1$H NMR (DMSO, 400 MHz) δ 12.35 (1H, s), 9.27(1H, t, J=6.5 Hz), 9.04 (1H, dd, J=4.4 and 1.4 Hz), 8.75 (1H, d, J=8.4 and 1.4 Hz), 7.71 (1H, dd, J=4.4 and 8.4 Hz), 7.40–7.10 (3H, m), 4.57 (2H, d, J=6.5 Hz) 4.00–3.00 (4H, m) ppm. FAB MS calcd for C$_{18}$H$_{16}$Cl$_2$N$_4$O$_3$ 407 (MH$^+$), found 407. FAB HRMS exact mass calc'd for C$_{18}$H$_{16}$Cl$_2$N$_4$O$_3$ 407.0672 (MH$^+$), found 407.0674.

EXAMPLE 117

N-(3,5-dichlorobenzyl)-8-hydroxy-5-(propylamino)-1,6-naphthyridine-7-carboxamide

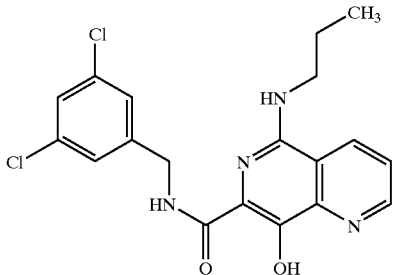

The title compound was prepared using the procedure described in Example 93 replacing 2-pyridin-3-ylethanamine with 1-aminopropane.

$^1$H NMR (DMSO, 400 MHz) δ 12.29 (1H, s), 9.21(1H, t, J=6.4 Hz), 9.03 (1H, dd, J=4.3 and 1.4 Hz), 8.75 (1H, d, J=8.4 and 1.4 Hz), 7.69 (1H, dd, J=4.3 and 8.4 Hz), 7.40–7.10 (3H, m), 4.57 (2H, d, J=6.4 Hz) 3.52 (2H, m), 1.67 (1H, quin, J=7.3 Hz), 0.97 (3H, t, J=7.4 Hz) ppm. FAB MS calcd for $C_{19}H_8Cl_2N_4O_2$ 405 (MH$^+$), found 405. FAB HRMS exact mass calc'd for $C_{19}H_{18}Cl_2N_4O_2$ 405.088 (MH$^+$), found 405.088.

EXAMPLE 118

N-(3,5-dichlorobenzyl)-8-hydroxy-5-[(1H-imidazol-4-ylethyl)amino]-1,6-naphthyridine-7-carboxamide

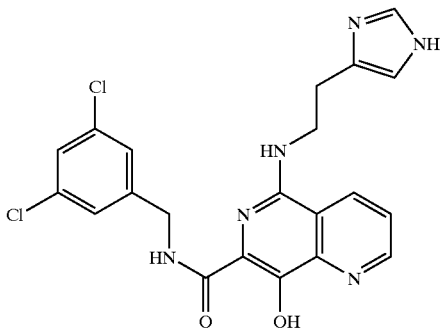

The title compound was prepared using the procedure described in Example 93 replacing 2-pyridin-3-ylethanamine with 2-(1H-imidazol-4-yl)ethanamine.

$^1$H NMR (DMSO, 400 MHz) δ 12.80 (1H, s), 9.29(1H, t, J=6.4 Hz), 9.05 (1H, dd, J=4.3 and 1.3 Hz), 8.91 (1H, s), 8.75 (1H, d, J=8.5 and 1.3 Hz), 7.70 (1H, dd, J=4.3 and 8.5 Hz), 7.52 (1H, s), 7.40–7.10 (3H, m), 4.60 (2H, d, J=6.3 Hz) 3.87(2H, m), 3.02 (2H, t, J=6.5 Hz) ppm. FAB MS calcd for $C_{21}H_{18}Cl_2N_6O_2$ 457 (MH$^+$), found 457. FAB HRMS exact mass calc'd for $C_{21}H_{18}Cl_2N_6O_2$ 457.0941 (MH$^+$), found 457.0946.

EXAMPLE 119

N-(3,5-dichlorobenzyl)-8-hydroxy-5-[(3-phenylprop-1-yl)amino]-1,6-naphthyridine-7-carboxamide

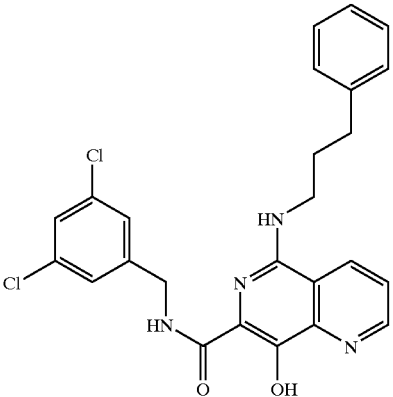

The title compound was prepared using the procedure described in Example 93 replacing 2-pyridin-3-ylethanamine with 3-phenpropylamine.

$^1$H NMR (DMSO, 400 MHz) δ 12.30 (1H, s), 9.18 (1H, t, J=6.5 Hz), 9.04 (1H, dd, J=4.3 and 1.3 Hz), 8.76 (1H, d, J=8.4 and 1.5 Hz), 7.71 (1H, dd, J=4.3 and 8.4 Hz), 7.60–7.10 (8H, m), 4.58 (2H, d, J=6.5 Hz) 3.61(2H, m), 2.72 (2H, t, J=7.9 Hz) 1.95 (2H, m) ppm. FAB MS calcd for $C_{25}H_{22}Cl_2N_4O_2$ 481 (MH$^+$), found 481. FAB HRMS exact mass calc'd for $C_{25}H_{22}Cl_2N_4O_2$ 481.1193 (MH$^+$), found 481.1188.

EXAMPLE 120

N-(3,5-dichlorobenzyl)-8-hydroxy-5-[(3-morpholin-4-ylpropyl)amino]-1,6-naphthyridine-7-carboxamide

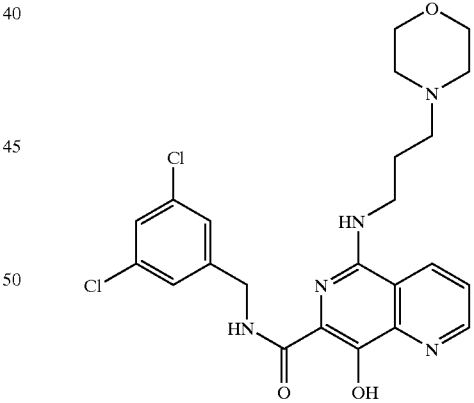

The title compound was prepared using the procedure described in Example 93 replacing 2-pyridin-3-ylethanamine with 3-morpholin-4-ylpropylamine.

$^1$H NMR (DMSO, 400 MHz) δ 12.40 (1H, s), 9.58 (1H, m), 9.29 (1H, t, J=6.5 Hz), 9.06 (1H, dd, J=4.3 and 1.5 Hz), 8.67 (1H, d, J=8.4 and 1.5 Hz), 7.74 (1H, dd, J=4.3 and 8.4 Hz), 7.30–7.10 (3H, m), 4.58 (2H, d, J=6.5 Hz) 3.94 (2H, d, J=12.8 Hz), 3.80–3.10 (8H, m), 3.00 (2H, m), 2.00 (2H, m) ppm. FAB MS calcd for $C_{23}H_{26}Cl_2N_5O_3$ 490 (MH$^+$), found 490. FAB HRMS exact mass calc'd for $C_{23}H_{26}Cl_2N_5O_3$ 490.1407 (MH$^+$), found 490.1405.

EXAMPLE 121

N-(3,5-dichlorobenzyl)-8-hydroxy-5-[4-(pyridin-2-ylmethyl)piperazin-1-yl]-1,6-naphthyridine-7-carboxamide

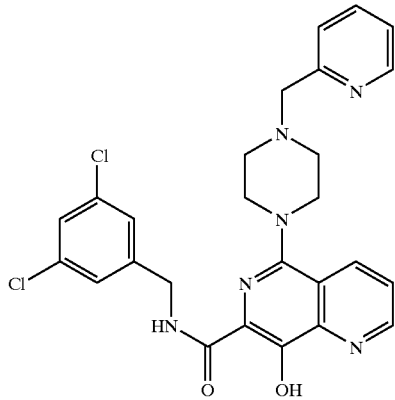

The title compound was prepared using the procedure described in Example 93 replacing 2-pyridin-3-ylethanamine with 1-(pyridin-2-ylmethyl)piperazine.

$^1$H NMR (DMSO, 400 MHz) δ 13.03 (1H, s), 9.41 (1H, t, J=6.5 Hz), 9.14 (1H, dd, J=4.2 and 1.5 Hz), 8.71 (1H, d, J=4.5 Hz), 8.56 (1H, d, J=8.5 and 1.5 Hz), 7.97 (1H, t, J=8.1 Hz), 7.78 (1H, dd, J=4.2 and 8.4 Hz), 7.57 (1H, d, J=7.8 Hz), 7.55–7.40 (4H, m), 4.80–4.40 (4H, m) 3.64 (4H, m), 3.51 (4H, m) ppm. FAB MS calcd for $C_{26}H_{24}Cl_2N_6O_2$ 523 (MH$^+$), found 523. FAB HRMS exact mass calc'd for $C_{26}H_{24}Cl_2N_6O_2$ 523.1407 (MH$^+$), found 523.1545.

EXAMPLE 122

N-(3,5-dichlorobenzyl)-8-hydroxy-5-[(2-morpholin-4-yl-2-pyridin-3-ylethyl)amino]-1,6-naphthyridine-7-carboxamide

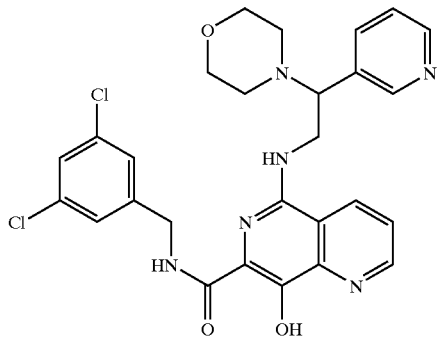

The title compound was prepared using the procedure described in Example 93 replacing 2-pyridin-3-ylethanamine with 2-morpholin-4-yl-2-pyridin-3-ylethylamine.

$^1$H NMR (DMSO, 400 MHz) δ 12.40 (1H, s), 9.14 (1H, m), 9.05 (1H, d, J=4.0 Hz), 8.68 (1H, s), 8.60–8.50 (2H, m), 8.00 (1H, m), 7.72 (1H, dd, J=4.2 and 8.4 Hz), 7.55–7.40 (4H, m), 4.63 (1H, dd, J=15.4 and 6.8 Hz), 4.53 (1H, dd, J=15.4 and 5.7 Hz), 4.00–3.00 (8H, m) ppm. FAB MS calcd for $C_{27}H_{26}Cl_2N_6O_3$ 553 (MH$^+$), found 553. FAB HRMS exact mass calc'd for $C_{27}H_{26}Cl_2N_6O_3$ 553.1516 (MH$^+$), found 553.1545.

EXAMPLE 123

N-(2,3-dimethoxybenzyl)-5-{[4-(dimethylamino)phenyl]thio}-8-hydroxy-1,6-naphthyridine-7-carboxamide

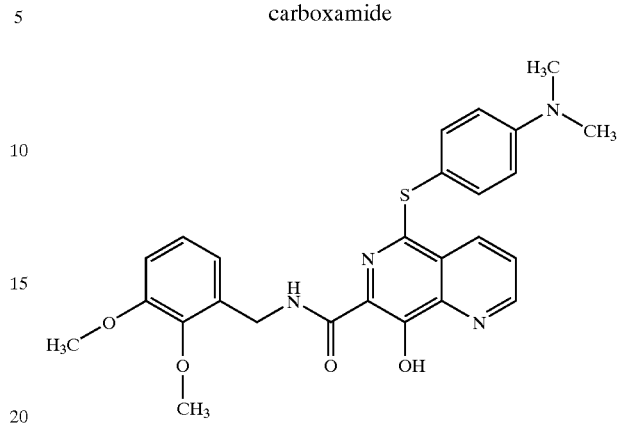

Into a pressure reactor was placed 5-bromo-N-(2,3-dimethoxybenzyl)-8-hydroxy-1,6-naphthyridine-7-carboxamide (0.1 g, 0.24 mmol), 4-(dimethylamino)benzenethiol (0.147 g, 0.96 mmol) and triethylamine (0.363 g, 0.5 mL, 3.59 mmol). The vessel was purged with nitrogen gas, sealed and heated to 135° C. for 18 hours, after which time it was cooled and the excess triethylamine removed in vacuo. The residue was partitioned between EtOAc/water and extracted. The combined organic extracts were washed with brine, dried over $Na_2SO_4$, filtered and the solvent removed. The resulting glass was triturated with diethyl ether and filtered to yield N-(2,3-dimethoxybenzyl)-5-{[4-(dimethylamino)phenyl]thio}-8-hydroxy-1,6-naphthyridine-7-carboxamide as a solid.

$^1$H NMR (CDCl$_3$, 400 MHz) δ 9.16 (1H, dd, J=1.6 Hz, 4.3 Hz); 8.61 (1H, dd, J=1.5 Hz, 8.4 Hz); 7.80 (1H, m); 7.63 (1H, dd, J=4.3 Hz, 8.4 Hz); 7.40 (2H, d, J=8.9 Hz); 7.02 (1H, t, J=8.0 Hz); 6.87 (1H, d, J=7.1 Hz); 6.77 (1H, d, J=7.7 Hz); 6.63 (2H, d, J=8.9 Hz); 4.56 (2H, d, J=6.3 Hz); 3.88 (3H, s); 3.80 (3H, s); 2.89 (6H, s) FAB MS calcd for $C_{26}H_{26}N_4O_4S$ 491 (MH$^+$), found 491.

EXAMPLE 124

8-hydroxy-6-methyl-[1,6]naphthyridine-7-carboxylic acid 3,5-dichloro-benzylamide

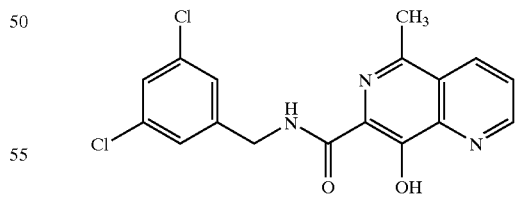

Step 1: Preparation of 2-bromo-6-methyl-pyridin-3-ol (124A)

To a solution of 5-hydroxy-2-methyl pyridine (20 g, 183.2 mmol) in dry pyridine (350 mL) was added a solution of bromine (10.3 mL, 201.5 mmol) in dry pyridine (100 mL) dropwise. After 1.5 h, the reaction mixture was filtered and the filtrate was concentrated under vacuum. The residue was treated with water (160 mL) and filtered. The resultant pale solid was washed with water (300 mL) and air dried. The crude product was recrystallized in EtOH (200 mL) to give the title compound as a solid.

Step 2: Preparation of 2-bromo-3-methoxy-6-methyl-pyridine

A mixture of 124A (19.9 g, 106 mmol), potassium carbonate (29.3 g, 212 mmol) and iodomethane (9.9 mL, 159 mmol) in acetone (300 mL) was refluxed overnight. The reaction mixture was filtered through Celite and the filtrate was concentrated. The residue was purified with flush chromatography (hexanes/ethyl acetate) to furnish 124B as a solid.

Step 3: Preparation of 2-bromo-3-methoxy-6-methyl-pyridine N-oxide (124C)

A mixture of 124B (14.8 g, 73.6 mmol) and urea hydrogen peroxide (14.5 g, 154.6 mmol) in dichloromethane (300 mL) was cooled to 0° C. Trifluoroacetic anhydride (20.7 mL, 147.2 mmol) was added slowly and the reaction mixture was allowed to warm to room temperature overnight. The reaction mixture was re-cooled to 0° C. and saturated aqueous sodium thiosulfate solution was added. After stirring for 30 min, the reaction mixture was acidified with 1N HCl to pH 1, extracted with dichloromethane. The organic phase was concentrated and the residue was purified with a short silica gel pad (eluted with 5% MeOH in chloroform) to give crude product. The crude product was recrystallized (hexanes/dichloromethane) to furnish 124C as a solid.

Step 4: Preparation of 2-bromo-3-methoxy-6-methyl-4-nitro-pyridine N-oxide (124D)

A solution of 124C (7.0 g, 32.4 mmol) in concentrate $H_2SO_4$ (9.5 mL) was added to a solution of concentrate $H_2SO_4$ (9.5 mL) and fuming $HNO_3$ (13 mL) and the mixture was heated at 60° C. for 30 min. After cooling to room temperature, the reaction mixture was added to iced 6M solution of NaOH (150 mL) and neutralized to pH 6 with 1N NaOH solution. The reaction mixture was extracted with dichloromethane (4×100 mL). The combined organic phases were dried over $Na_2SO_4$, filtered and concentrated to give 124D as a solid.

Step 5: Preparation of 2-bromo-3-methoxy-6-methyl-pyridin-4-ylamine (124E)

A mixture of 124D (0.75 g, 2.9 mmol), iron (0.48 g, 8.6 mmol) and ammonium chloride (0.46 g, 8.6 mmol) in EtOH/$H_2O$ (10 mL/3 mL) was refluxed (bath temperature 90° C.) for 4 h. After cooling to room temperature, the reaction mixture was diluted with water, extracted with dichloromethane three times. The combined organic phases were dried over $Na_2SO_4$, filtered and concentrated to give 124E as a oil.

Step 6: Preparation of 2-bromo-3-methoxy-6-methyl-[1,6]naphthyridine (124F)

To a mixture of 124E (1.97 g, 9.0 mmol) and sodium iodide (0.27 g, 1.8 mmol) in 70% $H_2SO_4$ (30 mL) at 110° C. under nitrogen was added acrolein (1.1 mL, 13.6 mmol) via syringe pump (1 mL/h). The reaction was stirred for another 30 min at 110° C. after complete addition. After cooling to room temperature, the reaction mixture was diluted with ice water (50 mL) then added to an aqueous solution (500 mL) of $Na_2CO_3$ (60 g) slowly. This mixture was extracted with chloroform (3×200 mL). The combined organic phases were dried over $Na_2SO_4$, filtered and concentrated. The residue was purified by flush chromatography (hexanes/ethyl acetate) to give 124F as a solid.

Step 7: Preparation of 8-methoxy-6-methyl-[1,6]naphthyridine-7-carboxylic acid methyl ester (124G)

A glass lined steel bomb was charge with 124F (1.0 g, 3.95 mmol), 1,3-bis(diphenylphosphino)propane (0.33 g, 0.8 mmol), sodium acetate (0.35 g, 4.35 mmol) and MeOH (30 mL). The mixture was purged with nitrogen for 10 min. Palladium acetate (0.19 g, 0.84 mmol) was then added. The vessel was sealed, purged with carbon monoxide (3×100 psi) then pressurized with carbon monoxide to 300 psi. The bomb was then heated at 100° C. overnight. The pressure was relieved and the reaction mixture was filtered through Celite and the filtrate was concentrated. The resultant residue was purified by flush chromatography (hexanes/ethyl acetate) to give 124G as a solid.

Step 8: Preparation of 8-hydroxy-6-methyl-[1,6]naphthyridine-7-carboxylic acid 3,5-dichloro-benzylamide (124H)

A mixture of 124G (150 mg, 0.64 mmol), 3,5-dichlorobenzylamine (153 mg, 0.87 mmol) and aluminum chloride (27 mg, 0.20 mmol) in toluene (8 mL) was refluxed for 4 h under nitrogen. After cooling to room temperature, the reaction mixture was treated with aqueous saturated $NaHCO_3$ solution and ethylenediaminetetraacetic acid (1 g, 3.4 mmol) to pH 7. The mixture was extracted with chloroform four times. The combined organic phases were dried over $Na_2SO_4$ and concentrated. The residue was purified by preparative reverse-phase HPLC to give 124H.

$^1$H NMR (400 MHz, DMSO) δ 13.2 (s, 1H), 9.73 (t, 1H), 9.15 (dd, 1H), 8.64 (dd, 1H), 7.83 (dd, 1H), 7.52 (s, 1H), 7.44 (s, 2H), 4.57 (d, 2H), 2.85 (s, 3H).

EXAMPLE 125

8-hydroxy-6-methyl-[1,6]naphthyridine-7-carboxylic acid 4-fluoro-benzylamide (125)

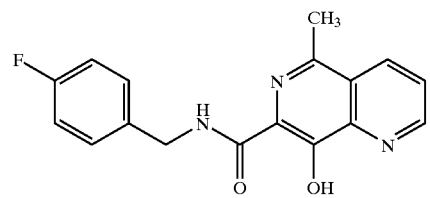

In a manner similar to that for the compound 124H in Example 124, Step 8, substituting 3,5-dichlorobenzylamine with 4-fluorobenzylamine in Step 8, 8-hydroxy-6-methyl-[1,6]naphthyridine-7-carboxylic acid the 4-fluoro-benzylamide (125) was prepared.

$^1$H NMR (400 MHz, $CD_3OD$) δ 9.10 (d, 1H), 8.72 (d, 1H), 7.84 (dd, 1H), 7.43 (dd, 2H), 7.06 (t, 2H), 4.64 (s, 2H), 2.88 (s, 3H).

EXAMPLE 126

5-bromo-N-(4-fluorobenzyl)-8-hydroxy-1,6-naphthyridine-7-carboxamide

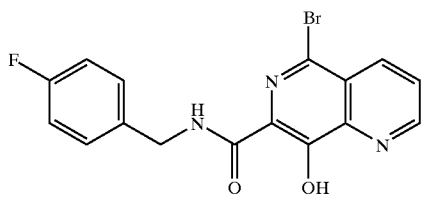

A slurry of the ester from example 113 step 1 (0.50 g, 0.177 mmol) and 4-fluorobenzylamine (0.243 g, 1.94 mmol) in toluene (2 mL) were heated at reflux for 20 hrs. Upon cooling to room temperature, the resulting solids were collected by filtration and washed with methanol (3 ml) and then with diethyl ether (5 ml) to afford the title compound as a white solid.

$^1$H NMR (CDCl$_3$, 400 MHz) δ 9.20 (1H, d, J=4.3 Hz), 8.56 (1H, d, J=8.4 Hz), 8.17 (1H, m), 7.74 (1H, dd, J=8.4 and 4.3 Hz), 7.39 (2H, m), 7.07 (2H, t, J=8.6 Hz), 4.67 (2H, d, J=6.2 Hz) ppm. FAB MS calcd for BrC$_{16}$H$_{11}$N$_3$O$_2$F 376 (MH$^+$), found 376.

EXAMPLE 127

1-(7-{[(4-fluorobenzyl)amino]carbonyl}-8-hydroxy-1,6-naphthyridin-5-yl)-4-methylpiperazine

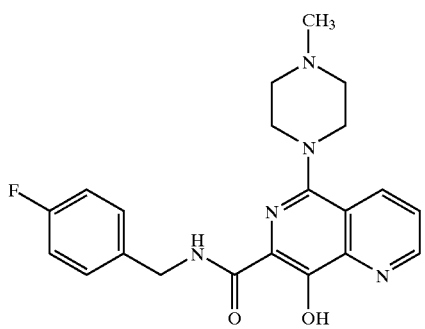

To a solution of 5-bromo-N-(4-fluorobenzyl)-8-hydroxy-1,6-naphthyridine-7-carboxamide from example 126 (45 mg, 0.120 mmol), N-methylpiperazine (79.8 ul, 0.72 mmol) in DMPU (0.50 ml) was heated at 135 C for 18 hrs. The resulting mixture was treated with TFA (100 ul) and purified by preparative HPLC (Gilson Semi Preparative HPLC System and a YMC Combiprep Pro Column (50×20 mm i.d., C18, S-5 um, 120A) eluting with 5–95% acetonitrile/water (0.1%) at 15 ml/min) to afford the piperazin-4-ium trifluoroacetate salt of the title compound after lyophillization.

$^1$H NMR (d6 DMSO, 400 MHz) δ 13.1 (1H, s), 9.33 (1H, t, J=6.4 Hz), 9.11 (1H, d, J=4.2 Hz), 8.51(1H, d, J=8.4 Hz), 7.76 (1H, dd, J=4.2 and 8.4 Hz), 7.43 (2H, m), 7.17 (2H, t, J=8.9 Hz), 4.57 (2H, d, J=6.4 Hz) and 3.80–3.10 (11H, m) FAB MS calcd for C$_{21}$H$_{22}$FN$_5$O$_2$ 396 (MH$^+$), found 396. FAB HRMS exact mass calcd for C$_{21}$H$_{22}$FN$_5$O$_2$ 396.1831 (MH$^+$), found 396.1846.

EXAMPLE 128

1-(7-{[(4-fluorobenzyl)amino]carbonyl}-8-hydroxy-1,6-naphthyridin-5-yl)piperazine

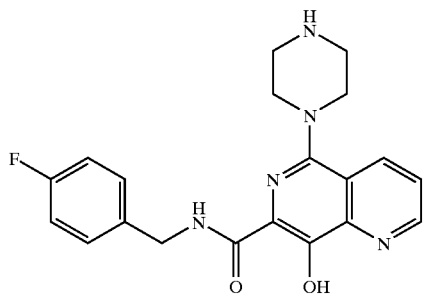

The title compound was prepared as the piperazin-4-ium trifluoroacetate salt using the procedure described in example 127 replacing N-methylpiperazine with piperazine.

$^1$H NMR (d6 DMSO, 400 MHz) δ 9.36 (1H, t, J=6.4 Hz), 9.13 (1H, dd, J=1.6 and 4.2 Hz), 8.51(1H, dd, J=8.4 and 1.6 Hz), 7.76 (1H, dd, J=4.2 and 8.4 Hz), 7.42 (2H, m), 7.18 (2H, t, J=8.9 Hz), 4.57(2H, d, J=6.4 Hz) and 3.60–3.10 (8H, m). FAB MS calcd for C$_{20}$H$_{20}$FN$_5$O$_2$ 382 (MH$^+$), found 382. FAB HRMS exact mass calcd for C$_{21}$H$_{22}$FN$_5$O$_2$ 382.1674 (MH$^+$), found 382.1687.

EXAMPLE 129

Benzyl 8-Hydroxyquinoline-7-carboxamide

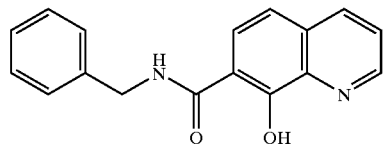

A mixture of 8-hydroxyquinoline-7-carboxylic acid (0.50 g, 2.64 mmol), benzylamine (0.34 g, 3.17 mmol), 1-hydroxybenzotriazole (0.45 g, 2.91 mmol), 1-(3-dimethylaminopropyl)-3-ethylcarbodiimide hydrochloride (0.56 g, 2.91 mmol), and triethylamine (1.6 mL, 11.6 mmol) in DMF (15 mL) was heated at 80° C. overnight. The reaction mixture was concentrated under vacuum. The residue was dissolved in methanol and subjected to HPLC purification on C-18 stationary phase eluted with water/acetonitrile/TFA mobile phase. Collection and lyophilization of appropriate fractions provide the title compound as yellow solid.

$^1$H NMR (400 MHz, CDCl$_3$) δ 9.01 (dd, 1H), 8.32 (dd, 1H), 8.23 (br s, 1H), 8.06 (d, 1H), 7.69 (dd, 1H), 7.45–7.25 (m), 4.70 (d, 2H).

EXAMPLE 130

1-Methyl-3-phenylpropyl 8-hydroxyquinoline-7-carboxamide

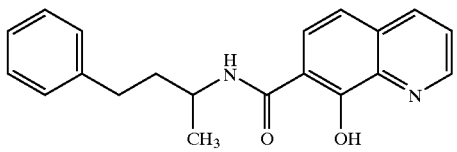

A mixture of 8-hydroxyquinoline-7-carboxylic acid (0.50 g, 2.64 mmol), 1-methy-3-phenylpropylamine (0.39 g, 2.64 mmol), 1-hydroxybenzotriazole (0.45 g, 2.91 mmol), 1-(3-dimethylaminopropyl)-3-ethylcarbodiimide hydrochloride (0.50 g, 2.64 mmol), and triethylamine (1.3 mL, 9.25 mmol) in DMF (15 mL) was stirred at room temp overnight. The reaction mixture was concentrated under vacuum. The residue was dissolved in DMSO and subjected to HPLC purification on C-18 stationary phase eluted with water/acetonitrile/TFA mobile phase. Collection and lyophilization of appropriate fractions provide the title compound as yellow solid.

$^1$H NMR (400 MHz, DMSO-d$_6$) δ 9.01 (br s, 1H), 8.88 (br s, 1H), 8.62 (br d, 1H), 8.17 (d, 1H), 7.84 (br s, 1H), 7.69 (dd, 1H), 7.57 (d, 1H), 7.29–7.17 (m, 5H), 4.14 (m, 1H), 2.66 (br s, 2H), 1.94 (br m, 1H), 1.85 (br m, 1H), 1.25 (d, 3H).

EXAMPLE 131

2-Phenylcyclopropyl 8-hydroxyquinoline-7-carboxyamide

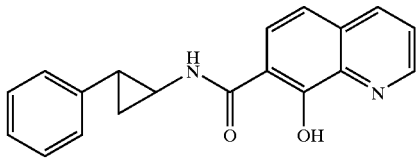

The title compound was prepared using a procedure similar to that described in Example 127, except that 1-amino-2-phenylcyclopropane was substituted for 1-methy-3-phenylpropylamine.

$^1$H NMR (400 MHz, DMSO-d$_6$) δ 9.35 (br s, 1H), 9.01 (br s, 1H), 8.62 (br s, 1H), 8.17 (br d, 1H), 7.84 (br s, 1H), 7.59 (dd, 1H), 7.32–7.18 (m, 5H), 3.14 (m, 1H), 2.22 (m, 1H), 1.47 (br m, 1H), 1.34 (br m, 1H).

EXAMPLE 132

1-Indanyl 8-hydroxyquinoline-7-carboxamide

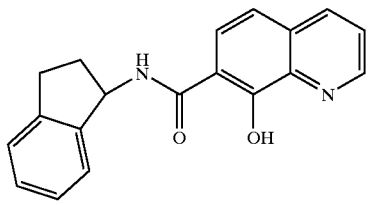

The title compound was prepared using a procedure similar to that described in Example 127, except that 1-aminoindane was substituted for 1-methy-3-phenylpropylamine.

$^1$H NMR (400 MHz, DMSO-d$_6$) δ 9.35 (br s, 1H), 9.01 (br s, 1H), 8.62 (br s, 1H), 8.17 (br d, 1H), 7.82 (br s, 1H), 7.59 (dd, 1H), 7.33–7.20 (m, 4H), 5.67 (m, 1H), 3.05 (m, 1H), 2.95 (m, 1H), 2.50 (m, 1H), 2.05 (m, 1H).

EXAMPLE 133

N-[(2E)-3-Phenyl-2-propenyl]8-hydroxyquinoline-7-carboxamide

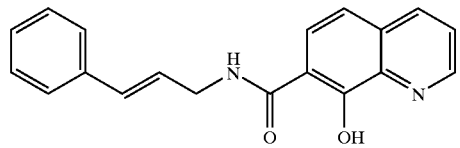

The title compound was prepared using a procedure similar to that described in Example 127, except that (2E)-3-phenyl-2-propenylamine was substituted for 1-methy-3-phenylpropylamine.

$^1$H NMR (400 MHz, DMSO-d$_6$) δ 9.18 (br s, 1H), 8.95 (d, 1H), 8.42 (d, 1H), 8.05 (d, 1H), 7.70 (m, 1H), 7,46 (m, 3H), 7.33 (m, 2H), 7.24 (m, 2H), 6.62 (d, 1H), 6.41 (m, 1H), 4.19 (dd, 2H).

EXAMPLE 134

Benzyl 5-chloro-8-hydroxyquinoline-7-carboxamide

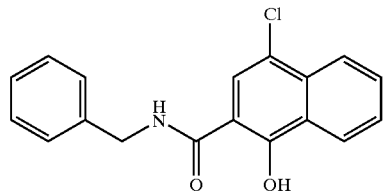

A mixture of 5-chloro-8-hydroxyquinoline-7-carboxylic acid (0.50 g, 2.24 mmol), benzylamine (0.29 g, 2.68 mmol), 1-hydroxy-7-azabenzotriazole (0.36 g, 2.68 mmol), 1-(3-dimethylaminopropyl)-3-ethylcarbodiimide hydrochloride (0.51 g, 2.68 mmol), and triethylamine (0.62 mL, 4.47 mmol) in DMF (15 mL) was stirred at room temperature overnight. The reaction mixture was concentrated under vacuum. The residue was dissolved in DMSO and subjected to HPLC purification on C-18 stationary phase eluted with water/acetonitrile/TFA mobile phase. Collection and lyophilization of appropriate fractions provide the title compound as yellow solid.

$^1$H NMR (400 MHz, DMSO-d$_6$) δ 9.40 (br s, 1H), 9.03 (br s, 1H), 8.54 (dd, 1H), 8.22 (s, 1H), 7.84 (dd, 1H), 7.40–7.28 (m, 4.60 (d, 2H).

EXAMPLE 135

5-[[2-(Dimethylamino)-2-oxoethyl](methyl)amino]-N-(4-fluorobenzyl)-8-hydroxy-1,6-naphthyridine-7-carboxamide

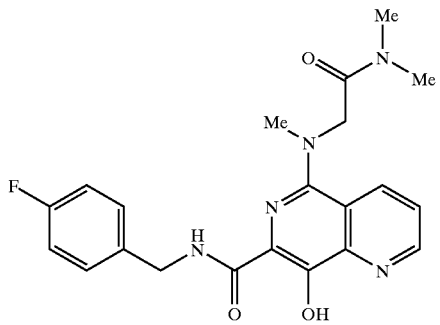

Into a 10 mL pressure vessel equipped with a magnetic stir bar was placed 0.1 g (0.266 mmol) 5-bromo-N-(4-fluorobenzyl)-8-hydroxy-1,6-naphthyridine-7-carboxamide (see Example 126), 0.031 g (0.27 mmol) N,N-dimethyl-2-(methylamino)acetamide, 0.726 mL (0.8 mmol) N,N-diisopropylethylamine and 5 mL DMF. The vessel was sealed and heated on an oil bath to 135° C. for 18 hrs., after which the mixture was cooled and the solvent removed in vacuo. The residue was purified by reverse phase HPLC on a $C_{18}$ column using acetonitrile/water as eluent to give 5-[[2-(dimethylamino)-2-oxoethyl](methyl)amino]-N-(4-fluorobenzyl)-8-hydroxy-1,6-naphthyridine-7-carboxamide.

$^1$H NMR (300 MHz, CDCl$_3$) δ 9.22 (dd, J=1.4 Hz, J=4.4 Hz, 1H); 8.57 (dd, J=1.4 Hz, J=8.6 Hz, 1H); 8.37 (t, J=4.5 Hz, 1H); 7.65 (dd, J=4.4 Hz, J=8.5 Hz, 1H); 7.41 (d, J=8.3 Hz, 1H); 7.40 (d, J=8.3 Hz, 1H); 7.06 (t, J=8.5 Hz, 2H); 4.65 (d, J=6.1 Hz, 2H); 4.08 (s, 2H); 3.15 (s, 3H); 2.99 (s, 3H); 2.80 (s, 3H)

HRMS calc for $C_{21}H_{22}FN_5O_3$ (M+1): calc, 412.1766; found, 412.1779

EXAMPLE 136

N-1-(7-{[(4-Fluorobenzyl)amino]carbonyl}-8-hydroxy-1,6-naphthyridin-5-yl)-N-1-,N-2-,N-2-trimethylethanediamide

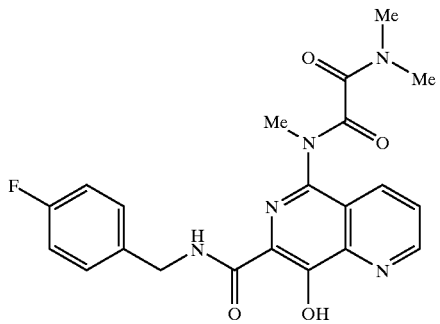

Step 1: 7-{[(4-Fluorobenzyl)amino]carbonyl}-5-[[methoxy(oxo)acetyl]-(methyl)amino]-1,6-naphthyridin-8-yl methyl oxalate

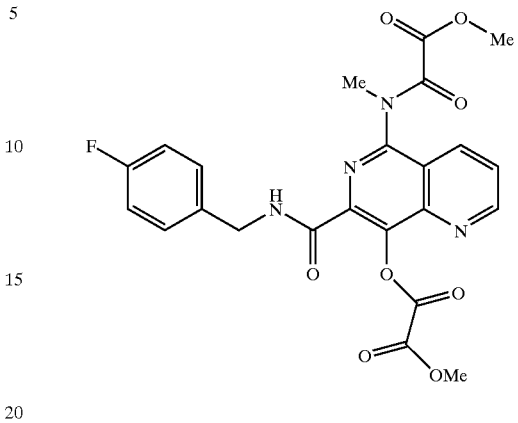

Into a 50 mL flask fitted with a gas inlet and magnetic stir bar was placed 0.3 g (0.92 mmol) N-(4-fluorobenzyl)-8-hydroxy-5-(methylamino)-1,6-naphthyridine-7-carboxamide, 0.961 mL (5.51 mmol) N,N-diisopropylethylamine and 20 mL CH$_2$Cl$_2$. The mixture was cooled to −78° C. and to it was added 0.338 mL (3.68 mmol) methyl chlorooxoacetate dropwise in 1 mL CH$_2$Cl$_2$. The reaction was then allowed to warm to ambient temperature and stirring was continued for 18 hrs, after which time the solvent was removed and the crude mixture was carried on without purification.

Step 2: N-1-(7-{[(4-Fluorobenzyl)amino]carbonyl}-8-hydroxy-1,6-naphthyridin-5-yl)-N-1-,N-2-,N-2-trimethylethanediamide hydrochloride Into a 50 mL flask fitted with a gas inlet and magnetic stir bar was placed the crude reaction mixture from Step 1 and 20 mL methanol. The mixture was cooled to 0° C. with an ice bath and dimethylamine gas was bubbled into the reaction until saturated. The ice bath was removed and stirring was continued for an additional hour, after which time the solvent was removed in vacuo to give crude product which was purified by reverse phase HPLC on a $C_{18}$ column using acetonitrile/water as eluent. The purified material was dissolved in 20 mL EtOAc, cooled to 0° C. and HCl gas bubbled through the solution briefly. The solvent was then removed in vacuo to give the title compound as a tan solid.

$^1$H NMR (400 MHz, DMSO, 135° C.) δ 9.16 (d, J=4.3 Hz, 1H), 8.86 (s, 1H), 8.36 (s, 1H), 7.81 (dd, J=4.3 Hz, 8.7 Hz, 1H), 7.43 (t, J=5.9 Hz, 2H), 7.11 (t, J=7.11 Hz, 2H), 4.61 (d, J=6.7 Hz, 2H), 3.39 (s, 3H), 2.97 (s, 3H), 2.51 (s, 3H). HRMS calc for $C_{21}H_{20}FN_5O_4$ (M+1): calc, 426.1572; found, 426.1570.

EXAMPLE 137

N-(4-Fluorobenzyl)-5-(2,6-dioxohexahydropyrimidin-4-yl)-8-hydroxy-[1,6]napthyridine-7-carboxamide

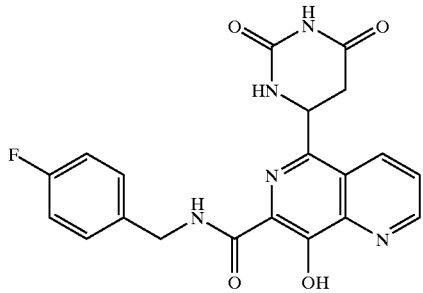

Step 1: Methyl (2E)-3-(7-{[(4-fluorobenzyl)amino]carbonyl}-8-hydroxy[1,6]-naphthyridin-5-yl)-2-propenoate

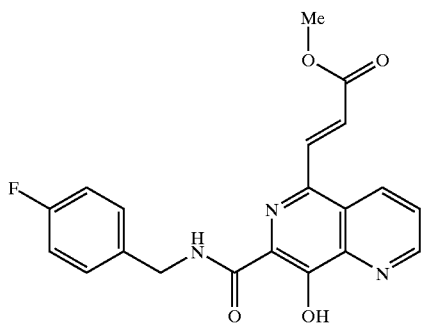

A mixture of 5-bromo-N-(4-fluorobenzyl)-8-hydroxy-[1,6]naphthyridine-7-carboxamide (2.00 g, 5.32 mmol), methyl acrylate (3.90 mL, 21.50 mmol), palladium acetate (0.60 g, 2.66 mmol), tri-o-tolylphosphine (1.62 g, 5.32 mmol), triethylamine (2.96 mL, 21.5 mmol) in DMF (75 mL) was purged with nitrogen and heated with stirring at 100° C. in a sealed tube for 18 hours. A second portion of palladium acetate (0.60 g, 2.66 mmol) was added, and reaction mixture was heated at the same temperature for 24 more hours. The resultant product mixture was filtered through a pad of Celite. The filtrate was concentrated under vacuum and the residue was triturated with diethyl ether. The resulting yellow solid was filtered, and recrystallized from absolute ethanol (500 mL) to provide the title propenoate.

$^1$H NMR (400 MHz, CDCl$_3$) δ 9.21 (dd, J=4.2, 1.9 Hz, 1H), 8.63 (dd, J=8.7, 1.4 Hz, 1H), 8.41 (br t, J=6.0, 1H), 8.31 (d, J=15.3 Hz, 1H), 7.71 (dd, J=8.6, 4.1 Hz, 1H), 7.40 (dd, J=9.3, 5.4 Hz, 2H), 7.08 (t, J=8.6 Hz, 2H), 7.01 (d, J=15.3 Hz, 1H), 4.72 (d, J=6.4 Hz, 1H), 3.87 (s, 3H).

Step 2: N-(4-Fluorobenzyl)-5-(2,6-dioxohexahydropyrimidin-4-yl)-8-hydroxy-[1,6]napthyridine-7-carboxamide To stirred, molten urea (50 g) heated in an oil bath at 165° C. under an atmosphere of nitrogen, propenoate from Step 1 (1.20 g, 3.15 mmol) was added. The resultant mixture was stirred at the same temperature for 2.5 hours. The product mixture was dissolved in water and the solution was acidified to pH 5–6. The resultant precipitate was filtered, dissolved in DMSO, and subjected to HPLC purification on C-18 stationary phase eluted with water/acetonitrile/TFA mobile phase. Collection and lyophilization of appropriate fractions provided the title compound as yellow solid.

$^1$H NMR (400 MHz, ~5:1 CDCl$_3$-DMSO-d$_6$) δ 13.35 (s, 1H), 9.19 (br d, 1H), 8.68–8.59 (m, 2H), 8.14 (br s, 1H), 7.71 (dd, J=8.6, 4.2 Hz, 1H), 7.42 (dd, J=8.4, 5.5 Hz, 2H), 7.06 (t, J=8.6 Hz, 2H), 5.36 (br d, 1H), 4.65 (br s, 2H), 3.03 (br s, 2H), 2.59 (br s, 1H). ES MS M+1=410

The enantiomers were separated by column chromatography on ChiralPak AD 50×5 eluted with a gradient of 80% 0.1% DEA in hexane, 10% ethanol, and 10% methanol to 50% 0.1% DEA in hexane, 25% ethanol, and 25% methanol at 70 mL/min over 60. Collection and concentration of appropriate fractions provided each of the enantiomers with >93% ee. The faster eluting enantiomers exhibited a +0.077° rotation at 1 mg/mL in MeOH observed at 578 nm and 25° C. The slower eluting enantiomers exhibited a −0.069° rotation under the same conditions.

EXAMPLE 138

5-(1,3-Dimethyl-2,6-dioxohexahydro-4-pyrimidinyl)-N-(4-fluorobenzyl)-8-hydroxy[1,6]-naphthyridine-7-carboxamide

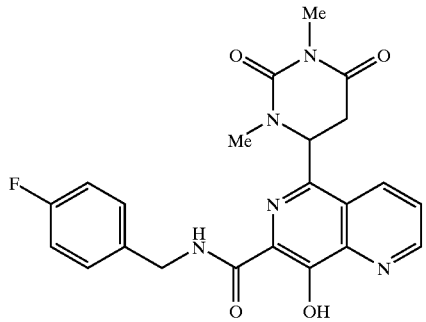

The title compound was prepared using a procedure similar to that described in Example 137, except that 1,3-dimethylurea was substituted for urea, and the reaction mixture was heated in on oil bath at 165° C. for 18 hours.

$^1$H NMR (400 MHz, CDCl$_3$) δ 13.32 (s, 1H), 9.23 (br dd, J=2.8, 1.5 Hz, 1H), 8.30 (br dd, J=7.2, 1.6 Hz, 1H), 8.11 (br t, 1H), 7.71 (dd, J=8.6, 4.2 Hz, 1H), 7.42 (dd, J=8.4, 5.5 Hz, 2H), 7.07 (t, J=8.6 Hz, 2H), 5.19 (br d, J=6.6 Hz, 1H), 4.73 (dd, J=14.5, 6.7 Hz, 1H), 4.56 (dd, J=14.6, 5.7 Hz, 1H), 3.37 (dd, J=16.3, 7.0 Hz, 1H), 3.01 (s, 3H), 2.97 (d, J=16.3 Hz, 1H), 2.90 (s, 3H). ES MS M+1=438

The enantiomers were separated by column chromatography on ChiralPak AD 50×5 eluted with 50% 0.1% DEA in hexane and 50% ethanol at 7 mL/min. Collection and concentration of appropriate fractions provided each of the enantiomers with >93% ee. The faster eluting enantiomers exhibited a +0.037° rotation at 1 mg/mL in MeOH observed at 578 nm and 25° C. The slower eluting enantiomers exhibited a −0.035° rotation under the same conditions.

EXAMPLES 139 & 140

5-(1-Methyl-2,6-dioxohexahydro-4-pyrimidinyl)-N-(4-fluorobenzyl)-8-hydroxy[1,6]-naphthyridine-7-carboxamide 5-(3-Methyl-2,6-dioxohexahydro-4-pyrimidinyl)-N-(4-fluorobenzyl)-8-hydroxy[1,6]-naphthyridine-7-carboxamide

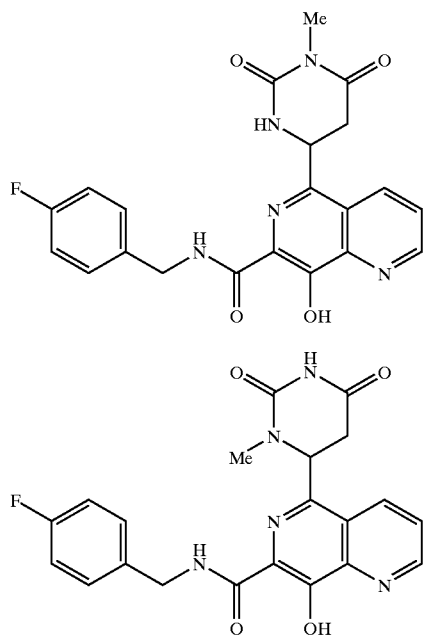

The title compounds were prepared using a procedure similar to that described in Example 137, except that methylurea was substituted for urea, and the reaction mixture was heated in on oil bath at 165° C. for 18 hours. The two regioisomers were separated by HPLC.

139: $^1$H NMR (400 MHz, DMSO-d$_6$) δ 13.33 (s, 1H), 9.19 (br d, J=2.8 Hz, 1H), 9.00 (br t, 6.6 Hz, 1H), 8.82 (br d, J=8.6 Hz, 1H), 8.42 (br s, 1H), 7.71 (dd, J=8.6, 4.4 Hz, 1H), 7.42 (dd, J=7.3, 5.5 Hz, 2H), 7.20 (t, J=9.2 Hz, 2H), 5.50 (br m, 1H), 4.66 (dd, J=14.8, 6.8 Hz, 1H), 4.57 (dd, J=14.8, 6.4 Hz, 1H), 3.18 (dd, J=16.1, 6.4 Hz, 1H), 3.03 (dd, J=16.1, 5.7 Hz, 1H), 2.90 (s, 3H). ES MS M+1=424

140: $^1$H NMR (400 MHz, CDCl$_3$) δ 13.4 (brs, 1H), 9.27 (dd, J=4.2, 1.8 Hz, 1H), 8.35 (dd, J=8.6, 1.5 Hz, 1H), 8.13 (br t, 1H), 7.75 (dd, J=8.6, 4.2 Hz, 1H), 7.52 (br s, 1H), 7.41 (dd, J=8.6, 5.3 Hz, 2H), 7.20 (t, J=8.6 Hz, 2H), 5.28 (dd, J=6.9, 1.7 Hz, 1H), 4.66 (dd, J=14.8, 6.8 Hz, 1H), 4.63 (d, J=6.4 Hz, 1H), 3.34 (dd, J=16.5, 7.0 Hz, 1H), 3.00 (s, 3H), 3.03 (br d, J=16.5 Hz, 1H). ES MS M+1=424

EXAMPLE 141

N-(4-Fluorobenzyl)-8-hydroxy-5-(5-oxo-1,4-thiazepan-7-yl)[1,6]naphthyridine-7-carboxamide

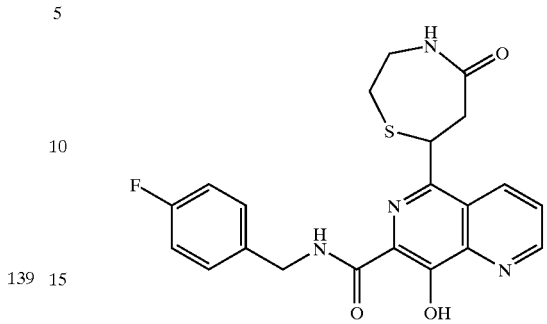

A mixture of methyl (2E)-3-(7-{[(4-fluorobenzyl)amino]carbonyl}-8-hydroxy[1,6]-naphthyridin-5-yl)-2-propenoate (Example 137, Step 1) (1.22 g, 3.20 mmol) and cysteamine (4.0 g) in DMF (15 mL) was heated in an oil bath at 80° C. under an atmosphere of nitrogen with stirring for 18 hours. The product mixture was treated with water and the mixture was acidified to pH 2. The resultant precipitate was filtered, dissolved in DMSO, and subjected to HPLC purification on C-18 stationary phase eluted with water/acetonitrile/TFA mobile phase. Collection and lyophilization of appropriate fractions provided the title compound as yellow solid.

$^1$H NMR (400 MHz, DMSO-d$_6$) δ 13.35 (s, 1H), 9.65 (t, J=6.5 Hz, 1H), 9.15 (dd, J=4.2, 1.5 Hz, 1H), 8.77 (dd, J=8.4, 1.3 Hz, 1H), 7.93 (br t, J=4.2 Hz, 1H), 7.81 (dd, J=8.6, 4.2 Hz, 1H), 7.43 (dd, J=8.6, 5.7 Hz, 2H), 7.18 (t, J=9.0 Hz, 2H), 4.67 (dd, J=8.1, 6.2 Hz, 1H), 4.58 (m, 2H), 3.79 (dd, J=15.8, 6.2 Hz, 1H), 3.49 (br m, 2H), 3.37 (dd, J=15.8, 8.2 Hz, 1H), 2.84 (br m, 2H). ES MS M+1=427

EXAMPLE 142

N-(4-Fluorobenzyl)-8-hydroxy-5-(1-oxido-5-oxo-1,4-thiazepan-7-yl)-[1,6]naphthyridine-7-carboxamide

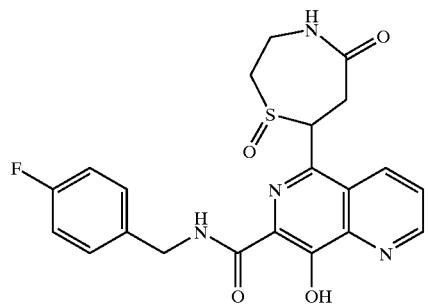

To a cold (0° C.) solution of N-(4-fluorobenzyl)-8-hydroxy-5-(5-oxo-1,4-thiazepan-7-yl)[1,6]naphthyridine-7-carboxamide (Example 141) (0.22 g, 0.52 mmol) in DMF (25 mL), a solution of 3-chloroperbenzoic acid in dichloromethane (0.57 mmol, 0.129 g/mL) was added and stirred at room temperature for 2 hours. The product mixture was treated with DMSO (1 mL), diethyl ether (200 mL), and cooled in an ice bath. The resultant precipitate was filtered, dissolved in DMSO, and subjected to HPLC purification on C-18 stationary phase eluted with water/acetonitrile/TFA mobile phase. Collection and lyophilization of appropriate fractions provided the title compound.

¹H NMR (400 MHz, DMSO-d₆) δ 13.38 (s, 1H), 9.94 (t, J=6.0 Hz, 0.25H), 9.58 (t, J=6.0 Hz, 0.75H), 9.18 (br s, 1H), 8.78 (br d, J=8.4 Hz, 0.75H), 8.74 (br d, J=9.0 Hz, 0.25H), 8.30 (br s, 0.25H), 8.18 (br s, 0.75H), 7.85 (dd, J=8.4, 4.2 Hz, 1H), 7.41 (m, 2H), 7.19 (m, 2H), 4.84 (dd, J=8.8,4.9 Hz, 0.75H), 4.59 (d, J=6.0 Hz, 2H), 4.43 (dd, J=13.9, 4.9 Hz, 0.25H), 4.03–2.93 (m, 6H). ES MS M+1=443

EXAMPLE 143

N-(4-Fluorobenzyl)-8-hydroxy-5-(1,1-dioxido-5-oxo-1,4-thiazepan-7-yl) [1,6]-naphthyridine-7-carboxamide

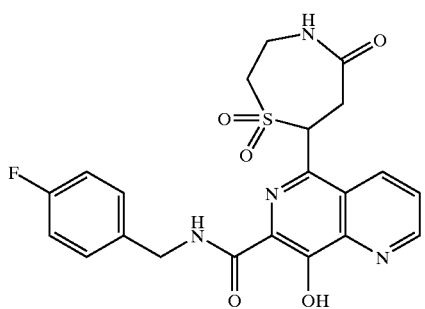

To a cold (0° C.) solution of N-(4-fluorobenzyl)-8-hydroxy-5-(5-oxo-1,4-thiazepan-7-yl)[1,6]naphthyridine-7-carboxamide (Example 141) (0.22 g, 0.52 mmol) in DMF (25 mL), a solution of 3-chloroperbenzoic acid in dichloromethane (1.14 mmol, 0.129 g/mL) was added and stirred at room temperature overnight. The product mixture was treated with DMSO (0.5 mL), diethyl ether (200 mL), and cooled in an ice bath. The resultant precipitate was filtered, dissolved in DMSO, and subjected to HPLC purification on C-18 stationary phase eluted with water/acetonitrile/TFA mobile phase. Collection and lyophilization of appropriate fractions provided the title compound.

¹H NMR (400 MHz, DMSO-d₆) δ 13.37 (s, 1H), 9.71 (t, J=6.2 Hz, 1H), 9.17 (br d, 1H), 8.82 (d, J=7.5 Hz, 1H), 8.42 (br s, 1H), 7.84 (dd, J=8.4, 4.2 Hz, 1H), 7.41 (dd, J=8.6, 5.9 Hz, 2H), 7.18 (t, J=9.0 Hz, 2H), 5.85 (dd, J=7.3, 5.1 Hz, 1H), 4.66 (dd, J=15.6, 7.0 Hz, 1H), 4.56 (dd, J=15.6, 5.9 Hz, 1H), 3.95–3.49 (m, 6H). ES MS M+1=459

EXAMPLE 144

N-(4-Fluorobenzyl)-5-{[2-(dimethylamino)-2-oxoethyl]sulfanyl}-8-hydroxy-[1,6]napthyridine-7-carboxamide

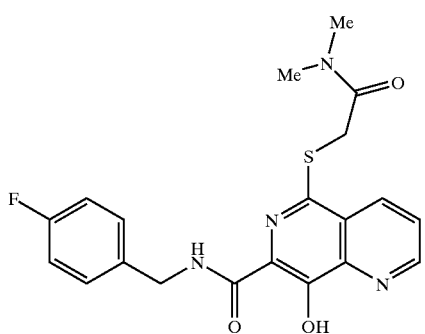

Step 1: [(7-{[(4-Fluorobenzyl)amino]carbonyl}-8-hydroxy[1,6]naphthyridin-5-yl)sulfanyl]acetic acid

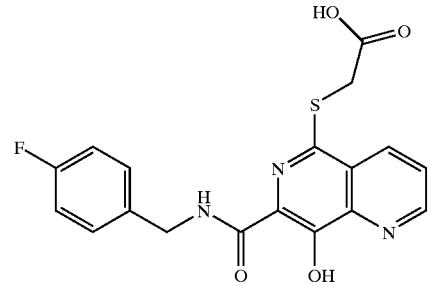

A mixture of 5-bromo-N-(4-fluorobenzyl)-8-hydroxy-[1,6]naphthyridine-7-carboxamide (0.40 g, 1.05 mmol), mercaptoacetic acid (0.11 mL, 1.60 mmol), triethylamine (0.59 mL, 4.2 mmol) in diglyme (2.5 mL) was heated with stirring at 130° C. under an atmosphere of nitrogen for 18 hours. The product mixture was treated with 1 M aq HCl at 0° C. The resulting yellow solid was filtered, washed with diethyl ether to provide the title acid.

Step 2: N-(4-Fluorobenzyl)-5-{[2-(dimethylamino)-2-oxoethyl]sulfanyl}-8-hydroxy-[1,6]naphthyridine-7-carboxamide A mixture of the carboxylic acid from Step 1 (0.18 g, 0.46 mmol), dimethylamine hydrochloride (56 mg, 0.69 mmol), 1-hydroxy-7-azabenzotriazole (62 mg, 0.46 mmol), 1-(3-dimethylaminopropyl)-3-ethylcarbodiimide hydrochloride (106 mg, 0.55 mmol), and diisopropylethylamine (0.2 mL, 0.46 mmol) in DMF (2.3 mL) was stirred at room temperature overnight. The product mixture was treated with 1 M aq HCl at 0° C. The resulting yellow solid was filtered, washed with diethyl ether. The solid was dissolved in DMSO and subjected to HPLC purification on C-18 stationary phase eluted with water/acetonitrile/TFA mobile phase. Collection and lyophilization of appropriate fractions provide the title compound as yellow solid.

¹H NMR (400 MHz, CDCl₃) δ 13.13 (s, 1H), 9.71 (br t, 1H), 9.16 (dd, J=4.3, 1.8 Hz, 1H), 8.35 (dd, J=8.2, 1.5 Hz, 1H), 7.61 (dd, J=8.2, 4.3 Hz, 1H), 7.47 (dd, J=8.4, 5.5 Hz, 2H), 7.03 (t, J=8.6 Hz, 2H), 4.69 (d, J=6.4 Hz, 2H), 3.97 (s, 2H), 3.13 (s, 3H), 2.84 (s, 3H). ES MS M+1=415

EXAMPLE 145

N-(4-Fluorobenzyl)-5-[2-(dimethylamino)-2-oxoethoxy]-8-hydroxy-[1,6]napthyridine-7-carboxamide

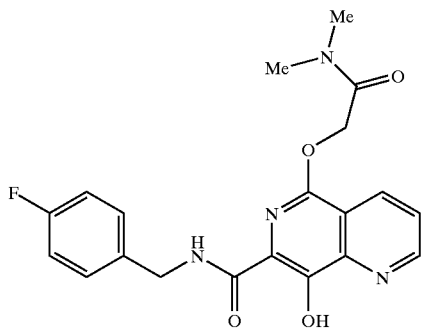

Step 1: Methyl 8-(benzoyloxy)-5-[2-(dimethylamino)-2-oxoethoxy][1,6]-naphthyridine-7-carboxylate

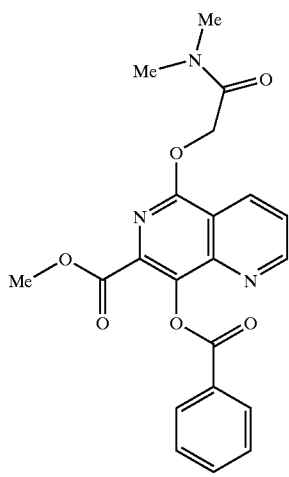

To a cold (0° C.) suspension of methyl 8-(benzoyloxy)-5-oxo-5,6-dihydro[1,6]-naphthyridine-7-carboxylate (3.24 g, 10 mmol), 2-hydroxy-N,N-dimethylacetamide (1.13 g, 11 mmol), and triphenylphosphine (5.24 g, 20 mmol) in THF (100 mL), diethyl azodicarboxylate (3.1 mL, 19.6 mmol) was added over a period of 3 minutes. The resultant mixture was stirred at room temperature for two days. The product mixture was treated with 1 M aq HCl and extracted with methylene chloride. The organic extract was dried over anhydrous sodium sulfate, filtered and concentrated under vacuum. The residual oil was subject to column chromatography on silica gel eluting with 1–2% methanol in ethyl acetate. Collection and concentration of the appropriate fractions provided the slower eluting o-alkylated isomer as white solid.

$^1$H NMR (400 MHz, CDCl$_3$) δ 9.09 (dd, J=4.2, 1.7 Hz, 2H), 8.74 (dd, J=8.3, 6.1 Hz, 2H), 8.32 (br d, J=7.1 Hz, 2H), 7.69–7.53 (m, 4H), 5.30 (s, 2H), 3.83 (s, 3H), 3.19 (s, 3H), 3.04 (s, 3H).

Step 2: N-(4-Fluorobenzyl)-5-[2-(dimethylamino)-2-oxoethoxy]-8-hydroxy-[1,6]napthyridine-7-carboxamide A mixture of methyl ester from Step 1 (0.28 g, 0.68 mmol) and 4-fluorobenzylamine (0.16 mL, 1.43 mmol) in toluene (5 mL) was heated in an oil bath at 110° C. overnight. The resultant precipitate was filtered, washed with diethyl ether, and dried under vacuum. The solid was dissolved in DMSO and subjected to HPLC purification on C-18 stationary phase eluted with water/acetonitrile/TFA mobile phase. Collection and lyophilization of appropriate fractions provided the title compound as yellow solid.

$^1$H NMR (400 MHz, CDCl$_3$) δ 12.66 (s, 1H), 9.17 (dd, J=4.3, 1.5 Hz, 1H), 8.54 (dd, J=8.2, 1.8 Hz, 1H), 8.33 (br t, J=5.8 Hz, 1H) 7.62 (dd, J=8.6, 4.6 Hz, 1H), 7.42 (dd, J=8.8, 5.5 Hz, 2H), 7.03 (t, J=8.9 Hz, 2H), 4.97 (s, 2H), 4.64 (d, J=6.1 Hz, 2H), 3.00 (s, 3H), 2.78 (s, 3H). ES MS M+1=399

EXAMPLE 146

N-(4-Fluorobenzyl)-5-{[2-(dimethylamino)-2-oxoethyl](methylsulfonyl)amino}-8-hydroxy-[1,6]napthyridine-7-carboxamide

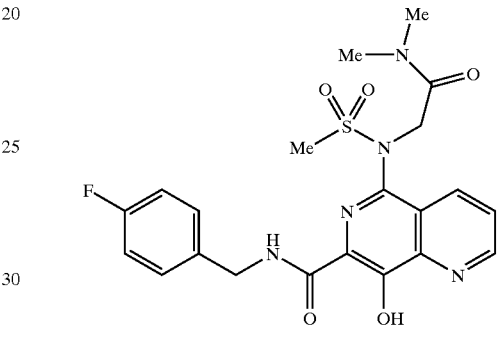

Step 1: N,N-dimethyl-2-[(methylsulfonyl)amino]acetamide

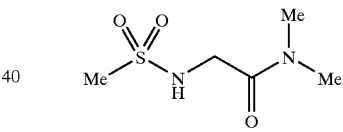

To a cold (0° C.) solution of 2-amino-N,N-dimethylacetamide (1.62 g, 10 mmol) and triethylamine (3.4 mL, 25 mmol) in dichloromethane (50 mL), methanesulfonyl chloride (0.85 mL, 11 mmol) was added over a period of 5 minutes. The resultant mixture was stirred at room temperature for overnight. The product mixture was diluted with dichloromethane and washed with sat. aq. sodium bicarbonate. The organic extract was dried over anhydrous magnesium sulfate, filtered and concentrated under vacuum to provide the title acetamide as white solid.

Step 2: N-(4-Fluorobenzyl) 5-{[2-(dimethylamino)-2-oxoethyl](methyl-sulfonyl)amino}-8-hydroxy-[1,6]napthyridine-7-carboxamide A mixture of 5-bromo-N-(4-fluorobenzyl)-8-hydroxy-[1,6]naphthyridine-7-carboxamide (0.57 g, 1.5 mmol), N,N-dimethyl-2-[(methylsulfonyl)amino]acetamide from Step 1 (0.25 g, 1.38 mmol) and copper (I) oxide (0.10 g, 0.70 mmol) in pyridine (5 mL) was heated in an oil bath at 115° C. overnight. The resultant mixture was concentrated under vacuum. To the residue, chloroform (200 mL) and a saturated aqueous solution of ethylenediamine tetraacetic acid, disodium salt (75 mL) was added. The mixture was stirred vigorously at room temp for 2 hours in the presence of air, and filtered through a pad of Celite. The organic extract was separated, dried over anhydrous magnesium sulfate, filtered and concentrated under vacuum. The residue was dissolved in DMSO and subjected to HPLC purification on C-18 stationary phase eluted with water/acetonitrile/TFA mobile phase. Collection and lyophilization of appropriate fractions provided the title compound as white solid.

$^1$H NMR (400 MHz, CDCl$_3$) δ 13.30 (br s, 1H), 9.18 (dd, J=4.2, 1.5 Hz, 1H), 8.90 (dd, J=8.6, 1.7 Hz, 1H), 8.06 (br t, J=6.4 Hz, 1H) 7.62 (dd, J=8.5, 4.4 Hz, 1H), 7.38 (dd, J=8.8,5.5 Hz, 2H), 7.06 (t, J=8.7 Hz, 2H), 4.68 (d, J=6.1 Hz, 2H), 4.66 (s, 2H), 3.17 (s, 3H), 2.97 (s, 3H), 2.82 (s, 3H). ES MS M+1=476

EXAMPLE 147

N-(4-Fluorobenzyl)-5-[3-(dimethylamino)-3-oxopropyl]-8-hydroxy-[1,6]napthyridine-7-carboxamide

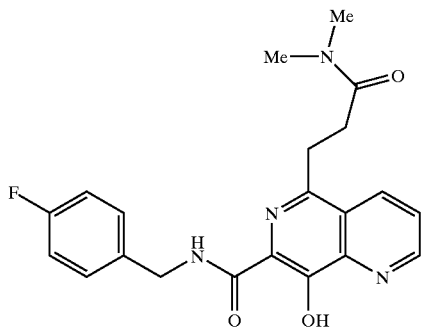

Step 1: Methyl 3-(7-{[(4-fluorobenzyl)amino]carbonyl}-8-hydroxy[1,6]-naphthyridin-5-yl)propanoate

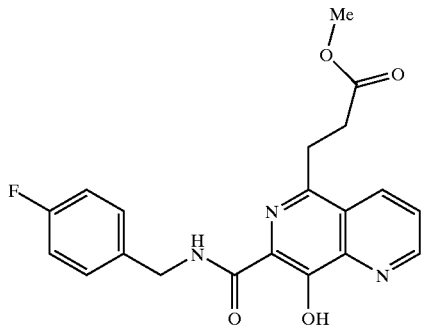

Methyl (2E)-3-(7-{[(4-fluorobenzyl)amino]carbonyl}-8-hydroxy[1,6]-naphthyridin-5-yl)-2-propenoate (Example 137, Step 1) (0.40 g, 1.05 mmol) was added to molten hydroxyurea (3.2 g) heated in an oil bath at 135–140° C. under an atmosphere of nitrogen. The mixture was heated with stirring for 0.5 hours. The product mixture was dissolved in water and the solution was acidified to pH 2. The resultant precipitate was filtered, dissolved in DMSO, and subjected to HPLC purification on C-18 stationary phase eluted with water/acetonitrile/TFA mobile phase. Collection and lyophilization of appropriate fractions provided the title methyl ester.

$^1$H NMR (400 MHz, DMSO-d$_6$) δ 13.3 (br s, 1H), 9.27 (br t, J=6.1, 1H), 9.16 (dd, J=4.2, 1.5 Hz, 1H), 8.72 (dd, J=8.5, 1.5 Hz, 1H), 7.83 (dd, J=8.5, 4.0 Hz, 1H), 7.44 (dd, J=8.6, 5.7 Hz, 2H), 7.19 (t, J=8.9 Hz, 2H), 4.60 (d, J=6.4 Hz, 2H), 3.51 (s, 3H), 3.48 (t, J=7.1 Hz, 2H), 3.01 (t, J=7.1 Hz, 2H). ES MS M+1=383

Step 2: N-(4-Fluorobenzyl)-5-[3-(dimethylamino)-3-oxopropyl]-8-hydroxy-[1,6]napthyridine-7-carboxamide A mixture of methyl ester from Step 1 (89 mg, 0.23 mmol) and aqueous NaOH (1M, 1.6 mL) in a mixture of methanol (5 mL) and THF (1 mL) was stirred at room temperature overnight. The resultant mixture was acidified to pH 2 and concentrated under vacuum. The residue was treated with a mixture of dimethylamine hydrochloride (28 mg, 0.34 mmol), 1-hydroxy-7-azabenzotriazole (35 mg, 0.26 mmol), 1-(3-dimethylaminopropyl)-3-ethylcarbodiimide hydrochloride (49 mg, 0.26 mmol), and diisopropylethylamine (0.11 mL, 0.60 mmol) in DMF (4 mL) and stirred at room temperature overnight. The product mixture was concentrated. The residue was partitioned between dichloromethane and aq HCl. The organic extract was isolated, dried over anhydrous magnesium sulfate, filtered and concentrated under vacuum. The residue was dissolved in DMSO and subjected to HPLC purification on C-18 stationary phase eluted with water/acetonitrile/TFA mobile phase. Collection and lyophilization of appropriate fractions provided the title compound as white solid.

$^1$H NMR (400 MHz, DMSO-d$_6$) δ 13.3 (br s, 1H), 9.45 (br t, J=6.2, 1H), 9.16 (br s, 1H), 8.75 (d, J=8.3 Hz, 1H), 7.83 (dd, J=8.3, 4.1 Hz, 1H), 7.43 (dd, J=8.6, 5.7 Hz, 2H), 7.19 (t, J=8.8 Hz, 2H), 4.58 (d, J=6.0 Hz, 2H), 3.40 (t, J=7.1 Hz, 2H), 2.97 (s, 3H), 2.94 (t, J=7.1 Hz, 2H), 2.75 (s, 3H). ES MS M+1=397

EXAMPLE 148

N-(4-Fluorobenzyl)-5-[(1E)-3-(dimethylamino)-3-oxo-1-propenyl]-8-hydroxy-[1,6]napthyridine-7-carboxamide

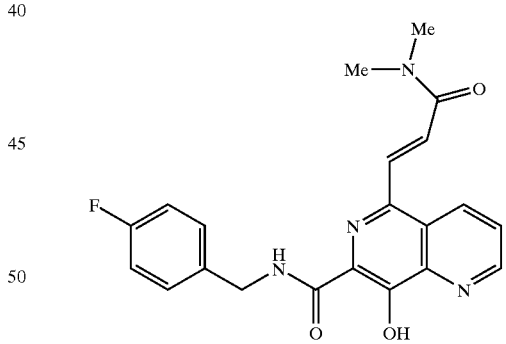

The title compound was prepared using a procedure similar to that described in Example 147, Step 2, except that methyl (2E)-3-(7-{[(4-fluorobenzyl)amino]carbonyl}-8-hydroxy[1,6]-naphthyridin-5-yl)-2-propenoate (Example 137, Step 1) was substituted for methyl 3-(7-{[(4-fluorobenzyl)amino]carbonyl}-8-hydroxy[1,6]-naphthyridin-5-yl)propanoate.

$^1$H NMR (400 MHz, DMSO-d$_6$) δ 13.8 (br s, 1H), 9.88 (br t, J=6.4, 1H), 9.18 (dd, J=4.0, 1.5 Hz, 1H), 8,92 (dd, J=8.8, 1.3 Hz, 1H), 8.17 (d, J=14.8 Hz, 1H), 7.93 (d, J=14.8 Hz, 1H), 7.85 (dd, J=8.6, 4.0 Hz, 1H), 7.45 (dd, J=8.6, 5.7 Hz, 2H), 7.19 (t, J=9.0 Hz, 2H), 4.64 (d, J=6.4 Hz, 2H), 3.23 (s, 3H), 2.99 (s, 3H). ES MS M+1=395

EXAMPLE 149

N-(4-Fluorobenzyl)-5-[2-(3-oxo-1-piperazinyl)ethyl]-8-hydroxy-[1,6]napthyridine-7-carboxamide

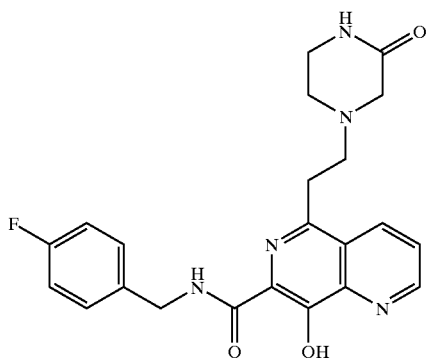

A mixture of 5-bromo-N-(4-fluorobenzyl)-8-hydroxy-[1,6]naphthyridine-7-carboxamide (0.40 g, 1.06 mmol), tri-n-butylvinyl tin (0.62 mL, 2.13 mmol), bis(triphenylphosphine)palladium(II) chloride (0.15 g, 0.21 mmol), 2-piperazinone (0.12 g, 1.17 mmol) in dioxane (10 mL) was purged with nitrogen and heated with stirring at 100° C. in a sealed tube for 24 hours. The resultant product mixture was filtered through a pad of Celite. The filtrate was concentrated under vacuum. The residue was dissolved in DMSO, and subjected to HPLC purification on C-18 stationary phase eluted with water/acetonitrile/TFA mobile phase. Collection and lyophilization of appropriate fractions provided the title compound as yellow solid.

$^1$H NMR (400 MHz, DMSO-d$_6$) δ 13.52 (s, 1H), 9.59 (br t, J=6.8, 1H), 9.20 (dd, J=4.0, 1.3 Hz, 1H), 8.75 (dd, J=8.6, 1.5 Hz, 1H), 8.44 (br s, 1H), 7.90 (dd, J=8.4, 4.2 Hz, 1H), 7.43 (dd, J=8.6, 5.7 Hz, 2H), 7.19 (t, J=9.0 Hz, 2H), 4.62 (d, J=5.7 Hz, 2H), 4.4–3.4 (m). ES MS M+1=424

EXAMPLE 150

N-(4-Fluorobenzyl)-5-[2-(2-oxo-1-imidazolidinyl)ethyl]-8-hydroxy-[1,6]napthyridine-7-carboxamide

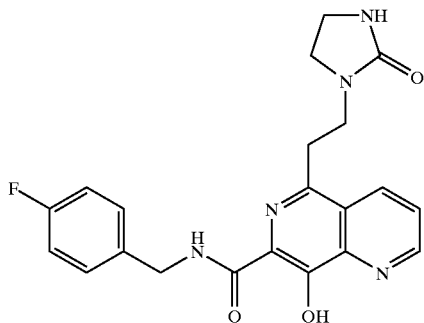

Step 1: tert-Butyl-2-{[2-(7-{[(4-fluorobenzyl)amino]carbonyl}-8-hydroxy[1,61-naphthyridin-5-yl)ethyl]amino}ethylcarbamate

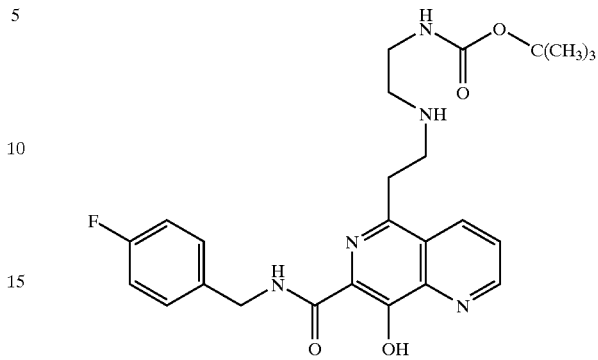

A mixture of 5-bromo-N-(4-fluorobenzyl)-8-hydroxy-[1,6]naphthyridine-7-carboxamide (2.00 g, 5.33 mmol), tri-n-butylvinyl tin (3.12 mL, 10.70 mmol), bis(triphenylphosphine)palladium(II) chloride (0.75 g, 1.10 mmol), N-Boc-ethylenediamine (4.23 g, 26.6 mmol) in dioxane (50 mL) was purged with nitrogen and heated with stirring at 100° C. in a sealed tube overnight. The resultant product mixture was filtered through a pad of Celite. The filtrate was concentrated under vacuum. The residue was dissolved in DMSO, and subjected to HPLC purification on C-18 stationary phase eluted with water/acetonitrile/TFA mobile phase. Collection and lyophilization of appropriate fractions provided the title N-Boc amino napthyridine.

Step 2: N-(4-fluorobenzyl)-5-{2-[(2-aminoethyl)amino]ethyl}-8-hydroxy[1,6]-naphthyridine-7-carboxamide

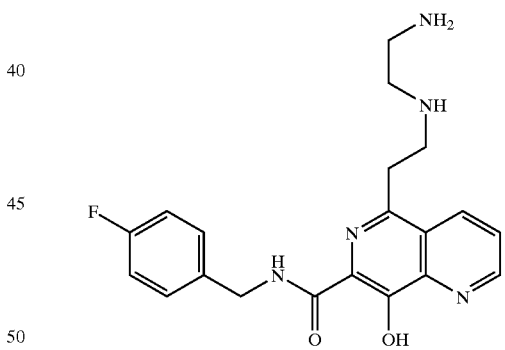

The solution of the above N-Boc amino napthyridine (0.5 g, 1.03 mmol) in dichloromethane (10 mL) was treated with trifluoroacetic acid (0.5 mL) and stirred at room temperature for 4 hours. The resultant mixture was concentrated under vacuum. The residue was dissolved in DMSO, and subjected to HPLC purification on C-18 stationary phase eluted with water/acetonitrile/TFA mobile phase. Collection and lyophilization of appropriate fractions provided the title diamine.

Step 3: N-(4-Fluorobenzyl)-5-[2-(2-oxo-1-imidazolidinyl)ethyl]-8-hydroxy-[1,6]napthyridine-7-carboxamide A mixture of the diamine from Step 2 (200 mg, 0.52 mmol), 1,1'-carbonyldiimidazole (100 mg, 0.62 mmol), and diisopropylethylamine (0.1 mL) in DMSO (2 mL) was stirred at room temperature overnight. The resultant mixture was subjected to HPLC purification on C-18 stationary phase eluted with water/acetonitrile/TFA mobile phase. Collection and lyophilization of appropriate fractions provided the title compound as white solid.

$^1$H NMR (400 MHz, DMSO-$d_6$) δ 13.4 (br s, 1H), 9.93 (t, J=6.4, 1H), 9.15 (br d, J=4.2 Hz, 1H), 8.71 (br d, J=8.6 Hz, 1H), 7.83 (ddd, J=8.6, 4.2, 1.1 Hz, 1H), 7.45 (dd, J=7.9, 5.7 Hz, 2H), 7.19 (td, J=8.9, 1.1 Hz, 2H), 4.55 (d, J=6.4 Hz, 2H), 3.70 (t, J=6.2 Hz, 2H), 3.42–3.37 (m, 4H), 3.15 (t, J=8.4 Hz, 2H). ES MS M+1=410

EXAMPLE 151

N-(4-Fluorobenzyl)-5-[2-(2-oxo-1-piperazinyl) ethyl]-8-hydroxy-[1,6]napthyridine-7-carboxamide

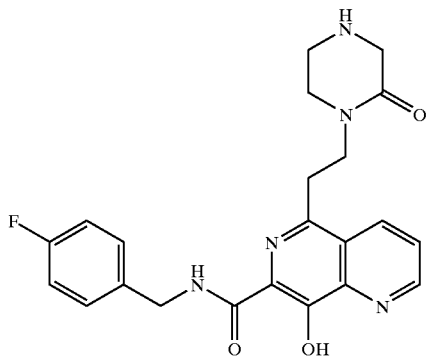

Step 1: N-(4-fluorobenzyl)-5-{2-[(2-aminoethyl) (chloroacetyl)amino]ethyl}-8-hydroxy[1,6] naphthyridine-7-carboxamide

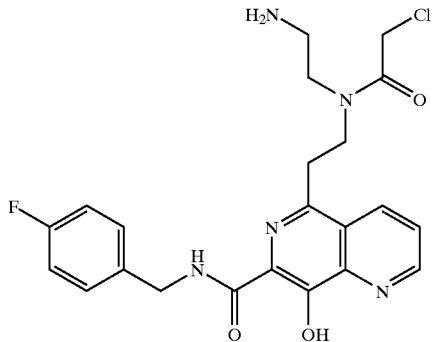

A mixture of tert-Butyl-2-{[2-(7-{[(4-fluorobenzyl) amino]carbonyl}-8-hydroxy[1,6]-naphthyridin-5-yl)ethyl] amino}ethylcarbamate (Example 150, Step 1) (0.10 g, 0.21 mmol), isopropylethylamine (0.11 mL, 0.62 mmol), and chloroacetyl chloride (18 µL, 0.23 mmol) in dioxane (10 mL) was stirred at room temperature for 1 hour. The resultant mixture was concentrated under vacuum. The residue was dissolved in dichloromethane (5 mL) and treated with trifluoroacetic acid (0.5 mL) and stirred at room temperature overnight. The resultant mixture was concentrated under vacuum and used in the following step without further purification. ES MS M+1=406

Step 2: N-(4-Fluorobenzyl)-5-[2-(2-oxo-1-piperazinyl)ethyl]-8-hydroxy-[1,6]napthyridine-7-carboxamide A mixture of the crude chloroamine from Step 1 (95 mg, 0.21 mmol) and diisopropylethylamine (0.5 mL, 2.87 mmol) in dichloromethane (5 mL) was stirred at room temperature for two hours. The resultant mixture was concentrated under vacuum. The residue was dissolved in DMSO and subjected to HPLC purification on C-18 stationary phase eluted with water/acetonitrile/TFA mobile phase. Collection and lyophilization of appropriate fractions provided the title compound as yellow solid.

$^1$H NMR (400 MHz, DMSO-$d_6$) δ 13.4 (br s, 1H), 9.65 (br t, 1H), 9.16 (br d, J=4.2 Hz, 1H), 9.16 (br s, 1H), 8.70 (br dd, J=7.2, 1.5 Hz, 1H), 7.85 (dd, J=8.4, 4.2 Hz, 1H), 7.44 (dd, J=8.5, 6.3 Hz, 2H), 7.19 (t, J=9.0 Hz, 2H), 4.59 (d, J=6.3 Hz, 2H), 3.99 (t, J=6.6 Hz, 2H), 3.64 (br s, 2H), 3.48 (t, J=6.6 Hz, 2H), 3.31 (br t, 2H). ES MS M+1=423

EXAMPLE 152

5-(1,1-dioxido-1,2-thiazinan-2-yl)-N-(4-fluorobenzyl)-8-hydroxy-1,6-naphthyridine-7-carboxamide

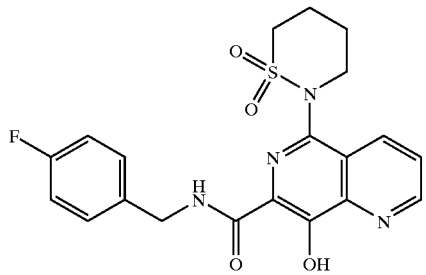

To a mixture of 1,4 butanesultam (prepared as in White et al, *J. Org Chem.* 1987, 52: 2162) (1.00 g, 7.40 mmol), 5-bromo-N-(4-fluorobenzyl)-8-hydroxy-1,6-naphthyridine-7-carboxamide (3.06 g, 8.14 mmol), and $Cu_2O$ (1.06 g, 7.40 mmol) under an atmosphere of argon was added pyridine (50 mL), and the suspension was stirred at reflux for 16 hr. The reaction was allowed to cool to room temperature and filtered to remove the solids. The solids were washed with chloroform (500 mL). The resulting filtrate was evaporated to dryness and the residue was dissolved in chloroform (1L) and vigorously stirred with a slurry of EDTA (4.0 g) in water (150 mL). After a period of 16 hr, the chloroform extracts were dried ($Na_2SO_4$) and evaporated in vacuo. The residue was purified by reverse phase HPLC. (Waters PrePak 500 cartridge C18, Gradient elution with Water:Acetonitrile 95:5 to 5:95 with 0.1% TFA at 75 mL/min over 45 mins). Lyophilization of the pure fractions afforded the title compound as an off-white solid.

$^1$H NMR ($d_6$ DMSO, 400 MHz) δ 9.25 (1H, t, J=6.4 Hz), 9.16 (1H, d, J=4.1 Hz), 8.56 (1H, d, J=8.4 Hz), 7.86 (1H, dd, J=8.4 and 4.1 Hz), 7.41 (2H, dd, J=8.4 and 5.7 Hz), 7.16 (2H, t, J=8.8 Hz), 4.60 (2H, d, J=6.3 Hz) 4.00–3.70(2H, m), 3.65–3.45 (2H, m), 2.35–2.10(3H, m), 1.70 (1H, m) ppm. FAB MS calcd for C20H19FN4O4S 431 (MH$^+$), found 431.

EXAMPLE 153

5-(1,1-dioxidoisothiazolidin-2-yl)-N-(4-fluorobenzyl)-8-hydroxy-1,6-naphthyridine-7-carboxamide

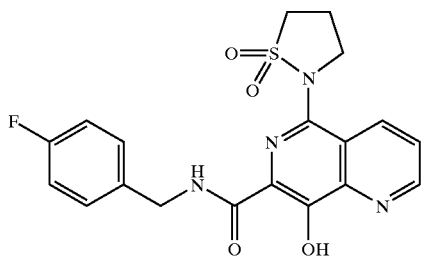

A mixture of 1,3 propanesultam (prepared as in White et al, *J. Org Chem.* 1987, 52: 2162) (0.081 g, 0.66 mmol), 5-bromo-N-(4-fluorobenzyl)-8-hydroxy-1,6-naphthyridine-7-carboxamide (0.10 g, 0.27 mmol), potassium carbonate (0.092 g, 0.66 mmol) and copper powder (0.017 g, 0.27 mmol) under an atmosphere of argon was stirred at 160C for 16 hr. The reaction was allowed to cool to room temperature and the residue was treated with DMF (5 mL) and TFA (1.5 mL) and filtered through a pad of celite to remove the solids. The filtrate was purified by reverse phase HPLC. (Waters PrePak 500 cartridge C18, Gradient elution with Water:Acetonitrile 95:5 to 5:95 with 0.1% TFA at 75 mL/min over 45 mins). Lyophilization of the pure fractions afforded the title compound as an off white solid.

$^1$H NMR (d$_6$DMSO, 400 MHz) δ 13.63 (1H, s), 9.57 (1H, t, J=6.0 Hz), 9.19 (1H, d, J=4.0 Hz), 8.79 (1H, d, J=8.0 Hz), 7.91 (1H, dd, J=8.0 and 4.0 Hz), 7.44 (2H, dd, J=8.0 and 6.0 Hz), 7.19 (2H, t, J=8.0 Hz), 4.60 (2H, d, J=6.0 Hz) 4.30 (2H, t, J=7.0 Hz), 3.51 (2H, t, J=7.0 Hz) 2.70–2.50(2H, m) ppm. FAB MS calcd for C19H17FN4O4S 417 (MH$^+$), found 417.

EXAMPLE 154

N-(4-fluorobenzyl)-8-hydroxy-5-[methyl (methylsulfonyl)amino]-1,6-naphthyridine-7-carboxamide

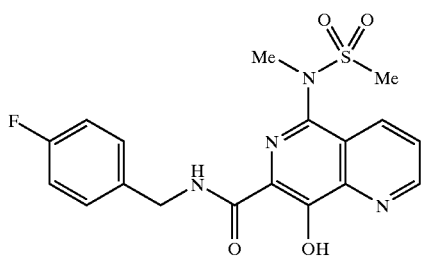

To a mixture of methyl-methanesulfonamide (1.06 g, 9.65 mmol), 5-bromo-N-(4-fluorobenzyl)-8-hydroxy-1,6-naphthyridine-7-carboxamide (1.21 g, 3.22 mmol), and Cu$_2$O (0.46 g, 3.22 mmol) under an atmosphere of argon was added pyridine (25 mL) and the suspension was stirred at reflux for 16 hr. The reaction was allowed to cool to room temperature and the solvent evaporated in vacuo. The residue was treated with DMF (12 mL) and TFA (0.5 mL) and filtered to remove the solids. The filtrate was purified by reverse phase HPLC. (Waters PrePak 500 cartridge C18, Gradient elution with Water:Acetonitrile 95:5 to 5:95 with 0.1% TFA at 75 mL/min over 45 mins). Lyophilization of the pure fractions afforded the title compound as an off white solid.

$^1$H NMR (d$_6$DMSO, 400 MHz) δ 13.80 (1H, s), 9.66 (1H, t, J=6.4 Hz), 9.19 (1H, d, J=4.2 Hz), 8.62 (1H, d, J=8.4 Hz), 7.88 (1H, dd, J=8.4 and 4.2 Hz), 7.41 (2H, dd, J=8.6 and 5.7 Hz), 7.18 (2H, t, J=8.9 Hz), 4.61 (2H, d, J=6.4 Hz) 3.38 (3H, s), 3.19 (3H, s) ppm. FAB MS calcd for C18H17FN4O4S 405 (MH$^+$), found 405.

EXAMPLE 155

5-[acetyl(methyl)amino]-N-(4-fluorobenzyl)-8-hydroxy-1,6-naphthyridine-7-carboxamide

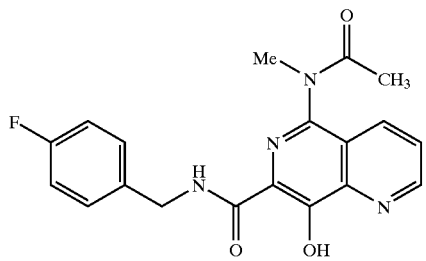

Step 1: N-(4-fluorobenzyl)-8-hydroxy-5-(methylamino)-1,6-naphthyridine-7-carboxamide A suspension of 5-bromo-N-(4-fluorobenzyl)-8-hydroxy-1,6-naphthyridine-7-carboxamide (12.0 g, 32 mmol) in DMSO (48 mL) was treated with methyl amine (48 mL of a 2M solution in THF, 96 mmol) and Hunig's base (11.1 mL, 86 mmol). The vessel was purged with argon, sealed and stirred at 135C for 3 days. The reaction was cooled, quenched with water (280 mL) and the pH adjusted to 5 by the addition of acetic acid. The reaction was stirred at room temperature for 1 hr and filtered. The solids were washed with water (100 mL) and then EtOAc (50 mL), and dried in vacuo to afford the title compound as a white solid.

$^1$H NMR (d$_6$DMSO, 400 MHz) δ 9.23 (1H, t, J=6.5 Hz), 9.03 (1H, d, J=4.0 Hz), 8.64 (1H, d, J=8.6 Hz), 7.69 (1H, dd, J=8.4 and 4.2 Hz), 7.42 (2H, dd, J=8.4 and 5.7 Hz), 7.37 (1H, q, J=4.4 Hz), 7.17 (2H, t, J=8.6 Hz), 4.56 (2H, d, J=6.6 Hz), 3.00 (3H, d, J=4.4 Hz) ppm. FAB MS calcd for C17H15FN4O2 327 (MH$^+$), found 327.

Step 2: 5-[Acetyl(methyl)amino]-N-(4-fluorobenzyl)-8-hydroxy-1,6-naphthyridine-7-carboxamide To a solution of N-(4-fluorobenzyl)-8-hydroxy-5-(methylamino)-1,6-naphthyridine-7-carboxamide (5.75 g, 17.6 mmol) in CH2Cl2 (60 mL) was added acetic anhydride (60 mL) and the mixture stirred at 55C for 16 hr. The solvent was evaporated in vacuo and the solids were collected by filtration and washed with EtOAc (50 mL) and dried in vacuo. The solids were recrystallized from acetonitrile to afford the title compound as a white crystalline solid.

$^1$H NMR (d$_6$ DMSO, 400 MHz) δ 13.85 ((⅓H, s), 13.70(⅓H, s), 9.77 (⅓H, t, J=4.0 Hz), 9.62(⅓H, s), 9.21 (⅓H, d, J=4.0 Hz), 9.18(⅓H, m), 8.41 (⅓H, d, J=8.2 Hz), 8.37(⅓H, d, J=8.0 Hz), 7.88 (⅓H, dd, J=8.4 and 4.2 Hz), 7.80(⅓H, m), 7.42 (2H, dd, J=8.4 and 5.6 Hz), 7.17 (2H, t, J=8.8 Hz), 4.54 (2H, m) 3.46 (⅔H, s), 3.24 (2⅔H, s), 2.32 (⅔H, s), 1.73 (2⅔H, s) ppm. FAB MS calcd for C19H17FN4O3 369 (MH$^+$), found 369.

EXAMPLE 156

5-[[(dimethylamino)carbonyl](methyl)amino]-N-(4-fluorobenzyl)-8-hydroxy-1,6-naphthyridine-7-carboxamide

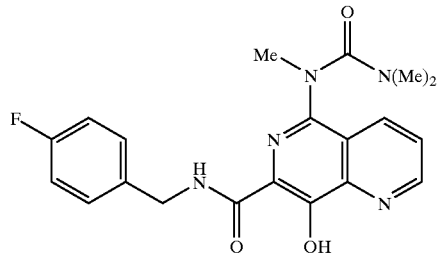

Step 1: N-(4-fluorobenzyl)-8-methoxy-5-(methylamino)-1,6-naphthyridine-7-carboxamide To a suspension of N-(4-fluorobenzyl)-8-hydroxy-5-(methylamino)-1,6-naphthyridine-7-carboxamide (2.65 g, 8.12 mmol) in methanol (50 mL) and CH2Cl2 (20 mL) was added trimethylsilyldiazomethane (12.1 ml of a 2M solution in hexanes, 24.4 mmol) and the mixture was stirred for 16 hr at rt. Additional trimethylsilyldiazomethane (24.0 ml of a 2M solution in hexanes, 48 mmol) was added and the reaction was stirred for 16 hr. The reaction was quenched by the addition of acetic acid (2 mL) and the solvent was evaporated in vacuo. The residue was purified by flash chromatography eluting with MeOH/CH2Cl2 (5–15% gradient elution), to afford the title compound.

$^1$H NMR (CDCl3, 400 MHz) δ 9.12 (1H, dd, J=1.6 and 4.4 Hz), 8.31 (1H, m), 8.10 (1H, d, J=6.4 Hz), 7.50 (1H, dd, J=4.4 and 8.4 Hz), 7.39 (2H, m), 7.04 (2H, t, J=8.8 Hz), 5.24 (1H, m), 4.68 (2H, d, J=6.0 Hz), 4.14(3H, s), 3.12 (3H, m) ppm. FAB MS calcd for C18H17FN4O2 341 (MH$^+$), found 341.

Step 2: 5-[[(dimethylamino)carbonyl](methyl)amino]-N-(4-fluorobenzyl)-8-methoxy-1,6-naphthyridine-7-carboxamide To a solution of N-(4-fluorobenzyl)-8-methoxy-5-(methylamino)-1,6-naphthyridine-7-carboxamide(93 mg, 0.27 mmol) in CH2Cl2 (1 mL) at 0C was added diisopropylethylamine (0.14 mL, 1.5 mmol) and triphosgene (0.04 g, 0.14 mmol) and the mixture was stirred at room temperature for 16 hr. Additional diisopropylethylamine (0.07 mL, 0.08 mmol) and triphosgene (0.02 g, 0.07 mmol) was added and the reaction was stirred an additional 16 hr at room temperature. A portion of this solution (0.5 mL) was treated with dimethylamine (0.41 mL of a 2M solution in THF, 0.82 mmol). The solvent was evaporated in vacuo and the residue dissolved in DMF (1 mL) and purified by reverse phase HPLC. (Vydak C18, Gradient elution with Water:Acetonitrile 95:5 to 5:95 with 0.1% TFA at 30 mL/min over 15 mins). Lyophilization of the pure fractions afforded the title compound as an off white solid which was used directly in step 3.

FAB MS calcd for C21H22FN5O3 412 (MH$^+$), found 412.

Step 3: 5-[[(dimethylamino)carbonyl](methyl)amino]-N-(4-fluorobenzyl)-8-hydroxy-1,6-naphthyridine-7-carboxamide To a solution of 5-[[(dimethylamino)carbonyl](methyl)amino]-N-(4-fluorobenzyl)-8-methoxy-1,6-naphthyridine-7-carboxamide from step 2 in CH2Cl2 (1 mL) at −78 C was added boron tribromide (0.10 mL of a 1M solution in CH2Cl2, 0.01 mmol). The reaction was allowed to warm to room temperature and stirred an additional 16 hr. The solvent was evaporated in vacuo and the residue dissolved in MeOH (2 mL) and the solvent again evaporated in vacuo. The residue was dissolved in DMF (1 mL) and purified by reverse phase HPLC. (Vydak C18, Gradient elution with Water:Acetonitrile 95:5 to 5:95 with 0.1% TFA at 30 mL/min over 15 mins). Lyophilization of the pure fractions afforded the title compound as an off white solid.

$^1$H NMR (d$_6$ DMSO, 400 MHz) δ 13.43 (1H, s), 9.43 (1H, t, J=6.2 Hz), 9.14 (1H, d, J=4.2 Hz), 8.20 (1H, dd, J=1.4 and 8.5 Hz), 7.80 (1H, dd, J=8.4 and 4.2 Hz), 7.42 (2H, m), 7.17 (2H, t, J=8.9 Hz), 4.57 (2H, d, J=6.6 Hz), 3.32 (3H, s), 2.77 (6H, s) ppm. FAB MS calcd for C20H20FN5O3 398 (MH$^+$), found 398.

EXAMPLE 157

N-(4-fluorobenzyl)-6-hydroxy-3-methyl-1-(2-morpholin-4-ylethyl)-2-oxo-2,3-dihydro-1H-pyrimido[4,5,6-de]-1,6-naphthyridine-5-carboxamide

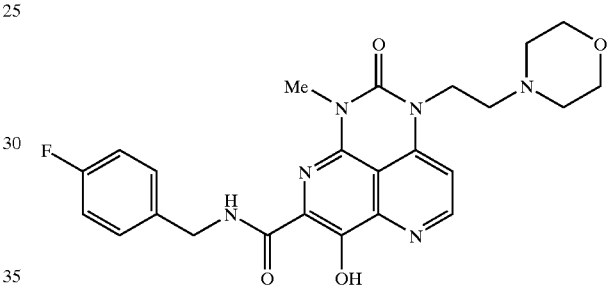

Step 1: N-(4-fluorobenzyl)-6-methoxy-3-methyl-1-(2-morpholin-4-ylethyl)-2-oxo-2,3-dihydro-1H-pyrimido[4,5,6-de]-1,6-naphthyridine-5-carboxamide To a solution of N-(4-fluorobenzyl)-8-methoxy-5-(methylamino)-1,6-naphthyridine-7-carboxamide (504 mg, 1.48 mmol) in CH2Cl2 (5 mL) at 0C was added diisopropylethylamine (0.77 mL, 4.4 mmol) and triphosgene (0.22 g, 0.74 mmol) and the mixture was stirred at room temperature for 16 hr. Additional diisopropylethylamine (0.77 mL, 4.4 mmol) and triphosgene (0.22 g, 0.74 mmol) was added and the reaction was stirred an additional 16 hr at room temperature. The reaction was diluted with CH2Cl2 and a portion of this solution (1.0 mL) was treated with 2-morpholinoethylamine (0.12 mL 0.89 mmol) at room temperature for 16 hr. The solvent was evaporated in vacuo and the residue dissolved in DMSO (0.5 mL) and purified by reverse phase HPLC. (Vydak C18, Gradient elution with Water:Acetonitrile 95:5 to 5:95 with 0.1% TFA at 30 mL/min over 15 mins). Lyophilization of the pure fractions afforded the title compound as an off white solid which was used directly in step 2.

FAB MS calcd for C25H27FN6O4 495 (MH$^+$), found 495.

Step 2: N-(4-fluorobenzyl)-6-hydroxy-3-methyl-1-(2-morpholin-4-ylethyl)-2-oxo-2,3-dihydro-1H-pyrimido[4,5,6-de]-1,6-naphthyridine-5-carboxamide To a solution of N-(4-fluorobenzyl)-6-methoxy-3-methyl-1-(2-morpholin-4-ylethyl)-2-oxo-2,3-dihydro-1H-pyrimido

[4,5,6-de]-1,6-naphthyridine-5-carboxamide from step 1 (0.038 g, 0.077 mmol) in CH2Cl2 (1 mL) at −78 C was added boron tribromide (0.077 mL of a 1M solution in CH2Cl2, 0.077 mmol). The reaction was allowed to warm to room temperature and stirred an additional 16 hr. The solvent was evaporated in vacuo and the residue dissolved in methanol (2 mL) and the solvent again evaporated in vacuo. The residue was dissolved in DMF (1 mL) and purified by reverse phase HPLC. (Vydak C18, Gradient elution with Water:Acetonitrile 95:5 to 5:95 with 0.1% TFA at 30 mL/min over 15 mins). Lyophilization of the pure fractions afforded the title compound as an off white solid.

$^1$H NMR (d$_6$ DMSO, 400 MHz) δ 13.14 (1H, s), 9.64 (1H, t, J=6.0 Hz), 9.50 (1H, m), 8.93 (1H, d, J=5.0 Hz), 7.42 (2H, m), 7.33 (1H, d, J=5.0 Hz), 7.19 (2H, t, J=8.7 Hz), 4.57 (2H, d, J=6.4 Hz), 4.45(2H, m), 4.00–3.96 (2H, m), 3.90–3.00 (10H, m) ppm. FAB MS calcd for C24H25FN 6O4 481 (MH$^+$), found 481.

EXAMPLE 158

N-(4-fluorobenzyl)-8-hydroxy-5-thiomorpholin-4-yl-1,6-naphthyridine-7-carboxamide

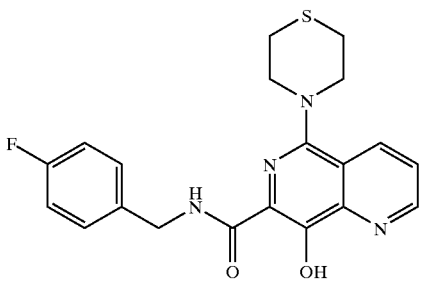

A solution of 5-bromo-N-(4-fluorobenzyl)-8-hydroxy-1,6-naphthyridine-7-carboxamide (0.25 g, 0.67 mmol), thiomorpholine (0.19 mL, 2.0 mmol) and diisopropylethylamine (0.06 mL, 0.67 mmol) in DMPU (3.0 mL) were heated at 135 C for 23 hr. The reaction was cooled to room temperature, neutralized by the addition of TFA and purified by reverse phase HPLC. (Vydak C18, Gradient elution with Water:Acetonitrile 95:5 to 5:95 with 0.1% TFA at 30 mL/min over 15 mins). Lyophilization of the pure fractions afforded the title compound as an off white solid.

$^1$H NMR (CDCl3, 400 MHz) δ 9.23 (1H, d, J=4.4 Hz), 8.46 (1H, d, J=8.4 Hz), 8.13 (1H, t, J=5.6 Hz), 7.67 (1H, dd, J=4.4 and 8.4 Hz), 7.37 (2H, dd, J=8.2 and 5.6 Hz), 7.07 (2H, t, J=8.7 Hz), 4.68 (2H, d, J=6.3 Hz), 3.51 (4H, m), 2.90 (4H, m) ppm. FAB MS calcd for C20H19FN 4O2S 399 (MH$^+$), found 399.

EXAMPLE 159

5-(1,1-dioxidothiomorpholin-4-yl)-N-(4-fluorobenzyl)-8-hydroxy-1,6-naphthyridine-7-carboxamide

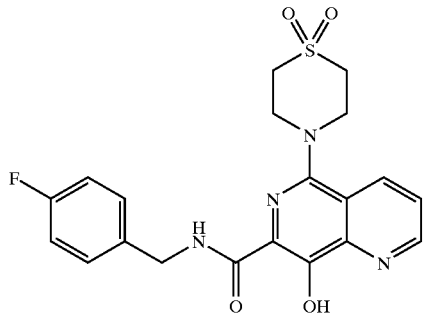

A solution of N-(4-fluorobenzyl)-8-hydroxy-5-thiomorpholin-4-yl-1,6-naphthyridine-7-carboxamide (0.19 g, 0.49 mmol) in methanol (25 mL) was treated with an aqueous solution of Oxone (7.5 mL of a 1M solution, 0.75 mmol) and stirred at room temperature for 28 hr. The solvent was evaporated in vacuo and the residue partitioned between water and CH2Cl2. The organic extracts were purified by reverse phase HPLC. (Vydak C18, Gradient elution with Water:Acetonitrile 95:5 to 5:95 with 0.1% TFA at 30 mL/min over 15 mins). Lyophilization of the pure fractions afforded the title compound as an off white solid.

$^1$H NMR (CDCl3, 400 MHz) δ 13.07 (1H, s), 9.21 (1H, dd, J=1.5 and 4.2 Hz), 8.38 (1H, dd, J=1.5 and 8.4 Hz), 7.98 (1H, t, J=6.0 Hz), 7.67 (1H, dd, J=4.3 and 8.4 Hz), 7.38 (2H, dd, J=8.5 and 5.4 Hz), 7.08 (2H, t, J=8.5 Hz), 4.67 (2H, d, J=6.4 Hz), 3.80 (4H, m), 3.30 (4H, m) ppm. FAB MS calcd for C20H19FN 4O4S 431 (MH$^+$), found 431.

EXAMPLE 160

N-(4-fluorobenzyl)-8-hydroxy-5-(4-methyl-3-oxopiperazin-1-yl)-1,6-naphthyridine-7-carboxamide

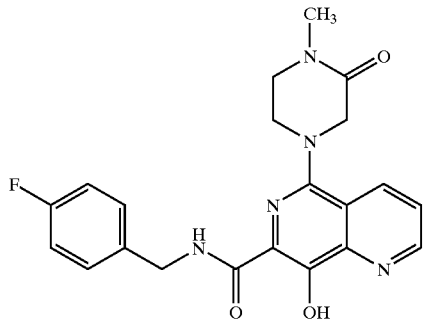

A solution of 5-bromo-N-(4-fluorobenzyl)-8-hydroxy-1,6-naphthyridine-7-carboxamide (0.20 g, 0.53 mmol), 1-methylpiperazin-2-one (0.21 g, 1.86 mmol) and diisopropylethylamine (0.19 mL, 1.06 mmol) in DMPU (2.0 mL) were heated at 135 C for 26 hr. Diisopropylethylamine (0.19 mL, 1.06 mmol) was added and the reaction heated at 135C for a further 24 hr. The reaction was cooled to room temperature, neutralized by the addition of TFA and purified by reverse phase HPLC. (Vydak C18, Gradient elution with Water:Acetonitrile 95:5 to 5:95 with 0.1% TFA at 30 mL/min over 15 mins). Lyophilization of the pure fractions afforded the title compound as an off white solid.

$^1$H NMR (CDCl3, 400 MHz) δ 12.95 (1H, s), 9.18 (1H, dd, J=1.6 and 4.4 Hz), 8.43 (1H, dd, J=1.7 and 8.4 Hz), 8.21 (1H, m), 7.63(1H, dd, J=4.3 and 8.4 Hz), 7.40(2H, m), 7.05(2H, t, J=8.7 Hz), 4.65 (2H, d, J=6.4 Hz), 4.01 (2H, s), 3.61 (2H, t, J=5.7 Hz), 3.34(2H, t, J=5.7 Hz), 2.95 (3H, s) ppm. FAB MS calcd for C21H20FN 5O3 410 (MH$^+$), found 410.

EXAMPLE 161

1-(7-{[(4-fluorobenzyl)amino]carbonyl}-8-hydroxy-1,6-naphthyridin-5-yl-L-prolinamide

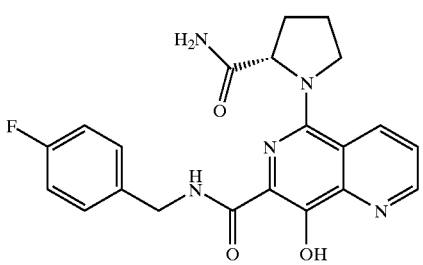

A solution of 5-bromo-N-(4-fluorobenzyl)-8-hydroxy-1,6-naphthyridine-7-carboxamide (0.21 g, 0.55 mmol), L-prolinamide (0.126 g, 1.10 mmol) and diisopropylethylamine (0.19 mL, 2.2 mmol) in DMPU (2.0 mL) were heated at 135 C for 26 hr. L-prolinamide (0.126 g, 1.10 mmol) and diisopropylethylamine (0.19 mL, 2.2 mmol) were added and the reaction heated at 135 C for a further 24 hr. The reaction was cooled to room temperature, diethyl ether added and the precipitate collected by filtration. The solids were washed with CH2Cl2 and then water. The solids were dried in vacuo to afford the title compound as an off white solid.

$^1$H NMR (CDCl3, 400 MHz) δ 9.18 (1H, d, J=4.4 Hz), 8.62(1H, d, J=8.4 Hz), 8.49(1H, m), 7.60(1H, dd, J=4.4 and 8.6 Hz), 7.41(2H, m), 7.04(2H, t, J=8.6 Hz), 6.61 (1H, s), 5.88(1H, s), 4.66 (1H, dd, J=15.0 and 6.8 Hz), 4.65–4.50 (2H, m), 4.20(1H, q, J=8.7 Hz), 3.72(1H, t, J=8.6 Hz), 2.47(1H, m), 2.23(1H, m), 2.15–1.90 (2H, m) ppm. FAB MS calcd for C21H20FN 5O3 410 (MH$^+$), found 410.

EXAMPLE 162

N-(4-fluorobenzyl)-8-hydroxy-5-(2-oxotetrahydropyrimidin-1(2H)-yl)-1,6-naphthyridine-7-carboxamide

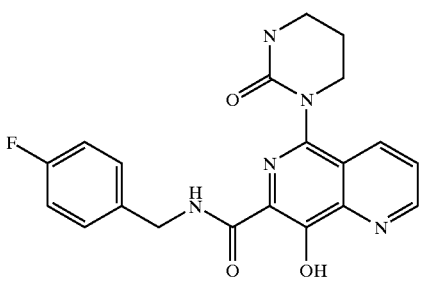

To a mixture of tetrahydro-2-pyrimidone (0.040 g, 0.4 mmol), 5-bromo-N-(4-fluorobenzyl)-8-hydroxy-1,6-naphthyridine-7-carboxamide (0.050 g, 0.13 mmol), and Cu$_2$O (0.0095 g, 0.07 mmol) under an atmosphere of argon was added pyridine (1.0 mL) and the suspension was stirred at reflux for 16 hr. Cu$_2$O (0.005 g, 0.04 mmol) was added and the reaction heated at 115 C for a further 16 hr. The reaction was allowed to cool to room temperature and the solvent evaporated in vacuo. The residue was treated with DMF (2 mL) and filtered to remove the solids. TFA (0.5 mL) was added to the filtrate which was purified by reverse phase HPLC. (Waters PrePak 500 cartridge C18, Gradient elution with Water:Acetonitrile 95:5 to 5:95 with 0.1% TFA at 75 mL/min over 45 mins). Lyophilization of the pure fractions afforded the title compound as an off white solid.

$^1$H NMR (d$_6$ DMSO, 400 MHz) δ 9.60 (1H, m), 9.12 (1H, m), 8.28 (1H, m), 7.77 (1H, m), 7.43 (2H, m), 7.17 (2H, m), 6.89 (1H, m), 4.56 (2H, m), 3.60–3.00(4H, m), 2.08(2H, m) ppm. FAB MS calcd for C20H18FN 5O3 396 (MH$^+$), found 396.

EXAMPLE 163

N-(4-fluorobenzyl)-8-hydroxy-5-(2-oxoimidazolidin-1-yl)-1,6-naphthyridine-7-carboxamide

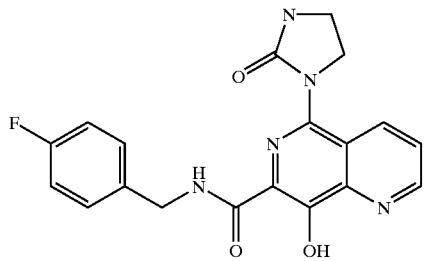

A solution of 5-bromo-N-(4-fluorobenzyl)-8-hydroxy-1,6-naphthyridine-7-carboxamide (0.21 g, 0.55 mmol), ethylene diamine (0.14 mL, 1.67 mmol) and diisopropylethylamine (0.29 mL, 1.67 mmol) in DMPU (2.0 mL) were heated at 140 C for 16 hr. Ethylene diamine (0.14 mL, 1.67 mmol) was added and the reaction heated at 140 C for a further 24 hr. The reaction was cooled to room temperature, and treated with carbonyldiimidazole (0.188 g 1.16 mmol) and diisopropylethylamine (0.29 mL, 1.67 mmol) and then heated at 120 C for 1 hr. The reaction was cooled to room temperature, acidified by the addition of TFA (0.5 mL) and purified by reverse phase HPLC. (Waters PrePak 500 cartridge C18, Gradient elution with Water:Acetonitrile 95:5 to 5:95 with 0.1% TFA at 75 mL/min over 45 mins). Lyophilization of the pure fractions afforded the title compound as an off white solid.

$^1$H NMR (d$_6$DMSO, 400 MHz) δ 9.52(1H, t, J=6.5 Hz), 9.10 (1H, d, J=4.2 Hz), 8.44(1H, dd, J=8.5 and 1.6 Hz), 7.73(1H, dd, J=8.5 and 4.2 Hz), 7.40(2H, m), 7.27 (1H, s), 7.14(2H, t, J=8.8 Hz), 4.54(2H, d, J=6.5 Hz), 4.22(2H, t, J=7.7 Hz), 3.51(2H, t, J=7.7 Hz) ppm. FAB MS calcd for C19H16FN 5O3 382 (MH$^+$), found 382.

EXAMPLE 164

N-7-(4-fluorobenzyl)-8-hydroxy-N 5,N 5-dimethyl-1,6-naphthyridine-5,7-dicarboxamide (HCl salt)

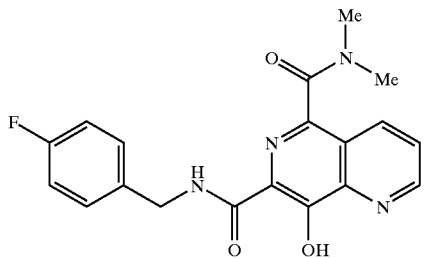

Step 1: Preparation of methyl 8-hydroxy-5-oxo-5,6-dihydro-1,6-naphthyridine-7-carboxylate This compound was prepared as described in M. Suzuki et.al., *Synthetic Communications*, 1978, pg. 461. To a solution of furo[3,4]pyridine-5,7-dione (130 g, 872 mmol) in anhydrous DMF (250 ml) was added 1 liter of dry THF and methyl isocyanoacetate (86.4 g, 872 mmol). This was stirred for 15 minutes at 40° C. under nitrogen, followed by dropwise addition of DBU (132.8 g, 130.4 ml, 872 mmol) which was dissolved in THF (300 ml). After one hour the solvent was removed under reduced pressure and the resultant crude 2-[4-(methoxycarbonyl)-1,3-oxazol-5-yl]nicotinic acid and regioisomeric 3-[4-(methoxycarbonyl)-1,3-oxazol-5-yl]pyridine-2-carboxylic acid products were taken up into MeOH (1 liter). Concentrated HCl (12 M, 291 ml) was then added dropwise while the solution stirred at 55° C. This was stirred for 0.5 hours at which time the crude solids were collected by vacuum filtration. The desired regioisomer was purified by successive recrystallizations in methanol. This provided pure yellow solids. TLC (silica, 90:10:3, dichloromethane, methanol, acetic acid), R f (desired regioisomer)=0.23, R f (undesired regioisomer)=0.62.

$^1$H NMR (DMSO, 400 MHz) δ 10.66 (1H, bs), 9.11 (1H, dd, J=1.6, 4.5 Hz), 8.63 (1H, dd, J=1.6, 8.1 Hz), 7.80 (1H, dd, J=4.6 and 8.1 Hz), and 3.90 (3H, s) ppm.

Step 2: Preparation of methyl 8-(benzoyloxy)-5-oxo-5,6-dihydro-1,6-naphthyridine-7-carboxylate To a mixture of the compound of Step 1 (20 g, 91 mmol) in dry DMF (250 ml) and dichloromethane (300 ml) under an atmosphere of argon at 0° C. was added diisopropyl ethylamine (59 g, 82 ml, 455 mmol) dropwise followed by the addition of benzoic anhydride (21 g, 91 mmol) dissolved in dichloromethane (50 ml). The reaction was allowed to warm slowly to ambient temperature and stirred for 18 hours. The dichloromethane and 75% of the DMF was then removed in vacuo and white solids crystallized out of the deep red solution. The white solids were collected by vacuum filtration to give the title compound.

$^1$H NMR (CDCl$_3$, 400 MHz) δ 9.36 (1H, bs), 8.99 (1H, dd, J=1.7, 4.5 Hz), 8.73 (1H, dd, J=1.7, 8.1 Hz), 8.28 (2H, d, J=8.4 Hz), 7.69 (1H, t, J=7.5 Hz), 7.59–7.54 (2H, m), 3.87 (3H, s) ppm.

Step 3: Preparation of methyl 8-hydroxy-5-{[(trifluoromethyl)sulfonyl]oxy}-1,6-naphthyridine-7-carboxylate To a stirring suspension of the compound of Step 2 (25 g, 77 mmol) in dry dichloromethane (150 ml) under argon was added pyridine (31 ml, 385 mmol). The suspension was then cooled to 0° C. and Tf$_2$O (32.6 g, 19.4 ml, 116 mmol) was added dropwise which caused the formation of a red color. The ice bath was then removed and after 1 hour the red solution was poured into a saturated aqueous solution of NaHCO$_3$ (200 ml). The organic phase was separated and the aqueous phase was extracted three times with chloroform. The combined organics were dried over sodium sulfate, filtered and concentrated to give a green solid.

$^1$H NMR (CDCl$_3$, 400 MHz) δ 9.24 (1H, dd, J=1.6, 4.3 Hz), 8.53(1H, dd, J=1.6 8.5 Hz), 8.32 (2H, d, J=7.2 Hz), 7.81 (1H, dd, J=4.3 and 8.5 Hz), 7.70 (1H, m), 7.57 (m, 2H), and 3.92 (3H, s) ppm.

Step 4: Preparation of dimethyl 8-(benzoyloxy)-1,6-naphthyridine-5,7-dicarboxylate To a solution of the compound of Step 3 (11.9 g, 26 mmol) in DMF (50 ml) was added methanol (11 ml, 290 mmol), diisopropylethylamine (6.7 g, 9.3 ml, 52 mmol), Pd(OAc)$_2$ (0.58 g, 2.6 mmol), and 1,1'-bis(diphenylphosphino) ferrocene (1.44 g, 2.6 mmol) while bubbling argon through the mixture. This was then placed in a bomb reactor and purged three times with carbon monoxide and finally filled to 80 p.s.i. and heated to 70° C. for two hours. The reaction mixture was then poured into water (~150 ml). Ethyl acetate (50 ml) was then added to the mixture and the aqueous phase was extracted six times. The combined organics were dried over sodium sulfate, filtered and concentrated. The crude material was allowed to dry on the hi-vac overnight and was then suspended in ethyl acetate. The undesired solids (methyl 8-(benzoyloxy)-5-oxo-5,6-dihydro-1,6-naphthyridine-7-carboxylate) that did not dissolve were collected by vacuum filtration and set aside. This was repeated twice. To the EtOAc solution was then added hexanes and a few drops of diethyl ether and the mixture was placed in a sonicator for 15 minutes which allowed solids to crystallize out of the solution. The solids were collected by vacuum filtration.

$^1$H NMR (CDCl$_3$, 400 MHz) δ 9.37 (1H, dd, J=1.5 and 8.8 Hz), 9.18(1H, d, J=4.2), 8.33 (1H, d, J=7.5 Hz), 7.74(1H, dd, J=4.2, and obscured Hz), 7.69 (2H, m), 7.56 (2H, m,), 4.12 (3H, s), 3.95 (3H, s).

Step 5: Preparation of 7-{[(4-fluorobenzyl)amino]carbonyl}-8-hydroxy-1,6-naphthyndine-5-carboxylic acid sodium salt To a solution of the compound of Step 4 (2.93 g, 11.17 mmol) in toluene (30 ml) under argon was added 4-fluorobenzylamine (3.1 g, 24.5 mmole) and the reaction was heated to reflux for 4 hours. The solvent was then removed under reduced pressure and the resulting crude product was triturated to pure solids by stirring in ether. The solids were collected by vacuum filtration and then dissolved in THF (80 ml). To this solution was added sodium hydroxide (18 mil, 3N) and this was heated to reflux for 0.5 hours. The reaction was allowed to cool and solid sodium salt crystallized out of the solution. The solids were collected by vacuum filtration.

$^1$H NMR (DMSO, 400 MHz) δ 12.9 (1H, bs), 10.26 (1H, bt), 9.62 (1H, d, J=8.6 Hz), 9.22 (1H, d, J=3.9 Hz), 7.93 (1H, dd, J=4.0 and 8.7 Hz), 7.46 (2H, m), 7.23 (2H, m), 4.65 (2H, d, J=6.0 Hz).

Step 6: Preparation of N 7-(4-fluorobenzyl)-8-hydroxy-N-5-N-5-dimethyl-1,6-naphthyridine-5,7-dicarboxamide HCl Salt To a solution of the salt of Step 5 (100 mg, 0.293 mmol) in DMSO (1 ml) under nitrogen was added BOP (0.16 g, 0.35 mmol) and a stream of dimethylamine gas (purged for 1 minute). After one hour of stirring at room temperature, the DMSO solution was purified by $C_{18}$ reverse phase preparative HPLC, eluting with a gradient of 95:5 to 5:95, water/acetonitrile (0.1% TFA). The pure fractions were combined then the solvent was removed and the resulting pure solids were suspended into EtOAc. A stream of HCl gas was passed over the suspension for 3 seconds and the solvent was removed under reduced pressure to give solids as the HCl salt.

$^1$H NMR (DMSO, 400 MHz) δ 9.75 (1H, t, J=6.4 Hz), 9.19 (1H, dd, J=1.6 J=4.2 Hz), 8.37 (1H, dd, J=1.6, J=8.5 Hz), 7.83 (1H, dd, J=4.2 and 8.5 Hz), 7.43 (2H, t, J=7.1 Hz), 7.16 (2H, t, J=8.9 Hz), 4.54 (2H, d, J=6.4 Hz), 3.13 (3H, s), 2.86 (3H, s). ES HRMS exact mass calcd for $C_{19}H_{18}FN_4O_3$ 369.1357 (MH$^+$), found 369.1368.

EXAMPLE 165

N 7-(4-fluorobenzyl)-8-hydroxy-N 5-isopropyl-N 5-methyl-1,6-naphthyridine-5,7-dicarboxamide HCl Salt

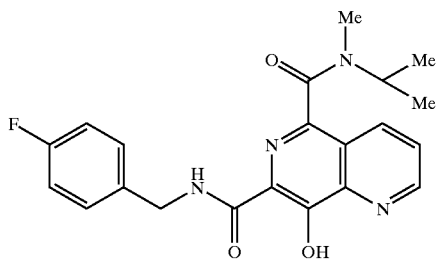

The title compound was prepared in the manner described in Step 6 of Example 164, wherein methyl isopropylamine was substituted for dimethylamine.
The NMR is complicated by the fact that the compounds exists as two separate rotamers in solution:

$^1$H NMR (DMSO, 400 MHz) δ 9.70 (1H, in), 9.20 (1H, d, J=4.1 Hz), 8.31–8.27 (1H, m), 7.86–7.82 (1H, in), 7.45–7.40 (2H, m), 7.19–7.13 (2H, m), 4.57–4.53 (2H, m), 3.56–3.52 (1H, in), (major rotamer) 2.98 (3H, s), (minor rotamer) 2.66 (3H, s), (minor rotamer) 1.25 (6H, d, J=6.78 Hz), (major rotamer) 1.09–1.06 (4H, d, J=6.5 Hz). ES HRMS exact mass calcd for $C_{21}H_{22}FN_4O_3$ 397.1671 (MH$^+$), found 397.1665

EXAMPLE 166

N 7-(4-fluorobenzyl)-8-hydroxy-N 5-(2-morpholin-4-ylethyl)-1,6-naphthyridine-5,7-dicarboxamide HCl Salt

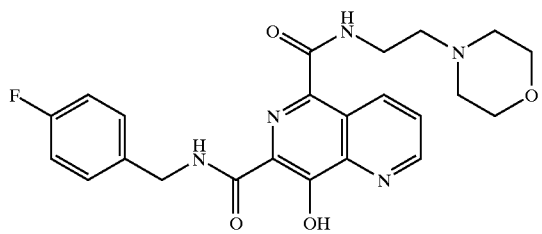

The title compound was prepared in the manner described in Step 6 of Example 164, wherein (2-(morpholin-4-yl)ethyl)amine was substituted for dimethylamine.

$^1$H NMR (DMSO, 400 MHz) δ 10.1 (1H, bt), 9.85(1H, d, J=8.7 Hz), 9.65(1H, bs), 9.55(1H, bs), 9.20(1H, d, J=4.1 Hz), 7.90 (1H, dd, J=4.1, 8.7 Hz), 7.45(2H, m), 7.20 (2H, m), 4.69 (2H, d, J=6.0, Hz), 4.0 (2H, m), 3.75 (2H, m), 3.65 (4H, m) 3.35 (2H, under H2O), 3.20 (2H, m). ES HRMS exact mass calcd for $C_{23}H_{25}FN_5O_4$ 454.1885 (MH$^+$), found 454.1892

EXAMPLE 167

N 5-[2-(dimethylamino)-2-oxoethyl]-N 7-(4-fluorobenzyl)-8-hydroxy-N 5-methyl-1,6-naphthyridine-5,7-dicarboxamide HCl salt

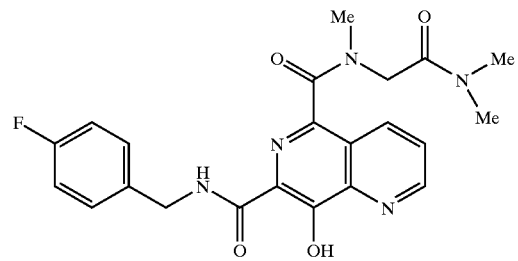

The title compound was prepared in the manner described in Step 6 of Example 164, wherein N-methyl-N-(2-(dimethylamino)-2-oxoethyl)amine was substituted for dimethylamine.

$^1$H NMR (DMSO, 400 MHz) mixture of rotamers, major: δ 9.73 (1H, t, J=6.3 Hz), 9.20 (1H, dd, J=1.0, 4.2 Hz), 8.84 (1H, dd, J=1.0, 8.4 Hz), 7.91 (1H, dd, J=4.2, 8.4 Hz), 7.45 (2H, m), 7.18 (2H, m), 4.55 (2H, m), 4.45 (2H, m), 3.05 (3H, s), 2.94 (3H, s), 2.78 (3H, s). minor 9.43 (1H, t, J=6.3 Hz), 9.14 (1H, dd, J=1.0, 4.2 Hz), 8.48 (1H, dd, J=1.0, 8.4 Hz), 7.80 (1H, dd, J=4.2, 8.4 Hz), 7.45 (2H, m), 7.18 (2H, m), 4.55 (2H, m), 4.45 (2H, m), 3.07 (3H, s), 2.65 (3H, s), 2.55 (3H, s). ES HRMS exact mass calcd for $C_{22}H_{23}FN_5O_4$ 440.1729 (MH$^+$), found 440.1722.

EXAMPLE 168

N-(4-Fluorobenzyl)-5-(1,1-dioxido-4-oxo-1,2,5-thiadiazepan-2-yl)-8-hydroxy-[1,6]napthyridine-7-carboxamide

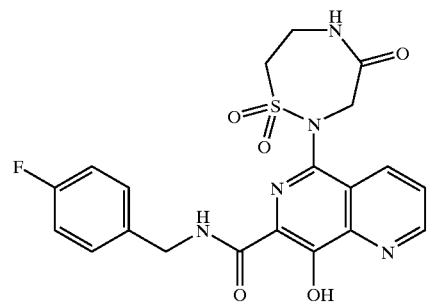

Step 1: 2-{[(Benzyloxy)carbonyl]amino}ethanesulfonyl chloride

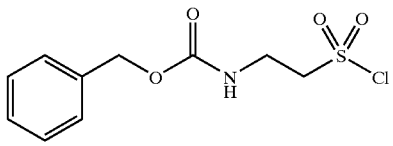

A mixture of taurine (12.5 g, 100 mmol), benzyl chloroformate (15.1 mL, 105 mmol) and sodium carbonate (10.6 g, 100 mmol) in water (250 mL) was stirred at room temperature for overnight. The product mixture was extracted with diethyl ether. The organic extract was concentrated under vacuum to provide 2-{[(benzyloxy)carbonyl]-amino}ethanesulfonic acid. Without further purification, the sulfonic acid was treated with thionyl chloride (15 mL, 206 mmol) with external ice-water bath cooling. The resultant mixture was stirred at room temperature for 1 hour, and poured into ice water. The mixture was extracted with diethyl ether. The organic extract was washed with brine, dried over anhydrous magnesium sulfate, filtered and concentrated under vacuum to provide the title compound as white solid.

Step 2: 1,2,5-Thiadiazepan-4-one 1,1-dioxide

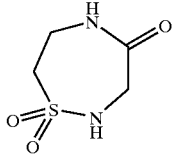

A cold (0° C.) mixture of sulfonyl chloride from Step 1 (5.54 g, 20 mmol) and glycine methyl ester hydrochloride (2.7 g, 21.5 mmol) in dichloromethane (125 mL) was treated with triethylamine (6.0 mL, 43 mmol). The resultant mixture was stirred at 0° C. for 2 hours. The product mixture was diluted with dichloromethane and was washed with water, dried over anhydrous magnesium sulfate, filtered and concentrated under vacuum. The residue was subjected to column chromatography on silica gel eluted with 50% ethyl acetate in hexane. Collection and concentration of appropriate fractions provided the intermediate methyl 3-oxo-1-phenyl-2-oxa-7-thia-4,8-diazadecan-10-oate 7,7-dioxide.

A mixture of the above ester (3.3 g, 10 mmol) and 5% palladium on charcoal (0.2 g) in methanol (100 mL) was shaken in a Parr hydrogenation under an atmosphere of hydrogen gas at 50 psi at room temperature over night. The resultant mixture was filtered through a pad of Celite. The filtrate was concentrated under vacuum. The residue was dissolved in absolute ethanol (500 mL). The alcoholic solution was heated under reflux overnight and concentrated to ~100 mL and cooled to 0° C. The white solid precipitated was collected by filtration to provide the title thiadiazepane.

Step 3: N-(4-Fluorobenzyl)-5-(1,1-dioxido-4-oxo-1,2,5-thiadiazepan-2-yl)-8-hydroxy-[1,6]napthyridine-7-carboxamide A mixture of 5-bromo-N-(4-fluorobenzyl)-8-hydroxy[1,6]naphthyridine-7-carboxamide (0.99 g, 2.66 mmol), 1,2,5-thiadiazepan-4-one 1,1-dioxide from step 2 (0.41 g, 2.5 mmol) and copper (I) oxide (0.18 g, 1.25 mmol) in pyridine (13 mL) was heated in an oil bath at 115° C. overnight. The resultant mixture was treated with a mixture of chloroform (200 mL) and a saturated aqueous solution of ethylenediamine tetraacetic acid, disodium salt (200 mL) and stirred vigorously at room temp overnight in the presence of air. The slurry was filtered through a pad of Celite. The organic extract was separated, dried over anhydrous sodium sulfate, filtered and concentrated under vacuum. The residue was dissolved in DMSO and subjected to HPLC purification on C-18 stationary phase eluted with water/acetonitrile/TFA mobile phase. Collection and lyophilization of appropriate fractions provided the title compound.

$^1$H NMR (400 MHz, CDCl$_3$) δ 13.22 (br s, 1H), 9.18 (dd, J=4.3, 1.8 Hz, 1H), 8.63 (dd, J=8.5, 1.5 Hz, 1H), 8.06 (br t, J=5.5 Hz, 1H) 7.69 (dd, J=8.5, 4.3 Hz, 1H), 7.38 (dd, J=8.6, 5.2 Hz, 2H), 7.06 (t, J=8.9 Hz, 2H), 5.89 (t, J=5.5 Hz, 1H), 4.77–4.57 (br m, 3H), 4.04–4.01 (br s, 2H), 3.59 (br s, 1H), 3.33–3.32 (m, 2H). HR ES MS calc for C$_{20}$H$_{18}$FN$_5$O$_5$S+H: calc, 460.1086; found, 460.1061.

EXAMPLE 169

N-(4-Fluorobenzyl)-5-(1,1-dioxido-5-methyl-4-oxo-1,2,5-thiadiazepan-2-yl)-8-hydroxy-[1,6]napthyridine-7-carboxamide

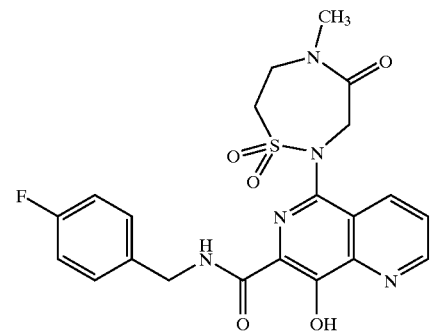

Step 1: Benzyl N-({2-[[(benzyloxy)carbonyl](methyl)amino]ethyl}sulfonyl)-glycinate

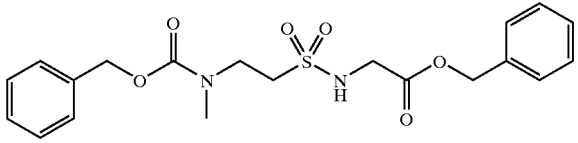

To a stirred solution of 2-methylaminoethane-1-sulfonic acid, sodium salt (16.1 g, 100 mmol), in aq. sodium hydroxide (1M, 100 mL, 100 mmol) at 0° C., benzyl chloroformate (16 mL, 112 mmol) was added over a period of 15 minutes. The resulting mixture was stirred at room temperature for 2 hours and extracted with hexane. The aqueous solution was freeze dried to provide 2-[[(benzyloxy)carbonyl](methyl)amino]-ethane-1-sulfonic acid, sodium salt.

Without further purification, the resultant sodium sulfonate was suspended in DMF (200 mL) and cooled to 10° C. Thionyl chloride (15 mL) was added to the suspension over a period of 10 minutes. The resulting mixture was stirred at room temp. for 1 hour, and poured into ice, and partitioned with diethyl ether. The organic extract was washed with brine, dried over anhydrous sodium sulfate, filtered and concentrated under vacuum to provide 2-[[(benzyloxy)carbonyl](methyl)-amino]ethane-1-sulfonyl chloride as yellow viscous liquid.

To a suspension of benzyl glycinate hydrochloride salt (6.83 g, 33.8 mmol) in dichloromethane (200 mL) at 0° C., a solution of the above sulfonyl chloride (9.0 g, 30.8 mmol) in dichloromethane (30 mL) was added over a period of 20 minutes. The reaction mixture was stirred at 0° C. for 2 hours, washed with ice water. The organic solution was dried over anhydrous sodium sulfate, filtered and concentrated under vacuum to provide benzyl N-({2-[[(benzyloxy)carbonyl](methyl)amino]ethyl}sulfonyl)-glycinate as yellow viscous liquid.

Step 2: 5-Methyl-1,2,5-thiadiazepan-4-one 1,1-dioxide

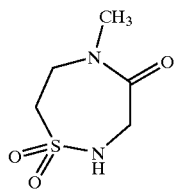

A mixture of the above glycinate (5.1 g, 12.1 mmol; step 1) and 5% palladium on charcoal (0.32 g) in methanol (75 mL) was shaken in a Parr hydrogenation under an atmosphere of hydrogen gas at 47 psi at room temperature for 2 hours. The resultant mixture was filtered through a pad of Celite. The solid filtered was washed with distilled water. The aqueous filtrate was freeze dried to provide N-(methylamino)ethyl-sulfonylglycine.

A mixture of this methylaminoglycine (0.21 g, 1.07 mmol), 1-hydroxy-7-azabenzotriazole (9 mg, 0.07 mmol), and 1-(3-dimethylaminopropyl)-3-ethylcarbodiimide hydrochloride (0.22 g, 1.14 mmol) in DMF (50 mL) was stirred at room temp overnight. The reaction mixture was concentrated under vacuum. The residue was subjected to column chromatography on silica gel eluted with 2.5% methanol in ethyl acetate. Collection and concentration of appropriate fractions provided 5-methyl-1,2,5-thiadiazepan-4-one 1,1-dioxide as white solid.

Step 3: N-(4-Fluorobenzyl)-5-(1,1-dioxido-5-methyl-4-oxo-1,2,5-thiadiazepan-2-yl)-8-hydroxy-[1,6]napthyridine-7-carboxamide A mixture of methyl 5-bromo-8-hydroxy[1,6]naphthyridine-7-carboxylate (0.28 g, 1.0 mmol), 5-methyl-1,2,5-thiadiazepan-4-one 1,1-dioxide from step 2 (0.178 g, 1.0 mmol) and copper (I) oxide (0.143 g, 1.0 mmol) in pyridine (5 mL) was heated in an oil bath at 115° C. overnight. The resultant mixture was filtered, and the filtrate concentrated under vacuum. The residue was treated with a mixture of chloroform (50 mL) and ethylenediamine tetraacetic acid, disodium salt (5 g) in water (30 mL) and stirred vigorously at room temp in the presence of air for 5 hours. The slurry was filtered through a pad of Celite. The organic extract was separated, dried over anhydrous sodium sulfate, filtered and concentrated under vacuum. The residue was triturated with methanol (25 mL) and the resultant suspension stirred at room temperature overnight. The solid was filtered, washed with cold (0° C.) methanol, and dried under vacuum to provide methyl 5-(1,1-dioxido-5-methyl-4-oxo-1,2,5-thiadiazepan-2-yl)-8-hydroxy[1,6]-naphthyridine-7-carboxylate as light brown solid.

A mixture of the above methyl ester (76 mg, 0.2 mmol) and 4-fluorobenzylamine (91 μL, 0.8 mmol) in 1,2-dimethoxyethane (1.3 mL) in a sealed tube was heated in an oil bath at 120° C. for 2 hours. The reaction mixture was cooled to 0° C., and the precipitate collected by filtration. The solid obtained was dissolved in DMSO and subjected to HPLC purification on C-18 stationary phase eluted with water/acetonitrile/TFA mobile phase. Collection and lyophilization of appropriate fractions provided the title compound.

$^1$H NMR (400 MHz, CDCl$_3$) δ 13.27 (br s, 1H), 9.18 (br s, 1H), 8.59 (br d, J=8.5 Hz, 1H), 8.21 (br s, 1H), 7.68 (br d, J=4.3 Hz, 1H), 7.43 (dd, J=8.2, 5.5 Hz, 2H), 7.06 (t, J=8.6 Hz, 2H), 4.79 (br s, 2H), 4.51 (br m, 1H), 4.35 (br m, 1H), 4.08 (d, J=15.9 Hz, 1H), 3.57 (br m, 2H), 2.84 (s, 3H). ES MS calcd for $C_{21}H_{20}FN_5O_5S$ 474 (MH$^+$), found 474.

EXAMPLE 170

N-(4-Fluorobenzyl)-5-(1,1-dioxido-5-ethyl-4-oxo-1,2,5-thiadiazepan-2-yl)-8-hydroxy-[1,6]napthyridine-7-carboxamide

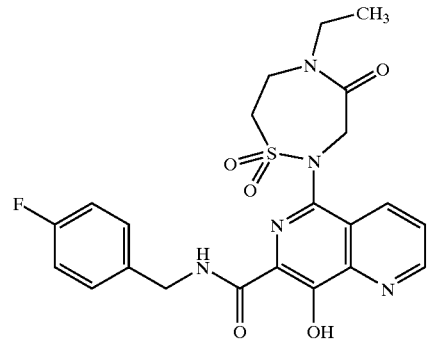

Step 1: tert-Butyl N-{[2-(ethylamino)ethyl]sulfonyl}glycinate

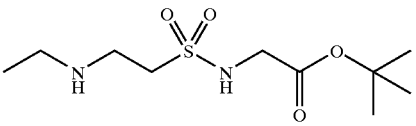

To a cold (−10° C.) stirred solution of glycine tert-butyl ester (3.0 g, 22.9 mmol) and triethylamine (7.1 mL, 50.9 mmol) in dichloromethane (150 mL), 2-chloroethanesulfonyl chloride (2.4 m/L, 23 mmol) in dichloromethane (10 mL) was added over a period of 15 minutes. The resulting mixture was stirred at 0° C. for 8 hours, and at room temperature overnight. The product mixture was concentrated under vacuum, and the residue was subjected to column chromatography on silica gel eluted with 40–50% ethyl acetate in hexane. Collection and concentration of appropriate fractions provided tert-butyl N-(ethenesulfonyl)glycinate.

A solution of the above vinylsulfonyl glycinate (4.07 g, 18.4 mmol) and ethylamine in methanol (50 mL, 2M) in methanol (700 mL) was stirred at room temp. overnight. The resultant solution was concentrated under vacuum to provide tert-butyl N-{[2-(ethylamino)ethyl]sulfonyl}glycinate as yellow viscous liquid which crystallized upon standing. This material was used in the following step without further purification.

Step 2: 5-Ethyl-1,2,5-thiadiazepan-4-one 1,1-dioxide

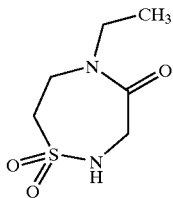

A solution of the above tert-butyl glycinate (18.4 mmol), anisole (30 mL), trifluoroacetic acid (20 mL) in dichloromethane (75 mL) was stirred at room temperature overnight. The resultant mixture was concentrated under vacuum. Residual anisole and trifluoroacetic acid was removed by co-evaporation with toluene (3×100 mL) to provide the required N-(ethylaminoethanesulfonyl)glycine TFA salt, which solidified upon standing.

To a mixture of the above N-sulfonylglycine TFA salt (0.32 g, 0.98 mmol), 1-hydroxy-7-azabenzotriazole (36 mg, 0.26 mmol), and 1-(3-dimethylaminopropyl)-3-ethylcarbodiimide hydrochloride (0.22 g, 1.13 mmol) in DMF (50 mL), diisopropyl-ethylamine was added dropwise to adjust the pH to 5–6, and the resultant mixture was stirred at room temp overnight. The reaction mixture was concentrated under vacuum. The residue was subjected to column chromatography on silica gel eluted with chloroform. Collection and concentration of appropriate fractions provided 5-ethyl-1,2,5-thiadiazepan-4-one 1,1-dioxide as white solid.

Step 3: N-(4-Fluorobenzyl)-5-(1,1-dioxido-5-ethyl-4-oxo-1,2,5-thiadiazepan-2-yl)-8-hydroxy-[1,6]napthyridine-7-carboxamide Following the procedure similar to that described in example 169 substituting 5-methyl-1,2,5-thiadiazepan-4-one 1,1-dioxide with 5-ethyl-1,2,5-thiadiazepan-4-one 1,1-dioxide, methyl 5-(1,1-dioxido-5-ethyl-4-oxo-1,2,5-thiadiazepan-2-yl)-8-hydroxy[1,6]naphthyridine-7-carboxylate was prepared.

A mixture of the above methyl ester (200 mg, 0.51 mmol) and 4-fluorobenzylamine (600 µL, 0.53 mmol) in ethyleneglycol diethyl ether (4 mL) in a sealed tube was heated in an oil bath at 120° C. for 1 hours. The reaction mixture was diluted with diethyl ether (4 mL) and cooled to 0° C. The pink solid precipitated was collected by filtration, dissolved in DMSO, and subjected to HPLC purification on C-18 stationary phase eluted with water/acetonitrile/TFA mobile phase. Collection and lyophilization of appropriate fractions provided the title compound.

$^1$H NMR (400 MHz, DMSO-d$_6$) δ 11.85 (t, J=5.7 Hz, 1H), 8.78 (dd, J=4.2, 1.7 Hz, 1H), 8.22 (dd, J=8.4, 1.7 Hz, 1H), 7.58 (dd, J=8.2, 4.2 Hz, 1H), 7.38 (dd, J=8.4, 5.7 Hz, 2H), 7.06 (t, J=8.9 Hz, 2H), 4.80 (d, J=15.8 Hz, 1H), 4.60–4.45 (br m, 3H), 4.13–4.06 (br m, 2H), 3.86 (br d, J=16.5 Hz, 1H), 3.71 (br d, J=15.8 Hz, 1H), 3.49–3.34 (m, 2H), 1.12 (t, J=7.1 Hz, 3H). ES MS calcd for C$_{22}$H$_{22}$FN$_5$O$_5$S 488 (MH$^+$), found 488.

EXAMPLE 171

N-(4-Fluorobenzyl)-5-(1,1-dioxido-1,5,2-dithiazepan-2-yl)-8-hydroxy-[1,6]napthyridine-7-carboxamide

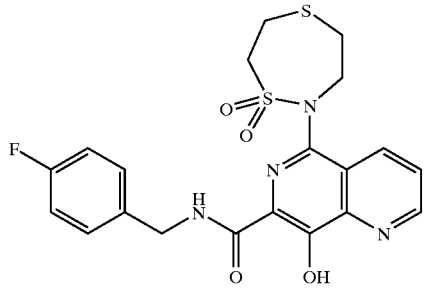

Step 1: 1,5,2-Dithiazepane 1,1-dioxide

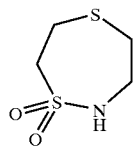

To a cold (−10° C.) stirred suspension of 2,2'-dithiobis (ethylamine) dihydrochloride (10.8 g, 48 mmol) and triethylamine (45.3 mL) in dichloromethane (500 mL), 2-chloroethanesulfonyl chloride (10.45 mL, 100 mmol) in dichloromethane (100 mL) was added over a period of 1 hour with the temperature kept <−5° C. The resulting mixture was allowed to warm up slowly to room temperature and stirred overnight. The product mixture was concentrated onto silica gel under vacuum, and the residue was loaded onto a column of silica gel and eluted with 70% ethyl acetate in hexane. Collection and concentration of appropriate fractions provided N,N'-divinylsulfonyl-2,2'-dithiobis (ethylamine) as yellow viscous oil.

To a solution of the above divinylsulfonamide disulfide (1.2 g, 3.6 mmol) in absolute ethanol at room temperature, sodium borohydride (0.14 g, 3.7 mmol) was added and stirred at room temperature overnight. The product mixture was concentrated onto silica gel under vacuum, and the residue was loaded onto a column of silica gel and eluted with 60–70% ethyl acetate in hexane. Collection and concentration of appropriate fractions provided 1,5,2-dithiazepane 1,1-dioxide as white solid.

Step 2: N-(4-Fluorobenzyl)-5-(1,1-dioxido-5-ethyl-4-oxo-1,2,5-thiadiazepan-2-yl)-8-hydroxy-[1,6]napthyridine-7-carboxamide Following the procedure similar to that described in example 169 substituting 5-methyl-1,2,5-thiadiazepan-4-one 1,1-dioxide with 1,5,2-dithiazepane 1,1-dioxide, methyl 5-(1,1-dioxido-5-ethyl-4-oxo-1,2,5-thiadiazepan-2-yl)-8-hydroxy[1,6]-naphthyridine-7-carboxylate was prepared.

A mixture of the above methyl ester (100 mg, 0.27 mmol) and 4-fluorobenzylamine (108 µL, 0.94 mmol) in absolute ethanol (1 mL) in a sealed tube was heated in an oil bath at 120° C. for 1 hours. The reaction mixture was concentrated under vacuum. The residue was dissolved in DMSO, and subjected to HPLC purification on C-18 stationary phase eluted with water/acetonitrile/TFA mobile phase. Collection and lyophilization of appropriate fractions provided the title compound.

$^1$H NMR (400 MHz, DMSO-d$_6$) δ 13.85 (br s, 1H), 9.21 (dd, J=4.2, 1.7 Hz, 1H), 9.11 (t, J=6.3 Hz, 1H), 8.65 (dd, J=8.6, 1.7 Hz, 1H), 7.92 (dd, J=8.5, 4.4 Hz, 1H), 7.45 (dd, J=8.8, 5.9 Hz, 2H), 7.19 (t, J=8.8 Hz, 2H), 4.63 (d, J=5.9 Hz, 2H), 3.94 (br s, 2H), 3.86 (br s, 2H), 3.13 (br m, 4H). ES MS calcd for C$_{20}$H$_{19}$FN$_4$O$_4$S$_2$ 463 (MH$^+$), found 463.

EXAMPLE 172

N-(4-Fluorobenzyl)-5-(1,1,5,5-tetraoxido-1,5,2-dithiazepan-2-yl)-8-hydroxy-[1,6]napthyridine-7-carboxamide

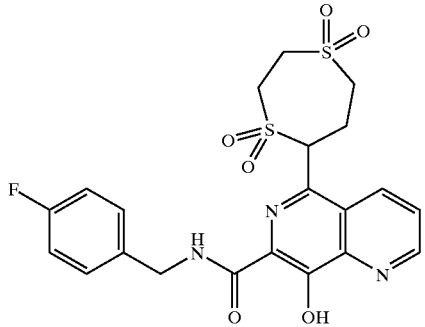

To a stirred suspension of N-(4-fluorobenzyl)-5-(1,1-dioxido-1,5,2-dithiazepan-2-yl)-8-hydroxy-[1,6]napthyridine-7-carboxamide (57 mg, 0.12 mmol, Example 171) in dichloromethane (1.2 mL), m-chloroperoxybenzoic acid (73 mg, 0.42 mmol) in dichloromethane (1 mL) was added. The resulting mixture was stirred at room temperature for 30 minutes. The product mixture was concentrated under vacuum. The residue was dissolved in DMSO, and subjected to HPLC purification on C-18 stationary phase eluted with water/acetonitrile/TFA mobile phase. Collection and lyophilization of appropriate fractions provided the title compound.

$^1$H NMR (400 MHz, DMSO-d$_6$) δ 13.70 (br s, 1H), 9.42 (t, J=6.1 Hz, 1H), 9.22 (dd, J=4.3, 1.5 Hz, 1H), 8.55 (dd, J=8.6, 1.5 Hz, 1H), 7.94 (dd, J=8.2, 4.0 Hz, 1H), 7.45 (dd, J=8.5, 5.5 Hz, 2H), 7.19 (t, J=8.9 Hz, 2H), 4.62 (br s, 2H), 3.47 (br s, 1H), 4.00 (br m, 6H), 3.61 (br s, 1H). ES MS calcd for C$_{20}$H$_{19}$FN$_4$O$_6$S$_2$ 495 (MH$^+$), found 495.

EXAMPLE 173

N-(4-Fluorobenzyl)-5-(1,4-dimethyl-7-oxo-1,4-diazepan-5-yl)-8-hydroxy-[1,6]-napthyridine-7-carboxamide

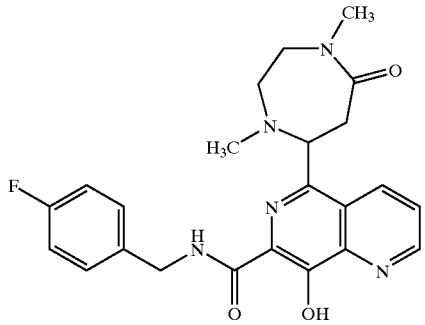

Step 1: tert-Butyl (2E)-3-(7-{[(4-fluorobenzyl)amino]carbonyl}-8-hydroxy[1,6]-naphthyridin-5-yl)-2-propenoate

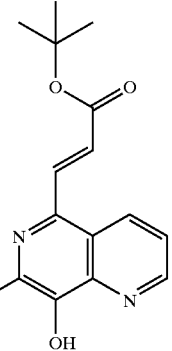

A mixture of 5-bromo-N-(4-fluorobenzyl)-8-hydroxy-[1,6]naphthyridine-7-carboxamide (3.00 g, 7.98 mmol), tert-butyl acrylate (5.0 mL, 34.1 mmol), allylpalladium(II) chloride dimer (0.25 g, 0.70 mmol), tri-o-tolylphosphine (0.51 g, 1.68 mmol), sodium acetate (2.09 g, 25.5 mmol) in xylene (50 mL) was purged with nitrogen and heated with stirring at 120° C. in a sealed tube for 18 hours. A second portion of allylpalladium(II) chloride dimer (0.25 g, 0.70 mmol) and tri-o-tolylphosphine (0.51 g, 1.68 mmol) was added, and reaction mixture was heated at the same temperature for 24 more hours. The resultant product mixture was filtered through a pad of Celite. The filtrate was diluted with diethyl ether and washed with water. The organic extract was dried over anhydrous sodium sulfate, filtered, and concentrated under vacuum. The residue was dissolved in DMSO, and subjected to HPLC purification on C-18 stationary phase eluted with water/acetonitrile/TFA mobile phase. Appropriate fractions were combined and concentrated to half of its volume. Aqueous sodium bicarbonate was added to adjust the pH to ~4. The solid precipitated was collected to provide the title propenoate.

Step 2: N-(4-Fluorobenzyl)-5-(1,4-dimethyl-7-oxo-1,4-diazepan-5-yl)-8-hydroxy-[1,6]napthyridine-7-carboxamide A mixture of the above propenoate (0.25 g, 0.59 mmol) in N,N'-dimethylethylenediamine (2.5 mL) was heated in a pressure tube in an oil bath at 60° C. for two days. The resultant mixture was diluted with chloroform and washed with aqueous ammonium chloride. The organic extract was dried over anhydrous sodium sulfate and filtered. Anhydrous hydrochloride was bubbled into the chloroform solution, and the resultant solution was stirred at room temperature for half an hour. The resultant mixture was concentrated under vacuum. The residual solid was dissolved in anhydrous DMF (30 mL) and treated with a mixture of 1-hydroxy-7-azabenzotriazole (52 mg, 0.38 mmol), 1-(3-dimethylaminopropyl)-3-ethylcarbodiimide hydrochloride (0.123 g, 0.64 mmol) and diisopropylethylamine (added dropwise to adjust the pH to 5–6). The resultant mixture was stirred at room temp overnight and concentrated under vacuum. The residue was dissolved in chloroform and washed with water. The organic extract was dried over anhydrous sodium sulfate, filtered, and concentrated under vacuum. The residue was dissolved in DMSO, and subjected to HPLC purification on C-18 stationary phase eluted with water/acetonitrile/TFA mobile phase. Collection and lyo-

EXAMPLE 174

N-(4-Fluorobenzyl)-5-(1-methyl-7-oxo-1,4-diazepan-5-yl)-8-hydroxy-[1,6]-napthyridine-7-carboxamide

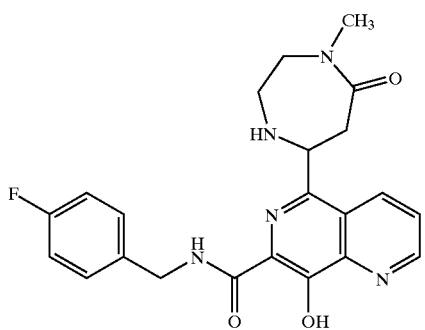

Following the procedure similar to that described in example 173 step 2, substituting N,N'-dimethylethylenediamine with N-methylethylenediamine, the title compound was prepared as TFA salt.

¹H NMR (400 MHz, DMSO-d₆) δ 13.80 (br s, 1H), 9.81 (t, J=6.0 Hz, 2H), 9.38 (br d, 1H), 9.26 (d, J=4.2 Hz, 1H), 8.61 (d, J=8.6 Hz, 1H), 8.01 (dd, J=8.2, 4.0 Hz, 1H), 7.44 (dd, J=8.5, 5.5 Hz, 2H), 7.21 (t, J=8.9 Hz, 2H), 5.66 (t, J=9.9 Hz, 1H), 4.69 (m, 2H), 4.14 (m, 1H), 3.41 (m, 3H), 2.98 (s, 3H). ES MS calcd for $C_{22}H_{22}FN_5O_3$ 424 (MH⁺), found 424.

EXAMPLE 175

N-(4-Fluorobenzyl)-5-(7-oxo-1,4-diazepan-5-yl)-8-hydroxy-[1,6]-napthyridine-7-carboxamide

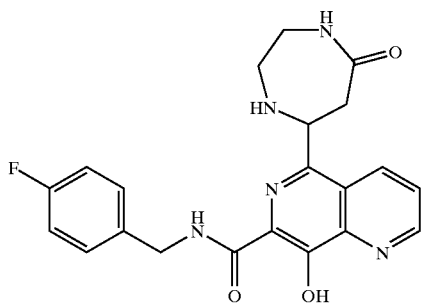

Following the procedure similar to that described in example 173 step 2, substituting N,N'-dimethylethylenediamine with ethylenediamine, the title compound was prepared as TFA salt.

¹H NMR (400 MHz, DMSO-d₆) δ 13.78 (br s, 1H), 9.77 (t, J=6.2 Hz, 2H), 9.34 (br d, 1H), 9.22 (d, J=4.2 Hz, 1H), 8.61 (d, J=8.6 Hz, 1H), 8.13 (br s, 1H), 7.96 (dd, J=8.6, 4.2 Hz, 1H), 7.41 (dd, J=8.6, 5.9 Hz, 2H), 7.17 (t, J=9.0 Hz, 2H), 5.66 (t, J=9.9 Hz, 1H), 4.65 (m, 2H), 3.74–3.20 (m). ES MS calcd for $C_{21}H_{20}FN_5O_3$ 410 (MH⁺), found 410.

EXAMPLE 176

N-(4-Fluorobenzyl)-5-[4-(methylsulfonyl)thiomorpholin-2-yl]-8-hydroxy-[1,6]napthyridine-7-carboxamide

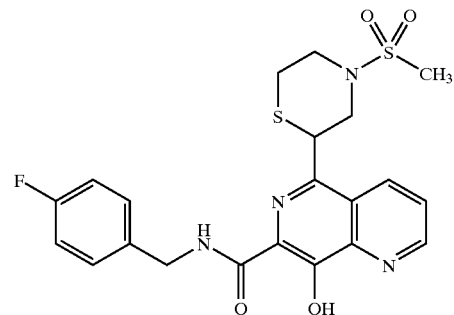

Step 1: Methyl 8-[(4-methoxybenzyl)oxy]-5-vinyl-[1,6]-naphthyridine-7-carboxylate

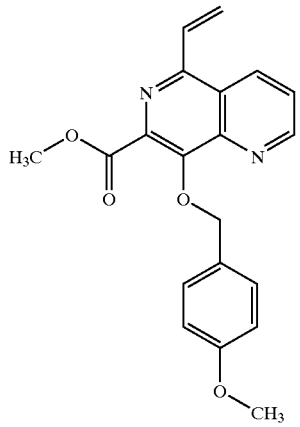

A mixture of methyl 5-bromo-8-hydroxy-[1,6]-naphthyridine-7-carboxylate (7.73 g, 27.4 mmol), 4-methoxybenzyl chloride (5.15 g, 32.9 mmol), and $Cs_2CO_3$ (10.7 g, 32.9 mmol) in DMF (150 mL) was stirred in an oil bath at 50° C. overnight. Additional quantity of 4-methoxybenzyl chloride (0.6 g), and $Cs_2CO_3$ (1 g) was added, and the mixture heated at the same temperature for 8 hour. The resulting mixture was filtered and concentrated under vacuum. The residue was partitioned between dichloromethane and brine. The organic extract was dried over anhydrous sodium sulfate, filtered, and concentrated under vacuum. The residue was dissolved in boiling ethyl acetate (150 mL), hexane was added until solution turn cloudy. The resultant slurry was stirred at room temperature overnight. The solid precipitated was collected by filtration to provide methyl 5-bromo-8-[(4-methoxybenzyl)oxy]-[1,6]-naphthyridine-7-carboxylate.

A mixture of the above bromoester (3.33 g, 8.3 mmol), tri-n-butyl(vinyl)tin (5.26 g, 16.6 mmol), tris(dibenzylideneacetone)dipalladium (0) (1.52 g, 1.6 mmol), tri(2-furyl)phosphine (0.78 g, 3.3 mmol), copper (I) iodide (0.47 g, 2.5 mmol) in DMF (120 mL) under an atmosphere of nitrogen in a sealed vessel was stirred in an oil bath at 80° C. for two hours. The resulting mixture was filtered through a pad of Celite, and the filtrated concentrated under vacuum. The residue was partitioned between ethyl acetate and brine.

The organic extract was dried over anhydrous sodium sulfate, filtered, and concentrated under vacuum. The residue was subjected to column chromatography on silica gel eluting with 40–50% ethyl acetate in hexane. Collection and concentration of appropriate fractions provided the vinyl-napthyridine as off-white solid.

Step 2: Methyl 5-{1-hydroxy-2-[(methylsulfonyl)amino]ethyl}-8-[(4-methoxybenzyl)oxy]-1,6-naphthyridine-7-carboxylate

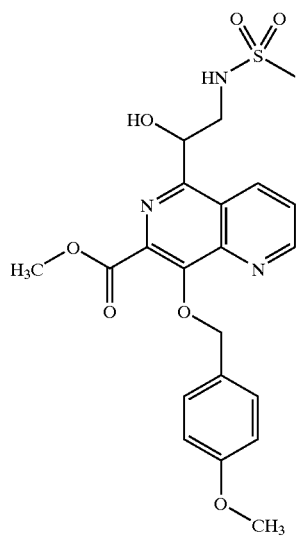

A suspension of the above vinylnapthyridine (1.2 g, 3.4 mmol) in a solution of chloramine-M (1.56 g, 10.3 mmol; Angew. Chem. Int. Ed. Engl. 1996, 35, 2810) and hydroquinidine 1,4-phthalazinediyl diether [0.26 g, 0.3 mmol; (DHQD)$_2$PHAL, no enantioselectivity was observed in the hydroxyamination of this vinylnapthyridine] in mixture of n-propanol (20 mL) and water (20 mL) was treated with a solution of osmium tetroxide in 2-methyl-2-propanol (2.5 wt. %, 0.2 mL, 19 μmol) and was stirred at room temperature for 30 minutes. The resultant clear solution was concentrated under vacuum. The residue was triturated with ethyl acetate, and the organic extract was concentrated under vacuum. The residue was subjected to column chromatography on silica gel eluting with 5% methanol in ethyl acetate. Collection and concentration of appropriate fractions provided the hydroxylamine derivative as racemic solid.

$^1$H NMR (400 MHz, DMSO-d$_6$) δ 9.27 (dd, J=4.0, 1.5 Hz, 1H), 8.98 (dd, J=8.6, 1.5 Hz, 1H), 7.85 (dd, J=8.6, 4.0 Hz, 1H), 7.42 (d, J=8.6 Hz, 2H), 7.06 (t, J=6.0 Hz, 1H), 6.95 (d, J=8.6 Hz, 2H), 6.03 (d, J=6.0 Hz, 1H), 5.43 (s, 2H), 5.30 (dd, J=12.5, 6.2 Hz, 1H), 3.81 (s, 3H), 3.76 (s, 3H), 3.50 (m, 2H), 2.89 (s, 3H).

Step 3: Methyl 8-[(4-methoxybenzyl)oxy]-5-[4-(methylsulfonyl)thiomorpholin-2-yl]-1,6-naphthyridine-7-carboxylate

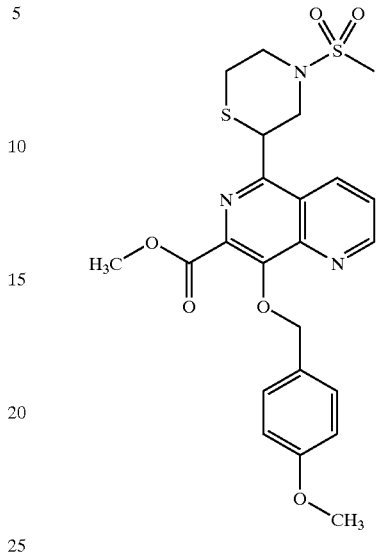

A cold (0° C.) solution of the above hydroxylsulfonamide (0.52 g, 1.12 mmol) and triethylamine (0.21 mL, 1.36 mmol) in dichloromethane (28 mL) was treated with methanesulfonyl chloride (0.12 mL, 1.55 mmol) and stirred at the same temperature for 1 hour. The resultant mixture was treated with 1,8-diazabicyclo[5.4.0]undec-7-ene (0.51 mL, 3.38 mmol) and stirred at room temperature for half an hour. The product mixture was concentrated under vacuum, and the residue was subjected to column chromatography on silica gel eluting with 20% ethyl acetate in dichloromethane. Collection and concentration of appropriate fractions provided the corresponding sulfonylaziridine.

A solution of the above sulfonylaziridine (0.42 g, 0.95 mmol) in chloroform (20 mL) was purged with nitrogen for 2 minutes. Triethylamine (0.58 g, 5.73 mmol) and 2-mercaptoethanol (0.44 g, 5.73 mmol) was added. The mixture was sealed and heated at 65° C. for 3 hours. The product mixture was concentrated under vacuum and the residue was subjected to column chromatography on silica gel eluting with ethyl acetate. Collection and concentration of appropriate fractions provided the corresponding ring opened hydroxyethylthioether.

A solution of the above hydroxyethylthioether (0.33 g, 0.63 mmol), triphenylphosphine (0.25 g, 0.95 mmol), and diethyl azodicarboxylate (0.16 g, 9.5 mmol) in anhydrous THF (40 mL) was stirred at room temperature overnight. The resultant mixture was concentrated onto silica gel, load onto a column of silica gel, and eluted with 50% ethyl acetate in chloroform. Appropriate fractions were collected and concentrated. The residue was triturated with anhydrous diethyl ether (2 mL), and the solid precipitated was collected by filtration to provide the title N-methylsulfonylthiomorpholine compound as off white solid.

$^1$H NMR (400 MHz, CDCl$_3$) δ 9.20 (dd, J=4.2, 1.7 Hz, 1H), 8.68 (dd, J=8.6, 1.7 Hz, 1H), 7.66 (dd, J=8.6, 4.2 Hz, 1H), 7.49 (d, J=8.7 Hz, 2H), 6.91 (d, J=8.7 Hz, 2H), 5.53 (d, J=10.3 Hz, 1H), 5.48 (d, J=10.3 Hz, 1H), 4.85 (dd, J=10.3, 2.7 Hz, 1H), 4.42 (dd, J=13.2, 2.0 Hz, 1H), 4.25 (dd, J=10.6, 2.7 Hz, 1H), 3.94 (s, 3H), 3.82 (s, 3H), 3.79 (d, J=10.3 Hz,

1H), 3.77 (d, J=10.3 Hz, 11), 3.29 (br t, J=11.7 Hz, 1H), 3.10 (br t, J=12.3 Hz, 1H), 2.89 (s, 3H), 2.75 (br d, J=13.6 Hz, 1H).

Step 4: N-(4-Fluorobenzyl)-5-[4-(methylsulfonyl) thiomorpholin-2-yl]-8-hydroxy-[1,6]napthyridine-7-carboxamide A solution of the above N-methylsulfonylthiomorpholine (120 mg, Step 3), water (1 mL), and TFA (0.4 mL) in acetonitrile (30 mL) was stirred at room temperature for 6 hours. The resultant mixture was concentrated under vacuum. Residual water and TFA was removed by co-evaporation with additional acetonitrile (3×20 mL). The residue was triturated with diethyl ether. The solid precipitated was filtered, and dried under vacuum to provide methyl 8-hydroxy-5-{4-(methylsulfonyl)thiomorpholin-2-}[1,6] naphthyridine-7-carboxylate as light brown solid.

A mixture of the above methyl ester (90 mg) and 4-fluorobenzylamine (0.3 mL) in a mixture of methanol (10 mL) and toluene (50 mL) in a sealed tube was heated in an oil bath at 120° C. for 2 hours. The reaction mixture was cooled to 0° C., and the precipitate was filtered to provide the title compound.

$^1$H NMR (400 MHz, DMSO-d$_6$) δ 13.60 (br s, 1H), 9.47 (br s, 1H), 9.16 (dd, J=4.1, 1.2 Hz, 1H), 8.90 (dd, J=8.6, 1.2 Hz, 1H), 7.85 (dd, J=8.6, 4.1 Hz, 1H), 7.44 (dd, J=8.6, 5.7 Hz, 2H), 7.18 (t, J=9.0 Hz, 2H), 4.97 (dd, J=9.3, 2.8 Hz, 1H), 4.61 (m, 2H), 4.16–3.97 (m, 4H), 3.19–1.09 (m, 2H), 3.06 (s, 3H), 2.79 (d, J=11.5 Hz, 1H). ES MS calcd for C$_{21}$H$_{21}$FN$_4$O$_5$S$_2$ 477 (MH$^+$), found 477.

EXAMPLES 177 & 178

N-(4-Fluorobenzyl)-5-[4-(methylsulfonyl)-1-oxidothiomorpholin-2-yl]-8-hydroxy-[1,6] napthyridine-7-carboxamide and N-(4-fluorobenzyl)-5-[4-(methylsulfonyl)-1,1-dioxidothiomorpholin-2-yl]-8-hydroxy-[1,6] napthyridine-7-carboxamide

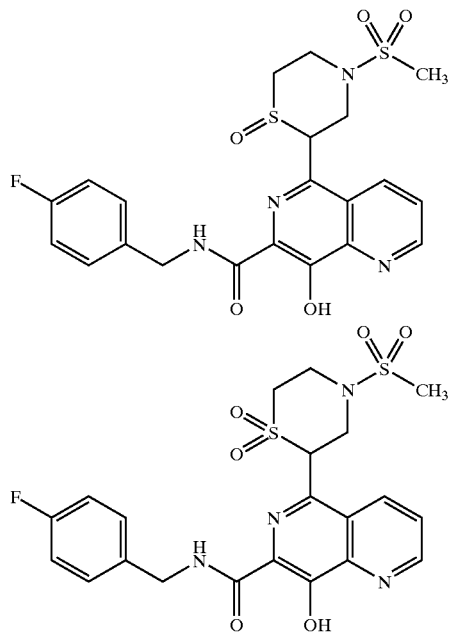

To a stirred solution of N-(4-fluorobenzyl)-5-[4-(methylsulfonyl)thiomorpholin-2-yl]-8-hydroxy-[1,6] napthyridine-7-carboxamide (55 mg, 0.115 mmol, example 176) in DMF (2 mL), m-chloroperoxybenzoic acid (0.6 mL of 73 mg m-CPBA/mL of dichloromethane) was added. The resulting mixture was stirred at room temperature for 5 hours. A second aliquot of 0.6 ml of m-CPBA solution was added and stirred at room temperature overnight. The product mixture was concentrated under vacuum. The residue was dissolved in trifluoroacetic acid, and subjected to HPLC purification on C-18 stationary phase eluted with water/acetonitrile/TFA mobile phase. Collection and lyophilization of appropriate fractions provided the title compounds.

EXAMPLE 177

Sulfoxide $^1$H NMR (500 MHz, DMSO-d$_6$) δ 13.71 (br s, 1H), 9.46 (t, J=6.0 Hz, 1H), 9.21 (dd, J=4.3, 1.5 Hz, 1H), 9.00 (br d, J=8.6 Hz, 1H), 7.88 (dd, J=8.6, 4.3 Hz, 1H), 7.43 (dd, J=8.5, 5.8 Hz, 2H), 7.18 (t, J=8.9 Hz, 2H), 5.11 (dd, J=11.3, 3.0 Hz, 1H), 4.62 (m, 2H), 4.39 (dd, J=14.3, 11.3 Hz, 1H), 3.96 (d, J=12.8 Hz, 1H), 3.83 (d, J=12.5 Hz, 1H), 3.56–3.45 (m, 2H), 3.18 (2H), 3.15 (s, 3H). ES MS calcd for C$_{21}$H$_{21}$FN$_4$O$_5$S$_2$ 493 (MH$^+$), found 493.

EXAMPLE 178

Sulfone $^1$H NMR (500 MHz, DMSO-d$_6$) δ 13.79 (br s, 1H), 9.54 (t, J=6.4 Hz, 1H), 9.18 (dd, J=4.3, 1.5 Hz, 1H), 8.96 (dd, J=8.6, 1.5 Hz, 1H), 7.88 (dd, J=8.9, 4.3 Hz, 1H), 7.44 (dd, J=8.5, 5.5 Hz, 2H), 7.19 (t, J=8.9 Hz, 2H), 5.75 (dd, J=10.9, 3.1 Hz, 1H), 4.69–4.54 (m, 3H), 4.19 (dd, J=14.0, 2.5 Hz, 2H), 3.76 (br t, J=13.7 Hz, 1H), 3.49 (d, J=12.2 Hz, 2H), 3.20 (s, 3H). ES MS calcd for C$_{21}$H$_{21}$FN$_4$O$_6$S$_2$ 509 (MH$^+$), found 509.

EXAMPLE 179

5-(2-Acetyl-1-methylpyrazolidin-3-yl)-N-(4-Fluorobenzyl)-8-hydroxy-[1,6]napthyridine-7-carboxamide

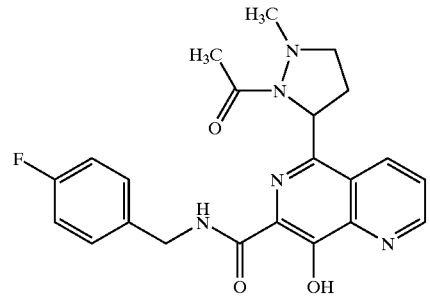

Step 1: Methyl 5-(2-acetyl-1-methylpyrazolidin-3-yl)-8-[(4-methoxybenzyl)oxy]-[1,6]-naphthyridine-7-carboxylate

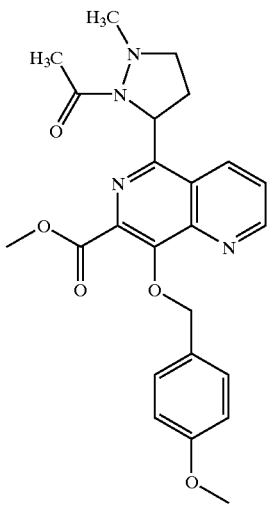

A mixture of methyl 8-[(4-methoxybenzyl)oxy]-5-vinyl-[1,6]-naphthyridine-7-carboxylate (0.26 g, 0.73 mmol), paraformaldehyde (96 mg), and 1-acetyl-2-methylhydrazine (0.22 g, 2.45 mmol; J. Org. Chem. 1972, 37, 3608) in toluene (15 mL) was heated in an oil bath at 120° C. for 1.5 hour. The resulting mixture was concentrated under vacuum. The residue was subjected to column chromatography on silica gel eluting first with a gradient of 0–5% methanol in ethyl acetate. Collection and concentration of appropriate fractions provided the title acetylpyrazolidine.

Step 2: 5-(2-Acetyl-1-methylpyrazolidin-3-yl)-N-(4-fluorobenzyl)-8-hydroxy-[1,6]napthyridine-7-carboxamide A solution of the above acetylpyrazolidine (50 mg, Step 1), water (0.25 mL), and TFA (0.15 mL) in acetonitrile (5 mL) was stirred at room temperature for 6 hours. The resultant mixture was concentrated under vacuum. Residual water and TFA was removed by co-evaporation with additional acetonitrile (3×5 mL). Without further purification, the residual oil was treated with 4-fluorobenzylamine (0.2 mL) in a mixture of methanol (1 mL) and toluene (8 mL) in a sealed tube was heated in an oil bath at 120° C. for 2 hours. The product mixture was concentrated under vacuum. The residue was dissolved in DMSO, and subjected to HPLC purification on C-18 stationary phase eluted with water/acetonitrile/TFA mobile phase. Collection and lyophilization of appropriate fractions provided the title compound.

$^1$H NMR (400 MHz, CDCl$_3$) δ 9.27 (d, J=4.3 Hz, 1H), 8.83 (d, J=8.5 Hz, 1H), 8.04 (br t, 1H), 7.75 (dd, J=8.3, 5.5 Hz, 1H), 7.08 (t, J=8.6 Hz, 2H), 5.89 (t, J=8.4 Hz, 1H), 4.64 (d, J=5.7 Hz, 2H), 3.2–2.4 (m), 2.58 (s, 3H), 2.17 (s, 1H). ES MS calcd for C$_{22}$H$_{22}$FN$_5$O$_3$ 424 (MH$^+$), found 424.

EXAMPLE 180

2-(7-{[(4-fluorobenzyl)amino]carbonyl}-8-hydroxy-1,6-naphthyridin-5-yl)-1,2,5-thiadiazepan-5-ium 1,1-dioxide trifluoroacetate

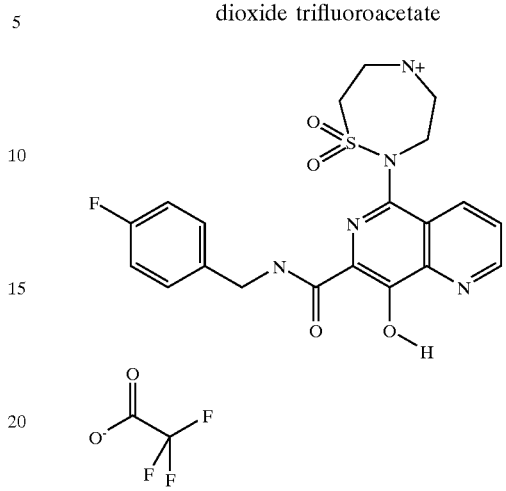

Step 1: Preparation of tert-butyl 2-[(vinylsulfonyl)amino]ethylcarbamate.

To a solution of N-Boc ethylenediamine (1.24 g, 7.74 mmol) in methylene chloride (35 ml) at −10 C, was added triethylamine (2.37 ml, 17.0 mmol). 2-chloro-1-ethanesulfonyl chloride (0.809 mL, 7.74 mmol). After 4 hr at −10 C the cold bath was removed and the reaction was stirred for 12 hr at room temperature. The reaction was quenched by the addition of Na$_2$CO$_3$ (sat aq.) and extracted with methylene chloride. The organic extracts were dried (MgSO$_4$) and the solvent evaporated in vacuo to afford the title compound as an oil which was used in the next step without further purification.

FAB MS calcd for C$_9$H$_{18}$N$_2$O$_4$S 151 (MH$^+$-Boc), found 151. $^1$H NMR (CDCl$_3$, 400 MHz) δ 6.53 (1H, dd, J=9.9 and 16.5 Hz), 6.24 (1H, d, J=16.5 Hz), 5.95 (1H, d, J=9.9 Hz), 5.09 (1H, s), 4.95 (1H, s), 3.28 (2H, m), 3.15 (2H, m), 1.45 (9H, s) ppm.

Step 2: Preparation of 2-[(vinylsulfonyl)amino]ethanaminium chloride

A solution of tert-butyl 2-[(vinylsulfonyl)amino]ethylcarbamate (1.60 g, 6.39 mmol) in EtOAc (55 ml) at 0 C, was saturated with HCl gas and then stirred for 1 hr. The solvent was evaporated in vacuo to afford the product as a viscous oil.

FAB MS calcd for C$_5$H$_{10}$N$_2$O$_2$S 151 (MH$^+$), found 151. $^1$H NMR (d$_6$DMSO, 400 MHz) δ 8.06 (3H, s), 7.64 (1H, t, J=5.7 Hz), 6.75 (1H, dd, J=9.9 and 16.5 Hz), 6.08 (1H, d, J=16.5 Hz), 6.05 (1H, d, J=9.9 Hz), 3.15 (2H, m), 2.88 (2H, m) ppm.

Step 3: Preparation of 1,2,5-thiadiazepane 1,1-dioxide

A solution of 2-[(vinylsulfonyl)amino]ethanaminium chloride (1.17 g, 6.24 mmol) in methanol (50 ml) at room temperature, was treated with triethylamine (0.87 mL, 6.24 mmol) and then stirred for 28 hr. Silica gel (10 g) was added to the solution. The solvent was evaporated in vacuo and the remaining silica gel was applied to a column of silica gel and chromatographed eluting with 4% ammonium hydroxide in acetonitrile to afford the title compound as an oil.

FAB MS calcd for $C_5H_{10}N_2O_2S$ 151 (MH$^+$), found 151. $^1$H NMR (d$_6$DMSO, 400 MHz) δ 7.19 (1H, s), 3.26 (2H, m), 2.95–2.85 (6H, m), 2.88 (2H, m) and 2.60 (1H, m) ppm.

Step 4: Preparation of tert-butyl 1,2,5-thiadiazepane-5-carboxylate 1,1-dioxide

To a solution of 1,2,5-thiadiazepane 1,1-dioxide 90.10 g, 0.67 mmol) in pyridine (1 mL) was added di-tert-butyldicarbonate 0.174 g, 0.799 mmol). After 24 hr the reaction was quenched with NaHCO$_3$ (sat aq.) and extracted into methylene chloride. The organic extracts were dried (MgSO$_4$) and the solvent evaporated in vacuo. The residue was purified by chromatography (SiO2, EtOAc/CH2Cl2: 1:1) to afford the title compound as a white solid.

FAB MS calcd for $C_9H_{18}N_2O_4S$ 151 (MH$^+$-Boc), found 151. $^1$H NMR (d$_6$DMSO, 400 MHz) δ 7.46 (1H, m), 3.55 (2H, m), 3.48 (2H, m), 3.36–3.26 (2H, m), 3.06 (2H, m), 1.41 (9H, s) ppm.

Step 5: Preparation of tert-butyl 2-(7-{[(4-fluorobenzyl)amino]carbonyl}-8-hydroxy-1,6-naphthyridin-5-yl)-1,2,5-thiadiazepane-5-carboxylate 1,1-dioxide To a solution of 5-bromo-N-(4-fluorobenzyl)-8-hydroxy-1,6-naphthyridine-7-carboxamide (0.188 g, 0.50 mmol), tert-butyl 1,2,5-thiadiazepane-5-carboxylate 1,1-dioxide (0.12 g, 0.45 mmol) and Cu2O (0.071 g, 0.50 mmol) in pyridine (3 mL) were heated at reflux for 16 hr. The reaction was filtered and the solids washed with CHCl3 (100 mL). The filtrate was stirred for 1 hr with disodium ethylenediamine tetraacetate (0.2 g in water 10 mL) in the presence of air. The organic extracts were stirred for 1 hr with disodium ethylenediamine tetraacetate (0.2 g in water 10 mL) in the presence of air. The organic extracts were dried (MgSO$_4$) and the solvent evaporated in vacuo. The residue was purified by preparative HPLC (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (d$_6$DMSO, 400 MHz) δ 9.28–9.18 (1.6H, m), 8.95(0.4H, m), 8.62 (0.6H, d, J=8.4 Hz), 8.48 (1H, d, J=8.4 Hz), 7.98–7.88 (1H, m), 7.54–7.42 (2H, m), 7.24–7.16 (2H, m), 4.75–4.45 (2H, m), 4.20–3.40 (8H, m), 1.43 (3.6H, s) 1.17 (5.4H, s) ppm. FAB MS calcd for $C_{25}H_{28}FN_5O_6S$ 546 (MH$^+$), found 546.

Step 6: Preparation of 2-(7-{[(4-fluorobenzyl)amino]carbonyl}-8-hydroxy-1,6-naphthyridin-5-yl)-1,2,5-thiadiazepan-5-ium 1,1-dioxide trifluoroacetate A solution of tert-butyl 2-(7-{[(4-fluorobenzyl)amino]carbonyl}-8-hydroxy-1,6-naphthyridin-5-yl)-1,2,5-thiadiazepane-5-carboxylate 1,1-dioxide (0.088 g, 0.185 mmol) in methylene chloride (5 mL) was treated with trifluoroacetic acid (2 mL) at room temperature. After 6 hr the solvent was evaporated in vacuo and the residue purified by preparative HPLC (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (d$_6$DMSO, 400 MHz) δ 9.46 (1H, s), 9.24 (1H, d, J=4.1 Hz), 8.59 (1H, d, J=8.4 Hz), 7.95 (1H, dd, J=4.1 and 8.4 Hz), 7.44 (2H, m), 7.19 (2H, m), 4.66 (2H, d, J=6.0 Hz), 4.40–3.00 (8H, m), ppm. FAB MS calcd for $C_{20}H_{20}FN_5O_4S$ 446 (MH$^+$), found 446.

EXAMPLE 181

N-(4-fluorobenzyl)-8-hydroxy-5-[5-(methylsulfonyl)-1,1-dioxido-1,2,5-thiadiazepan-2-yl]-1,6-naphthyridine-7-carboxamide

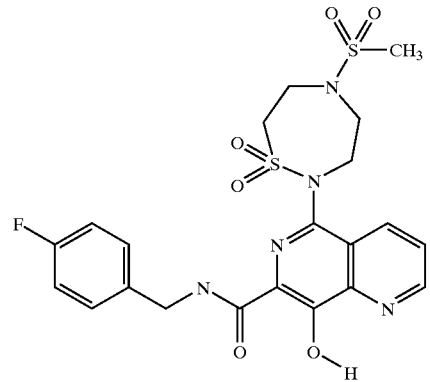

Step 1: Preparation of 5-(methylsulfonyl)-1,2,5-thiadiazepane 1,1-dioxide

To a solution of 1,2,5-thiadiazepane 1,1-dioxide (0.10 g, 0.67 mmol) in methylene chloride (2 mL) at −10 C was added methane sulfonyl chloride (0.06 mL, 0.77 mmol) and triethylamine (0.108 mL, 0.77 mmol). After 72 hr the reaction was quenched with NaHCO$_3$ (sat. aq.) and extracted into methylene chloride. The organic extracts were dried (MgSO$_4$) and the solvent evaporated in vacuo. The residue was purified by chromatography (SiO2, EtOAc/CH$_2$Cl$_2$: 1:1) to afford the title compound as a white solid.

$^1$H NMR (d$_6$DMSO, 400 MHz) δ 7.57 (1H, t, J=5.8 Hz), 3.55 (2H, t, J=5.4 Hz), 3.49 (2H, t, J=5.8 Hz), 3.35 (2H, m), 3.10 (2H, q, J=5.7 Hz), 2.99 (3H, s) ppm.

Step 2: Preparation of N-(4-fluorobenzyl)-8-hydroxy-5-[5-(methylsulfonyl)-1,1-dioxido-1,2,5-thiadiazepan-2-yl]-1,6-naphthyridine-7-carboxamide To a solution of 5-bromo-N-(4-fluorobenzyl)-8-hydroxy-1,6-naphthyridine-7-carboxamide (0.147 g, 0.39 mmol), 5-(methylsulfonyl)-1,2,5-thiadiazepane 1,1-dioxide (0.081 g, 0.355 mmol) and Cu2O (0.056 g, 0.39 mmol) in pyridine (2.4 mL) were heated at reflux for 16 hr. The reaction was filtered and the solids washed with CHCl$_3$ (100 mL). The filtrate was stirred for 1 hr with disodium ethylenediamine tetraacetate (0.2 g in water 10 mL) in the presence of air. The organic extracts were stirred for 1 hr with disodium ethylenediamine tetraacetate (0.2 g in water 10mL) in the presence of air. The organic extracts were dried (MgSO$_4$) and the solvent evaporated in vacuo. The residue was purified by preparative HPLC (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (d$_6$DMSO, 400 MHz) δ 9.23 (1H, d, J=1.5 Hz), 9.04 (1H, t, J=6.0 Hz), 8.66 (1H, d, J=8.5 Hz), 7.74 (1H, dd, J=4.3 and 8.5 Hz), 7.42 (2H, m), 7.02 (2H, m), 4.61 (2H, m), 4.20–4.00 (2H, m), 4.00–3.80 (2H, m), 3.75–3.60 (1H, m), 3.47 (1H, t, J=14.0 Hz), 3.30 (1H, m, J=14.0 Hz), 2.97 (3H, s) ppm. FAB MS calcd for $C_{21}H_{22}FN_5O_6S_2$ 524 (MH$^+$), found 524.

EXAMPLE 182

N-(4-fluorobenzyl)-8-hydroxy-5(6-methyl-1,1-dioxido-1,2,6-thiadiazinan-2yl)-1,6-naphthyridine-7-carboxamide

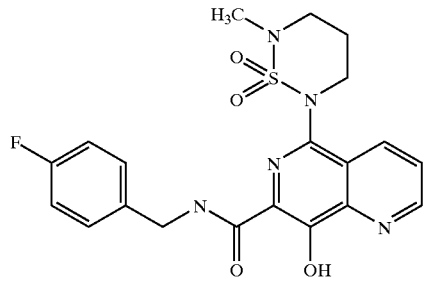

Step 1: Preparation of 2-methyl-1,2,6-thiadiazinane 1,1-dioxide

To a solution of N-methyl-1,3-diaminopropane (37.6 mL, 312 mmol) and sulfamide (10.0 g, 104 mmol) were heated at reflux for 16 hr. The solvent was evaporated in vacuo and the residue was purified by chromatography (SiO2, EtOAc/CH2Cl2: 1:1) to afford the title compound as an oil.

$^1$H NMR (CDCl$_3$, 400 MHz) δ 4.06 (1H, s), 3.52 (2H, m), 3.30 (2H, m), 2.76 (3H, s), 1.79 (2H, m) ppm. FAB MS calcd for C$_4$H$_9$N$_2$O$_2$S 151 (MH$^+$), found 151.

Step 2: Preparation of N-(4-fluorobenzyl)-8-hydroxy-5(6-methyl-1,1-dioxido-1,2,6-thiadiazinan-2yl)-1,6-naphthyridine-7-carboxamide To a solution of 5-bromo-N-(4-fluorobenzyl)-8-hydroxy-1,6-naphthyridine-7-carboxamide (0.300 g, 0.80 mmol), 2-methyl-1,2,6-thiadiazinane 1,1-dioxide (0.144 g, 0.96 mmol) and Cu2O (0.086 g, 0.60 mmol) in pyridine (6.0 mL) were heated at reflux for 16 hr. The reaction was filtered and the solids washed with CHCl3 (100 mL). The filtrate was stirred for 1 hr with disodium ethylenediamine tetraacetate (0.5 g) in water (25 mL) in the presence of air. The organic extracts were stirred for 1 hr with disodium ethylenediamine tetraacetate (0.50 g in water 50 mL) in the presence of air. The organic extracts were dried (MgSO$_4$) and the solvent evaporated in vacuo. The residue was purified by preparative HPLC (Gilson semi preparative HPLC system and a YMC Combiprep Pro Column (50×20 mm I.D., C18, S-5 um, 120A) eluting with 5–95% acetonitrile/water (0.1% TFA) at 15 ml/min) to afford the title compound after lyophilization.

$^1$H NMR (d$_6$DMSO, 400 MHz) δ 13.70 (1H, s), 9.36 (1H, t, J=6.3 Hz), 9.16 (1H, d, J=4.2 Hz), 8.67 (1H, d, J=8.4 Hz), 7.86 (1H, dd, J=4.2 and 8.4 Hz), 7.43 (2H, m), 7.18 (2H, m), 4.60 (2H, d, J=6.2 Hz), 4.55–4.20 (1H, m), 4.00–3.40 (3H, m), 3.05 (3H, s), 2.30–1.90 (2H, m) ppm. FAB MS calcd for C$_{20}$H$_{20}$FN$_5$O$_4$S 446 (MH$^+$), found 446.

EXAMPLE 183

N-(4-fluorobenzyl)-8-hydroxy-5-{methyl [(1-methyl-1H-imidazol-4-yl)sulfonyl]amino}-1,6-naphthyridine-7-carboxamide

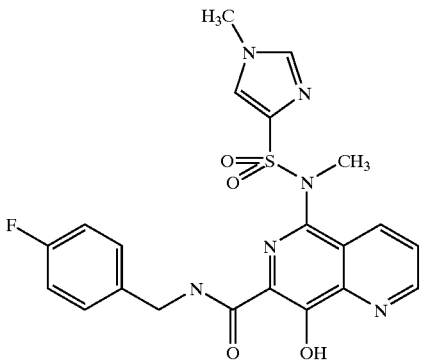

Step 1: Preparation of N,1-dimethyl-1H-imidazole-4-sulfonamide

To a solution of (1-methyl-1H-imidazol-4-yl)sulfonyl chloride (3.14 g, 17.4 mmol) in methylene chloride was added a solution of methylamine (26 mL of a 2M solution in THF, 52 mmol). The resulting mixture was stirred at room temperature for 16 hr. Water (25 mL) was added and the mixture was extracted with methylene chloride (2×100 mL). The combined organic extracts were washed with water (10 mL) and dried (MgSO$_4$). The solvent was evaporated in vacuo to afford the title compound.

$^1$H NMR (CDCl$_3$, 400 MHz) δ 7.51 (1H, s), 7.49 (1H, s), 4.71 (1H, s), 3.77 (3H, s), 2.70 (3H, m) ppm.

Step 2: Preparation of methyl 8-hydroxy-5-{methyl [(1-methyl-1H-imidazol-4-yl) sulfonyl]amino}-1,6-naphthyridine-7-carboxylate A solution of methyl-5-bromo-8-hydroxy-1,6-naphthyridine-7-carboxylate (0.969 g, 3.42 mmol), N,1-dimethyl-1H-imidazole-4-sulfonamide (0.60 g, 3.42 mmol) and Cu2O (0.49 g, 3.42 mmol) in pyridine (15 mL) was heated at reflux for 16 hr. The reaction was filtered and the solids washed with CHCl3 (100 mL). The filtrate was stirred for 1 hr with disodium ethylenediamine tetraacetate (1.0 g) in water (20 mL) in the presence of air. The organic extracts were stirred for 1 hr with disodium ethylenediamine tetraacetate (1.0 g in water 20 mL) in the presence of air. The organic extracts were dried (MgSO$_4$) and the solvent evaporated in vacuo. The residue was suspended in acetonitrile (10 mL) and the resulting solid collected by filtration. The solids were washed with diethyl ether (5 mL) and dried in vacuo to afford the title compound as a solid.

$^1$H NMR (d$_6$DMSO, 400 MHz) δ 11.45 (1H, s), 9.22 (1H, dd, J=4.2 and 1.6 Hz), 8.85 (1H, dd, J=1.6 and 8.6 Hz), 7.93 (1H, dd, J=4.2 and 8.4 Hz), 7.88 (1H, s), 7.80 (1H, d, J=1.1 Hz), 3.91 (3H, s), 3.74 (3H, s), 3.18 (3H, s) ppm. FAB MS calcd for C$_{13}$H$_{15}$N$_5$O$_5$S 378 (MH$^+$), found 378.

Step 3: Preparation of N-(4-fluorobenzyl)-8-hydroxy-5-{methyl[(1-methyl-1H-imidazol-4-yl)sulfonyl]amino}-1,6-naphthyridine-7-carboxamide A solution of the methyl ester from step 2 (0.10 g, 0.265 mmol) and 4-fluorobenzylamine (0.033 mL, 0.29 mmol) in toluene (1 mL) was heated at 130 C in a sealed tube for 72 hr. 4-fluorobenzylamine (0.033 mL, 0.29 mmol) was added and heating continued at 130 C for 16 hr. The solvent was evaporated in vacuo. The residue was purified by preparative HPLC (Waters PrepPak Column, C18 eluting with 5–95% acetonitrile/water (0.1% TFA) at 100 ml/min) to afford the title compound after lyophilization.

$^1$H NMR (d$_6$DMSO, 400 MHz) δ 9.26 (1H, d, J=2.9 Hz), 8.84 (1H, d, J=8.0 Hz), 8.51 (1H, m), 7.78 (1H, dd, J=4.2 and 8.4 Hz), 7.39 (2H, m), 7.31 (1H, s), 7.10 (2H, m), 7.00 (1H, s) 4.64 (2H, d, J=3.8 Hz), 3.52 (3H, s) and 3.34 (3H, s) ppm. FAB MS calcd for $C_{21}H_{19}FN_6O_4S$ 471 (MH$^+$), found 471.

EXAMPLE 184

N-[4-fluoro-2-(methylsulfonyl)benzyl]-8-hydroxy-5-{methyl[(1-methyl-1H-imidazol-4-yl)sulfonyl]amino}-1,6-naphthyridine-7-carboxamide

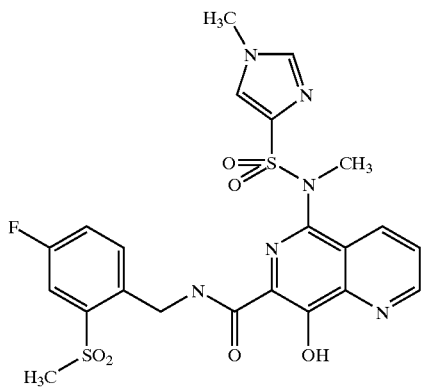

Step 1: Preparation of N-[4-fluoro-2-(methylthio)benzyl]-8-hydroxy-5-{methyl[(1-methyl-1H-imidazol-4-yl)sulfonyl]amino}-1,6-naphthyridine-7-carboxamide A solution of methyl 8-hydroxy-5-{methyl[(1-methyl-1H-imidazol-4-yl) sulfonyl]amino}-1,6-naphthyridine-7-carboxylate. (0.14 g, 0.371 mmol) and 1-[4-fluoro-2-(methylthio)phenyl]methanamine (0.102 g, 0.594 mmol) in toluene (1 mL) were heated at 130 C in a sealed tube for 72 hr. The solvent was evaporated in vacuo. The residue was purified by preparative HPLC (Waters PrepPak Column, C18 eluting with 5–95% acetonitrile/water (0.1% TFA) at 100 ml/min) to afford the title compound after lyophilization.

$^1$H NMR (CDCl$_3$, 400 MHz) δ 9.26 (1H, d, J=4.2 Hz), 8.89 (1H, dd, J=8.4 and 1.5 Hz), 8.23 (1H, t, J=6.1 Hz), 7.80 (1H, dd, J=4.4 and 8.6 Hz), 7.40–7.30 (2H, m), 7.25 (1H, m), 7.00 (1H, dd, J=9.4 and 2.5 Hz), 6.88 (1H, dt, J=2.5 and 9.8 Hz) 4.65 (2H, d, J=6.2 Hz), 3.59 (3H, s) and 3.37 (3H, s) and 2.53 (3H, s) ppm. FAB MS calcd for $C_{22}H_{21}FN_6O_4S_2$ 517 (MH$^+$), found 517.

Step 2: Preparation of N-[4-fluoro-2-(methylsulfonyl)benzyl]-8-hydroxy-5-{methyl[(1-methyl-1H-imidazol-4-yl)sulfonyl]amino}-1,6-naphthyridine-7-carboxamide To a solution of the thioether from step 1 (0.06 g, 0.116 mmol) in methylene chloride (2 mL) was added 3-chloroperbenzoic acid (0.08 g, 0.46 mmol of 50% solid) and stirred for 1 hr at room temperature. The reaction was quenched by the addition of sodium thiosulfate (0.2 g) and NaHCO$_3$ (sat. aq. 10 mL) and extracted with methylene choride (2×20 mL). The organic extracts were dried (MgSO$_4$) and the solvent was evaporated in vacuo. The residue was purified by preparative HPLC (Gilson semi preparative HPLC system and a Xterra RP18 Column (50× 20 mm I.D., C18, 5 um) eluting with 5–95% acetonitrile/water (0.1% TFA) at 15 ml/min) to afford the title compound after lyophilization.

$^1$H NMR (CDCl$_3$, 400 MHz) δ 13.10 (1H, s), 9.26 (1H, dd, J=4.2 and 1.5 Hz), 8.85 (1H, dd, J=8.5 and 1.5 Hz), 8.78 (1H, t, J=5.0 Hz), 7.84 (1H, dd, J=4.8 and 8.5 Hz), 7.80–7.70 (2H, m), 7.63 (1H, m), 7.45–7.34 (2H, m), 4.89 (2H, d, J=6.6 Hz), 3.74 (3H, s) and 3.31 (3H, s) and 3.20 (3H, s) ppm. FAB MS calcd for $C_{22}H_{21}FN_6O_6S_2$ 549 (MH$^+$), found 549.

EXAMPLE 185

N-7-[4-fluoro-2-(methylsulfonyl)benzyl]-8-hydroxy-N-5-,N-5-dimethyl-1,6-naphthyridine-5,7-dicarboxamide

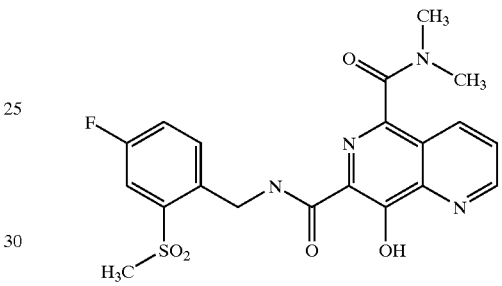

Step 1: Preparation of 4-fluoro-2-(methylthio)benzoic acid

A solution of 2-bromo-4-fluorobenzoic acid (15 g, 68.5 mmol, Aldrich) in THF (150 mL) under Argon at 0 degrees C. was treated with chloro(methyl)magnesium (5.64 g, 75.34 mmol, 2.94 M in THF) over 5 minutes. The temperature during addition was maintained below 10 degrees C. The resulting solution was cooled to −78 degrees C. and n-butyllithium (9.65 g, 150.7 mmol, 2.5M in hexanes) was added over 10 minutes. The reaction was kept below −65 degrees C. during the addition. The reaction was stirred at −78 degrees C. for 50 minutes. A solution of (methyldithio)methane (38.71 g, 410.9 mmol) in THF (20 mL), precooled to −78 degrees C., was added by cannula. The reaction was stirred for 10 minutes, warmed to zero degrees C. and stirred at zero degrees C. for 2 hours until a solid began to precipitate. The reaction was allowed to warm to 25 degrees C. The material was filtered and the solid partitioned between ethyl acetate (400 mL) and water (400 mL). The water layer was acidified with HCl to pH of less than 1 and then extracted with ethyl acetate (4×500 mL). The organic was dried over Na$_2$SO$_4$, filtered, and reduced to a small volume in vacuo to produce crystals. The crystals were filtered and dried in vacuo to afford the title compound.

$^1$H NMR (d-DMSO, 400 MHz) δ 7.98 (1H, dd, J=8.8, 6.4 Hz), 7.15 (1H, d, J=10.8 Hz), 7.05 (1H, dd, J=8.8, 6.4 Hz), 2.41 (3H, bs) ppm. EI HRMS exact mass calcd for $C_8H_7FO_2S$ 186.0151 (M), found 186.0151.

Step 2: Preparation of 4-fluoro-2-(methylthio)benzamide

To a solution of 4-fluoro-2-(methylthio)benzoic acid (8.1 g, 43.6 mmol) in degassed DMF (100 mL) under nitrogen was added ammonium chloride (4.66 g, 87.2 mmol) followed by 1-hydroxy-7-azabenzotriazole (11.87 g, 87.2 mmol) and N,N,N-diisopropylethylamine (30.38 mL, 174.4 mmol). To this mixture was added N-[3-(dimethylamino) propyl]-N'-ethylcarbodiimide hydrochloride and the reaction was stirred for 16 hour. LCMS analysis indicated that the reaction was complete. The DMF was removed in vacuo and the residue was partitioned between methylene chloride (800 mL) and 5% aqueous HCl (400 ml). The organic phase was washed with water (400 mL), saturated sodium bicarbonate solution (400 mL), and brine (400 mL). The organics were dried over $Na_2SO_4$, filtered, and reduced to a small volume in vacuo. The product crystallized upon solvent reduction. The crystals were filtered and dried in vacuo to afford the title compound.

$^1$H NMR (CDCl$_3$, 400 MHz) δ 7.67 (1H, dd, J=8.4, 5.86 Hz), 7.00 (1H, dd, J=9.89, 2.4 Hz), 6.88 (1H, dd, J=8.4, 2.4 Hz), 2.48 (3H, s) ppm. APCI HRMS exact mass calcd for $C_8H_8FNOS$ 186.0783 (MH$^+$), found 186.0365.

Step 3: Preparation of 1-[4-fluoro-2-(methylthio) phenyl]methanamine

A slurry of 4-fluoro-2-(methylthio)benzamide (9 g, 48.6 mmol) in diethyl ether (500 mL) was cooled to zero degrees C. under nitrogen and lithium aluminum hydride (5.53 g, 145.8 mmol, 1.0 M in diethyl ether) was added dropwise. The reaction was allowed to stir with slow warming to 25 degrees C. overnight. The reaction was quenched via the addition of water (5.53 mL), 15% NaOH (5.53 μL) and water (16 mL). The mixture was stirred, the lithium salts precipitated out and were filtered off. The organic filtrate was washed with saturated sodium bicarbonate (300 mL) and brine (300 mL), dried over $Na_2SO_4$, filtered and reduced to a small volume. The resulting brown oil was placed under high vacuum to give the desired compound as a free base.

$^1$H NMR (d-DMSO, 400 MHz) δ 7.43 (1H, t, J=7 Hz), 7.03 (1H, dd, J=10.0, 2.4 Hz), 6.94 (1H, ddd, J=8.8, 6.4, 2.4 Hz), 3.64 (2H, s), 2.50 (3H, s) ppm. APCI HRMS exact mass calcd for $C_8H_{10}FNS$ 172.0591 (MH$^+$), found 172.0566.

Step 4: Preparation of dimethyl 8-hydroxy-1,6-naphthyridine-5,7-dicarboxylate

Dimethyl 8-(benzoyloxy)-1,6-naphthyridine-5,7-dicarboxylate (2.0 g, 5.46 mmol, prepared as in Example 164) was dissolved in dry methanol (4.0 ml) in a pressure tube. Benzylamine (0.58 g, 5.46 mmol) was added and the reaction capped and heated to 80 degrees C. under nitrogen for 16 hours. LCMS analysis indicated that the reaction was complete. The reaction was transferred to an Erlenmeyer flask and then diethyl ether was added to precipitate the product. Filtered and dried the solid in vacuo to obtain the desired compound.

$^1$H NMR (d-DMSO, 400 MHz) δ 9.21 (1H, dd, J=8.8, 1.46 Hz), 8.92 (1H, m), 7.71 (1H, dd, J=8.8, 4.0 Hz), 3.86 (3H, s), 3.81 (3H, s) ppm. FAB HRMS exact mass calculated for $C_{12}H_{10}N_2O_5$ 263.0663 (MH$^+$), found 263.0663.

Step 5: Preparation of methyl 7-({[4-fluoro-2-(methylthio)benzyl]amino}-carbonyl)-8-hydroxy-1, 6-naphthyridine-5-carboxylate A slurry of dimethyl 8-hydroxy-1,6-naphthyridine-5,7-dicarboxylate (0.25 g, 0.953 mmol), 1-[4-fluoro-2-(methylthio)phenyl]methanamine (0.326 g, 1.91 mmol) and N,N,N-diisopropylethylamine (170 uL, 0.953 mmol) in toluene (4.0 mL) were heated in a pressure tube at 110 degrees C. for 18 hrs. The reaction was incomplete by LCMS analysis and solids remained undissolved. DMF (1 mL) was added to solubilize the reagents and the reaction was again heated in a pressure tube at 110 degrees C. for 18 hrs. Upon cooling to room temperature, the resulting solution was transferred to a round bottom flask and reduced to a small volume. The residue was partitioned between methylene chloride and water. The organic layer was dried with Na2SO4, filtered and reduced in vacuo. The material was crystallized with a small amount of chloroform. The solid was filtered and dried in vacuo to afford the desired compound as a white solid.

$^1$H NMR (d-DMSO, 400 MHz) δ 9.55 (1H, bs), 9.18 (1H, d, J=4.0 Hz), 9.10 (1H, d, J=8.4 Hz), 7.90 (1H, m), 7.30 (1H, dd, J=8.4,7.2 Hz), 7.14 (1H, dd, J=10.4, 2.4 Hz), 6.97 (1H, m), 4.56 (2H, d, J=6.0 Hz), 3.90 (3H, s), 2.55 (3H, s) ppm. FAB HRMS exact mass calcd for $C_{19}H_{16}FN_3O_4S$ 402.0919 (MH$^+$), found 402.0916.

Step 6: Preparation of 7-({[4-fluoro-2-(methylthio) benzyl]amino}carbonyl)-8-hydroxy-1,6-naphthyridine-5-carboxylic acid To a solution of methyl 7-({[4-fluoro-2-(methylthio) benzyl]amino}carbonyl)-8-hydroxy-1,6-naphthyridine-5-carboxylate (0.180 g, 0.448 mmol) in 4 mL of dioxane: methanol (3:1) was added 1.34 mL of a stock solution of 1 N NaOH (1.34 mmol). The reaction was stirred for 3 hours at 80 degrees C. The reaction was determined to be complete by LCMS analysis. The solvent was removed in vacuo and the residue partitioned between 5% HCl and methylene chloride. The organics were reduced to give desired compound as a solid.

$^1$H NMR (d-DMSO, 400 MHz) δ 10.16 (1H, bs), 9.64 (1H, d, J=8.8 Hz), 9.21 (1H, d, J=4.0 Hz), 7.93 (1H, dd, J=8.4, 3.6 Hz), 7.37 (1H, dd, J=8.4, 6.0 Hz), 7.17 (1H, dd, J=10.0, 2.4 Hz), 7.01 (1H, m), 4.61 (2H, d, J=6.0 Hz), 2.55 (3H, m) ppm. FAB HRMS exact mass calcd for $C_{18}H_{14}FN_3O_4S$ 388.0762 (MH$^+$), found 388.0787.

Step 7: Preparation of N-7-[4-fluoro-2-(methylthio) benzyl]-8-hydroxy-N-5-,N-5-dimethyl-1,6-naphthyridine-5,7-dicarboxamide To a stirred solution of 7-({[4-fluoro-2-(methylthio) benzyl]amino}-carbonyl)-8-hydroxy-1,6-naphthyridine-5-carboxylic acid (0.174 g, 0.448 mmol) in DMF at 25 degrees C. was bubbled in gaseous dimethylamine for 5 minutes. To this was added BOP (0.238 g, 0.54 mmol). The reaction was stirred for 1 hour and was determined to be complete by LCMS analysis. The DMF was removed in vacuo and the residue was partitioned between methylene chloride and water. The organic phase was washed with brine, dried over $Na_2SO_4$, filtered and reduced to a small volume in vacuo. The residue was crystallized from methanol. The product was filtered and dried in vacuo to afford the desired compound.

$^1$H NMR (d-DMSO, 400 MHz) δ 9.14 (1H, bs), 8.35 (1H, m), 8.17 (1H, m), 7.78 (1H, m), 7.28 (1H, dd, J=8.0, 6.8 Hz), 7.13 (1H, dd, J=8.0, 2.0 Hz), 6.95 (1H, m), 4.51 (2H, d, J=6.4 Hz), 3.12 (3H, s), 2.89 (3H, s), 2.55 (3H, s) ppm. FAB HRMS exact mass calcd for $C_{20}H_{19}FN_4O_3S$ 415.1235 (MH$^+$), found 415.1210.

Step 8: Preparation of N-7-[4-fluoro-2-(methylsulfonyl)benzyl]-8-hydroxy-N-5-,N-5-dimethyl-1,6-naphthyridine-5,7-dicarboxamide To a solution of the N-7-[4-fluoro-2-(methylthio)benzyl]-8-hydroxy-N-5-,N-5-dimethyl-1,6-naphthyridine-5,7- dicarboxamide (0.150 g, 0.362 mmol) in methylene chloride (4 mL) under nitrogen was added 3-chloroperoxybenzoic acid (60% by weight, 0.187 g, 1.09 mmol) and the reaction was stirred 1 hour. The reaction was incomplete by LCMS analysis so an additional 30 mg of 3-chloroperoxybenzoic acid was added. The reaction was complete in 1 hour. To destroy residual oxidizing agent a drop of DMSO was added to the reaction and stirring was continued for 18 hours. The reaction solution was diluted with methylene chloride and extracted with a saturated solution of aqueous sodium bicarbonate (3 times). The organic was dried over $Na_2SO_4$, filtered and reduced to a small volume. Diethyl ether was used to triturate the product which crystallized. The crystals were filtered and dried in vacuo to afford the title compound.

$^1$H NMR (d-DMSO, 400 MHz) δ 13.5 (1H, bs), 9.80 (1H, bs), 9.18 (1H, bs), 8.38 (1H, d, J=8.4 Hz), 7.82 (1H, m), 7.74–7.66 (2H, m), 7.60 (1H, m), 4.93 (2H, d, J=6.4 Hz), 3.46 (3H, m), 3.13 (3H, m), 2.89 (3H, m) ppm. FAB HRMS exact mass calcd for $C_{20}H_{19}FN_4O_5S$ 447.1133 (MH$^+$), found 447.1138. C, H, N calculated for $C_{20}H_{19}FN_4O_5S$ 2.1H$_2$O, 0.2 Et2O % C, 50.05; % H, 5.09; % N, 11.23; found % C, 50.08; % H, 4.59; % N, 10.75.

EXAMPLE 186

Sodium 5-(1,1-dioxido-1,2-thiazinan-2-yl)-7-({[4-fluoro-2-(methylsulfonyl)benzyl]-amino}carbonyl)-1,6-naphthyridin-8-olate

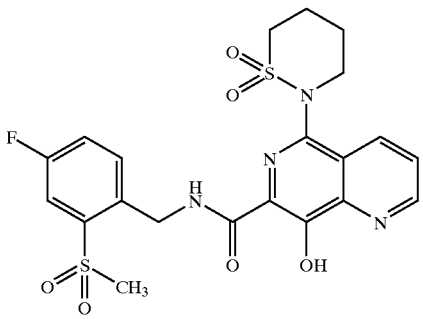

Step 1: Preparation of 4-fluoro-2-(methylthio) benzonitrile 2,4-difluorobenzonitrile (2.0 g, 14.38 mmol) and thiomethoxide (1.02 g, 14.38 mmol) were placed in an oven dried 100 mL round bottom flask fitted with a reflux condenser. Toluene (40 mL) was added and the reaction solution was put under an atmosphere of Argon. The reaction was heated to 90 deg C. over 48 hours. The crude reaction was cooled and concentrated in vacuo. The residue was taken up in methylene chloride and extracted with water. The organic phase was dried (MgSO4), filtered and concentrated to afford a white solid. The solid was dissolved in a minimal amount of methylene chloride and purified on an ISCO column (110 g silica) with a gradient of 100% hexanes to 80% hexanes/20% ethylacetate over 15 min, then 20% EtOAc/80% Hexanes for 5 min. The collected fractions were evaporated in vacuo to afford the desired material in a 7.5:1 ratio 4-fluoro-2-(methylthio)benzonitrile: 2-fluoro-4-(methylthio)benzonitrile. The white solid was carried on to the next step without further purification.

$^1$H NMR (CDCl$_3$, 400 MHz, major regioisomer) δ 7.56 (1H, dd, J=5.58, 8.51 Hz), 6.95 (1H, dd, J=2.38, 9.34 Hz), 6.88 (1H, dt, J=2.38, 8.24 Hz), 2.54 (3H, s) ppm. EI HRMS exact mass calcd for $C_8H_6FNS$ 167.0203, found 167.0205

Step 2: Preparation of 4-fluoro-2-(methylsulfonyl) benzonitrile 4-fluoro-2-(methylthio)benzonitrile (1.59 g, 9.51 mmol, 7.5:1 mixture of regioisomers from Step 1) was dissolved in methylene chloride (50 mL) and 3-chloroperoxybenzoic acid (60% by weight, 4.6 g, 16 mmol) was added. The reaction was put under an atmosphere of Argon and stirred overnight at ambient temperature. The reaction was quenched with saturated aqueous sodium bicarbonate (2×100 mL). The organic phase still contained some 3-chloroperoxybenzoic acid by LCMS analysis so 1 mL DMSO was added and stirred for 1 hour. The organic phase was then extracted again with saturated aqueous sodium bicarbonate (100 mL), dried (MgSO4), filtered and concentrated to afford the desired material as a 7:1 ratio of 4-fluoro-2-(methylsulfonyl)benzonitrile:2-fluoro-4-(methylsulfonyl)-benzonitrile. Selective crystallization from methanol, filtration and drying in vacuo afforded the desired 4-fluoro-2-(methylsulfonyl)benzonitrile as white crystals.

$^1$H NMR (CDCl$_3$, 400 MHz, major regioisomer) δ 7.93 (1H, dd, J=4.77, 8.51 Hz), 7.90 (1H, dd, J=2.36, 7.70 Hz), 7.45 (1H, ddd, J=2.56, 7.24, 8.47 Hz), 3.28 (3H, s) ppm. EI HRMS exact mass calcd for $C_8H_6FNSO_2$ 199.0103, found 199.0103

Step 3: Preparation of 1-[4-fluoro-2-(methylsulfonyl)phenyl]methanaminium chloride 4-fluoro-2-(methylsulfonyl)benzonitrile (5.6 g, 28.11 mmol) was added to a dry Parr bottle. Ethanol (50 mL) and conc HCl (10 mL) were added and the reaction solution put under an Argon atmosphere. 10% Pd/C (1 gram) was added and the reaction vessel placed on a Parr hydrogenation apparatus. The reaction was placed under an atmosphere of H2 (50 psi) and shaken overnight. After overnight the ratio of starting material to product was 50:50. The reaction was filtered through celite and concentrated slightly. Conc. HCl (10 mL) and 10% Pd/C (1 gram) were added and the reaction was again put under H2 (50 psi). The reaction was again shaken overnight. The crude reaction was filtered through celite and concentrated to afford the desired material as a white solid.

$^1$H NMR (CDCl$_3$, 400 MHz) δ 7.86 (1H, dd, J=2.74, 8.24 Hz), 7.74 (1H, dd, J=5.03, 8.51 Hz), 7.57 (1H, dt, J=2.75, 8.15 Hz), 4.45 (2H, s), 3.27 (3H, s) ppm. MS calcd for $C_8H_{10}FNO_2S$ 203 (MH$^+$), found 204. EI HRMS exact mass calcd for $C_8H_{10}FNO_2S$ 203.0410, found 203.0416 C, H, N calcd for $C_8H_{10}FNO_2S$ 1.1 HCl % C, 39.49; % H, 4.6; % N, 5.76; found % C, 39.50; % H, 4.34; % N, 5.56

Step 4: Preparation of methyl 5-bromo-8-{[(4-methylphenyl)sulfonyl]oxy}-1,6-naphthyridine-7-carboxylate To a slurry of methyl 5-bromo-8-hydroxy-1,6-naphthyridine-7-carboxylate (5.0 g, 17.66 mmol, prepared as in Example 113) in chloroform (20 mL) under nitrogen was added N,N,N-diisopropylethylamine (3.72 mL, 26.49 mmol). 4-Methylbenzenesulfonyl chloride (4.04 g, 21.20 mmol) was added over 5 minutes and the reaction was heated to 40 degrees C. and stirred one hour. The completed reaction was cooled to 25 degrees C. and 1:1 methanol:water was added to precipitate the product which was filtered, washed with more 1:1 methanol:water and dried in vacuo. This afforded the desired product as a solid.

$^1$H NMR (d-DMSO, 400 MHz) δ 9.03 (1H, dd, J=4.4, 1 Hz), 8.64 (1H, dd, J=8.8, 1.0 Hz), 7.92 (1H, dd, J=8.8, 4.4

Hz), 7.70 (2H, d, J=8.0), 7.40 (2H, d, J=8.0 Hz), 3.76 (3H, m), 2.42 (3H, m) ppm. FAB HRMS exact mass calcd for $C_{17}H_{13}BrN_2O_5S$ 436.9802 (MH$^+$), found 436.9807

Step 5: Preparation of methyl 5-(1,1-dioxido-1,2-thiazinan-2-yl)-8-{[(4-methylphenyl)sulfonyl]oxy}-1,6-naphthyridine-7-carboxylate To a slurry of methyl 5-bromo-8-{[(4-methylphenyl)sulfonyl]oxy}-1,6-naphthyridine-7-carboxylate (7.55 g, 17.27 mmol) in degassed DMF (20 mL) in a pressure tube was added 1,2-thiazinane-1,1-dioxide (2.8 g, 20.7 mmol, prepared as in White et al, *J. Org Chem.* 1987, 52: 2162) followed by 2,2'-bipyridine (3.24 g, 20.7 mmol) and copper (I) oxide powder (2.96 g, 20.7 mmol). The pressure tube was closed and heated to 118 degrees C. overnight. Celite (0.5 g) was added to the resulting slurry and this was filtered through a plug of DMF wetted celite. The solids were washed with more DMF (10 mL) and the filtrate transferred to a large Erlenmeyer flask (1L) fitted with a 2 inch stirring bar. The volume was brought up to 200 mL with chloroform and a solution of ethylenediaminetetraacetic acid monohydrate (13.3 g, 35.7 mmol) in 140 mL of water was added. The biphasic mixture was vigorously stirred, open to the air, for 3 hours. The organic phase was separated and retreated with another solution of ethylenediaminetetraacetic acid monohydrate (13.3 g, 35.7 mmol) in 140 mL of water overnight (16 hrs). The organic was separated and washed with water and dried over $Na_2SO_4$, filtered, and reduced to a small volume in vacuo. The product solidified during solvent reduction. The solid was broken up and dried to afford the desired product.

LCMS calcd for $C_{21}H_{21}N_3O_7S_2$ 492.082 (MH$^+$), found 492.51

Step 6: Preparation of methyl 5-(1,1-dioxido-1,2-thiazinan-2-yl)-8-hydroxy-1,6-naphthyridine-7-carboxylate To a solution of methyl 5-(1,1-dioxido-1,2-thiazinan-2-yl)-8-{[(4-methylphenyl)sulfonyl]oxy}-1,6-naphthyridine-7-carboxylate (6.0 g, 12.2 mmol) in DMF (50 mL) under nitrogen at zero degrees C. was added sodium methoxide (49.40 mL, 24.70 mmol, 0.5 M in Methanol). The cold solution was allowed to stir for one hour. Acetic acid (1.64 mL, 27.4 mmol) was added followed by water to precipitate the product. The mixture was allowed to stand for one hour. The crude reaction was filtered and the solids were washed with 1:1 methanol:water and dried in vacuo to afford the desired product.

$^1$H NMR (d-DMSO, 400 MHz) δ 9.20 (1H, d, J=4.0 Hz), 8.61 (1H, d, J=8.4 Hz), 7.91 (1H, dd, J=8.4, 4.0 Hz), 3.96 (3H, m), 3.87 (1H, bs), 3.79 (1H, bs), 3.32 (2H, m), 2.27 (3H, m), 1.66 (1H, m) ppm. FAB HRMS exact mass calcd for $C_{14}H_{15}N_3O_5S$ 338.0805 (MH$^+$), found 338.0793 C, H, N calculated for $C_{14}H_{15}N_3O_5S$ -0.40$H_2O$ % C, 48.80; % H, 4.62; % N, 12.20; found % C, 48.79; % H, 4.35; % N, 12.15.

Step 7: Preparation of 5-(1,1-dioxido-1,2-thiazinan-2-yl)-N-[4-fluoro-2-(methylsulfonyl)benzyl]-8-hydroxy-1,6-naphthyridine-7-carboxamide To a slurry of methyl 5-(1,1-dioxido-1,2-thiazinan-2-yl)-8-hydroxy-1,6-naphthyridine-7-carboxylate (2.11 g, 6.26 mmol) in ethanol (30 mL) in a pressure flask was added 1-[4-fluoro-2-(methylsulfonyl)phenyl]methanaminium chloride followed by N,N,N-diisopropylethylamine (2.17 mL, 12.52 mmol). The pressure flask was purged with nitrogen and closed. The reaction was heated to 80 degrees C. for 16 hours. The reaction containing residual solids was cooled and determined to be incomplete by LCMS analysis. Added degassed DMF (10 mL) to solubilize the remaining solids, resealed the pressure tube and reheated to 80 degrees C. overnight. The reaction was cooled, transferred to a round bottom flask and reduced to a small volume in vacuo. The residue was partitioned between methylene chloride and saturated aqueous sodium bicarbonate. The organic layer was washed with water, dried over Na2SO4, filtered and reduced to a small volume in vacuo. The residue was crystallized via the addition of 5 mL of methanol. The crystals were filtered and dried in vacuo to afford the title compound.

$^1$H NMR (d-DMSO, 400 MHz) δ 13.41 (1H, s), 9.19 (2H, d, J=4.0 Hz), 8.60 (1H, d, J=8.4 Hz), 7.89 (1H, dd, J=8.4,4.0 Hz), 7.79–7.71 (2H, m), 7.64 (1H, dd, J=8.4, 2.4 Hz), 4.98 (2H, d, J=3.6 Hz), 3.84 (2H, m), 3.48 (5H, m), 2.29 (3H, m), 1.69 (1H, bs) ppm. APCI HRMS exact mass calcd for $C_{21}H_{21}FN_4O_6S_2$ 509.0960 (MH$^+$), found 509.0936 C, H, N calculated for $C_{21}H_{21}FN_4O_6S_2$ 0.15$H_2O$ % C, 49.33; % H, 4.20; % N, 10.96; found % C, 49.37; % H, 4.08; % N, 10.85.

Step 8: Preparation of sodium 5-(1,1-dioxido-1,2-thiazinan-2-yl)-7-({[4-fluoro-2-(methylsulfonyl)benzyl]amino}carbonyl)-1,6-naphthyridin-8-olate To a slurry of the free base (0.25 g, 0.5 mmol) from step 7 in acetone (10 mL) was added methanol (2 mL) and 1 N aqueous NaOH (0.49 mL, 0.49 mmol). The yellow solution was reduced to a small volume and the residue was crystallized from methanol. The crystals were filtered and dried in vacuo to afford the sodium salt form of the title compound.

$^1$H NMR (d-DMSO, 400 MHz) δ 12.41 (1H, m), 8.79 (1H, dd, J=4.0, 1.6 Hz), 8.26 (1H, dd, J=8.4, 1.6 Hz), 7.71–7.57 (3H, m), 7.54 (1H, dd, J=8.4, 4.0 Hz), 4.90 (2H, d, J=6.0 Hz), 3.88–3.77 (2H, m), 3.48 (4H, m), 3.20 (1H, m), 2.50 (1H, m), 2.22 (2H, m), 1.49 (1H, m) ppm. APCI HRMS exact mass calcd for $C_{21}H_{20}FN_4O_6S_2$ 531.0779 (M+Na), found 531.0811 C, H, N calculated for $C_{21}H_{20}FN_4NaO_6S_2$ 0.85$H_2O$ % C, 46.21; % H, 4.01; % N, 10.27; found % C, 46.19; % H, 3.68; % N, 10.02.

EXAMPLE 187

Sodium 5-(1,1-dioxido-1,2-thiazinan-2-yl)-7-({[2-(methylsulfonyl)benzyl]-amino}carbonyl)-1,6-naphthyridin-8-olate

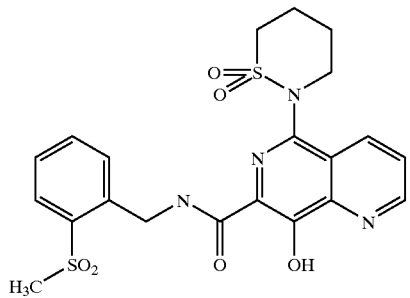

Step 1: Preparation of 2-(methylsulfonyl)benzonitrile 2-(methylthio)benzonitrile (17.6 grams, 112 mmol) was dissolved in $CH_2Cl_2$ (100 mL) and cooled to 0 deg C. A solution of mCPBA (51 g, 250 mmol) in $CH_2Cl_2$ (470 mL)

was added and the solution allowed to warm to room temperature. The reaction was stirred overnight. Added more mCPBA (18 grams, 88 mmol) and the reaction went to completion over 2 hours. The reaction solution was quenched with aqueous saturated NaHCO$_3$ and then washed with H$_2$O and brine. The organic phase was dried (MgSO$_4$), filtered and concentrated in vacuo to afford a white solid. The solid was dissolved in ethanol (100 mL) and cooled in the refrigerator overnight. The white crystals that formed were collected by filtration to afford the desired material.

$^1$H NMR (CDCl$_3$, 400 MHz) δ 8.20 (1H, dd, J=1.20, 7.78 Hz), 7.91 (1H, dd, J=1.38, 7.42 Hz), 7.82 (1H, ddd, J=1.56, 7.78, 14.64 Hz), 7.78 (1H, ddd, J=1.46, 6.14, 13.56 Hz), 3.27 (3H, s) ppm. MS calcd for C$_8$H$_7$NO$_2$S 181 (M), found 182 (MH$^+$).

Step 2: Preparation of 1-[2-(methylsulfonyl)phenyl]methanamine

Raney Ni (1.5 grams) was washed with methanol and placed in a Parr flask with methanol saturated with NH$_3$ (50 mL). 2-(Methylsulfonyl)benzonitrile (3.0 grams, 16.6 mmol) was added to the Parr flask and the reaction mixture was put under an atmosphere of H2 (45 psi). The reaction vessel was shaken on a Parr apparatus overnight, depressurized and the filtered through a pad of celite. The solvent was removed in vacuo to afford the desired product.

$^1$H NMR (CDCl$_3$, 400 MHz) δ 8.05 (1H, bs), 7.63 (1H, bs), 7.43 (1H, bs), 7.31 (1H, bs), 4.2 (2H, bs), 3.16 (3H, s) ppm. MS calcd for C$_8$H$_{11}$NO$_2$S 185 (M), found 186 (MH$^+$).

Step 3: Preparation of 5-bromo-8-hydroxy-N-[2-(methylsulfonyl)benzyl]-1,6-naphthyridine-7-carboxamide Methyl 5-bromo-8-hydroxy-1,6-naphthyridine-7-carboxylate (500 mg, 1.77 mmol, prepared as in Example 113) and 1-[2-(methylsulfonyl)phenyl]methanamine (491 mg, 2.65 mmol) were suspended in 10 mL methanol in an oven-dried Schlenck tube. The solution was purged with Argon for 1 minute and capped. The solution was heated to 80 deg C. with stirring over 4 days. Upon cooling a white solid precipitated out of the methanol. LCMS analysis indicated that the precipitate was the desired product. Filtration and subsequent washing with methanol (10 mL) afforded the desired material as a white solid.

$^1$H NMR (CDCl$_3$, 400 MHz) δ 9.16 (1H, dd, J=1.64, 5.21 Hz), 8.71 (1H, m), 8.53 (dd, 1H, J=1.64, 8.43 Hz), 8.06 (1H, dd, J=1.28, 7.88 Hz), 7.70 (2H, m), 7.64 (1H, dt, J=1.28, 7.69 Hz), 7.51 (1H, dt, J=1.28, 8.0 Hz), 5.03 (2H, d, J=5.35 Hz), 4.20 (1H, bs), 3.22 (3H, s) ppm. MS calcd for C$_{17}$H$_{14}$BrN$_3$O$_4$S 436 (M), found 437 (MH$^+$). APCI HRMS exact mass calcd for C$_{17}$H$_{14}$BrN$_3$O$_4$S 435.9961 (MH$^+$), found 435.9948 (MH$^+$).

Step 4: Preparation of 5-bromo-7-({[2-(methylsulfonyl)benzyl]amino}carbonyl)-1,6-naphthyridine-8-yl-4-methylbenzenesulfonate 5-bromo-8-hydroxy-N-[2-(methylsulfonyl)benzyl]-1,6-naphthyridine-7-carboxamide (700 mg, 1.60 mmol.), p-toluenesulfonylchloride (367 mg, 1.92 mmol) and triethylamine (335 uL, 2.41 mmol) were dissolved in CH2Cl2 (20 mL) and warmed to 40 deg C. with stirring. After overnight most of the starting material was consumed and product was present. The crude reaction was diluted with saturated aqueous NaHCO3 (20 mL) and the aqueous back extracted with CH$_2$Cl$_2$ (2×20 mL). The organic phase was dried with MgSO$_4$, filtered and concentrated in vacuo. The crude white solid was carried on to the next step without further purification. MS calcd for C$_{24}$H$_{20}$BrN$_3$O$_6$S$_2$ 589 (M), found 590 (MH$^+$). APCI HRMS exact mass calcd for C$_{24}$H$_{20}$BrN$_3$O$_6$S$_2$ 590.0050 (MH$^+$), found 590.0048 (MH$^+$).

Step 5: Preparation of 5-(1,1-dioxido-1,2-thiazinan-2-yl)-7-({[2-(methylsulfonyl)-benzyl]amino}carbonyl)-1,6-naphthyridine-8-yl-4-methylbenzenesulfonate Into an oven dried Schlenck tube was placed 5-bromo-7-({[2-(methylsulfonyl)benzyl]amino}carbonyl)-1,6-naphthyridine-8-yl-4-methylbenzenesulfonate (200 mg, 0.35 mmol), 2,2'-dipyridyl (65 mg, 0.42 mmol), copper(I) oxide (59.6 mg, 0.42 mmol) and 1,2-thiazinane 1,1-dioxide (56 mg, 0.42 mmol, prepared as in Example 152). DMF (1.0 mL) was added and the suspension degassed with Argon for 1 minute. The tube was sealed and heated to 120 deg C. for 2 hours. LCMS analysis of the crude reaction after 2 hours showed starting material consumed and desired product the major component of the reaction mixture. The crude reaction was diluted with 10 mL chloroform and 15 mL 10% EDTA disodium salt. The reaction mixture was stirred vigorously overnight and the layers separated. The organic phase was washed once with 10% EDTA solution and the aqueous phase back extracted with 20 mL chloroform. The organic phase was dried (MgSO4), filtered and concentrated in vacuo to afford a yellowish solid. The crude solid was taken forward to the next step without further purification.

MS calcd for C$_{28}$H$_{28}$N$_4$O$_8$S$_3$ 644 (M), found 645 (MH$^+$).

Step 6: Preparation of 5-(1,1-dioxido-1,2-thiazinan-2-yl)-8-hydroxy-N-[2-(methylsulfonyl)-benzyl]-1,6-naphthyridine-7-carboxamide 5-(1,1-dioxido-1,2-thiazinan-2-yl)-7-({[2-(methylsulfonyl)benzyl]amino}carbonyl)-1,6-naphthyridin-8-yl-4-methylbenzenesulfonate (220 mg, 0.34 mmol) was dissolved in methanol (10 mL) and NaOMe (55 mg, 1.02 mmol) was added. The reaction was stirred overnight at room temperature. The crude reaction was diluted with water (10 mL) and extracted with CH$_2$Cl$_2$ (2×10 mL). The organic phase was dried (MgSO$_4$), filtered and concentrated in vacuo to afford a yellow oily solid. The material was suspended in methanol and a yellow precipitate fell out of solution. Washing with fresh methanol (2×10 mL) gave the desired product as an off-white solid.

$^1$H NMR (CDCl$_3$, 400 MHz) δ 13.3 (1H, s), 9.13 (1H, dd, J=1.65, 4.21 Hz), 8.83 (1H, t, J=6.78 Hz), 8.62 (1H, dd, J=1.65, 8.43 Hz), 8.02 (1H, dd, J=0.92, 7.88 Hz), 7.78 (d, 1H, J=7.51 Hz), 7.67, (1H, dt, J=1.28, 6.86 Hz), 7.64 (1H, dd, J=4.22, 8.43 Hz), 7.54 (1H, dt, J=1.28, 7.69 Hz), 4.91 (2H, d, J=6.78 Hz), 4.12 (1H, t, J=12.2 Hz), 3.56 (1H, t, J=12.2 Hz), 3.25 (1H, m), 3.16 (3H, s), 2.46 (4H, m), 1.66 (1H, m) ppm. MS calcd for C$_{21}$H$_{22}$N$_4$O$_6$S$_2$ 490 (M), found 491 (MH$^+$). APCI HRMS exact mass calcd for C$_{21}$H$_{22}$N$_4$O$_6$S$_2$ 491.1034 (MH$^+$), found 491.1054 (MH$^+$). C, H, N calculated for C$_{21}$H$_{22}$N$_4$O$_6$S$_2$ 0.55 MeOH % C, 50.93; % H, 4.48; % N, 11.02; found % C, 50.93; % H, 4.80; % N 11.03.

Step 7: Preparation of sodium 5-(1,1-dioxido-1,2-thiazinan-2-yl)-7-({[2-(methylsulfonyl)benzyl]amino}carbonyl)-1,6-naphthyridin-8-olate 5-(1,1-dioxido-1,2-thiazinan-2-yl)-8-hydroxy-N-[2-(methylsulfonyl)benzyl]-1,6-naphthyridine-7-carboxamide (53 mg, 0.108 mmol) was suspended in a 1:1 mixture of ethanol and acetone (1 mL each). NaOH (130 uL, 1 M) was added and the starting material dissolved. After 1 hour the sodium salt precipitated. The sample was concentrated in vacuo to afford the desired material as a yellow solid.

$^1$H NMR (CD$_3$OD, 400 MHz) δ 8.80 (1H, bs), 8.45 (1H, d, J=8.06 Hz), 8.00 (1H, d, J=7.87 Hz), 7.79 (1H, d, J=8.06 Hz), 7.64 (1H, t, J=7.60 Hz), 7.56 (1H, dd, J=4.03, 8.24 Hz), 7.48 (1H, t, J=7.60 Hz) 5.10 (2H, s), 3.98–3.83 (2H, m), 3.63 (1H, m), 3.30 (3H, s), 3.14–3.10 (1H, m), 2.70–2.60 (1H, m), 2.40–2.33 (2H, m), 1.60–1.57 (1H, m) ppm. ESI HRMS exact mass calcd for C$_{21}$H$_{22}$N$_4$O$_6$S$_2$ 513.0873 (M+Na), found 513.0909 (M+Na). C, H, N calcd for C$_{21}$H$_{21}$N$_4$O$_6$S$_2$.1.75 Na, 0.8H$_2$O, % C, 46.35; % H, 4.19; % N, 10.3; found % C, 46.79; % H, 4.20; % N, 9.70.

EXAMPLE 188

Sodium 7-[({2-[(dimethylamino)sulfonyl]-4-fluorobenzyl}amino) carbonyl]-5-(1,1-dioxido-1,2-thiazinan-2-yl)-1,6-naphthyridin-8-olate

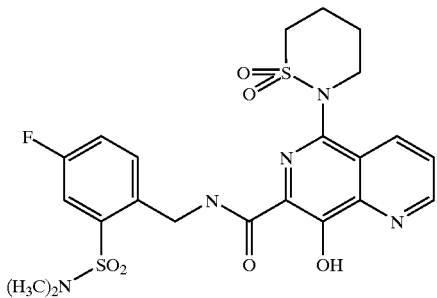

Step 1: Preparation of 5-fluoro-N,N,2-trimethylbenzenesulfonamide

A solution of 5-fluoro-2-methyl-benzenesulphonyl chloride (5.0 g, 24.0 mmol, Lancaster cat # 12627) dissolved in THF (100 mL) was saturated with dimethylamine gas and left to stir at room temperature for one hour. The ammonium chloride salts were then removed by vacuum filtration and the filtrate was concentrated to a yellow oil. The oil was dissolved in a minimal amount of ethyl acetate and purified on an Isco column (110 g silica) running a 10 to 25% EtOAc/Hexane gradient over 40 minutes. The collected fractions were concentrated in vacuo to afford the desired material as a yellow oil.

$^1$H NMR (CDCl$_3$, 400 MHz) δ 7.60 (1H, dd, J=2.75, 8.61 Hz), 7.29 (1H, dd, J=2.93, 8.43 Hz), 7.16 (1H, ddd, J=2.75, 8.14, 8,14 Hz), 2.93 (6H, s), and 2.59 (3H, s) ppm. MS calc'd for C$_9$H$_{12}$FNO$_2$S 217 (M), found 218 (MH$^+$).

Step 2: Preparation of 2-(bromomethyl)-5-fluoro-N,N-dimethylbenzenesulfonamide

A mixture of 5-fluoro-N,N,2-trimethylbenzenesulfonamide (5.20 g, 24.0 mmol) and N-bromosuccinimide (4.69 g, 26.4 mmol) in dry CCl4 (100 mL) was refluxed overnight under nitrogen. Cooled the reaction and filtered off the succinimide salts by vacuum filtration, washing with CCl4. The concentrated filtrate was dissolved in a minimal amount of ethyl acetate and purified on an Isco column (110 g silica) running a 0 to 20% EtOAc/Hexane gradient over 40 minutes. The collected fractions were concentrated in vacuo to afford the desired material as a yellow oil in a ratio of 3.5:1 with the starting material.

$^1$H NMR (CDCl3, 400 MHz) δ 7.64 (2H, m), 7.31 (1H, m), 4.87 (2H, s), and 2.88 (6H, s).

Step 3: Preparation of 2-(azidomethyl)-5-fluoro-N,N-dimethylbenzenesulfonamide

Sodium azide (2.36 g, 36.3 mmol) was added to 2-(bromomethyl)-5-fluoro-N,N-dimethylbenzenesulfonamide (4.30 g, 14.5 mmol) dissolved in DMF (100 mL). The reaction was stirred for one hour at room temperature under nitrogen. The excess sodium azide was filtered off by vacuum filtration and the filtrate was concentrated to a brown oil. The crude material was purified on an Isco column (110 g silica) running a 0 to 20% EtOAc/Hexane gradient over 40 minutes. The collected fractions were concentrated in vacuo to afford the desired material as a yellow oil in a ratio of 3.5:1 with 2-(bromomethyl)-5-fluoro-N,N-dimethylbenzenesulfonamide.

$^1$H NMR (CDCl$_3$, 400 MHz) δ 7.61 (2H, m), 7.32 (1H, m), 4.79 (1H, s), and 2.85 (6H, s).

Step 4: Preparation of 2-(aminomethyl)-5-fluoro-N,N-dimethylbenzenesulfonamide

A mixture of 2-(azidomethyl)-5-fluoro-N,N-dimethylbenzenesulfonamide (3.57 g, 13.8 mmol) and 5% palladium on carbon (0.89 g, 25% w/w) in absolute ethanol (100 mL) was stirred under a balloon of hydrogen gas for one hour. The reaction was filtered through a small pack of celite and the filtrate was concentrated in vacuo to a yellow oil. The crude material was purified by preparative HPLC. (Gilson semi preparative HPLC system using a Waters Delta pak column (3(10×40 mm I.D.)cartridges, C18, 15 µm pore size) eluting with 5–95% acetonitrile/water (0.1% TFA) at 30 ml/min) to afford the desired product as a white solid.

$^1$H NMR (DMSO, 400 MHz) δ 8.24 (2H, bs), 7.75 (2H, m), 7.67 (1H, dd, J=2.48, 8.61 Hz), 4.34 (2H, s) and 2.78 (6H, s).

Step 5: Preparation of 5-bromo-N-{2-[(dimethylamino)sulfonyl]-4-fluorobenzyl}-8-hydroxy-1,6-naphthyridine-7-carboxamide A mixture of 5-bromo-8-hydroxy-1,6-naphthyridine-7-carboxylic acid methyl ester (1.00 g, 3.53 mmol, see Example 113), 2-(aminomethyl)-5-fluoro-N,N-dimethylbenzenesulfonamide (1.64 g, 7.07 mmol), and triethylamine (0.99 mL, 7.07 mmol) in EtOH (8 mL) and DMF (2 mL) was heated to 78° C. overnight. The mixture was cooled to 40° C. and glacial acetic acid (0.81 mL, 14.1 mmol) was added. The mixture was allowed to cool to room temperature and water was added dropwise while sonicating to facilitate the product precipitating out of solution. The solids were collected by vacuum filtration to afford the desired product as a light yellow solid.

$^1$H NMR (DMSO, 400 MHz) δ 13.5 (1H, bs), 9.62 (1H, bs), 9.24 (1H, d, J=3.84 Hz), 8.60 (1H, d, J=8.42 Hz), 7.97 (1H, dd, J=4.21, 8.42 Hz), 7.58 (3H, m), 4.90 (2H, d, J=5.86 Hz) and 2.85 (6H, s).

Step 6: Preparation of 5-bromo-7-[({2-[(dimethylamino)sulfonyl]-4-fluorobenzyl}amino) carbonyl]-1,6-naphthyridin-8-yl 4-methylbenzenesulfonate Triethylamine (0.65 mL, 4.66 mmol) was added slowly to a suspension of 5-bromo-N-{2-[(dimethylamino)sulfonyl]-4-fluorobenzyl}-8-hydroxy-1,6-naphthyridine-7- carboxamide (1.50 g, 3.10 mmol) in chloroform (15 mL) to give a yellow cloudy solution. p-Toluenesulfonyl chloride (0.71 g, 3.73 mmol) was then added slowly and the mixture was aged at 40° C. for five hours. The mixture was quenched with 10% KHSO$_4$ solution and the layers were separated. The aqueous layer was extracted twice more with CHCl$_3$. The combined organic extracts were washed once with brine, dried over Na$_2$SO$_4$, filtered, and concentrated in vacuo to a crude yellow oil. The oil was dissolved in a minimal amount of CHCl$_3$ and purified on an Isco column (110 g silica) running a 0 to 2.5% MeOH/CHCl$_3$ gradient over 30 minutes. The collected fractions were concentrated in vacuo to afford the desired material as a white solid foam.

$^1$H NMR (CDCl$_3$, 400 MHz) δ 8.94 (1H, dd, J=1.65, 4.20 Hz), 8.55 (1H, dd, J=1.46, 8.61 Hz), 8.39 (1H, t, J=6.32 Hz), 7.89 (2H, d, J=8.24 Hz), 7.78 (1H, dd, J=5.31, 8.61 Hz), 7.66 (1H, dd, J=4.21, 8.43 Hz), 7.61 (1H, dd, J=2.65, 8.52 Hz), 7.32 (2H, d, J=8.43 Hz), 7.25 (1H, m), 4.91 (2H, d, J=6.59 Hz), 2.93 (6H, s) and 2.48 (3H, s).

Step 7: Preparation of 7-[({2-[(dimethylamino) sulfonyl]-4-fluorobenzyl}amino)carbonyl]-5-(1,1-dioxido-1,2-thiazinan-2-yl)-1,6-naphthyridin-8-yl 4-methylbenzenesulfonate In a similar manner to 5-(1,1-dioxido-1,2-thiazinan-2-yl)-7-({[4-fluoro-2-(methylsulfonyl)benzyl]amino}carbonyl)-1,6-naphthyridin-8-yl 4-methylbenzenesulfonate (Example 187), the title compound was prepared and the crude solid was taken forward to the next step without further purification.

MS calcd for C$_{29}$H$_{30}$FN$_5$O$_8$S$_3$ 691 (M), found 692 (MH+).

Step 8: Preparation of N-{2-[(dimethylamino) sulfonyl]-4-fluorobenzyl}-5-(1,1-dioxido-1,2-thiazinan-2-yl)-8-hydroxy-1,6-naphthyridine-7-carboxamide Dissolved 7-[({2-[(dimethylamino)sulfonyl]-4-fluorobenzyl}amino)carbonyl]-5-(1,1-dioxido-1,2-thiazinan-2-yl)-1,6-naphthyridin-8-yl 4-methylbenzenesulfonate (271 mg, 0.39 mmol) in DMF (0.5 mL) and added to a solution of sodium methoxide (53 mg, 0.98 mmol) in methanol (3.0 mL). The reaction was stirred at 50° C. for one hour, cooled, and glacial acetic acid (56 μL, 0.78 mmol) was added. The reaction was stripped down three times from methanol. Ethanol was added while sonicating the flask to crash out the product. Collected the solids by vacuum filtration to afford the desired compound as a yellowish solid.

MS calcd for C$_{22}$H$_{24}$FN$_5$O$_6$S$_2$ 537 (M), found 538 (MH+). APCI HRMS exact mass calcd for C$_{22}$H$_{24}$FN$_5$O$_6$S$_2$ 538.1225(MH+), found 538.1195 (MH+). $^1$H NMR (DMSO, 400 MHz) δ 13.5 (1H, bs), 9.19 (1H, d, J=4.21 Hz), 9.14 (1H, m), 8.61(1H, d, J=8.43 Hz), 7.90 (1H, dd, J=4.22, 8.52 Hz), 7.69–7.56 (3H, m), 4.92 (2H, m), 3.85 (2H, bs), 3.51 (2H, bs), 2.87 (6H, s), 2.28 (3H, m), and 1.68 (1H, bs).

Step 9: Preparation of sodium 7-[({2-[(dimethylamino)sulfonyl]-4-fluorobenzyl}amino) carbonyl]-5-(1,1-dioxido-1,2-thiazinan-2-yl)-1,6-naphthyridin-8-olate To a suspension of N-{2-[(dimethylamino)sulfonyl]-4-fluorobenzyl}-5-(1,1-dioxido-1,2-thiazinan-2-yl)-8-hydroxy-1,6-naphthyridine-7-carboxamide (147 mg, 0.27 mmol) in acetonitrile (1 mL) was added 1N sodium hydroxide (287 μL, 0.29 mmol). After the solution became homogeneous, the sample was concentrated in vacuo to afford the title compound as a yellow solid.

$^1$H NMR (DMSO, 400 MHz) δ 12.2 (1H, t, J=5.86 Hz), 8.79 (1H, d, J=4.03 Hz), 8.30 (1H, d, J=8.43 Hz), 7.70 (1H, dd, J=5.68, 8.42 Hz), 7.61–7.526 (3H, m), 4.87 (2H, m), 3.87–3.78 (2H, m), 3.51 (1H, m), 3.31–3.17 (2H, m), 2.84 (6H, s), 2.24 (2H, bs), and 1.52 (1H, m). Anal. calcd for C$_{22}$H$_{23}$FN$_5$NaO$_6$S$_2$·1.35 H$_2$O: C, 45.26; H, 4.44; N, 11.99. Found: C, 45.25; H, 4.09; N, 11.84.

EXAMPLE 189

N-(4-fluorobenzyl)-8-hydroxy-5-(1-methyl-5-oxopyrrolidin-3-yl)-1,6-naphthyridine-7-carboxamide

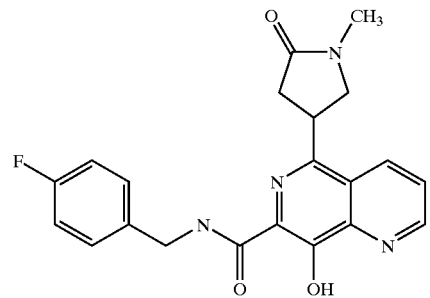

Step 1: Preparation of N-(4-fluorobenzyl)-8-hydroxy-1,6-naphthyridine-7-carboxamide Methyl 8-hydroxy-1,6-naphthyridine-7-carboxylate (10.0 grams, 48.9 mmol) prepared as described in Example 1 was dissolved/suspended in MeOH (100 mL) and treated with 4-fluorobenzylamine (6.1 g, 48.9 mmol). The reaction was brought to reflux and the MeOH allowed to evaporate until the total volume was approximately 30 mL. The reaction was refluxed for 5 hours more and a white solid precipitated. The reaction was cooled and the solid collected by filtration, washed with a minimum of MeOH and dried on the pump to give the product as a white solid.

$^1$H NMR (d-DMSO, 400 MHz) δ 13.7 (s, 1H), 9.88 (1H, t, J=5.7 Hz), 9.17(1H, d, J=3.5 Hz), 8.92 (1H, s), 8.61 (1H, d, J=8.2 Hz), 7.83 (1H, dd, J=4.2, 8.2 Hz), 7.43 (2H, m), 7.16 (2H, m), 4.55 (2H, d, J=6.4 Hz). ESI HRMS exact mass calcd for C$_{16}$H$_{12}$N$_3$O$_2$F 298.0987 (MH$^+$), found 298.1029 (MH$^+$).

Step 2: Preparation of N-(4-fluorobenzyl)-8-hydroxy-5-iodo-1,6-naphthyridine-7-carboxamide To a solution of N-(4-fluorobenzyl)-8-hydroxy-1,6-naphthyridine-7-carboxamide (7.0 g, 23.6 mmol) in chloroform (125 ml) and DMF (10 ml) was added N-Iodosuccinimide (10.6 g, 47.1 mmol) and this was stirred under nitrogen for 0.5 hours. The chloroform was then removed under reduced pressure leaving just the DMF solution. Water was then added which caused oily solids to crash out of the solution. The flask containing the product was then placed in a sonicator and the resulting beige solids were collected by vacuum filtration.

$^1$H NMR (d-DMSO, 400 MHz) δ 13.67 (1H, s), 9.67 (1H, bs), 9.15 (1H, d, J=4.2 Hz), 8.40 (1H, d, J=8.6 Hz), 7.91 (1H, dd, J=4.2, 8.5 Hz), 7.44 (2H, dd, J=5.6, 8.4 Hz), 7.17 (2H, m), 4.55 (2H, d, J=6.4 Hz). C, H, N calcd for $C_{16}H_{11}N_3O_2FI\cdot 0.5\ H_2O$, % C, 44.47; % H, 2.80; % N, 9.72; found % C, 44.38; % H, 2.62; % N, 9.60.

Step 3: Preparation of N-(4-fluorobenzyl)-8-hydroxy-5-(5-oxo-2,5-dihydrofuran-3-yl)-1,6-naphthyridine-7-carboxamide The iodide from step 2 (4.37 g, 10.32 mmol) was dissolved in anhydrous toluene (40 ml) in an oven dried flask that was purged with nitrogen. Dichlorobis (triphenylphospine)palladium (II) (660 mgs., 0.94 mmol) and 4-(tributylstannyl)furan-2(5H)-one, (3.85 g, 10.32 mmol) (prepared as described by Gregory J. Hollingworth, Gemma Perkins, and Joseph Sweeney, *J. Chem. Soc., Perkins 1.* 1996, 1913) were then added to the reaction. After four hours at reflux the reaction was cooled and the solids that precipitated from the solution were collected by vacuum filtration. The product contained 17% of an impurity: N,N'-bis(4-fluorobenzyl)-8,8'-dihydroxy-5,5'-bi-1,6-naphthyridine-7,7'-dicarboxamide.

Major component of sample:

$^1$H NMR (DMSO, 400 MHz) δ 9.77 (1H, t, J=6.4 Hz), 9.23 (1H, d, J=3.4 Hz), 8.92 (1H, d, J=8.0 Hz), 7.91–7.88 (1H, dd, J=8.6 and 4.2 Hz), 7.46–7.42 (2H, dd, J=8.6 and 5.6 Hz), 7.18 (2H, t, J=8.9 Hz), 6.99 (1H, s), 5.69 (2H, s), 4.60 (2H, d, J=6.4 Hz) ppm. ES HRMS exact mass calcd. for $C_{20}H_{14}N_3O_4F$ 380.1041 (MH$^+$), found 380.1050.

Step 4: Preparation of N-(4-fluorobenzyl)-8-hydroxy-5-[1-methyl-2-(methylamino)-5-oxopyrrolidin-3-yl]-1,6-naphthyridine-7-carboxamide (TFA salt)

The butenolide from step 3 (1.0 g, 2.64 mmol) was placed into a glass pressure vessel which contained a saturated solution of methylamine in MeOH (13 ml). After two hours of stirring at 55° C. the reaction was concentrated and it was redissolved into DMF, (solids that did not dissolve were filtered away) and this was purified by preparative HPLC. (Gilson semi preparative HPLC system using a Waters Nova pak column (10×40 mm I.D., C18, 6 um) eluting with 5–95% acetonitrile/water (0.1% TFA) at 30 ml/min) to afford a mixture of the trans and cis diastereomers, with the trans being the major component after concentrating.

Major component of sample (trans diastereomer):

$^1$H NMR (DMSO, 400 MHz) δ 13.45 (1H, bs), 9.28 (1H, bs), 9.45–9.25 (1H, bs), 9.21 (1H, J=4.2 and 1.4 Hz), 8.78–8.75 (1H, dd, J=8.7 and 1.3 Hz), ), 7.93–7.90 (1H, dd, J=8.6 and 4.2 Hz), 7.44–7.41 (2H, dd, J=8.6 and 5.6 Hz), 7.20 (2H, t, J=8.9 Hz), 5.95 (1H, bs), 4.71–4.57 (3H, bs), 3.29–3.22 (1H, dd, J=17.2 and 9.6 Hz), 2.92 (3H, s), 2.64 (3H, s), 2.38–2.34 (1H, d, J=18.5 Hz) ppm. ES HRMS exact mass calcd. for $C_{22}H_{22}N_5O_3F$ 424.1786 (MH$^+$), found 424.1781

Step 5: Preparation of N-(4-fluorobenzyl)-8-hydroxy-5-(1-methyl-5-oxopyrrolidin-3-yl)-1,6-naphthyridine-7-carboxamide A solution of the aminal from step 4 (0.45 g, 1.063 mmol) in TFA (3 ml) was heated to 105° C. in a glass pressure vessel until the methylamine was eliminated as determined by 1 c-ms. The reaction was then cooled to room temperature and triethylsilane (0.85 ml, 0.618 g, 5.31 mmol) was added to the solution. After stirring for 1.5 hours at 75° C. the reaction was complete. The solution was then concentrated and was redissolved into DMF and purified by preparative HPLC. (Gilson semi preparative HPLC system using a waters Nova pak column (10×40 mm I.D., C18, 6 um) eluting with 5–95% acetonitrile/water (0.1% TFA) at 30 ml/min) to afford a mixture enantiomers after concentrating down the solvent on the speed vac.

$^1$H NMR (DMSO, 400 MHz) δ 13.55 (1H, bs), 9.63 (1H, t, J=6.6 Hz), 9.16 (1H, dd, J=4.2 and 1.4 Hz), 8.82–8.79 (1H, dd, J=8.5 and 1.2 Hz), ), 7.85–7.82 (1H, dd, J=8.5 and 4.2 Hz), 7.45–7.41 (2H, dd, J=8.6 and 5.7 Hz), 7.18 (2H, t, J=8.8 Hz), 4.60–4.50 (3H, bs), 3.81 (1H, t, J=9.0 Hz), 3.67 (1H, t, J=8.7 Hz), 3.28–3.22 (1H, dd, J=16.5 and 9.1 Hz), 2.78 (3H, s), 2.64–2.58 (1H, dd, J=16.5 and 9.1 Hz) ppm. ES HRMS exact mass calcd. for $C_{21}H_{19}N_4O_3F$ 395.1514 (MH$^+$), found 395.1514. CHN Anal. Calcd for $C_{21}H_{19}N_4O_3F+0.15$ TFA: C, 62.17; H, 4.69; N, 13.62. Found: C, 62.27; H, 4.45; N, 13.29.

EXAMPLE 190

Preparation of 1,4-Butanesultam

| | Weight | FW | Moles | E-quiv. | Density | Volume |
|---|---|---|---|---|---|---|
| MsCl (1) | 2.36 Kg | 114.55 | 20.6 | 1.03 | 1.480 | 1.59 L |
| 3-bromopropyl-amine (2) HBr salt | 4.40 Kg | 220 | 20.0 | 1.00 | | |
| TEA | 4.07 Kg | 101.19 | 40.2 | 2.01 | 0.726 | 5.60 L |
| THF | | | | | | 43 + 4 + 8 = 55 L |
| DIPA | 481 g | 101.19 | 4.75 | 0.25 | 0.722 | 666 mL |
| 1,10-Phenanthroline | 4.11 g | 180.21 | | | | |
| n-BuLi, 1.6 M in hexane | | | | | | |

The 3-bromopropylamine-HBr salt (2) and THF (43 L) were placed in a 72 L round-bottomed-flask under $N_2$ and the resulting slurry was cooled to 0° C. Two dropping funnels were fitted to the flask. One was charged with the TEA and the other with a solution of the MsCl (1) and THF (4 L). The contents of the addition funnels were added at roughly the same rate (the TEA was added slightly faster than the MsCl) while maintaining an internal reaction temperature below 10° C. The addition required 2 h. The resulting white suspension was warmed to 23° C. and aged for 1 h. The suspended solids (a mixture of TEA-HBr and TEA-HCl) were removed by filtration through a dry frit. The cake was washed with THF (8 L). The combined filtrate and cake-rinse, a THF solution of 3, was collected in a 100 L round-bottomed-flask under $N_2$. To the solution of 3 was added the 1,10-phenanthroline and the DIPA and the resulting solution was cooled to −30° C. The n-BuLi was added over about 4 h maintaining the internal temperature below −20° C. After 1.25 eq of the n-BuLi was added the reaction mixture became deep brown and the color remained as the addition was completed. The reaction mixture was warmed to 0° C. over 3 h. A small aliquot was removed, and partitioned between saturated $NH_4Cl$ and EtOAc. The EtOAc was evaporated and the residue examined by $^1$H NMR to confirm consumption of 3 and conversion to 4. To the reaction mixture at 0° C. was added saturated aqueous NH₄Cl (12 L, the first 1L slowly, a heat kick to 6° C. was observed) and then brine (12 L). The phases were partitioned and the aqueous phase was extracted with EtOAc (20 L). The organic phases were combined, washed with brine (4 L) and then concentrated under vacuum to about 12 L. The solvent was switched to EtOAc (20 L used) maintaining a volume of 12 L. After the solvent switch, a yellow slurry resulted. n-Heptane (20 L) was added with stirring and the slurry was cooled to 5° C. After a 1 h age the solids were collected on a frit and rinsed with cold (5° C.) 3:5 EtOAc/n-heptane. The wet cake was dried for 24 h under a stream of dry N₂ to provide 1.44 Kg (53% from 2) of sultam 4 as a crystalline yellow solid.

EXAMPLE 191

Preparation of 5-(1,1-dioxido-1,2-thiazinan-2-yl)-N-(4-fluorobenzyl)-8-hydroxy-1,6-naphthyridine-7-carboxamide from methyl 5-bromo-8-hydroxy-1,6-naphthyridine-7-carboxylate Step 1: 5-Bromo-8-hydroxy-1,6-naphthyridine-7-carboxylic acid methyl ester

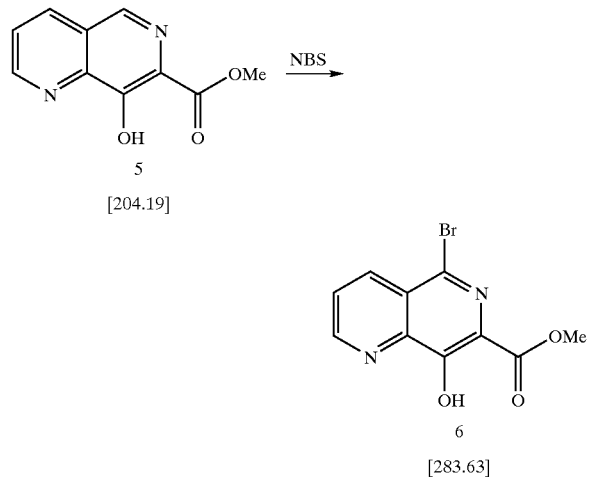

N-bromosuccinimide (7.83 g, 44.0 mmol) was added to a solution of 8-hydroxy-1,6-naphthyridine-7-carboxylic acid methyl ester (5, 8.17 g, 40.0 mmol) in chloroform (32 mL) over 20 min maintaining the temperature at 20–50° C. and the mixture was aged for 30 min at 50° C. The mixture became a thick, stirrable slurry and HPLC analysis indicated <2% starting material remaining. The mixture was cooled to 30° C. over 15 min. MeOH (64 mL) was added over 30 min then a 1:1 mixture of MeOH-water (64 mL) was added over 30 min. The mixture was cooled to −40° C. over 30 min and aged at −40° C. for 30 min. The cold mixture was filtered and the solid was washed with 1:1 MeOH:water (100 mL) at 10–20° C. The off white crystalline solid was dried under a stream of nitrogen to provide 10.48 g (93% yield) of 5-bromo-8-hydroxy-1,6-naphthyridine-7-carboxylic acid methyl ester (6).

HPLC retention times: 5=2.2 min, 6=6.0 min, HPLC conditions: 150×4.6 mm ACE 3 C18 column, isocratic elution with 30% MeCN in 0.025% aq H₃PO₄ at 1 mL/min, 25° C. with detection at 254 nm;

HPLC retention times: 5=1.8 min, 6=3.1 min, 1HPLC conditions: 150×4.6 mm ACE 3 C18 column, isocratic elution with 46% MeCN in 0.025% aq H₃PO₄ at 1 mL/min, 25° C. with detection at 254 nm.

¹³CNMR of 6 (CDCl₃, 100 MHz): 169.7, 156.3, 154.5, 143.9, 137.1, 132.4, 128.0, 126.1, 124.2, 53.4.

Step 2: 5-Bromo-8-(4-toluenesulfonyloxy)-1,6-naphthyridin-7-carboxylic acid methyl ester

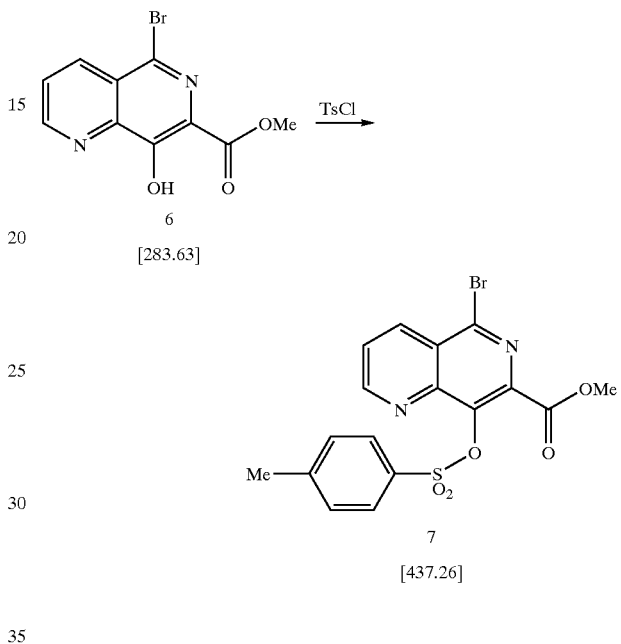

Triethylamine (0.759 g, 7.50 mmol) was added to a suspension of 5-bromo-8-hydroxy-1,6-naphthyridine-7-carboxylic acid methyl ester (6, 1.415 g, 5.000 mmol) in chloroform (5 mL) over 5 min maintaining the temperature at 20–50° C. to give a yellow suspension. p-Toluenesulfonyl chloride (1.15 g, 6.00 mmol) was added over 5 min maintaining the temperature at 20–40° C. to give a yellow solution. The mixture was aged at 40° C. for 2 h during which a crystalline solid precipitated out of the mixture and the color faded (HPLC analysis indicated <0.5% starting material remaining). The mixture was cooled to 20° C. over 15 min. MeOH (10 mL) was added over 30 min then a 1:1 mixture of MeOH:water (10 mL) was added over 30 min. The mixture was cooled to −40° C. over 30 min and aged at −40° C. for 30 min. The cold mixture was filtered and the solid was washed with 1:1 MeOH:water (10 mL), MeOH (5 mL), MTBE (10 mL) and hexanes (10 mL) all at 10–20° C. The off-white crystalline solid was dried under a stream of nitrogen to provide 2.112 g (97% yield) of 5-bromo-8-(p-toluenesulfonyloxy)-1,6-naphthyridine-7-carboxylic acid methyl ester (7)

HPLC retention times: 6=3.1 min, 7=12.4 min, HPLC conditions: 150×4.6 mm ACE 3 C18 column, isocratic elution with 46% MeCN in 0.025% aq H₃PO₄ at 1 mL/min, 25° C. with detection at 254 nm.

¹³C NMR of 7 (d6-DMSO, 100 MHz): 163.2, 157.0, 146.5, 145.8, 141.9, 141.3, 139.2, 137.2, 132.3, 130.4, 129.0, 127.6, 127.1, 53.3, 21.7.

Step 3: 5-(1,1-Dioxido-1,2-thiazinan-2-yl)-8-(4-toluenesulfonyloxy)-1,6-naphthyridine-7-carboxylic acid methyl ester

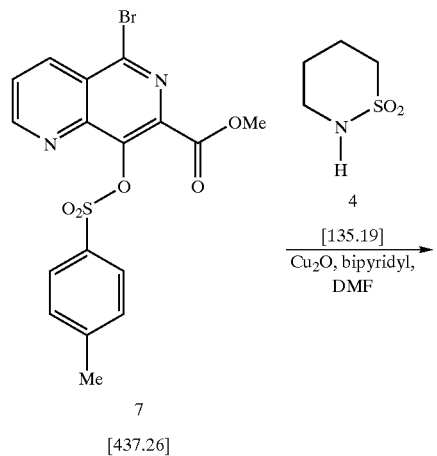

7
[437.26]

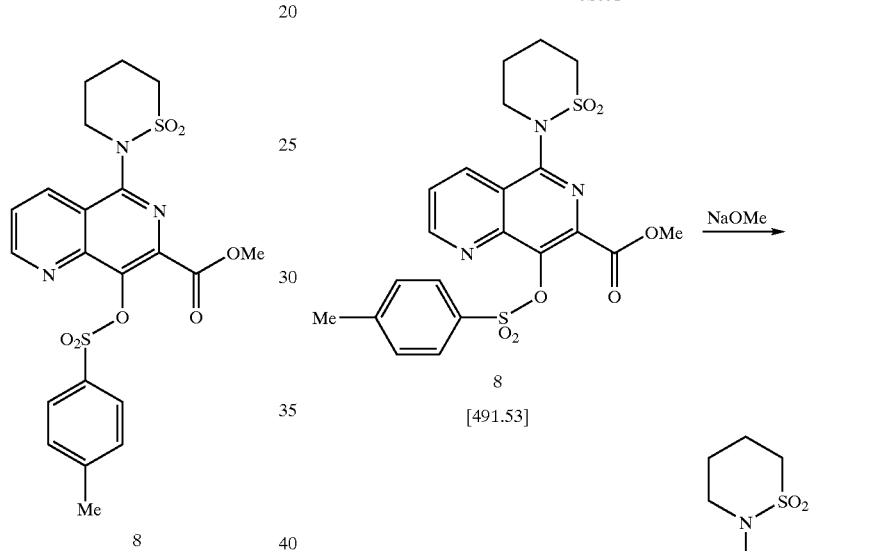

A mixture of 5-bromo-8-(p-toluenesulfonyloxy)-1,6-naphthyridine-7-carboxylic acid methyl ester (7, 2.186 g, 5.000 mmol), 1,4-butane sultam (4, 811 mg, 6.00 mmol), copper (I) oxide (858 mg, 6.00 mmol, <5 micron), 2,2'-bipyridyl (937 mg, 6.00 mmol) and DMF (10 mL) was degassed by stirring under a stream of nitrogen for 1 min and heated to 120° C. for 4 h. The brown suspension became a dark red solution with a small amount of undissolved copper (I) oxide remaining (HPLC analysis indicated <0.5% starting material remaining). The mixture was diluted with chloroform (10 mL), Solkaflok (200 mg) was added and the resulting mixture was filtered through a plug of Solkaflok. The plug was washed with chloroform (10 mL) and the combined filtrates were stirred vigorously with a solution of EDTA disodium salt dihydrate (3.8 g, 10.2 mmol) in water (40 mL) while air was slowly bubbled in for 40 min. The upper aqueous phase became turquoise while the lower organic phase became yellow. The organic phase was washed with a solution of EDTA disodium salt (1.9 g, 5.1 mmol) in water (30 mL) and a solution of sodium bisulfate monohydrate (0.87 g, 6.3 mmol) in water (30 mL). Each of the above three aqueous phases was back extracted sequentially with one portion of chloroform (15 mL). The organic phases were dried over sodium sulfate and filtered. The dried organic extracts were concentrated and solvent switched to a final volume of 15 mL MeOH using a total of 30 mL MeOH for the switch at atmospheric pressure. Product crystallized during the solvent switch. The resulting slurry was cooled to 0° C. over 30 min and aged at 0° C. for 30 min. The slurry was filtered cold and the solid was washed with MeOH (15 mL). The off white solid was dried under a stream of nitrogen to provide 1.910 g (78%) of 5-(N-1,4-butanesultam)-8-(p-toluenesulfonyloxy)-1,6-naphthyridine-7-carboxylic acid methyl ester (8).

HPLC retention times: 7=12.4 min, 8=10.3 min, DMF =1.3 min, Bipy =1.5 min, HPLC conditions: 150×4.6 mm ACE 3 C18 column, isocratic elution with 46% MeCN in 0.025% aq $H_3PO_4$ at 1 mL/min, 25° C. with detection at 254 nm.

$^{13}$C NMR of 8 (CDCl$_3$, 100 MHz): 164.2, 155.3, 151.9, 146.7, 145.4, 141.2, 137.8, 135.3, 133.6, 129.6, 128.9, 125.4, 124.3, 53.4, 52.9, 48.7, 24.2, 22.0, 21.7.

Step 4: 5-(1,1-Dioxido-1,2-thiazinan-2-yl)-8-hydroxy-1,6-naphthyridine-7-carboxylic acid methyl ester 5-(N-1,4-butanesultam)-8-(p-toluenesulfonyloxy)-1,6-naphthyridine-7-carboxylic acid methyl ester (8, 1.597 g, 3.250 mmol) was dissolved in DMF (3.25 mL) at 40° C. and transferred to a solution of 0.5M NaOMe in MeOH (16.25 mL, 8.125 mmol) over ca 1–2 min at 20–25° C. The resulting yellow homogenous mixture was heated to 50° C. and aged for 5 min (HPLC analysis indicated <0.5% starting material remaining). Mixture was cooled to 25° C. over 15 min and aged at 25° C. for 15 min during which a yellow crystalline precipitate was deposited. Acetic acid (390 mg, 6.50 mmol) was added over 1 min (yellow color faded) then water (32.5 mL) was added over 15 min at 25° C. The slurry was aged for 30 min 25° C. and filtered. The filter cake was washed with 1:1 MeOH:water (32.5 mL) and then with 1:1 MTBE:hexanes (8 mL). The filter cake was dried under a stream of nitrogen to provide 1.064 g (97%) of 5-(N-1,4-butanesultam)-8-hydroxy-1,6-naphthyridine-7-carboxylic acid methyl ester (9) as an off white crystalline solid.

HPLC retention times: 8=10.3 min, 9=2.9 min, HPLC conditions: 150×4.6 mm ACE 3 C18 column, isocratic elution with 46% MeCN in 0.025% aq $H_3PO_4$ at 1 mL/min, 25° C. with detection at 254 nm.

$^{13}C$ NMR of 9 (d6-DMSO, 100 MHz): 167.8, 154.4, 153.5, 143.9, 143.7, 135.2, 125.9, 125.2, 124.4, 53.2, 53.1, 49.1, 24.4, 21.9.

Step 5: 5-(1,1-Dioxido-1,2-thiazinan-2-yl)-N-(4-fluorobenzyl)-8-hydroxy-1,6-naphthyridine-7-carboxamide, monoethanolate

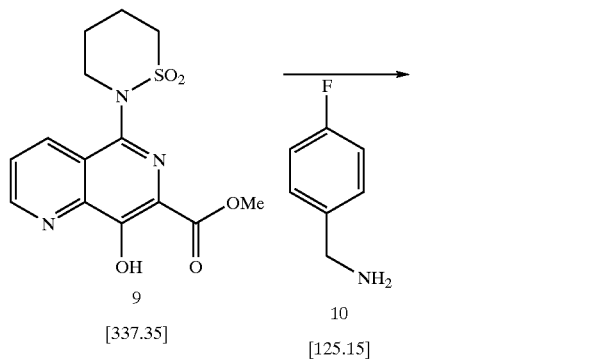

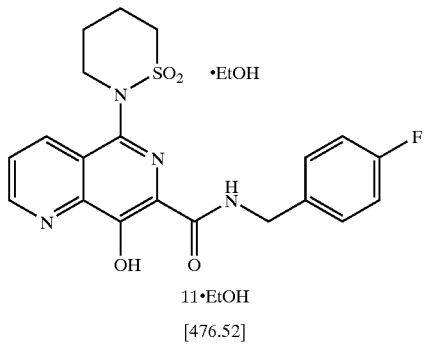

A suspension of 5-(N-1,4-butanesultam)-8-hydroxy-1,6-naphthyridine-7-carboxylic acid methyl ester (9, 1.012 g, 3.00 mmol) and 4-fluorobenzylamine (10, 1.314 g, 10.5 mmol) in EtOH (9.0 mL) was heated to 75–77° C. for 2 h during which the mixture became a yellow homogeneous solution (HPLC analysis indicated <0.5% starting material remaining). Acetic acid (0.630 mg, 10.5 mmol) was added over 1 min (yellow color faded) then water (9.0 mL) was added over 10 min at 75° C. An off white crystalline solid began to precipitate near the end of addition of the water. The slurry was cooled to 0° C. over 30 min then aged for 30 min at 0° C. and filtered. The filter cake was washed with 5% HOAc in 1:1 EtOH:water (5 mL) then with 1:1 EtOH:water (10 mL) and then with EtOH (5 mL). The filter cake was dried under a stream of nitrogen to provide 1.343 g (94%) of the monoethanolate of 5-(N-1,4-butanesultam)-N-(4-fluorobenzyl)-8-hydroxy-1,6-naphthyridine-7-carboxamide (11) as an off white crystalline solid.

HPLC retention times: 9=2.9 min, 11=6.7 min, 10=1.4 min, impurity present in 10=4.3 min, HPLC conditions: 150×4.6 mm ACE 3 C18 column, isocratic elution with 46% MeCN in 0.025% aq $H_3PO_4$ at 1 ml/min, 25° C. with detection at 254 nm;

HPLC retention time: 9=10.9 min, PLC conditions: 150×4.6 mm ACE 3 C18 column, isocratic elution with 24% MeCN in 0.025% aq $H_3PO_4$ at 1 mL/min, 25° C. with detection at 254 nm.

$^1H$ NMR (d6-DMSO, 400 MHz): 9.25 (t, J=6.4, 1H), 9.16 (d, J=8.4, 1H), 8.56 (d, J=8.4, 1H), 7.86 (dd, J=8.4, 1H), 7.41 (dd, J=8.4, 5.7, 2H), 7.16, t, J=8.8, 2H), 4.60 (d, 6.3, 2H), 4.00–3.70 (m, 2H), 3.65–3.45 (m, 2H), 2.35–2.10 (m, 3H), 1.7 (m, 1H).

Step 6: Sodium salt of 5-(1,1-Dioxido-1,2-thiazinan-2-yl)-N-(4-fluorobenzyl)-8-hydroxy-1,6-naphthyridine-7-carboxamide,

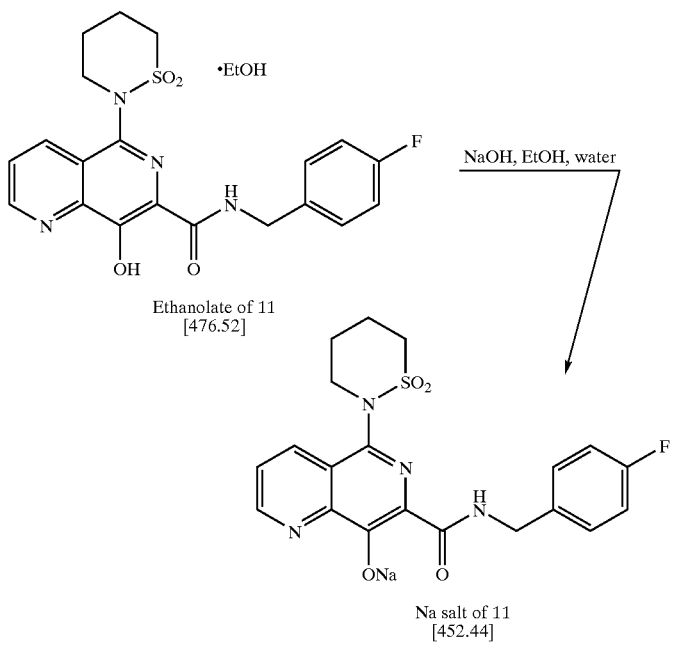

5-(N-1,4-Butanesultam)-N-(4-fluorobenzyl)-8-hydroxy-1,6-naphthyridine-7-carboxamide (11) monoethanolate (1.207 g, 2.533 mmol) was dissolved in a mixture of EtOH (24 mL) and water (11 mL) by heating to 78° C. for 1 h. A solution of 5M aq NaOH (0.608 mL, 3.04 mmol) was added over 15 min at 78° C. A yellow crystalline precipitate was deposited. The mixture was aged at 78° C. for 20 min, then cooled to 20° C. over 30 min and aged for 30 min at 20° C. The slurry was filtered and the filter cake was washed with 2:1 EtOH:water (5 mL) and EtOH (15 mL). The filter cake was dried under a stream of nitrogen to provide 1.088 g (95%) of 5-(N-1,4-butanesultam)-N-(4-fluorobenzyl)-8-hydroxy-1,6-naphthyridine-7-carboxamide sodium salt (11 sodium salt) as a yellow crystalline solid.

The Na salt was analyzed by differential scanning calorimetry at a heating rate of 10° C./min in an open cup under flowing nitrogen and was found to have a DSC curve exhibiting an endotherm with a peak temperature of about 348° C. and an associated heat of fusion of about 45 J/gm followed by an exotherm with a peak temperature of about 352° C. and an associated heat of fusion of about 45 J/gm.

The XRPD pattern of the Na salt was generated on a Philips Analytical X-ray powder diffraction (XRPD) instrument with XRG 3100 generator using a continuous scan from 2 to 40 degrees 2 theta over about 126 minutes. The resulting XRPD pattern was analyzed using Philips X'Pert Graphics and Identify software. Copper K-Alpha 1 radiation was used as the source. The experiment was run under ambient conditions. The XRPD pattern was found to have characteristic diffraction peaks corresponding to d-spacings of 12.63, 5.94, 5.05, 4.94, 4.81, 4.61, 4.54, 4.34, 3.88, 3.73, 3.49, 3.45, 3.22, 3.15, 3.12, and 2.86 angstroms.

The Na salt has been jet-milled to provide crystals with a mean particle size of about 3 to 5 microns (v. about 20 to 25 microns for unmilled material) for use in orally administered formulations. The jet-milled salt has exhibited improved oral bioavailability over the unmilled salt.

EXAMPLE 192

Oral Composition

As a specific embodiment of an oral composition of a compound of this invention, 50 mg of compound of Example 1 is formulated with sufficient finely divided lactose to provide a total amount of 580 to 590 mg to fill a size 0 hard gelatin capsule.

EXAMPLE 193

HIV Integrase Assay: Strand Transfer Catalyzed by Recombinant Integrase

Assays for the strand transfer activity of integrase were conducted in accordance with Wolfe, A. L. et al., *J. Virol.* 1996, 70: 1424–1432, for recombinant integrase, except that: (i) the assays used preassembled integrase strand transfer complexes; (ii) the strand transfer reaction was performed in the presence of inhibitor in 2.5 MM $MgCl_2$ using 0.5 to 5 nM of a 3' FITC labeled target DNA substrate (SEQ. ID. NO: 1 and SEQ. ID. NO: 2)

```
5'      TGA CCA AGG GCT AAT TCA CT fitc    3'

3' fitc   ACT GGT TCC CGA TTA AGT GA       5';
``` and (iii) strand transfer products were detected using an alkaline phosphatase conjugated anti-FITC antibody and a chemiluminescent alkaline phosphatase substrate. Representative compounds tested in the integrase assay demonstrated $IC_{50}$'s of less than about 100 micromolar.

Further description on conducting the assay using preassembled complexes is found in Hazuda et al., *J. Virol.* 1997, 71: 7005–7011; Hazuda et al., *Drug Design and Discovery* 1997, 15: 17–24; and Hazuda et al., *Science* 2000, 287: 646–650.

EXAMPLE 194

Assay for Inhibition of UV Replication

Assays for the inhibition of acute HIV infection of T-lymphoid cells were conducted in accordance with Vacca, J. P. et al., (1994), Proc. Natl. Acad. Sci. USA 91, 4096. Representative compounds tested in the present assay demonstrated $IC_{95}$'s of less than about 20 micromolar.

While the foregoing specification teaches the principles of the present invention, with examples provided for the purpose of illustration, the practice of the invention encompasses all of the usual variations, adaptations and/or modifications that come within the scope of the following claims.

---

What is claimed is:
1. A compound of Formula (I):

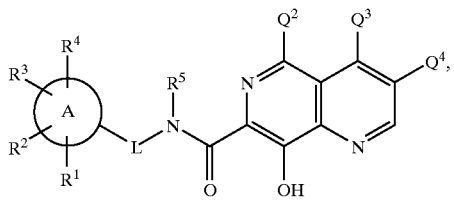

wherein A is phenyl or phenyl fused to a carbocycle to form a fused carbocyclic ring system;
A is substituted by $R^1$, $R^2$, $R^3$, and $R^4$;
L is a linker connecting a ring atom of A to the nitrogen of the —N($R^5$)— moiety, wherein L is
 (i) a single bond,
 (ii) —($C_{1-6}$ alkyl)-,
 (iii) —($C_{2-6}$ alkenyl)-,
 (iv) —($C_{0-6}$ alkyl)—($C_{3-6}$ cycloalkyl)—($C_{0-6}$ alkyl)-, or
 (v) —($C_{0-6}$ alkyl)-M—($C_{0-6}$ alkyl)-, wherein M is —N($R^a$)—, —OC(=O)—, or —C(=O)O—;
wherein the alkenyl in (iii) and the alkyls in (ii), (iv), and (v) are independently and optionally substituted with 1, 2, or 3 substituents independently selected from the group consisting of halogen, —OH, —$C_{1-6}$ alkyl, —O—$C_{1-6}$ alkyl, —$CO_2R^a$, —$CO_2(CH_2)_{1-2}R^k$, —$C_{1-6}$ alkyl-$OR^a$, —$R^k$, —$(CH_2)_{1-2}R^k$, —CH($OR^a$)—$R^k$, and —CH(N($R^a$)$_2$)—$R^k$;
each of $Q^2$, $Q^3$, and $Q^4$ is independently
 (1) —H,
 (2) —$C_{1-6}$ alkyl,
 (3) —$C_{1-6}$ haloalkyl,
 (4) —O—$C_{1-6}$ alkyl,
 (5) —O—$C_{1-6}$ haloalkyl,
 (6) halo,
 (7) —CN,
 (8) —$C_{1-6}$ alkyl-$OR^a$,
 (9) —$C_{0-6}$ alkyl-C(=O)$R^a$,
 (10) —$C_{0-6}$ alkyl-$CO_2R^a$,
 (11) —$C_{0-6}$ alkyl-$SR^a$,
 (12) —N($R^a$)$_2$,
 (13) —$C_{1-6}$ alkyl-N($R^a$)$_2$,
 (14) —$C_{0-6}$ alkyl-C(=O)N($R^a$)$_2$,
 (15) —$C_{0-6}$ alkyl-G—$C_{1-6}$ alkyl-C(=O)N($R^a$)$_2$, wherein G is O, S, N($R^a$), or N($SO_2R^a$),
 (16) —N($R^a$)—C($R^a$)=O,
 (17) —$C_{1-6}$ alkyl-N($R^a$)—C($R^a$)=O,
 (18) —C(=O)—N($R^a$)—$C_{1-6}$ alkyl-[C(=O)]$_{0-1}$—N($R^a$)$_2$,
 (19) —C(=O)—N($R^a$)—$C_{1-6}$ alkyl substituted with 1 or 2 —$OR^a$,
 (20) —$C_{0-6}$ alkyl-$SO_2R^a$,
 (21) —$C_{0-6}$ alkyl-N($R^a$)$SO_2R^a$,
 (22) —$C_{2-6}$ alkenyl,
 (23) —$C_{2-6}$ alkenyl-C(=O)—N($R^a$)$_2$,
 (24) —$C_{2-5}$ alkynyl,
 (25) —$C_{2-5}$ alkynyl-$CH_2$N($R^a$)$_2$,
 (26) —$C_{2-5}$ alkynyl-$CH_2OR^a$,
 (27) —$C_{2-5}$ alkynyl-$CH_2$S(O)$_n$—$R^a$, (28)

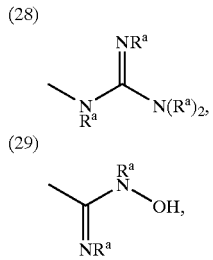

(29)

(30) —C(=N$R^a$)—N($R^a$)$_2$,
 (31) —N($R^a$)—$C_{1-6}$ alkyl-S(O)$_n R^a$,
 (32) —N($R^a$)—$C_{1-6}$ alkyl-$OR^a$,
 (33) —N($R^a$)—$C_{1-6}$ alkyl-N($R^a$)$_2$,
 (34) —N($R^a$)—$C_{1-6}$ alkyl-N($R^a$)—C($R^a$)=O,
 (35) —N($R^a$)—$C_{0-6}$ alkyl-[C(=O)]$_{1-2}$N($R^a$)$_2$,
 (36) —N($R^a$)—$C_{1-6}$ alkyl-$CO_2R^a$,
 (37) —N($R^a$)C(=O)N($R^a$)—$C_{1-6}$ alkyl-C(=O)N($R^a$)$_2$,
 (38) —N($R^a$)C(=O)—$C_{1-6}$ alkyl-N($R^a$)$_2$,
 (39) —N($R^a$)—$SO_2$—N($R^a$)$_2$,
 (40) —$R^k$,
 (41) —$C_{1-6}$ alkyl substituted with $R^k$,
 (42) —$C_{1-6}$ haloalkyl substituted with $R^k$,
 (43) —$C_{2-5}$ alkenyl-$R^k$,
 (44) —$C_{2-5}$ alkynyl-$R^k$,
 (45) —$C_{0-6}$ alkyl-O—$R^k$,
 (46) —$C_{0-6}$ alkyl-O—$C_{1-6}$ alkyl-$R^k$,
 (47) —$C_{0-6}$ alkyl-S(O)$_n$—$R^k$,
 (48) —$C_{0-6}$ alkyl-S(O)$_n$—$C_{1-6}$ alkyl-$R^k$,
 (49) —O—$C_{1-6}$ alkyl-$OR^k$,
 (50) —O—$C_{1-6}$ alkyl-O—$C_{1-6}$ alkyl-$R^k$,
 (51) —O—$C_{1-6}$ alkyl-S(O)$_n R^k$,
 (52) —$C_{0-6}$ alkyl-N($R^c$)—$R^k$,
 (53) —$C_{0-6}$ alkyl-N($R^c$)—$C_{1-6}$ alkyl substituted with one or two $R^k$ groups,
 (54) —$C_{0-6}$ alkyl-N($R^c$)—$C_{1-6}$ alkyl-$OR^k$,
 (55) —$C_{0-6}$ alkyl-C(=O)—$R^k$,
 (56) —$C_{0-6}$ alkyl-C(=O)N($R^a$)—$R^k$,
 (57) —$C_{0-6}$ alkyl-N($R^a$)C(=O)—$R^k$,
 (58) —$C_{0-6}$ alkyl-C(=O)N($R^a$)—$C_{1-6}$ alkyl-$R^k$, or
 (59) —$C_{0-6}$ alkyl-N($R^a$)—$C_{0-6}$ alkyl-S(O)$_n R^k$;
each of $R^1$ and $R^2$ is independently:
 (1) —H,
 (2) —$C_{1-6}$ alkyl,
 (3) —$C_{1-6}$ haloalkyl,
 (4) —O—$C_{1-6}$ alkyl,
 (5) —O—$C_{1-6}$ haloalkyl,
 (6) —OH
 (7) halo,
 (8) —$NO_2$, (9) —CN,
(10) —$C_{1-6}$ alkyl-$OR^a$,
(11) —$C_{0-6}$ alkyl-C(=O)$R^a$,
(12) —$C_{0-6}$ alkyl-$CO_2R^a$,
(13) —$C_{0-6}$ alkyl-$SR^a$,
(14) —$N(R^a)_2$,
(15) —$C_{1-6}$ alkyl-$N(R^a)_2$,
(16) —$C_{0-6}$ alkyl-C(=O)$N(R^a)_2$,
(17) —$C_{1-6}$ alkyl-$N(R^a)$—C($R^a$)=O,
(18) —$SO_2R^a$,
(19) —$N(R^a)SO_2R^a$,
(20) —$C_{2-5}$ alkenyl,
(21) —O—$C_{1-6}$ alkyl-$OR^a$,
(22) —O—$C_{1-6}$ alkyl-$SR^a$,
(23) —O—$C_{1-6}$ alkyl-NH—$CO_2R^a$,
(24) —O—$C_{2-6}$ alkyl-$N(R^a)_2$,
(25) —$N(R^a)$—$C_{1-6}$ alkyl-$SR^a$,
(26) —$N(R^a)$—$C_{1-6}$ alkyl-$OR^a$,
(27) —$N(R^a)$—$C_{1-6}$ alkyl-$N(R^a)_2$,
(28) —$N(R^a)$—$C_{1-6}$ alkyl-$N(R^a)$—C($R^a$)=O,
(29) —$R^k$,
(30) —$C_{1-6}$ alkyl substituted with 1 or 2 $R^k$ groups,
(31) —$C_{1-6}$ haloalkyl substituted with 1 or 2 $R^k$ groups,
(32) —$C_{2-5}$ alkenyl-$R^k$,
(33) —$C_{2-5}$ alkynyl-$R^k$,
(34) —O—$R^k$,
(35) —O—$C_{1-6}$ alkyl-$R^k$,
(36) —$S(O)_n$—$R^k$,
(37) —$S(O)_n$—$C_{1-6}$ alkyl-$R^k$,
(38) —O—$C_{1-6}$ alkyl-$OR^k$,
(39) —O—$C_{1-6}$ alkyl-O—$C_{1-6}$ alkyl-$R^k$,
(40) —O—$C_{1-6}$ alkyl-$S(O)_nR^k$,
(41) —$C_{1-6}$ alkyl ($OR^b$)($R^k$),
(42) —$C_{1-6}$ alkyl ($OR^b$)(—$C_{1-6}$ alkyl-$R^k$),
(43) —$C_{0-6}$ alkyl-$N(R^b)(R^k)$,
(44) —$C_{0-6}$ alkyl-$N(R^b)$(—$C_{1-6}$ alkyl-$R^k$),
(45) —$C_{1-6}$ alkyl $S(O)_n$—$R^k$,
(46) —$C_{1-6}$ alkyl $S(O)_n$—$C_{1-6}$ alkyl-$R^k$,
(47) —$C_{0-6}$ alkyl C(O)—$R^k$, or
(48) —$C_{0-6}$ alkyl C(O)—$C_{1-6}$ alkyl-$R^k$, each of $R^3$ and $R^4$ is independently
(1) —H,
(2) halo,
(3) —CN,
(4) —$NO_2$,
(5) —OH,
(6) $C_{1-6}$ alkyl,
(7) $C_{1-6}$ haloalkyl,
(8) —O—$C_{1-6}$ alkyl,
(9) —O—$C_{1-6}$ haloalkyl,
(10) —$C_{1-6}$ alkyl-$OR^a$,
(11) —$C_{0-6}$ alkyl-C(=O)$R^a$,
(12) —$C_{0-6}$ alkyl-$CO_2R^a$,
(13) —$C_{0-6}$ alkyl-$SR^a$,
(14) —$N(R^a)_2$,
(15) —$C_{1-6}$ alkyl-$N(R^a)_2$,
(16) —$C_{0-6}$ alkyl-C(=O)$N(R^a)_2$,
(17) —$SO_2R^a$,
(18) —$N(R^a)SO_2R^a$,
(19) —$C_{2-5}$ alkenyl,
(20) —O—$C_{1-6}$ alkyl-$OR^a$,
(21) —O—$C_{1-6}$ alkyl-$SR^a$,
(22) —O—$C_{1-6}$ alkyl-NH—$CO_2R^a$, or
(23) —O—$C_{2-6}$ alkyl-$N(R^a)_2$;

$R^5$ is
(1) —H,
(2) —$C_{1-6}$ alkyl, optionally substituted with from 1 to 5 substituents independently selected from halogen, —O—$C_{1-6}$ alkyl, —O—$C_{1-6}$ haloalkyl, —$N(R^a)_2$, and —$CO_2R^a$;
(3) aryl optionally substituted with from 1 to 5 substituents independently selected from halogen, $C_{1-6}$ alkyl, $C_{1-6}$ haloalkyl, —O—$C_{1-6}$ alkyl, —O—$C_{1-6}$ haloalkyl, —S—$C_{1-6}$ alkyl, —CN, and —OH, or
(4) —$C_{1-6}$ alkyl substituted with $R^k$;

each $R^a$ is independently —H, —$C_{1-6}$ alkyl, or —$C_{1-6}$ haloalkyl;

each $R^b$ is independently:
(1) —H,
(2) —$C_{1-4}$ alkyl,
(3) —$C_{1-4}$ haloalkyl,
(4) —$R^k$,
(5) —$C_{2-3}$ alkenyl,
(6) —$C_{1-4}$ alkyl-$R^k$,
(7) —$C_{2-3}$ alkenyl-$R^k$,
(8) —$S(O)_n$—$R^k$, or
(9) —C(O)—$R^k$;

each $R^c$ is independently
(1) —H,
(2) —$C_{1-6}$ alkyl,
(3) —$C_{1-6}$ alkyl substituted with —$N(R^a)_2$, or
(4) —$C_{1-4}$ alkyl-aryl, wherein aryl is optionally substituted with 1 to 5 substituents independently selected from halogen, $C_{1-6}$ alkyl, $C_{1-6}$ haloalkyl, —O—$C_{1-6}$ alkyl, —O—$C_{1-6}$ haloalkyl, —S—$C_{1-6}$ alkyl, —CN, and —OH;

each $R^k$ is independently carbocycle or heterocycle, wherein the carbocycle and heterocycle are unsubstituted or substituted with from 1 to 5 substituents each of which is independently selected from
(a) halogen,
(b) —$C_{1-6}$ alkyl,
(c) —$C_{1-6}$ haloalkyl,
(d) —O—$C_{1-6}$ alkyl,
(e) —O—$C_{1-6}$ haloalkyl,
(f) —S—$C_{1-6}$ alkyl,
(g) —CN,
(h) —OH,
(i) oxo,
(j) —$C_{0-6}$ alkyl-C(=O)$N(R^a)_2$,
(k) —$C_{0-6}$ alkyl-C(=O)$R^a$,
(l) —$N(R^a)$—C(=O)$R^a$,
(m) —$N(R^a)$—$CO_2R^a$,
(n) —$C_{1-6}$ alkyl-$N(R^a)$—C(=O)$R^a$,
(o) —$N(R^a)_2$,
(p) —$C_{1-6}$ alkyl-$N(R^a)_2$,
(q) —$C_{1-6}$ alkyl-$OR^a$,
(r) —$C_{0-6}$ alkyl-$CO_2R^a$,
(s) —$C_{0-6}$ alkyl-O—$C_{1-6}$ alkyl-$OR^a$,
(t) —$SO_2R^a$,
(u) —$SO_2N(R^a)_2$,
(v) —$C_{0-6}$ alkyl-$CO_2$—$C_{2-5}$ alkenyl,
(w) aryl,
(x) aryloxy-,
(y) —$C_{1-4}$ alkyl substituted with aryl,
(z) $R^t$,
(aa) —$C_{1-4}$ alkyl substituted with $R^t$,
(bb) —$C_{0-6}$ alkyl-C(=O)$R^t$, and
(cc) —$N(C_{1-6}$ alkyl)$R^t$, and
wherein the aryl group in (w) aryl, (x) aryloxy, and (y) —$C_{1-4}$ alkyl substituted with aryl, is optionally substituted with from 1 to 4 substituents independently selected from halogen, $C_{1-6}$ alkyl, —O—$C_{1-6}$ alkyl, $C_{1-6}$ alkyl substituted with $N(R^a)_2$, $C_{1-6}$ haloalkyl, and —OH; and wherein R' in (z), (aa), (bb) and (cc) is a hetero-monocycle which is optionally substituted with from 1 to 4 substituents independently selected from halogen, $C_{1-6}$ alkyl, —O—$C_{1-6}$ alkyl, $C_{1-6}$ haloalkyl, oxo, and —OH; and each n is independently an integer equal to 0, 1 or 2;

or a pharmaceutically acceptable salt thereof.

2. The compound according to claim 1, wherein

A is phenyl; and $Q^3$ and $Q^4$ are both —H;

or a pharmaceutically acceptable salt thereof.

3. A compound of Formula (II):

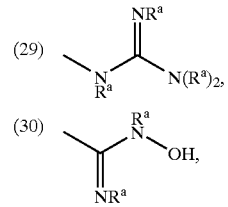

(II)

wherein

A is

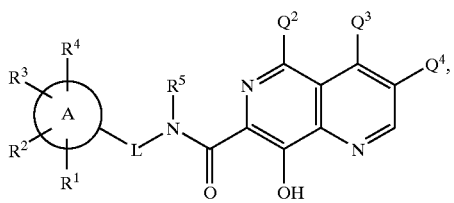

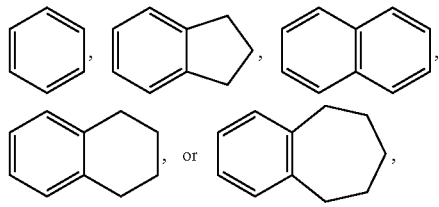, or

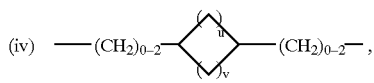,

L is
- (i) a single bond;
- (ii) —$(CH_2)_{1-3}$—, which is optionally substituted with 1 or 2 substituents independently selected from the group consisting of halogen, —OH, —$C_{1-4}$ alkyl, —O—$C_{1-4}$ alkyl, —$CO_2CH_3$, —$CO_2CH_2$-phenyl, phenyl, benzyl, —$(CH_2)_{1-2}OH$, —CH(OH)-phenyl, and —$CH(NH_2)$-phenyl;
- (iii) —$(CH_2)_{0-1}$—CH=CH—$(CH_2)$—, which is optionally substituted with 1 or 2 substituents independently selected from the group consisting of halogen, —OH, —$C_{1-4}$ alkyl, and —O—$C_{1-4}$ alkyl;
- (iv) —$(CH_2)_{0-2}$—⟨⟩—$(CH_2)_{0-2}$—, wherein u and v are each integers having a value of from 0 to 4, provided that the sum of u+v is 1, 2, 3 or 4; or

- (v) a heteroatom-containing chain which is —$N(R^a)$—$(CH_2)_{1-2}$—, —$CH_2$—OC(=O)—$CH_2$—, or —$CH_2$—C(=O)O—$CH_2$—;

$Q^2$ is
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo,
(7) —CN,
(8) —$C_{1-4}$ alkyl-$OR^a$,
(9) —$(CH_2)_{0-2}C(=O)R^a$,
(10) —$(CH_2)_{0-2}CO_2R^a$,
(11) —$(CH_2)_{0-2}SR^a$,
(12) —$N(R^a)_2$,
(13) —$C_{1-4}$ alkyl —$N(R^a)_2$,
(14) —$(CH_2)_{0-2}C(=O)N(R^a)_2$,
(15) —G—$C_{1-6}$ alkyl-$C(=O)N(R^a)_2$, wherein G is O, S, $N(R^a)$, or $N(SO_2R^a)$,
(16) —$N(R^a)$—$C(R^a)$=O,
(17) —$(CH_2)_{1-3}$—$N(R^a)$—$C(R^a)$=O,
(18) —$C(=O)$—$N(R^a)$—$(CH_2)_{1-3}$—$[C(=O)]_{0-1}$—$N(R^a)_2$,
(19) —$C(=O)$—$N(R^a)$—$C_{1-4}$ alkyl substituted with 1 or 2 —$OR^a$,
(20) —$SO_2R^a$,
(21) —$N(R^a)SO_2R^a$,
(22) —$C_{2-4}$ alkenyl,
(23) —$C_{2-4}$ alkenyl-$C(=O)$—$N(R^a)_2$,
(24) —$C_{2-3}$ alkynyl,
(25) —C≡C—$CH_2N(R^a)_2$,
(26) —C≡C—$CH_2OR^a$,
(27) —C≡C—$CH_2SR^a$,
(28) —C≡C—$CH_2SO_2R^a$,

(29) ![structure with NR^a, N(R^a)_2, R^a],

(30) ![structure with NR^a, R^a, OH],

(31) —$N(R^a)$—$C_{1-4}$ alkyl-$SR^a$,
(32) —$N(R^a)$—$C_{1-4}$ alkyl-$OR^a$,
(33) —$N(R^a)$—$C_{1-4}$ alkyl-$N(R^a)_2$,
(34) —$N(R^a)$—$C_{1-4}$ alkyl-$N(R^a)$—$C(R^a)$=O,
(35) —$N(R^a)$—$C_{0-4}$ alkyl-$[C(=O)]_{1-2}N(R^a)_2$,
(36) —$N(R^a)$—$C_{1-4}$ alkyl-$CO_2R^a$,
(37) —$N(R^a)C(=O)N(R^a)$—$C_{1-4}$ alkyl-$C(=O)N(R^a)_2$,
(38) —$N(R^a)C(=O)$—$C_{1-4}$ alkyl-$N(R^a)_2$,
(39) —$N(R^a)$—$SO_2$—$N(R^a)_2$,
(40) —$R^k$,
(41) —$C_{1-4}$ alkyl substituted with $R^k$,
(42) —$C_{1-4}$ fluoroalkyl substituted with $R^k$,
(43) —$C_{2-5}$ alkenyl-$R^k$,
(44) —$C_{2-5}$ alkynyl-$R^k$,
(45) —O—$R^k$,
(46) —O—$C_{1-4}$ alkyl-$R^k$,
(47) —$S(O)_n$—$R^k$,
(48) —$S(O)_n$—$C_{1-4}$ alkyl-$R^k$,
(49) —O—$C_{1-4}$ alkyl-$OR^k$,
(50) —O—$C_{1-4}$ alkyl-O—$C_{1-4}$ alkyl-$R^k$,
(52) —$N(R^c)$—$R^k$, —O—$C_{1-4}$ alkyl-$S(O)_nR^k$,
(53) —$N(R^c)$—$C_{1-4}$ alkyl substituted with one or two $R^k$ groups,
(54) —$N(R^c)$—$C_{1-4}$ alkyl-$OR^k$,
(55) —$C(=O)$—$R^k$,
(56) —$C(=O)N(R^a)$—$R^k$,
(57) —$N(R^a)C(=O)$—$R^k$,
(58) —$C(=O)N(R^a)$—$C_{1-4}$ alkyl-$R^k$, or
(59) —$N(R^a)$—$C_{0-4}$ alkyl-$S(O)_nR^k$;

$Q^3$ is
- (1) —H,
- (2) —$C_{1-4}$ alkyl,
- (3) —$C_{1-4}$ fluoroalkyl,
- (4) —O—$C_{1-4}$ alkyl,
- (5) —O—$C_{1-4}$ fluoroalkyl,
- (6) halo selected from —F, —Cl, and —Br,
- (7) —CN,
- (8) —$C_{1-4}$ alkyl-$OR^a$, or
- (9) —$C_{1-4}$ alkyl substituted with $R^k$;

$Q^4$ is:
- (1) —H,
- (2) —$C_{1-4}$ alkyl,
- (3) —$C_{1-4}$ fluoroalkyl,
- (4) —O—$C_{1-4}$ alkyl,
- (5) —O—$C_{1-4}$ fluoroalkyl,
- (6) halo selected from —F, —Cl, and —Br,
- (7) —CN,
- (8) —$C_{1-6}$ alkyl-$OR^a$,
- (9) —$N(R^a)_2$, or
- (10) —$C_{1-6}$ alkyl-$N(R^a)_2$;

each of $R^1$ and $R^2$ is independently:
- (1) —H,
- (2) —$C_{1-4}$ alkyl,
- (3) —$C_{1-4}$ fluoroalkyl,
- (4) —O—$C_{1-4}$ alkyl,
- (5) —O—$C_{1-4}$ fluoroalkyl,
- (6) —OH,
- (7) halo,
- (8) —CN,
- (9) —$C_{1-4}$ alkyl-$OR^a$,
- (10) —$(CH_2)_{0-2}C(=O)R^a$,
- (11) —$(CH_2)_{0-2}CO_2R^a$,
- (12) —$(CH_2)_{0-2}SR^a$,
- (13) —$N(R^a)_2$,
- (14) —$C_{1-4}$ alkyl $N(R^a)_2$,
- (15) —$(CH_2)_{0-2}C(=O)N(R^a)_2$,
- (16) —$C_{1-4}$ alkyl-$N(R^a)$—$C(R^a)=O$,
- (17) —$SO_2R^a$,
- (18) —$N(R^a)SO_2R^a$,
- (19) —O—$C_{1-4}$ alkyl-$OR^a$,
- (20) —O—$C_{1-4}$ alkyl-$SR^a$,
- (21) —O—$C_{1-4}$ alkyl-NH—$CO_2R^a$,
- (22) —O—$C_{2-4}$ alkyl-$N(R^a)_2$,
- (23) —$N(R^a)$—$C_{1-4}$ alkyl-$SR^a$,
- (24) —$N(R^a)$—$C_{1-4}$ alkyl-$OR^a$,
- (25) —$N(R^a)$—$C_{1-4}$ alkyl-$N(R^a)_2$,
- (26) —$N(R^a)$—$C_{1-4}$ alkyl-$N(R^a)$—$C(R^a)=O$,
- (27) —$R^k$,
- (28) —$C_{1-4}$ alkyl substituted with 1 or 2 $R^k$ groups,
- (29) —$C_{1-4}$ fluoroalkyl substituted with 1 or 2 $R^k$ groups,
- (30) —O—$R^k$,
- (31) —O—$C_{1-4}$ alkyl-$R^k$,
- (32) —$S(O)_n$—$R^k$,
- (33) —$S(O)_n$—$C_{1-4}$ alkyl-$R^k$,
- (34) —O—$C_{1-4}$ alkyl-$OR^k$,
- (35) —O—$C_{1-4}$ alkyl-O—$C_{1-4}$ alkyl-$R^k$,
- (36) —O—$C_{1-4}$ alkyl-$S(O)_nR^k$, or
- (37) —$C_{0-4}$ alkyl-$N(R^b)(R^c)$;

each of $R^3$ and $R^4$ is independently
- (1) —H,
- (2) halo,
- (3) —CN,
- (4) —OH,
- (5) $C_{1-4}$ alkyl,
- (6) $C_{1-4}$ fluoroalkyl,
- (7) —O—$C_{1-4}$ alkyl,
- (8) —O—$C_{1-4}$ fluoroalkyl,
- (9) —$C_{1-4}$ alkyl-$OR^a$,
- (10) —O—$C_{1-4}$ alkyl-$OR^a$,
- (11) —O—$C_{1-4}$ alkyl-$SR^a$,
- (12) —O—$C_{1-4}$ alkyl-NH—$CO_2R^a$, or
- (13) —O—$C_{2-4}$ alkyl-$N(R^a)_2$;

$R^5$ is
- (1) —H,
- (2) —$C_{1-4}$ alkyl, optionally substituted with 1 or 2 substituents independently selected from halogen, —O—$C_{1-4}$ alkyl, —O—$C_{1-4}$ fluoroalkyl, —$N(R^a)_2$, and —$CO_2R^a$;
- (3) phenyl optionally substituted with from 1 to 3 substituents independently selected from halogen, $C_{1-4}$ alkyl, $C_{1-4}$ fluoroalkyl, —O—$C_{1-4}$ alkyl, —O—$C_{1-4}$ fluoroalkyl, —S—$C_{1-4}$ alkyl, —CN, and —OH, or
- (4) —$C_{1-4}$ alkyl substituted with phenyl;

each $R^a$ is independently —H or —$C_{1-4}$ alkyl;

each $R^b$ is independently:
- (1) —H,
- (2) —$C_{1-4}$ alkyl,
- (3) —$C_{1-4}$ fluoroalkyl,
- (4) —$R^k$,
- (5) —$C_{1-4}$ alkyl-$R^k$,
- (6) —$S(O)_n$—$R^k$, or
- (7) —$C(=O)$—$R^k$;

each $R^c$ is independently
- (1) —H,
- (2) —$C_{1-4}$ alkyl,
- (3) —$C_{1-4}$ alkyl substituted with —$N(R^a)_2$, or
- (4) —$C_{1-4}$ alkyl-phenyl, wherein the phenyl is optionally substituted with 1 to 3 substituents independently selected from halogen, $C_{1-4}$ alkyl, $C_{1-4}$ fluoroalkyl, —O—$C_{1-4}$ alkyl, —O—$C_{1-4}$ fluoroalkyl, —S—$C_{1-4}$ alkyl, —CN, and —OH;

each $R^k$ is independently:
- (1) aryl selected from phenyl and naphthyl, wherein aryl is unsubstituted or substituted with from 1 to 5 substituents independently selected from:
  - (a) halogen,
  - (b) $C_{1-6}$ alkyl,
  - (c) $C_{1-6}$ fluoroalkyl,
  - (d) —O—$C_{1-6}$ alkyl,
  - (e) —O—$C_{1-6}$ fluoroalkyl,
  - (f) phenyl,
  - (g) —S—$C_{1-6}$ alkyl,
  - (h) —CN,
  - (i) —OH,
  - (j) phenyloxy, unsubstituted or substituted with from 1 to 3 substituents independently selected from:
    - (i) halogen,
    - (ii) $C_{1-6}$ alkyl,
    - (iii) $C_{1-6}$ fluoroalkyl, and
    - (iv) —OH,
  - (k) —$N(R^a)_2$,
  - (l) —$C_{1-6}$ alkyl-$N(R^a)_2$,
  - (m) naphthyl, which is unsubstituted or substituted with from 1 to 4 substituents independently selected from halogen, $C_{1-4}$ alkyl, and —O—$C_{1-4}$ alkyl,
  - (n) —$R^t$,
  - (o) —$(CH_2)_{0-3}C(=O)N(R^a)_2$, and
  - (p) —$(CH_2)_{0-3}C(=O)R^a$;
- (2) —$C_{3-7}$ cycloalkyl, unsubstituted or substituted with from 1 to 3 substituents independently selected from:

(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) phenyl, and
(h) —OH;
(3) —$C_{3-7}$ cycloalkyl fused with a phenyl ring, unsubstituted or substituted with from 1 to 5 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN, and
(g) —OH;
(4) a 5- or 6-membered heteroaromatic ring containing from 1 to 4 heteroatoms independently selected from oxygen, nitrogen and sulfur, wherein the heteroaromatic ring is unsubstituted or substituted on nitrogen or carbon with from 1 to 5 substituents independently selected from:
(a) halogen,
(b) $C_{1-6}$ alkyl,
(c) $C_{1-6}$ fluoroalkyl,
(d) —O—$C_{1-6}$ alkyl,
(e) —O—$C_{1-6}$ fluoroalkyl,
(f) phenyl,
(g) —S—$C_{1-6}$ alkyl,
(h) —CN,
(i) —OH,
(j) phenyloxy, unsubstituted or substituted with from 1 to 3 substituents independently selected from:
  (i) halogen,
  (ii) $C_{1-6}$ alkyl,
  (iii) $C_{1-6}$ fluoroalkyl, and
  (iv) —OH,
(k) —N($R^a$)$_2$,
(l) —$C_{1-6}$ alkyl-N($R^a$)$_2$,
(m) naphthyl, which is unsubstituted or substituted with from 1 to 4 substituents independently selected from halogen, $C_{1-4}$ alkyl, and —O—$C_{1-4}$ alkyl,
(n) —$R^t$,
(o) oxo,
(p) —(CH$_2$)$_{0-3}$C(=O)N($R^a$)$_2$, and
(q) —(CH$_2$)$_{0-3}$C(=O)$R^a$;
(5) a 5- or 6- or 7-membered saturated heterocyclic ring containing from 1 to 3 heteroatoms independently selected from oxygen, nitrogen and sulfur, wherein the heterocyclic ring is unsubstituted or substituted with from 1 to 4 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) oxo,
(h) phenyl
(i) benzyl,
(j) phenylethyl,
(k) —OH,
(l) —(CH$_2$)$_{0-3}$C(=O)N($R^a$)$_2$,
(m) —(CH$_2$)$_{0-3}$C(=O)$R^a$,
(n) —N($R^a$)—C(=O)$R^a$,
(o) —N($R^a$)—CO$_2$$R^a$,
(p) —(CH$_2$)$_{1-3}$N($R^a$)—C(=O)$R^a$,
(q) —N($R^a$)$_2$,
(r) —(CH$_2$)$_{1-3}$N($R^a$)$_2$,
(s) —(CH$_2$)$_{1-3}$O$R^a$,
(t) —(CH$_2$)$_{0-3}$CO$_2$$R^a$,
(u) —(CH$_2$)$_{0-3}$—O—(CH$_2$)$_{1-3}$—O$R^a$,
(v) —SO$_2$$R^a$,
(w) —SO$_2$N($R^a$)$_2$,
(x) —(CH$_2$)$_{0-3}$C(O)O(CH$_2$)$_{1-2}$CH=CH$_2$,
(y) naphthyl, which is unsubstituted or substituted with from 1 to 4 substituents independently selected from halogen, $C_{1-4}$ alkyl, and —O—$C_{1-4}$ alkyl,
(z) —(CH$_2$)$_{1-3}$-naphthyl, wherein the naphthyl is unsubstituted or substituted with from 1 to 4 substituents independently selected from halogen, $C_{1-4}$ alkyl, and —O—$C_{1-4}$ alkyl,
(aa) $R^t$,
(bb) —(CH$_2$)$_{1-3}$$R^t$,
(cc) —(CH$_2$)$_{0-3}$C(=O)$R^t$, and
(dd) —N(H)$R^t$ or —N($C_{1-4}$ alkyl)$R^t$; or
(6) an 8- to 10- membered heterobicyclic ring containing from 1 to 4 heteroatoms independently selected from oxygen, nitrogen and sulfur, wherein the heterobicyclic ring is saturated or unsaturated, and is unsubstituted or substituted with from 1 to 5 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) =O, and
(h) —OH;

$R^t$ is a 5- or 6-membered heteromonocylic ring containing from 1 to 4 nitrogen atoms, wherein the heteromonocyclic ring is saturated or unsaturated, and wherein the heteromonocyclic ring is unsubstituted or substituted with from 1 to 4 substituents independently selected from halogen, oxo, $C_{1-4}$ alkyl, and —O—$C_{1-4}$ alkyl; and n is an integer equal to 0, 1 or 2;

or a pharmaceutically acceptable salt thereof.

4. The compound according to claim 3,
wherein
$Q^2$ is
(1) —H,
(2) —$C_{1-4}$ alkyl,
(3) —(CH$_2$)$_{0-2}$CF$_3$,
(4) —O—$C_{1-4}$ alkyl,
(5) —O—(CH$_2$)$_{0-2}$CF$_3$,
(6) halo selected from —F, —Cl and —Br,
(7) —CN,
(8) —(CH$_2$)$_{1-3}$O$R^a$,
(9) —(CH$_2$)$_{0-2}$C(=O)$R^a$,
(10) —(CH$_2$)$_{0-2}$CO$_2$$R^a$,
(11) —(CH$_2$)$_{0-2}$S$R^a$,
(12) —N($R^a$)$_2$,
(13) —(CH$_2$)$_{1-3}$N($R^a$)$_2$,
(14) —(CH$_2$)$_{0-2}$C(=O)N($R^a$)$_2$,
(15) —G—(CH$_2$)$_{1-2}$—C(=O)N($R^a$)$_2$, wherein G is O, S, N($R^a$), or N(SO$_2$$R^a$),
(16) —N($R^a$)—C($R^a$)=O,

(17) —(CH$_2$)$_{1-2}$—N(R$^a$)—C(R$^a$)=O,
(18) —C(=O)—N(R$^a$)—(CH$_2$)$_{1-3}$—[C(=O)]$_{0-1}$—N(R$^a$)$_2$,
(19) —C(=O)—N(R$^a$)—(CH$_2$)$_{1-2}$H substituted with 1 or 2—OR$^a$,
(20) —SO$_2$R$^a$,
(21) —N(R$^a$)SO$_2$R$^a$,
(22) —CH=CH—(CH$_2$)$_{0-1}$—C(=O)—N(R$^a$)$_2$,
(23) —C≡C—CH$_2$OR$^a$,
(24) —C≡C—CH$_2$SR$^a$,
(25) —C≡C—CH$_2$SO$_2$R$^a$,

(26) 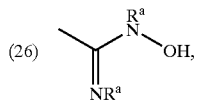

(27) —N(R$^a$)—(CH$_2$)$_{1-4}$SR$^a$,
(28) —N(R$^a$)—(CH$_2$)$_{1-4}$OR$^a$,
(29) —N(R$^a$)—(CH$_2$)$_{1-4}$—N(R$^a$)$_2$,
(30) —N(R$^a$)—(CH$_2$)$_{1-4}$N(R$^a$)—C(R$^a$)=O,
(31) —N(R$^a$)—(CH$_2$)$_{0-2}$—[C(=O)]$_{1-2}$N(R$^a$)$_2$,
(32) —N(R$^a$)—(CH$_2$)$_{1-4}$—CO$_2$R$^a$,
(33) —N(R$^a$)C(=O)N(R$^a$)—(CH$_2$)$_{1-4}$—C(=O)N(R$^a$)$_2$,
(34) —N(R$^a$)C(=O)—(CH$_2$)$_{1-4}$—N(R$^a$)$_2$,
(35) —N(R$^a$)—SO$_2$—N(R$^a$)$_2$,
(36) —R$^k$,
(37) —(CH$_2$)$_{1-4}$R$^k$,
(38) —C≡C—CH$_2$R$^k$,
(39) —O—R$^k$,
(40) —S(O)$_n$—R$^k$,
(41) —N(R$^c$)—R$^k$,
(42) —N(R$^c$)—(CH$_2$)$_{1-4}$H substituted with one or two R$^k$ groups,
(43) —N(R$^c$)—(CH$_2$)$_{1-4}$OR$^k$,
(44) —C(=O)—R$^k$,
(45) —C(=O)N(R$^a$)—R$^k$,
(46) —N(R$^a$)C(=O)—R$^k$,
(47) —C(=O)N(R$^a$)—(CH$_2$)$_{1-4}$R$^k$, or
(48) —N(R$^a$)—S(O)$_n$R$^k$;

Q$^3$ is —H;
Q$^4$ is —H;
each of R$^1$ and R$^2$ is independently:
(1) —H,
(2) —C$_{1-4}$ alkyl,
(3) —(CH$_2$)$_{0-2}$CF$_3$,
(4) —O—C$_{1-4}$ alkyl,
(5) —O—(CH$_2$)$_{0-2}$CF$_3$,
(6) —OH,
(7) halo selected from —F, —Cl and —Br,
(8) —CN,
(9) —(CH$_2$)$_{1-3}$OR$^a$,
(10) —(CH$_2$)$_{0-2}$C(=O)R$^a$,
(11) —(CH$_2$)$_{0-2}$CO$_2$R$^a$,
(12) —(CH$_2$)$_{0-2}$SR$^a$,
(13) —N(R$^a$)$_2$,
(14) —(CH$_2$)$_{1-3}$N(R$^a$)$_2$,
(15) —(CH$_2$)$_{0-2}$C(=O)N(R$^a$)$_2$,
(16) —C$_{1-4}$ alkyl-N(R$^a$)—C(R$^a$)=O,
(17) —SO$_2$R$^a$,
(18) —N(R$^a$)SO$_2$R$^a$,
(19) —O—(CH$_2$)$_{1-4}$OR$^a$,
(20) —O—(CH$_2$)$_{1-4}$SR$^a$,
(21) —O—(CH$_2$)$_{1-4}$NH—CO$_2$R$^a$,
(22) —O—(CH$_2$)$_{2-4}$N(R$^a$)$_2$,
(23) —N(R$^a$)—(CH$_2$)$_{1-4}$SR$^a$,
(24) —N(R$^a$)—(CH$_2$)$_{1-4}$OR$^a$,
(25) —N(R$^a$)—(CH$_2$)$_{1-4}$N(R$^a$)$_2$,
(26) —N(R$^a$)—(CH$_2$)$_{1-4}$N(R$^a$)—C(R$^a$)=O,
(27) —R$^k$,
(28) —(CH$_2$)$_{1-4}$H substituted with 1 or 2 R$^k$ groups,
(29) —O—R$^k$,
(30) —O—(CH$_2$)$_{1-4}$R$^k$,
(31) —S(O)$_n$—R$^k$,
(32) —S(O)$_n$—(CH$_2$)$_{1-4}$R$^k$,
(33) —O—(CH$_2$)$_{1-4}$OR$^k$,
(34) —O—(CH$_2$)$_{1-4}$—O—(CH$_2$)$_{1-4}$R$^k$,
(35) —O—(CH$_2$)$_{1-4}$SR$^k$, or
(36) —(CH$_2$)$_{0-4}$N(R$^b$)(R$^k$);

each of R$^3$ and R$^4$ is independently
(1) —H,
(2) halo selected from —F, —Cl and —Br,
(3) —CN,
(4) —OH,
(5) C$_{1-4}$ alkyl,
(6) —(CH$_2$)$_{0-2}$CF$_3$,
(7) —O—C$_{1-4}$ alkyl, or
(8) —O(CH$_2$)$_{0-2}$CF$_3$; and R$^5$ is
(1) —H,
(2) —C$_{1-4}$ alkyl,
(3) —(CH$_2$)$_{1-4}$N(R$^a$)$_2$,
(4) —(CH$_2$)$_{1-4}$CO$_2$R$^a$,
(5) phenyl optionally substituted with from 1 to 3 substituents independently selected from halogen, C$_{1-4}$ alkyl, —(CH$_2$)$_{0-2}$CF$_3$, —O—C$_{1-4}$ alkyl, —O(CH$_2$)$_{0-2}$CF$_3$, —S—C$_{1-4}$ alkyl, —CN, and —OH, or
(6) —(CH$_2$)$_{1-4}$-phenyl;

or a pharmaceutically acceptable salt thereof.

5. The compound according to claim 4, which is a compound of Formula (III):

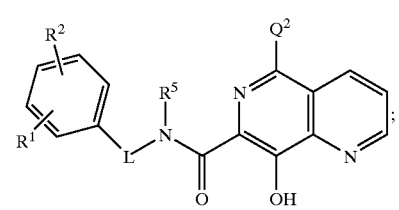

(III)

or a pharmaceutically acceptable salt thereof.

6. The compound according to claim 5, wherein

L is
(i) a single bond;
(ii) —(CH$_2$)$_{1-3}$—, which is optionally substituted with 1 or 2 substituents independently selected from the group consisting of —F, —Cl, —Br, —OH, methyl, ethyl, —CO$_2$CH$_3$, —CO$_2$CH$_2$-phenyl, phenyl, benzyl, —(CH$_2$)$_{1-2}$OH, —CH(OH)-phenyl, and —CH(NH$_2$)-phenyl; or (iii) 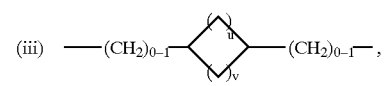

wherein u and v are each integers having a value of from 0 to 3, provided that the sum of u+v is 1, 2, 3 or 4;

each of $R^1$ and $R^2$ is independently:
(1) —H,
(2) methyl,
(3) ethyl,
(4) $CF_3$,
(5) methoxy,
(6) ethoxy
(7) —$OCF_3$
(8) halo selected from —F, —Cl and —Br,
(9) —CN,
(10) —$CH_2OR^a$,
(11) —$CO_2R^a$,
(12) —$SR^a$,
(13) —$N(R^a)_2$,
(14) —$(CH_2)_{1-3}N(R^a)_2$,
(15) —$SO_2R^a$,
(16) —$(CH_2)_{1-2}N(R^a)$—$C(R^a)$=O,
(17) —$R^k$,
(18) —$(CH_2)_{1-3}H$ substituted with 1 or 2 $R^k$ groups,
(19) —O—$R^k$, or
(20) —O—$(CH_2)_{1-3}R^k$;
$R^5$ is
(1) —H,
(2) methyl,
(3) —$(CH_2)_{1-2}N(R^a)_2$,
(4) —$(CH_2)_{1-2}CO_2CH_3$, or
(5) —$(CH_2)_{1-2}CO_2CH_2CH_3$;
(6) phenyl, or
(7) benzyl;
each $R^a$ is independently —H or —$C_{1-4}$ alkyl;
each $R^c$ is independently
(1) —H,
(2) —$C_{1-4}$ alkyl,
(3) —$(CH_2)_{1-4}N(R^a)_2$, or
(4) —$(CH_2)_{1-4}$-phenyl, wherein the phenyl is optionally substituted with 1 to 3 substituents independently selected from halogen, $C_{1-4}$ alkyl, $C_{1-4}$ fluoroalkyl, —O—$C_{1-4}$ alkyl, —O—$C_{1-4}$ fluoroalkyl, —S—$C_{1-4}$ alkyl, —CN, and —OH; and
each $R^k$ is independently:
(1) aryl selected from phenyl and naphthyl, wherein aryl is unsubstituted or substituted with from 1 to 4 substituents independently selected from:
(a) halogen,
(b) $C_{1-4}$ alkyl,
(c) $C_{1-4}$ fluoroalkyl,
(d) —O—$C_{1-4}$ alkyl,
(e) —O—$C_{1-4}$ fluoroalkyl,
(f) phenyl,
(g) —S—$C_{1-4}$ alkyl,
(h) —CN,
(i) —OH,
(j) phenyloxy, unsubstituted or substituted with from 1 to 3 substituents independently selected from:
(i) halogen,
(ii) $C_{1-4}$ alkyl,
(iii) $C_{1-4}$ fluoroalkyl, and
(iv) —OH,
(k) —$N(R^a)_2$,
(l) —$C_{1-4}$ alkyl-$N(R^a)_2$,
(m) naphthyl, which is unsubstituted or substituted with 1 or 2 substituents independently selected from halogen, $C_{1-4}$ alkyl, and —O—$C_{1-4}$ alkyl,
(n) —$R^t$,
(o) —$(CH_2)_{0-3}C(=O)N(R^a)_2$, and
(p) —$(CH_2)_{0-3}C(=O)R^a$;
(2) —$C_{3-6}$ cycloalkyl, unsubstituted or substituted with from 1 to 3 substituents independently selected from:
(a) halogen,
(b) $C_{1-4}$ alkyl,
(c) —O—$C_{1-4}$ alkyl,
(d) $C_{1-4}$ fluoroalkyl,
(e) —O—$C_{1-4}$ fluoroalkyl,
(f) —CN,
(g) phenyl, and
(h) —OH;
(3) —$C_{3-6}$ cycloalkyl fused with a phenyl ring, unsubstituted or substituted with from 1 to 4 substituents independently selected from:
(a) halogen,
(b) $C_{1-4}$ alkyl,
(c) —O—$C_{1-4}$ alkyl,
(d) $C_{1-4}$ fluoroalkyl,
(e) —O—$C_{1-4}$ fluoroalkyl,
(f) —CN, and
(g) —OH;
(4) a 5- or 6-membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with from 1 to 4 substituents independently selected from:
(a) halogen,
(b) $C_{1-4}$ alkyl,
(c) $C_{1-4}$ fluoroalkyl,
(d) —O—$C_{1-4}$ alkyl,
(e) —O—$C_{1-4}$ fluoroalkyl,
(f) phenyl,
(g) —S—$C_{1-4}$ alkyl,
(h) —CN,
(i) —OH,
(j) phenyloxy, unsubstituted or substituted with from 1 to 3 substituents independently selected from:
(i) halogen,
(ii) $C_{1-4}$ alkyl,
(iii) $C_{1-4}$ fluoroalkyl, and
(iv) —OH,
(k) —$N(R^a)_2$,
(l) —$C_{1-4}$ alkyl-$N(R^a)_2$,
(m) naphthyl, which is unsubstituted or substituted with 1 or 2 substituents independently selected from halogen, $C_{1-4}$ alkyl, and —O—$C_{1-4}$ alkyl,
(n) —$R^t$,
(o) oxo,
(p) —$(CH_2)_{0-3}C(=O)N(R^a)_2$, and
(q) —$(CH_2)_{0-3}C(=O)R^a$;
(5) a 5- or 6- or 7- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, azepanyl, thiadiazepanyl, dithiazepanyl, diazepanyl, and thiadiazinanyl, and wherein the heterocyclic ring is unsubstituted or substituted with from 1 to 4 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) oxo, (h) phenyl
(i) benzyl,
(j) phenylethyl,
(k) —OH,
(l) —(CH$_2$)$_{0-3}$C(=O)N(R$^a$)$_2$,
(m) —(CH$_2$)$_{0-3}$C(=O)R$^a$,
(n) —N(R$^a$)—C(=O)R$^a$,
(o) —N(R$^a$)—CO$_2$R$^a$,
(p) —(CH$_2$)$_{1-3}$N(R$^a$)—C(=O)R$^a$,
(q) —N(R$^a$)$_2$,
(r) —(CH$_2$)$_{1-3}$N(R$^a$)$_2$,
(s) —(CH$_2$)$_{1-3}$—OR$^a$,
(t) —(CH$_2$)$_{0-3}$CO$_2$R$^a$,
(u) —(CH$_2$)$_{0-3}$—O—(CH$_2$)$_{1-3}$—OR$^a$,
(v) —SO$_2$R$^a$,
(w) —SO$_2$N(R$^a$)$_2$,
(x) —(CH$_2$)$_{0-3}$C(=O)O(CH$_2$)$_{1-2}$CH=CH$_2$,
(y) naphthyl, which is unsubstituted or substituted with 1 or 2 substituents independently selected from halogen, C$_{1-4}$ alkyl, and —O—C$_{1-4}$ alkyl,
(z) —(CH$_2$)$_{1-3}$-naphthyl, wherein the naphthyl is unsubstituted or substituted with 1 or 2 substituents independently selected from halogen, C$_{1-4}$ alkyl, and —O—C$_{1-4}$ alkyl,
(aa) —R$^t$,
(bb) —(CH$_2$)$_{1-3}$R$^t$,
(cc) —(CH$_2$)$_{0-3}$C(=O)R$^t$, and
(dd) —N(H)R$^t$ or —N(C$_{1-4}$ alkyl)R$^t$; or
(6) an 8- to 10-membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, isochromanyl, hexahydropyrazolo[4,3-c]pyridinyl, hexahydropurinyl, hexahydrooxazolo[3,4a]pyrazinyl, and 1,2,3,4-tetrahydro-1,8-naphthyridinyl; and wherein the bicyclic ring is unsubstituted or substituted with from 1 to 3 substituents independently selected from:
(a) halogen,
(b) C$_{1-4}$ alkyl,
(c) —O—C$_{1-4}$ alkyl,
(d) C$_{1-4}$ fluoroalkyl,
(e) —O—C$_{1-4}$ fluoroalkyl,
(f) —CN,
(g) =O, and
(h) —OH;

R$^t$ is a 5- or 6-membered heteromonocylic ring selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; and wherein the heteromonocyclic ring is unsubstituted or substituted with 1 or 2 substituents independently selected from halogen, oxo, C$_{1-4}$ alkyl, and —O—C$_{1-4}$ alkyl;

or a pharmaceutically acceptable salt thereof.

7. A compound of Formula (IV):

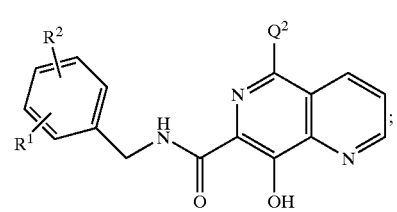

(IV)

wherein
Q$^2$ is
(1) —H,
(2) —C$_{1-4}$ alkyl,
(3) —(CH$_2$)$_{0-2}$CF$_3$,
(4) —O—C$_{1-4}$ alkyl,
(5) —O—(CH$_2$)$_{0-2}$CF$_3$,
(6) halo selected from —F, —Cl and —Br,
(7) —CN,
(8) —(CH$_2$)$_{1-3}$OR$^a$,
(9) —(CH$_2$)$_{0-2}$C(=O)R$^a$,
(10) —(CH$_2$)$_{0-2}$CO$_2$R$^a$,
(11) —(CH$_2$)$_{0-2}$SR$^a$,
(12) —N(R$^a$)$_2$,
(13) —(CH$_2$)$_{1-3}$N(R$^a$)$_2$,
(14) —(CH$_2$)$_{0-2}$C(=O)N(R$^a$)$_2$,
(15) —G—(CH$_2$)$_{1-2}$—C(=O)N(R$^a$)$_2$, wherein G is O, S, N(R$^a$), or N(SO$_2$R$^a$),
(16) —N(R$^a$)—C(R$^a$)=O,
(17) —(CH$_2$)$_{1-2}$—N(R$^a$)—C(R$^a$)=O,
(18) —C(=O)—N(R$^a$)—(CH$_2$)$_{1-3}$—[C(=O)]$_{0-1}$—N(R$^a$)$_2$,
(19) —C(=O)—N(R$^a$)—(CH$_2$)$_{1-2}$H substituted with 1 or 2 —OR$^a$,
(20) —SO$_2$R$^a$,
(21) —N(R$^a$)SO$_2$R$^a$,
(22) —CH=CH—(CH$_2$)$_{0-1}$—C(=O)—N(R$^a$)$_2$,
(23) —C≡C—CH$_2$OR$^a$,
(24) —C≡C—CH$_2$SR$^a$,
(25) —C≡C—CH$_2$SO$_2$R$^a$,

(26) 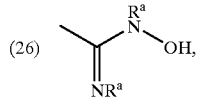

(27) —N(R$^a$)—(CH$_2$)$_{1-4}$SR$^a$,
(28) —N(R$^a$)—(CH$_2$)$_{1-4}$OR$^a$,
(29) —N(R$^a$)—(CH$_2$)$_{1-4}$—N(R$^a$)$_2$,
(30) —N(R$^a$)—(CH$_2$)$_{1-4}$N(R$^a$)—C(R$^a$)=O,
(31) —N(R$^a$)—(CH$_2$)$_{0-2}$—[C(=O)]$_{1-2}$N(R$^a$)$_2$,
(32) —N(R$^a$)—(CH$_2$)$_{1-4}$—CO$_2$R$^a$,
(33) —N(R$^a$)C(=O)N(R$^a$)—(CH$_2$)$_{1-4}$—C(=O)N(R$^a$)$_2$,
(34) —N(R$^a$)C(=O)—(CH$_2$)$_{1-4}$—N(R$^a$)$_2$,
(35) —N(R$^a$)—SO$_2$—N(R$^a$)$_2$,
(36) —R$^k$,
(37) —(CH$_2$)$_{1-4}$R$^k$,
(38) —C≡C—CH$_2$R$^k$,
(39) —O—R$^k$,
(40) —S(O)$_n$—R$^k$,
(41) —N(R$^c$)—R$^k$,
(42) —N(R$^c$)—(CH$_2$)$_{1-4}$H substituted with one or two R$^k$ groups,
(43) —N(R$^c$)—(CH$_2$)$_{1-4}$OR$^k$,

(44) —C(=O)—R$^k$,
(45) —C(=O)N(R$^a$)—R$^k$,
(46) —N(R$^a$)C(=O)—R$^k$,
(47) —C(=O)N(R$^a$)—(CH$_2$)$_{1-4}$R$^k$; or
(48) —N(R$^a$)—S(O)$_n$R$^k$;

each of R$^1$ and R$^2$ is independently:
(1) —H,
(2) methyl,
(3) ethyl,
(4) CF$_3$,
(5) methoxy,
(6) ethoxy
(7) —OCF$_3$
(8) halo selected from —F, —Cl and —Br,
(9) —CN,
(10) —CH$_2$OR$^a$,
(11) —CO$_2$R$^a$,
(12) —SR$^a$,
(13) —N(R$^a$)$_2$,
(14) —(CH$_2$)$_{1-3}$N(R$^a$)$_2$,
(15) —SO$_2$R$^a$,
(16) —(CH$_2$)$_{1-2}$N(R$^a$)—C(R$^a$)=O,
(17) —R$^k$,
(18) —(CH$_2$)$_{1-3}$H substituted with 1 or 2 R$^k$ groups,
(19) —O—R$^k$, or
(20) —O—(CH$_2$)$_{1-3}$R$^k$;

each R$^a$ is independently —H or —C$_{1-4}$ alkyl;
each R$^c$ is independently
(1) —H,
(2) —C$_{1-4}$ alkyl,
(3) —(CH$_2$)$_{1-4}$N(R$^a$)$_2$, or
(4) —(CH$_2$)$_{1-4}$-phenyl, wherein the phenyl is optionally substituted with 1 to 3 substituents independently selected from halogen, C$_{1-4}$ alkyl, C$_{1-4}$ fluoroalkyl, —O—C$_{1-4}$ alkyl, —O—C$_{1-4}$ fluoroalkyl, —S—C$_{1-4}$ alkyl, —CN, and —OH; and each R$^k$ is independently:
(1) aryl selected from phenyl and naphthyl, wherein aryl is unsubstituted or substituted with from 1 to 4 substituents independently selected from:
(a) halogen,
(b) C$_{1-4}$ alkyl,
(c) C$_{1-4}$ fluoroalkyl,
(d) —O—C$_{1-4}$ alkyl,
(e) —O—C$_{1-4}$ fluoroalkyl,
(f) phenyl,
(g) —S—C$_{1-4}$ alkyl,
(h) —CN,
(i) —OH,
(j) phenyloxy, unsubstituted or substituted with from 1 to 3 substituents independently selected from:
  (i) halogen,
  (ii) C$_{1-4}$ alkyl,
  (iii) C$_{1-4}$ fluoroalkyl, and
  (iv) —OH,
(k) —N(R$^a$)$_2$,
(l) —C$_{1-4}$ alkyl-N(R$^a$)$_2$,
(m) naphthyl, which is unsubstituted or substituted with from 1 or 2 substituents independently selected from halogen, C$_{1-4}$ alkyl, and —O—C$_{1-4}$ alkyl,
(n) —R$^t$,
(o) —(CH$_2$)$_{0-3}$C(=O)N(R$^a$)$_2$, and
(p) —(CH$_2$)$_{0-3}$C(=O)R$^a$;
(2) —C$_{3-6}$ cycloalkyl, unsubstituted or substituted with from 1 to 3 substituents independently selected from:
(a) halogen,
(b) C$_{1-4}$ alkyl,
(c) —O—C$_{1-4}$ alkyl,
(d) C$_{1-4}$ fluoroalkyl,
(e) —O—C$_{1-4}$ fluoroalkyl,
(f) —CN,
(g) phenyl, and
(h) —OH;
(3) —C$_{3-6}$ cycloalkyl fused with a phenyl ring, unsubstituted or substituted with from 1 to 4 substituents independently selected from:
(a) halogen,
(b) C$_{1-4}$ alkyl,
(c) —O—C$_{1-4}$ alkyl,
(d) C$_{1-4}$ fluoroalkyl,
(e) —O—C$_{1-4}$ fluoroalkyl,
(f) —CN, and
(g) —OH;
(4) a 5- or 6- membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with from 1 to 4 substituents independently selected from:
(a) halogen,
(b) C$_{1-4}$ alkyl,
(c) C$_{1-4}$ fluoroalkyl,
(d) —O—C$_{1-4}$ alkyl,
(e) —O—C$_{1-4}$ fluoroalkyl,
(f) phenyl,
(g) —S—C$_{1-4}$ alkyl,
(h) —CN,
(i) —OH,
(j) phenyloxy, unsubstituted or substituted with from 1 to 3 substituents independently selected from:
  (i) halogen,
  (ii) C$_{1-4}$ alkyl,
  (iii) C$_{1-4}$fluoroalkyl, and
  (iv) —OH,
(k) —N(R$^a$)$_2$,
(l) —C$_{1-4}$ alkyl-N(R$^a$)$_2$,
(m) naphthyl, which is unsubstituted or substituted with from 1 or 2 substituents independently selected from halogen, C$_{1-4}$ alkyl, and —O—C$_{1-4}$ alkyl,
(n) —R$^t$,
(o) oxo,
(p) —(CH$_2$)$_{0-3}$C(=O)N(R$^a$)$_2$, and
(q) —(CH$_2$)$_{0-3}$C(=O)R$^a$;
(5) a 5- or 6- or 7- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, azepanyl, thiadiazepanyl, dithiazepanyl, diazepanyl, and thiadiazinanyl, and wherein the heterocyclic ring is unsubstituted or substituted with from 1 to 4 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(g) oxo, (h) phenyl
(i) benzyl,
(j) phenylethyl,
(k) —OH,
(l) —(CH$_2$)$_{0-3}$C(=O)N(R$^a$)$_2$,
(m) —(CH$_2$)$_{0-3}$C(=O)R$^a$,
(n) —N(R$^a$)—C(=O)R$^a$,
(o) —N(R$^a$)—CO$_2$R$^a$,
(p) —(CH$_2$)$_{1-3}$N(R$^a$)—C(=O)R$^a$,
(q) —N(R$^a$)$_2$,
(r) —(CH$_2$)$_{1-3}$N(R$^a$)$_2$,
(s) —(CH$_2$)$_{1-3}$—OR$^a$,
(t) —(CH$_2$)$_{0-3}$CO$_2$R$^a$,
(u) —(CH$_2$)$_{0-3}$—O—(CH$_2$)$_{1-3}$—OR$^a$,
(v) —SO$_2$R$^a$,
(w) —SO$_2$N(R$^a$)$_2$,
(x) —(CH$_2$)$_{0-3}$C(=O)O(CH$_2$)$_{1-2}$CH=CH$_2$,
(y) naphthyl, which is unsubstituted or substituted with from 1 or 2 substituents independently selected from halogen, C$_{1-4}$ alkyl, and —O—C$_{1-4}$ alkyl,
(z) —(CH$_2$)$_{1-3}$-naphthyl, wherein the naphthyl is unsubstituted or substituted with 1 or 2 substituents independently selected from halogen, C$_{1-4}$ alkyl, and —O—C$_{1-4}$ alkyl,
(aa) R$^t$,
(bb) —(CH$_2$)$_{1-3}$R$^t$,
(cc) —(CH$_2$)$_{0-3}$C(=O)R$^t$, and
(dd) —N(H)R$^t$ or —N(C$_{1-4}$ alkyl)R$^t$; or
(6) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, isochromanyl, hexahydropyrazolo[4,3-c]pyridinyl, hexahydropurinyl, hexahydrooxazolo[3,4a]pyrazinyl, and 1,2,3,4-tetrahydro-1,8-naphthyridinyl; and wherein the bicyclic ring is unsubstituted or substituted with from 1 to 3 substituents independently selected from:
(a) halogen,
(b) C$_{1-4}$ alkyl,
(c) —O—C$_{1-4}$ alkyl,
(d) C$_{1-4}$ fluoroalkyl,
(e) —O—C$_{1-4}$ fluoroalkyl,
(f) —CN,
(g) =O, and
(h) —OH;

R$^t$ is a 5- or 6-membered heteromonocylic ring selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; and wherein the heteromonocyclic ring is unsubstituted or substituted with 1 or 2 substituents independently selected from halogen, oxo, C$_{1-4}$ alkyl, and —O—C$_{1-4}$ alkyl; and
each n is an integer equal to zero, 1 or 2;
or a pharmaceutically acceptable salt thereof.

8. The compound according to claim 7, wherein
Q$^2$ is
(1) —H,
(2) methyl,
(3) ethyl,
(4) CF$_3$,
(5) methoxy,
(6) ethoxy
(7) —OCF$_3$
(8) halo selected from —F, —Cl and —Br,
(9) —CN,
(10) —CH$_2$OH,
(11) —CH$_2$OCH$_3$
(12) —(CH$_2$)$_{0-2}$C(=O)CH$_3$,
(13) —(CH$_2$)$_{0-2}$CO$_2$CH$_3$,
(14) —SR$^a$,
(15) —N(R$^a$)$_2$,
(16) —(CH$_2$)$_{1-2}$N(R$^a$)$_2$,
(17) —(CH$_2$)$_{0-2}$C(=O)N(R$^a$)$_2$,
(18) —S—CH$_2$—C(=O)N(R$^a$)$_2$,
(19) —O—CH$_2$—C(=O)N(R$^a$)$_2$,
(20) —N(SO$_2$R$^a$)—CH$_2$—C(=O)N(R$^a$)$_2$,
(21) —N(R$^a$)—C(R$^a$)=O,
(22) —C(=O)—N(R$^a$)—(CH$_2$)$_{1-2}$—C(=O)N(R$^a$)$_2$,
(23) —C(=O)—N(R$^a$)—(CH$_2$)$_{1-2}$OR$^a$,
(24) —C(=O)—N(R$^a$)—(CH$_2$)$_{1-3}$—N(R$^a$)$_2$,
(25) —SO$_2$R$^a$,
(26) —N(R$^a$)SO$_2$R$^a$,
(27) —CH=CH—C(=O)—N(R$^a$)$_2$,
(28) —C≡C—CH$_2$OR$^a$,
(29) —C≡C—CH$_2$SR$^a$,
(30) —C≡C—CH$_2$SO$_2$R$^a$, (31)

![structure: C(CH$_3$)(=NH)—NH—OH]

(32) —N(R$^a$)—(CH$_2$)$_{1-3}$ SR$^a$,
(33) —N(R$^a$)—(CH$_2$)$_{1-3}$OR$^a$,
(34) —N(R$^a$)—(CH$_2$)$_{1-3}$N(R$^a$)$_2$,
(35) —N(R$^a$)—(CH$_2$)$_{1-3}$N(R$^a$)—C(R$^a$)=O,
(36) —N(R$^a$)CH$_2$—C(=O)N(R$^a$)$_2$,
(37) —N(R$^a$)—C(=O)—C(=O)—N(R$^a$)$_2$,
(38) —N(R$^a$)—C(=O)—N(R$^a$)$_2$,
(39) —N(R$^a$)—(CH$_2$)$_{1-2}$—CO$_2$R$^a$,
(40) —N(R$^a$)—C(=O)—N(R$^a$)—(CH$_2$)$_{1-2}$—C(=O)—N(R$^a$)$_2$,
(41) —N(R$^a$)—C(=O)—(CH$_2$)$_{1-2}$—N(R$^a$)$_2$,
(42) —N(R$^a$)—SO$_2$—N(R$^a$)$_2$,
(43) R$^k$,
(44) —(CH$_2$)$_{1-4}$R$^k$,
(45) —C≡C—CH$_2$R$^k$,
(46) —O—R$^k$,
(47) —S—R$^k$,
(48) —SO$_2$—R$^k$,
(49) —N(R$^c$)—R$^k$,
(50) —N(R$^c$)—(CH$_2$)$_{1-4}$H substituted with one or two R$^k$ groups,
(51) —N(R$^c$)—(CH$_2$)$_{1-4}$OR$^k$,
(52) —C(=O)—R$^k$,
(53) —C(=O)N(R$^a$)—R$^k$,
(54) —N(R$^a$)—C(=O)—R$^k$,
(55) —C(=O)N(R$^a$)—(CH$_2$)$_{1-4}$R$^k$, or
(56) —N(R$^a$)—SO$_2$R$^k$, each of $R^1$ and $R^2$ is independently:
  (1) —H,
  (2) methyl,
  (3) ethyl,
  (4) $CF_3$,
  (5) methoxy,
  (6) ethoxy
  (7) —$OCF_3$,
  (8) halo selected from —F and —Cl,
  (9) —CN,
  (10) —$CH_2OR^a$,
  (11) —$CO_2R^a$,
  (12) —$SR^a$,
  (13) —$N(R^a)_2$,
  (14) —$(CH_2)_{1-3}N(R^a)_2$,
  (15) —$SO_2R^a$,
  (16) —$R^k$,
  (17) —$(CH_2)_{1-3}R^k$,
  (18) —O—$R^k$, or
  (19) —O—$(CH_2)_{1-3}R^k$;
each $R^a$ is independently —H or —$C_{1-4}$ alkyl;
each $R^c$ is independently —H, —$C_{1-4}$ alkyl, or —$(CH_2)_{1-3}$ $N(R^a)_2$;
each $R^k$ is independently:
  (1) phenyl which is unsubstituted or substituted with from 1 to 4 substituents independently selected from:
    (a) halogen selected from —F, —Cl, and —Br,
    (b) methyl or ethyl,
    (c) —$CF_3$,
    (d) methoxy,
    (e) —$OCF_3$,
    (f) phenyl,
    (g) —S—$CH_3$,
    (h) —CN,
    (i) —OH,
    (j) phenyloxy
    (k) —$N(R^a)_2$,
    (l) —$(CH_2)_{1-3}N(R^a)_2$,
    (m) —$R^t$,
    (n) —$(CH_2)_{0-3}C(=O)N(R^a)_2$, and
    (o) —$(CH_2)_{0-3}C(=O)R^a$;
  (2) —$C_{3-6}$ cycloalkyl,
  (3) a 5- or 6- membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with 1 or 2 substituents independently selected from:
    (a) halogen selected from —F, —Cl, and —Br,
    (b) methyl or ethyl,
    (c) —$CF_3$,
    (d) methoxy,
    (e) —$OCF_3$,
    (f) —S—$C_{1-6}$ alkyl,
    (g) —CN,
    (h) —OH,
    (i) —$N(R^a)_2$,
    (j) —$C_{1-6}$ alkyl-$N(R^a)_2$,
    (k) —$R^t$,
    (l) oxo,
    (m) —$(CH_2)_{0-3}C(=O)N(R^a)_2$, and
    (n) —$(CH_2)_{0-3}C(=O)R^a$;
  (4) a 5- or 6- or 7- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, azepanyl, thiadiazepanyl, dithiazepanyl, diazepanyl, and thiadiazinanyl; and wherein the heterocyclic ring is unsubstituted or substituted with 1 to 4 substituents independently selected from:
    (a) halogen selected from —F, —Cl, and —Br,
    (b) methyl or ethyl,
    (c) —$CF_3$,
    (d) methoxy,
    (e) —$OCF_3$,
    (f) —CN,
    (g) =O,
    (h) phenyl,
    (i) benzyl,
    (j) phenylethyl,
    (k) —OH,
    (l) —$(CH_2)_{0-3}C(=O)N(R^a)_2$,
    (m) —$(CH_2)_{0-3}C(=O)R^a$,
    (n) $N(R^a)$—$C(=O)R^a$,
    (o) $N(R^a)$—$CO_2R^a$,
    (p) $(CH_2)_{1-3}N(R^a)$—$C(=O)R^a$,
    (q) $N(R^a)_2$,
    (r) $(CH_2)_{1-3}N(R^a)_2$,
    (s) $SO_2R^a$,
    (t) —$(CH_2)_{0-3}C(=O)R^t$,
    (u) —$R^t$,
    (v) —$N(H)R^t$ or —$N(C_{1-4}$ alkyl)$R^t$, and
    (w) —$(CH_2)_{1-3}R^t$; and
  (5) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, isochromanyl, and 1,2,3,4-tetrahydro-1,8-naphthyridinyl, wherein the bicyclic ring is unsubstituted or substituted with 1 or 2 substituents independently selected from:
    (a) halogen selected from —F, —Cl, and —Br,
    (b) methyl or ethyl,
    (c) —$CF_3$,
    (d) methoxy,
    (e) —$OCF_3$,
    (f) —CN,
    (g) =O, and
    (h) —OH;

$R^t$ is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;

or a pharmaceutically acceptable salt thereof.

9. The compound according to claim 8, which is a compound of Formula (VI):

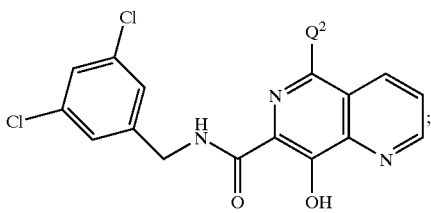

(VI)

or a pharmaceutically acceptable salt thereof.
10. A compound of Formula (V-A):

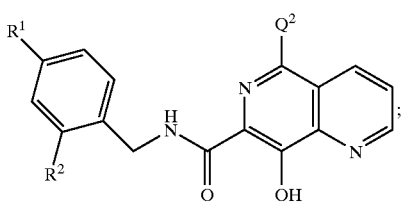

(V-A)

$Q^2$ is
(1) —H,
(2) methyl,
(3) ethyl,
(4) $CF_3$,
(5) methoxy,
(6) ethoxy
(7) —$OCF_3$
(8) halo selected from —F, —Cl and —Br,
(9) —CN,
(10) —$CH_2OH$,
(11) —$CH_2OCH_3$,
(12) —$(CH_2)_{0-2}C(=O)CH_3$,
(13) —$(CH_2)_{0-2}CO_2CH_3$,
(14) —$SR^a$,
(15) —$N(R^a)_2$,
(16) —$(CH_2)_{1-2}N(R^a)_2$,
(17) —$(CH_2)_{0-2}C(=O)N(R^a)_2$,
(18) —S—$CH_2$—$C(=O)N(R^a)_2$,
(19) —O—$CH_2$—$C(=O)N(R^a)_2$,
(20) —$N(SO_2R^a)$—$CH_2$—$C(=O)N(R^a)_2$,
(21) —$N(R^a)$—$C(R^a)$=O,
(22) —$C(=O)$—$N(R^a)$—$(CH_2)_{1-2}$—$C(=O)N(R^a)_2$,
(23) —$C(=O)$—$N(R^a)$—$(CH_2)_{1-2}OR^a$,
(24) —$C(=O)$—$N(R^a)$—$(CH_2)_{1-3}$—$N(R^a)_2$,
(25) —$SO_2R^a$,
(26) —$N(R^a)SO_2R^a$,
(27) —CH=CH—$C(=O)$—$N(R^a)_2$,
(28) —C≡C—$CH_2OR^a$,
(29) —C≡C—$CH_2SR^a$,
(30) —C≡C—$CH_2SO_2R^a$,

(31) 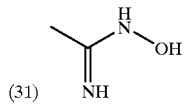

(32) —$N(R^a)$—$(CH_2)_{1-3}SR^a$,
(33) —$N(R^a)$—$(CH_2)_{1-3}OR^a$,
(34) —$N(R^a)$—$(CH_2)_{1-3}N(R^a)_2$,
(35) —$N(R^a)$—$(CH_2)_{1-3}N(R^a)$—$C(R^a)$=O,
(36) —$N(R^a)CH_2$—$C(=O)N(R^a)_2$,
(37) —$N(R^a)$—$C(=O)$—$C(=O)$—$N(R^a)_2$,
(38) —$N(R^a)$—$C(=O)$—$N(R^a)_2$,
(39) —$N(R^a)$—$(CH_2)_{1-2}$—$CO_2R^a$,
(40) —$N(R^a)$—$C(=O)$—$N(R^a)$—$(CH_2)_{1-2}$—$C(=O)$—$N(R^a)_2$,
(41) —$N(R^a)$—$C(=O)$—$(CH_2)_{1-2}$—$C(=O)$—$N(R^a)_2$,
(42) —$N(R^a)$—$SO_2$—$N(R^a)_2$,
(43) —$R^k$,
(44) —$(CH_2)_{1-4}R^k$,
(45) —C≡C—$CH_2R^k$,
(46) —O—$R^k$,
(47) —S—$R^k$,
(48) —$SO_2$—$R^k$,
(49) —$N(R^c)$—$R^k$,
(50) —$N(R^c)$—$(CH_2)_{1-4}H$ substituted with one or two $R^k$ groups,
(51) —$N(R^c)$—$(CH_2)_{1-4}OR^k$,
(52) —$C(=O)$—$R^k$,
(53) —$C(=O)N(R^a)$—$R^k$,
(54) —$N(R^a)$—$C(=O)$—$R^k$,
(55) —$C(=O)N(R^a)$—$(CH_2)_{1-4}R^k$, or
(56) —$N(R^a)$—$SO_2R^k$,
each of $R^1$ and $R^2$ is independently:
(1) —H,
(2) methyl,
(3) ethyl,
(4) $CF_3$,
(5) methoxy,
(6) ethoxy
(7) —$OCF_3$
(8) halo selected from —F and —Cl,
(9) —CN,
(10) —$CH_2OR^a$,
(11) —$CO_2R^a$,
(12) —$SR^a$,
(13) —$N(R^a)_2$,
(14) —$(CH_2)_{1-3}N(R^a)_2$,
(15) —$SO_2R^a$,
(16) —$R^k$,
(17) —$(CH_2)_{1-3}R^k$,
(18) —O—$R^k$, or
(19) —O—$(CH_2)_{1-3}R^k$;
each $R^a$ is independently —H or —$C_{1-4}$ alkyl;
each $R^c$ is independently —H, —$C_{1-4}$ alkyl, or —$(CH_2)_{1-3}N(R^a)_2$;
each $R^k$ is independently:
(1) phenyl which is unsubstituted or substituted with from 1 to 4 substituents independently selected from:
(a) halogen selected from —F, —Cl, and —Br,
(b) methyl or ethyl,
(c) —$CF_3$,
(d) methoxy,
(e) —$OCF_3$,
(f) phenyl,
(g) —S—$CH_3$,
(h) —CN,
(i) —OH,
(j) phenyloxy
(k) —$N(R^a)_2$,
(l) —$(CH_2)_{1-3}N(R^a)_2$,
(m) —$R^t$,
(n) —$(CH_2)_{0-3}C(=O)N(R^a)_2$, and
(o) —$(CH_2)_{0-3}C(=O)R^a$;
(2) —$C_{3-6}$ cycloalkyl,
(3) a 5- or 6- membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with 1 or 2 substituents independently selected from:
(a) halogen selected from —F, —Cl, and —Br,
(b) methyl or ethyl,
(c) —$CF_3$,
(d) methoxy,
(e) —$OCF_3$,
(f) —S—$C_{1-6}$ alkyl,
(g) —CN,
(h) —OH,
(i) —N($R^a$)$_2$,
(j) —$C_{1-6}$ alkyl-N($R^a$)$_2$,
(k) —$R^t$,
(l) oxo,
(m) —$(CH_2)_{0-3}C(=O)N(R^a)_2$, and
(n) —$(CH_2)_{0-3}C(=O)R^a$;
(4) a 5- or 6- or 7- membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, thiazinanyl, thiazepanyl, azepanyl, thiadiazepanyl, dithiazepanyl, diazepanyl, and thiadiazinanyl; and wherein the heterocyclic ring is unsubstituted or substituted with 1 to 4 substituents independently selected from:
(a) halogen selected from —F, —Cl, and —Br,
(b) methyl or ethyl,
(c) —$CF_3$,
(d) methoxy,
(e) —$OCF_3$,
(f) —CN,
(g) =O,
(h) phenyl,
(i) benzyl,
(j) phenylethyl,
(k) —OH,
(l) —$(CH_2)_{0-3}C(=O)N(R^a)_2$,
(m) —$(CH_2)_{0-3}C(=O)R^a$,
(n) N($R^a$)—C(=O)$R^a$,
(o) N($R^a$)—$CO_2R^a$,
(p) $(CH_2)_{1-3}$N($R^a$)—C(=O)$R^a$,
(q) N($R^a$)$_2$,
(r) $(CH_2)_{1-3}$N($R^a$)$_2$,
(s) $SO_2R^a$,
(t) —$(CH_2)_{0-3}C(=O)R^t$,
(u) —$R^t$,
(v) —N(H)$R^t$ or —N($C_{1-4}$ alkyl)$R^t$, and
(w) —$(CH_2)_{1-3}R^t$; and
(5) an 8- to 10- membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, isochromanyl, and 1,2,3,4-tetrahydro-1,8-naphthyridinyl, wherein the bicyclic ring is unsubstituted or substituted with 1 or 2 substituents independently selected from:
(a) halogen selected from —F, —Cl, and —Br,
(b) methyl or ethyl,
(c) —$CF_3$,
(d) methoxy,
(e) —$OCF_3$,
(f) —CN,
(g) =O, and
(h) —OH;

$R^t$ is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;
or a pharmaceutically acceptable salt thereof.

11. The compound according to claim 10, wherein $R^1$ is H or F, and $R^2$ is H or —$SO_2CH_3$, with the proviso that $R^1$ and $R^2$ are not both H;
or a pharmaceutically acceptable salt thereof.

12. The compound according to claim 11, which is a compound of Formula (VIII):

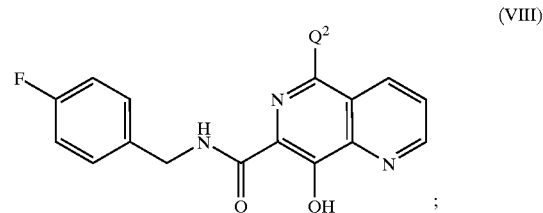

(VIII)

or a pharmaceutically acceptable salt.

13. The compound according to claim 11, wherein $Q^2$ is:
(1) —C(=O)N($R^a$)$_2$,
(2) —$CH_2$C(=O)N($R^a$)$_2$,
(3) —$CH_2CH_2$C(=O)N($R^a$)$_2$,
(4) —S—$CH_2$—C(=O)N($R^a$)$_2$,
(5) —O—$CH_2$—C(=O)N($R^a$)$_2$,
(6) —N($R^a$)—C($R^a$)=O,
(7) —N($SO_2R^a$)—$CH_2$—C(=O)N($R^a$)$_2$,
(8) —N($R^a$)—C(=O)—C(=O)—N($R^a$)$_2$,
(9) —N($R^a$)$SO_2R^a$,
(10) —CH=CH—C(=O)—N($R^a$)$_2$,
(11) —N($R^a$)$CH_2$—C(=O)N($R^a$)$_2$,
(12) —N($R^a$)—C(=O)—N($R^a$)$_2$,
(13) —$R^k$,
(14) —$(CH_2)_{1-3}R^k$, or
(15) —N($R^c$)—$(CH_2)_{1-3}R^k$, each $R^a$ is independently —H or —$C_{1-4}$ alkyl;
each $R^c$ is independently —H or —$C_{1-4}$ alkyl; and
$R^k$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, 1,2-thiazinanyl, 1,4-thiazepanyl, 1,2,5-thiadiazepanyl, 1,5,2-dithiazepanyl, 1,4-diazepanyl, and 1,2,6-thiadiazinanyl, wherein the heterocyclic ring is unsubstituted or substituted with 1 to 4 substituents independently selected from:
(a) methyl or ethyl,
(b) =O,
(c) —C(=O)N($R^a$)$_2$,
(d) —$CH_2$C(=O)N($R^a$)$_2$,
(e) —C(=O)$R^a$, or
(f) —$SO_2R^a$;
or a pharmaceutically acceptable salt thereof.

14. The compound according to claim 13, wherein Q² is:
(1) —C(=O)N(R$^a$)$_2$,
(2) —CH$_2$C(=O)N(R$^a$)$_2$,
(3) —CH$_2$CH$_2$C(=O)N(R$^a$)$_2$,
(4) —S—CH$_2$—C(=O)N(R$^a$)$_2$,
(5) —O—CH$_2$—C(=O)N(R$^a$)$_2$,
(6) —N(SO$_2$R$^a$)—CH$_2$—C(=O)N(R$^a$)$_2$,
(7) —N(R$^a$)—C(=O)—C(=O)—N(R$^a$)$_2$,
(8) —N(R$^a$)SO$_2$R$^a$,
(9) —CH=CH—C(=O)—N(R$^a$)$_2$,
(10) —N(R$^a$)CH$_2$—C(=O)N(R$^a$)$_2$,
(11) —N(R$^a$)—C(=O)—N(R$^a$)$_2$,
(12) —R$^k$,
(13) —(CH$_2$)$_{1-2}$R$^k$, or
(14) —NH—(CH$_2$)$_{1-2}$R$^k$;

each R$^a$ is independently methyl, ethyl, or isopropyl; and
R$^k$ is a saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, pyrazolidinyl, hexahydropyrimidinyl, 1,2-thiazinanyl, 1,4-thiazepanyl, 1,2,5-thiadiazepanyl, 1,5,2-dithiazepanyl, 1,4-diazepanyl, and 1,2,6-thiadiazinanyl, wherein the heterocyclic ring is unsubstituted or substituted with 1 to 4 substituents independently selected from:
(a) methyl or ethyl,
(b) =O,
(c) —C(=O)NH$_2$,
(d) —C(=O)CH$_3$, or
(e) —SO$_2$CH$_3$;
or a pharmaceutically acceptable salt thereof.

15. A compound selected from the group consisting of
N-(3,5-dichlorobenzyl)-8-hydroxy-1,6-naphthyridine-7-carboxamide;
N-(2,5-dichlorobenzyl)-8-hydroxy-1,6-naphthyridine-7-carboxamide;
N-[(1R,S)-2,3-dihydro-1H-inden-1-yl]-8-hydroxy-1,6-naphthyridine-7-carboxamide;
N-[2-(3-chlorophenyl)ethyl]-8-hydroxy-1,6-naphthyridine-7-carboxamide;
N-[2-(2-chlorophenyl)ethyl]-8-hydroxy-1,6-naphthyridine-7-carboxamide;
N-[2-(1,1'-biphenyl-4-yl)ethyl]-8-hydroxy-1,6-naphthyridine-7-carboxamide;
8-hydroxy-N-[2-(4-phenoxyphenyl)ethyl]-1,6-naphthyridine-7-carboxamide;
8-hydroxy-N-(3-phenylpropyl)-1,6-naphthyridine-7-carboxamide;
N-(1,1'-biphenyl-2-ylmethyl)-8-hydroxy-1,6-naphthyridine-7-carboxamide;
N-(1,1'-biphenyl-3-ylmethyl)-8-hydroxy-1,6-naphthyridine-7-carboxamide;
8-hydroxy-N-phenyl-1,6-naphthyridine-7-carboxamide;
8 N-(2-chlorobenzyl)-8-hydroxy-1,6-naphthyridine-7-carboxamide;
N-benzyl-8-hydroxy-N-methyl-1,6-naphthyridine-7-carboxamide;
8-hydroxy-N-(1-methyl-1-phenylethyl)-1,6-naphthyridine-7-carboxamide;
8-hydroxy-N-(2-phenylethyl)-1,6-naphthyridine-7-carboxamide;
8-hydroxy-N-(1-naphthylmethyl)-1,6-naphthyridine-7-carboxamide;
N-benzyl-8-hydroxy-N-phenyl-1,6-naphthyridine-7-carboxamide;
N-(3-chlorobenzyl)-8-hydroxy-1,6-naphthyridine-7-carboxamide;
N-(4-chlorobenzyl)-8-hydroxy-1,6-naphthyridine-7-carboxamide;
Methyl (2S)-{[(8-hydroxy-1,6-naphthyridin-7-yl)carbonyl]amino}(phenyl)ethanoate;
Ethyl N-benzyl-N-[(8-hydroxy-1,6-naphthyridin-7-yl)carbonyl]glycinate;
N-benzyl-8-hydroxy-N-(2-phenylethyl)-1,6-naphthyridine-7-carboxamide;
N-(1,2-diphenylethyl)-8-hydroxy-1,6-naphthyridine-7-carboxamide;
N-(2,3-dihydro-1H-inden-2-yl)-8-hydroxy-1,6-naphthyridine-7-carboxamide;
N-benzyl-8-hydroxy-1,6-naphthyridine-7-carboxamide;
N-(2-anilinoethyl)-8-hydroxy-1,6-naphthyridine-7-carboxamide;
N-(2,2-diphenylethyl)-8-hydroxy-1,6-naphthyridine-7-carboxamide;
N-(3,3-diphenylpropyl)-8-hydroxy-1,6-naphthyridine-7-carboxamide;
N-(2-chloro-6-phenoxybenzyl)-8-hydroxy-1,6-naphthyridine-7-carboxamide;
Methyl (2R)-{[(8-hydroxy-1,6-naphthyridin-7-yl)carbonyl]amino}(phenyl)ethanoate;
8-hydroxy-N-(1,2,3,4-tetrahydronaphthalen-1-yl)-1,6-naphthyridine-7-carboxamide;
N-(2,3-dihydro-1H-inden-1-ylmethyl)-8-hydroxy-1,6-naphthyridine-7-carboxamide;
8-hydroxy-N-(6,7,8,9-tetrahydro-5H-benzo [a][7]annulen-6-ylmethyl)-1,6-naphthyridine-7-carboxamide;
8-hydroxy-N-[2-(1-naphthylamino)ethyl]-1,6-naphthyridine-7-carboxamide;
N-(2,3-dihydro-1H-inden-2-yl methyl)-8-hydroxy-1,6-naphthyridine-7-carboxamide;
8-hydroxy-N-[(1R)-1-phenylethyl]-1,6-naphthyridine-7-carboxamide;
8-hydroxy-N-[(1S)-1-phenylethyl]1,6-naphthyridine-7-carboxamide;
8-hydroxy-N-(3-hydroxy-1-phenylpropyl)-1,6-naphthyridine-7-carboxamide;
N-[2-(4-chlorophenyl)ethyl]-8-hydroxy-1,6-naphthyridine-7-carboxamide;
8-hydroxy-N-[(1R)-2-hydroxy-1-phenylethyl]-1,6-naphthyridine-7-carboxamide;
N-[(1S)-1-benzyl-2-hydroxyethyl]-8-hydroxy-1,6-naphthyridine-7-carboxamide;
N-[(1R)-1-benzyl-2-hydroxyethyl]-8-hydroxy-1,6-naphthyridine-7-carboxamide;
8-hydroxy-N-(2-hydroxy-2-phenylethyl)-1,6-naphthyridine-7-carboxamide;
5-chloro-N-(3,5-dichlorobenzyl)-8-hydroxy-1,6-naphthyridine-7-carboxamide;
N-(3,5-dichlorobenzyl)-8-hydroxy-5-piperidin-1-yl-1,6-naphthyridine-7-carboxamide;
N-(3,5-dichlorobenzyl)-8-hydroxy-5-phenyl-1,6-naphthyridine-7-carboxamide;

N-(3,5-dichlorobenzyl)-8-hydroxy-5-(1H-imidazol-1-yl)-1,6-naphthyridine-7-carboxamide;

N-(3,5-dichlorobenzyl)-8-hydroxy-5-morpholin-4-yl-1,6-naphthyridine-7-carboxamide;

(±)-8-hydroxy-N-[(cis)-3-phenyl-2,3-dihydro-1H-inden-1-yl]-1,6-naphthyridine-7-carboxamide 5-bromo-N-(3,5-dichlorobenzyl)-8-hydroxy-1,6-naphthyridine-7-carboxamide;

N-(benzyl)-8-hydroxy-5-phenyl-1,6-naphthyridine-7-carboxamide;

N-(2,3-dihydro-1H-inden-1-yl)-8-hydroxy-5-phenyl-1,6-naphthyridine-7-carboxamide;

8-hydroxy-N-(1-naphthylmethyl)-5-phenyl-1,6-naphthyridine-7-carboxamide;

N-(2,5-dichlorobenzyl)-8-hydroxy-5-phenyl-1,6-naphthyridine-7-carboxamide;

N-(3-chlorobenzyl)-8-hydroxy-5-phenyl-1,6-naphthyridine-7-carboxamide;

N-[(1S)-2,3-dihydro-1H-inden-1-yl]-8-hydroxy-1,6-naphthyridine-7-carboxamide;

N-(3,5-dichlorobenzyl)-8-hydroxy-5-phenoxy-1,6-naphthyridine-7-carboxamide;

N-(3,5-dichlorobenzyl)-8-hydroxy-5-(4-methylpiperazin-1-yl)-1,6-naphthyridine-7-carboxamide;

5-(4-benzylpiperazin-1-yl)-N-(3,5-dichlorobenzyl)-8-hydroxy-1,6-naphthyridine-7-carboxamide;

N-(3,5-dichlorobenzyl)-5-{4-[2-(formylamino)ethyl]piperazin-1-yl}-8-hydroxy-1,6-naphthyridine-7-carboxamide;

N-(3,5-dichlorobenzyl)-8-hydroxy-5-(4-pyridin-2-ylpiperazin-1-yl)-1,6-naphthyridine-7-carboxamide;

N-(3,5-dichlorobenzyl)-8-hydroxy-5-(4-pyrrolidin-1-ylpiperidin-1-yl)-1,6-naphthyridine-7-carboxamide;

5-anilino-N-(3,5-dichlorobenzyl)-8-hydroxy-1,6-naphthyridine-7-carboxamide;

N-(3,5-dichlorobenzyl)-5-{[3-(formylamino)propyl]amino}-8-hydroxy-1,6-naphthyridine-7-carboxamide;

N-(3,5-dichlorobenzyl)-5-{[2-(dimethylamino)ethyl]amino}-8-hydroxy-1,6-naphthyridine-7-carboxamide;

N-(3,5-dichlorobenzyl)-8-hydroxy-5-[(2-morpholin-4-ylethyl)amino]-1,6-naphthyridine-7-carboxamide;

5-[(1-benzylpiperidin-4-yl)amino]-N-(3,5-dichlorobenzyl)-8-hydroxy-1,6-naphthyridine-7-carboxamide;

N-(3,5-dichlorobenzyl)-5-[[2-(dimethylamino)ethyl](methyl)amino]-8-hydroxy-1,6-naphthyridine-7-carboxamide;

8-Hydroxy-5-phenylsulfanyl-[1,6]naphthyridine-7-carboxylic acid 3,5-dichlorobenzylamide;

5-benzenesulfonyl-8-hydroxy-[1,6]naphthyridine-7-carboxylic acid 3,5-dichlorobenzylamide;

tert-butyl 1-(7-{[(3,5-dichlorobenzyl)amino]carbonyl}-8-hydroxy-1,6-naphthyridin-5-yl)pyrrolidin-3-ylcarbamate;

5-(3-aminopyrrolidin-1-yl)-N-(3,5-dichlorobenzyl)-8-hydroxy-1,6-naphthyridine-7-carboxamide trifluoroacetate;

N-(3,5-dichlorobenzyl)-8-hydroxy-5-(4H-1,2,4-triazol-4-yl)-1,6-naphthyridine-7-carboxamide;

N-(3,5-dichlorobenzyl)-8-hydroxy-5-(1H-1,2,4-triazol-1-yl)-1,6-naphthyridine-7-carboxamide;

N-(3,5-dichlorobenzyl)-8-hydroxy-5-(3-hydroxypyrrolidin-1-yl)-1,6-naphthyridine-7-carboxamide;

5-[3-(acetylamino)pyrrolidin-1-yl]-N-(3,5-dichlorobenzyl)-8-hydroxy-1,6-naphthyridine-7-carboxamide;

N-(3,5-dichlorobenzyl)-5-(4-formylpiperazin-1-yl)-8-hydroxy-1,6-naphthyridine-7-carboxamide;

1-(7-{[(3,5-dichlorobenzyl)amino]carbonyl}-8-hydroxy-1,6-naphthyridin-5-yl)piperazine;

8-Hydroxy-5-(3-hydroxy-prop-1-ynyl)-[1,6]naphthyridine-7-carboxylic acid 3,5-dichlorobenzylamide;

1-(7-{[(3,5-dichlorobenzyl)amino]carbonyl}-8-hydroxy-1,6-naphthyridin-5-yl)-4-(2-oxo-2-pyrrolidin-1-ylethyl)piperazine;

8-Hydroxy-5-(3-piperidin-1-yl-prop-1-ynyl)-[1,6]naphthyridine-7-carboxylic acid 3,5-dichlorobenzylamide;

N-(3,5-dichlorobenzyl)-8-hydroxy-5-thiomorpholin-4-yl-1,6-naphthyridine-7-carboxamide;

5-[3-(aminocarbonyl)piperidin-1-yl]-N-(3,5-dichlorobenzyl)-8-hydroxy-1,6-naphthyridine-7-carboxamide;

1-(7-{[(3,5-dichlorobenzyl)amino]carbonyl}-8-hydroxy-1,6-naphthyridin-5-yl)-4-(2-phenylethyl)piperazine;

4-[(7-{[(3,5-dichlorobenzyl)amino]carbonyl}-8-hydroxy-1,6-naphthyridin-5-yl)amino]pyridine;

5-[(cyclopropylmethyl)amino]-N-(3,5-dichlorobenzyl)-8-hydroxy-1,6-naphthyridine-7-carboxamide;

N-(3,5-dichlorobenzyl)-5-{[2-(formylamino)ethyl]amino}-8-hydroxy-1,6-naphthyridine-7-carboxamide;

2-[(7-{[(3,5-dichlorobenzyl)amino]carbonyl}-8-hydroxy-1,6-naphthyridin-5-yl)amino]ethanamine;

N-(3,5-dichlorobenzyl)-8-hydroxy-5-[(2-methoxyethyl)amino]-1,6-naphthyridine-7-carboxamide;

N-(3,5-dichlorobenzyl)-8-hydroxy-5-{[2-(methylthio)ethyl]amino}-1,6-naphthyridine-7-carboxamide;

1-{2-[(7-{[(3,5-dichlorobenzyl)amino]carbonyl}-8-hydroxy-1,6-naphthyridin-5-yl)amino]ethyl}pyrrolidine;

1 N-(3,5-dichlorobenzyl)-8-hydroxy-5-pyrrolidin-1-yl-1,6-naphthyridine-7-carboxamide;

3-{2-[(7-{[(3,5-dichlorobenzyl)amino]carbonyl}-8-hydroxy-1,6-naphthyridin-5-yl)amino]ethyl}pyridine;

1-{3-[(7-{[(3,5-dichlorobenzyl)amino]carbonyl}-8-hydroxy-1,6-naphthyridin-5-yl)amino]propyl}-1H-imidazoline;

1-{3-[(7-{[(3,5-dichlorobenzyl)amino]carbonyl}-8-hydroxy-1,6-naphthyridin-5-yl)amino]propyl}pyrrolidine;

1-(2-aminoethyl)-4-(7-{[(3,5-dichlorobenzyl)amino]carbonyl}-8-hydroxy-1,6-naphthyridin-5-yl)piperazine;

N-(3,5-dichlorobenzyl)-8-hydroxy-5-[(2-phenoxyethyl)amino]-1,6-naphthyridine-7-carboxamide;

N-(3,5-dichlorobenzyl)-8-hydroxy-5-{[3-(2-oxopyrrolidin-1-yl)propyl]amino}-1,6-naphthyridine-7-carboxamide;

2-[benzyl(7-{[(3,5-dichlorobenzyl)amino]carbonyl}-8-hydroxy-1,6-naphthyridin-5-yl)amino]ethanamine;

1-{3-[(7-{[(3,5-dichlorobenzyl)amino]carbonyl}-8-hydroxy-1,6-naphthyridin-5-yl)amino]propyl}-4-methylpiperazine;

1:1 mixture of 1-(7-{[(3,5-dichlorobenzyl)amino]carbonyl}-8-hydroxy-1,6-naphthyridin-5-yl)-1H- imidazo[4,5-b]pyridine and 3-(7-{[(3,5-dichlorobenzyl)amino]carbonyl}-8-hydroxy-1,6-naphthyridin-5-yl)-3H-imidazo[4,5-b]pyridine;

N-(3,5-dichlorobenzyl)-8-hydroxy-5-{[4-(3-methyl-2-oxoimidazolidin-1-yl)phenyl]amino}-1,6-naphthyridine-7-carboxamide;

N-(3,5-dichlorobenzyl)-8-hydroxy-5-(1,4,6,7-tetrahydro-5H-pyrazolo[4,3-c]pyridin-5-yl)-1,6-naphthyridine-7-carboxamide;

N-(3,5-dichlorobenzyl)-8-hydroxy-5-({[(2R)-5-oxopyrrolidin-2-yl]methyl}amino)-1,6-naphthyridine-7-carboxamide;

N-(3,5-dichlorobenzyl)-8-hydroxy-5-{[(5-oxo-4,5-dihydro-1H-1,2,4-triazol-3-yl)methyl]amino}-1,6-naphthyridine-7-carboxamide;

2-(7-{[(3,5-dichlorobenzyl)amino]carbonyl}-8-hydroxy-1,6-naphthyridin-5-yl)octahydropyrrolo[1,2-a]pyrazine;

N-(3,5-dichlorobenzyl)-8-hydroxy-5-[4-(pyrimidin-2-ylamino)piperidin-1-yl]-1,6-naphthyridine-7-carboxamide 2-{2-[(7-{[(3,5-dichlorobenzyl)amino]carbonyl}-8-hydroxy-1,6-naphthyridin-5-yl)(methyl)amino]ethyl}pyridine;

N-(3,5-dichlorobenzyl)-5-(dimethylamino)-8-hydroxy-1,6-naphthyridine-7-carboxamide;

8-Hydroxy-5-(3-morpholin-4-yl-prop-1-ynyl)-[1,6]naphthyridine-7-carboxylic acid 3,5-dichloro-benzylamide;

N-(3,5-difluorobenzyl)-8-hydroxy-5-(methylsulfonyl)-1,6-naphthyridine-7-carboxamide;

5-cyano-N-(2,3-dimethoxybenzyl)-8-hydroxy-1,6-naphthyridine-7-carboxyamide;

N-(3,5-dichlorobenzyl)-8-hydroxy-5-thien-2-yl-1,6-naphthyridine-7-carboxamide;

8-hydroxy-5-phenylsulfanyl-[1,6]naphthyridine-7-carboxylic acid 2-methylsulfanylbenzylamide;

N-(2,3-dimethoxybenzyl)-8-hydroxy-5-(methylsulfonyl)-1,6-naphthyridine-7-carboxamide;

N-(3,5-dichlorobenzyl)-8-hydroxy-5-[(2-hydroxyethyl)amino]-1,6-naphthyridine-7-carboxamide;

N-(3,5-dichlorobenzyl)-8-hydroxy-5-(propylamino)-1,6-naphthyridine-7-carboxamide;

N-(3,5-dichlorobenzyl)-8-hydroxy-5-[(1H-imidazol-4-ylethyl)amino]-1,6-naphthyridine-7-carboxamide;

N-(3,5-dichlorobenzyl)-8-hydroxy-5-[(3-phenylprop-1-yl)amino]-1,6-naphthyridine-7-carboxamide;

N-(3,5-dichlorobenzyl)-8-hydroxy-5-[(3-morpholin-4-ylpropyl)amino]-1,6-naphthyridine-7-carboxamide;

N-(3,5-dichlorobenzyl)-8-hydroxy-5-[4-(pyridin-2-ylmethyl)piperazin-1-yl]-1,6-naphthyridine-7-carboxamide;

N-(3,5-dichlorobenzyl)-8-hydroxy-5-[(2-morpholin-4-yl-2-pyridin-3-ylethyl)amino]-1,6-naphthyridine-7-carboxamide;

N-(2,3-dimethoxybenzyl)-5-{[4-(dimethylamino)phenyl]thio}-8-hydroxy-1,6-naphthyridine-7-carboxamide;

8-hydroxy-5-methyl-[1,6]naphthyridine-7-carboxylic acid 3,5-dichloro-benzylamide;

8-hydroxy-5-methyl-[1,6]naphthyridine-7-carboxylic acid 4-fluoro-benzylamide;

5-bromo-N-(4-fluorobenzyl)-8-hydroxy-1,6-naphthyridine-7-carboxamide;

1-(7-{[(4-fluorobenzyl)amino]carbonyl}-8-hydroxy-1,6-naphthyridin-5-yl)-4-methylpiperazine;

1-(7-{[(4-fluorobenzyl)amino]carbonyl}-8-hydroxy-1,6-naphthyridin-5-yl)piperazine;

5-[[2-(dimethylamino)-2-oxoethyl](methyl)amino]-N-(4-fluorobenzyl)-8-hydroxy-1,6-naphthyridine-7-carboxamide;

N-1-(7-{[(4-fluorobenzyl)amino]carbonyl}-8-hydroxy-1,6-naphthyridin-5-yl)-N-1-,N-2-,N-2-trimethylethanediamide;

N-(4-fluorobenzyl)-5-(2,6-dioxohexahydropyrimidin-4-yl)-8-hydroxy-[1,6]napthyridine-7-carboxamide;

5-(1,3-dimethyl-2,6-dioxohexahydro-4-pyrimidinyl)-N-(4-fluorobenzyl)-8-hydroxy[1,6]-naphthyridine-7-carboxamide;

5-(1-methyl-2,6-dioxohexahydro-4-pyrimidinyl)-N-(4-fluorobenzyl)-8-hydroxy[1,6]-naphthyridine-7-carboxamide;

5-(3-methyl-2,6-dioxohexahydro-4-pyrimidinyl)-N-(4-fluorobenzyl)-8-hydroxy[1,6]-naphthyridine-7-carboxamide;

N-(4-fluorobenzyl)-8-hydroxy-5-(5-oxo-1,4-thiazepan-7-yl)[1,6]naphthyridine-7-carboxamide;

N-(4-fluorobenzyl)-8-hydroxy-5-(1-oxido-5-oxo-1,4-thiazepan-7-yl)-[1,6]naphthyridine-7-carboxamide;

N-(4-fluorobenzyl)-8-hydroxy-5-(1,1-dioxido-5-oxo-1,4-thiazepan-7-yl)[1,6]-naphthyridine-7-carboxamide;

N-(4-fluorobenzyl)-5-{[2-(dimethylamino)-2-oxoethyl]sulfanyl}-8-hydroxy-[1,6]napthyridine-7-carboxamide;

N-(4-fluorobenzyl)-5-[2-(dimethylamino)-2-oxoethoxy]-8-hydroxy-[1,6]napthyridine-7-carboxamide;

N-(4-fluorobenzyl)-5-{[2-(dimethylamino)-2-oxoethyl](methylsulfonyl)amino}-8-hydroxy-[1,6]napthyridine-7-carboxamide;

N-(4-fluorobenzyl)-5-[3-(dimethylamino)-3-oxopropyl]-8-hydroxy-[1,6]napthyridine-7-carboxamide;

N-(4-fluorobenzyl)-5-[(1E)-3-(dimethylamino)-3-oxo-1-propenyl]-8-hydroxy-[1,6]napthyridine-7-carboxamide;

N-(4-fluorobenzyl)-5-[2-(3-oxo-1-piperazinyl)ethyl]-8-hydroxy-[1,6]napthyridine-7-carboxamide;

N-(4-fluorobenzyl)-5-[2-(2-oxo-1-imidazolidinyl)ethyl]-8-hydroxy-[1,6]napthyridine-7-carboxamide;

N-(4-fluorobenzyl)-5-[2-(2-oxo-1-piperazinyl)ethyl]-8-hydroxy-[1,6]napthyridine-7-carboxamide;

5-(1,1-dioxido-1,2-thiazinan-2-yl)-N-(4-fluorobenzyl)-8-hydroxy-1,6-naphthyridine-7-carboxamide;

5-(1,1-dioxidoisothiazolidin-2-yl)-N-(4-fluorobenzyl)-8-hydroxy-1,6-naphthyridine-7-carboxamide;

N-(4-fluorobenzyl)-8-hydroxy-5-[methyl(methylsulfonyl)amino]-1,6-naphthyridine-7-carboxamide;

5-[acetyl(methyl)amino]-N-(4-fluorobenzyl)-8-hydroxy-1,6-naphthyridine-7-carboxamide;

5-[[(dimethylamino)carbonyl](methyl)amino]-N-(4-fluorobenzyl)-8-hydroxy-1,6-naphthyridine-7-carboxamide;

N-(4-fluorobenzyl)-8-hydroxy-5-thiomorpholin-4-yl-1,6-naphthyridine-7-carboxamide;

5-(1,1-dioxidothiomorpholin-4-yl)-N-(4-fluorobenzyl)-8-hydroxy-1,6-naphthyridine-7-carboxamide;

N-(4-fluorobenzyl)-8-hydroxy-5-(4-methyl-3-oxopiperazin-1-yl)-1,6-naphthyridine-7-carboxamide;
1-(7-{[(4-fluorobenzyl)amino]carbonyl}-8-hydroxy-1,6-naphthyridin-5-yl)-L-prolinamide;
N-(4-fluorobenzyl)-8-hydroxy-5-(2-oxotetrahydropyrimidin-1(2H)-yl)-1,6-naphthyridine-7-carboxamide;
N-(4-fluorobenzyl)-8-hydroxy-5-(2-oxoimidazolidin-1-yl)-1,6-naphthyridine-7-carboxamide;
N-7-(4-fluorobenzyl)-8-hydroxy-N 5, N 5-dimethyl-1,6-naphthyridine-5,7-dicarboxamide;
N-7-(4-fluorobenzyl)-8-hydroxy-N 5-isopropyl-N 5-methyl-1,6-naphthyridine-5,7-dicarboxamide;
N-7-(4-fluorobenzyl)-8-hydroxy-N 5-(2-morpholin-4-ylethyl)-1,6-naphthyridine-5,7-dicarboxamide;
N 5-[2-(dimethylamino)-2-oxoethyl]-N 7-(4-fluorobenzyl)-8-hydroxy-N 5-methyl-1,6-naphthyridine-5,7-dicarboxamide;
N-(4-fluorobenzyl)-5-(1,1-dioxido-4-oxo-1,2,5-thiadiazepan-2-yl)-8-hydroxy-[1,6]napthyridine-7-carboxamide;
N-(4-fluorobenzyl)-5-(1,1-dioxido-5-methyl-4-oxo-1,2,5-thiadiazepan-2-yl)-8-hydroxy-[1,6]napthyridine-7-carboxamide;
N-(4-fluorobenzyl)-5-(1,1-dioxido-5-ethyl-4-oxo-1,2,5-thiadiazepan-2-yl)-8-hydroxy-[1,6]napthyridine-7-carboxamide;
N-(4-fluorobenzyl)-5-(1,1-dioxido-1,5,2-dithiazepan-2-yl)-8-hydroxy-[1,6]napthyridine-7-carboxamide;
N-(4-fluorobenzyl)-5-(1,1,5,5-tetraoxido-1,5,2-dithiazepan-2-yl)-8-hydroxy-[1,6]napthyridine-7-carboxamide;
N-(4-fluorobenzyl)-5-(1,4-dimethyl-7-oxo-1,4-diazepan-5-yl)-8-hydroxy-[1,6]-napthyridine-7-carboxamide;
N-(4-fluorobenzyl)-5-(1-methyl-7-oxo-1,4-diazepan-5-yl)-8-hydroxy-[1,6]-napthyridine-7-carboxamide;
N-(4-Fluorobenzyl)-5-(7-oxo-1,4-diazepan-5-yl)-8-hydroxy-[1,6]-napthyridine-7-carboxamide;
N-(4-fluorobenzyl)-5-[4-(methylsulfonyl)thiomorpholin-2-yl]-8-hydroxy-[1,6]napthyridine-7-carboxamide;
N-(4-fluorobenzyl)-5-[4-(methylsulfonyl)-1-oxidothiomorpholin-2-yl]-8-hydroxy-[1,6]napthyridine-7-carboxamide;
N-(4-fluorobenzyl)-5-[4-(methylsulfonyl)-1,1-dioxidothiomorpholin-2-yl]-8-hydroxy-[1,6]napthyridine-7-carboxamide;
N-(4-fluorobenzyl)-5-(2-Acetyl-1-methylpyrazolidin-3-yl)-8-hydroxy-[1,6]napthyridine-7-carboxamide;
N-(4-fluorobenzyl)-5-(1,1-dioxido-1,2,5-thiadiazepan-2-yl)-8-hydroxy-[1,6]napthyridine-7-carboxamide;
N-(4-fluorobenzyl)-8-hydroxy-5-[5-(methylsulfonyl)-1,1-dioxido-1,2,5-thiadiazepan-2-yl]-1,6-naphthyridine-7-carboxamide;
N-(4-fluorobenzyl)-8-hydroxy-5(6-methyl-1,1-dioxido-1,2,6-thiadiazinan-2yl)-1,6-naphthyridine-7-carboxamide;
N-(4-fluorobenzyl)-8-hydroxy-5-{methyl[(1-methyl-1H-imidazol-4-yl)sulfonyl]amino}-1,6-naphthyridine-7-carboxamide;
N-[4-fluoro-2-(methylsulfonyl)benzyl]-8-hydroxy-5-{methyl[(1-methyl-1H-imidazol-4-yl)sulfonyl]amino}-1,6-naphthyridine-7-carboxamide;
N-7-[4-fluoro-2-(methylsulfonyl)benzyl]-8-hydroxy-N-5-, N-5-dimethyl-1,6-naphthyridine-5,7-dicarboxamide;
N-[4-fluoro-2-(methylsulfonyl)benzyl]-8-hydroxy-5-(1,1-dioxido-1,2-thiazinan-2-yl)-1,6-naphthyridine-7-carboxamide
N-(2-(methylsulfonyl)benzyl)-5-(1,1-dioxido-1,2-thiazinan-2-yl)-8-hydroxy-1,6-naphthyridine-7-carboxamide;
N-(4-fluorobenzyl)-8-hydroxy-5-(1-methyl-5-oxopyrrolidin-3-yl)-1,6-naphthyridine-7-carboxamide;
and pharmaceutically acceptable salts thereof.

16. A compound selected from the group consisting of
1-(7-{[(4-fluorobenzyl)amino]carbonyl}-8-hydroxy-1,6-naphthyridin-5-yl)-4-methylpiperazine;
1-(7-{[(4-fluorobenzyl)amino]carbonyl}-8-hydroxy-1,6-naphthyridin-5-yl)piperazine;
N-(3,5-dichlorobenzyl)-5-(4-formylpiperazin-1-yl)-8-hydroxy-1,6-naphthyridine-7-carboxamide;
N-(3,5-dichlorobenzyl)-5-{4-[2-(formylamino)ethyl]piperazin-1-yl}-8-hydroxy-1,6-naphthyridine-7-carboxamide;
N-(3,5-dichlorobenzyl)-8-hydroxy-5-[4-(pyridin-2-ylmethyl)piperazin-1-yl]-1,6-naphthyridine-7-carboxamide;
1-(7-{[(3,5-dichlorobenzyl)amino]carbonyl}-8-hydroxy-1,6-naphthyridin-5-yl)-4-(2-oxo-2-pyrrolidin-1-ylethyl)piperazine;
1-(7-{[(3,5-dichlorobenzyl)amino]carbonyl}-8-hydroxy-1,6-naphthyridin-5-yl)piperazine;
2-(7-{[(3,5-dichlorobenzyl)amino]carbonyl}-8-hydroxy-1,6-naphthyridin-5-yl)octahydropyrrolo[1,2-a]pyrazine;
N-(3,5-dichlorobenzyl)-8-hydroxy-5-(1,4,6,7-tetrahydro-5H-pyrazolo[4,3-c]pyridin-5-yl)-1,6-naphthyridine-7-carboxamide;
N-(3,5-dichlorobenzyl)-8-hydroxy-5-{[4-(3-methyl-2-oxoimidazolidin-1-yl)phenyl]amino}-1,6-naphthyridine-7-carboxamide;
5-[3-(aminocarbonyl)piperidin-1-yl]-N-(3,5-dichlorobenzyl)-8-hydroxy-1,6-naphthyridine-7-carboxamide;
N-(3,5-dichlorobenzyl)-8-hydroxy-5-(4-pyrrolidin-1-ylpiperidin-1-yl)-1,6-naphthyridine-7-carboxamide;
N-(3,5-dichlorobenzyl)-8-hydroxy-5-[(2-morpholin-4-ylethyl)amino]-1,6-naphthyridine-7-carboxamide;
N-(3,5-dichlorobenzyl)-8-hydroxy-5-(4-methylpiperazin-1-yl)-1,6-naphthyridine-7-carboxamide;
8-hydroxy-5-methyl-[1,6]naphthyridine-7-carboxylic acid 3,5-dichloro-benzylamide;
N-(3,5-dichlorobenzyl)-8-hydroxy-5-[4-(pyrimidin-2-ylamino)piperidin-1-yl]-1,6-naphthyridine-7-carboxamide
N-(3,5-dichlorobenzyl)-8-hydroxy-5-[(3-morpholin-4-ylpropyl)amino]-1,6-naphthyridine-7-carboxamide;
N-(3,5-dichlorobenzyl)-8-hydroxy-5-[(2-morpholin-4-yl-2-pyridin-3-ylethyl)amino]-1,6-naphthyridine-7-carboxamide;
2-{2-[(7-{[(3,5-dichlorobenzyl)amino]carbonyl}-8-hydroxy-1,6-naphthyridin-5-yl)(methyl)amino]ethyl}pyridine;
N-(3,5-dichlorobenzyl)-8-hydroxy-5-(4-pyridin-2-ylpiperazin-1-yl)-1,6-naphthyridine-7-carboxamide;
and pharmaceutically acceptable salts thereof.

17. A compound selected from the group consisting of
5-[[2-(dimethylamino)-2-oxoethyl](methyl)amino]-N-(4-fluorobenzyl)-8-hydroxy-1,6-naphthyridine-7-carboxamide;

N-1-(7-{[(4-fluorobenzyl)amino]carbonyl}-8-hydroxy-1,
6-naphthyridin-5-yl)-N-1-,N-2-,N-2-trimethylethane-
diamide;

N-(4-fluorobenzyl)-5-(2,6-dioxohexahydropyrimidin-4-
yl)-8-hydroxy-[1,6]napthyridine-7-carboxamide;

5-(1,3-dimethyl-2,6-dioxohexahydro-4-pyrimidinyl)-N-
(4-fluorobenzyl)-8-hydroxy[1,6]-naphthyridine-7-
carboxamide;

5-(1-methyl-2,6-dioxohexahydro-4-pyrimidinyl)-N-(4-
fluorobenzyl)-8-hydroxy[1,6]-naphthyridine-7-
carboxamide;

5-(3-methyl-2,6-dioxohexahydro-4-pyrimidinyl)-N-(4-
fluorobenzyl)-8-hydroxy[1,6]-naphthyridine-7-
carboxamide;

N-(4-fluorobenzyl)-8-hydroxy-5-(5-oxo-1,4-thiazepan-7-
yl)[1,6]naphthyridine-7-carboxamide;

N-(4-fluorobenzyl)-8-hydroxy-5-(1-oxido-5-oxo-1,4-
thiazepan-7-yl)-[1,6]naphthyridine-7-carboxamide;

N-(4-fluorobenzyl)-8-hydroxy-5-(1,1-dioxido-5-oxo-1,4-
thiazepan-7-yl)[1,6]-naphthyridine-7-carboxamide;

N-(4-fluorobenzyl)-5-{[2-(dimethylamino)-2-oxoethyl]
sulfanyl}-8-hydroxy-[1,6]napthyridine-7-
carboxamide;

N-(4-fluorobenzyl)-5-[2-(dimethylamino)-2-oxoethoxy]-
8-hydroxy-[1,6]napthyridine-7-carboxamide;

N-(4-fluorobenzyl)-5-{[2-(dimethylamino)-2-oxoethyl]
(methylsulfonyl)amino}-8-hydroxy-[1,6]napthyridine-
7-carboxamide;

N-(4-fluorobenzyl)-5-[3-(dimethylamino)-3-oxopropyl]-
8-hydroxy-[1,6]napthyridine-7-carboxamide;

N-(4-fluorobenzyl)-5-[(1E)-3-(dimethylamino)-3-oxo-1-
propenyl]-8-hydroxy-[1,6]napthyridine-7-
carboxamide;

N-(4-fluorobenzyl)-5-[2-(3-oxo-1-piperazinyl)ethyl]-8-
hydroxy-[1,6]napthyridine-7-carboxamide;

N-(4-Fluorobenzyl)-5-[2-(2-oxo-1-imidazolidinyl)ethyl]-
8-hydroxy-[1,6]napthyridine-7-carboxamide;

N-(4-fluorobenzyl)-5-[2-(2-oxo-1-piperazinyl)ethyl]-8-
hydroxy-[1,6]napthyridine-7-carboxamide;

5-(1,1-dioxido-1,2-thiazinan-2-yl)-N-(4-fluorobenzyl)-8-
hydroxy-1,6-naphthyridine-7-carboxamide;

5-(1,1-dioxidoisothiazolidin-2-yl)-N-(4-fluorobenzyl)-8-
hydroxy-1,6-naphthyridine-7-carboxamide;

N-(4-fluorobenzyl)-8-hydroxy-5-[methyl
(methylsulfonyl)amino]-1,6-naphthyridine-7-
carboxamide;

5-[acetyl(methyl)amino]-N-(4-fluorobenzyl)-8-hydroxy-
1,6-naphthyridine-7-carboxamide;

5-[[(dimethylamino)carbonyl](methyl)amino]-N-(4-
fluorobenzyl)-8-hydroxy-1,6-naphthyridine-7-
carboxamide;

N-(4-fluorobenzyl)-8-hydroxy-5-thiomorpholin-4-yl-1,6-
naphthyridine-7-carboxamide;

5-(1,1-dioxidothiomorpholin-4-yl)-N-(4-fluorobenzyl)-8-
hydroxy-1,6-naphthyridine-7-carboxamide;

N-(4-fluorobenzyl)-8-hydroxy-5-(4-methyl-3-
oxopiperazin-1-yl)-1,6-naphthyridine-7-carboxamide;

1-(7-{[4-fluorobenzyl)amino]carbonyl}-8-hydroxy-1,6-
naphthyridin-5-yl)-L-prolinamide;

N-(4-fluorobenzyl)-8-hydroxy-5-(2-oxotetrahydro-
pyrimidin-1(2H)-yl)-1,6-naphthyridine-7-
carboxamide;

N-(4-fluorobenzyl)-8-hydroxy-5-(2-oxoimidazolidin-1-
yl)-1,6-naphthyridine-7-carboxamide;

N-7-(4-fluorobenzyl)-8-hydroxy-N 5, N 5-dimethyl-1,6-
naphthyridine-5,7-dicarboxamide;

N 7-(4-fluorobenzyl)-8-hydroxy-N 5-isopropyl-N
5-methyl-1,6-naphthyridine-5,7-dicarboxamide;

N 7-(4-fluorobenzyl)-8-hydroxy-N 5-(2-morpholin-4-
ylethyl)-1,6-naphthyridine-5,7-dicarboxamide;

N 5-[2-(dimethylamino)-2-oxoethyl]-N 7-(4-
fluorobenzyl)-8-hydroxy-N 5-methyl-1,6-
naphthyridine-5,7-dicarboxamide;

N-(4-fluorobenzyl)-5-(1,1-dioxido-4-oxo-1,2,5-
thiadiazepan-2-yl)-8-hydroxy-[1,6]napthyridine-7-
carboxamide;

and pharmaceutically acceptable salts thereof.

18. The compound according to claim 17, which is 5-(1,1
-dioxido-1,2-thiazinan-2-yl)-N-(4-fluorobenzyl)-8-
hydroxy-1,6-naphthyridine-7-carboxamide; or a pharma-
ceutically acceptable salt thereof.

19. A compound selected from the group consisting of
N-(4-fluorobenzyl)-5-(1,1-dioxido-5-methyl-4-oxo-1,2,
5-thiadiazepan-2-yl)-8-hydroxy-[1,6]napthyridine-7-
carboxamide;

N-(4-fluorobenzyl)-5-(1,1-dioxido-5-ethyl-4-oxo-1,2,5-
thiadiazepan-2-yl)-8-hydroxy-[1,6]napthyridine-7-
carboxamide;

N-(4-fluorobenzyl)-5-(1,1-dioxido-1,5,2-dithiazepan-2-
yl)-8-hydroxy-[1,6]napthyridine-7-carboxamide;

N-(4-fluorobenzyl)-5-(1,1,5,5-tetraoxido-1,5,2-
dithiazepan-2-yl)-8-hydroxy-[1,6]napthyridine-7-
carboxamide;

N-(4-fluorobenzyl)-5-(1,4-dimethyl-7-oxo-1,4-diazepan-
5-yl)-8-hydroxy-[1,6]-napthyridine-7-carboxamide;

N-(4-fluorobenzyl)-5-(1-methyl-7-oxo-1,4-diazepan-5-
yl)-8-hydroxy-[1,6]-napthyridine-7-carboxamide;

N-(4-Fluorobenzyl)-5-(7-oxo-1,4-diazepan-5-yl)-8-
hydroxy-[1,6]-napthyridine-7-carboxamide N-(4-fluorobenzyl)-5-[4-(methylsulfonyl)thiomorpholin-
2-yl]-8-hydroxy-[1,6]napthyridine-7-carboxamide;

N-(4-fluorobenzyl)-5-[4-(methylsulfonyl)-1-
oxidothiomorpholin-2-yl]-8-hydroxy-[1,6]
napthyridine-7-carboxamide;

N-(4-fluorobenzyl)-5-[4-(methylsulfonyl)-1,1-
dioxidothiomorpholin-2-yl]-8-hydroxy-[1,6]
napthyridine-7-carboxamide;

N-(4-fluorobenzyl)-5-(2-Acetyl-1-methylpyrazolidin-3-
yl)-8-hydroxy-[1,6]napthyridine-7-carboxamide;

N-(4-fluorobenzyl)-5-(1,1-dioxido-1,2,5-thiadiazepan-2-
yl)-8-hydroxy-[1,6]napthyridine-7-carboxamide;

N-(4-fluorobenzyl)-8-hydroxy-5-[5-(methylsulfonyl)-1,
1-dioxido-1,2,5-thiadiazepan-2-yl]-1,6-naphthyridine-
7-carboxamide;

N-(4-fluorobenzyl)-8-hydroxy-5(6-methyl-1,1-dioxido-1,
2,6-thiadiazinan-2yl)-1,6-naphthyridine-7-
carboxamide;

N-(4-fluorobenzyl)-8-hydroxy-5-{methyl[(1-methyl-1H-
imidazol-4-yl)sulfonyl]amino}-1,6-naphthyridine-7-
carboxamide;

N-[4-fluoro-2-(methylsulfonyl)benzyl]-8-hydroxy-5-
{methyl[(1-methyl-1H-imidazol-4-yl)sulfonyl]
amino}-1,6-naphthyridine-7-carboxamide;

N-7-[4-fluoro-2-(methylsulfonyl)benzyl]-8-hydroxy-N-
5-,N-5-dimethyl-1,6-naphthyridine-5,7-
dicarboxamide;

N-[4-fluoro-2-(methylsulfonyl)benzyl]-8-hydroxy-5-(1,1-dioxido-1,2-thiazinan-2-yl)-1,6-naphthyridine-7-carboxamide N-(2-(methylsulfonyl)benzyl)-5-(1,1-dioxido-1,2-thiazinan-2-yl)-8-hydroxy-1,6-naphthyridine-7-carboxamide;

N-(2-[(dimethylamino)sulfonyl]-4-fluorobenzyl)-5-(1,1-dioxido-1,2-thiazinan-2-yl)-8-hydroxy-1,6-naphthyridine-7-carboxamide;

N-(4-fluorobenzyl)-8-hydroxy-5-(1-methyl-5-oxopyrrolidin-3-yl)-1,6-naphthyridine-7-carboxamide;

and pharmaceutically acceptable salts thereof.

20. A pharmaceutical composition comprising a therapeutically effective amount of a compound according to claim 1, or a pharmaceutically acceptable salt thereof, and a pharmaceutically acceptable carrier.

21. A method for treating infection by HIV or for treating or delaying the onset of AIDS in a subject in need thereof which comprises administering to the subject a therapeutically effective amount of the compound according to claim 1 or a pharmaceutically acceptable salt thereof.

22. A method for treating infection by HIV or for treating, or delaying the onset of AIDS in a subject in need thereof which comprises administering to the subject a therapeutically effective amount of the composition according to claim 20.

23. A pharmaceutical composition which comprises the product prepared by combining an effective amount of a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 6,921,759 B2
DATED : July 26, 2005
INVENTOR(S) : Anthony et al.

It is certified that error appears in the above-identified patent and that said Letters Patent is hereby corrected as shown below:

Column 251,
Line 39, after "alkyl-$R^k$", delete "," and insert therefor -- ; --.

Column 254,
Line 59, delete:
    "(52)      -$N(R^c)$-$R^k$, -O-$C_{1-4}$ alkyl-$S(O)_nR^k$,"
and insert therefor:
    -- (51)      -O-$C_{1-4}$ alkyl-$S(O)_nR^k$,
       (52)      -$N(R^c)$-$R^k$, --.

Column 269,
Line 56, after "(f)", delete "-S-$C_{1-6}$ alkyl," and insert therefor -- -S-$C_{1-4}$ alkyl, --.
Line 60, after "(j)", delete "-$C_{1-6}$ alkyl-$N(R^a)_2$," and insert therefor
-- -$C_{1-4}$ alkyl-$N(R^a)_2$, --.

Signed and Sealed this

Twenty-fifth Day of October, 2005

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
tgaccaaggg ctaattcact                                           20

<210> SEQ ID NO 2
<211> LENGTH: 20
<212> TYPE: DNA
<213> ORGANISM: Artificial Sequence
<220> FEATURE:
```

-continued

<223> OTHER INFORMATION: Synthetic DNA

<400> SEQUENCE: 2
actggttccc gattaagtga                                               20